(12) United States Patent
Lukashev et al.

(10) Patent No.: US 12,012,422 B2
(45) Date of Patent: Jun. 18, 2024

(54) COPPER COMPLEXES FOR TREATMENT OF NEURODEGENERATIVE DISORDERS

(71) Applicant: ALS Therapy Development Institute, Cambridge, MA (US)

(72) Inventors: Matvey Lukashev, Upton, MA (US); Alexei Pushechnikov, San Diego, CA (US); Peter Demin, Moscow (RU); Kyle Denton, Medford, MA (US)

(73) Assignee: ALS THERAPY DEVELOPMENT INSTITUTE, Cambridge, MA (US)

( * ) Notice: Subject to any disclaimer, the term of this patent is extended or adjusted under 35 U.S.C. 154(b) by 150 days.

(21) Appl. No.: 17/458,021

(22) Filed: Aug. 26, 2021

(65) Prior Publication Data

US 2023/0054997 A1    Feb. 23, 2023

Related U.S. Application Data

(60) Provisional application No. 63/070,792, filed on Aug. 26, 2020.

(51) Int. Cl.
| | | |
|---|---|---|
| *C07F 1/08* | (2006.01) | |
| *A61P 25/28* | (2006.01) | |
| *C07F 9/54* | (2006.01) | |

(52) U.S. Cl.
CPC .............. *C07F 1/08* (2013.01); *A61P 25/28* (2018.01); *C07F 9/5442* (2013.01)

(58) Field of Classification Search
None
See application file for complete search history.

(56) References Cited

U.S. PATENT DOCUMENTS

2020/0062703 A1    2/2020    Grapperhaus et al.

FOREIGN PATENT DOCUMENTS

| WO | WO2008/061306 A1 | 5/2008 |
| WO | WO2015/070177 A2 | 5/2015 |
| WO | WO2019/046761 A1 | 3/2019 |

OTHER PUBLICATIONS

Andres et al., "Synthesis, Characterization, and Biological Activity of Hybrid Thiosemicarbazone-Alkylthiocarbamate Metal Complexes", *Inorganic Chemistry* 59:4924-4935 (2020).
Bates "Cancer, Copper, & Mysterious Mechanisms", obtained Nov. 2021.
International Search Report and Written Opinion for International Application No. PCT/US2021/047727, dated Jan. 31, 2022, 15 pages.
Attia, et al., "Some glyoxalbis(thiosemicarbazone)copper(II) chelates of pronounced antimicrobial activity", *Egyptian Journal of Chemistry* 26(5):453-459 (1983), graphical abstract only.

*Primary Examiner* — Po-Chih Chen
(74) *Attorney, Agent, or Firm* — LATHROP GPM LLP; Brian C. Trinque

(57) ABSTRACT

The present disclosure relates to copper complexes, pharmaceutical compositions comprising these complexes, chemical processes for preparing these complexes, and their use in the treatment of neurodegenerative disease, e.g., amyotrophic lateral sclerosis (ALS).

14 Claims, 22 Drawing Sheets

COPPER COMPLEXES FOR TREATMENT OF NEURODEGENERATIVE DISORDERS

CROSS-REFERENCE TO RELATED APPLICATIONS

This application claims the benefit of U.S. Ser. No. 63/070,792, filed Aug. 26, 2020, the disclosure of which is incorporated herein by reference in its entirety.

BACKGROUND

Neurodegenerative diseases are age-dependent disorders that are becoming increasingly prevalent, in part due to the increasing elderly population (Heemels, *Nature* (2016) 539: 179).

For example, amyotrophic lateral sclerosis (ALS), also known as motor neuron disease, Lou Gehrig's disease, or Charcot's disease, is estimated to affect 30,000 Americans and over 400,000 people worldwide at any given time. Approximately 5,000 Americans are diagnosed with ALS every year. The disease causes the unrelenting death of motor neurons, resulting in a progressive paralysis that kills its victims within one to five years on average. Most people diagnosed with ALS live 3-5 years after their first signs of disease. About 10% of people with ALS survive at least 10 years. The variable rate of disease progression makes prognosis difficult to predict, and therapies challenging to develop.

Only two agents (riluzole and edaravone) have been approved by the FDA for treating ALS, and while both slow disease progression in a subset of patients, and can extend life by up to a few months, neither is able to treat or cure the disease.

Some inherited forms of ALS are caused by genetic mutations. The genetic change alters an enzyme within cells called copper-zinc superoxide dismutase (Cu—Zn superoxide dismutase, now called commonly SOD1). This enzyme serves to keep cells safe from metabolic waste that can cause damage if not rendered harmless.

The compound CuATSM has been shown by the rigorous methods established in the art to be protective in transgenic mouse models of ALS where the transgenic mice were engineered to express human SOD1 harboring mutations found in SOD1 familial ALS.

However, there is a need in the art for improved therapeutic agents that can treat neurological diseases and/or copper deficiency-related disorders.

SUMMARY

Provided herein are compounds useful in methods of treating or preventing a neurodegenerative disease in a subject in need thereof.

In one aspect, the disclosure provides a compound of Formula (I):

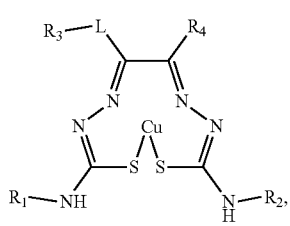

(I)

or a pharmaceutically acceptable salt thereof, wherein L, $R_1$, $R_2$, $R_3$, and $R_4$ are as defined herein.

In an embodiment, the compound of Formula (I) is selected from the group consisting of Compounds 1-22, or pharmaceutically acceptable salts thereof.

In another aspect, the disclosure provides a compound of Formula (II):

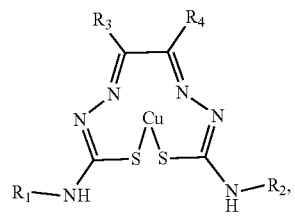

(II)

or a pharmaceutically acceptable salt thereof, wherein $R_1$, $R_2$, $R_3$, and $R_4$ are as defined herein.

In an embodiment, the compound of Formula (II) is selected from the group consisting of Compounds 23-46.

In another aspect, the disclosure provides a compound of Formula (III):

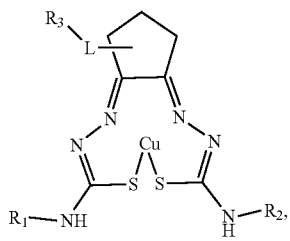

(III)

or a pharmaceutically acceptable salt thereof, wherein L, $R_1$, $R_2$, and $R_3$ are as defined herein.

In an embodiment, the compound of Formula (III) is selected from the group consisting of Compounds 47-53.

In another aspect, the disclosure provides a compound of Formula (IV):

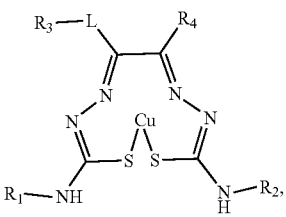

(IV)

or a pharmaceutically acceptable salt thereof, wherein L, $R_1$, $R_2$, $R_3$, and $R_4$ are as defined herein.

In an embodiment, the compound of Formula (IV) is selected from the group consisting of Compounds 1-22, 57, 59-61, and 66-78.

In another aspect, the disclosure provides a compound of Formula (V):

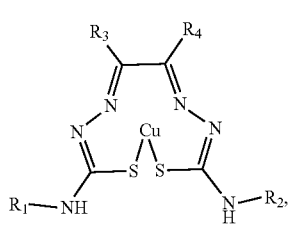

or pharmaceutically acceptable salts thereof, wherein $R_1$, $R_2$, $R_3$, and $R_4$ are as defined herein.

In an embodiment, the compound of Formula (V) is selected from the group consisting of Compounds 23-46 and 79-127.

In another aspect, the disclosure provides a compound selected from the group consisting of Compounds 56-65.

In another aspect, the disclosure provides a pharmaceutical composition comprising a compound of the disclosure, or a pharmaceutically acceptable salt thereof, and at least one pharmaceutically acceptable excipient, diluent, or carrier.

In another aspect, the disclosure provides a method of treating or preventing a neurodegenerative disease in a subject in need thereof, the method comprising administering to the subject a therapeutically effective amount of a compound of the disclosure.

In an embodiment, the neurodegenerative disease is amyotrophic lateral sclerosis (ALS), frontal temporal dementia (FTD), Parkinson's disease, Huntington's disease, and Alzheimer's disease. In another embodiment, the neurodegenerative disease is ALS. In a further embodiment, the ALS is familial or sporadic.

In another aspect, the disclosure provides a method of making a compound of the disclosure.

BRIEF DESCRIPTION OF THE FIGURES

FIG. 4A illustrates the age of onset of neurological disease, FIG. 4B illustrates extended survival, FIG. 4C demonstrates improved body weight maintenance in Compound 25-treated mice, and FIG. 4D illustrates differences in neurological disease progression.

DETAILED DESCRIPTION

Figure 1A:
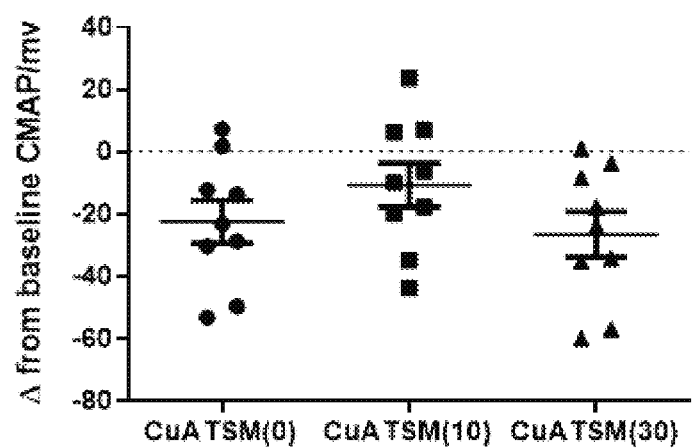
FIG. 1A illustrates the compound muscle action potential (CMAP) change from baseline in male SOD1$^{G93A}$ mice after being treated with 10 mg/kg or 30 mg/kg CuATSM or vehicle daily for four weeks.

Provided herein are compounds of Formula (I):

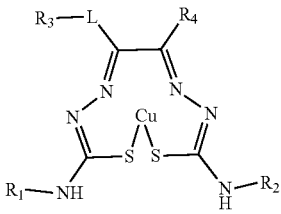

(I)

and pharmaceutically acceptable salts thereof, compounds of Formula (II):

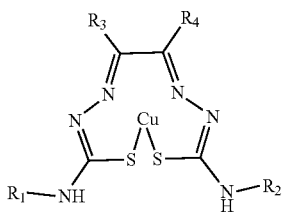

(II)

and pharmaceutically acceptable salts thereof, compounds of Formula (III):

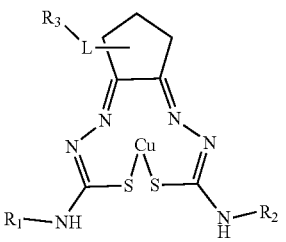

(III)

and pharmaceutically acceptable salts thereof, compound of Formula (IV):

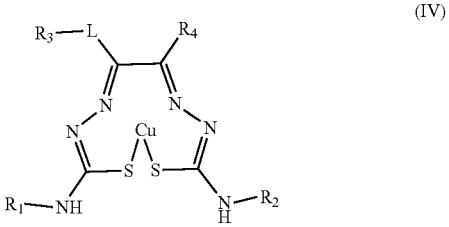

(IV)

and pharmaceutically acceptable salts thereof, and compound of Formula (V):

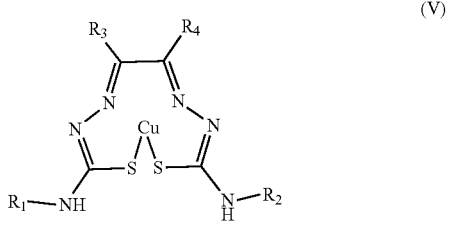

(V)

and pharmaceutically acceptable salts thereof, all of which are useful in the treatment of neurological diseases and/or copper deficiency-related disorders.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, 1%, and ±0.1% from the specified value, as such variations are appropriate to perform the disclosed methods.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert-butyl, pentyl, neopentyl, and 1-hexyl.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "halo" or "halogen" alone or as part of another substituent means, unless otherwise stated, a fluorine, chlorine, bromine, or iodine atom.

As used herein, the term "cycloalkyl" means a non-aromatic carbocyclic system that is partially or fully saturated having the number of carbon atoms designated. The cycloalkyl group may be a monocyclic, a fused polycyclic, a bridged polycyclic, or a spiro polycyclic carbocycle. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "heterocyclyl" or "heterocycloalkyl" means a non-aromatic saturated or partially saturated monocyclic, fused polycyclic, bridged polycyclic, or spiro polycyclic ring system containing the number of ring atoms designated, and wherein the ring atoms are carbon atoms and 1, 2, 3, or 4 heteroatoms selected independently from N, O, and S. The term "heterocyclyl" includes cyclic esters (i.e., lactones) and cyclic amides (i.e., lactams) and also includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. Unless otherwise noted, the heterocycle or heterocycloalkyl is attached to its pendant group at any heteroatom or carbon atom that results in a stable structure.

As used herein, the term "aromatic" refers to a carbocycle or heterocycle with one or more polyunsaturated rings and having aromatic character, i.e., having (4n+2) delocalized rr (pi) electrons, where n is an integer.

As used herein, the term "aryl" means an aromatic carbocyclic system containing the designated number of ring atoms. Aryl groups can be a single rings or multiple rings (up to three rings) which are fused together or linked covalently. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl.

As used herein, the term "heteroaryl" means an aromatic carbocyclic system containing 1, 2, 3, or 4 heteroatoms selected independently from N, O, and S. Heteroaryl groups may be single rings or multiple rings (up to three rings) which are fused together or linked covalently. If the rings are fused, one of the rings must be fully unsaturated and the fused ring(s) may be fully saturated, partially unsaturated or fully unsaturated. The term "heteroaryl" includes, but is not limited to, furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, benzo[d][1,3]dioxolyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. Unless otherwise noted, the heterocycle or heterocycloalkyl is attached to its pendant group at any heteroatom or carbon atom that results in a stable structure.

As used herein, the term "substituted" means that an atom or group of atoms has replaced hydrogen as the substituent attached to another group.

A "pharmaceutically acceptable salt" is intended to mean a salt of a free acid or base of compounds of the disclosure that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", J. Med. Chem., 2007, 50:6665-72, S. M. Berge, et al., "Pharmaceutical Salts", J Pharm Sci., 1977, 66:1-19, and Handbook of Pharmaceutical Salts, Properties, Selection, and Use, Stahl and Wermuth, Eds., Wiley-VCH and VHCA, Zurich, 2002.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "use" includes any one or more of the following embodiments of the invention, respectively: the use in the treatment of pain the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise.

As used herein, the term "patient," "individual," or "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from, ALS. In another embodiment, the subject is a cell. The terms term "patient," "individual," or "subject" do not denote a particular age or sex.

When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "composition" or "pharmaceutical composition" refers to a mixture of at least one compound useful within the invention with a pharmaceutically acceptable diluent, excipient, or carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The terms "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

The term "sporadic" refers to a neurodegenerative disease, ALS for example, that is not inherited. Sporadic ALS accounts for about 90% of cases, where the affected individual is the only member of the family with the disease. The cause of sporadic ALS is not well understood, but may be due to a combination of environmental and genetic risk factors.

The term "familial" refers to a neurodegenerative disease, ALS for example, that is inherited. Familial ALS accounts for about 10% of cases, where more than one person in the family has ALS and sometimes family members have frontotemporal dementia as well. People with familial ALS often start showing symptoms at earlier ages than in sporadic ALS. Familial ALS is most often autosomal dominant.

Compounds of the Disclosure

In one aspect, provided herein are compounds of Formula (I):

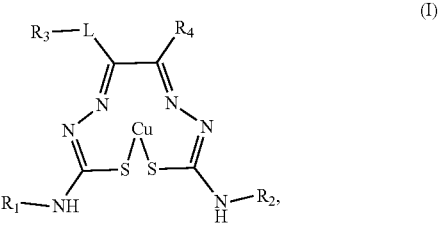

or pharmaceutically acceptable salts thereof, wherein:
L is $C_3$-$C_7$ cycloalkyl, $C_1$-$C_6$ alkyl, or absent
$R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl$)_2$;
$R_2$ is $C_1$-$C_6$ alkyl optionally substituted with 5- to 10-membered heteroaryl, $NH_2$, $NH(C_1$-$C_6$ alkyl), or $N(C_1$-$C_5$ alkyl$)_2$;
$R_3$ is $C_6$-$C_{10}$ aryl, 5- to 10-membered heteroaryl, C(O)NH—($C_1$-$C_6$ alkyl)-$PPh_3$, hydroxy, $C_1$-$C_6$ alkoxy, or O—($C_1$-$C_6$ alkyl)-O—($C_1$-$C_6$ alkyl), wherein the $C_6$-$C_{10}$ aryl is substituted one, two, or three times with the group $R_{3a}$, and wherein the 5- to 10-membered heteroaryl is optionally substituted one, two, or three times with the group $R_{3b}$;
$R_{3a}$ independently for each occurrence is $C_3$-$C_7$ cycloalkyl or 4- to 8-membered heterocycle, wherein the 4- to 8-membered heterocycle is optionally further substituted one, two, or three times with $C_1$-$C_3$ alkyl;
$R_{3b}$ independently for each occurrence is $C_1$-$C_3$ alkoxy, $C_3$-$C_7$ cycloalkyl, or 4- to 8-membered heterocycle, wherein the heterocycle is optionally further substituted one, two, or three times with $C_1$-$C_3$ alkyl; and
$R_4$ is hydrogen, $C_1$-$C_3$ alkyl, or $C_6$-$C_{10}$ aryl;
provided that when L is absent, $R_3$ is $C_6$-$C_{10}$ aryl substituted one, two, or three times with the group $R_{3a}$; or when L is absent, $R_3$ is 6- to 10-membered heteroaryl substituted one, two, or three times with the group $R_{3b}$.

In an embodiment, L is $C_3$-$C_7$ cycloalkyl or $C_1$-$C_6$ alkyl. In an embodiment, L is $C_3$-$C_7$ cycloalkyl. In an embodiment, L is $C_1$-$C_6$ alkyl. In an embodiment, L is $C_3$-$C_5$ cycloalkyl or $C_1$-$C_3$ alkyl. In an embodiment, L is is $C_3$-$C_5$ cycloalkyl. In an embodiment, L is $C_1$-$C_3$ alkyl.

In an embodiment, L is —$CH_2$—. In an embodiment, L is —$CH_2CH_2$—. In an embodiment, L is —$CH_2CH_2CH_2$—. In an embodiment, L is —$CH_2CH_2CH_2CH_2$—. In an embodiment, L is —$CH(CH_3)$—. In an embodiment, L is —$CH(CH_2CH_3)$—. In an embodiment, L is —$C(CH_3)_2$—.

In an embodiment, L is $C_3$-$C_7$ cycloalkyl or $C_3$-$C_5$ cycloalkyl, wherein the cycloalkyl group comprises a quaternary carbon that forms the point of attachment to group $R_3$ and to the rest of the scaffold. Accordingly, in an embodiment, L is represented by one of the following groups:

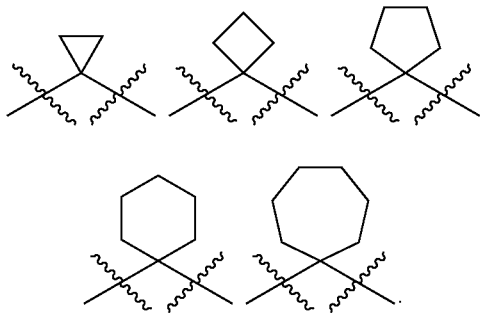

In an embodiment, $R_1$ is $C_{1-6}$ alkyl. In an embodiment, $R_1$ is $C_{1-3}$ alkyl. In an embodiment, $R_1$ is methyl or ethyl. In an embodiment, $R_1$ is methyl. In an embodiment, $R_1$ is ethyl.

In an embodiment, $R_2$ is $C_{1-6}$ alkyl. In an embodiment, $R_2$ is $C_{1-3}$ alkyl. In an embodiment, $R_2$ is methyl or ethyl. In an embodiment, $R_2$ is methyl. In an embodiment, $R_2$ is ethyl.

In an embodiment, $R_1$ and $R_2$ are identical.

In an embodiment, $R_3$ is $C_6$-$C_{10}$ aryl, 6- to 10-membered heteroaryl, C(O)NH—($C_1$-$C_6$ alkyl)-PPh$_3$, hydroxy, $C_1$-$C_6$ alkoxy, or O—($C_1$-$C_6$ alkyl)-O—($C_1$-$C_6$ alkyl), wherein the $C_6$-$C_{10}$ aryl is substituted one, two, or three times with the group $R_{3a}$, and wherein the 5- to 10-membered heteroaryl is optionally substituted one, two, or three times with the group $R_{3b}$.

In an embodiment, $R_3$ is phenyl, pyridinyl, C(O)NH—($C_1$-$C_6$ alkyl)-PPh$_3$, hydroxy, $C_1$-$C_6$ alkoxy, or O—($C_1$-$C_6$ alkyl)-O—($C_1$-$C_6$ alkyl), wherein the phenyl is substituted one, two, or three times with the group $R_{3a}$, and wherein the pyridinyl is optionally substituted one, two, or three times with the group $R_{3b}$.

In an embodiment, $R_3$ is phenyl, pyridinyl, C(O)NH—($C_1$-$C_6$ alkyl)-PPh$_3$, hydroxy, $C_1$-$C_6$ alkoxy, or O—($C_1$-$C_6$ alkyl)-O—($C_1$-$C_6$ alkyl), wherein the phenyl is substituted one time with the group $R_{3a}$, and wherein the pyridinyl is optionally substituted one time with the group $R_{3b}$.

In an embodiment, $R_{3a}$ independently for each occurrence is 4- to 8-membered heterocycle optionally further substituted one, two, or three times with $C_1$-$C_3$ alkyl. In an embodiment, $R_{3a}$ independently for each occurrence is 4- to 8-membered heterocycle optionally further substituted one time with methyl.

In an embodiment, $R_{3a}$ independently for each occurrence is pyrrolidinyl, pyrrolidinonyl, tetrahydrofuranyl, morpholinyl, thiomorpholinyl, piperidinyl, or piperazinyl, each of which is optionally further substituted one, two, or three times with $C_1$-$C_3$ alkyl. In an embodiment, $R_{3a}$ independently for each occurrence is pyrrolidinyl, pyrrolidinonyl, tetrahydrofuranyl, morpholinyl, thiomorpholinyl, piperidinyl, or piperazinyl, each of which is optionally further substituted one time with methyl. In an embodiment, $R_{3a}$ independently for each occurrence is pyrrolidinyl, pyrrolidinonyl, or morpholinyl. In an embodiment, $R_{3a}$ independently for each occurrence is represented by a group selected from the following:

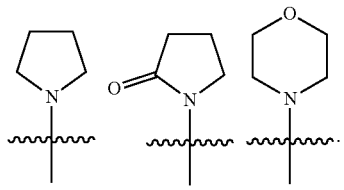

In an embodiment, $R_{3b}$ independently for each occurrence is $C_1$-$C_3$ alkoxy or 4- to 8-membered heterocycle, wherein the heterocycle is optionally further substituted one, two, or three times with $C_1$-$C_3$ alkyl. In an embodiment, $R_{3b}$ independently for each occurrence is $C_1$-$C_3$ alkoxy or 4- to 8-membered heterocycle, wherein the heterocycle is optionally further substituted one time with methyl.

In an embodiment, $R_{3b}$ independently for each occurrence is $C_1$-$C_3$ alkoxy or a heterocycle selected from the group consisting of pyrrolidinyl, pyrrolidinonyl, tetrahydrofuranyl, morpholinyl, thiomorpholinyl, piperidinyl, and piperazinyl, wherein the heterocycle is optionally further substituted one, two, or three times with $C_1$-$C_3$ alkyl. In an embodiment, $R_{3b}$ independently for each occurrence is $C_1$-$C_3$ alkoxy or a heterocycle selected from the group consisting of pyrrolidinyl, pyrrolidinonyl, tetrahydrofuranyl, morpholinyl, thiomorpholinyl, piperidinyl, and piperazinyl, wherein the heterocycle is optionally further substituted one time with methyl. In an embodiment, $R_{3b}$ independently for each occurrence is methoxy or a heterocycle selected from the group consisting of pyrrolidinyl and morpholinyl. In an embodiment, $R_{3b}$ independently for each occurrence is represented by a group selected from the following:

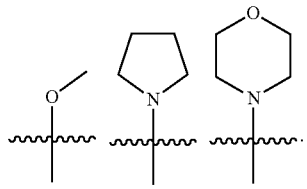

In an embodiment, $R_4$ is hydrogen, $C_1$-$C_3$ alkyl, or phenyl. In an embodiment, $R_4$ is hydrogen, methyl, or phenyl. In an embodiment, $R_4$ is hydrogen or $C_1$-$C_3$ alkyl. In an embodiment, $R_4$ is hydrogen or methyl. In an embodiment, $R_4$ is hydrogen. In an embodiment, $R_4$ is methyl. In an embodiment, $R_4$ is phenyl.

In an embodiment, the group represented by $R_3$-L has one of the following structures:

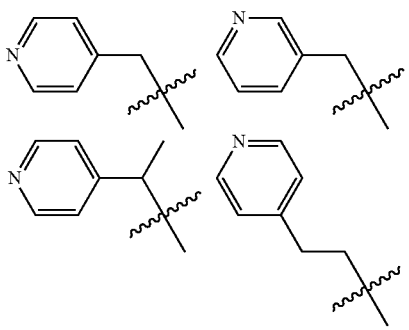

-continued

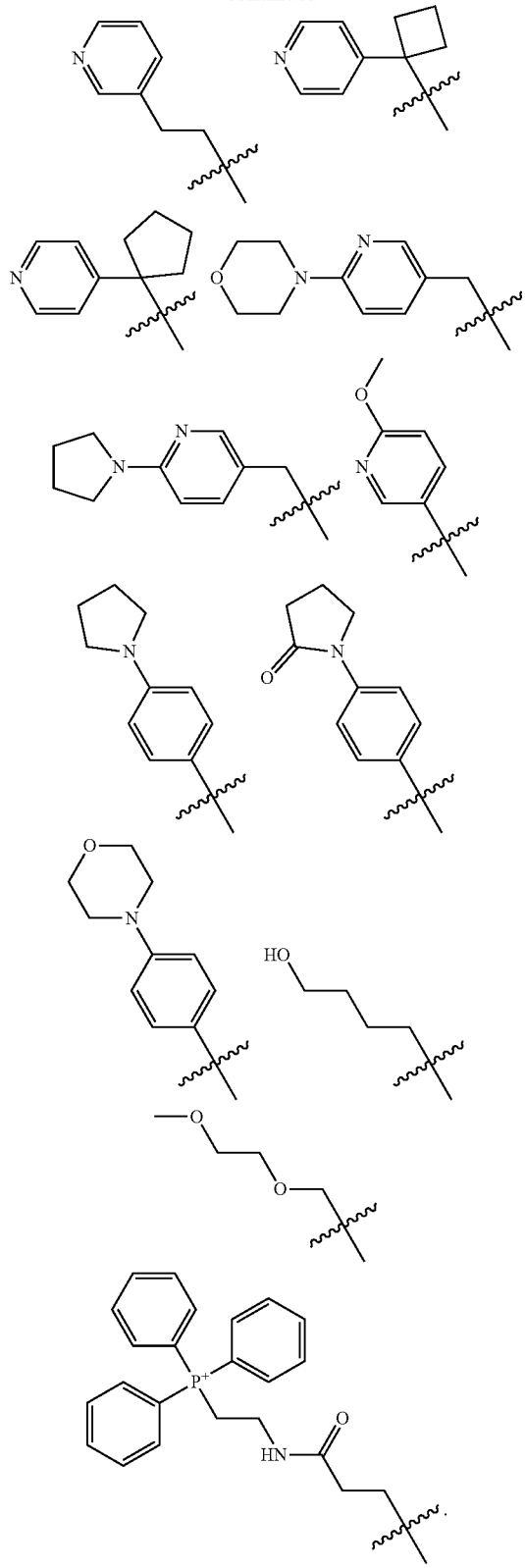

In an embodiment, $R_3$ is pyridinyl optionally substituted one, two, or three times with $C_1$-$C_3$ alkoxy or 4- to 8-membered heterocycle, wherein the 4- to 8-membered heterocycle is optionally substituted one time with $C_1$-$C_3$ alkyl.

In an embodiment, L is absent and $R_3$ is pyridinyl substituted one, two, or three times with $C_1$-$C_3$ alkoxy.

In an embodiment, L is absent and $R_3$ is phenyl substituted with 4- to 8-membered heterocycle.

In an embodiment, L is $C_3$-$C_5$ cycloalkyl or $C_1$-$C_3$ alkyl; $R_3$ is pyridinyl optionally substituted one, two, or three times with 4- to 8-membered heterocycle; and $R_4$ is methyl.

In an embodiment, the compound of Formula (I) has the structure of Compound 9:

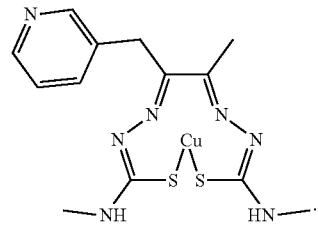

Exemplary compounds of Formula (I) include the compounds described below, or pharmaceutically acceptable salts thereof:

Compound 1

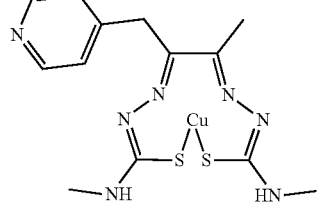

Compound 2

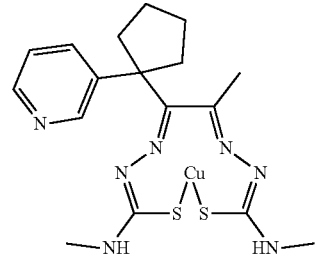

Compound 3

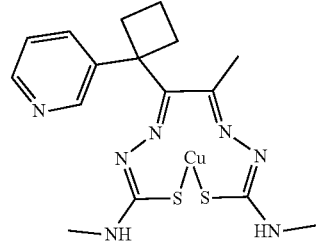

Compound 4

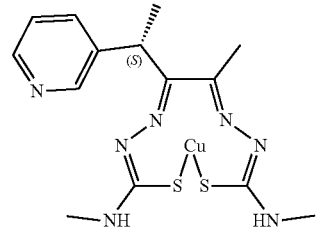

Compound 5
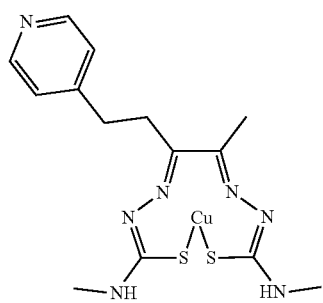
Compound 6
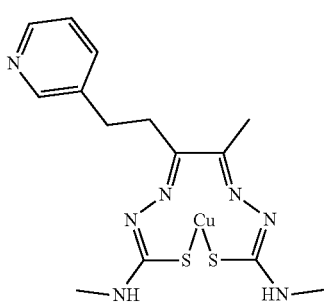
Compound 7
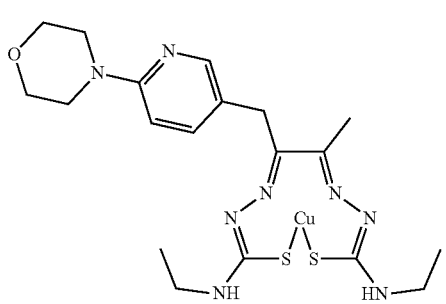
Compound 8
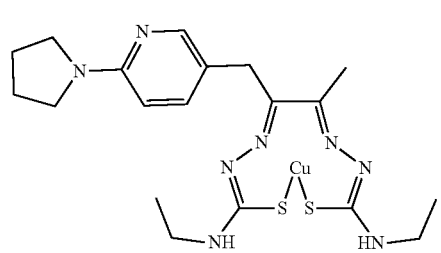
Compound 9
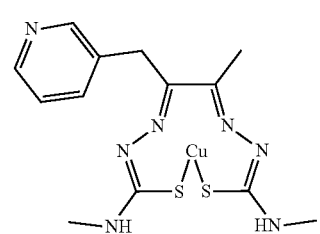
Compound 10
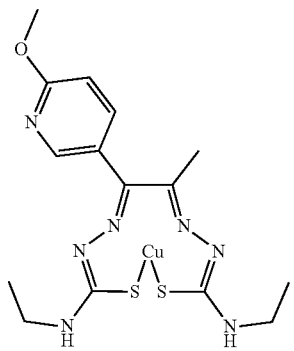
Compound 11
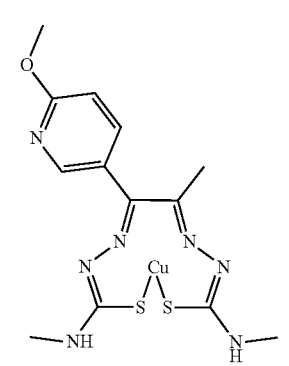
Compound 12
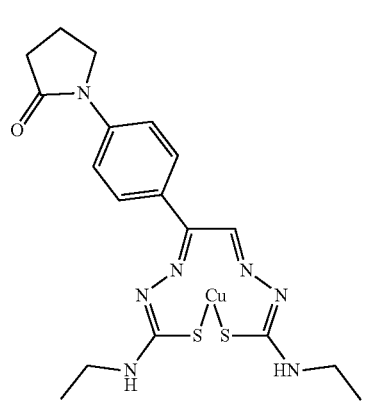
Compound 13
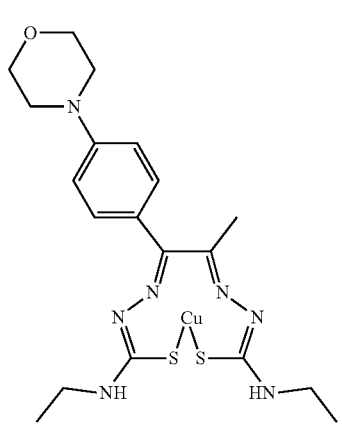

-continued
Compound 14
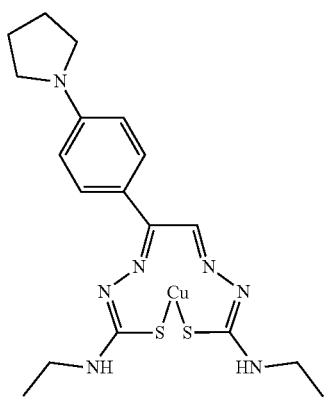
Compound 15
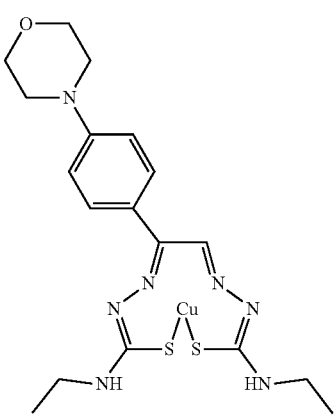
Compound 16
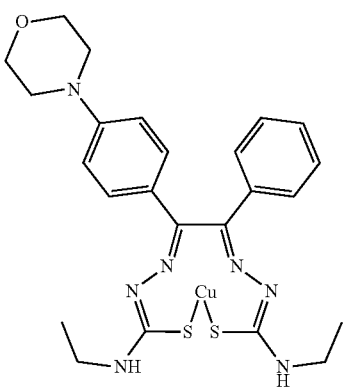
Compound 17
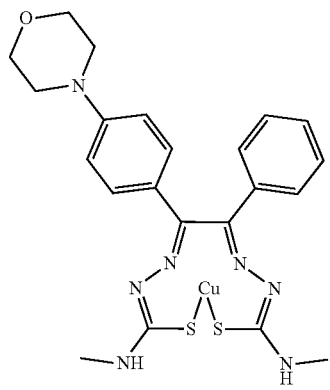
-continued
Compound 18
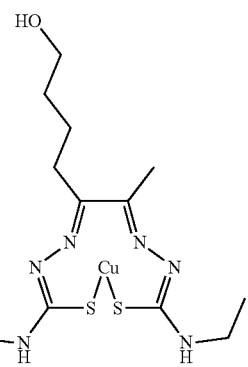
Compound 19
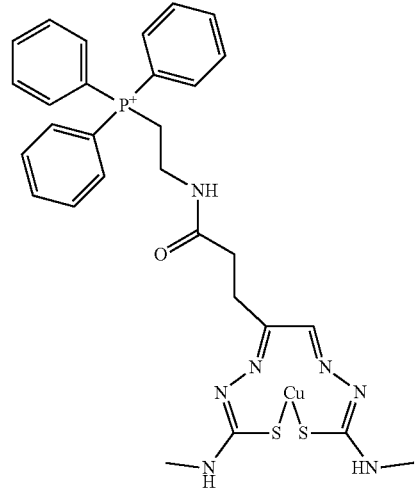
Compound 21
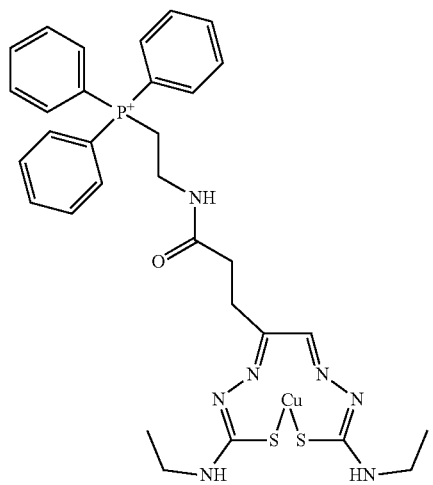
Compound 22
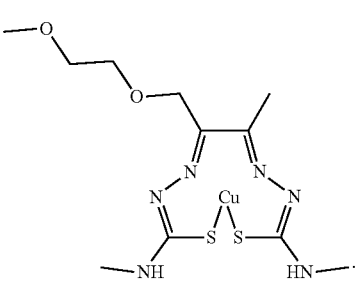

In another aspect, provided herein are compounds of Formula (II):

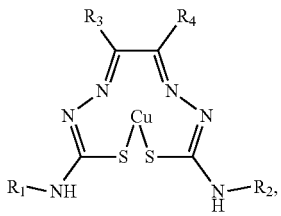

(II)

or pharmaceutically acceptable salts thereof, wherein:
- $R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
- $R_2$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
- $R_3$ is 4- to 8-membered heterocycle or 5-membered heteroaryl, wherein the 4- to 8-membered heterocycle is optionally substituted one, two, or three times with the group $R_{3a}$, and wherein the 5-membered heteroaryl is optionally substituted one, two, or three times with the group $R_{3b}$;
- $R_{3a}$ independently for each occurrence is $C_1$-$C_6$ alkyl, $C_1$-$C_6$ alkyl-($C_6$-$C_{10}$ aryl), $S(O)_2H$, $S(O)_2$—($C_1$-$C_6$ alkyl), $S(O)_2$—($C_3$-$C_7$ cycloalkyl), or $S(O)_2$—($C_6$-$C_{10}$ aryl);
- $R_{3b}$ independently for each occurrence is $C_1$-$C_6$ alkyl, $C_1$-$C_6$ alkoxy, $C_1$-$C_6$ haloalkyl, halo, nitro, cyano, C(O)-(4- to 8-membered heterocycle), or $C_1$-$C_6$ alkyl-(4- to 8-membered heterocycle), wherein each 4- to 8-membered heterocycle is optionally further substituted one, two, or three times with $C_1$-$C_3$ alkyl; and
- $R_4$ is hydrogen or $C_{1-3}$ alkyl.

In an embodiment, $R_1$ is $C_{1-6}$ alkyl. In an embodiment, $R_1$ is $C_{1-3}$ alkyl. In an embodiment, $R_1$ is methyl or ethyl. In an embodiment, $R_1$ is methyl. In an embodiment, $R_1$ is ethyl.

In an embodiment, $R_2$ is $C_{1-6}$ alkyl. In an embodiment, $R_2$ is $C_{1-3}$ alkyl. In an embodiment, $R_2$ is methyl or ethyl. In an embodiment, $R_2$ is methyl. In an embodiment, $R_2$ is ethyl.

In an embodiment, $R_1$ and $R_2$ are identical.

In an embodiment, $R_3$ is 6-membered heterocycle or 5-membered heteroaryl, wherein the 6-membered heterocycle is optionally substituted one, two, or three times with the group $R_{3a}$, and wherein the 5-membered heteroaryl is optionally substituted one, two, or three times with the group $R_{3b}$.

In an embodiment, $R_3$ is morpholinyl, piperidinyl, furyl, thiophenyl, or pyrazolyl, wherein the morpholinyl and piperidinyl are optionally substituted one, two, or three times with the group $R_{3a}$, and wherein the furyl, thiophenyl, and pyrazolyl are optionally substituted one, two, or three times with the group $R_{3b}$.

In an embodiment, $R_3$ is furyl, thiophenyl, or pyrazolyl optionally substituted one, two, or three times with the group $R_{3b}$. In an embodiment, $R_3$ is furyl, thiophenyl, or pyrazolyl substituted one, two, or three times with the group $R_{3b}$.

In an embodiment, $R_3$ is furyl optionally substituted one, two, or three times with the group $R_{3b}$. In an embodiment, $R_3$ is furyl substituted one, two, or three times with the group $R_{3b}$.

In an embodiment, $R_3$ is morpholinyl or piperidinyl optionally substituted one, two, or three times with the group $R_{3a}$.

In an embodiment, $R_{3a}$ independently for each occurrence is $C_1$-$C_6$ alkyl, $C_1$-$C_6$ alkyl-($C_6$-$C_{10}$ aryl), $S(O)_2$—($C_1$-$C_6$ alkyl), or $S(O)_2$—($C_6$-$C_{10}$ aryl).

In an embodiment, $R_{3a}$ independently for each occurrence is $C_1$-$C_6$ alkyl, $C_1$-$C_6$ alkyl-(phenyl), $S(O)_2$—($C_1$-$C_6$ alkyl), or $S(O)_2$-(phenyl).

In an embodiment, $R_{3a}$ independently for each occurrence is represented by a group selected from the following:

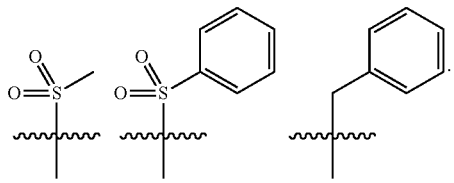

In an embodiment, $R_{3b}$ independently for each occurrence is $C_1$-$C_6$ alkyl, halo, nitro, C(O)-(4- to 8-membered heterocycle), or $C_1$-$C_6$ alkyl-(4- to 8-membered heterocycle), wherein each 4- to 8-membered heterocycle is optionally further substituted one, two, or three times with $C_1$-$C_3$ alkyl.

In an embodiment, $R_{3b}$ independently for each occurrence is $C_1$-$C_6$ alkyl, halo, nitro, C(O)-(4- to 8-membered heterocycle), or $C_1$-$C_6$ alkyl-(4- to 8-membered heterocycle), wherein each 4- to 8-membered heterocycle is independently selected from the group consisting of pyrrolidinyl, pyrrolidinonyl, tetrahydrofuranyl, morpholinyl, thiomorpholinyl, piperidinyl, and piperazinyl, and wherein each 4- to 8-membered heterocycle is optionally further substituted one, two, or three times with $C_1$-$C_3$ alkyl.

In an embodiment, $R_{3b}$ independently for each occurrence is $C_1$-$C_6$ alkyl, halo, nitro, C(O)-(4- to 8-membered heterocycle), or $C_1$-$C_6$ alkyl-(4- to 8-membered heterocycle), wherein each 4- to 8-membered heterocycle is independently selected from the group consisting of morpholinyl, piperidinyl, and piperazinyl, and wherein each 4- to 8-membered heterocycle is optionally further substituted one, two, or three times with methyl.

In an embodiment, $R_{3b}$ independently for each occurrence is represented by a group selected from the following:

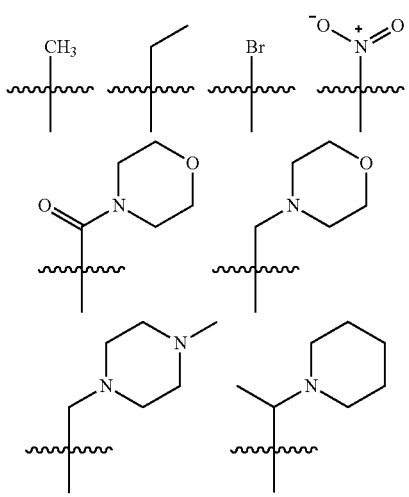

-continued

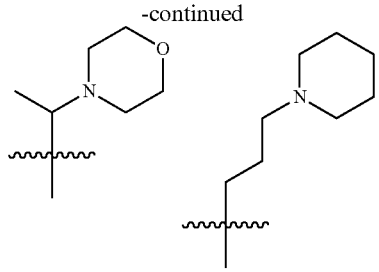

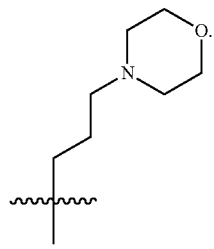

In an embodiment, $R_4$ is hydrogen or methyl. In an embodiment, $R_4$ is hydrogen. In an embodiment, $R_4$ is methyl.

In an embodiment, $R_3$ is furyl substituted one, two, or three times with C(O)-(4- to 8-membered heterocycle) or $C_1$-$C_6$ alkyl-(4- to 8-membered heterocycle), wherein each 4- to 8-membered heterocycle is optionally further substituted one, two, or three times with $C_1$-$C_3$ alkyl.

In an embodiment, $R_3$ is furyl substituted one, two, or three times with C(O)-(4- to 8-membered heterocycle) or $C_1$-$C_6$ alkyl-(4- to 8-membered heterocycle), wherein each 4- to 8-membered heterocycle is independently selected from the group consisting of pyrrolidinyl, pyrrolidinonyl, tetrahydrofuranyl, morpholinyl, thiomorpholinyl, piperidinyl, and piperazinyl, and wherein each 4- to 8-membered heterocycle is optionally further substituted one, two, or three times with $C_1$-$C_3$ alkyl.

In an embodiment, $R_3$ is furyl substituted one, two, or three times with C(O)-(4- to 8-membered heterocycle) or $C_1$-$C_6$ alkyl-(4- to 8-membered heterocycle), wherein each 4- to 8-membered heterocycle is independently selected from the group consisting of morpholinyl, piperidinyl, and piperazinyl, and wherein each 4- to 8-membered heterocycle is optionally further substituted one, two, or three times with $C_1$-$C_3$ alkyl.

In an embodiment, $R_3$ is furyl substituted one, two, or three times with C(O)-(morpholinyl) or $C_1$-$C_6$ alkyl-(morpholinyl).

In an embodiment, $R_3$ is represented by a group selected from the following:

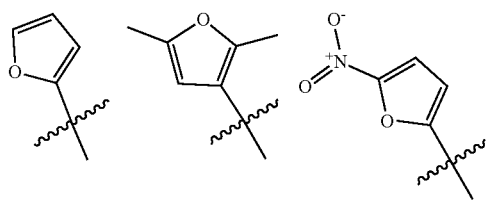

-continued

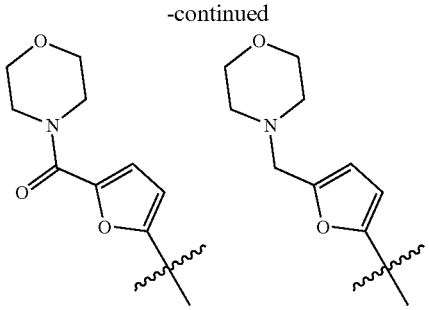

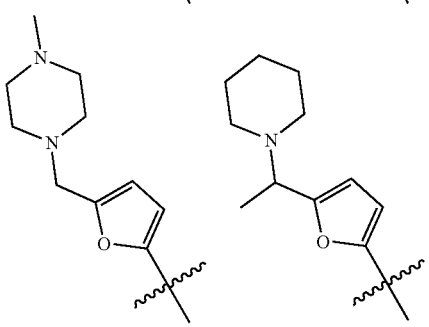

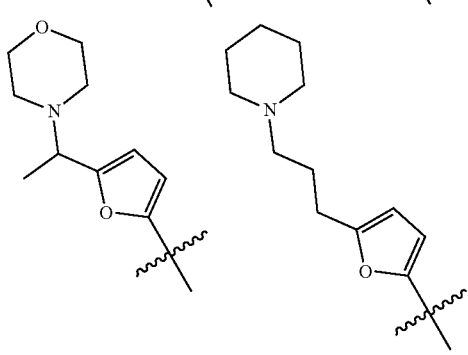

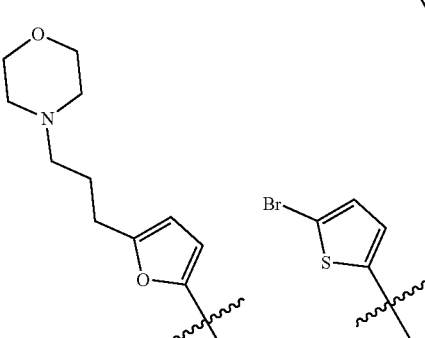

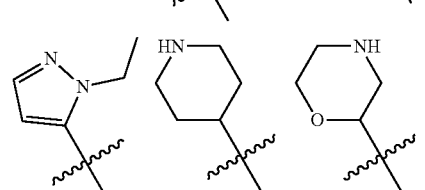

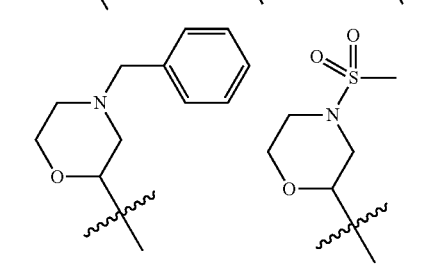

-continued

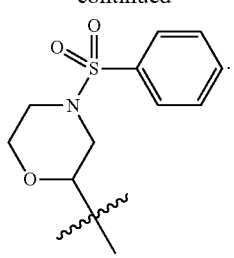

In an embodiment, the compound of Formula (II) has the structure of Compound 24:

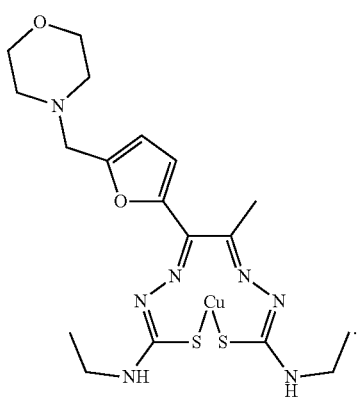

In an embodiment, the compound of Formula (II) has the structure of Compound 25:

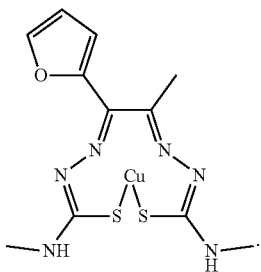

In an embodiment the compound of Formula (II) has the structure of Compound 37:

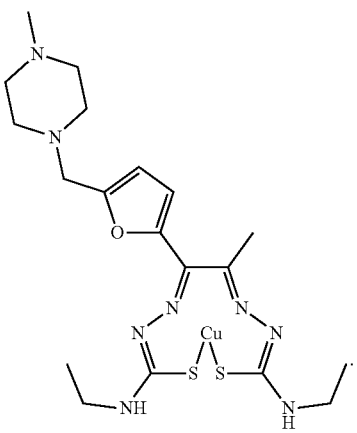

Exemplary compounds of Formula (II) include the compounds described below, or pharmaceutically acceptable salts thereof:

Compound 23

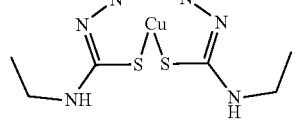

Compound 24

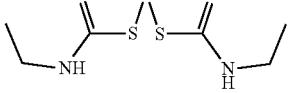

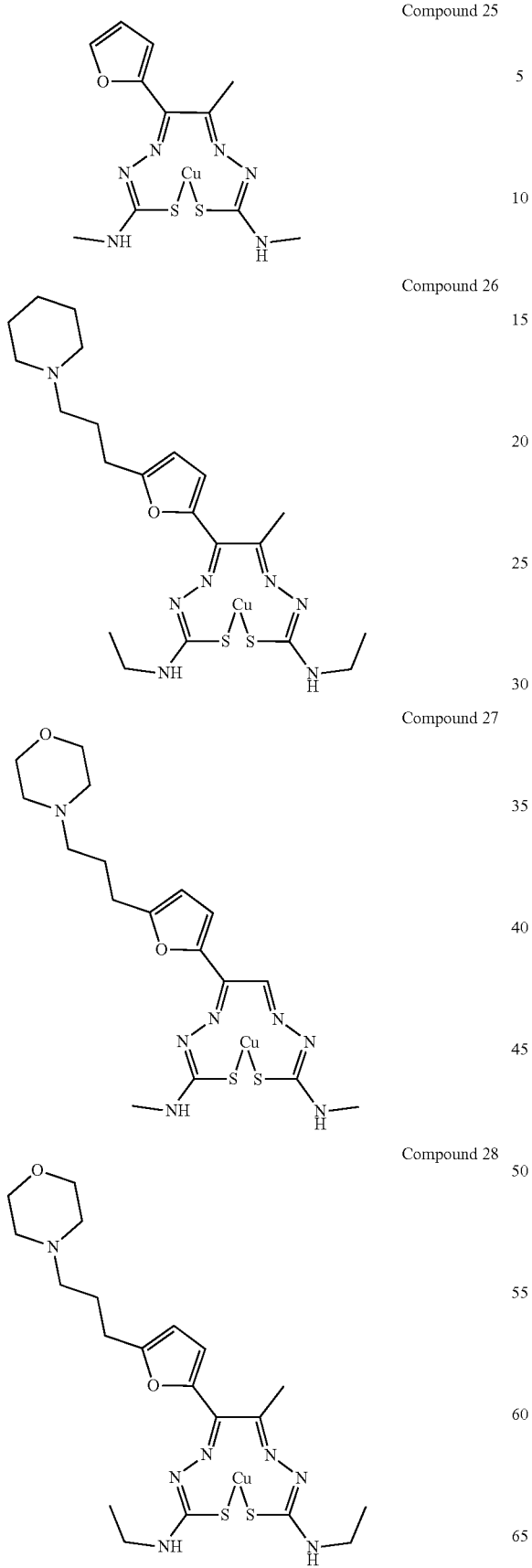

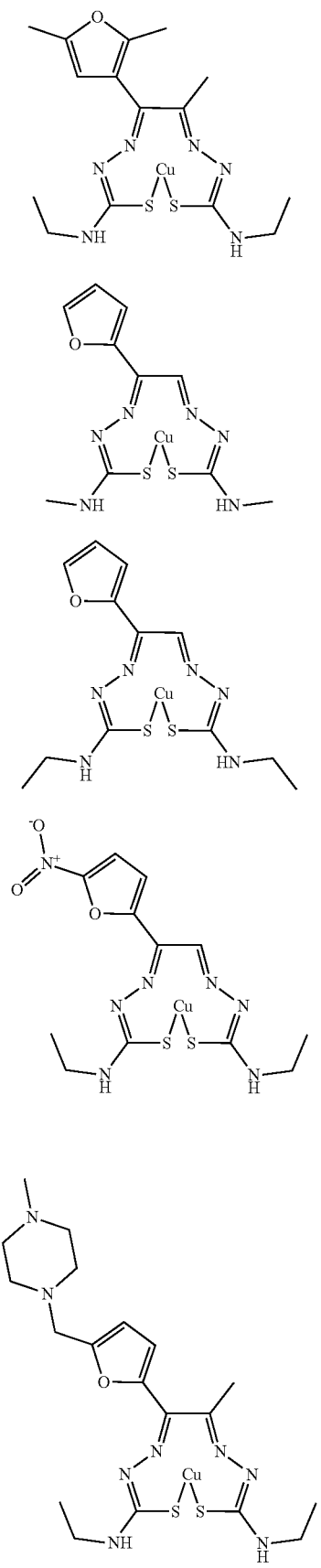
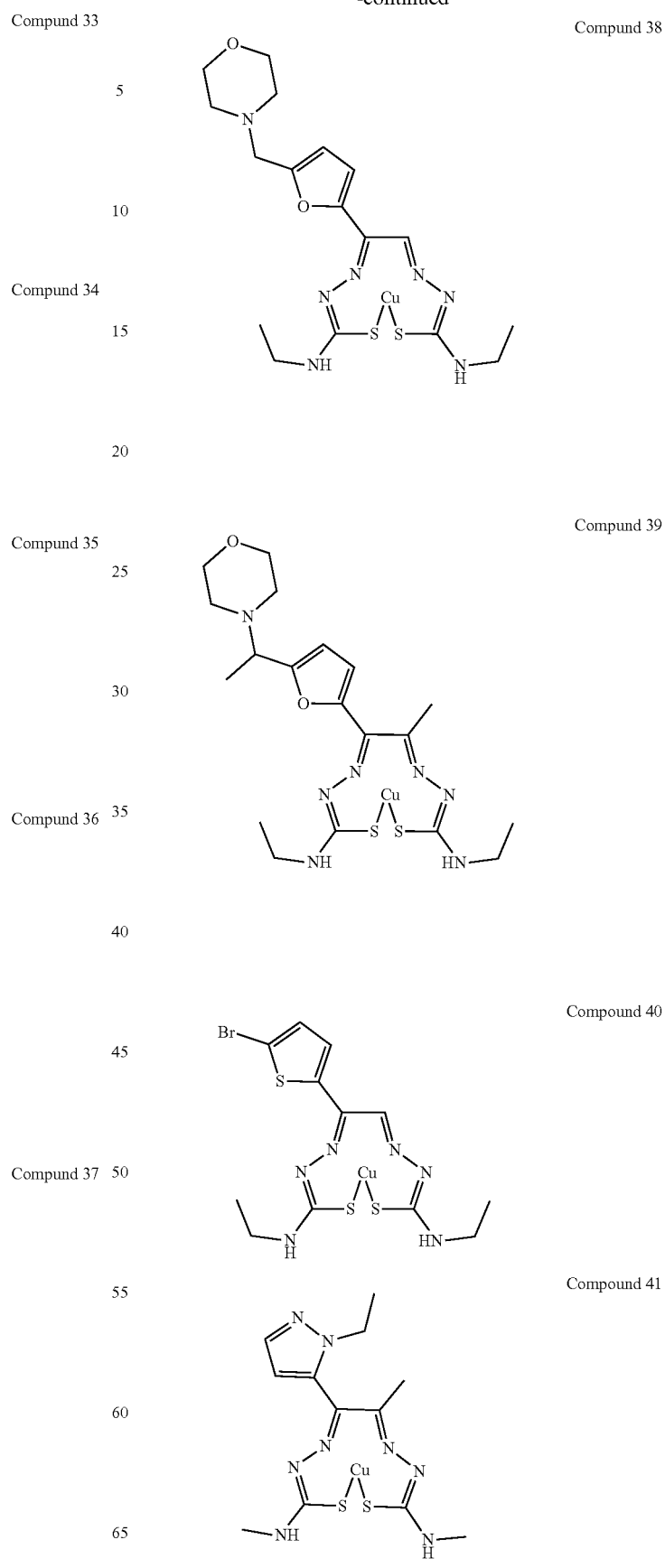

Compound 42

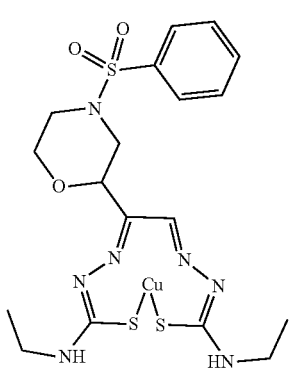

Compound 43

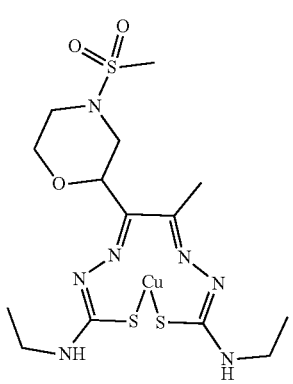

Compound 44

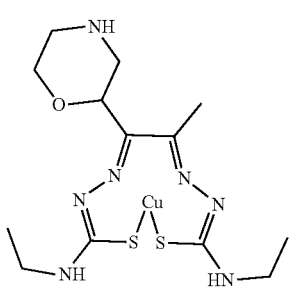

Compound 45

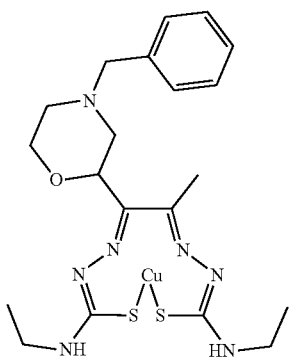

Compound 46

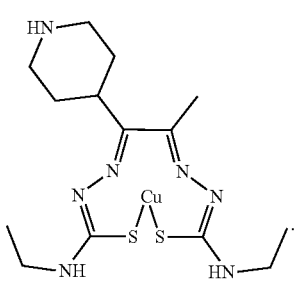

In yet another aspect, provided herein are compounds of Formula (III):

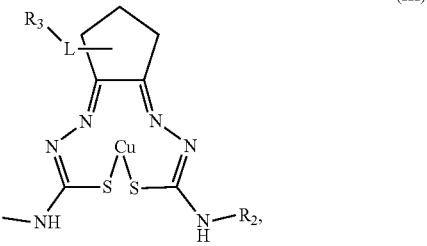

(III)

or pharmaceutically acceptable salts thereof, wherein:
L is $C_1$-$C_6$ alkyl or absent
$R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_2$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_3$ is $C_1$-$C_6$ alkyl, $C_1$-$C_6$ alkoxy, $C_1$-$C_6$ haloalkyl, halo, hydroxy, C(O)$NH_2$, C(O)NH($C_1$-$C_6$ alkyl), C(O)N($C_1$-$C_6$ alkyl)$_2$, or C(O)-(4- to 8-membered heterocycle), wherein the $C_1$-$C_6$ alkyl and the $C_1$-$C_6$ alkoxy are optionally substituted one, two, or three times with $C_6$-$C_{10}$ aryl, and wherein the C(O)-(4- to 8-membered heterocycle) is optionally substituted one, two, or three times with $C_1$-$C_3$ alkyl.

In an embodiment, L is $C_1$-$C_3$ alkyl or absent. In an embodiment, L is $C_1$-$C_3$ alkyl. In an embodiment, L is absent.

In an embodiment, $R_1$ is $C_1$-$C_6$ alkyl optionally substituted with $NH_2$, $NH(C_1$-$C_6$ alkyl), or $N(C_1$-$C_6$ alkyl)$_2$. In an embodiment, $R_1$ is $C_1$-$C_6$ alkyl optionally substituted with $N(C_1$-$C_6$ alkyl)$_2$.

In an embodiment, $R_1$ is $C_1$-$C_3$ alkyl optionally substituted with $N(C_1$-$C_3$ alkyl)$_2$. In an embodiment, $R_1$ is methyl or ethyl, wherein the ethyl is optionally substituted with $N(CH_2CH_3)_2$.

In an embodiment, $R_2$ is $C_1$-$C_6$ alkyl optionally substituted with $NH_2$, $NH(C_1$-$C_6$ alkyl), or $N(C_1$-$C_6$ alkyl)$_2$. In an embodiment, $R_2$ is $C_1$-$C_6$ alkyl optionally substituted with $N(C_1$-$C_6$ alkyl)$_2$.

In an embodiment, $R_2$ is $C_1$-$C_3$ alkyl optionally substituted with $N(C_1$-$C_3$ alkyl)$_2$. In an embodiment, $R_2$ is methyl or ethyl, wherein the ethyl is optionally substituted with $N(CH_2CH_3)_2$.

In an embodiment, $R_1$ and $R_2$ are identical.
In an embodiment, $R_3$ is $C_1$-$C_6$ alkyl, $C_1$-$C_6$ alkoxy, hydroxy, or C(O)-(4- to 8-membered heterocycle), wherein the $C_1$-$C_6$ alkyl and the $C_1$-$C_6$ alkoxy are optionally substituted one time with $C_6$-$C_{10}$ aryl and wherein the C(O)-(4- to 8-membered heterocycle) is optionally substituted one time with $C_1$-$C_3$ alkyl.

In an embodiment, $R_3$ is $C_1$-$C_3$ alkyl, $C_1$-$C_3$ alkoxy, hydroxy, or C(O)-(6-membered heterocycle), wherein the $C_1$-$C_3$ alkyl and the $C_1$-$C_3$ alkoxy are optionally substituted one time with phenyl.

In an embodiment, $R_3$ is $C_1$-$C_3$ alkyl, $C_1$-$C_3$ alkoxy, hydroxy, or C(O)-(morpholinyl), wherein the $C_1$-$C_3$ alkyl and the $C_1$-$C_3$ alkoxy are optionally substituted one time with phenyl.

In an embodiment, the group represented by $R_3$-L has one of the following structures:

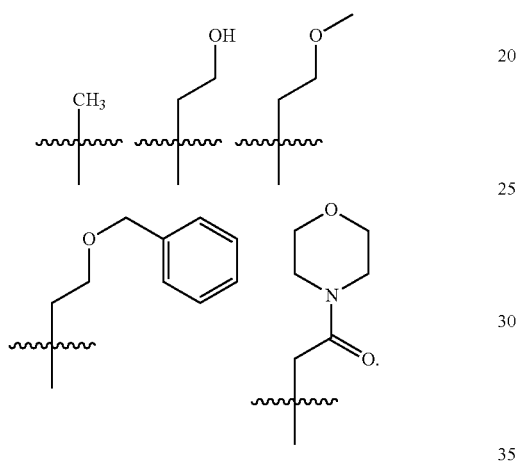

In an embodiment, L is absent and $R_3$ is $C_1$-$C_6$ alkyl.

Exemplary compounds of Formula (III) include the compounds described below, or pharmaceutically acceptable salts thereof:

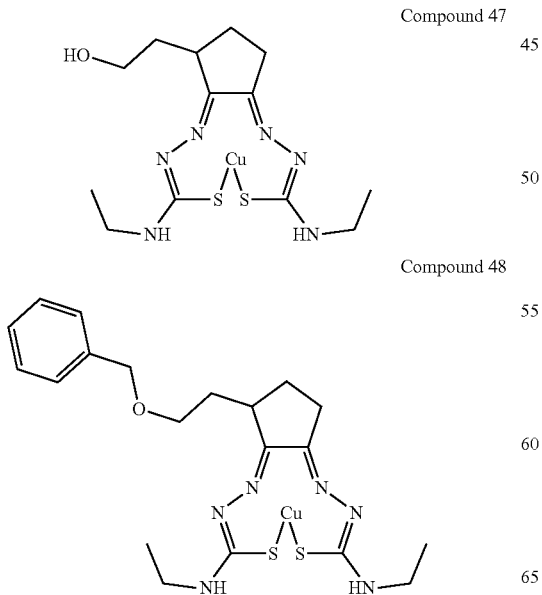

Compound 47

Compound 48

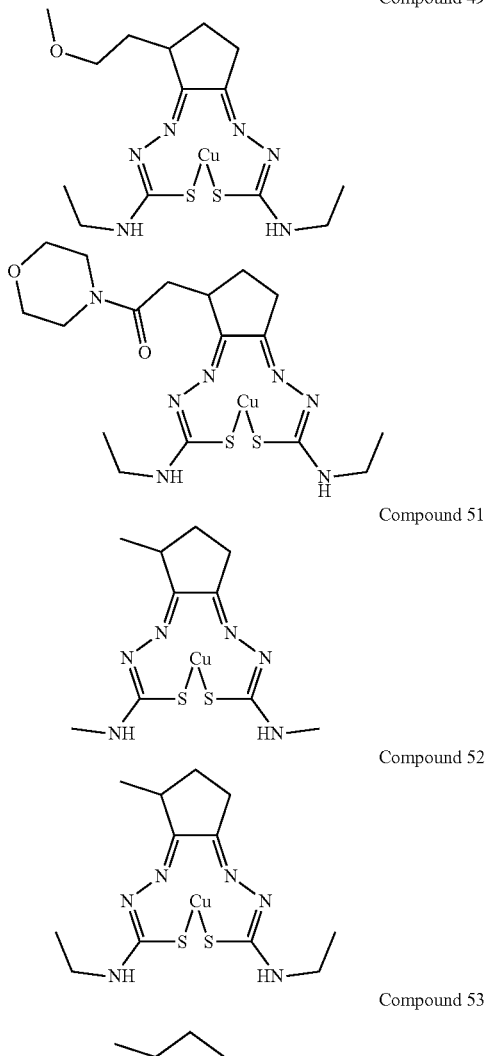

Compound 49

Compound 51

Compound 52

Compound 53

In another aspect, provided herein are compounds of Formula (IV):

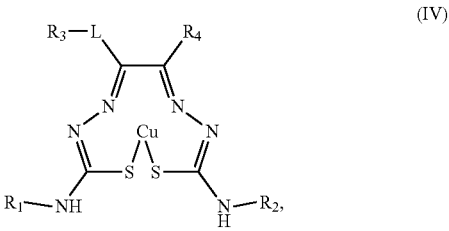

(IV)

or pharmaceutically acceptable salts thereof, wherein:

L is $C_3$-$C_7$ cycloalkyl, $C_1$-$C_6$ alkyl, or absent;

$R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;

$R_2$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;

$R_3$ is $C_6$-$C_{10}$ aryl, 5- to 10-membered heteroaryl, $C_3$-$C_1$ cycloalkyl, $C(O)NH$—$(C_1$-$C_6$ alkyl)-$PPh_3$, hydroxy, $C_1$-$C_6$ alkoxy, or O—$(C_1$-$C_6$ alkyl)-O—$(C_1$-$C_6$ alkyl), wherein the $C_6$-$C_{10}$ aryl is substituted one, two, or three times with the group $R_{3a}$, and wherein the 5- to 10-membered heteroaryl is optionally substituted one, two, or three times with the group $R_{3b}$;

$R_{3a}$ independently for each occurrence is $C_3$-$C_7$ cycloalkyl or 4- to 8-membered heterocycle, wherein the 4- to 8-membered heterocycle is optionally further substituted one, two, or three times with $C_1$-$C_3$ alkyl;

$R_{3b}$ independently for each occurrence is $C_1$-$C_3$ alkyl, $C_1$-$C_3$ alkoxy, $C_3$-$C_7$ cycloalkyl, or 4- to 8-membered heterocycle, wherein the heterocycle is optionally further substituted one, two, or three times with $C_1$-$C_3$ alkyl; and $R_4$ is hydrogen, $C_1$-$C_3$ alkyl, or $C_6$-$C_{10}$ aryl;

provided that when L is absent, $R_3$ is $C_6$-$C_{10}$ aryl substituted one, two, or three times with the group $R_{3a}$; or when L is absent, $R_3$ is 6- to 10-membered heteroaryl substituted one, two, or three times with the group $R_{3b}$; or when L is absent, $R_3$ is 6- to 10-membered heteroaryl optionally substituted one, two, or three times with the group $R_{3b}$, and $R_4$ is H.

In an embodiment, L is $C_3$-$C_7$ cycloalkyl or $C_1$-$C_6$ alkyl. In an embodiment, L is $C_3$-$C_7$ cycloalkyl. In an embodiment, L is $C_1$-$C_6$ alkyl. In an embodiment, L is $C_3$-$C_5$ cycloalkyl or $C_1$-$C_3$ alkyl. In an embodiment, L is is $C_3$-$C_5$ cycloalkyl. In an embodiment, L is $C_1$-$C_3$ alkyl.

In an embodiment, L is —$CH_2$—. In an embodiment, L is —$CH_2CH_2$—. In an embodiment, L is —$CH_2CH_2CH_2$—. In an embodiment, L is —$CH_2CH_2CH_2CH_2$—. In an embodiment, L is —$CH(CH_3)$—. In an embodiment, L is —$CH(CH_2CH_3)$—. In an embodiment, L is —$C(CH_3)_2$—.

In an embodiment, L is $C_3$-$C_7$ cycloalkyl or $C_3$-$C_5$ cycloalkyl, wherein the cycloalkyl group comprises a quaternary carbon that forms the point of attachment to group $R_3$ and to the rest of the scaffold. Accordingly, in an embodiment, L is represented by one of the following groups:

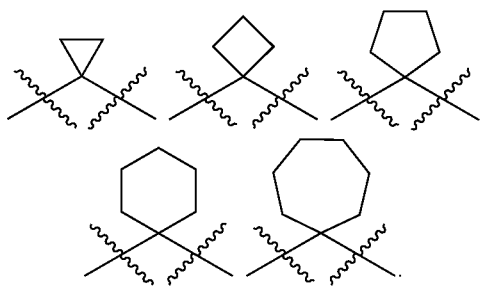

In an embodiment, $R_1$ is $C_{1-6}$ alkyl. In an embodiment, $R_1$ is $C_{1-3}$ alkyl. In an embodiment, $R_1$ is methyl or ethyl. In an embodiment, $R_1$ is methyl. In an embodiment, $R_1$ is ethyl.

In an embodiment, $R_1$ is $C_1$-$C_6$ alkyl optionally substituted with 5-membered heteroaryl. In an embodiment, $R_1$ is $C_1$-$C_6$ alkyl optionally substituted with furyl. In an embodiment, $R_1$ is $CH_2$-furyl.

In an embodiment, $R_2$ is $C_{1-6}$ alkyl. In an embodiment, $R_2$ is $C_{1-3}$ alkyl. In an embodiment, $R_2$ is methyl or ethyl. In an embodiment, $R_2$ is methyl. In an embodiment, $R_2$ is ethyl.

In an embodiment, $R_2$ is $C_1$-$C_6$ alkyl optionally substituted with 5-membered heteroaryl.

In an embodiment, $R_2$ is $C_1$-$C_6$ alkyl optionally substituted with furyl. In an embodiment, $R_2$ is $CH_2$-furyl.

In an embodiment, $R_1$ and $R_2$ are identical.

In an embodiment, $R_3$ is $C_6$-$C_{10}$ aryl, 5- to 10-membered heteroaryl, $C_3$-$C_{10}$ cycloalkyl, or $C_1$-$C_6$ alkoxy, wherein the $C_6$-$C_{10}$ aryl is substituted one, two, or three times with the group $R_{3a}$, and wherein the 5- to 10-membered heteroaryl is optionally substituted one, two, or three times with the group $R_{3b}$.

In an embodiment, $R_3$ is 5- to 10-membered heteroaryl or $C_3$-$C_{10}$ cycloalkyl, wherein the 5- to 10-membered heteroaryl is optionally substituted one, two, or three times with the group $R_{3b}$.

In an embodiment, $R_3$ is phenyl, pyrazolyl, pyridinyl, benzofuranyl, benzothiazolyl, benzodioxolyl, $C_3$-$C_6$ cycloalkyl, adamantyl, $C(O)NH$—$(C_1$-$C_6$ alkyl)-$PPh_3$, hydroxy, $C_1$-$C_6$ alkoxy, or O—$(C_1$-$C_6$ alkyl)-O—$(C_1$-$C_6$ alkyl), wherein the phenyl is substituted one, two, or three times with the group $R_{3a}$; and wherein the pyrazolyl, pyridinyl, benzofuranyl, benzothiazolyl, and benzodioxolyl are optionally substituted one, two, or three times with the group $R_{3b}$.

In an embodiment, $R_3$ is phenyl, pyrazolyl, pyridinyl, benzofuranyl, benzothiazolyl, benzodioxolyl, or $C_1$-$C_6$ alkoxy, wherein the pyrazolyl, pyridinyl, benzofuranyl, benzothiazolyl, and benzodioxolyl are optionally substituted one or two times with the group $R_{3b}$.

In an embodiment, $R_3$ is pyridinyl, benzofuranyl, or benzodioxolyl, wherein the pyridinyl, benzofuranyl, and benzodioxolyl are optionally substituted one or two times with the group $R_{3b}$.

In an embodiment, $R_3$ is benzofuranyl or benzodioxolyl, wherein the benzofuranyl and benzodioxolyl are optionally substituted one or two times with the group $R_{3b}$.

In an embodiment, $R_{3a}$ independently for each occurrence is 4- to 8-membered heterocycle optionally further substituted one, two, or three times with $C_1$-$C_3$ alkyl. In an embodiment, $R_{3a}$ independently for each occurrence is 4- to 8-membered heterocycle optionally further substituted one time with methyl.

In an embodiment, $R_{3a}$ independently for each occurrence is pyrrolidinyl, pyrrolidinonyl, tetrahydrofuranyl, morpholinyl, thiomorpholinyl, piperidinyl, or piperazinyl, each of which is optionally further substituted one, two, or three times with $C_1$-$C_3$ alkyl. In an embodiment, $R_{3a}$ independently for each occurrence is pyrrolidinyl, pyrrolidinonyl, tetrahydrofuranyl, morpholinyl, thiomorpholinyl, piperidinyl, or piperazinyl, each of which is optionally further substituted one time with methyl. In an embodiment, $R_{3a}$ independently for each occurrence is pyrrolidinyl, pyrrolidinonyl, or morpholinyl. In an embodiment, $R_{3a}$ independently for each occurrence is represented by a group selected from the following:

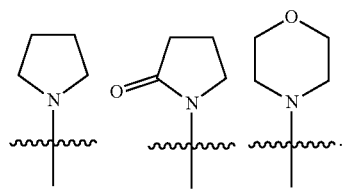

In an embodiment, $R_{3b}$ independently for each occurrence is $C_1$-$C_3$ alkyl, $C_1$-$C_3$ alkoxy, or 4- to 8-membered heterocycle, wherein the heterocycle is optionally further substituted one, two, or three times with $C_1$-$C_3$ alkyl. In an embodiment, $R_{3b}$ independently for each occurrence is $C_1$-$C_3$ alkoxy or 4- to 8-membered heterocycle, wherein the heterocycle is optionally further substituted one time with methyl.

In an embodiment, $R_{3b}$ independently for each occurrence is $C_1$-$C_3$ alkyl, $C_1$-$C_3$ alkoxy, or a heterocycle selected from the group consisting of pyrrolidinyl, pyrrolidinonyl, tetrahydrofuranyl, morpholinyl, thiomorpholinyl, piperidinyl, and piperazinyl, wherein the heterocycle is optionally further substituted one, two, or three times with $C_1$-$C_3$ alkyl. In an embodiment, $R_{3b}$ independently for each occurrence is $C_1$-$C_3$ alkyl, $C_1$-$C_3$ alkoxy or a heterocycle selected from the group consisting of pyrrolidinyl, pyrrolidinonyl, tetrahydrofuranyl, morpholinyl, thiomorpholinyl, piperidinyl, and piperazinyl, wherein the heterocycle is optionally further substituted one time with methyl. In an embodiment, $R_{3b}$ independently for each occurrence is methyl, methoxy or a heterocycle selected from the group consisting of pyrrolidinyl and morpholinyl. In an embodiment, $R_{3b}$ independently for each occurrence is represented by a group selected from:

In an embodiment, $R_4$ is hydrogen, $C_1$-$C_3$ alkyl, or phenyl. In an embodiment, $R_4$ is hydrogen, methyl, or phenyl. In an embodiment, $R_4$ is hydrogen or $C_1$-$C_3$ alkyl. In an embodiment, $R_4$ is hydrogen or methyl. In an embodiment, $R_4$ is hydrogen. In an embodiment, $R_4$ is methyl. In an embodiment, $R_4$ is phenyl.

In an embodiment, L is $C_1$-$C_6$ alkyl, and $R_3$ is $C_1$-$C_6$ alkoxy.

In an embodiment, the group represented by $R_3$-L is represented by one of the following:

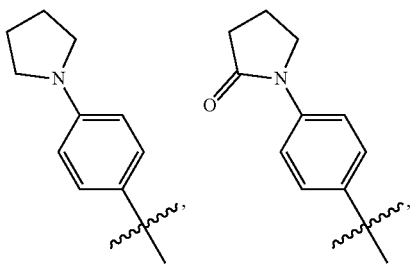

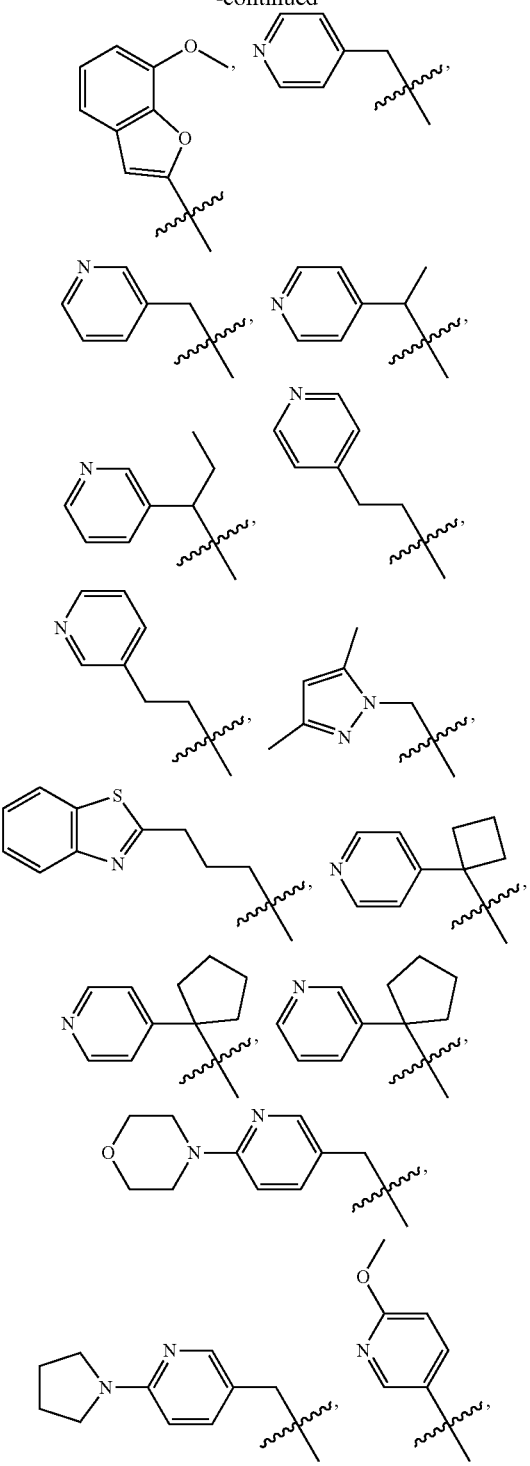

-continued

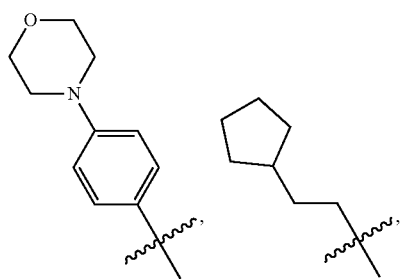

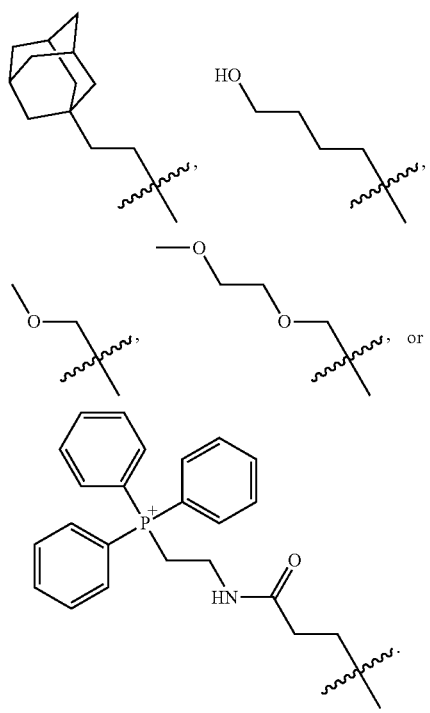

In an embodiment, the group represented by R₃-L is represented by one of the following:

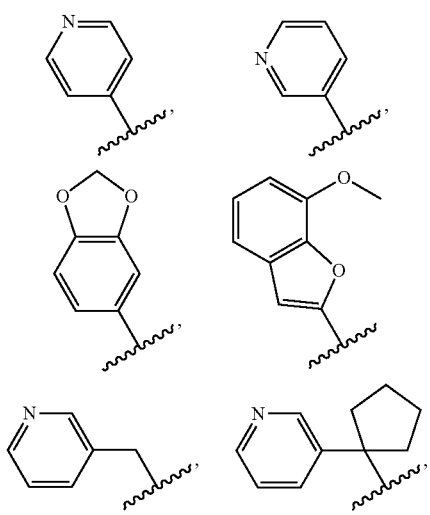

-continued

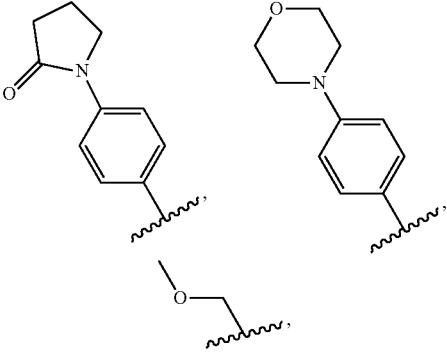

In an embodiment, $R_3$ is pyridinyl optionally substituted one, two, or three times with $C_1$-$C_3$ alkoxy or 4- to 8-membered heterocycle, wherein the 4- to 8-membered heterocycle is optionally substituted one time with $C_1$-$C_3$ alkyl.

In an embodiment, when L is absent, $R_3$ is $C_6$-$C_{10}$ aryl substituted one, two, or three times with the group $R_{3a}$; or when L is absent, $R_3$ is 6- to 10-membered heteroaryl substituted one, two, or three times with the group $R_{3b}$. In another embodiment, when L is absent, $R_3$ is $C_6$-$C_{10}$ aryl substituted one, two, or three times with the group $R_{3a}$; or when L is absent, $R_3$ is 6- to 10-membered heteroaryl optionally substituted one, two, or three times with the group $R_{3b}$, and $R_4$ is H.

In an embodiment, when L is absent, $R_3$ is pyridinyl substituted one, two, or three times with $C_1$-$C_3$ alkoxy.

In an embodiment, when L is absent, $R_3$ is phenyl substituted with 4- to 8-membered heterocycle.

In an embodiment, when L is absent, $R_3$ is $C_6$-$C_{10}$ aryl substituted one, two, or three times with the group $R_{3a}$; or when L is absent, $R_3$ is 6- to 10-membered heteroaryl substituted one, two, or three times with the group $R_{3b}$.

In an embodiment, L is $C_3$-$C_5$ cycloalkyl or $C_1$-$C_3$ alkyl; $R_3$ is pyridinyl optionally substituted one, two, or three times with 4- to 8-membered heterocycle; and $R_4$ is methyl.

Exemplary compounds of Formula (IV) include the following compounds, or pharmaceutically acceptable salts thereof:

Compound 1

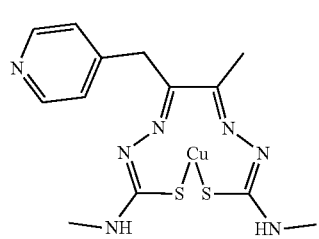

Compound 2

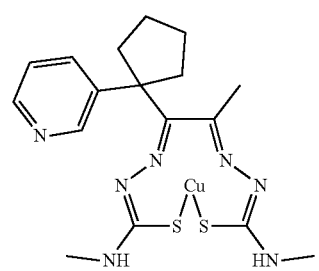

-continued
Compound 3
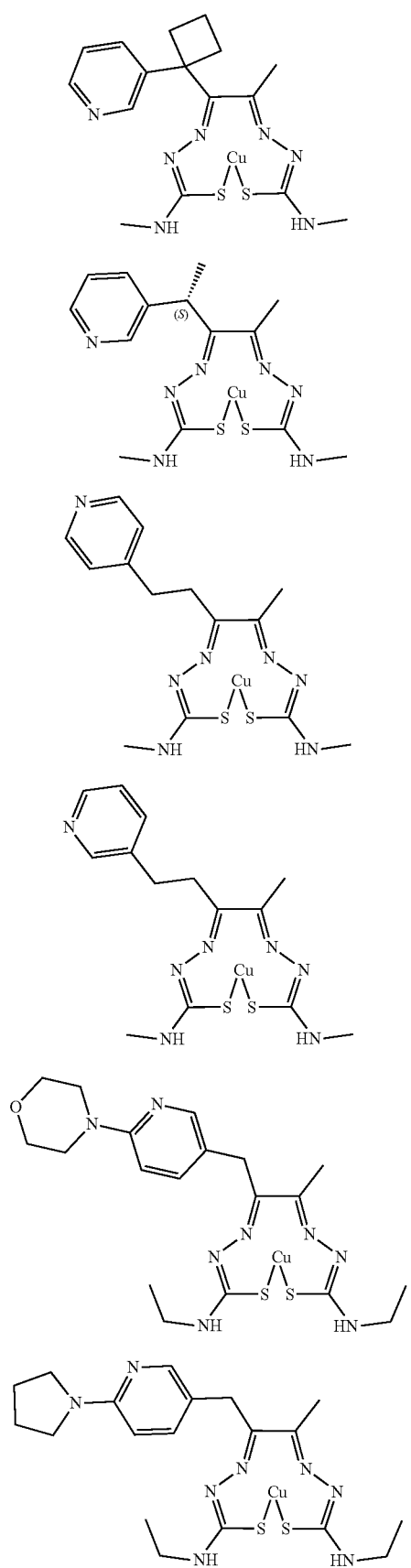
Compound 4
Compound 5
Compound 6
Compound 7
Compound 8
-continued
Compound 9
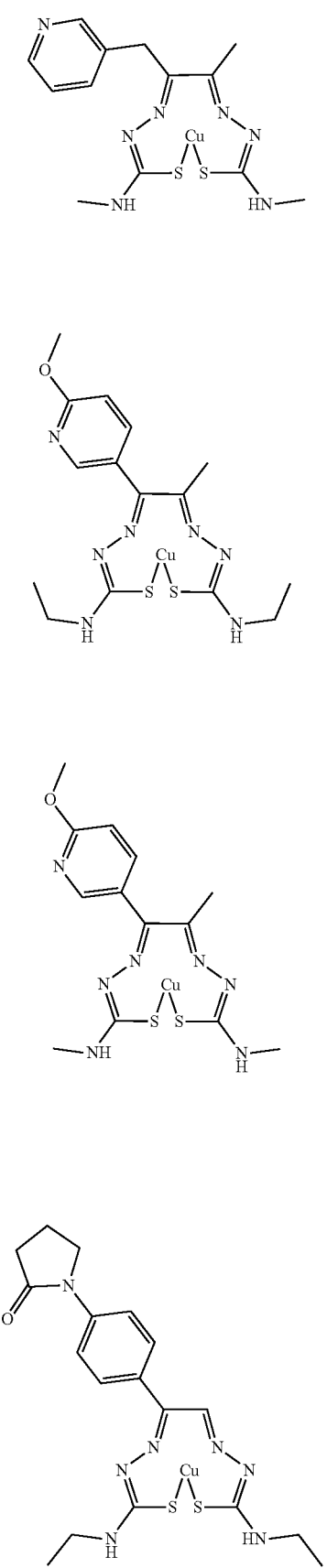
Compound 10
Compound 11
Compound 12

Compound 13
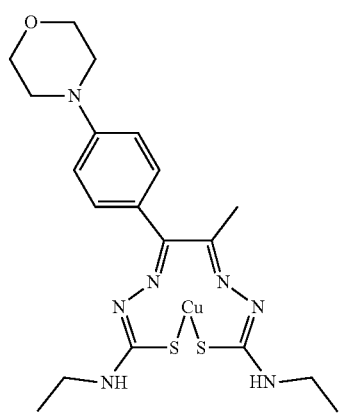
Compound 14
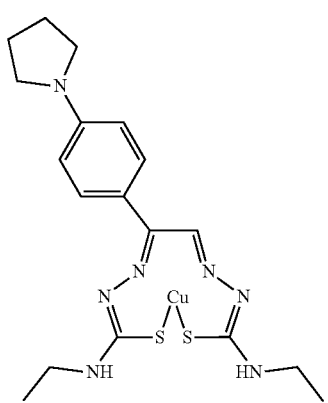
Compound 15
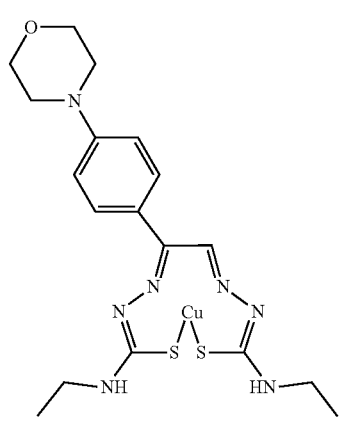
Compound 16
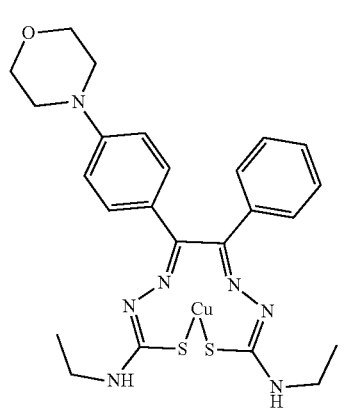
Compound 17
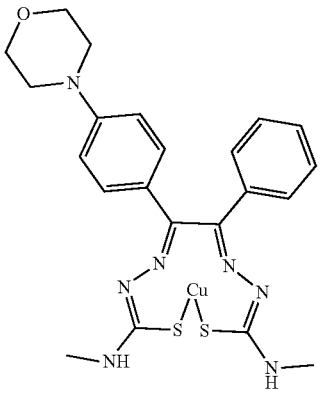
Compound 18
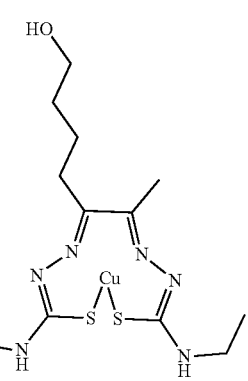
Compound 19
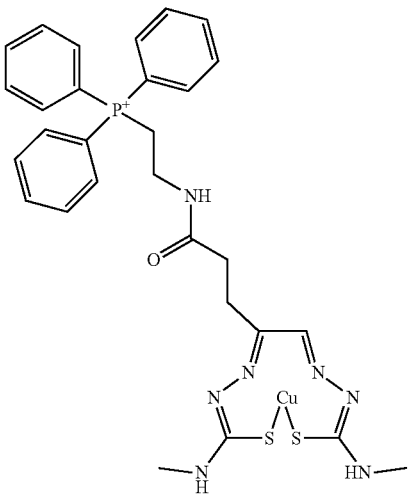

Compound 21
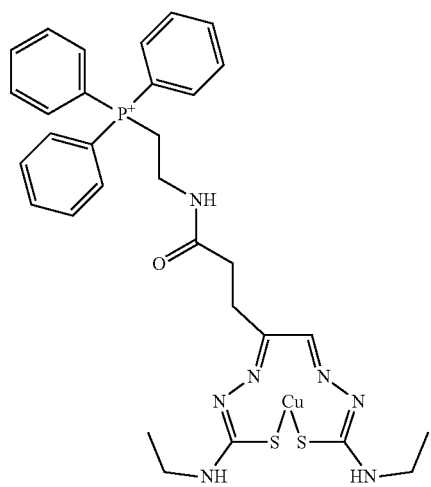
Compound 22
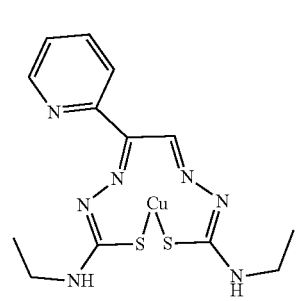
Compound 57
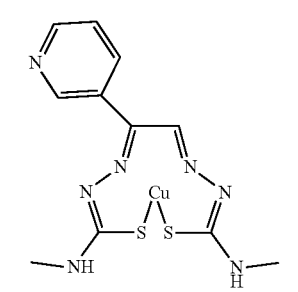
Compound 59
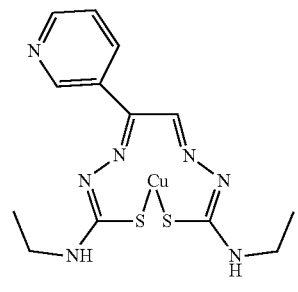
Compound 60
Compound 61
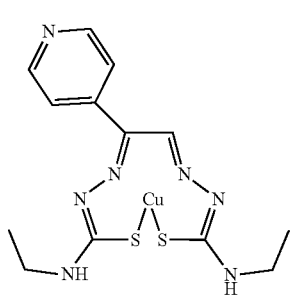
Compound 66
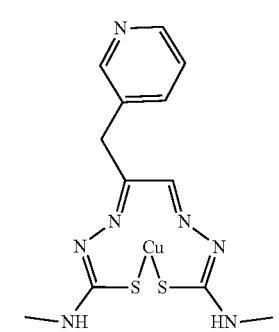
Compound 67
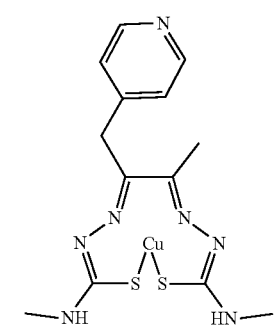
Compound 68
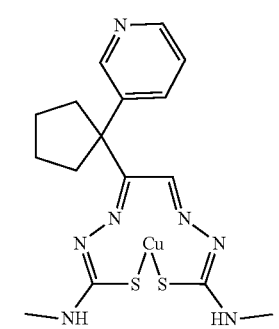
Compound 69
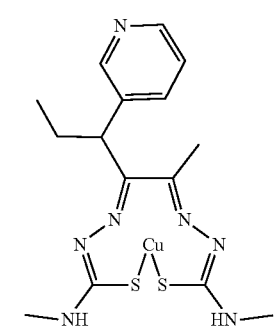

-continued
Compound 70
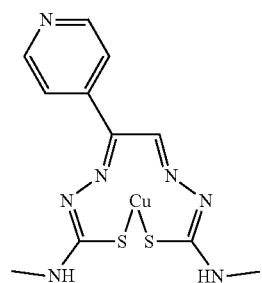
Compound 71
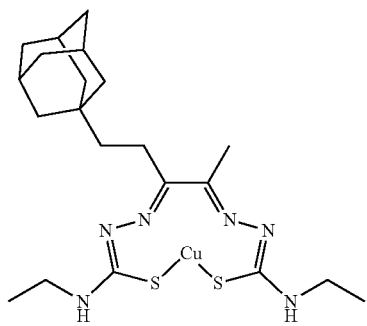
Compound 72
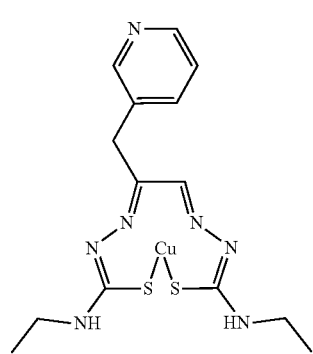
Compound 73
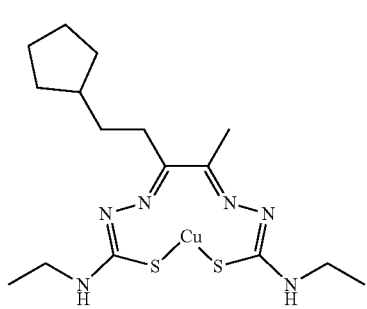
Compound 74
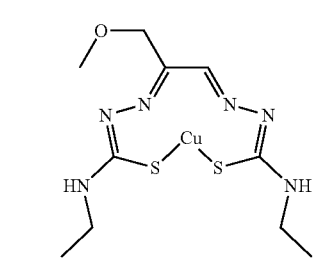
-continued
Compound 75
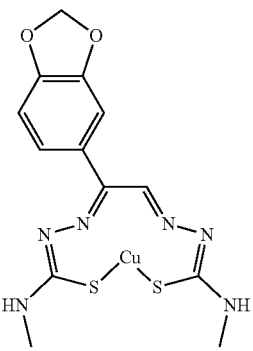
Compound 76
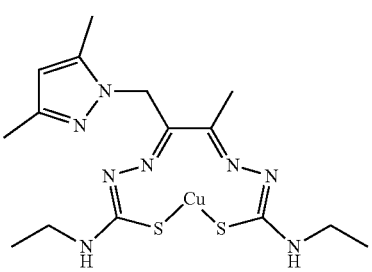
Compound 77
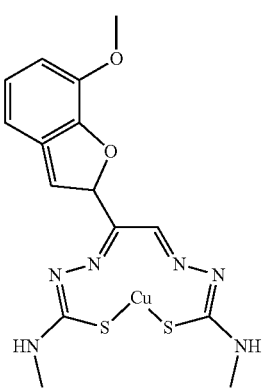
Compound 78
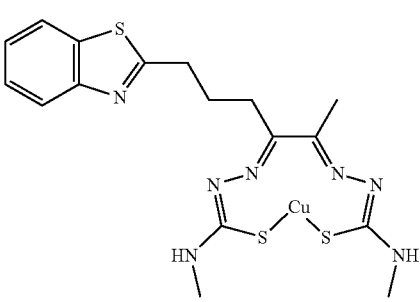
In an embodiment, the compound of Formula (IV) is one of the following compounds, or a pharmaceutically acceptable salt thereof:

Compound 2
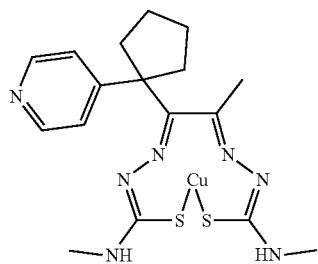
Compound 12
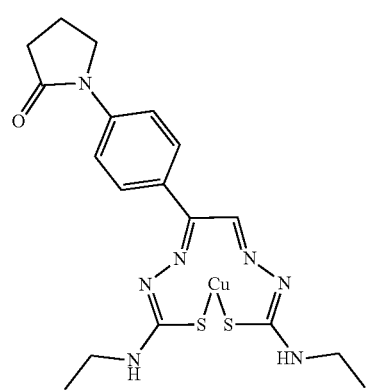
Compound 15
Compound 17
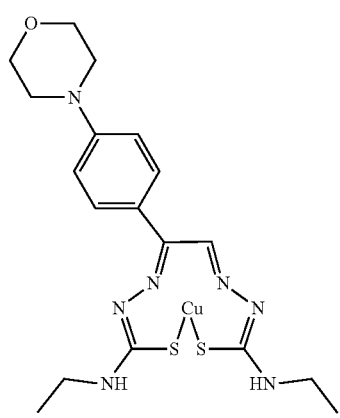
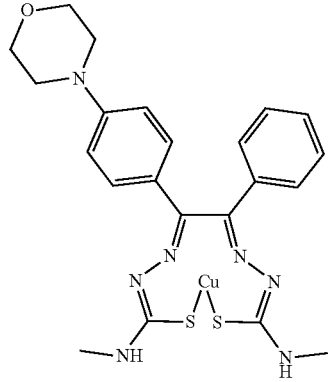
-continued
Compound 59
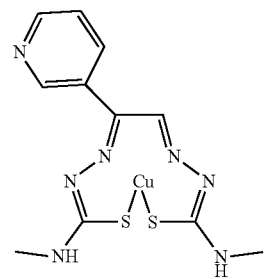
Compound 60
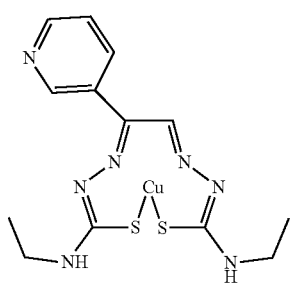
Compound 61
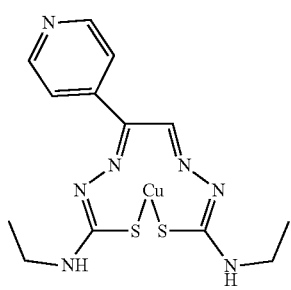
Compound 66
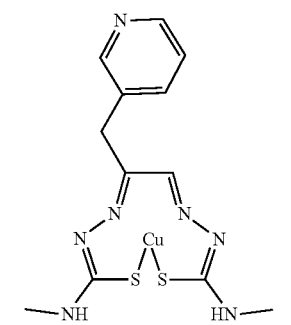
Compound 74
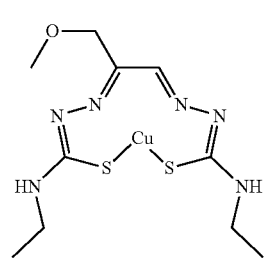

-continued

Compound 77

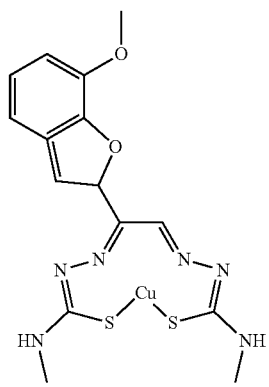

In an embodiment, the compound of Formula (IV) has the structure of Compound 2:

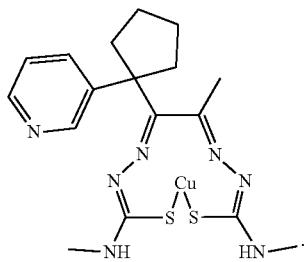

In an embodiment, the compound of Formula (IV) has the structure of Compound 59:

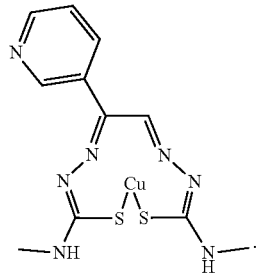

In an embodiment, the compound of Formula (IV) has the structure of Compound 60:

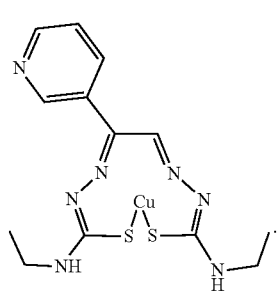

In an embodiment, the compound of Formula (IV) has the structure of Compound 61:

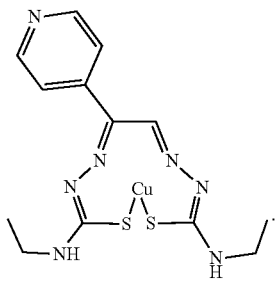

In an embodiment, the compound of Formula (IV) has the structure of Compound 74:

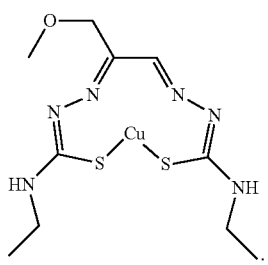

In an embodiment, the compound of Formula (IV) has the structure of Compound 74:

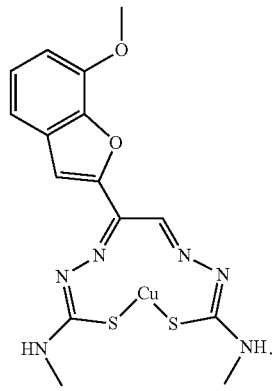

In another aspect, provided herein are compounds of Formula (V):

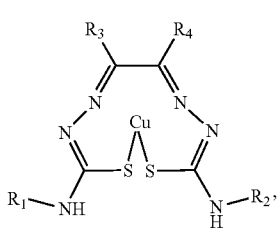

(V)

or pharmaceutically acceptable salts thereof, wherein:
$R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_2$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_6$ is 4- to 8-membered heterocycle or 5-membered heteroaryl, wherein the 4- to 8-membered heterocycle is optionally substituted one, two, or three times with the group $R_{3a}$, and wherein the 5-membered heteroaryl is optionally substituted one, two, or three times with the group $R_{3b}$;
$R_{3a}$ independently for each occurrence is $C_1$-$C_6$ alkyl, $C_1$-$C_6$ alkyl-($C_6$-$C_{10}$ aryl), $C_1$-$C_6$ alkyl-(5- to 10-membered heteroaryl), $S(O)_2H$, $S(O)_2$—($C_1$-$C_6$ alkyl), $S(O)_2$—($C_3$-$C_7$ cycloalkyl), or $S(O)_2$—($C_6$-$C_{10}$ aryl); wherein each heteroaryl is optionally further substituted one to four times with $C_1$-$C_6$ alkyl or $C_6$-$C_{10}$ aryl; and wherein each $C_6$-$C_{10}$ aryl is optionally further substituted one to four times with $C_1$-$C_6$ alkyl;
$R_{3b}$ independently for each occurrence is $C_1$-$C_6$ alkyl, $C_1$-$C_6$ alkoxy, $C_1$-$C_6$ haloalkyl, $C_1$-$C_6$ alkyl-N($R_5$)$_2$, ($C_1$-$C_6$ alkyl)-O—($C_1$-$C_6$ alkyl), halo, nitro, cyano, $C_6$-$C_{10}$ aryl, C(O)-(4- to 8-membered heterocycle), $C_1$-$C_6$ alkyl-($C_6$-$C_{10}$ aryl), $C_1$-$C_6$ alkyl-(5- to 10-membered heteroaryl), or $C_1$-$C_6$ alkyl-(4- to 8-membered heterocycle), wherein each 4- to 8-membered heterocycle, $C_6$-$C_{10}$ aryl, and 5- to 10-membered heteroaryl are optionally further substituted one to four times with $C_1$-$C_3$ alkyl, $C_1$-$C_3$ alkoxy, $C_1$-$C_3$ haloalkyl, or halo;
$R_4$ is hydrogen or $C_{1-3}$ alkyl; and
$R_5$ independently for each occurrence is hydrogen, $C_1$-$C_6$ alkyl, or $C_1$-$C_3$ alkyl-($C_6$-$C_{10}$ aryl).

In an embodiment, $R_1$ is $C_{1-6}$ alkyl. In an embodiment, $R_1$ is $C_{1-3}$ alkyl. In an embodiment, $R_1$ is methyl or ethyl. In an embodiment, $R_1$ is methyl. In an embodiment, $R_1$ is ethyl.

In an embodiment, $R_1$ is $C_1$-$C_6$ alkyl optionally substituted with 5-membered heteroaryl.

In an embodiment, $R_1$ is $C_1$-$C_6$ alkyl optionally substituted with furyl. In an embodiment, $R_1$ is $CH_2$-furyl.

In an embodiment, $R_2$ is $C_{1-6}$ alkyl. In an embodiment, $R_2$ is $C_{1-3}$ alkyl. In an embodiment, $R_2$ is methyl or ethyl. In an embodiment, $R_2$ is methyl. In an embodiment, $R_2$ is ethyl.

In an embodiment, $R_2$ is $C_1$-$C_6$ alkyl optionally substituted with 5-membered heteroaryl. In an embodiment, $R_2$ is $C_1$-$C_6$ alkyl optionally substituted with furyl. In an embodiment, $R_2$ is $CH_2$-furyl.

In an embodiment, $R_1$ and $R_2$ are identical.

In an embodiment, $R_3$ is 5- to 6-membered heterocycle or 5-membered heteroaryl, wherein the 5- to 6-membered heterocycle is optionally substituted one, two, or three times with the group $R_{3a}$, and wherein the 5-membered heteroaryl is optionally substituted one, two, or three times with the group $R_{3b}$ In an embodiment, $R_3$ is tetrahydrofuranyl, morpholinyl, piperidinyl, furyl, thiophenyl, pyrrolyl, oxazolyl, pyrazolyl, or imidazolyl, wherein the tetrahydrofuranyl, morpholinyl, and piperidinyl are optionally substituted one, two, or three times with the group $R_{3a}$, and wherein the furyl, thiophenyl, pyrrolyl, oxazolyl, pyrazolyl, and imidazolyl are optionally substituted one, two, or three times with the group $R_{3b}$.

In an embodiment, $R_3$ is furyl, thiophenyl, oxazolyl, pyrazolyl, or imidazolyl optionally substituted one, two, or three times with the group $R_{3b}$. In another embodiment, $R_3$ is furyl, thiophenyl, oxazolyl, pyrazolyl, or imidazolyl substituted one, two, or three times with the group $R_{3b}$.

In an embodiment, $R_3$ is furyl optionally substituted one, two, or three times with the group $R_{3b}$. In another embodiment, $R_3$ is furyl substituted one, two, or three times with the group $R_{3b}$.

In an embodiment, $R_3$ is thiophenyl optionally substituted one, two, or three times with the group $R_{3b}$. In another embodiment, $R_3$ is thiophenyl substituted one, two, or three times with the group $R_{3b}$.

In an embodiment, $R_3$ is oxazolyl optionally substituted one, two, or three times with the group $R_{3b}$. In another embodiment, $R_3$ is oxazolyl substituted one, two, or three times with the group $R_{3b}$.

In an embodiment, $R_3$ is pyrazolyl optionally substituted one, two, or three times with the group $R_{3b}$. In another embodiment, $R_3$ is pyrazolyl substituted one, two, or three times with the group $R_{3b}$.

In an embodiment, $R_3$ is imidazolyl optionally substituted one, two, or three times with the group $R_{3b}$. In another embodiment, $R_3$ is imidazolyl substituted one, two, or three times with the group $R_{3b}$.

In an embodiment, $R_3$ is tetrahydrofuranyl, morpholinyl, or piperidinyl, each of which is optionally substituted one, two, or three times with the group $R_{3a}$.

In an embodiment, $R_{3a}$ independently for each occurrence is $C_1$-$C_6$ alkyl, $C_1$-$C_6$ alkyl-($C_6$-$C_{10}$ aryl), $C_1$-$C_6$ alkyl-(5- to 10-membered heteroaryl), $S(O)_2$—($C_1$-$C_6$ alkyl), or $S(O)_2$—($C_6$-$C_{10}$ aryl), wherein each heteroaryl is optionally further substituted one to four times with $C_1$-$C_6$ alkyl or $C_6$-$C_{10}$ aryl; and wherein each $C_6$-$C_{10}$ aryl is optionally further substituted one to four times with $C_1$-$C_6$ alkyl.

In an embodiment, $R_{3a}$ independently for each occurrence is $C_1$-$C_6$ alkyl, $C_1$-$C_6$ alkyl-(phenyl), $C_1$-$C_6$ alkyl-(5- to 6-membered heteroaryl), $S(O)_2$—($C_1$-$C_5$ alkyl), or $S(O)_2$-(phenyl), wherein each heteroaryl is optionally further substituted one to four times with $C_1$-$C_3$ alkyl or phenyl; and wherein each phenyl is optionally further substituted one to four times with $C_1$-$C_3$ alkyl.

In an embodiment, $R_{3a}$ independently for each occurrence is:

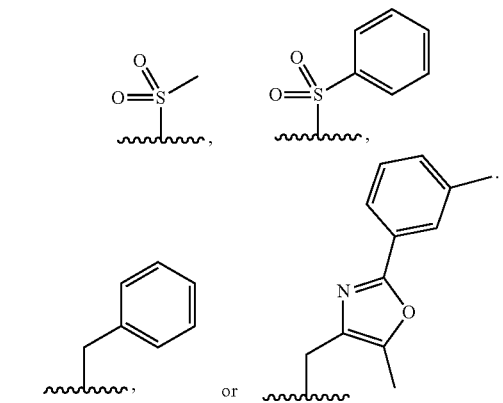

In an embodiment, $R_{3b}$ independently for each occurrence is $C_1$-$C_6$ alkyl, $C_1$-$C_6$ alkyl-N($R_5$)$_2$, ($C_1$-$C_6$ alkyl)-O—($C_1$-$C_6$ alkyl), halo, nitro, $C_6$-$C_{10}$ aryl, C(O)-(4- to 8-membered heterocycle), $C_1$-$C_6$ alkyl-($C_6$-$C_{10}$ aryl), $C_1$-$C_6$ alkyl-(5- to 10-membered heteroaryl), or $C_1$-$C_6$ alkyl-(4- to 8-membered heterocycle), wherein each 4- to 8-membered heterocycle, $C_6$-$C_{10}$ aryl, and 5- to 10-membered heteroaryl are optionally further substituted one to four times with $C_1$-$C_3$ alkyl, $C_1$-$C_3$ alkoxy, $C_1$-$C_3$ haloalkyl, or halo.

In an embodiment, $R_{3b}$ independently for each occurrence is $C_1$-$C_6$ alkyl, $C_1$-$C_6$ alkyl-$N(R_5)_2$, halo, $C_6$-$C_{10}$ aryl, $C_1$-$C_6$ alkyl-(4- to 8-membered heterocycle), or $C_1$-$C_6$ alkyl-($C_6$-$C_{10}$ aryl), wherein each 4- to 8-membered heterocycle and $C_6$-$C_{10}$ aryl are optionally further substituted one to four times with $C_1$-$C_3$ alkyl, $C_1$-$C_3$ alkoxy, $C_1$-$C_3$ haloalkyl, or halo.

In an embodiment, $R_{3b}$ independently for each occurrence is $C_1$-$C_6$ alkyl, $C_1$-$C_3$ alkyl-$N(R_5)_2$, halo, phenyl, $C_1$-$C_3$ alkyl-(5- to 6-membered heterocycle), or $C_1$-$C_6$ alkyl-phenyl, wherein each 5- to 6-membered heterocycle and phenyl are optionally further substituted one to four times with $C_1$-$C_3$ alkyl or halo.

In an embodiment, $R_{3b}$ independently for each occurrence is $C_1$-$C_6$ alkyl, $C_1$-$C_6$ alkyl-$N(R_5)_2$, ($C_1$-$C_6$ alkyl)-O—($C_1$-$C_6$ alkyl), halo, nitro, $C_6$-$C_{10}$ aryl, C(O)-(4- to 8-membered heterocycle), $C_1$-$C_6$ alkyl-($C_6$-$C_{10}$ aryl), $C_1$-$C_6$ alkyl-(5- to 10-membered heteroaryl), or $C_1$-$C_6$ alkyl-(4- to 8-membered heterocycle), wherein each 4- to 8-membered heterocycle, $C_6$-$C_{1a}$ aryl, and 5- to 10-membered heteroaryl are optionally further substituted one to four times with —$CH_3$, —$CH_2CH_3$, —$OCH_3$, —$CH_2F$, $CHF_2$, —$CF_3$, —F, or —Cl.

In an embodiment, $R_{3b}$ independently for each occurrence is $C_1$-$C_6$ alkyl, $C_1$-$C_6$ alkyl-$N(R_5)_2$, ($C_1$-$C_6$ alkyl)-O—($C_1$-$C_6$ alkyl), halo, nitro, phenyl, C(O)-(4- to 8-membered heterocycle), $C_1$-$C_6$ alkyl-phenyl, $C_1$-$C_6$ alkyl-(5- to 10-membered heteroaryl), or $C_1$-$C_6$ alkyl-(4- to 8-membered heterocycle); wherein each 4- to 8-membered heterocycle is independently selected from the group consisting of pyrrolidinyl, pyrrolidinonyl, tetrahydrofuranyl, morpholinyl, thiomorpholinyl, piperidinyl, and piperazinyl; wherein each 5- to 10-membered heteroaryl is selected from the group consisting of furyl and tetrahydroisoquinolinyl; and wherein each 4- to 8-membered heterocycle, phenyl, and 5- to 10-membered heteroaryl are optionally further substituted one to four times with —$CH_3$, —$CH_2CH_3$, —$OCH_3$, —$CH_2F$, $CHF_2$, —$CF_3$, —F, or —Cl.

In an embodiment, $R_{3b}$ independently for each occurrence is $C_1$-$C_6$ alkyl, $C_1$-$C_6$ alkyl-$N(R_5)_2$, ($C_1$-$C_6$ alkyl)-O—($C_1$-$C_6$ alkyl), halo, nitro, phenyl, C(O)-(4- to 8-membered heterocycle), $C_1$-$C_6$ alkyl-phenyl, $C_1$-$C_6$ alkyl-(5- to 10-membered heteroaryl), or $C_1$-$C_6$ alkyl-(4- to 8-membered heterocycle); wherein each 4- to 8-membered heterocycle is independently selected from the group consisting of pyrrolidinyl, morpholinyl, piperidinyl, and piperazinyl; wherein each 5- to 10-membered heteroaryl is selected from the group consisting of furyl and tetrahydroisoquinolinyl; and wherein each 4- to 8-membered heterocycle, phenyl, and 5- to 10-membered heteroaryl are optionally further substituted one to four times with —$CH_3$, —$OCH_3$, —$CF_3$, or —F.

In an embodiment, $R_{3b}$ independently for each occurrence is:

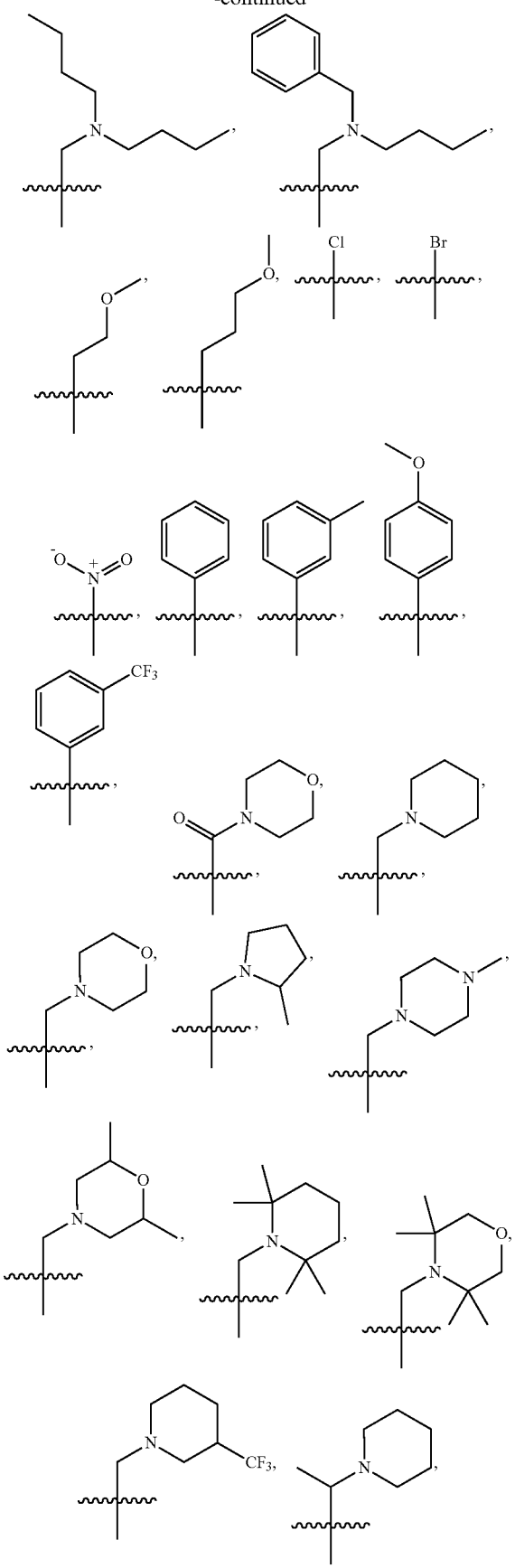

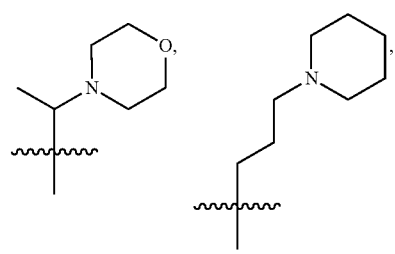
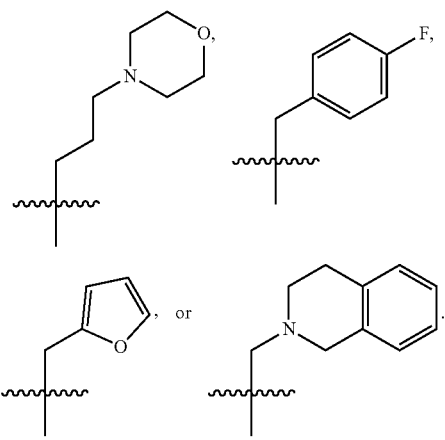
In an embodiment, $R_{3b}$ independently for each occurrence is:
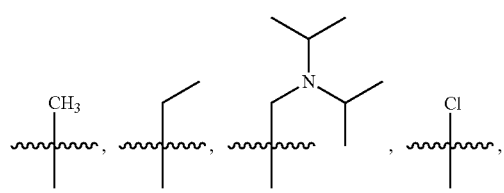
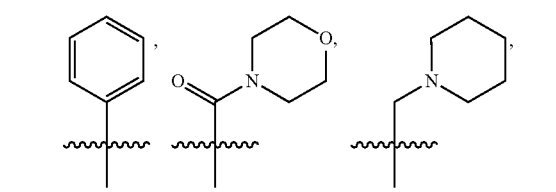
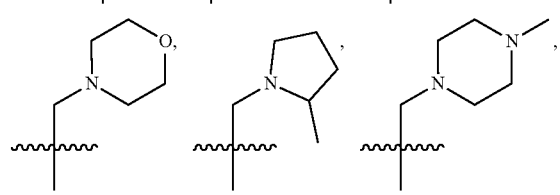
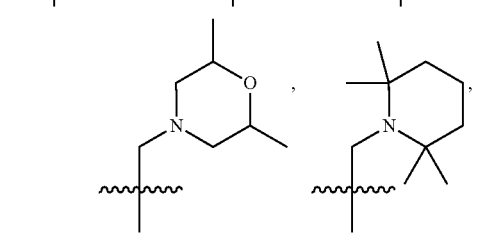
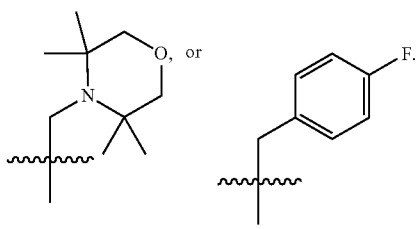
In an embodiment, $R_{3b}$ independently for each occurrence is:
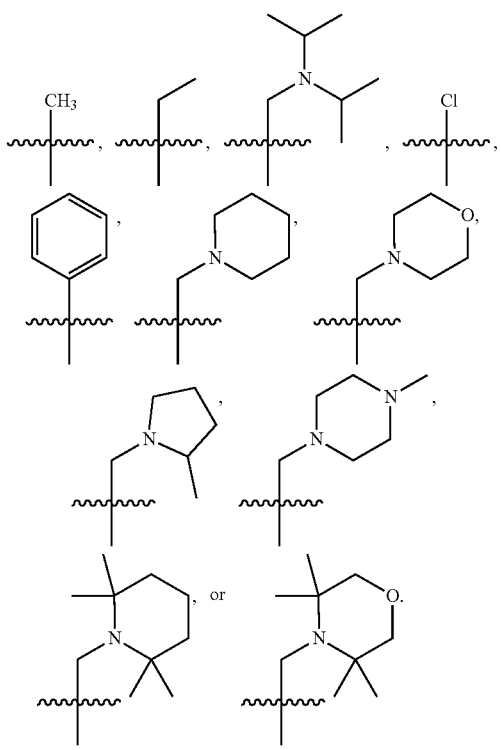
In an embodiment, $R_{3b}$ independently for each occurrence is:
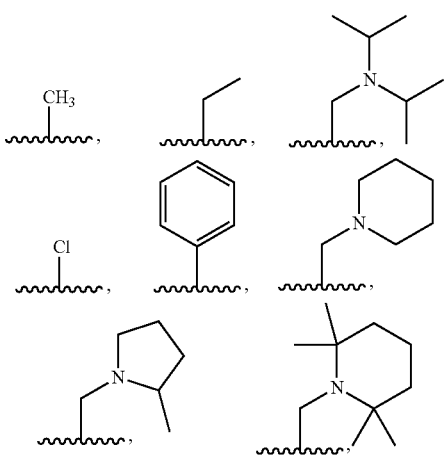

In an embodiment, R$_{3b}$ independently for each occurrence is:

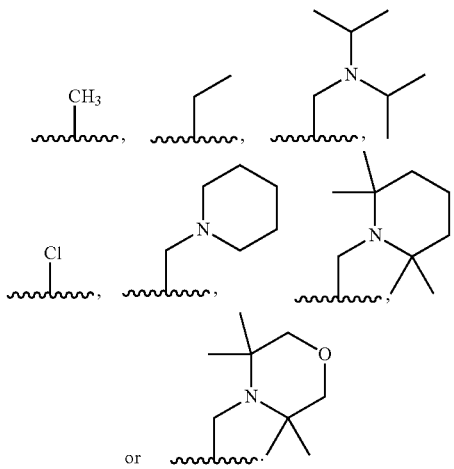

In an embodiment, R$_3$ is furyl optionally substituted one, two, or three times with C$_1$-C$_6$ alkyl, C$_1$-C$_6$ alkoxy, C$_1$-C$_6$ haloalkyl, C$_1$-C$_6$ alkyl-N(R$_5$)$_2$, (C$_1$-C$_6$ alkyl)-O—(C$_1$-C$_6$ alkyl), halo, nitro, cyano, C$_6$-C$_{10}$ aryl, C(O)-(4- to 8-membered heterocycle), C$_1$-C$_6$ alkyl-(C$_6$-C$_{10}$ aryl), C$_1$-C$_6$ alkyl-(5- to 10-membered heteroaryl), or C$_1$-C$_6$ alkyl-(4- to 8-membered heterocycle), wherein each 4- to 8-membered heterocycle, C$_6$-C$_{10}$ aryl, and 5- to 10-membered heteroaryl are optionally further substituted one to four times with C$_1$-C$_3$ alkyl, C$_1$-C$_3$ alkoxy, C$_1$-C$_3$ haloalkyl, or halo.

In an embodiment, R$_3$ is furyl optionally substituted one, two, or three times with C$_1$-C$_6$ alkyl, C$_1$-C$_6$ alkyl-N(R$_5$)$_2$, halo, C(O)-(4- to 8-membered heterocycle), or C$_1$-C$_6$ alkyl-(4- to 8-membered heterocycle), wherein each 4- to 8-membered heterocycle is optionally further substituted one to four times with C$_1$-C$_3$ alkyl, C$_1$-C$_3$ alkoxy, C$_1$-C$_3$ haloalkyl, or halo.

In an embodiment, R$_3$ is furyl optionally substituted one, two, or three times with C$_1$-C$_6$ alkyl-N(R$_5$)$_2$ or C$_1$-C$_6$ alkyl-(4- to 8-membered heterocycle), wherein each 4- to 8-membered heterocycle is optionally further substituted one to four times with C$_1$-C$_3$ alkyl, C$_1$-C$_3$ alkoxy, C$_1$-C$_3$ haloalkyl, or halo.

In an embodiment, R$_3$ is furyl optionally substituted one time with C$_1$-C$_3$ alkyl-N(C$_1$-C$_4$ alkyl)$_2$ or C$_1$-C$_3$ alkyl-(5- to 6-membered heterocycle), wherein the 5- to 6-membered heterocycle is optionally further substituted one to four times with C$_1$-C$_3$ alkyl.

In an embodiment, R$_3$ is furyl substituted one time with C$_1$-C$_3$ alkyl-N(C$_1$-C$_4$ alkyl)$_2$ or C$_1$-C$_3$ alkyl-(5- to 6-membered heterocycle), wherein the 5- to 6-membered heterocycle is optionally further substituted one to four times with C$_1$-C$_3$ alkyl.

In an embodiment, R$_3$ is thiophenyl, oxazolyl, pyrazolyl, or imidazolyl, optionally substituted one, two, or three times with C$_1$-C$_6$ alkyl, halo, C$_6$-C$_{10}$ aryl, or C$_1$-C$_6$ alkyl-(C$_6$-C$_{10}$ aryl), wherein each C$_6$-C$_{10}$ aryl is optionally further substituted one to four times with C$_1$-C$_3$ alkyl, C$_1$-C$_3$ alkoxy, C$_1$-C$_3$ haloalkyl, or halo.

In an embodiment, R$_3$ is thiophenyl, oxazolyl, pyrazolyl, or imidazolyl, optionally substituted one, two, or three times with methyl, ethyl, halo, phenyl, or C$_1$-C$_3$ alkyl-phenyl, wherein each phenyl is optionally further substituted one to four times with C$_1$-C$_3$ alkyl or halo.

In an embodiment, R$_3$ is:

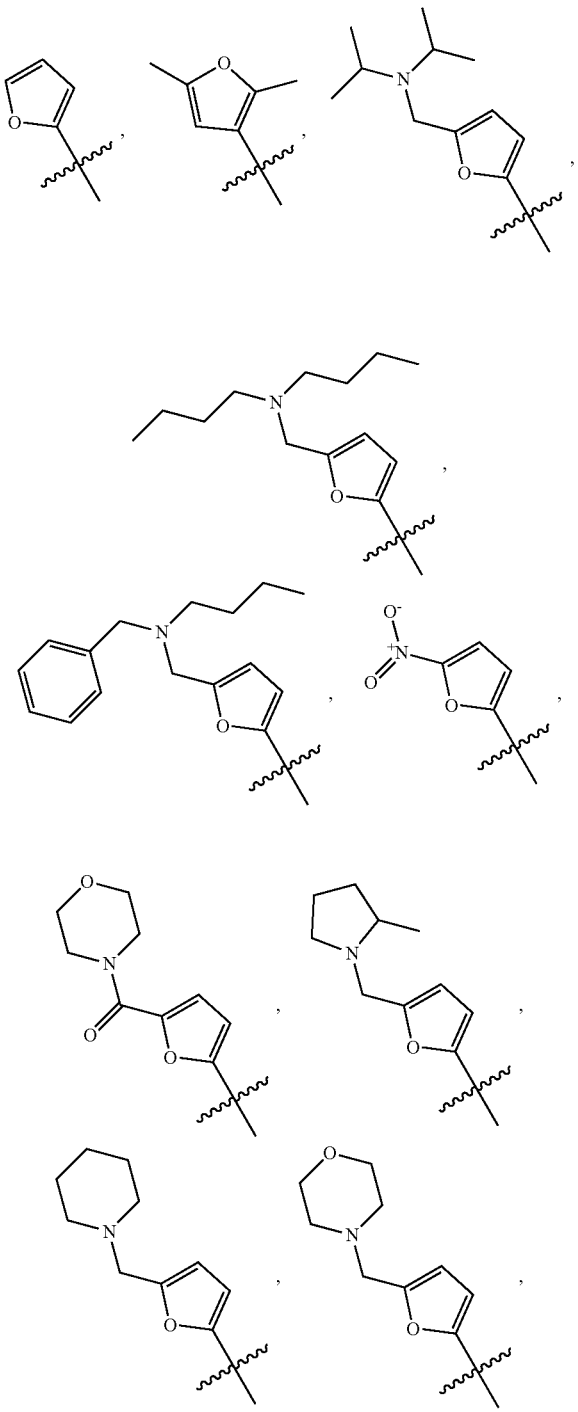

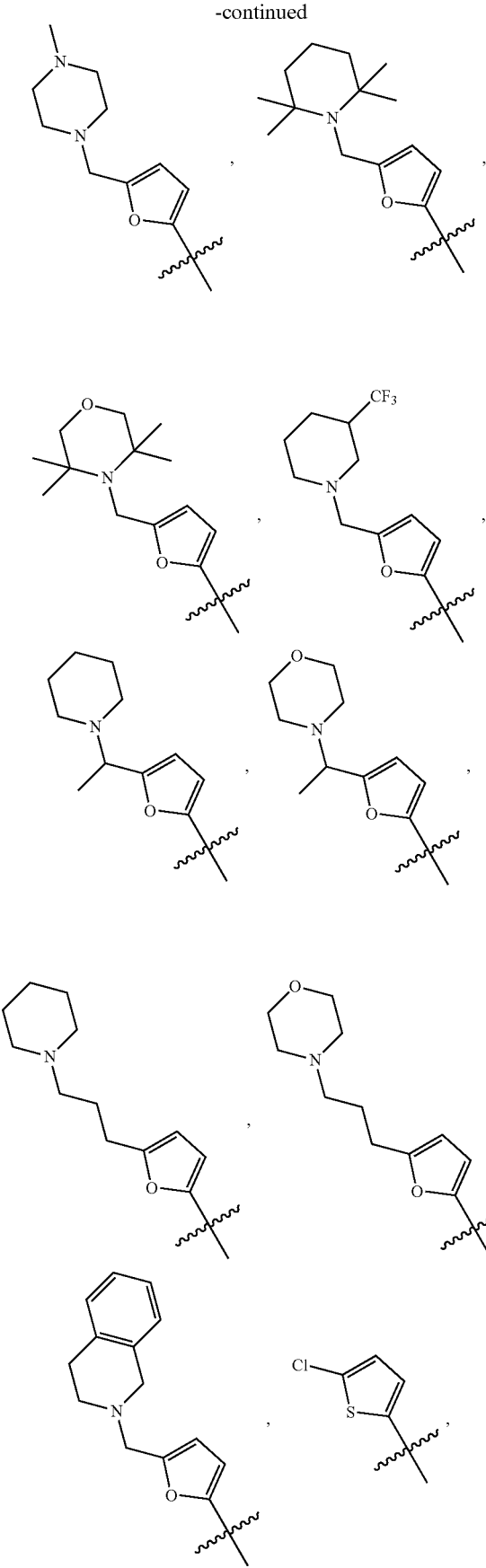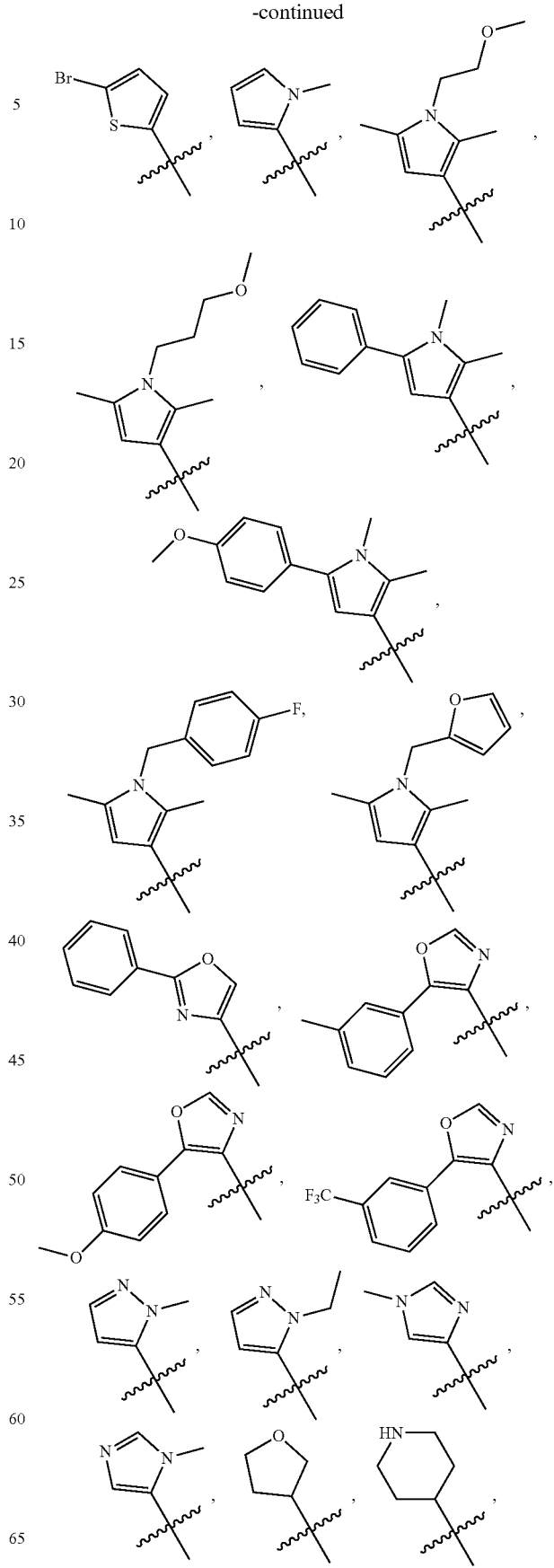

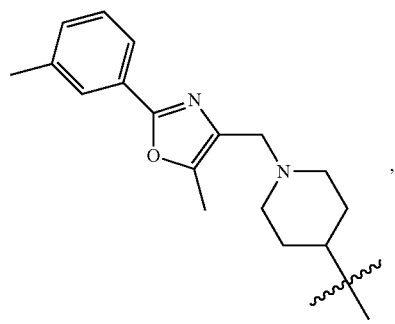
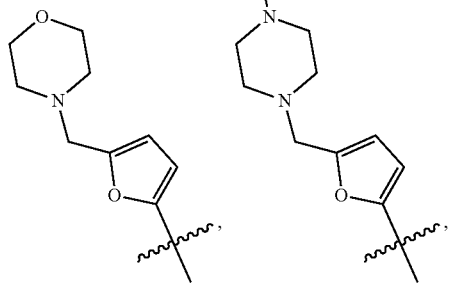
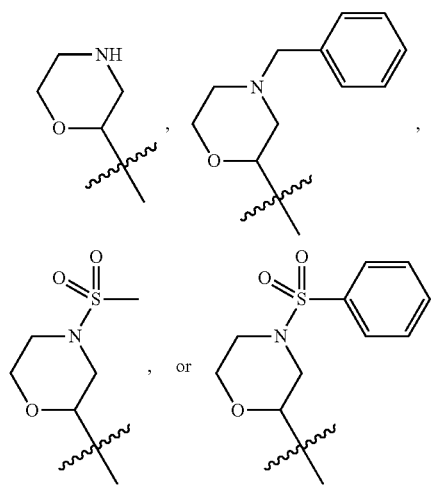
In an embodiment, R$_3$ is:
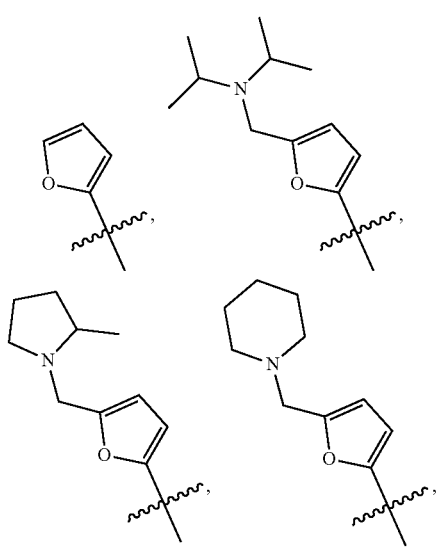
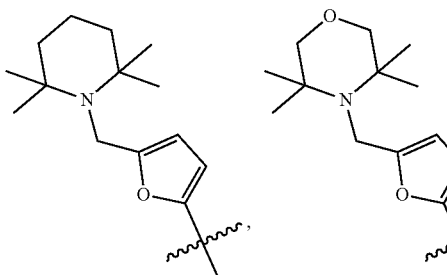
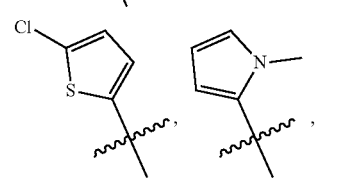
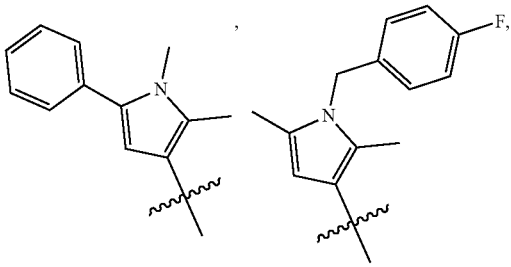
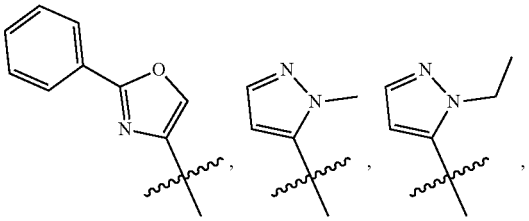
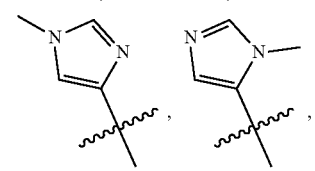

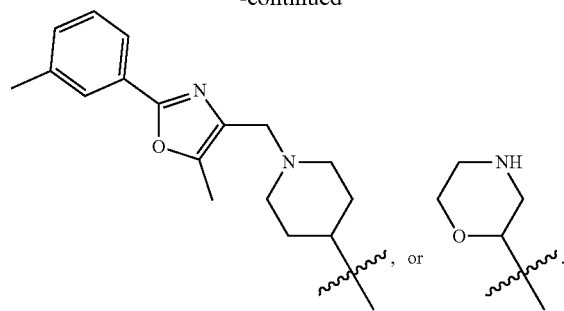, or 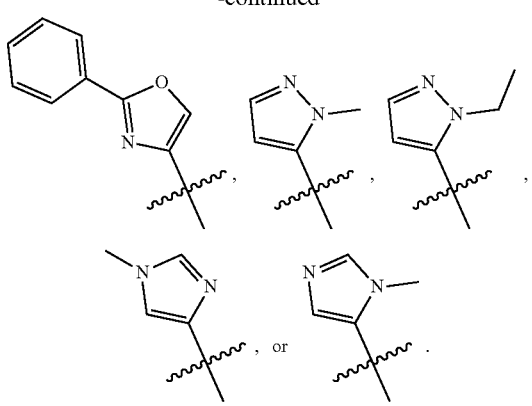
In an embodiment, $R_3$ is:
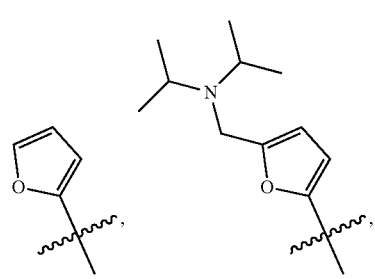
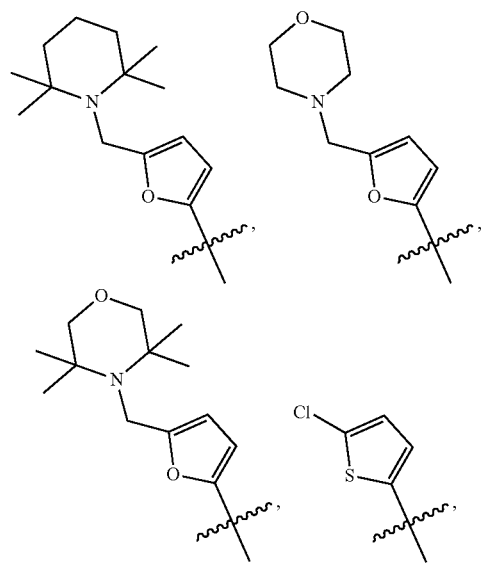
In an embodiment, $R_3$ is:
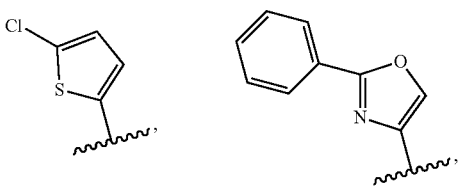
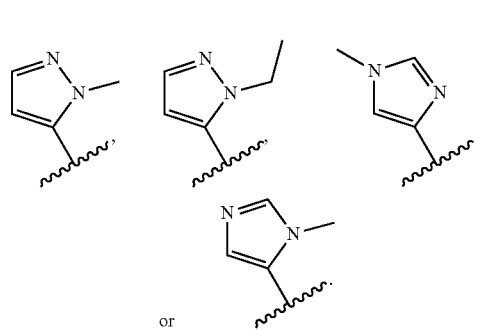
or
In an embodiment, $R_3$ is:
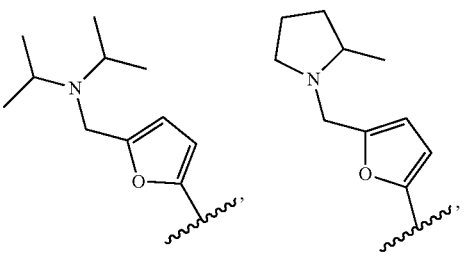
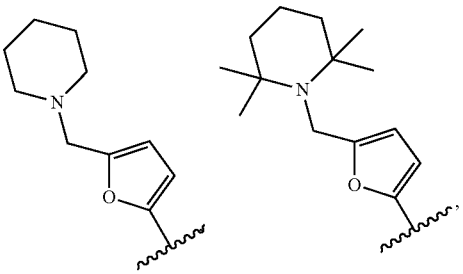

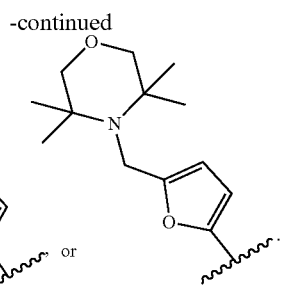

In an embodiment, $R_4$ is hydrogen or methyl. In an embodiment, $R_4$ is hydrogen. In an embodiment, $R_4$ is methyl.

In an embodiment, $R_5$ is $C_1$-$C_6$ alkyl or $C_1$-$C_3$ alkyl-($C_6$-$C_{10}$ aryl). In another embodiment, $R_5$ is $C_1$-$C_4$ alkyl or $C_1$-$C_3$ alkyl-phenyl. In another embodiment, $R_5$ is $C_1$-$C_4$ alkyl or benzyl.

In an embodiment, when $R_1$ is not methyl, $R_2$ is not methyl, and $R_4$ is not hydrogen, then $R_{3b}$ independently for each occurrence is $C_1$-$C_6$ alkyl, $C_1$-$C_6$ alkoxy, $C_1$-$C_6$ haloalkyl, $C_1$-$C_6$ alkyl-N($R_5$)$_2$, ($C_1$-$C_6$ alkyl)-O—($C_1$-$C_6$ alkyl), halo, nitro, cyano, $C_6$-$C_{10}$ aryl, C(O)-(4- to 8-membered heterocycle), $C_1$-$C_6$ alkyl-($C_6$-$C_{10}$ aryl), $C_1$-$C_6$ alkyl-(5- to 10-membered heteroaryl), or $C_1$-$C_6$ alkyl-(4- to 8-membered heterocycle), wherein each 4- to 8-membered heterocycle, $C_6$-$C_{10}$ aryl, and 5- to 10-membered heteroaryl are optionally further substituted one or two times with $C_1$-$C_3$ alkyl, $C_1$-$C_3$ alkoxy, $C_1$-$C_3$ haloalkyl, or halo.

In an embodiment, when $R_4$ is not hydrogen, then $R_{3b}$ independently for each occurrence is $C_1$-$C_6$ alkyl, $C_1$-$C_6$ alkoxy, $C_1$-$C_6$ haloalkyl, $C_1$-$C_6$ alkyl-N($R_5$)$_2$, ($C_1$-$C_6$ alkyl)-O—($C_1$-$C_6$ alkyl), halo, nitro, cyano, $C_6$-$C_{10}$ aryl, C(O)-(4- to 8-membered heterocycle), $C_1$-$C_6$ alkyl-($C_6$-$C_{10}$ aryl), $C_1$-$C_6$ alkyl-(5- to 10-membered heteroaryl), or $C_1$-$C_6$ alkyl-(4- to 8-membered heterocycle), wherein each 4- to 8-membered heterocycle, $C_6$-$C_{10}$ aryl, and 5- to 10-membered heteroaryl are optionally further substituted one or two times with $C_1$-$C_3$ alkyl, $C_1$-$C_3$ alkoxy, $C_1$-$C_3$ haloalkyl, or halo.

In an embodiment, when $R_3$ is oxazolyl, $R_3$ does not have the following structure:

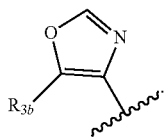

In a particular embodiment of the compound of Formula (V), or a pharmaceutically acceptable salt thereof:
$R_1$ is $C_1$-$C_3$ alkyl;
$R_2$ is $C_1$-$C_3$ alkyl;
$R_3$ is a 5-membered heteroaryl that is optionally substituted one, two, or three times with the group $R_{3b}$;
$R_{3b}$ independently for each occurrence is $C_1$-$C_6$ alkyl, $C_1$-$C_6$ alkyl-N($R_5$)$_2$, ($C_1$-$C_6$ alkyl)-O—($C_1$-$C_6$ alkyl), halo, $C_6$-$C_{10}$ aryl, C(O)-(4- to 8-membered heterocycle), $C_1$-$C_6$ alkyl-($C_6$-$C_{10}$ aryl), $C_1$-$C_6$ alkyl-(5- to 10-membered heteroaryl), or $C_1$-$C_6$ alkyl-(4- to 8-membered heterocycle), wherein each 4- to 8-membered heterocycle, $C_6$-$C_{10}$ aryl, and 5- to 10-membered heteroaryl are optionally further substituted one to four times with $C_1$-$C_3$ alkyl, $C_1$-$C_3$ alkoxy, $C_1$-$C_3$ haloalkyl, or halo;
$R_4$ is hydrogen or methyl; and
$R_5$ independently for each occurrence is $C_1$-$C_4$ alkyl or benzyl.

In another embodiment of the compound of Formula (V), or a pharmaceutically acceptable salt thereof:
$R_1$ is $C_1$-$C_3$ alkyl;
$R_2$ is $C_1$-$C_3$ alkyl;
$R_3$ is a furyl that is optionally substituted one, two, or three times with the group $R_{3b}$;
$R_{3b}$ independently for each occurrence is $C_1$-$C_6$ alkyl-N($R_5$)$_2$ or $C_1$-$C_6$ alkyl-(4- to 8-membered heterocycle), wherein each 4- to 8-membered heterocycle is optionally further substituted one to four times with $C_1$-$C_3$ alkyl, $C_1$-$C_3$ alkoxy, $C_1$-$C_3$ haloalkyl, or halo;
$R_4$ is hydrogen or methyl; and
$R_5$ independently for each occurrence is $C_1$-$C_4$ alkyl or benzyl.

In another embodiment of the compound of Formula (V), or a pharmaceutically acceptable salt thereof:
$R_1$ is $C_1$-$C_3$ alkyl;
$R_2$ is $C_1$-$C_3$ alkyl;
$R_3$ is a furyl that is optionally substituted one, two, or three times with the group $R_{3b}$;
$R_{3b}$ independently for each occurrence is $C_1$-$C_6$ alkyl-N($R_5$)$_2$ or $C_1$-$C_6$ alkyl-(4- to 8-membered heterocycle), wherein each 4- to 8-membered heterocycle is optionally further substituted one to four times with $C_1$-$C_3$ alkyl, $C_1$-$C_3$ alkoxy, $C_1$-$C_3$ haloalkyl, or halo;
$R_4$ is hydrogen or methyl; and
$R_5$ independently for each occurrence is $C_1$-$C_4$ alkyl or benzyl;
provided that when $R_1$ is $C_2$-$C_3$ alkyl, $R_2$ is $C_2$-$C_3$ alkyl, and $R_4$ is methyl, then $R_{3b}$ independently for each occurrence is $C_1$-$C_6$ alkyl-N($R_5$)$_2$ or $C_1$-$C_6$ alkyl-(4- to 8-membered heterocycle), wherein each 4- to 8-membered heterocycle is optionally further substituted one or two times with $C_1$-$C_3$ alkyl, $C_1$-$C_3$ alkoxy, $C_1$-$C_3$ haloalkyl, or halo.

In another embodiment of the compound of Formula (V), or a pharmaceutically acceptable salt thereof:
$R_1$ is $C_1$-$C_3$ alkyl;
$R_2$ is $C_1$-$C_3$ alkyl;
$R_3$ is a furyl that is optionally substituted one, two, or three times with the group $R_{3b}$;
$R_{3b}$ independently for each occurrence is $C_1$-$C_6$ alkyl-N($R_5$)$_2$ or $C_1$-$C_6$ alkyl-(4- to 8-membered heterocycle), wherein each 4- to 8-membered heterocycle is optionally further substituted one to four times with $C_1$-$C_3$ alkyl, $C_1$-$C_3$ alkoxy, $C_1$-$C_3$ haloalkyl, or halo;
$R_4$ is hydrogen or methyl; and
$R_5$ independently for each occurrence is $C_1$-$C_4$ alkyl or benzyl;
provided that when $R_4$ is methyl, then $R_{3b}$ independently for each occurrence is $C_1$-$C_6$ alkyl-N($R_5$)$_2$ or $C_1$-$C_6$ alkyl-(4- to 8-membered heterocycle), wherein each 4- to 8-membered heterocycle is optionally further substituted one or two times with $C_1$-$C_3$ alkyl, $C_1$-$C_3$ alkoxy, $C_1$-$C_3$ haloalkyl, or halo.

Exemplary compounds of Formula (V) include the following compounds, or pharmaceutically acceptable salts thereof:

Compound 23
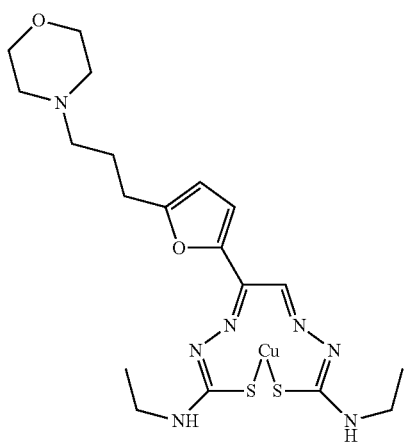
Compound 24
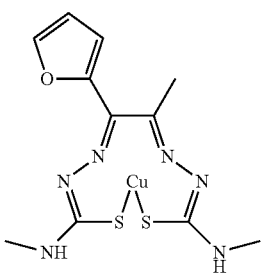
Compound 25
Compound 26
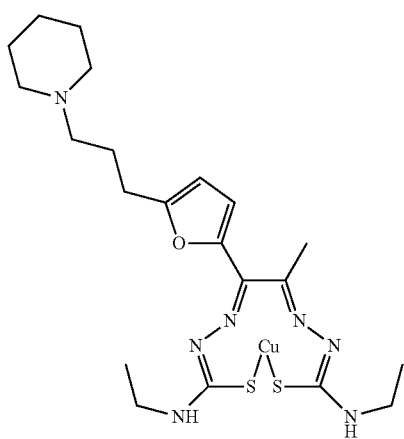
Compound 27
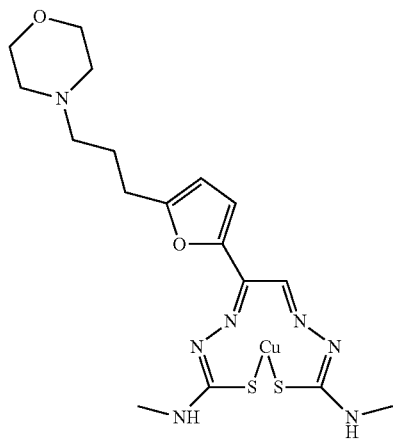
Compound 28
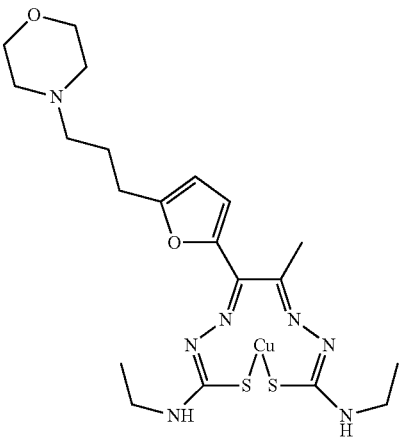
Compound 29
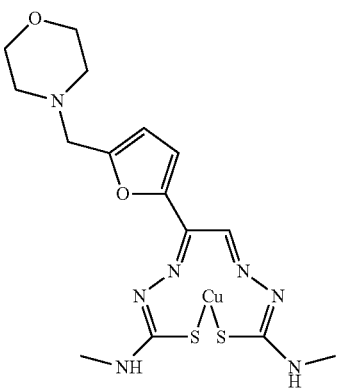
Compound 30
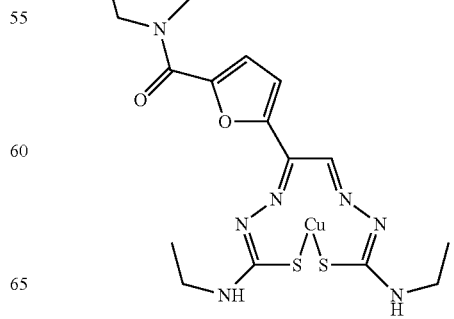

Compound 31
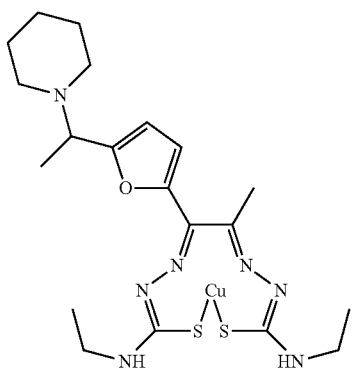
Compound 32
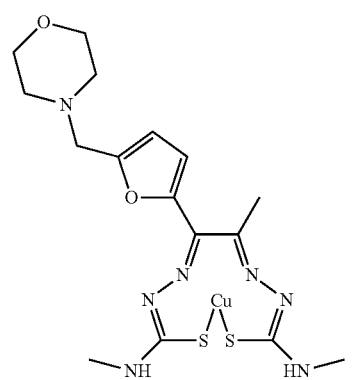
Compound 33
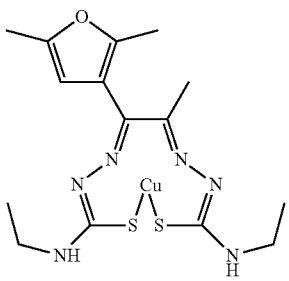
Compound 34
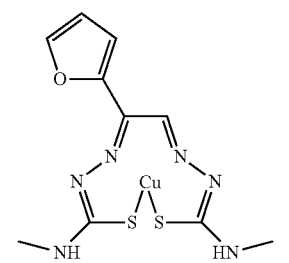
Compound 35
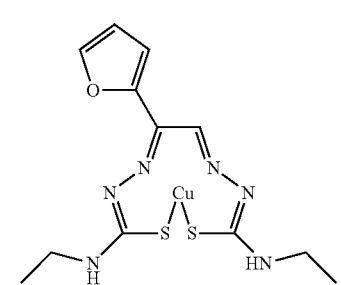
Compound 36
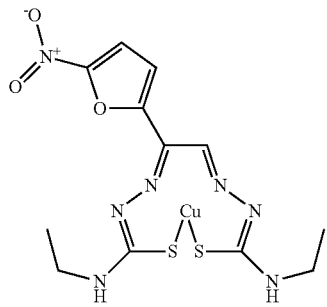
Compound 37
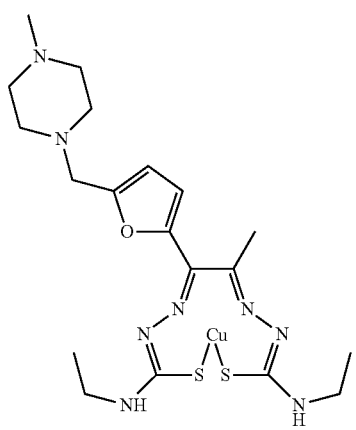
Compound 38
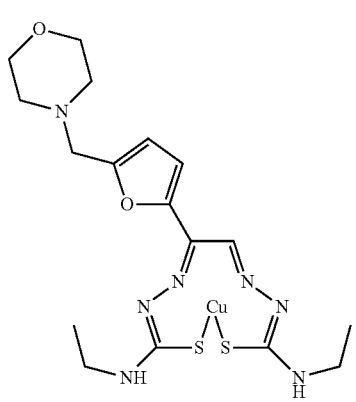
Compound 39
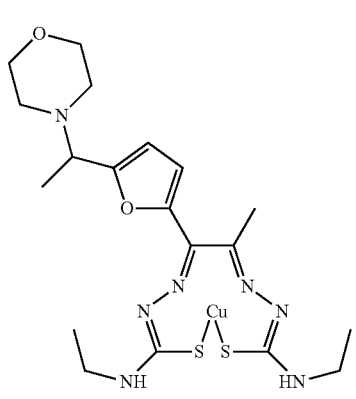

-continued
Compound 40
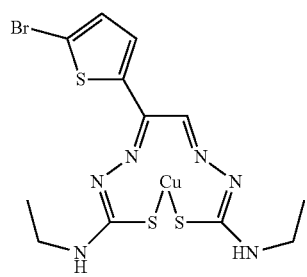
Compound 41
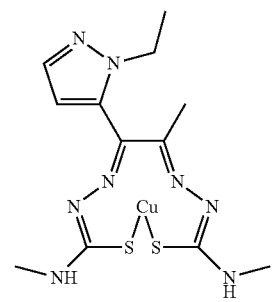
Compound 42
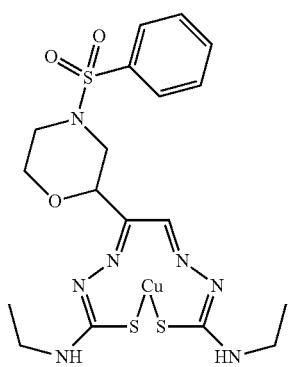
Compound 43
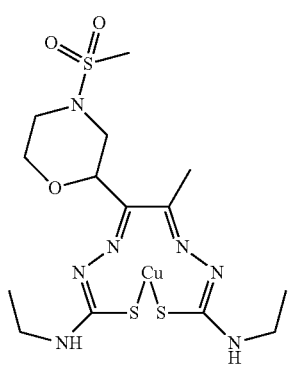
Compound 44
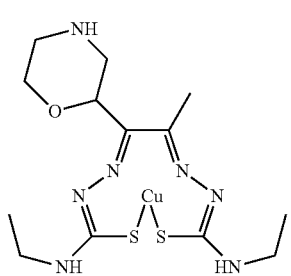
-continued
Compound 45
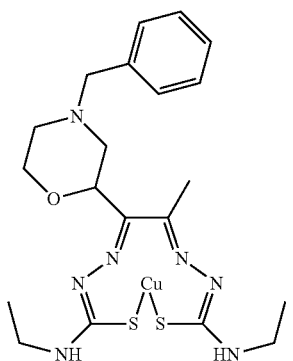
Compound 46
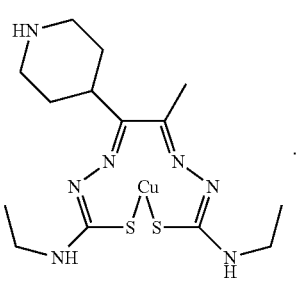
Compound 79
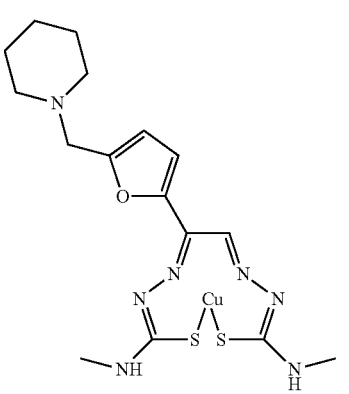
Compound 80

Compound 81
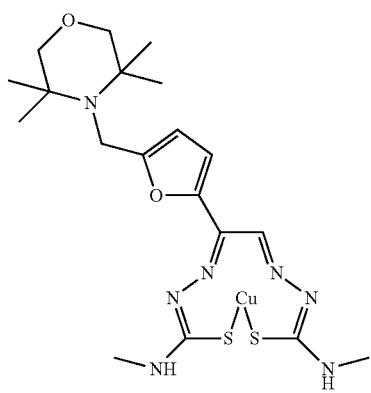
Compound 82
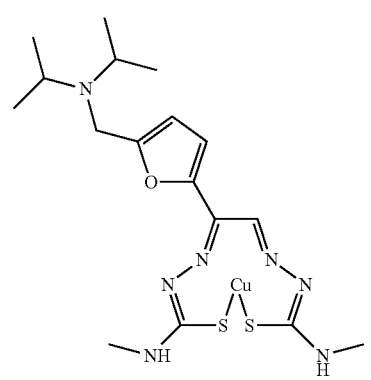
Compound 83
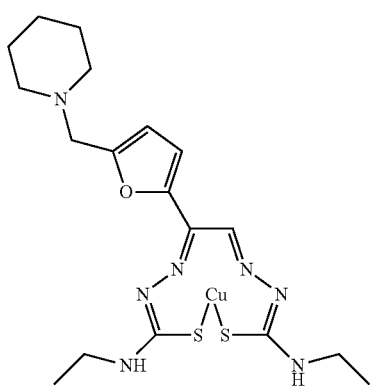
Compound 84
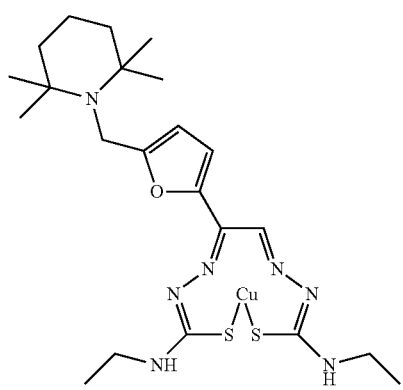
Compound 85
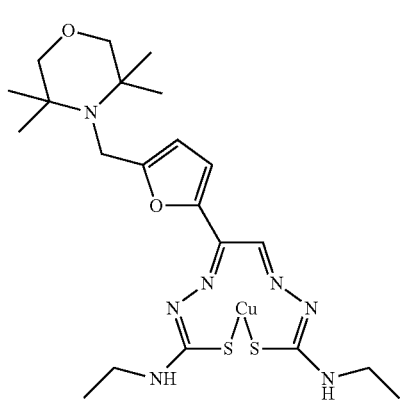
Compound 86
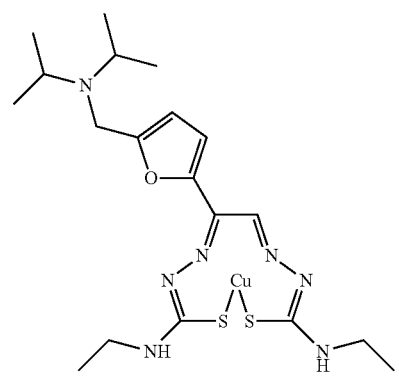
Compound 87
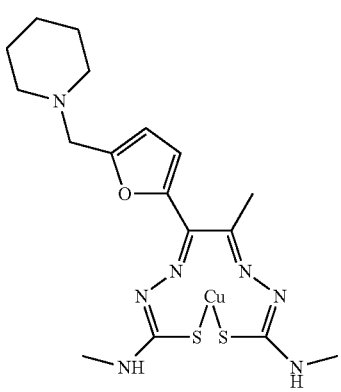
Compound 88
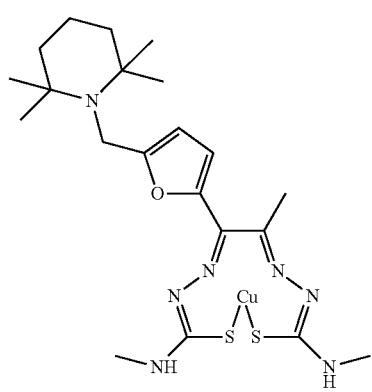

Compound 89
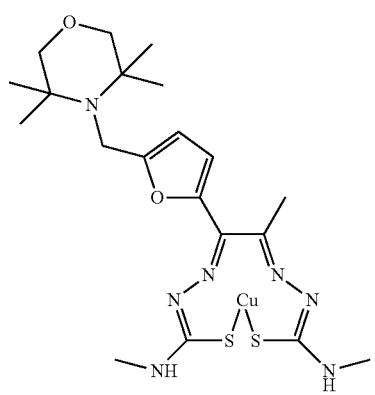
Compound 90
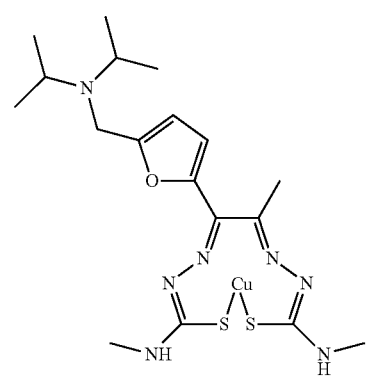
Compound 91
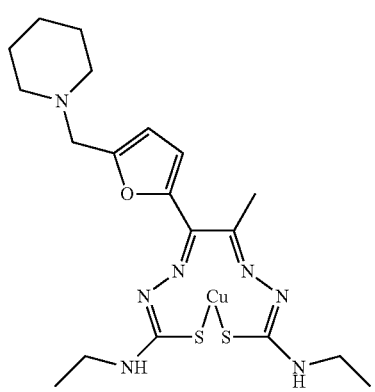
Compound 92
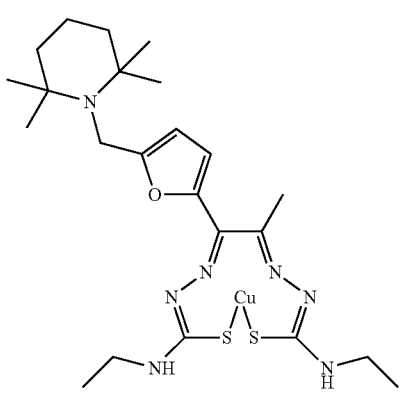
Compound 93
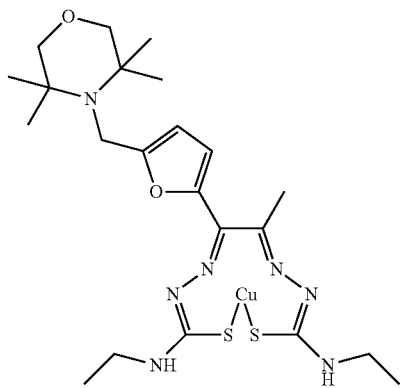
Compound 94
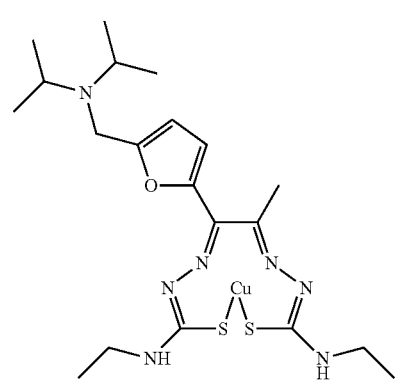
Compound 95
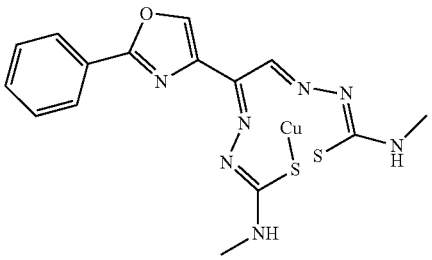
Compound 96
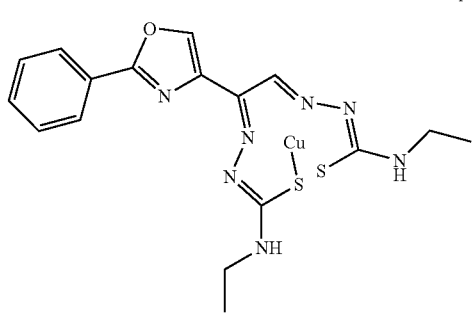
Compound 97
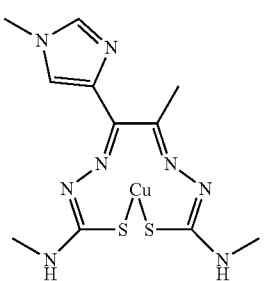

Compound 98
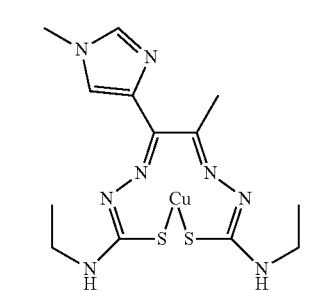
Compound 103
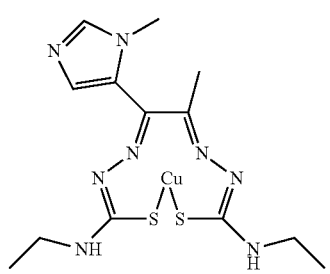
Compound 99
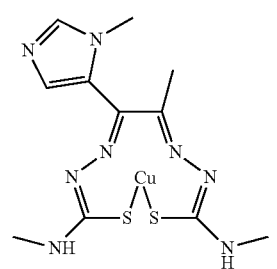
Compound 100
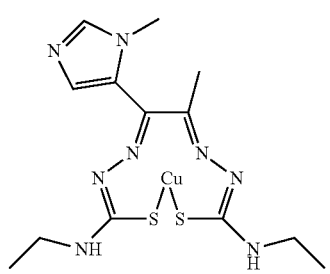
Compound 104
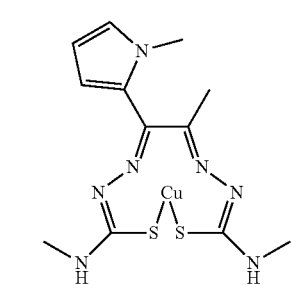
Compound 101
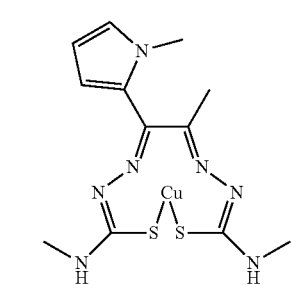
Compound 105
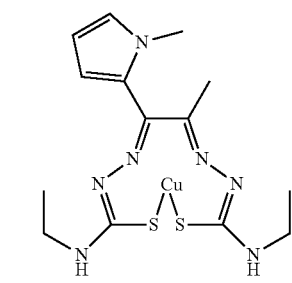
Compound 102
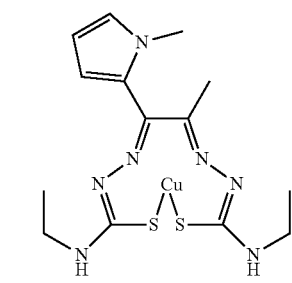
Compound 106
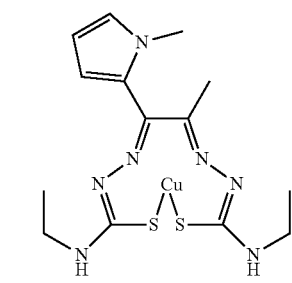

-continued
Compound 107
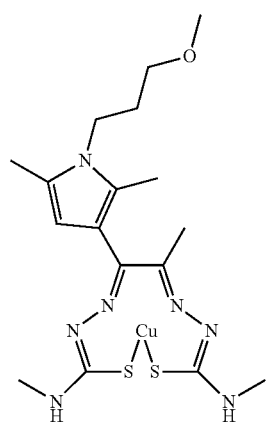
Compound 108
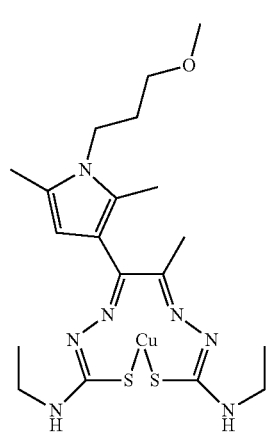
Compound 109
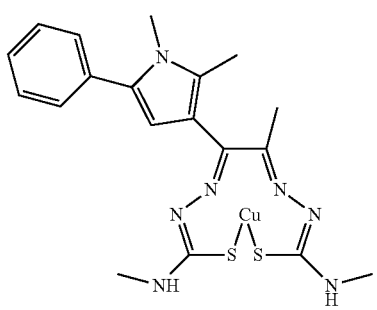
Compound 110
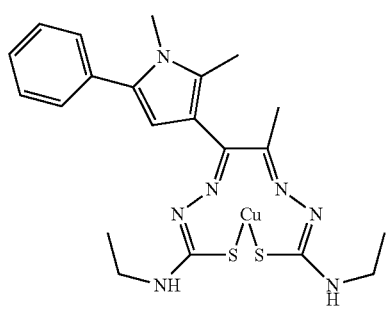
-continued
Compound 111
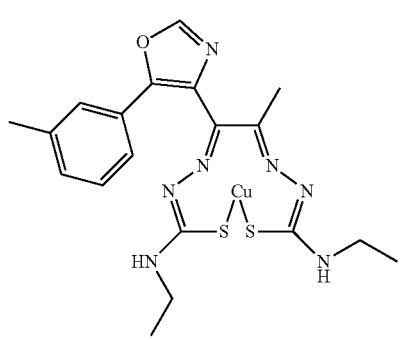
Compound 112
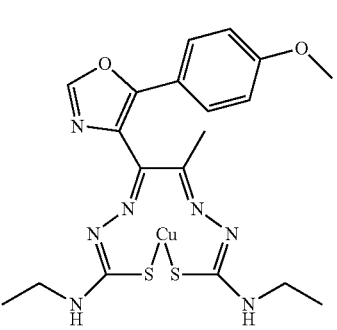
Compound 113
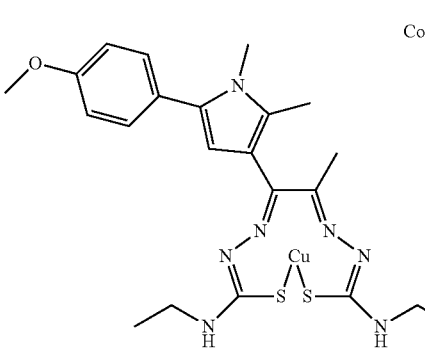
Compound 114
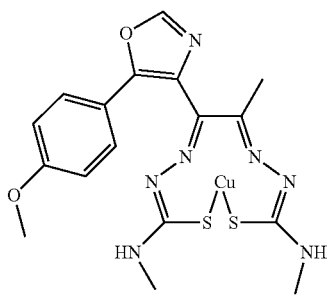
Compound 115
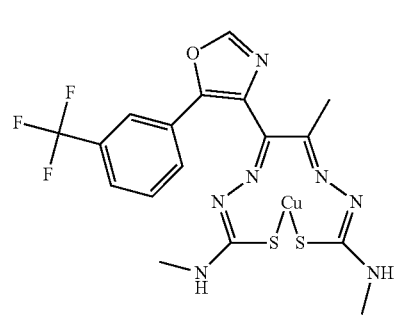

Compound 116
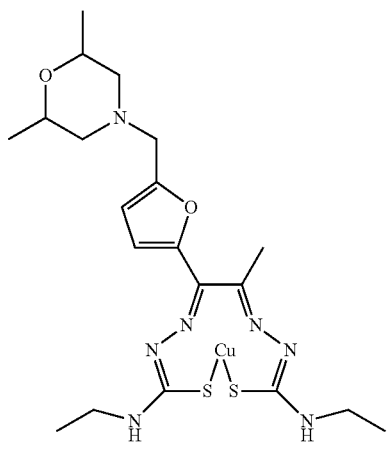
Compound 117
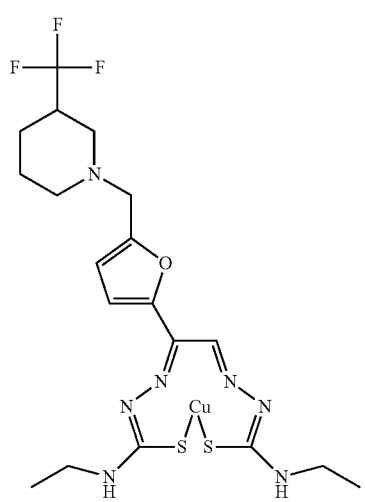
Compound 118
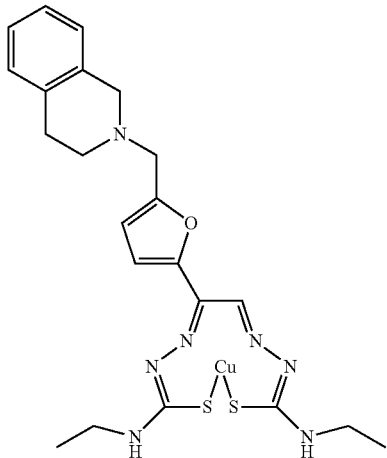
Compound 119
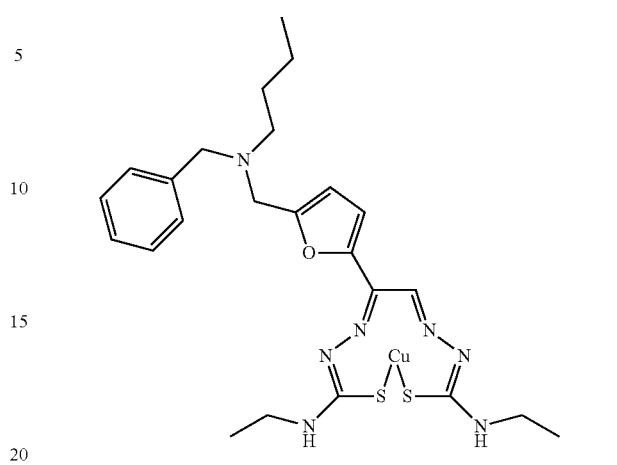
Compound 120
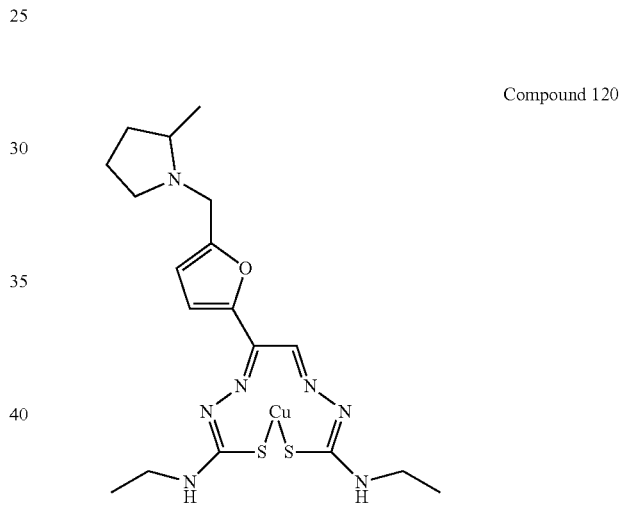
Compound 121
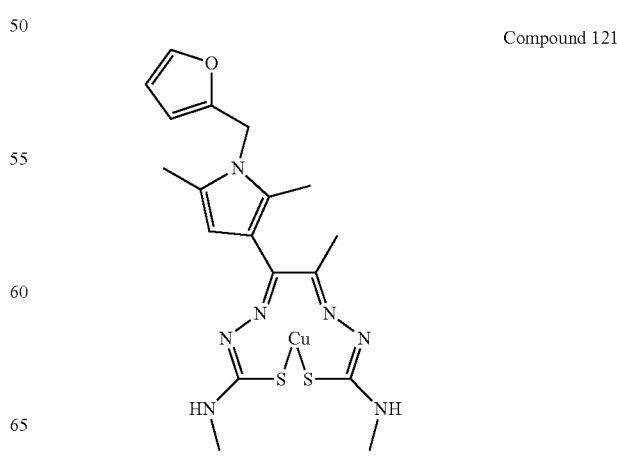

Compound 122
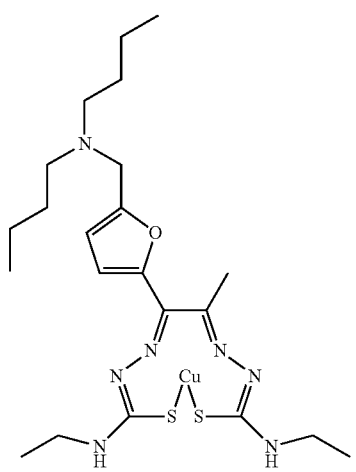
Compound 123
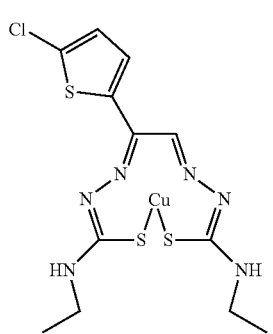
Compound 124
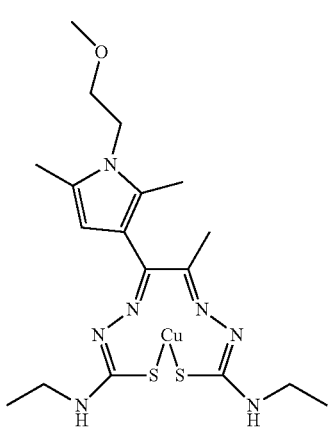
Compound 125
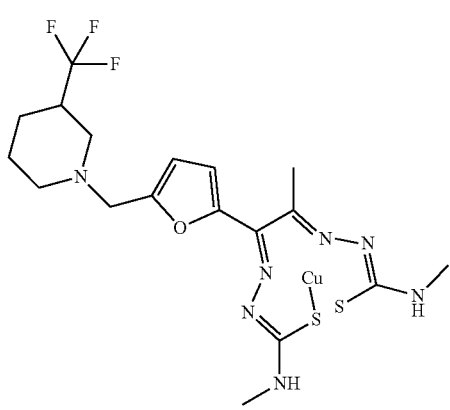
Compound 126
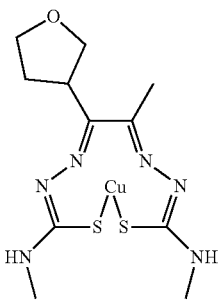
Compound 127
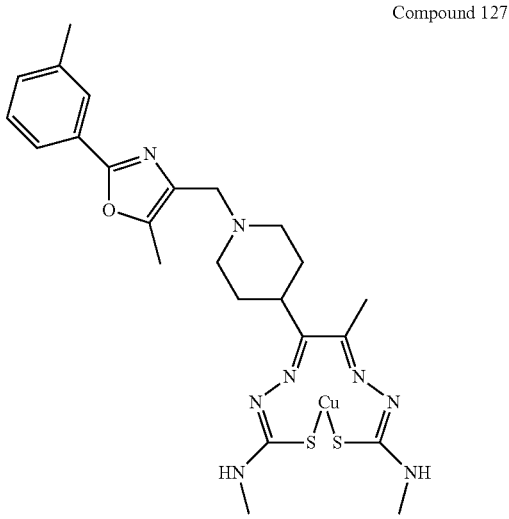
In an embodiment, the compound of Formula (V) is one of the following compounds, or a pharmaceutically acceptable salt thereof:
Compound 25
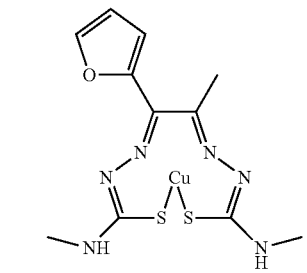
Compound 29
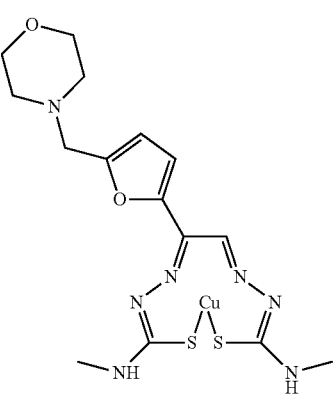

Compound 32
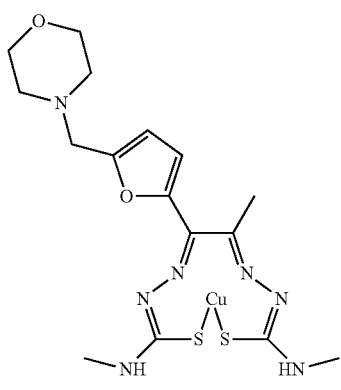
Compound 79
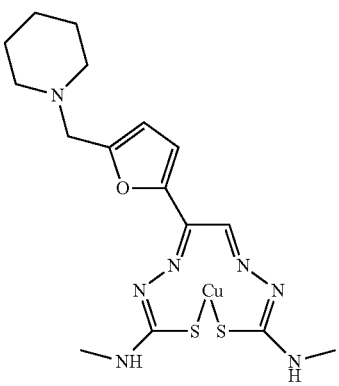
Compound 34
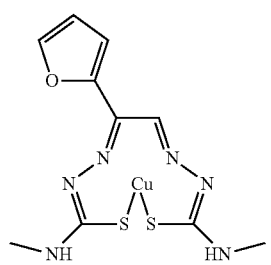
Compound 80
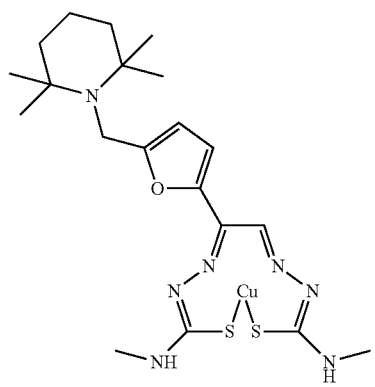
Compound 41
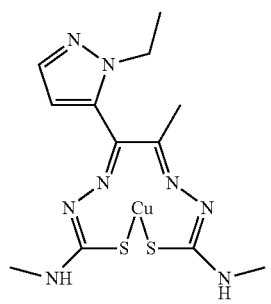
Compound 81
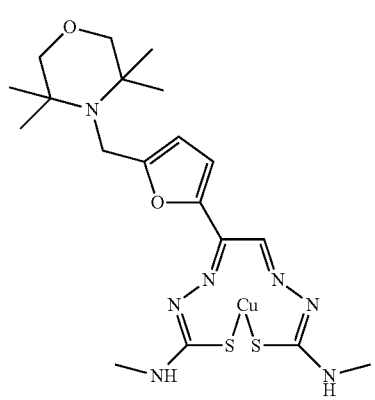
Compound 43
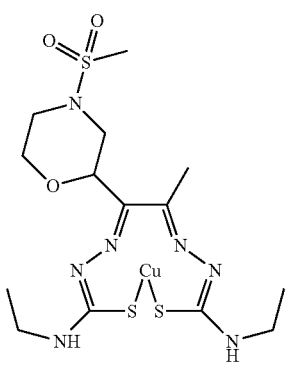
Compound 82
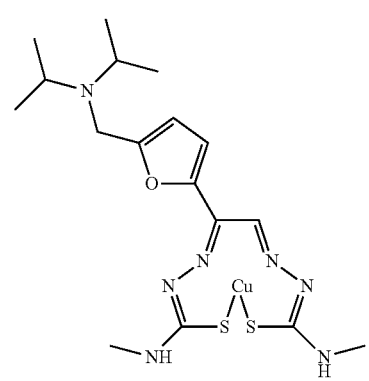
Compound 44
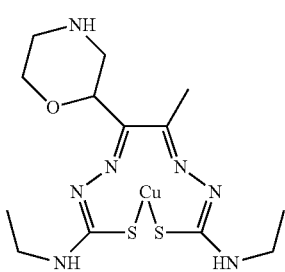

Compound 83
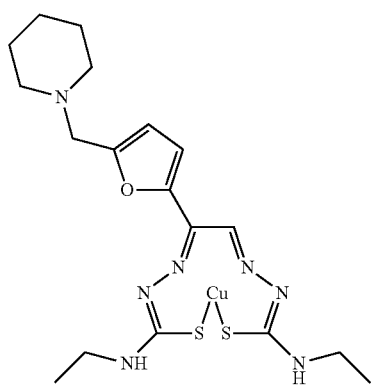
Compound 84
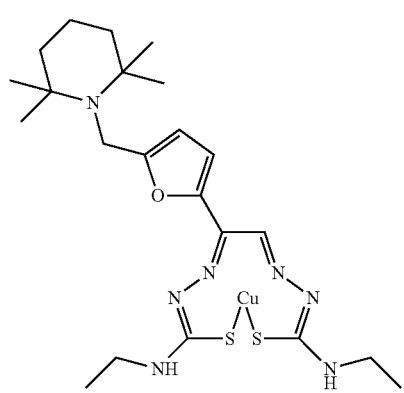
Compound 85
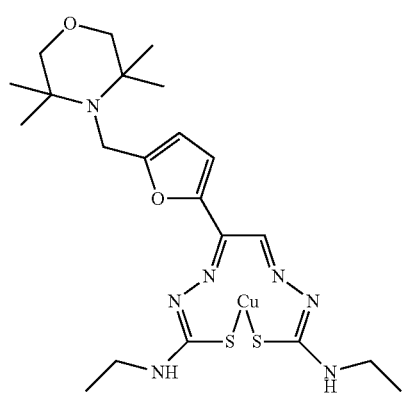
Compound 86
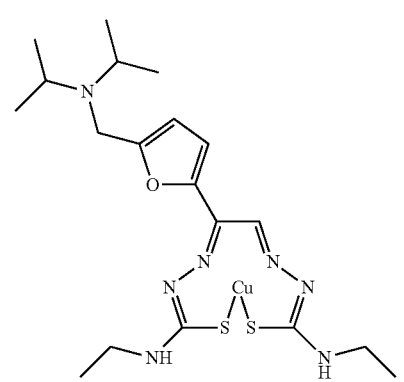
Compound 87
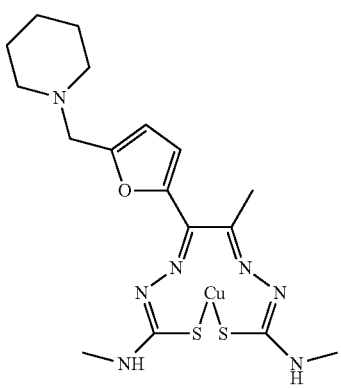
Compound 88
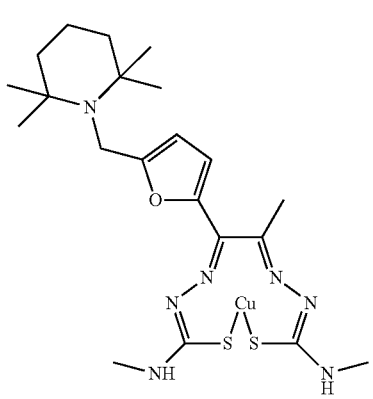
Compound 90
Compound 91
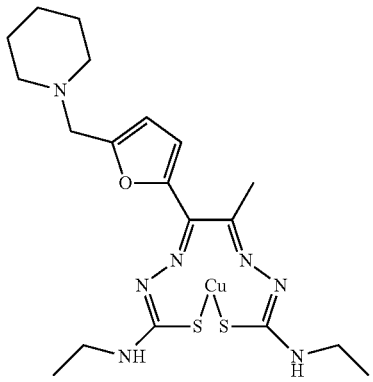

Compound 94
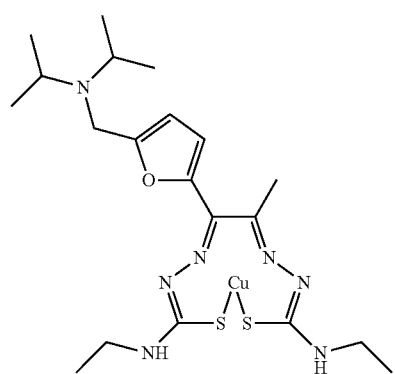
Compound 95
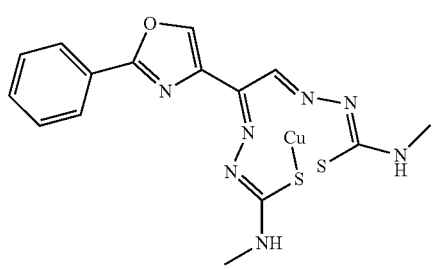
Compound 96
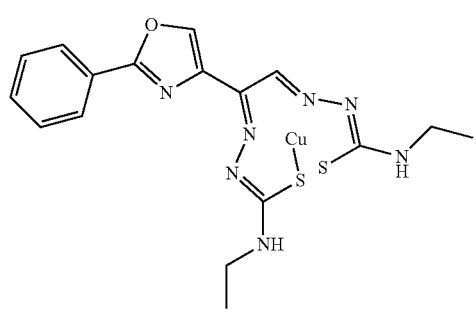
Compound 98
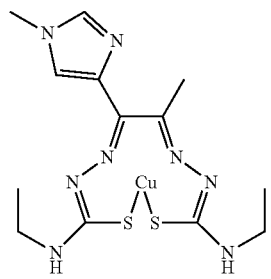
Compound 100
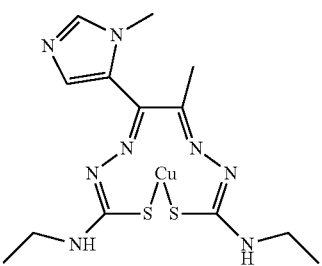
Compound 104
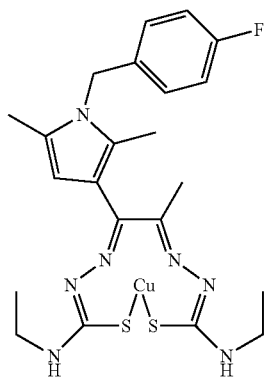
Compound 105
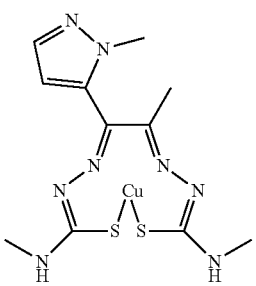
Compound 106
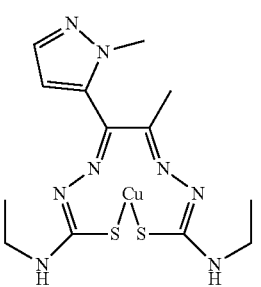
Compound 120
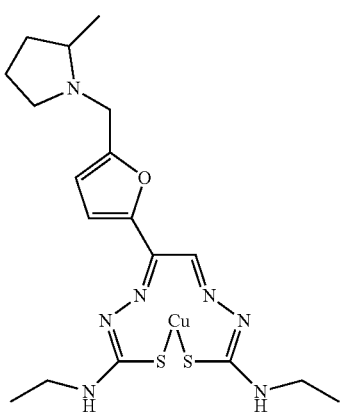

-continued

Compound 123

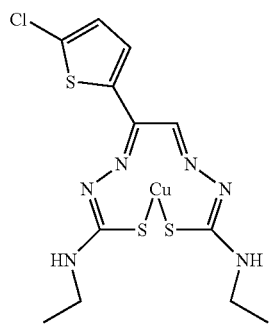

In an embodiment, the compound of Formula (V) has the structure of Compound 25:

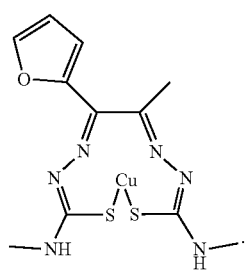

In an embodiment, the compound of Formula (V) has the structure of Compound 32:

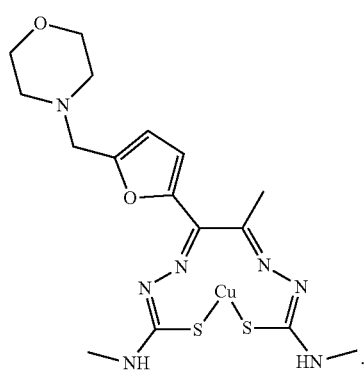

In an embodiment the compound of Formula (V) has the structure of Compound 34:

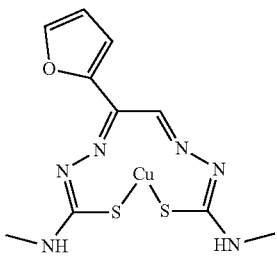

In an embodiment the compound of Formula (V) has the structure of Compound 35:

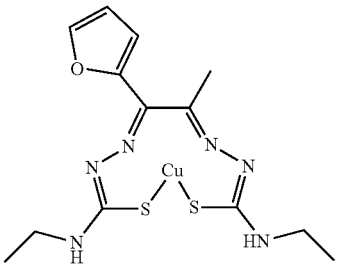

In an embodiment the compound of Formula (V) has the structure of Compound 37:

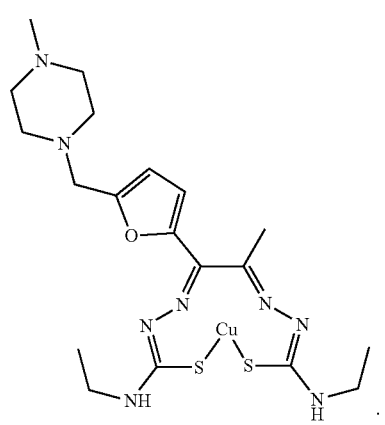

In an embodiment the compound of Formula (V) has the structure of Compound 80:

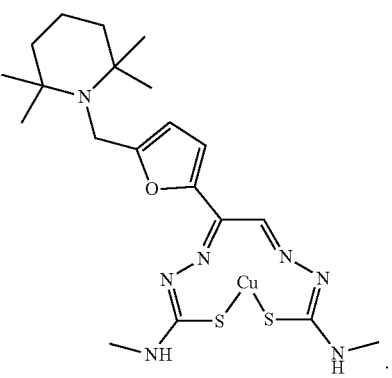

In an embodiment the compound of Formula (V) has the structure of Compound 81:

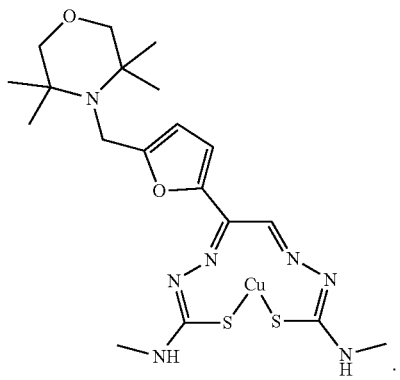

In an embodiment the compound of Formula (V) has the structure of Compound 82:

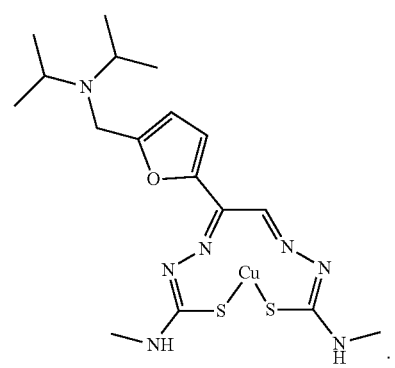

In an embodiment the compound of Formula (V) has the structure of Compound 84:

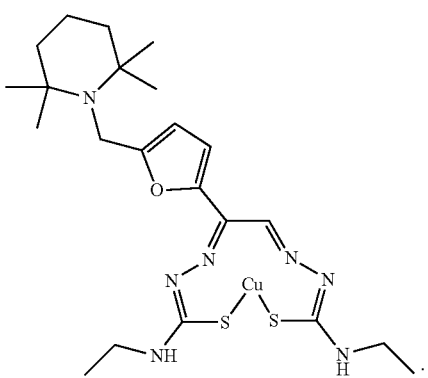

In an embodiment the compound of Formula (V) has the structure of Compound 85:

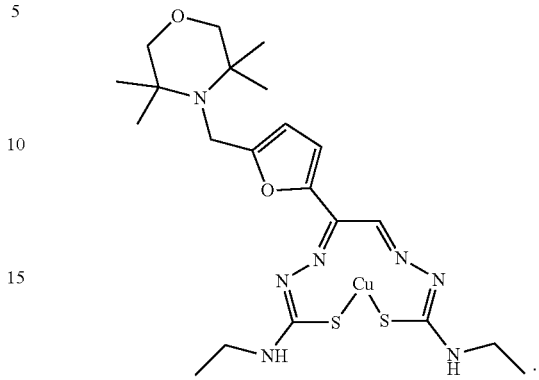

In an embodiment the compound of Formula (V) has the structure of Compound 86:

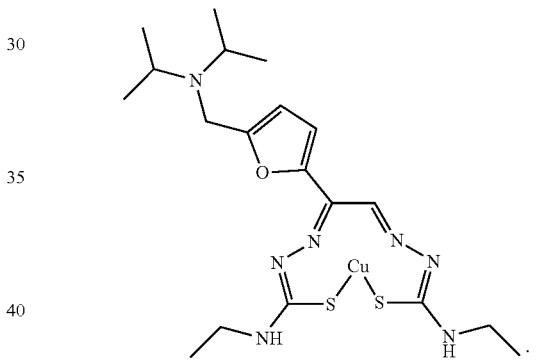

In an embodiment the compound of Formula (V) has the structure of Compound 87:

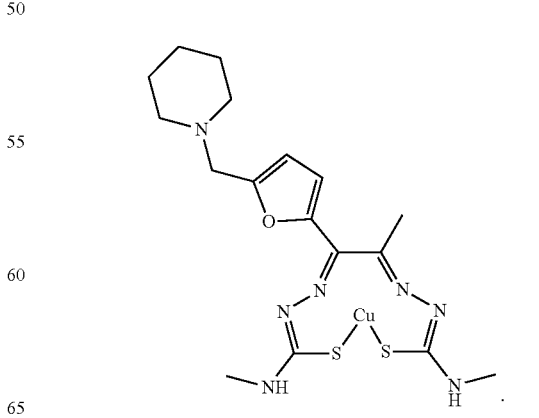

In an embodiment the compound of Formula (V) has the structure of Compound 88:

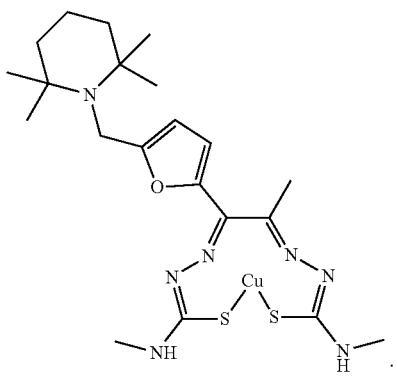

In an embodiment the compound of Formula (V) has the structure of Compound 90:

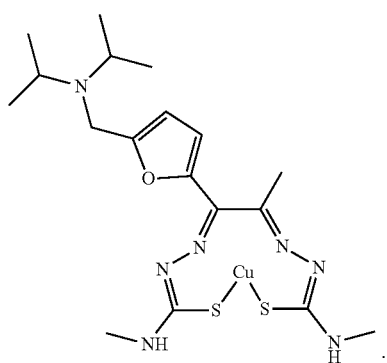

In an embodiment the compound of Formula (V) has the structure of Compound 94:

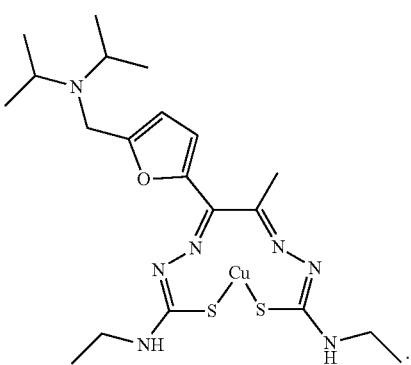

In an embodiment the compound of Formula (V) has the structure of Compound 95:

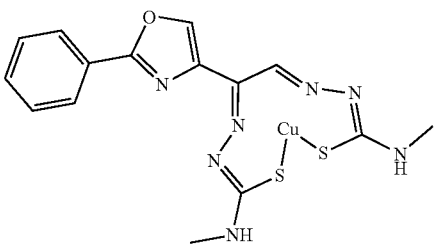

In an embodiment the compound of Formula (V) has the structure of Compound 96:

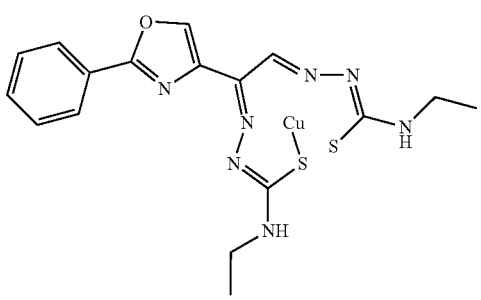

In an embodiment the compound of Formula (V) has the structure of Compound 98:

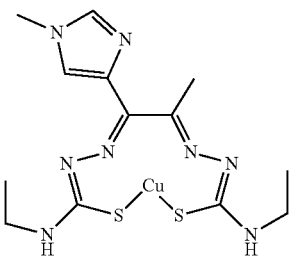

In an embodiment the compound of Formula (V) has the structure of Compound 100:

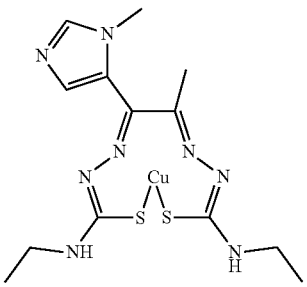

In an embodiment the compound of Formula (V) has the structure of Compound 105:

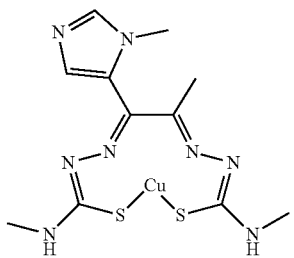

In an embodiment the compound of Formula (V) has the structure of Compound 106:

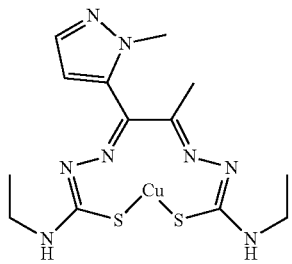

In an embodiment the compound of Formula (V) has the structure of Compound 120:

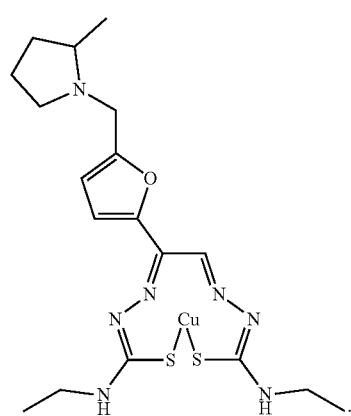

In an embodiment the compound of Formula (V) has the structure of Compound 123:

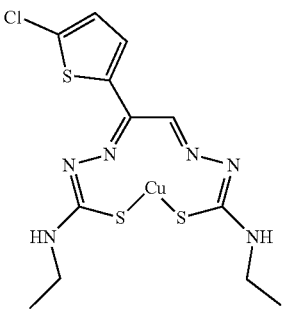

Another aspect of the present disclosure is a compound selected from the group consisting of the compounds described below, or a pharmaceutically acceptable salt thereof:

Compound 54

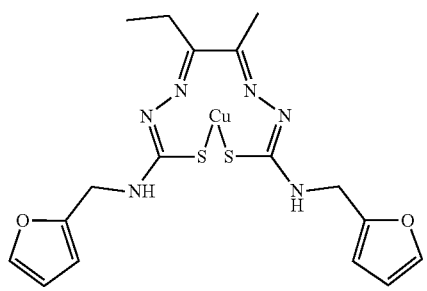

Compound 55

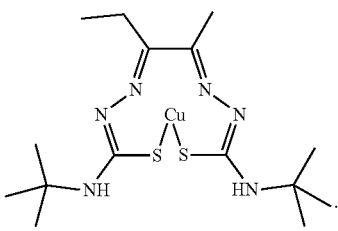

In an embodiment the disclosure provides a compound having the structure of Compound 54:

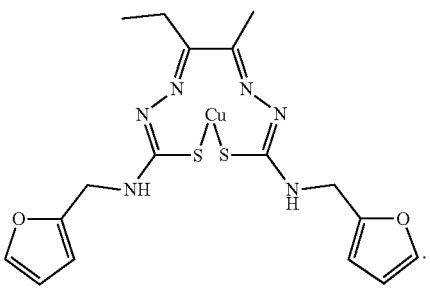

In another aspect, the present disclosure provides a compound having the structure of Compound 20:

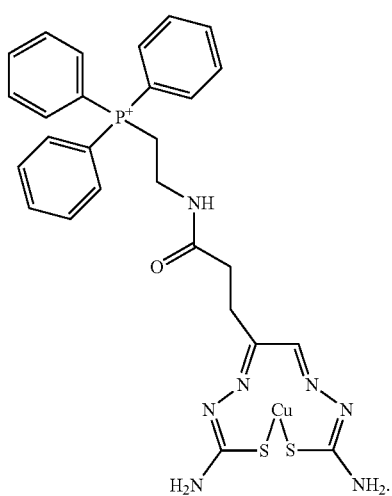
A further aspect of the present disclosure is a compound selected from the group consisting of the compounds described below, or a pharmaceutically acceptable salt thereof:
Compound 56
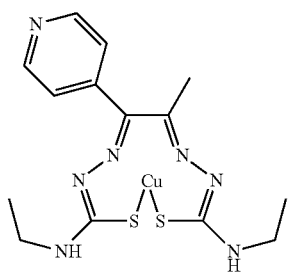
Compound 57
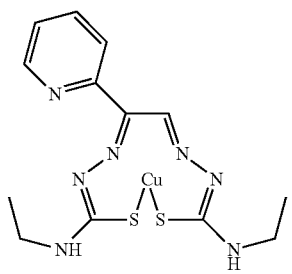
Compound 58
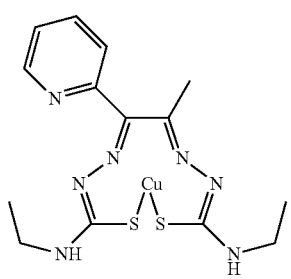
Compound 59
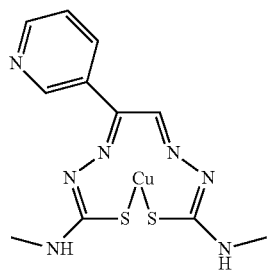
Compound 60
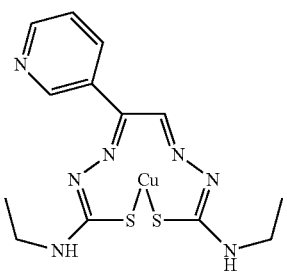
Compound 61
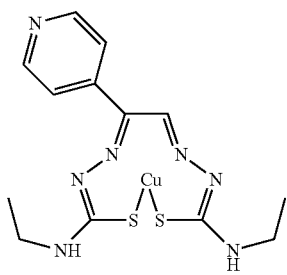
Compound 62
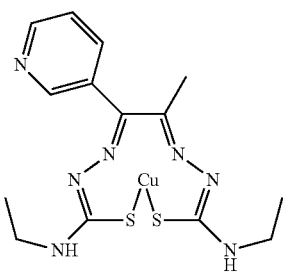
Compound 63
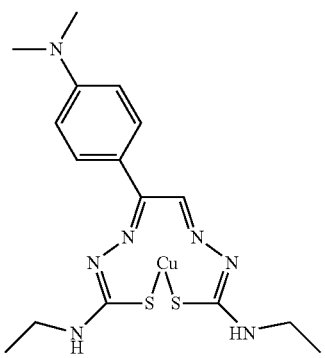

Compound 64

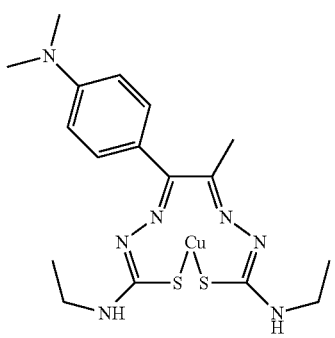

ZN-50

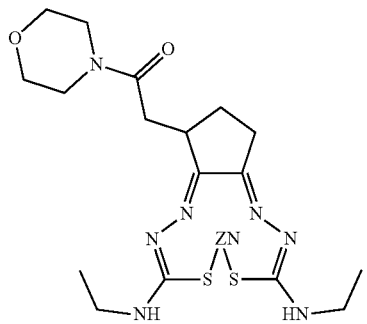

Compound 65

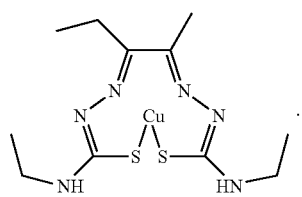

A further aspect of the present disclosure is a compound selected from the group consisting of the compounds described below, or a pharmaceutically acceptable salt thereof:

ZN-75

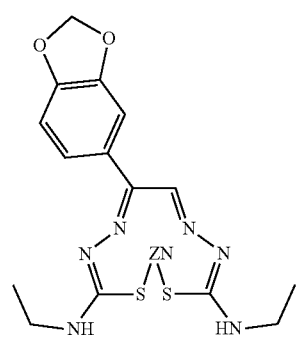

ZN-30

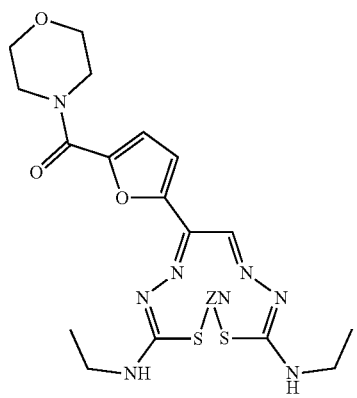

Synthetic Intermediates

In another aspect, the present disclosure also relates to synthetic intermediates of the copper complexes described herein. In some embodiments, the synthetic intermediate has a structure represented by Formula (I-A):

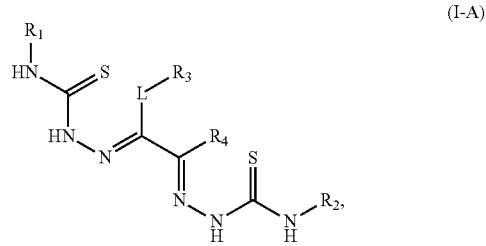

(I-A)

wherein variables L, $R_1$, $R_2$, $R_3$, and $R_4$ correspond to the variables of the same name as defined in Formula (I).

Exemplary synthetic intermediates represented by Formula (I-A) include the following:

ZN-47

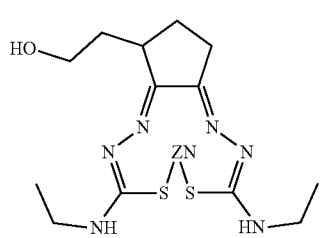

INT-1

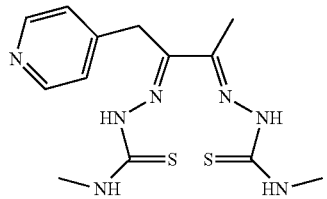

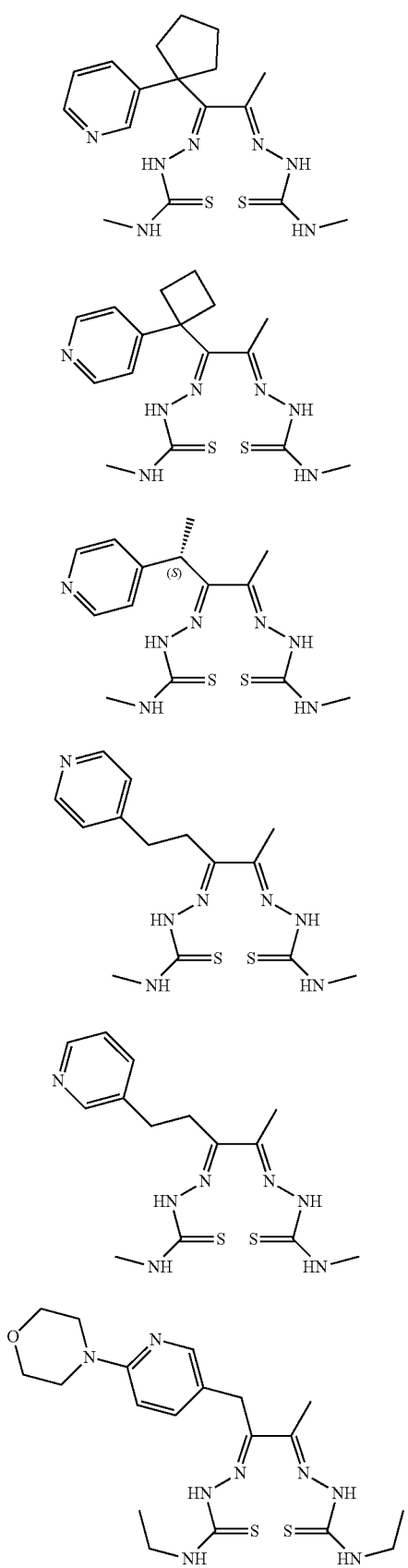
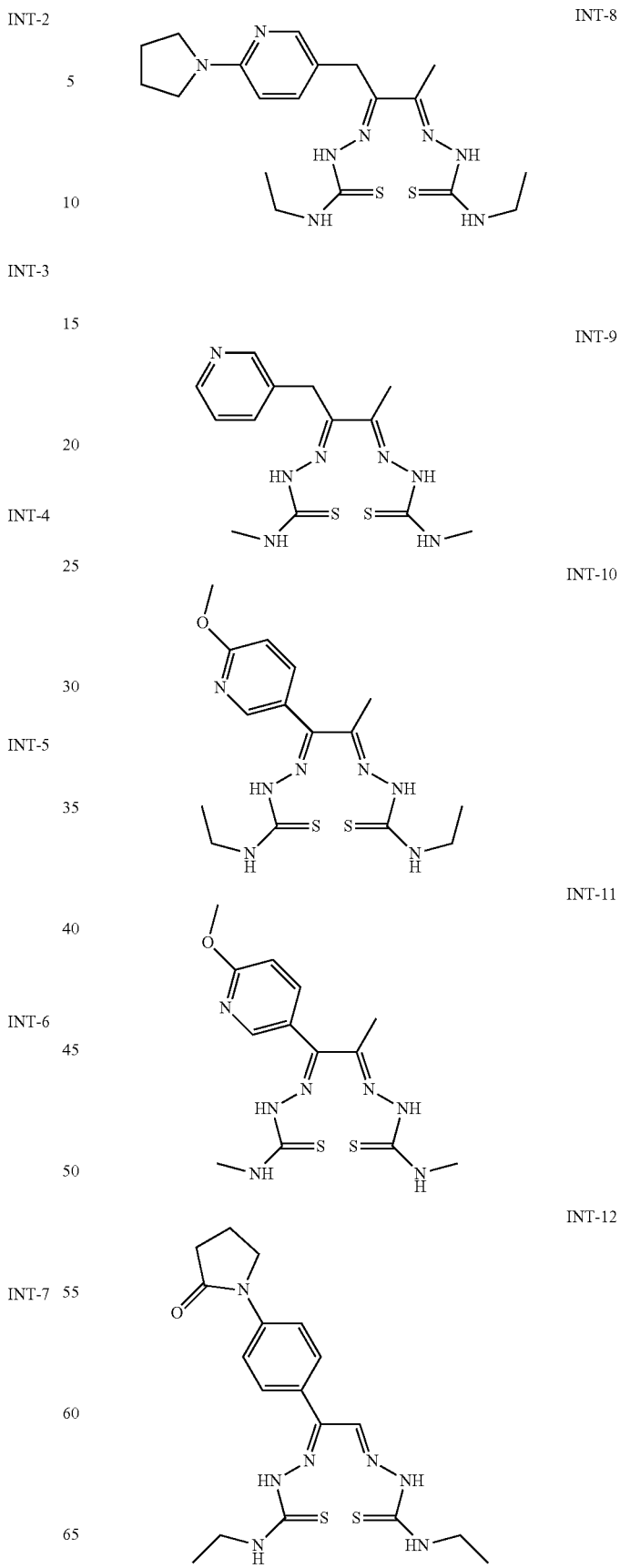

INT-13
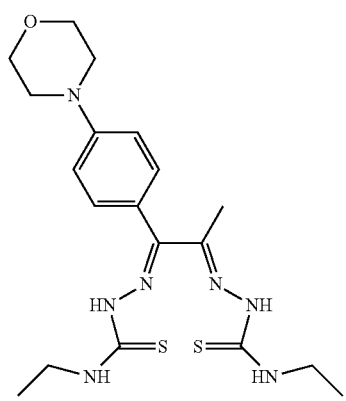
INT-14
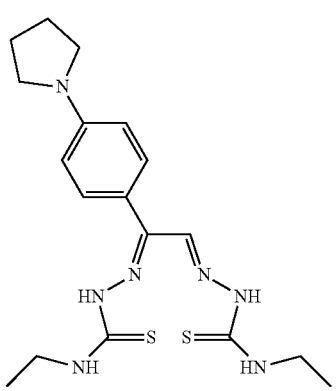
INT-15
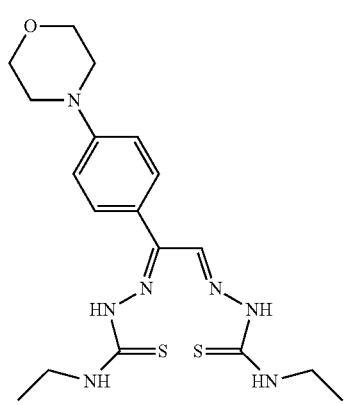
INT-16
INT-17
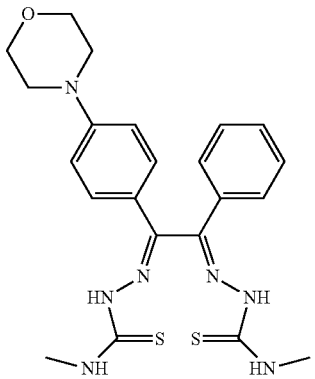
INT-18
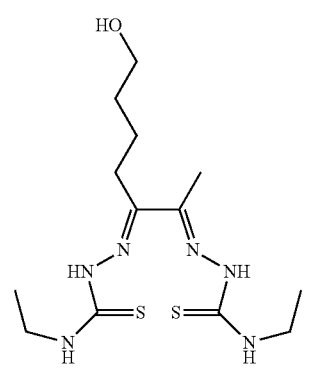
INT-19
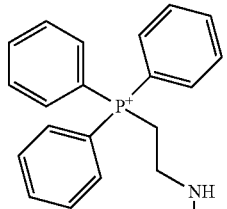
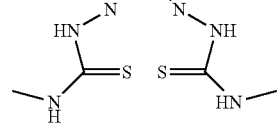

Exemplary synthetic intermediates represented by Formula (II-A) include the following:
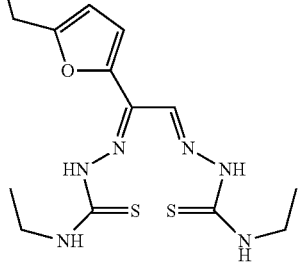
In some embodiments, the synthetic intermediate has a structure represented by Formula (II-A):
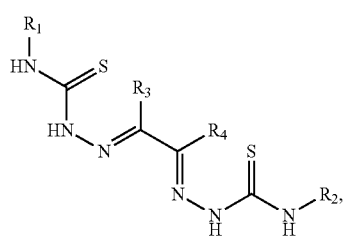
wherein variables $R_1$, $R_2$, $R_3$, and $R_4$ correspond to the variables of the same name as defined in Formula (II).

INT-27
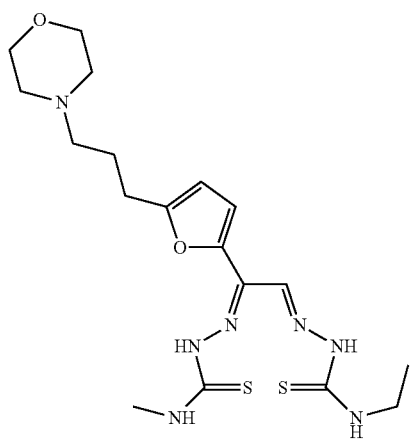
INT-28
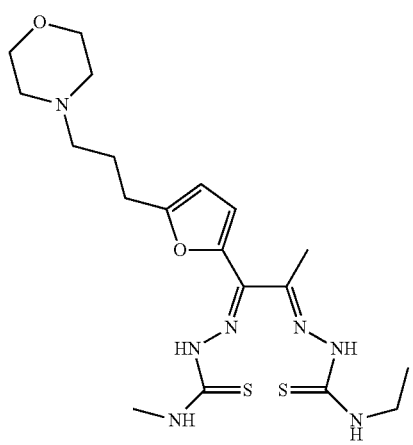
INT-29
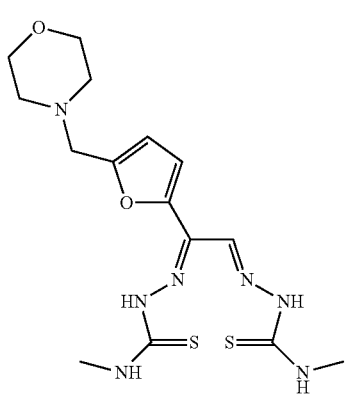
INT-30
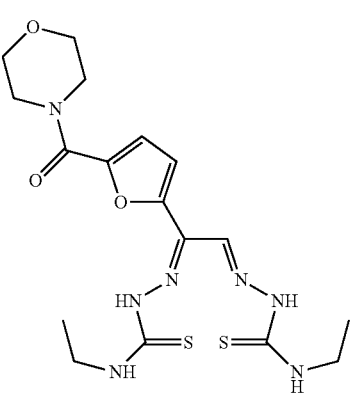
INT-31
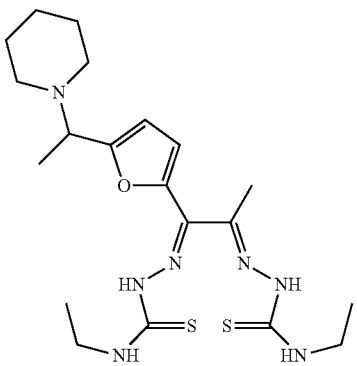
INT-32
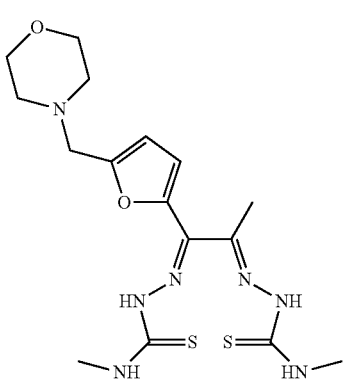
INT-33
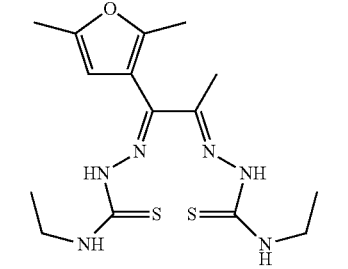
INT-34
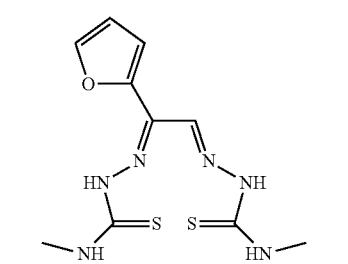
INT-35
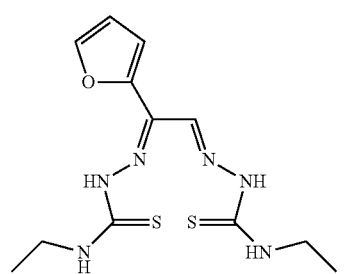

INT-36
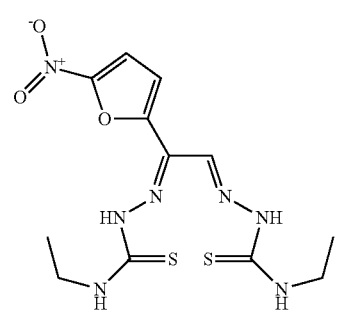
INT-37
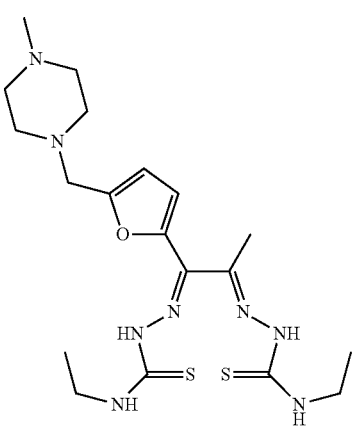
INT-38
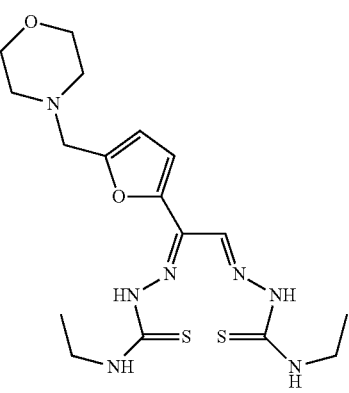
INT-39
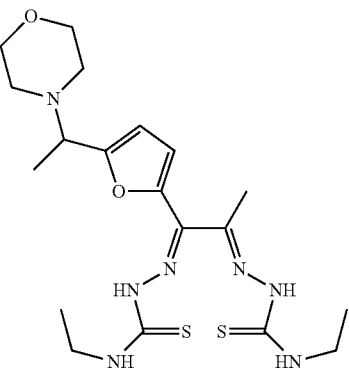
INT-40
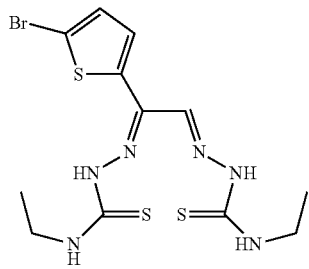
INT-41
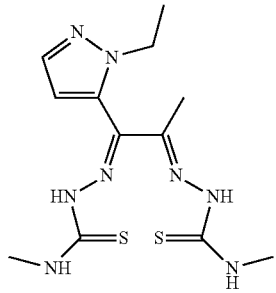
INT-42
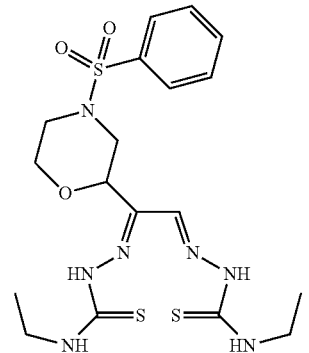
INT-43
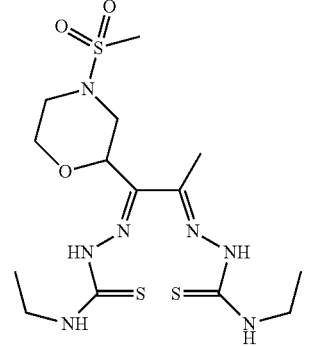
INT-44
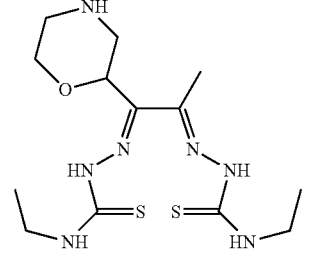

-continued

INT-45

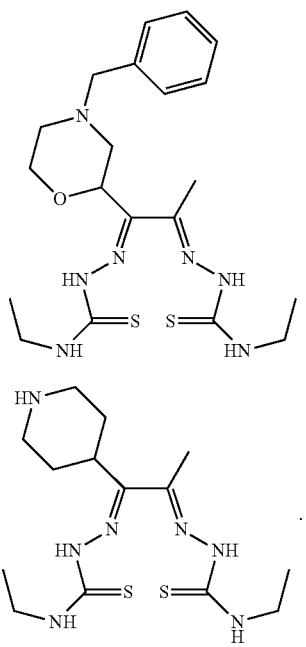

INT-46

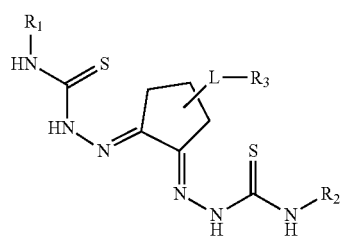

In some embodiments, the synthetic intermediate has a structure represented by Formula (III-A):

(III-A)

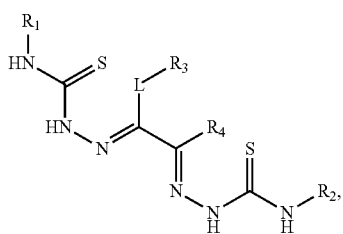

wherein variables L, $R_1$, $R_2$, and $R_3$ correspond to the variables of the same name as defined in Formula (III).

Exemplary synthetic intermediates represented by Formula (III-A) include the following:

(IV-A)

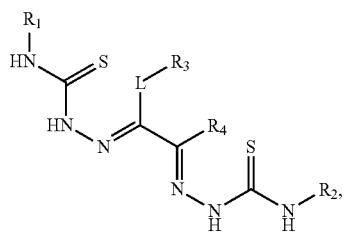

In another aspect, the present disclosure also relates to synthetic intermediates of the copper complexes described herein. In some embodiments, the synthetic intermediate has a structure represented by Formula (IV-A):

wherein variables L, $R_1$, $R_2$, $R_3$, and $R_4$ correspond to the variables of the same name as defined in Formula (IV).

Exemplary synthetic intermediates represented by Formula (IV-A) include the following:

INT-66

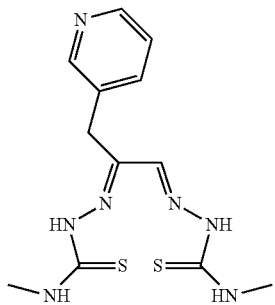

INT-67

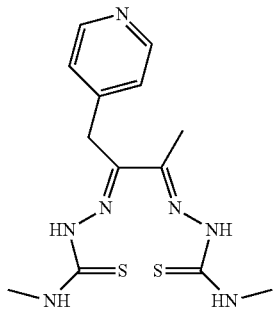

INT-68

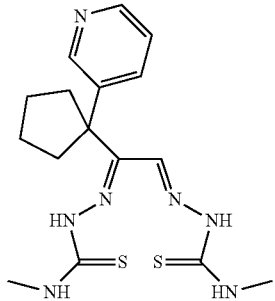

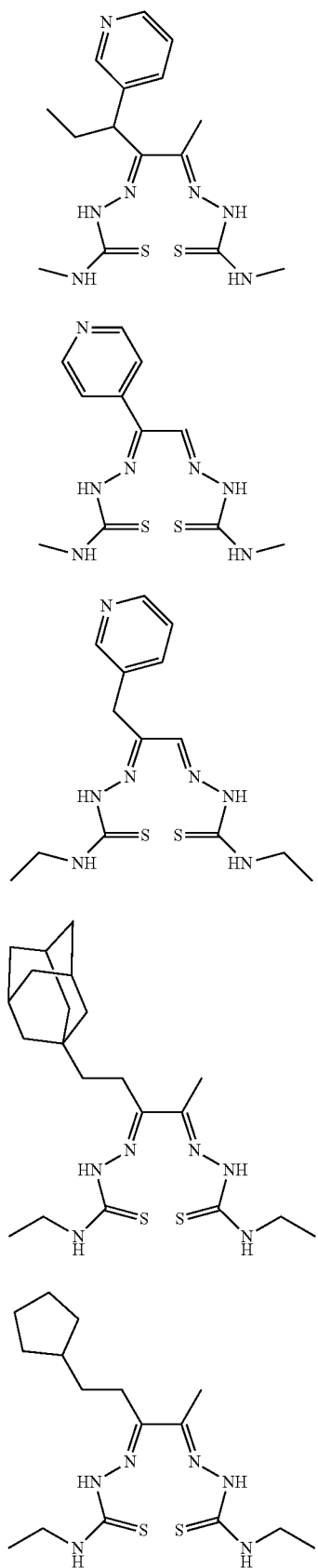
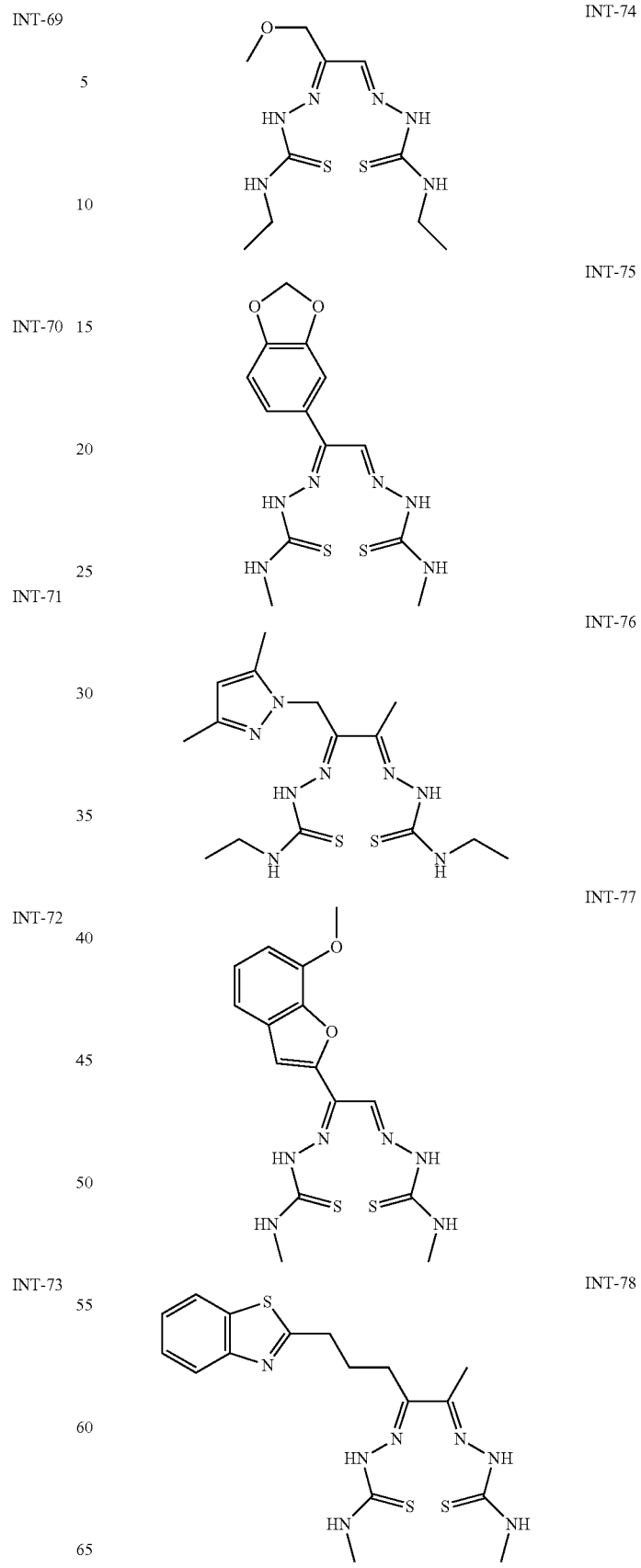

In some embodiments, the synthetic intermediate has a structure represented by Formula (V-A):
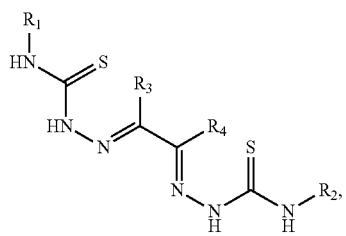
(V-A)
wherein variables $R_1$, $R_2$, $R_3$, and $R_4$ correspond to the variables of the same name as defined in Formula (V).
Exemplary synthetic intermediates represented by Formula (V-A) include the following:
INT-79
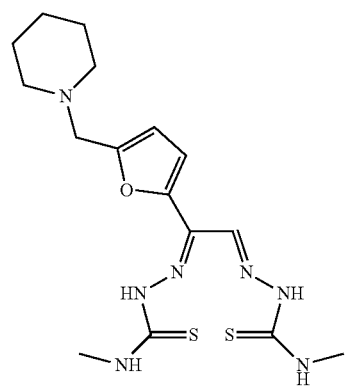
INT-80
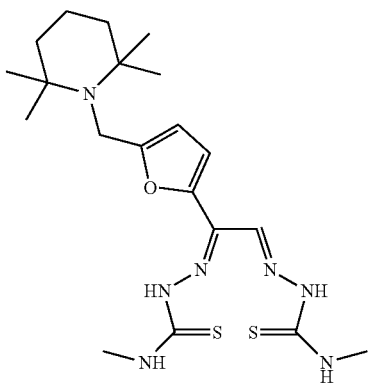
INT-81
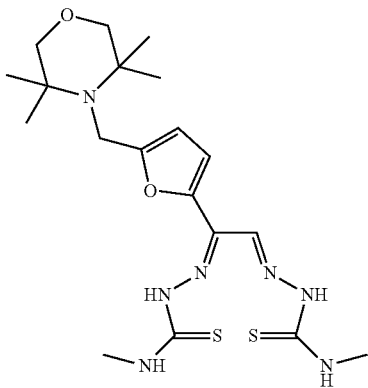
INT-82
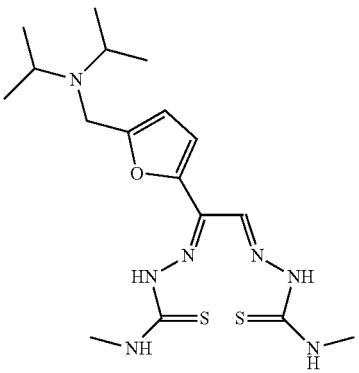
INT-83
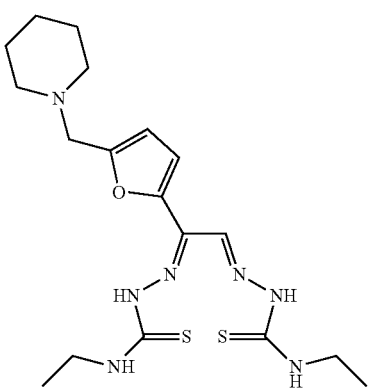
INT-84
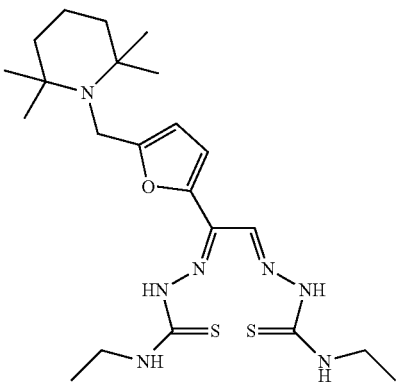
INT-85
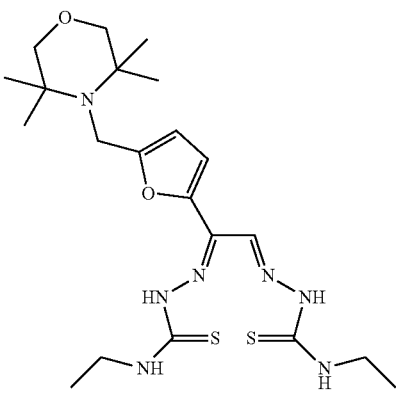

INT-86
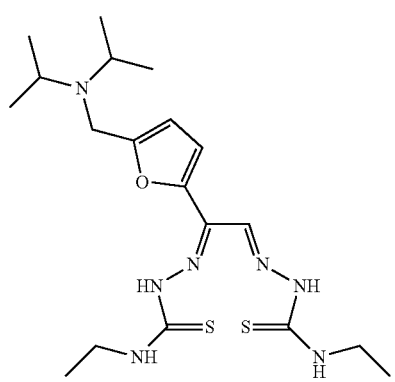
INT-87
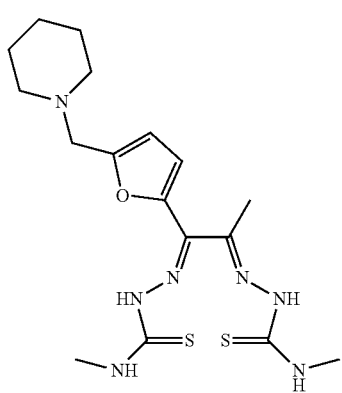
INT-88
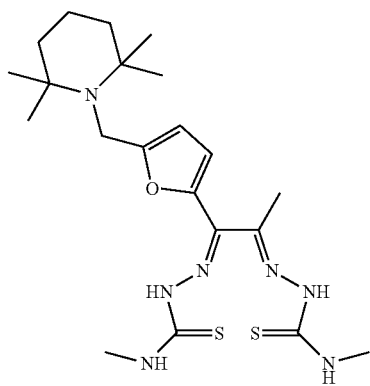
INT-89
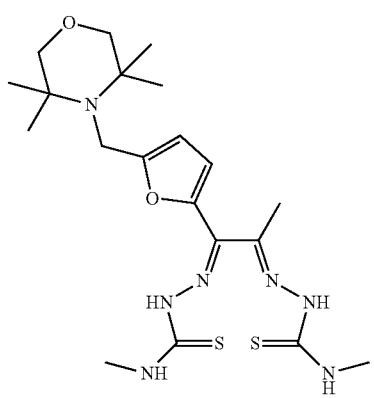
INT-90
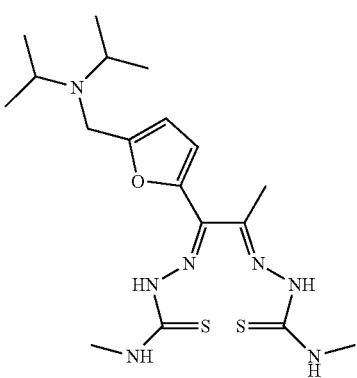
INT-91
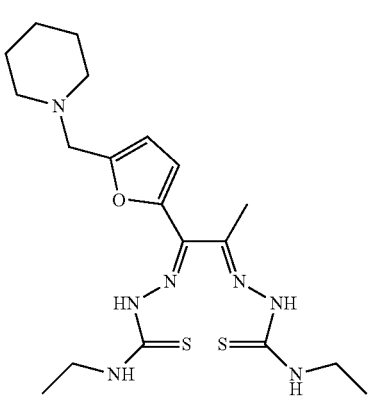
INT-92
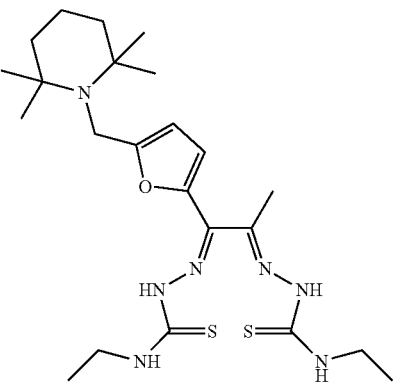
INT-93
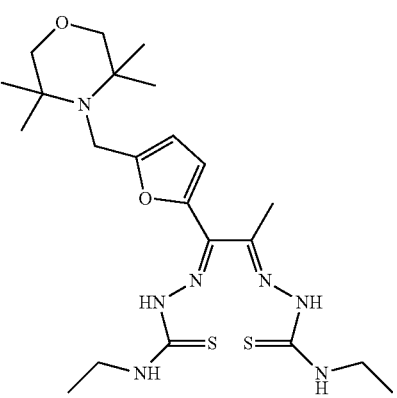

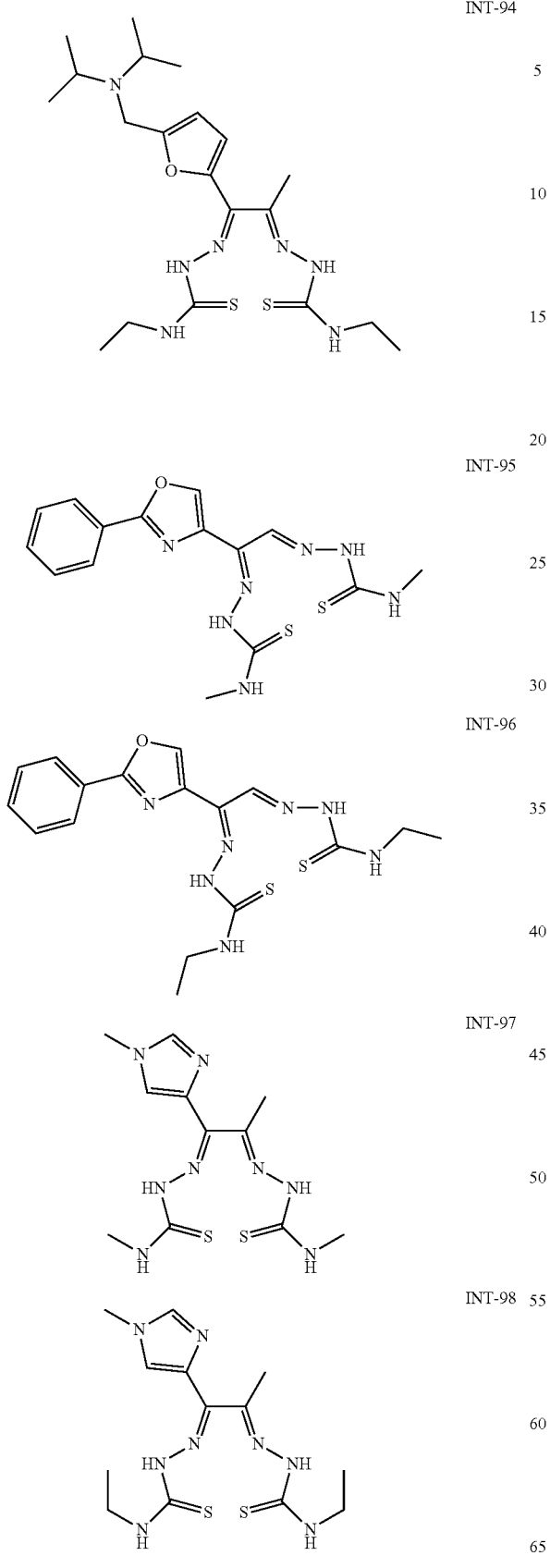
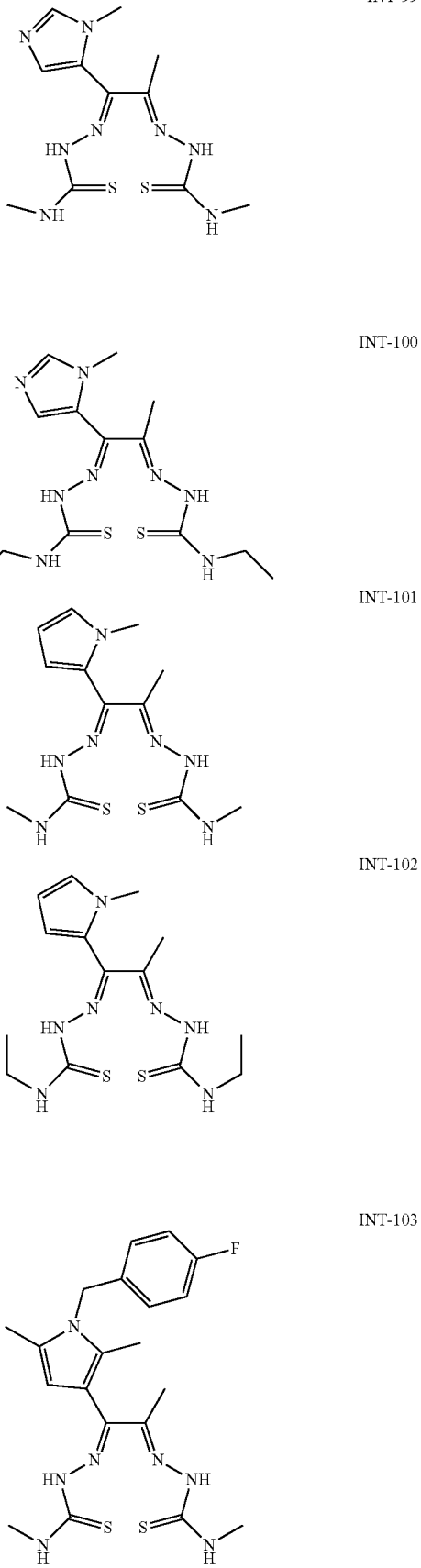

-continued
INT-104
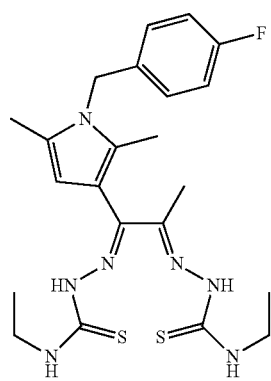
INT-105
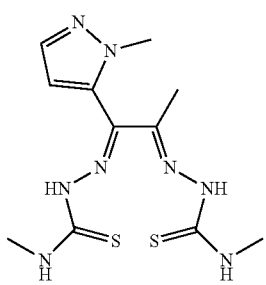
INT-106
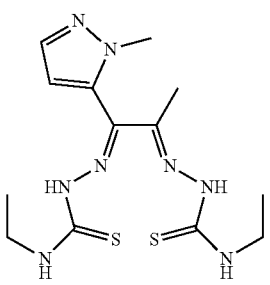
-continued
INT-108
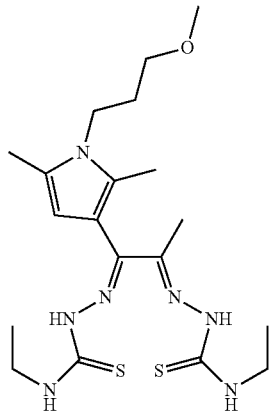
INT-109
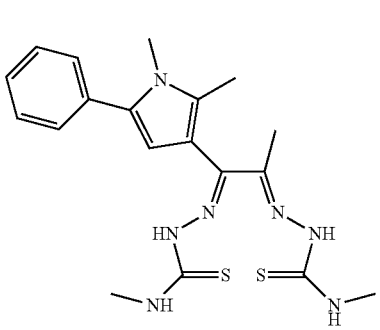
INT-110
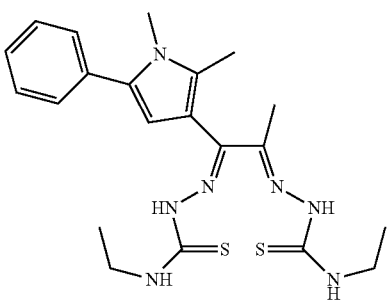
INT-111
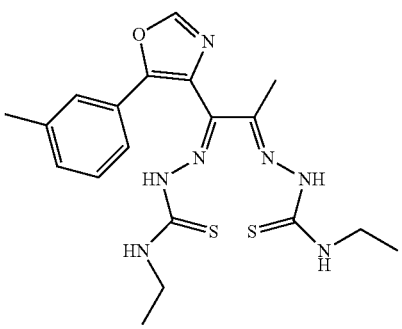
INT-107

INT-112
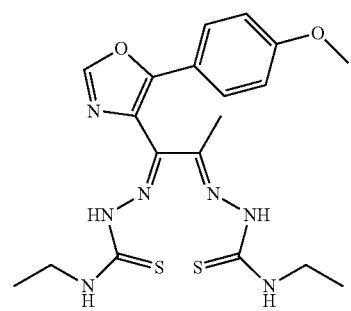
INT-113
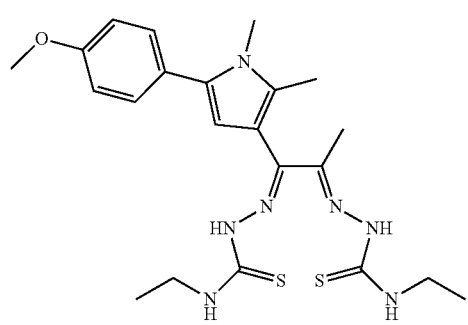
INT-114
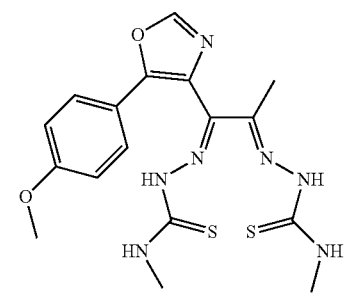
INT-115
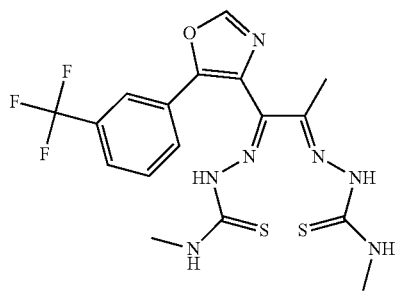
INT-116
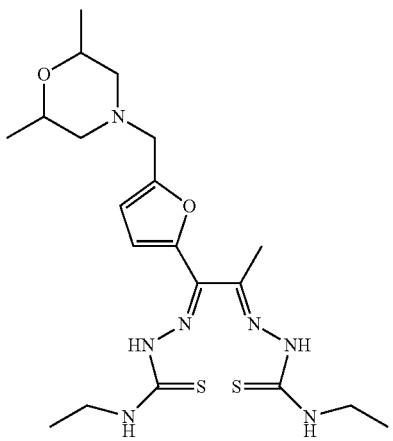
INT-117
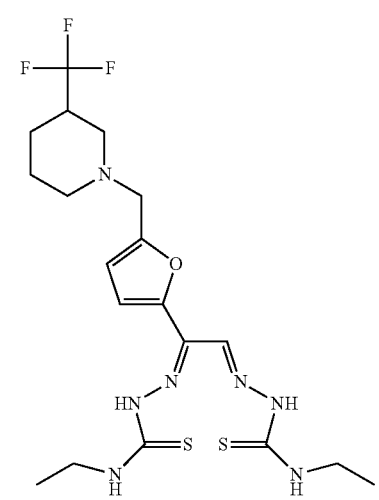
INT-118
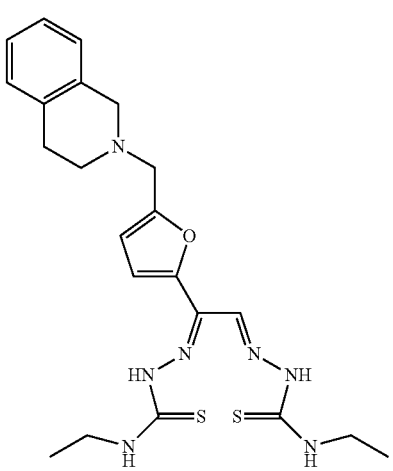

INT-119
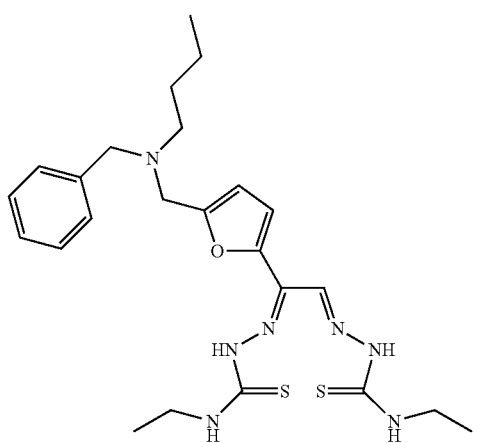
INT-120
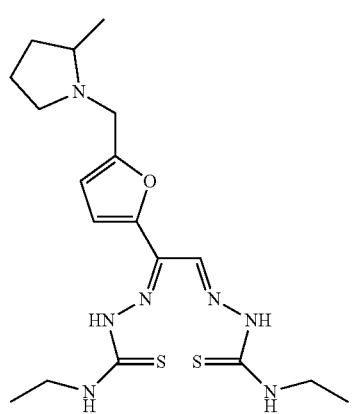
INT-121
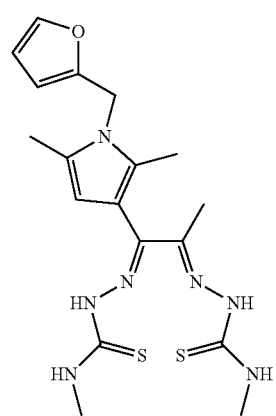
INT-122
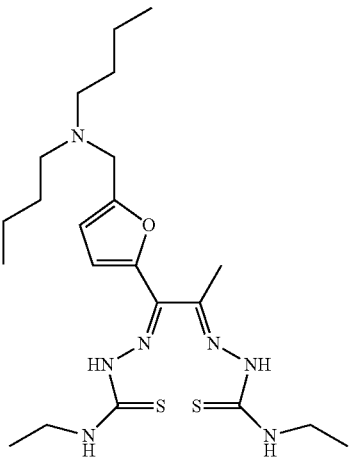
INT-123
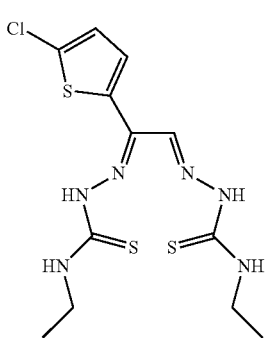
INT-124
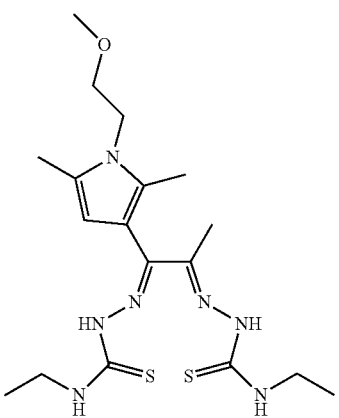
INT-125
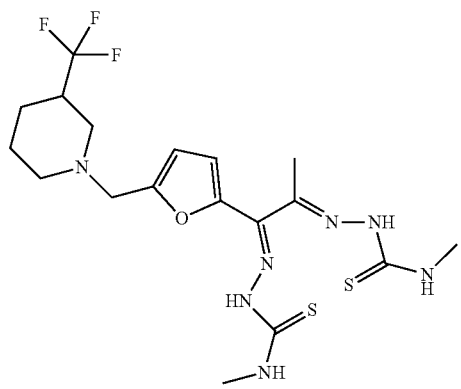

INT-126
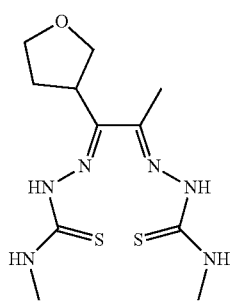
INT-127
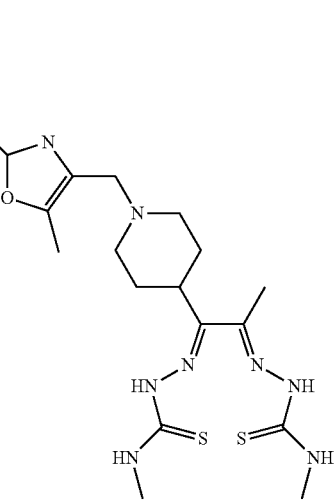
Further exemplary synthetic intermediates of the disclosure include the following compounds:
INT-54

INT-55
INT-56
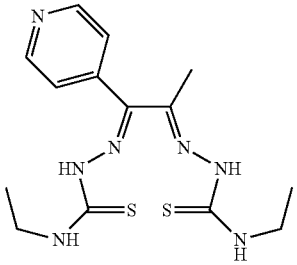
INT-57
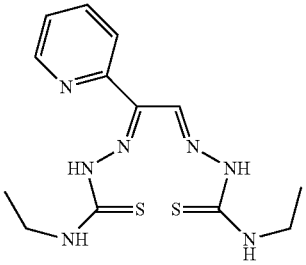
INT-58
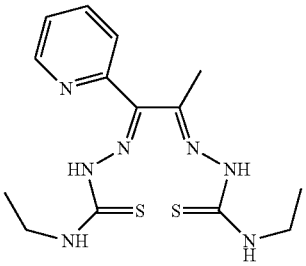
INT-59
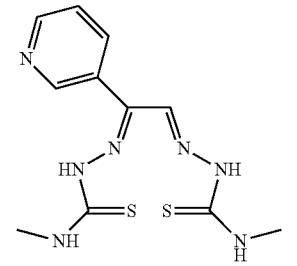
INT-60
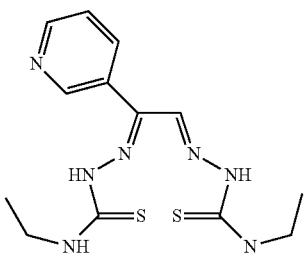
INT-61
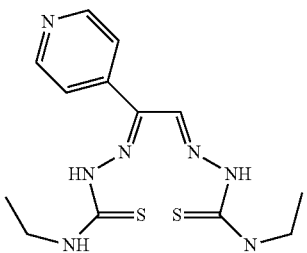

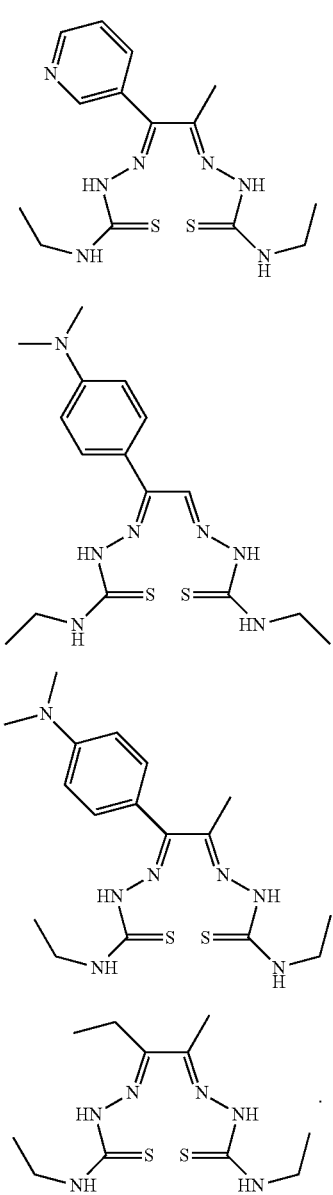

Pharmaceutical Compositions

In another aspect, provided herein are pharmaceutical compositions comprising a compound of the disclosure, or a pharmaceutically acceptable salt thereof, and at least one pharmaceutically acceptable excipient, diluent, or carrier.

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potencies of the compounds of the disclosure, and can generally be estimated based on $EC_{50}$ values found to be effective in in vitro and in vivo animal models. In general, dosage is from 0.01 µg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein a compound of the disclosure is administered in maintenance doses, ranging from 0.01 µg to 100 g/kg of body weight, once or more daily, to once every 20 years.

Different dosage regiments may be used to treat neurodegenerative diseases (e.g., ALS). In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

In an aspect, the compound of the disclosure may be administered alone or in combination with at least one pharmaceutically acceptable excipient. The expression "pharmaceutically acceptable" means acceptable for use in the pharmaceutical and veterinary arts, i.e., not being unacceptably toxic or otherwise unsuitable. Examples of pharmaceutically acceptable adjuvants, diluents, excipients and the like can be found in "Remington's: The Science and Practice of Pharmacy," 21st Ed., Lippincott Williams and Wilkins, 2005, the contents of which are incorporated herein by reference.

The compounds of the disclosure, in pure form or in appropriate pharmaceutical compositions, can be administered via any of the accepted modes of administration or agents known in the art. The compounds of the disclosure can be administered, for example, orally, nasally, parenterally (intravenous, intramuscular, or subcutaneous), topically, transdermally, intravaginally, intravesically, intracistemally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methylcellulose, and cellulose acetate phthalate; gelatin; talc; stearic acid; magnesium stearate; vegetable oils such as peanut oil, cottonseed oil; sesame oil, olive oil, corn oil, and oil of *theobroma*; propylene glycol, glycerin; sorbitol; polyethylene glycol; water; agar; alginic acid; isotonic saline, and phosphate buffer solutions; as well as other compatible substances normally used in pharmaceutical formulations. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Emulsifiers can include polysorbates, such as TWEEN, for example TWEEN-20 and TWEEN-80. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release a compound of the disclosure in a certain part of the intestinal tract in a delayed manner. Examples of embedded compositions that can be used are polymeric substances and waxes. The compound of the disclosure also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound of the disclosure, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to 99% by weight of a compound disclosed herein, and 99% to 1% by weight of a pharmaceutically acceptable excipient. In one example, the composition will be between about 5% and about 75% by weight of a compound of the disclosure, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Methods of Treatment

The methods described herein comprise administering a therapeutically effective amount of a compound disclosed herein to a subject in need thereof. A "therapeutically effective amount" is an amount of a compound of the disclosure that, when administered to a patient by itself, effectively treats a neurodegenerative disease. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of a compound of the disclosure that corresponds to a therapeutically effective amount is strongly dependent on the type of disease, stage of the disease, the age of the patient being treated, and other facts.

Accordingly, in an aspect, the disclosure provides a method of treating or preventing a neurodegenerative disease in a subject in need thereof, the method comprising administering to the subject a therapeutically effective amount of a compound of the disclosure. In particular, the method comprises administering to the subject a therapeutically effective amount of a compound of Formula (I), (II), (III), (IV), or (V). Non-limiting examples of neurodegenerative diseases that can be treated or prevented with the compounds disclosed herein include amyotrophic lateral sclerosis (ALS), frontal temporal dementia (FTD), Parkinson's disease, Huntington's disease, and Alzheimer's disease. In a preferred embodiment, the neurodegenerative disease to be treated or prevented by a compound of the disclosure is ALS. In an embodiment, the ALS is familial ALS. In an embodiment, the ALS is sporadic ALS.

While the amounts of the compounds disclosed herein should result in the effective treatment or prevention of neurodegenerative disease, the amounts are preferably not excessively toxic to the patient (i.e., the amounts are preferably within toxicity limits as established by medical guidelines). In some embodiments, either to prevent excessive toxicity or provide a more efficacious treatment, or both, of the neurodegenerative disease, a limitation on the total administered dosage is provided. Typically, the amounts considered herein are per day; however, half-day and two-day or three-day cycles are also considered herein.

In certain embodiments, the subject in need thereof is treatment naïve. In certain embodiments, the subject in need thereof has received previous treatment for ALS, wherein the previous treatment is other than administration of a compound of the disclosure, and wherein said previous treatment has been inadequate (e.g., assessed by the subject and/or a physician), ineffective, and/or has not resulted in a detectable improvement in one or more parameters or symptoms associated with ALS and/or has not caused a biological effect that is correlated with the underlying pathology giving rise to the symptoms of ALS.

In certain embodiments, the subject in need thereof is human, and the human has a genetic mutation associated with ALS. In further embodiments, the genetic mutation associated with ALS comprises a mutation in the SOD1 gene.

In certain embodiments, the compound of the disclosure is administered to the subject in combination with an additional ALS treatment therapy. Current treatment for ALS includes administration of riluzole and edaravone, which have been shown to be modestly effective. Other therapies for ALS include medications to treat specific symptoms associated with the disease, for example muscle relaxants such as baclofen or diazepam may be prescribed to treat muscle cramps, spasms, and spasticity. Gabapentin may be prescribed to help control pain. Such medicines like amitriptyline, trihexyphenidyl, scopaderm, and glycopyrrolate can be administered to treat excess saliva in the mouth due to difficulty swallowing. Medication may also be required for the treatment of constipation, fatigue, depression, difficulty sleeping, and pseudobulbar affect associated with ALS.

In certain embodiments, the compound of the disclosure is administered at a dose that achieves a plasma $C_{max}$ of about 50-650 ng/mL in the subject. The term "$C_{max}$" is defined as the maximum concentration of active compound achieved in the plasma or spinal cord following administration of the drug.

In another aspect, the disclosure provides a method of treating, preventing, or diagnosing cancer in a subject in need thereof, the method comprising administering to the subject a therapeutically effective amount of a compound of the disclosure. In particular, isotopes (e.g., $^{64}Cu$) of the compounds disclosed herein may be used in PET imaging to detect the presence of cancer cells in a subject in need thereof. Accordingly, in another aspect, the disclosure provides a method of performing positron emission tomography (PET) imaging of a subject in need thereof, the method comprising administering to the subject an effective amount of a compound of the disclosure and subsequently performing a PET scan on the subject.

In yet another aspect, the disclosure provides a method of treating or preventing an infection in a subject in need thereof, the method comprising administering to the subject a therapeutically effective amount of a compound of the disclosure.

In a further aspect, the disclosure provides a method of treating a disease or disorder associated with aberrant copper metabolism (e.g., Menkes disease or Wilson's disease) in a subject in need thereof, the method comprising administering to the subject a therapeutically effective amount of a compound of the disclosure. In some embodiments, the subject has a congenital SOD1 deficiency or mutation. In some embodiments, the subject does not have a congenital SOD1 deficiency or mutation.

Preparation Methods

An aspect of the disclosure relates to a process for the preparation of a compound of Formula (I), or a pharmaceutically acceptable salt thereof, as described herein.

In an embodiment, the process comprises at least the step of mixing a compound of Formula (I-A):

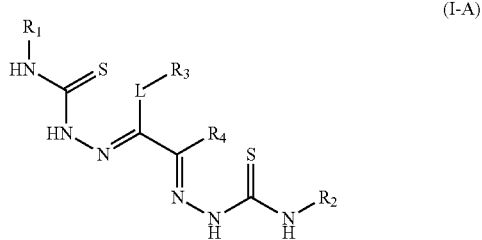

(I-A)

with a copper (II) salt to form the compound of Formula (I), or a pharmaceutically acceptable salt thereof;
wherein:
L is $C_3$-$C_7$ cycloalkyl, $C_1$-$C_6$ alkyl, or absent
$R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_2$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_3$ is $C_6$-$C_{10}$ aryl, 5- to 10-membered heteroaryl, C(O)NH—($C_1$-$C_6$ alkyl)-PPh$_3$, hydroxy, $C_1$-$C_6$ alkoxy, or O—($C_1$-$C_6$ alkyl)-O—($C_1$-$C_6$ alkyl), wherein the $C_6$-$C_{10}$ aryl is substituted one, two, or three times with the group $R_{3a}$, and wherein the 5-10-membered heteroaryl is optionally substituted one, two, or three times with the group $R_{3b}$;
$R_{3a}$ independently for each occurrence is $C_3$-$C_7$ cycloalkyl or 4- to 8-membered heterocycle, wherein the 4- to 8-membered heterocycle is optionally further substituted one, two, or three times with $C_1$-$C_3$ alkyl;
$R_{3b}$ independently for each occurrence is $C_1$-$C_3$ alkoxy, $C_3$-$C_7$ cycloalkyl, or 4- to 8-membered heterocycle, wherein the heterocycle is optionally further substituted one, two, or three times with $C_1$-$C_3$ alkyl; and
$R_4$ is hydrogen, $C_1$-$C_3$ alkyl, or $C_6$-$C_{10}$ aryl;
provided that when L is absent, $R_3$ is $C_6$-$C_{10}$ aryl substituted one, two, or three times with the group $R_{3a}$; or when L is absent, $R_3$ is 6- to 10-membered heteroaryl substituted one, two, or three times with the group $R_{3b}$.

In an embodiment, the copper (II) salt is $CuCl_2$ or $Cu(OAc)_2$, or a hydrate thereof.

Another aspect of the disclosure relates to a process for the preparation of a compound of Formula (II), or a pharmaceutically acceptable salt thereof, as described herein.

In an embodiment, the process comprises at least the step of mixing a compound of Formula (II-A):

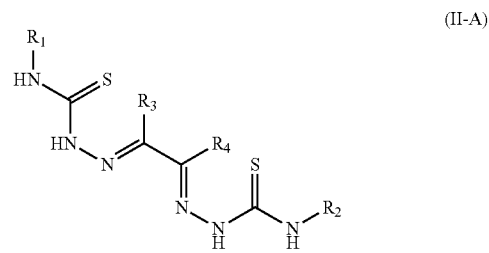

(II-A)

with a copper (II) salt to form the compound of Formula (II);
wherein:
$R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_2$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;
$R_3$ is 4- to 8-membered heterocycle or 5-membered heteroaryl, wherein the 4- to 8-membered heterocycle is optionally substituted one, two, or three times with the group $R_{3a}$, and wherein the 5-membered heteroaryl is optionally substituted one, two, or three times with the group $R_{3b}$;
$R_{3a}$ independently for each occurrence is $C_1$-$C_6$ alkyl, $C_1$-$C_6$ alkyl-($C_6$-$C_{10}$ aryl), $S(O)_2H$, $S(O)_2$—($C_1$-$C_6$ alkyl), $S(O)_2$—($C_3$-$C_7$ cycloalkyl), or $S(O)_2$—($C_6$-$C_{10}$ aryl);
$R_{3b}$ independently for each occurrence is $C_1$-$C_6$ alkyl, $C_1$-$C_6$ alkoxy, $C_1$-$C_6$ haloalkyl, halo, nitro, cyano, C(O)-(4- to 8-membered heterocycle), or $C_1$-$C_6$ alkyl-(4- to 8-membered heterocycle), wherein each 4- to 8-membered heterocycle is optionally further substituted one, two, or three times with $C_1$-$C_3$ alkyl; and
$R_4$ is hydrogen or $C_{1-3}$ alkyl.

In an embodiment, the copper (II) salt is $CuCl_2$ or $Cu(OAc)_2$, or a hydrate thereof.

In another embodiment, the process comprises at least the steps of mixing a compound of Formula (II-A) with a zinc salt to form a compound of Formula (II-B):

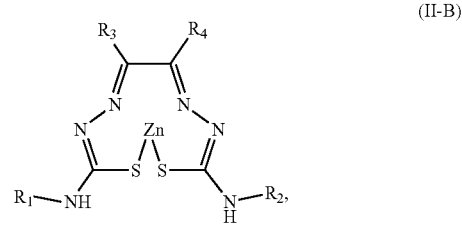

(II-B)

and mixing the compound of Formula (II-B) with a copper (II) salt to form the compound of Formula (II).

In an embodiment, the zinc salt is Zn(OAc)$_2$ or a hydrate thereof.

In an embodiment, the copper (II) salt is CuCl$_2$ or Cu(OAc)$_2$, or a hydrate thereof.

Yet another aspect of the disclosure relates to a process for the preparation of a compound of Formula (III), or a pharmaceutically acceptable salt thereof, as described herein.

In an embodiment, the process comprises at least the step of mixing a compound of Formula (III-A):

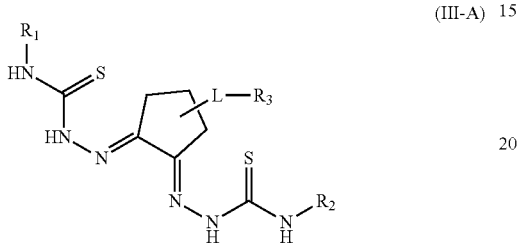

(III-A)

with a copper (II) salt to form the compound of Formula (III);
wherein:
L is C$_1$-C$_6$ alkyl or absent
R$_1$ is C$_1$-C$_6$ alkyl optionally substituted with 5- to 10-membered heteroaryl, NH$_2$, NH(C$_1$-C$_6$ alkyl), or N(C$_1$-C$_6$ alkyl)$_2$;
R$_2$ is C$_1$-C$_6$ alkyl optionally substituted with 5- to 10-membered heteroaryl, NH$_2$, NH(C$_1$-C$_6$ alkyl), or N(C$_1$-C$_6$ alkyl)$_2$;
R$_3$ is C$_1$-C$_6$ alkyl, C$_1$-C$_6$ alkoxy, C$_1$-C$_6$ haloalkyl, halo, hydroxy, C(O)NH$_2$, C(O)NH(C$_1$-C$_6$ alkyl), C(O)N(C$_1$-C$_6$ alkyl)$_2$, or C(O)-(4- to 8-membered heterocycle), wherein the C$_1$-C$_6$ alkyl and the C$_1$-C$_6$ alkoxy are optionally substituted one, two, or three times with C$_6$-C$_{10}$ aryl, and wherein the C(O)-(4- to 8-membered heterocycle) is optionally substituted one, two, or three times with C$_1$-C$_3$ alkyl.

In an embodiment, the copper (II) salt is CuCl$_2$ or Cu(OAc)$_2$, or a hydrate thereof.

In another embodiment, the process comprises at least the steps of mixing a compound of Formula (III-A) with a zinc salt to form a compound of Formula (III-B):

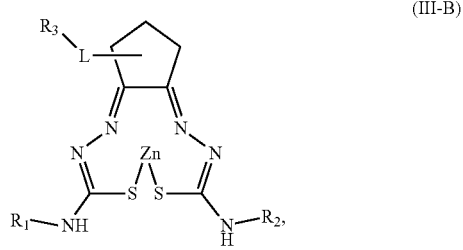

(III-B)

and mixing the compound of Formula (III-B) with a copper (II) salt to form the compound of Formula (III).

In an embodiment, the zinc salt is Zn(OAc)$_2$ or a hydrate thereof.

In an embodiment, the copper (II) salt is CuCl$_2$ or Cu(OAc)$_2$, or a hydrate thereof.

Another aspect of the disclosure relates to a process for the preparation of a compound of Formula (IV), or a pharmaceutically acceptable salt thereof, as described herein.

In an embodiment, the process comprises at least the step of mixing a compound of Formula (IV-A):

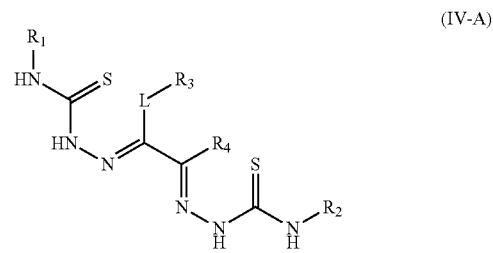

(IV-A)

with a copper (II) salt to form the compound of Formula (IV), or a pharmaceutically acceptable salt thereof;
wherein variables L, R$_1$, R$_2$, R$_3$, and R$_4$ correspond to the variables of the same name as defined in Formula (IV).

In an embodiment, the copper (II) salt is CuCl$_2$ or Cu(OAc)$_2$, or a hydrate thereof In yet another aspect of the disclosure relates to a process for the preparation of a compound of Formula (V), or a pharmaceutically acceptable salt thereof, as described herein.

In an embodiment, the process comprises at least the step of mixing a compound of Formula (V-A):

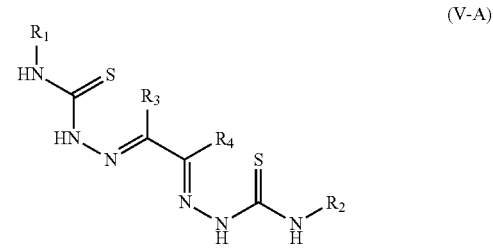

(V-A)

with a copper (II) salt to form the compound of Formula (V), or a pharmaceutically acceptable salt thereof;
wherein variables R$_1$, R$_2$, R$_3$, and R$_4$ correspond to the variables of the same name as defined in Formula (V).

In an embodiment, the copper (II) salt is CuCl$_2$ or Cu(OAc)$_2$, or a hydrate thereof.

In another embodiment, the process comprises at least the steps of mixing a compound of Formula (V-A) with a zinc salt to form a compound of Formula (V-B):

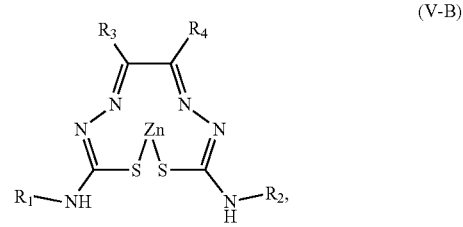

(V-B)

and mixing the compound of Formula (V-B) with a copper (II) salt to form the compound of Formula (V).

In an embodiment, the zinc salt is Zn(OAc)$_2$ or a hydrate thereof.

In an embodiment, the copper (II) salt is CuCl$_2$ or Cu(OAc)$_2$, or a hydrate thereof.

EXAMPLES

The disclosure further relates to the following experimental examples. These examples are included merely for purposes of illustration of certain aspects and embodiments of the present disclosure, and are not intended to limit the disclosure. Thus, the disclosure should in no way be construed as being limited to the following examples, but rather, should be construed to encompass any and all variation which become evident as a result of the teaching provided herein.

Example 1: Preparation of Compounds 1-22

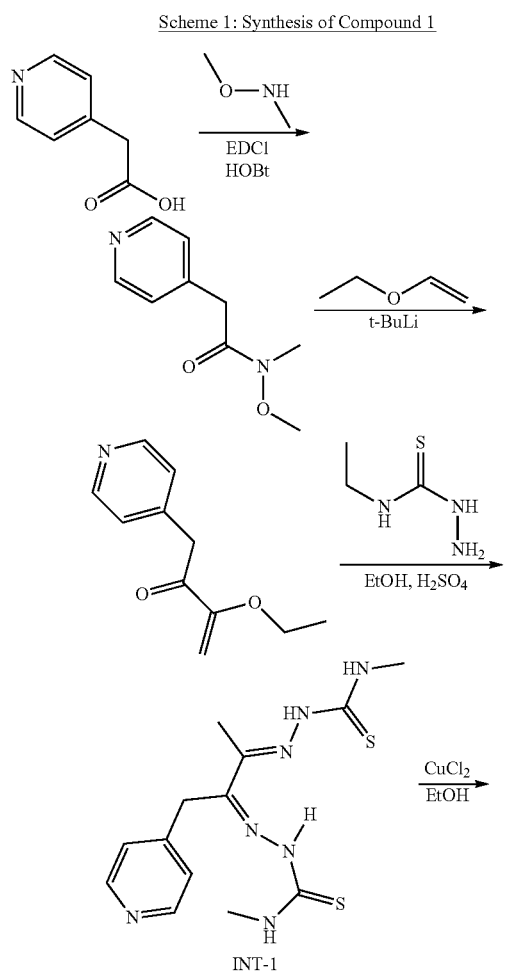

Scheme 1: Synthesis of Compound 1

Synthesis of N-methoxy-N-methyl-2-(pyridin-4-yl)acetamide

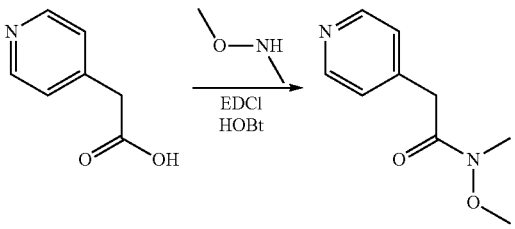

To a stirred mixture of 4-pyridineacetic acid (4.2 g, 24.2 mmol), N,O-dimethylhydroxylamine (2.8 g, 29.1 mmol), HOBt (3.9 g, 29.1 mmol) and TEA (12 ml, 84.7 mmol) in DCM (100 ml) at 4° C. EDCl (5.6 g, 29.1 mmol) was added. The reaction was stirred overnight at ambient temperature. The mixture was washed with water (100 ml), and brine (100 ml). The organic layer was dried over anhydrous Na$_2$SO$_4$, filtered, and then concentrated under reduced pressure. The residue was purified by column chromatography (silica gel, eluent 100% DCM to 5% MeOH). Yield 2.9 g (66%). LCMS (C18 column 20×2 mm, particle size 2.5 µm, pore size 100A, water-acetonitrile+0.1% TFA, gradient 5 to 87% for 3 min, retention time 1.14 min). MS (ESI) m/z 232.3 [MH]+. $^1$H-NMR (400 MHz, CDCl$_3$): δ (ppm) 3.21 (s, 3H), 3.66 (s, 3H), 3.78 (s, 2H), 7.24 (d, 2H), 8.55 (d, 2H).

Synthesis of 3-ethoxy-1-(pyridin-4-yl)but-3-en-2-one

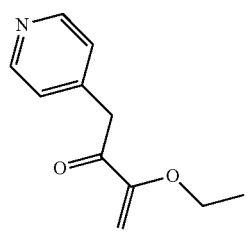

A solution of ethyl vinyl ether (3.1 g, 42.9 mmol) in tetrahydrofuran (100 ml) was cooled to −78° C., and tert-butyllithium (1.7M, 23.0 ml, 38.8 mmol) in pentane was added. The mixture was warmed to 0° C. over 1 h period, stirred for 45 min, and cooled down to −30° C. A solution of N-methoxy-N-methyl-2-(pyridin-4-yl)acetamide (0.7 g, 3.8 mmol) in tetrahydrofuran (20 mL) was added, and reaction was stirred at 0° C. for 2 h. The progress of the reaction was monitored by TLC. The mixture was poured into aq. NH$_4$Cl (100 ml) and extracted with Et$_2$O (3×50 ml). The combined extracts were dried over Na$_2$SO$_4$, solution was decanted, and solvents were removed under reduced pressure. The titular compound was used for the next step without further purification. Yield 0.2 g (27%). LCMS (C18 column 20×2 mm, particle size 2.5 μm, pore size 100A, water-acetonitrile+0.1% TFA, gradient 5 to 87% for 3 min, retention time 0.72 min). MS (ESI) m/z 192.4 [MH]+. $^1$H-NMR (400 MHz, CDCl$_3$): δ (ppm) 1.40 (t, 3H), 3.83 (q, 2H), 3.99 (s, 2H), 4.41 (d, 1H), 5.25 (d, 1H), 7.18 (dd, 1H), 8.55 (dd, 1H), 8.54 (dd, 2H).

Synthesis of INT-1 ((2Z,2'E)-2,2'-(1-(pyridin-4-yl)butane-2,3-diylidene)bis(N-methylhydrazine-1-carbothioamide))

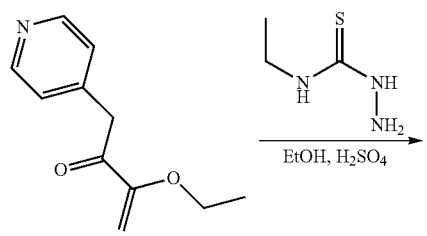

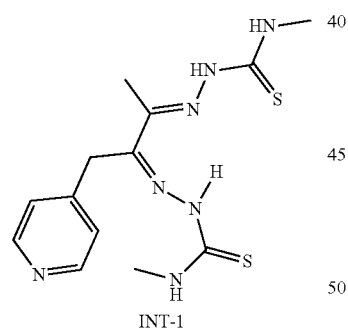

INT-1

3-Ethoxy-1-(pyridin-4-yl)but-3-en-2-one (0.2 g, 1.04 mmol) was dissolved in EtOH (5 ml), methyl thiosemicarbazide (0.22 g, 2.08 mmol) and 3 drops of H$_2$SO$_4$ were added and the reaction mixture was stirred for 4 h reflux and overnight at ambient temperature. The progress of the reaction was monitored by TLC. The precipitate was filtered, washed with EtOH, Et$_2$O, and dried. Yield 0.21 g (60%). LCMS (C18 column 20×2 mm, particle size 2.5 μm, pore size 100A, water-acetonitrile+0.1% TFA, gradient 5 to 87% for 3 min, retention time 0.98 min). MS (ESI) m/z 338.9 [MH]+. $^1$H-NMR (400 MHz, DMSO-d$_6$): δ (ppm) 2.28 (s, 3H), 2.98 (d, 3H), 3.02 (d, 3H), 4.76 (s, 2H), 7.72 (d, 2H), 8.36 (dd, 1H), 8.50 (dd, 1H), 8.78 (d, 2H), 10.35 (s, 1H), 10.85 (s, 1H).

Synthesis of INT-5 ((2Z,2'E)-2,2'-(5-(pyridin-4-yl)pentane-2,3-diylidene)bis(N-methylhydrazine-1-carbothioamide))

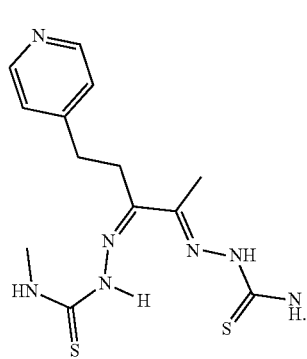

INT-5

INT-5 was made using a procedure analogous to the procedure to prepare INT-1. Yield 1.54 g (85%). LCMS (C18 column 20×2 mm, particle size 2.5 μm, pore size 100A, water-acetonitrile+0.1% TFA, gradient 5 to 87% for 3 min, retention time 0.94 min). MS (ESI) m/z 352.5 [MH]+. $^1$H-NMR (400 MHz, DMSO-d$_6$): δ (ppm) 2.15 (s, 3H), 2.66 (t, 2H), 3.01 (d, 6H), 3.28 (t, 2H), 7.32 (d, 2H), 8.21 (dd, 1H), 8.33 (dd, 1H), 8.45 (d, 2H), 10.21 (s, 1H), 10.67 (s, 1H).

Synthesis of INT-6 ((2Z,2'E)-2,2'-(5-(pyridin-3-yl)pentane-2,3-diylidene)bis(N-methylhydrazine-1-carbothioamide))

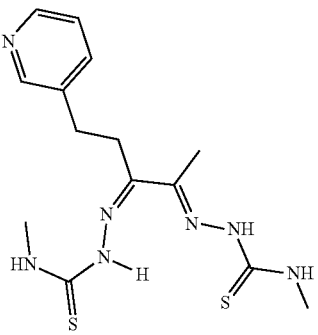

INT-6

INT-6 was made using a procedure analogous to the procedure to prepare INT-1. Yield 0.42 g (49%). LCMS (C18 column 20×2 mm, particle size 2.5 μm, pore size 100A, water-acetonitrile+0.1% TFA, gradient 5 to 87% for 3 min, retention time 0.94 min). MS (ESI) m/z 352.4 [MH]+.

Synthesis of INT-9 ((2E,2'E)-2,2'-(1-(pyridin-3-yl)butane-2,3-diylidene)bis(N-methylhydrazine-1-carbothioamide))

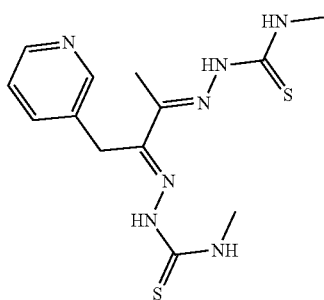

INT-9

INT-9 was made using a procedure analogous to the procedure to prepare INT-1. Yield 8.6 g (76%). LCMS (C18 column 20×2 mm, particle size 2.5 µm, pore size 100A, water-acetonitrile+0.1% TFA, gradient 5 to 87% for 3 min, retention time 0.91 min). MS (ESI) m/z 338.4 [MH]+.

Synthesis of INT-10 ((2E,2'E)-2,2'-(1-(6-methoxy-pyridin-3-yl)propane-1,2-diylidene)bis(N-ethylhydrazine-1-carbothioamide))

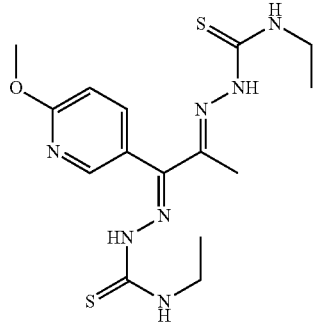

INT-10

INT-10 was made using a procedure analogous to the procedure to prepare INT-1. Yield 1.2 g (46.2%). LCMS (C18 column 20×2 mm, particle size 2.5 µm, pore size 100A, water-acetonitrile+0.1% TFA, gradient 5 to 87% for 3 min, retention time 1.52 min, MS (ESI) m/z 382.0 [MH]+. $^1$H-NMR (400 MHz, CDCl$_3$): δ (ppm) 0.94 (t, 3H), 1.15 (t, 3H), 2.35 (s, 3H), 3.34 (q, 2H), 3.60 (q, 2H), 3.91 (s, 3H), 6.44 (d, 1H), 7.62 (d, 1H), 8.05 (s, 1H), 8.68 (br.s, 1H), 9.54 (s, 1H), 10.71 (s, 1H).

Synthesis of INT-11 ((2E,2'E)-2,2'-(1-(6-methoxy-pyridin-3-yl)propane-1,2-diylidene)bis(N-methylhydrazine-1-carbothioamide))

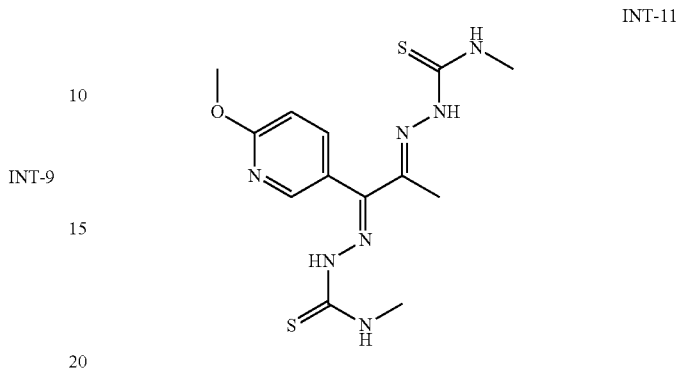

INT-11

INT-11 was made using a procedure analogous to the procedure to prepare INT-1. Yield 0.7 g (56.6%). LCMS (C18 column 20×2 mm, particle size 2.5 µm, pore size 100A, water-acetonitrile+0.1% TFA, gradient 5 to 87% for 3 min, retention time 1.41 min, MS (ESI) m/z 354.5 [MH]+. $^1$H-NMR (400 MHz, CDCl$_3$): δ (ppm) 2.36 (s, 3H), 2.87 (s, 3H), 3.03 (s, 3H), 3.92 (s, 3H), 6.95 (d, 1H), 7.15 (br.s, 1H), 7.61 (d, 1H), 8.04 (s, 1H), 8.62 (br.s, 1H), 9.54 (s, 1H), 10.56 (s, 1H).

Synthesis of Compound 1

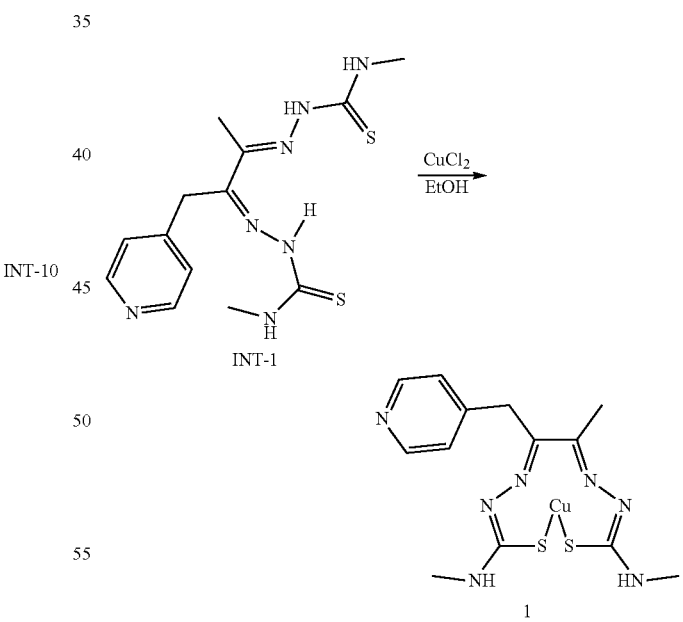

CuCl$_2$·2H$_2$O (0.08 g, 0.48 mmol) was added to INT-1 (0.15 g, 0.44 mmol) in ethanol (6 ml). The mixture was stirred overnight at ambient temperature. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.075 g (42%). LCMS (C18 column 20×2 mm, particle size 2.5

μm, pore size 100A, water-acetonitrile+0.1% TFA, gradient 5 to 87% for 4 min, retention time 1.29). MS (ESI) m/z 399.1 [MH]+.

Synthesis of Compound 5

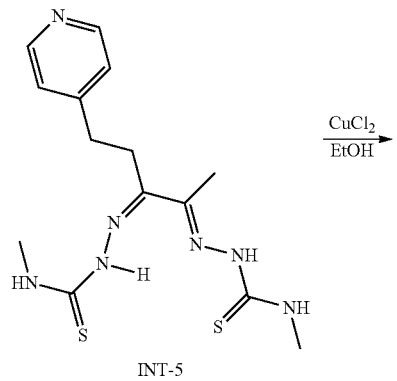

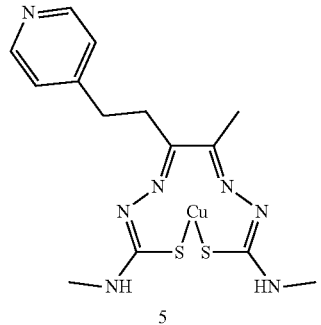

The titular compound was prepared from INT-5 according to the method to prepare compound 1. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.5 g (78%). LCMS (C18 column 20×2 mm, particle size 2.5 μm, pore size 100A, water-acetonitrile+0.1% TFA, gradient 5 to 87% for 4 min, retention time 1.26). MS (ESI) m/z 413.4 [MH]+.

Synthesis of Compound 6

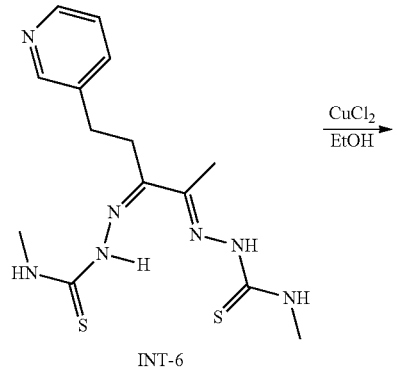

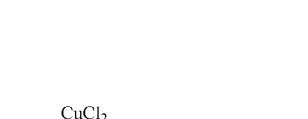

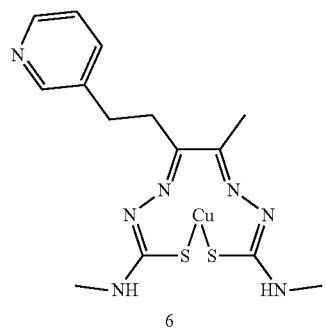

The titular compound was prepared from INT-6 according to the method to prepare compound 1. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.18 g (95%). LCMS (C18 column 20×2 mm, particle size 2.5 μm, pore size 100A, water-acetonitrile+0.1% TFA, gradient 5 to 87% for 4 min, retention time 1.25). MS (ESI) m/z 412.9 [MH]+.

Synthesis of Compound 9

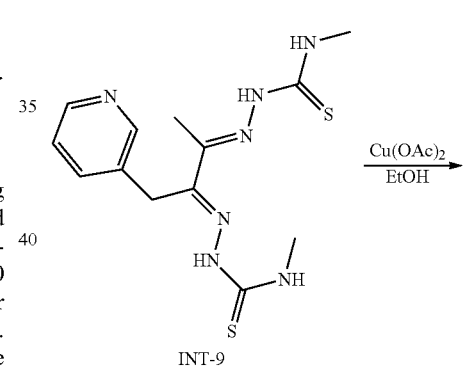

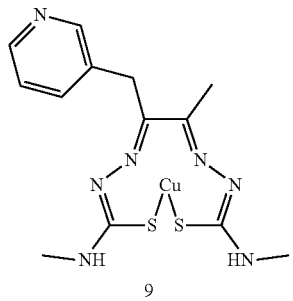

The titular compound was prepared from INT-9 according to the method to prepare compound 1. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 2.3 g (97%). LCMS (C18 column 20×2 mm, particle size 2.5 μm, pore size 100A, water-acetonitrile+0.1% TFA, gradient 5 to 87% for 4 min, retention time 1.30). MS (ESI) m/z 399.1 [MH]+.

Synthesis of Compound 10

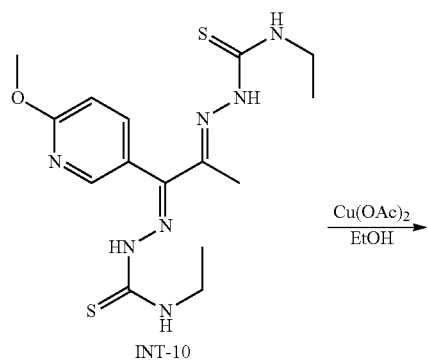

INT-10

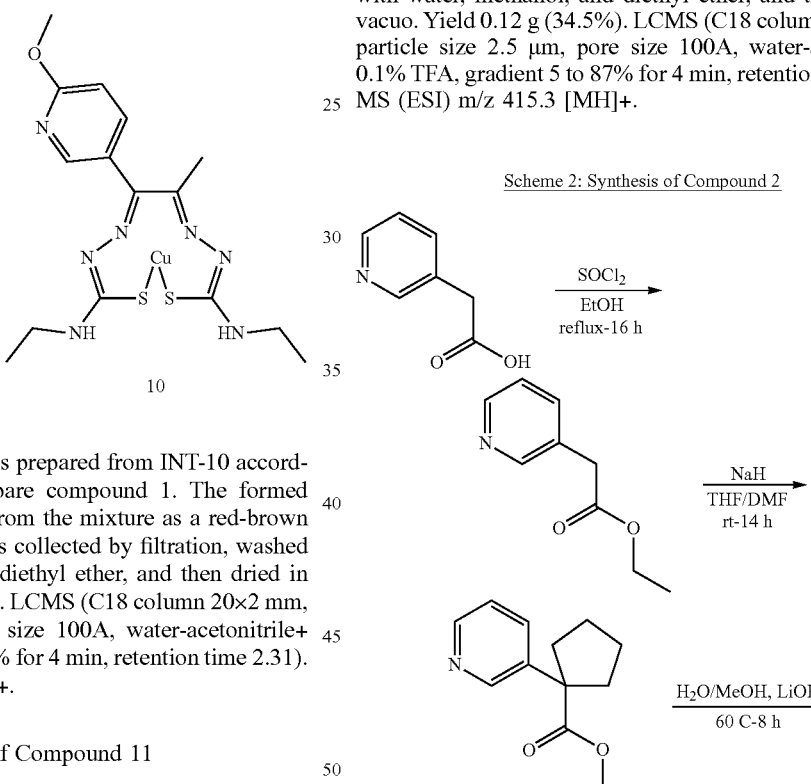

10

The titular compound was prepared from INT-10 according to the method to prepare compound 1. The formed complex was precipitated from the mixture as a red-brown powder. The precipitate was collected by filtration, washed with water, methanol, and diethyl ether, and then dried in vacuo. Yield 0.13 g (37.3%). LCMS (C18 column 20×2 mm, particle size 2.5 μm, pore size 100A, water-acetonitrile+ 0.1% TFA, gradient 5 to 87% for 4 min, retention time 2.31). MS (ESI) m/z 443.5 [MH]+.

Synthesis of Compound 11

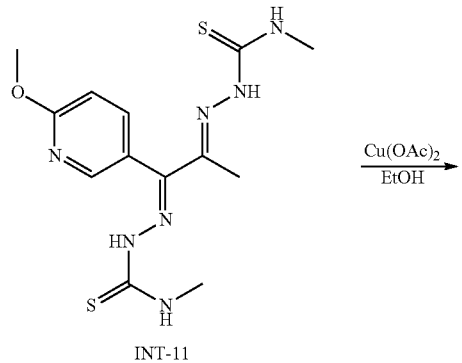

INT-11

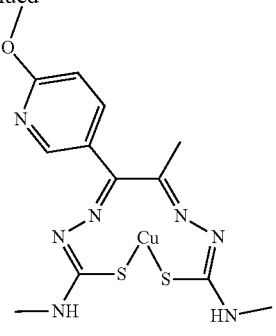

11

The titular compound was prepared from INT-11 according to the method to prepare compound 1. The formed complex was precipitated from the mixture as a red-brown powder. The precipitate was collected by filtration, washed with water, methanol, and diethyl ether, and then dried in vacuo. Yield 0.12 g (34.5%). LCMS (C18 column 20×2 mm, particle size 2.5 μm, pore size 100A, water-acetonitrile+ 0.1% TFA, gradient 5 to 87% for 4 min, retention time 1.97). MS (ESI) m/z 415.3 [MH]+.

Scheme 2: Synthesis of Compound 2

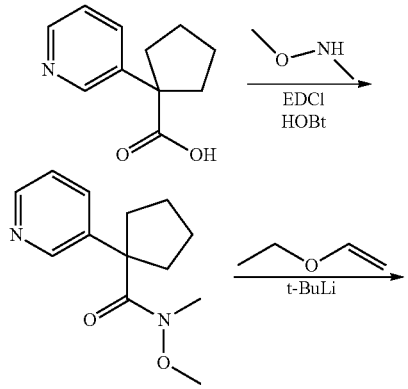

-continued

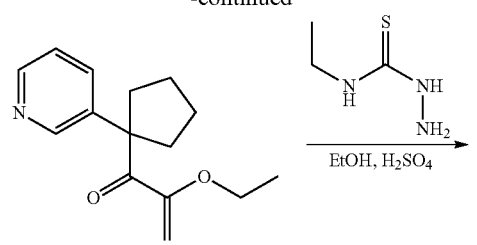

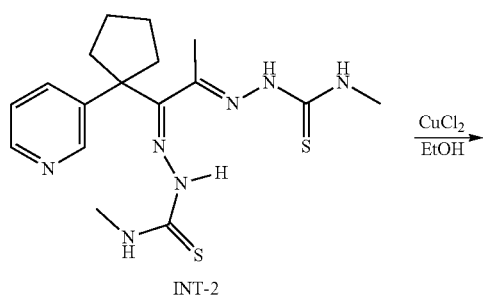

INT-2

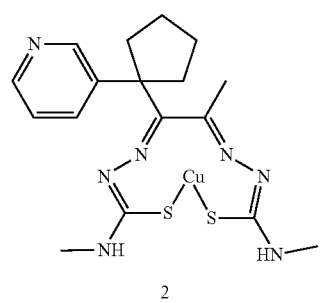

2

Synthesis of ethyl 2-(pyridin-3-yl)acetate

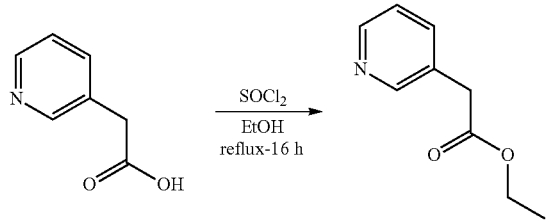

To a stirred solution of 3-pyridineacetic acid (25.0 g, 145 mmol) in EtOH (250 ml) at 0-5° C. was added SOCl$_2$ (11.6 ml, 160 mmol) over period of 15 min. Then the reaction was heated to reflux for additional 16 h. EtOH was evaporated under reduced pressure. To the residue was added aq. 2M Na$_2$CO$_3$ (30 ml), and the resulting mixture was extracted with EtOAc (3×400 ml). Combined organic layers were washed with brine (100 mL), dried over anhydrous Na$_2$SO$_4$, filtered, and concentrated giving the titular compound as a colorless liquid. Yield 22.3 g (93%). $^1$H-NMR (400 MHz, CDCl$_3$): δ (ppm): 1.26 (t, 3H), 3.62 (s, 2H), 4.17 (q, 2H), 7.27-7.28 (m, 1H), 7.64-7.65 (m, 1H), 8.53 (m, 2H).

Synthesis of ethyl 1-(pyridin-3-yl)cyclopentane-1-carboxylate

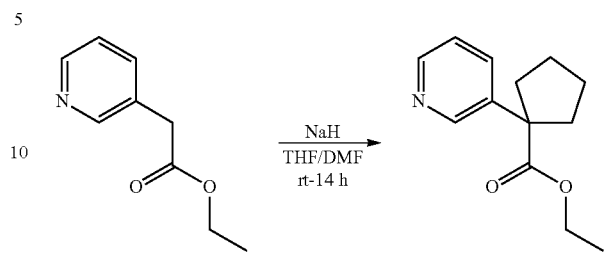

To a stirred suspension of sodium hydride (7.3 g, 181 mmol, 60% in oil) in dry THF (160 ml) at 0° C. was added dropwise a solution of ethyl 2-(pyridin-3-yl)acetate (10.0 g, 60.5 mmol) in dry THF (35 ml). The reaction mixture was stirred at 0° C. for 30 min (until ending gas formation). Then dibromo butane (19.6 g, 90.5 mmol) was added at 0° C. and the reaction mixture was stirred at ambient temperature for 14 h. Subsequently, the reaction mixture was quenched with aqueous saturated ammonium chloride (60 ml). The reaction mixture was extracted with EtOAc (3×40 ml). The organic phase was washed with brine (100 ml), dried over anhydrous Na$_2$SO$_4$, filtered, and concentrated. The obtained dark solid was purified by flash chromatography (silica gel, eluting with hexane-ethyl acetate, 4:1 to 1:1). Yield 9.8 g (74%). LCMS (C18 column 20×2 mm, particle size 2.5 μm, pore size 100A, water-acetonitrile+0.1% TFA, gradient 5 to 87% for 3 min, retention time 1.01 min). MS (ESI) m/z 220.6 [MH]+. $^1$H-NMR (400 MHz, CDCl$_3$): δ (ppm) 1.16 (t, 3H), 1.74-1.78 (m, 4H), 1.88-1.98 (m, 2H), 2.67-2.73 (m, 2H), 4.09 (q, 2H), 7.23-7.27 (m, 1H), 7.67-7.71 (m, 1H), 8.49 (dd, 1H), 8.65 (dd, 1H).

Synthesis of 1-(pyridin-3-yl)cyclopentane-1-carboxylic Acid

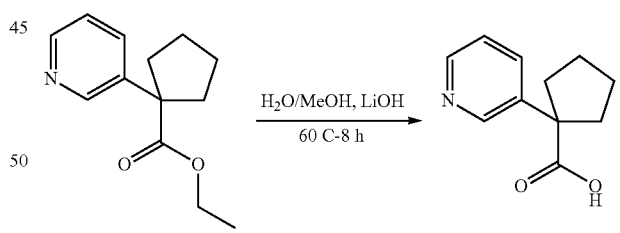

A solution of ethyl 1-(pyridin-3-yl)cyclopentane-1-carboxylate (8.4 g, 38.5 mmol) in MeOH (60 ml) was added to 20% aqueous solution of LiOH (2.5 g, 96.2 mmol). The reaction mixture was stirred for 8 h at 60° C. Then the solvent was removed by freeze-drying, and the corresponding crude product was used for the next step without further purification. Yield 7 g (80%). LCMS (C18 column 20×2 mm, particle size 2.5 μm, pore size 100A, water-acetonitrile+0.1% TFA, gradient 5 to 87% for 3 min, retention time 0.82 min). MS (ESI) m/z 192.1 [MH]+. $^1$H-NMR (400 MHz, DMSO-d$_6$): δ (ppm) 1.66-1.70 (m, 4H), 1.85-1.92 (m, 2H), 2.52-2.58 (m, 2H), 7.56 (dd, 1H), 7.98-8.02 (m, 1H), 8.58 (dd, 1H), 8.66 (d, 1H), 12.66 (br.s, 1H).

Synthesis of N-methoxy-N-methyl-1-(pyridin-3-yl)cyclopentane-1-carboxamide

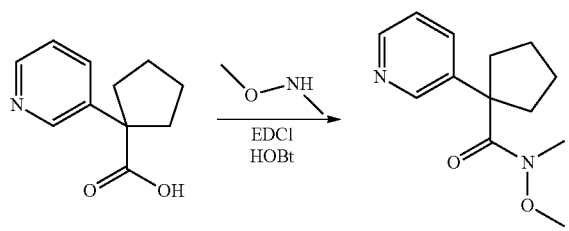

To a stirred mixture of 1-(pyridin-3-yl)cyclopentane-1-carboxylic acid (5.0 g, 22.0 mmol), N,O-dimethylhydroxylamine (2.6 g, 26.4 mmol), HOBt (3.6 g, 26.4 mmol) and TEA (10.8 ml, 77 mmol) in DCM (150 ml) at 4° C. EDCl (5.1 g, 26.4 mmol) was added. The reaction was stirred overnight at ambient temperature. The mixture was washed with water (100 ml), and brine (100 ml). The organic layer was dried over anhydrous Na$_2$SO$_4$, filtered, and concentrated under reduced pressure. The residue was purified by column chromatography (silica gel, eluent 100% DCM to 5% MeOH) to afford the titular compound. Yield 2.5 g (49%). LCMS (C18 column 20×2 mm, particle size 2.5 μm, pore size 100A, water-acetonitrile+0.1% TFA, gradient 5 to 87% for 3 min, retention time 0.84 min). MS (ESI) m/z 235.3 [MH]+. $^1$H-NMR (400 MHz, CDCl$_3$): δ (ppm) 1.66-1.81 (m, 4H), 2.05-2.11 (m, 2H), 2.42-2.48 (m, 2H), 2.89 (s, 3H), 3.13 (s, 3H), 7.34 (q, 1H), 7.65 (d, 1H), 8.49 (d, 1H), 8.59 (d, 1H).

Synthesis of 2-ethoxy-1-(1-(pyridin-3-yl)cyclopentyl)prop-2-en-1-one

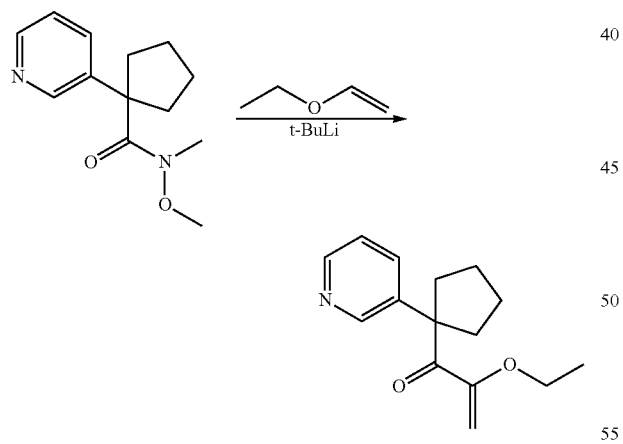

A solution of ethyl vinyl ether (1.69 g, 23.6 mmol) in tetrahydrofuran (40 ml) was cooled to −78° C., and tert-butyllithium (1.7M, 13.0 ml, 21.5 mmol) in pentane was added. The mixture was warmed to 0° C. over 1 h period, stirred for 45 min, and cooled down to −30° C. A solution of N-methoxy-N-methyl-1-(pyridin-3-yl)cyclopentane-1-carboxamide (1.0 g, 4.3 mmol) in THF (15 ml) was added, and the reaction was stirred at 0° C. for 4 h. The progress of the reaction was monitored by TLC. The mixture was poured into aq NH$_4$Cl (100 ml) and extracted with Et$_2$O (3×50 ml). The combined extracts were dried over Na$_2$SO$_4$. The solution was decanted, and solvents were removed under reduced pressure. The titular compound was used without further purification. Yield 0.85 g (81%). LCMS (C18 column 20×2 mm, particle size 2.5 μm, pore size 100A, water-acetonitrile+0.1% TFA, gradient 5 to 87% for 3 min, retention time 1.11 min). MS (ESI) m/z 246.4 [MH]+. $^1$H-NMR (400 MHz, CDCl$_3$): δ (ppm) 1.05 (t, 3H), 1.69-1.73 (m, 4H), 2.06-2.08 (m, 2H), 2.46-2.52 (m, 2H), 3.50 (q, 2H), 4.30 (d, 1H), 5.18 (d, 1H), 7.21-7.25 (m, 1H), 7.51-7.54 (m, 1H), 8.45 (dd, 1H), 8.52 (d, 1H).

Synthesis of INT-2 ((2Z,2'E)-2,2'-(1-(1-(pyridin-3-yl)cyclopentyl)propane-1,2-diylidene)bis(N-methylhydrazine-1-carbothioamide))

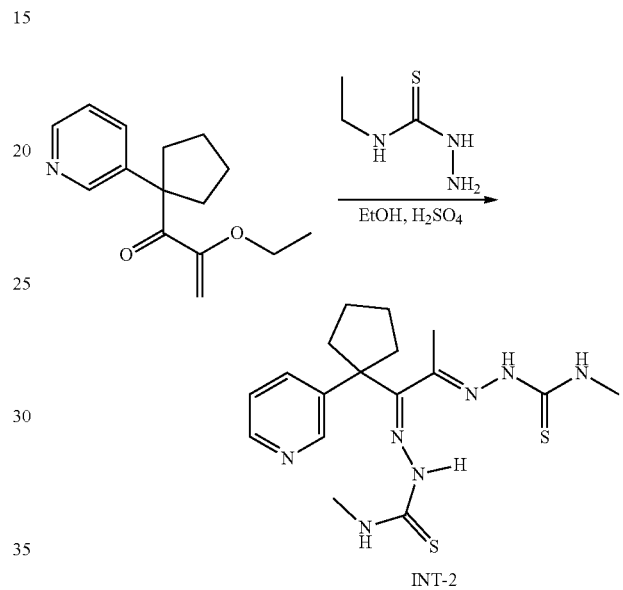

2-Ethoxy-1-(1-(pyridin-3-yl)cyclopentyl)prop-2-en-1-one (0.85 g, 3.5 mmol) was dissolved in EtOH (5 ml), methyl thiosemicarbazide (0.80 g, 7.7 mmol) and 3 drops of H$_2$SO$_4$ were added and the reaction mixture was stirred for 4 h at reflux and overnight at ambient temperature. The progress of the reaction was monitored by TLC. The precipitate was filtered, washed with EtOH, Et$_2$O, and dried. Yield 0.21 g (15%). LCMS (C18 column 20×2 mm, particle size 2.5 μm, pore size 100A, water-acetonitrile+0.1% TFA, gradient 5 to 87% for 3 min, retention time 1.00 min). MS (ESI) m/z 392.3 [MH]+.

Synthesis of INT-3 ((2Z,2'E)-2,2'-(1-(1-(pyridin-3-yl)cyclobutyl)propane-1,2-diylidene)bis(N-methylhydrazine-1-carbothioamide))

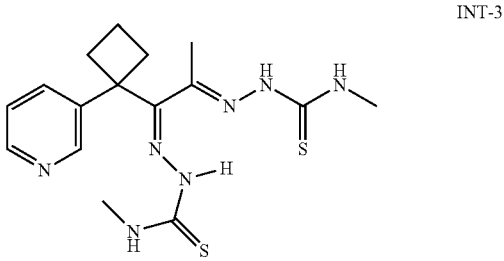 [SMILES: CNC(=S)N/N=C(\C(C)=N\NC(=S)NC)C1(c2cccnc2)CCC1]

INT-3 was made using a procedure analogous to the procedure to prepare INT-2. Yield 0.08 g (10%). LCMS (C18 column 20×2 mm, particle size 2.5 μm, pore size 100A, water-acetonitrile+0.1% TFA, gradient 5 to 87% for 3 min, retention time 1.01 min). MS (ESI) m/z 378.5 [MH]+.

Synthesis of INT-4 ((2Z,2'E)-2,2'-(4-(pyridin-3-yl)pentane-2,3-diylidene)bis(N-methylhydrazine-1-carbothioamide))

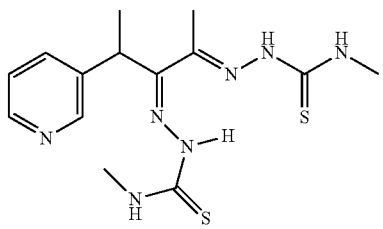

INT-4

INT-4 was made using a procedure analogous to the procedure to prepare INT-2. Yield 0.58 g (42%). LCMS (C18 column 20×2 mm, particle size 2.5 μm, pore size 100A, water-acetonitrile+0.1% TFA, gradient 5 to 87% for 3 min, retention time 0.96 min). MS (ESI) m/z 352.3 [MH]+. $^1$H-NMR (400 MHz, DMSO-$d_6$): δ (ppm) 1.52 (d, 3H), 2.24 (s, 3H), 2.90 (d, 3H), 3.00 (d, 3H), 5.23 (q, 1H), 7.32-7.34 (m, 1H), 7.39-7.42 (m, 1H), 7.62 (d, 1H), 8.40 (s, 1H), 8.46 (d, 2H), 9.84 (s, 1H), 10.30 (s, 1H).

Synthesis of Compound 2

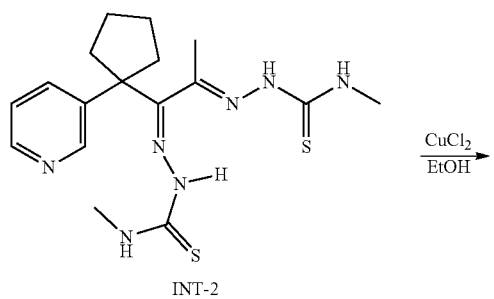

CuCl$_2$·2H$_2$O (0.08 g, 0.5 mmol) was added to INT-2 (0.18 g, 0.46 mmol) in ethanol (6 mL). The mixture was stirred overnight at ambient temperature. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.08 g (39%). LCMS (C18 column 20×2 mm, particle size 2.5 μm, pore size 100A, water-acetonitrile+0.1% TFA, gradient 5 to 87% for 4 min, retention time 2.01). MS (ESI) m/z 453.4 [MH]+.

Synthesis of Compound 3

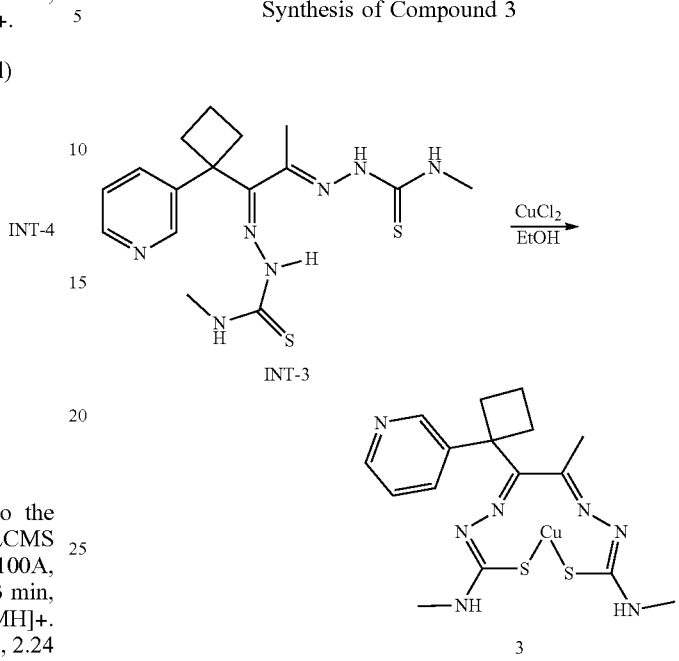

The titular compound was prepared from INT-3 according to the method to prepare compound 2. The formed complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.05 g (61%). LCMS (C18 column 20×2 mm, particle size 2.5 μm, pore size 100A, water-acetonitrile+0.1% TFA, gradient 5 to 87% for 4 min, retention time 1.49). MS (ESI) m/z 439.0 [MH]+.

Synthesis of Compound 4

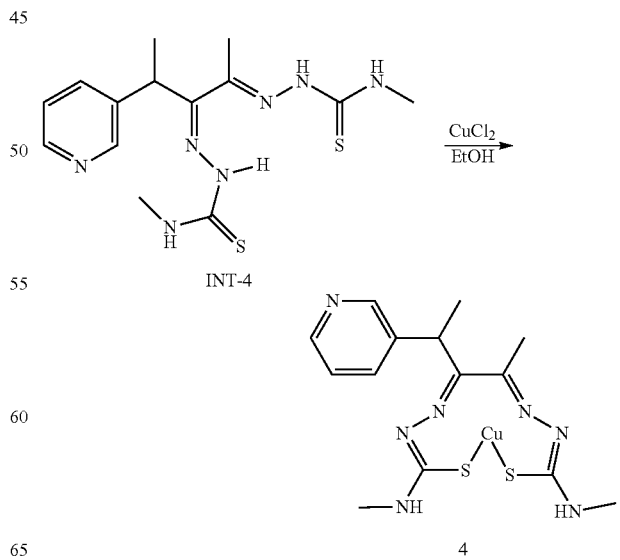

The titular compound was prepared from INT-4 according to the method to prepare compound 2. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.61 g (89%). LCMS (C18 column 20×2 mm, particle size 2.5 μm, pore size 100A, water-acetonitrile+0.1% TFA, gradient 5 to 87% for 4 min, retention time 1.30). MS (ESI) m/z 413.5 [MH]+.

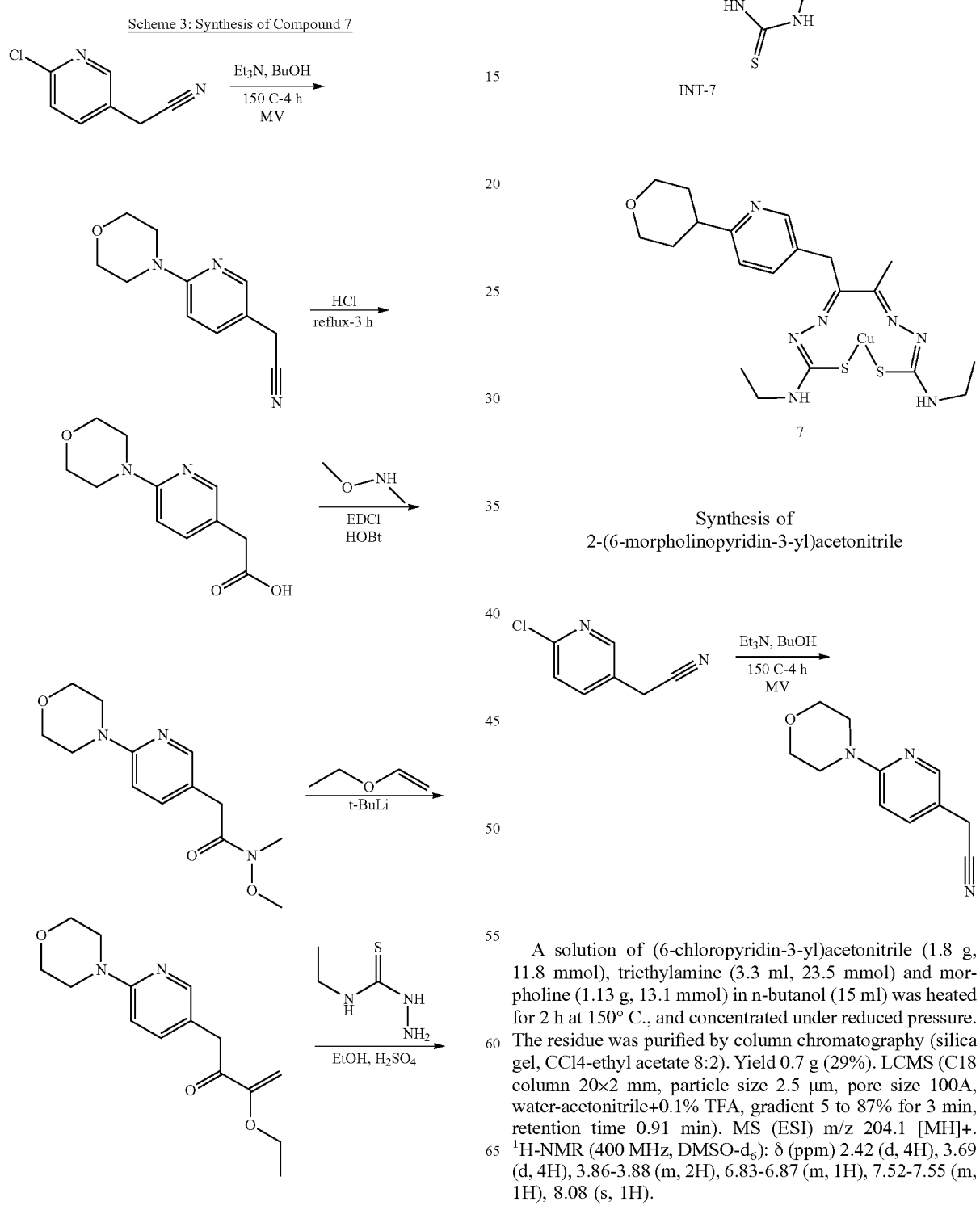

Synthesis of 2-(6-morpholinopyridin-3-yl)acetonitrile

A solution of (6-chloropyridin-3-yl)acetonitrile (1.8 g, 11.8 mmol), triethylamine (3.3 ml, 23.5 mmol) and morpholine (1.13 g, 13.1 mmol) in n-butanol (15 ml) was heated for 2 h at 150° C., and concentrated under reduced pressure. The residue was purified by column chromatography (silica gel, CCl4-ethyl acetate 8:2). Yield 0.7 g (29%). LCMS (C18 column 20×2 mm, particle size 2.5 μm, pore size 100A, water-acetonitrile+0.1% TFA, gradient 5 to 87% for 3 min, retention time 0.91 min). MS (ESI) m/z 204.1 [MH]+. $^1$H-NMR (400 MHz, DMSO-d$_6$): δ (ppm) 2.42 (d, 4H), 3.69 (d, 4H), 3.86-3.88 (m, 2H), 6.83-6.87 (m, 1H), 7.52-7.55 (m, 1H), 8.08 (s, 1H).

Synthesis of 2-(6-morpholinopyridin-3-yl)acetic Acid

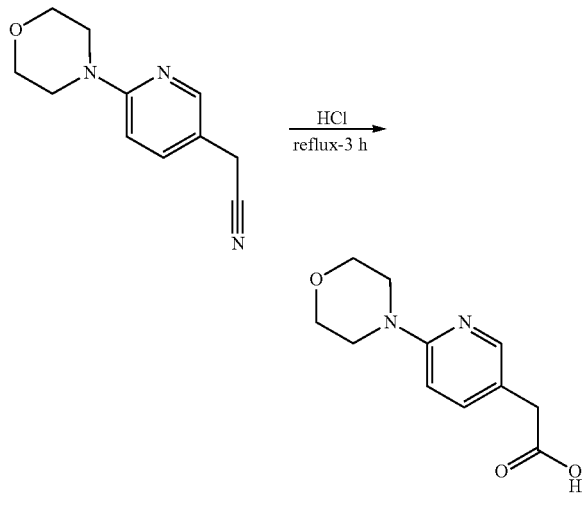

A mixture of 2-(6-morpholinopyridin-3-yl)acetonitrile (1.0 g, 5.2 mmol) in conc. hydrochloric acid (15 mL) was refluxed for 3 h. The liquids were stripped off in vacuo to yield the crude product as a white solid (1.40 g, 86.8%). LCMS (C18 column 20×2 mm, particle size 2.5 μm, pore size 100A, water-acetonitrile+0.1% TFA, gradient 5 to 87% for 3 min, retention time 0.51 min). MS (ESI) m/z 223.6 [MH]+. $^1$H-NMR (400 MHz, DMSO-$d_6$): δ (ppm) 3.66 (s, 2H), 3.73 (s, 8H), 7.36 (d, 1H), 7.94 (dd, 1H), 7.97 (d, 1H), 13.94 (br.s, 1H).

Synthesis of N-methoxy-N-methyl-2-(6-morpholinopyridin-3-yl)acetamide

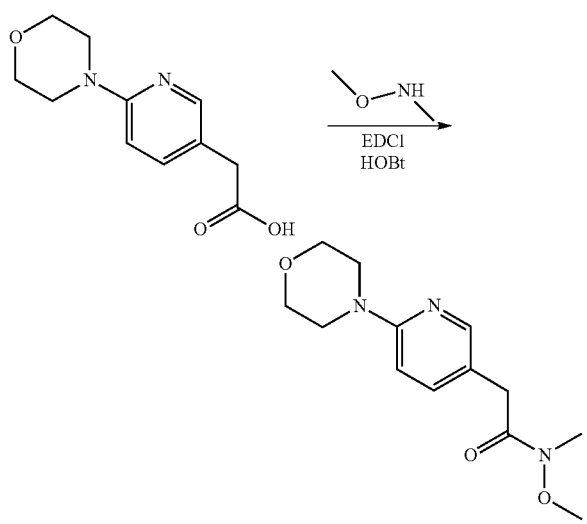

To a mixture of 2-(6-morpholinopyridin-3-yl)acetic acid (1.4 g, 4.5 mmol), N,O-dimethylhydroxylamine (0.53 g, 5.4 mmol), HOBt (0.73 g, 5.4 mmol) and TEA (2.2 ml, 15.7 mmol) in DCM (25 ml) at 4° C. EDCl (1.03 g, 5.4 mmol) was added. The reaction was stirred overnight at ambient temperature. The mixture was washed with water (100 ml), brine (100 ml). The organic layer was dried over anhydrous Na$_2$SO$_4$, filtered, and then concentrated under reduced pressure. The residue was purified by column chromatography (silica gel, eluent 100% DCM to 5% MeOH) to afford the crude titular product. Yield 1.0 g (84%). LCMS (C18 column 20×2 mm, particle size 2.5 μm, pore size 100A, water-acetonitrile+0.1% TFA, gradient 5 to 87% for 3 min, retention time 0.91 min). MS (ESI) m/z 266.5 [MH]+. $^1$H-NMR (400 MHz, CDCl$_3$): δ (ppm) 3.20 (s, 3H), 3.48 (t, 4H), 3.65 (s, 2H), 3.68 (s, 3H), 3.82 (t, 4H), 6.63 (d, 1H), 7.52 (dd, 1H), 8.09 (d, 1H).

Synthesis of 3-ethoxy-1-(6-morpholinopyridin-3-yl)but-3-en-2-one

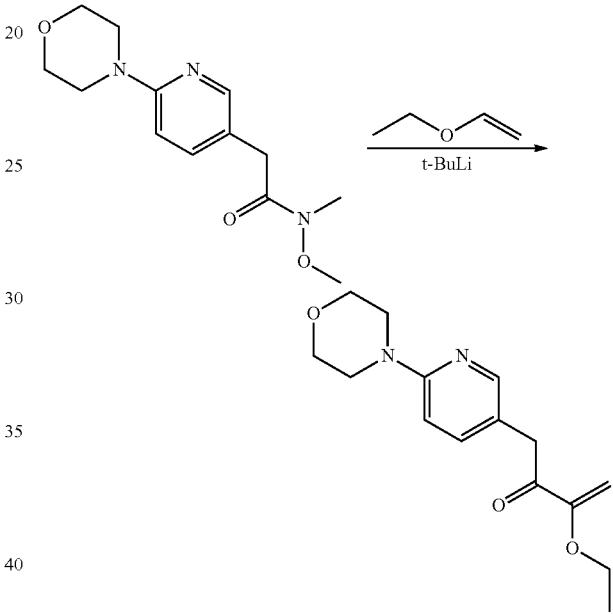

A solution of ethyl vinyl ether (3.0 g, 41.8 mmol) in tetrahydrofuran (50 ml) was cooled to −78° C., and tert-butyllithium (1.7M, 20.2 ml, 34.6 mmol) in pentane was added. The mixture was warmed to 0° C. over 1 h period, stirred for 45 min, cooled down to −30° C., and magnesium bromide etherate (8.9 g, 34.6 mmol) was added. The mixture was warmed to 0° C. over a period of 15 min and a solution of N-methoxy-N-methyl-2-(6-morpholinopyridin-3-yl)acetamide (1.0 g, 3.8 mmol) in tetrahydrofuran (20 mL) was added. The mixture was allowed to reach r.t. on its own accord and stirred overnight. The progress of the reaction was monitored by TLC. The mixture was poured into aq. NH$_4$Cl (100 ml) and extracted with Et$_2$O (3×50 ml). The combined extracts were dried over Na$_2$SO$_4$. The solution was decanted, and solvents were removed under reduced pressure. The titular compound was used for the next step without further purification. Yield 0.26 g (25%). LCMS (C18 column 20×2 mm, particle size 2.5 μm, pore size 100A, water-acetonitrile+0.1% TFA, gradient 5 to 87% for 3 min, retention time 0.96 min). MS (ESI) m/z 277.5 [MH]+. $^1$H-NMR (400 MHz, CDCl$_3$): δ (ppm) 1.43 (t, 3H), 2.01-2.04 (m, 4H), 3.46-3.51 (m, 4H), 3.82 (q, 2H), 3.84 (s, 2H), 4.41 (d, 1H), 5.22 (d, 1H), 6.39 (dd, 1H), 7.38 (dd, 1H), 8.01 (dd, 1H).

Synthesis of INT-7 ((2E,2'E)-2,2'-(1-(6-morpholino-pyridin-3-yl)butane-2,3-diylidene)bis(N-ethylhydrazine-1-carbothioamide))

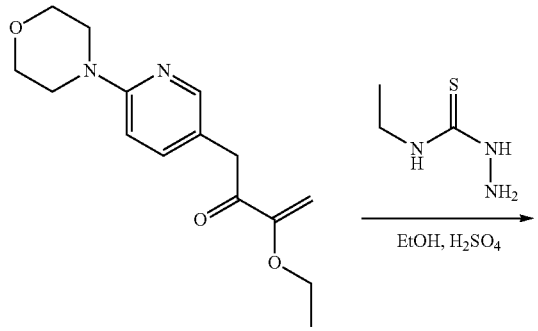

Synthesis of INT-8 ((2E,2'E)-2,2'-(1-(6-(pyrrolidin-1-yl)pyridin-3-yl)butane-2,3-diylidene)bis(N-ethyl-hydrazine-1-carbothioamide))

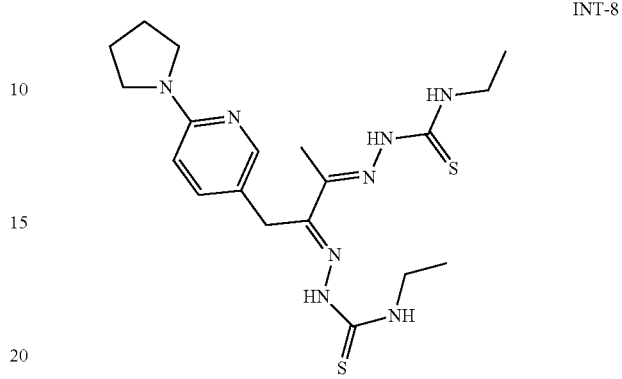

INT-8 was made using a procedure analogous to the procedure to prepare INT-7. Yield 0.25 g (99%). LCMS (C18 column 20×2 mm, particle size 2.5 μm, pore size 100A, water-acetonitrile+0.1% TFA, gradient 5 to 87% for 3 min, retention time 1.17 min). MS (ESI) m/z 435.5 [MH]+.

Synthesis of Compound 7

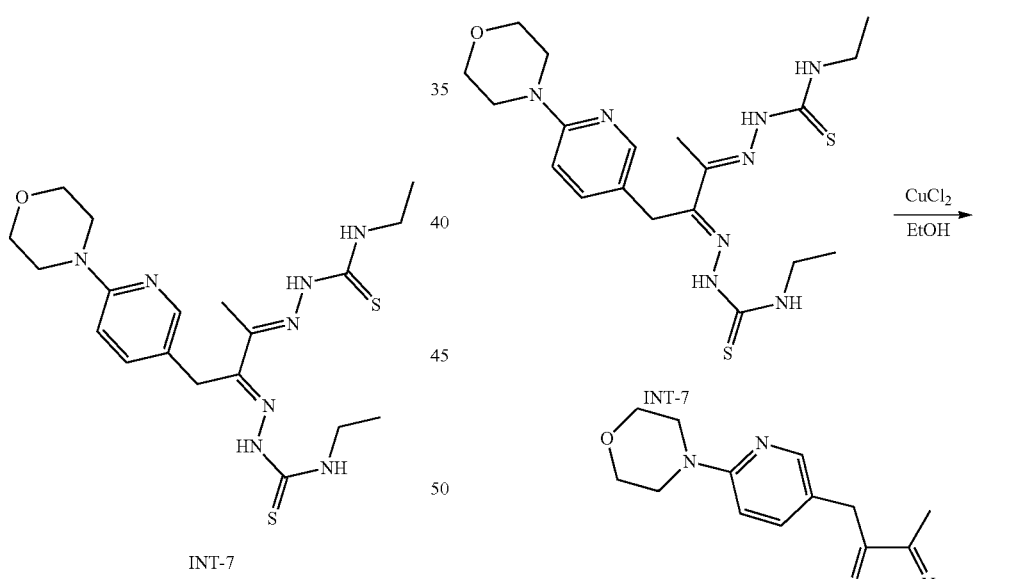

3-Ethoxy-1-(6-morpholinopyridin-3-yl)but-3-en-2-one (0.26 g, 0.94 mmol) was dissolved in EtOH (5 ml), ethyl thiosemicarbazide (0.22 g, 1.88 mmol) and 3 drops of $H_2SO_4$ were added and the reaction mixture was stirred for 4 h at reflux and overnight at ambient temperature. The progress of the reaction was monitored by TLC. The precipitate was filtered, washed with EtOH, $Et_2O$, and dried. Yield 0.41 g (97%). LCMS (C18 column 20×2 mm, particle size 2.5 μm, pore size 100A, water-acetonitrile+0.1% TFA, gradient 5 to 87% for 3 min, retention time 1.14 min). MS (ESI) m/z 451.5 [MH]+.

$CuCl_2 \cdot 2H_2O$ (0.07 g, 0.4 mmol) was added to INT-7 (0.18 g, 0.4 mmol) in ethanol (6 mL). The mixture was stirred overnight at ambient temperature. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.03 g (14%). LCMS (C18 column 20×2 mm, particle size 2.5 µm, pore size 100A, water-acetonitrile+0.1% TFA, gradient 5 to 87% for 4 min, retention time 1.55). MS (ESI) m/z 512.7 [MH]+.

Synthesis of Compound 8

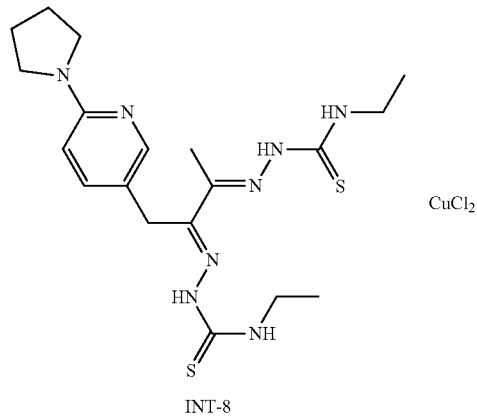

INT-8

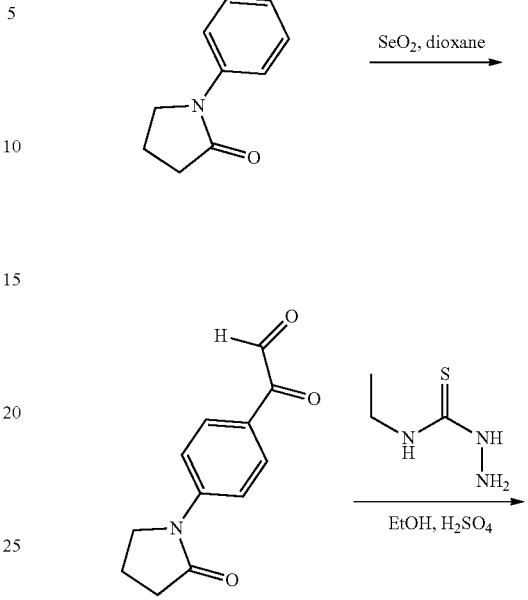

The titular compound was prepared from INT-8 according to the method to prepare compound 7. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.05 g (16%). LCMS (C18 column 20×2 mm, particle size 2.5 µm, pore size 100A, water-acetonitrile+0.1% TFA, gradient 5 to 87% for 4 min, retention time 1.57). MS (ESI) m/z 496.5 [MH]+.

Scheme 4: Synthesis of Compound 12

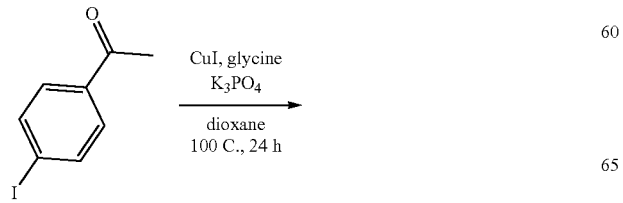

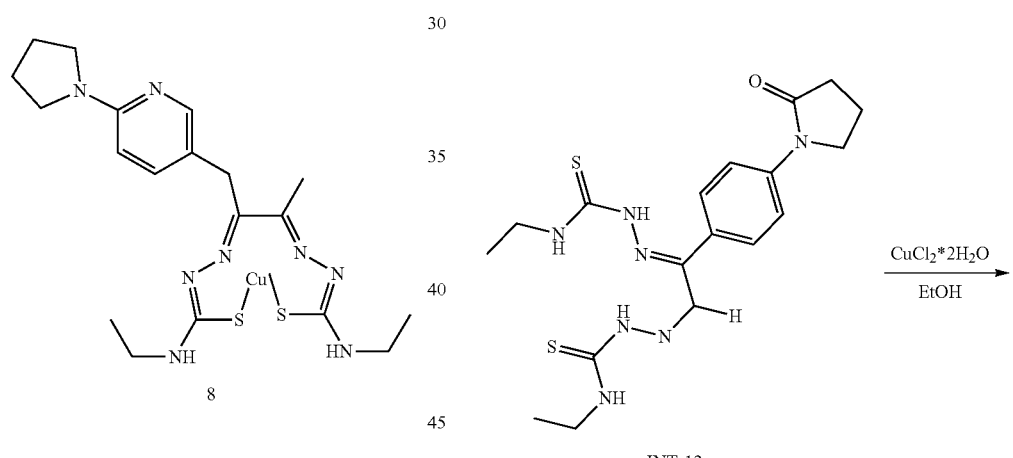

INT-12

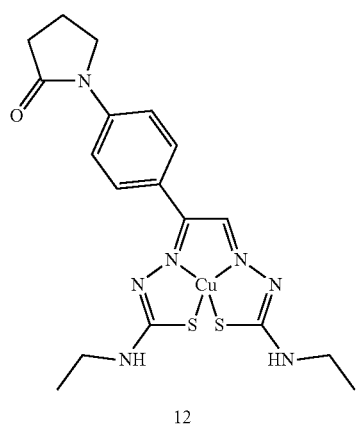

12

Synthesis of 1-(4-acetylphenyl)pyrrolidin-2-one

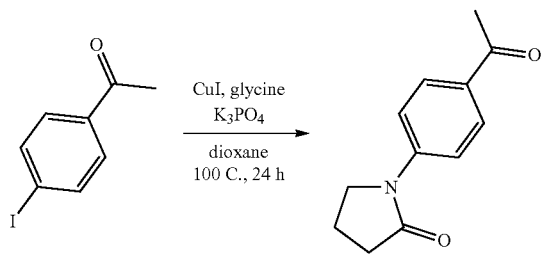

To a mixture of pyrrolidin-2-one (1.7 g, 20.0 mmol), 1-(4-iodophenyl)ethanone (4.1 g, 16.7 mmol), CuI (0.32 g, 1.67 mmol), glycine (0.25 g, 3.34 mmol) was added potassium phosphate (2.1 g, 40.0 mmol). A glass tube was evacuated, filled with argon at room temperature, and sealed. DMF (0.5 mL) was added under argon via syringe. The mixture was then stirred for 24 h at 100° C. The cooled mixture was partitioned between water and ethyl acetate. The organic layer was separated, and the aqueous layer was extracted with ethyl acetate. The combined organic extracts were washed with brine, dried over $Na_2SO_4$, filtered, and concentrated in vacuo. The residue was purified by column chromatography (silica gel, eluting with gradient 1:8 to 1:2 ethyl acetate-hexanes) to give the titular compound. Yield 3.2 g (94%). $^1$H-NMR (400 MHz, $CDCl_3$): δ (ppm) 2.22 (m, 2H), 2.60 (s, 3H), 2.66 (t, 2H), 3.92 (t, 2H), 7.77 (dd, 2H), 7.99 (dd, 2H).

Synthesis of 2-oxo-2-(4-(2-oxopyrrolidin-1-yl)phenyl)acetaldehyde

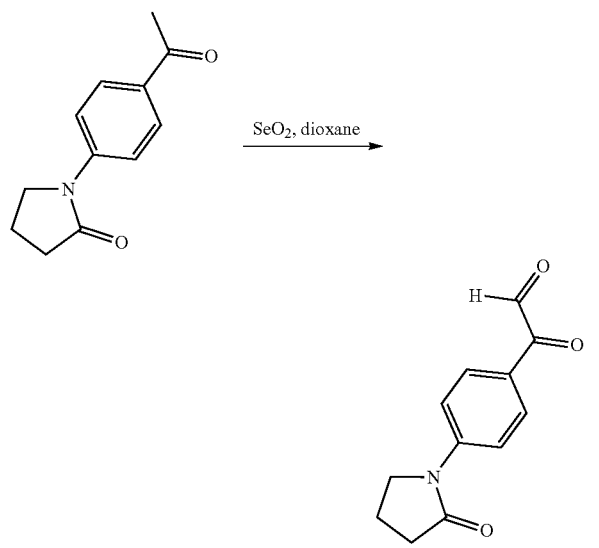

A flask was charged with $SeO_2$ (0.16 g, 1.5 mmol), 1,4-dioxane (3 ml), and water (0.5 ml). The mixture was heated to 50° C. and stirred until most of $SeO_2$ was dissolved. 1-(4-acetylphenyl)pyrrolidin-2-one (0.3 g, 1.47 mmol) was added, and the reaction was heated at gentle reflux overnight. The progress of the reaction was monitored by TLC ($CCl_4$-EtOAc 7:3). Selenium solids precipitated over the course of the reaction. The mixture was cooled over an ice bath and filtered through diatomaceous earth to remove the selenium. The filter cake was washed with portions of 1,4-dioxane. The filtrate was concentrated in vacuo until most of 1,4-dioxane was removed. The crude product was used for the next step without purification. Yield 0.25 g (83%).

Synthesis of INT-12 (2Z,2'E)-2,2'-(1-(4-(2-oxopyrrolidin-1-yl)phenyl)ethane-1,2-diylidene)bis(N-ethylhydrazine-1-carbothioamide)

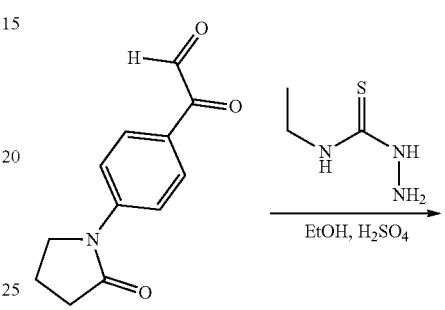

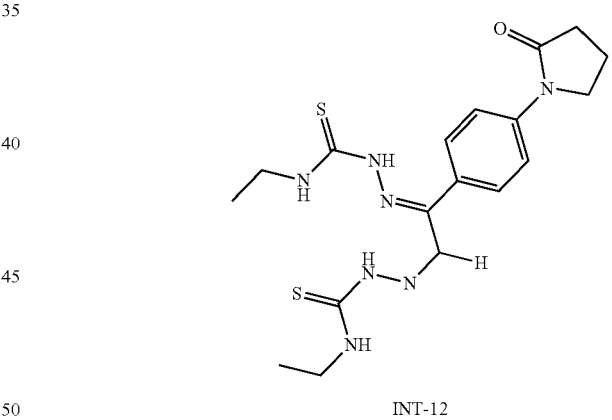

INT-12

2-Oxo-2-(4-(2-oxopyrrolidin-1-yl)phenyl)acetaldehyde (0.25 g, 1.2 mmol) was dissolved in EtOH (5 mL), ethyl thiosemicarbazide (0.35 g, 2.4 mmol) and 3 drops of $H_2SO_4$ were added and the reaction mixture was stirred for 4 h at reflux and for 15 h at ambient temperature. The progress of the reaction was monitored by TLC ($CCl_4$-EtOAc 7:3). The formed precipitate was filtered, washed with EtOH, water, $Et_2O$, and dried. Yield 0.45 g (73%). LCMS (C18 column 20×2 mm, particle size 2.5 μm, pore size 100A, water-acetonitrile+0.1% TFA, gradient 5 to 87% for 3 min, retention time 1.49 min). MS (ESI) m/z 420.5 [MH]+. $^1$H-NMR (400 MHz, DMSO-$d_6$): δ (ppm) 1.15 (t, 3H), 1.19 (t, 3H), 2.94-2.11 (m, 2H), 2.28 (s, 1H0, 3.36-3.47 (m, 1H), 3.57-3.65 (m, 4H), 3.82 (t, 2H), 7.69-7.82 (m, 4H), 7.94 (d, 1H), 8.23 (s, 1H), 8.91 (t, 1H), 11.77 (s, 1H), 12.31 (s, 1H).

Synthesis of INT-14 ((2Z,2'E)-2,2'-(1-(4-(pyrrolidin-1-yl)phenyl)ethane-1,2-diylidene)bis(N-ethylhydrazine-1-carbothioamide))

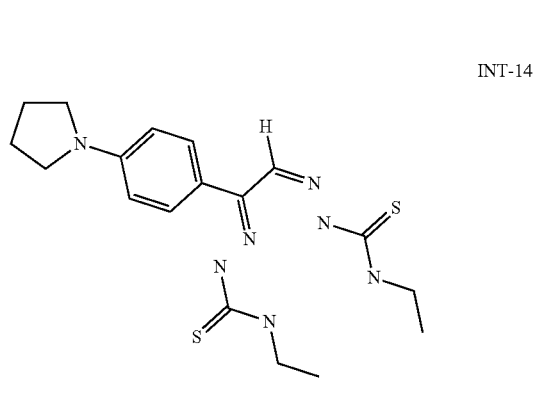

INT-14

INT-14 was made using a procedure analogous to the procedure to prepare INT-12. Yield 0.3 g (15.5%). LCMS (C18 column 20×2 mm, particle size 2.5 μm, pore size 100A, water-acetonitrile+0.1% TFA, gradient 5 to 87% for 3 min, retention time 1.92 min, MS (ESI) m/z 406.3 [MH]+. $^1$H-NMR (400 MHz, DMSO-$d_6$): δ (ppm) 1.12-1.24 (m, 6H), 1.91-2.06 (m, 4H), 3.19-3.29 (m, 4H), 3.53-3.66 (m, 4H), 6.58 (d, 2H), 7.65 (d, 2H), 7.93 (br.s, 1H), 8.22 (s, 1H), 8.74 (br.s, 1H), 11.73 (s, 1H), 12.16 (s, 1H).

Synthesis of INT-15 ((2Z,2'E)-2,2'-(1-(4-morpholinophenyl)ethane-1,2-diylidene)bis(N-ethylhydrazine-1-carbothioamide))

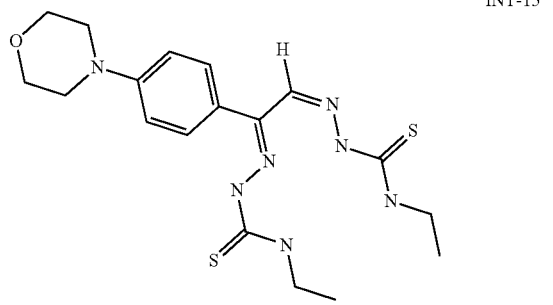

INT-15

INT-15 was made using a procedure analogous to the procedure to prepare INT-12. Yield 1.1 g (53.5%). LCMS (C18 column 20×2 mm, particle size 2.5 μm, pore size 100A, water-acetonitrile+0.1% TFA, gradient 5 to 87% for 3 min, retention time 1.66 min, MS (ESI) m/z 422.4 [MH]+. $^1$H-NMR (400 MHz, DMSO-$d_6$): δ (ppm) 1.16 (t, 3H), 1.20 (t, 3H), 3.16-3.24 (m, 4H), 3.54-3.66 (m, 4H), 3.71-3.79 (m, 4H), 7.00 (d, 2H), 7.23 (br.s, 1H), 7.70 (d, 2H), 7.95 (br.s, 1H), 8.83 (br.s, 1H), 11.74 (s, 1H), 12.23 (s, 1H).

Synthesis of Compound 12

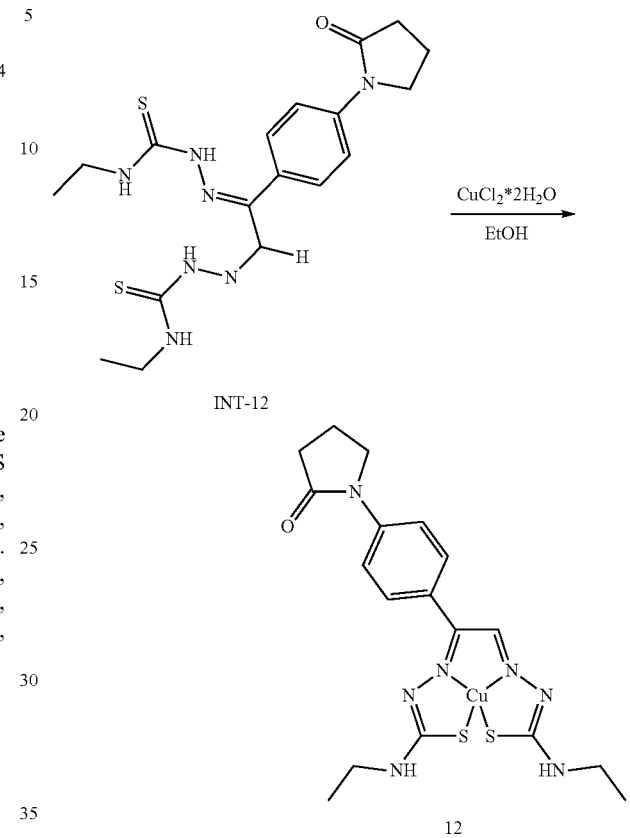

CuCl$_2$·2H$_2$O (0.16 g, 0.9 mmol) was added to INT-12 (0.4 g, 0.9 mmol) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.016 g (4%). LCMS (C18 column 20×2 mm, particle size 2.5 μm, pore size 100A, water-acetonitrile+0.1% TFA, gradient 5 to 87% for 4 min, retention time 1.84). MS (ESI) m/z 481.3 [MH]+.

Synthesis of Compound 14

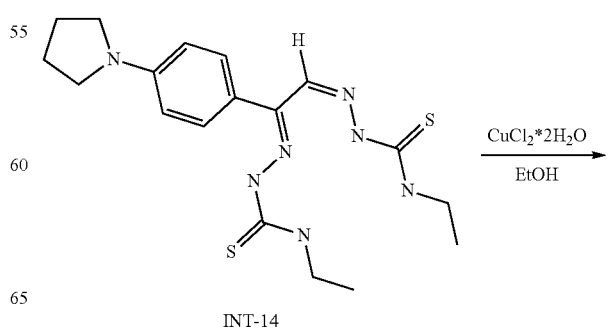

INT-14

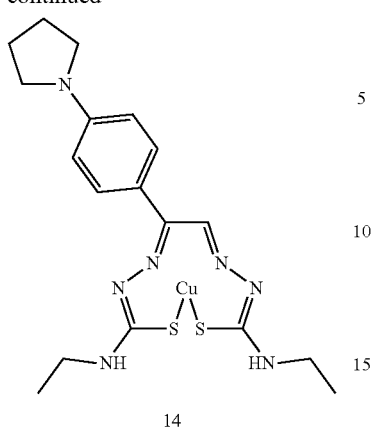

14

The titular compound was prepared from INT-14 according to the method to prepare compound 12. The formed complex precipitated as a red-brown powder. The precipitate was collected by filtration, washed with water, methanol, and diethyl ether, and then dried in vacuo. Yield 0.057 g (49.6%). LCMS (C18 column 20×2 mm, particle size 2.5 μm, pore size 100A, water-acetonitrile+0.1% TFA, gradient 5 to 87% for 4 min, retention time 2.34). MS (ESI) m/z 467.0 [MH]+.

Synthesis of Compound 15

The titular compound was prepared from INT-15 according to the method to prepare compound 12. The formed complex precipitated as a red-brown powder. The precipitate was collected by filtration, washed with water, methanol, and diethyl ether, and then dried in vacuo to afford the titular product. Yield 0.17 g (85%). LCMS (C18 column 20×2 mm, particle size 2.5 μm, pore size 100A, water-acetonitrile+0.1% TFA, gradient 5 to 87% for 4 min, retention time 1.97). MS (ESI) m/z 483.5 [MH]+.

Scheme 5: Synthesis of Compound 13

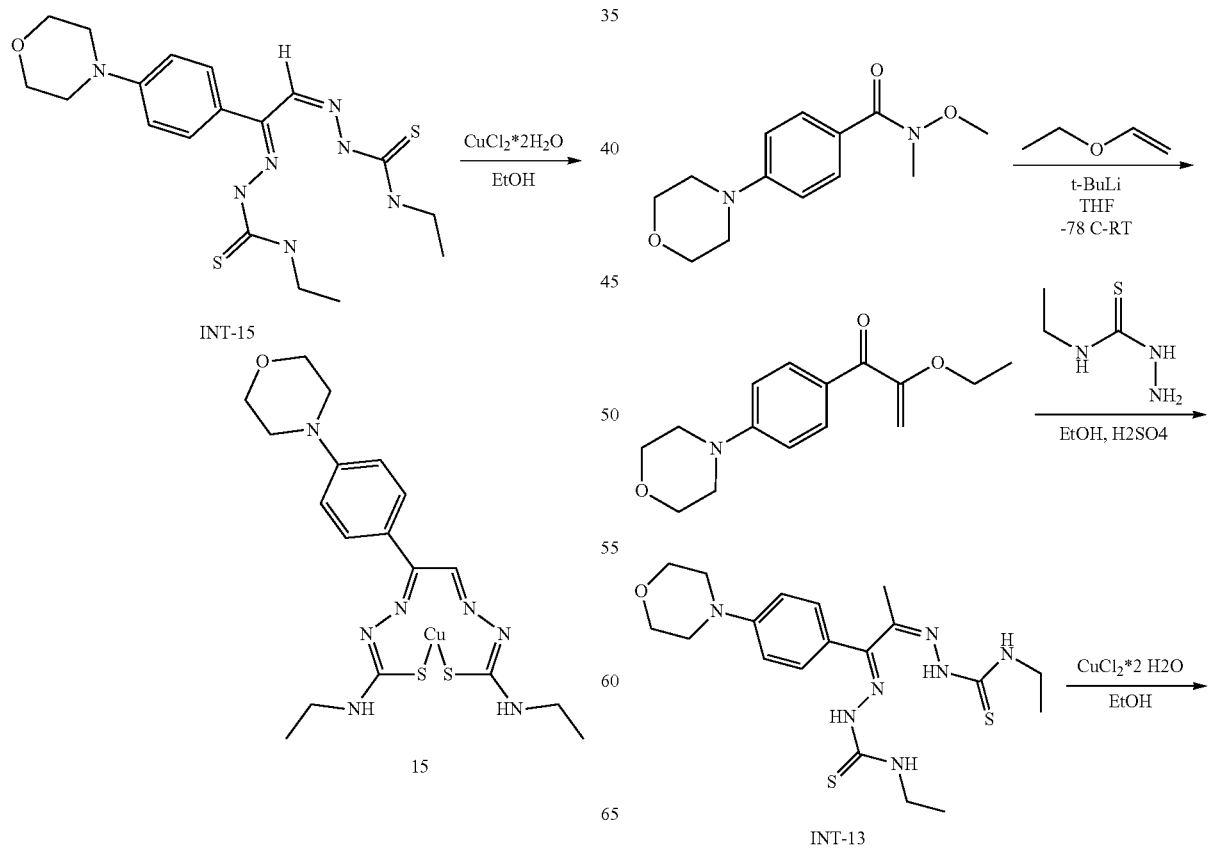

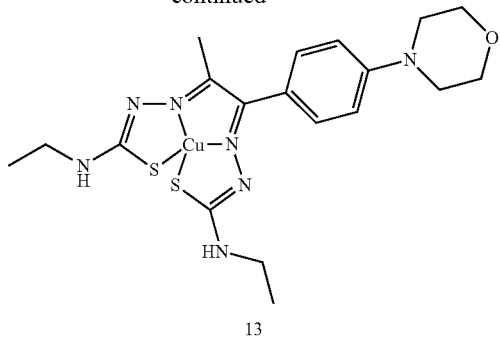

13

Synthesis of 4-morpholinobenzonitrile

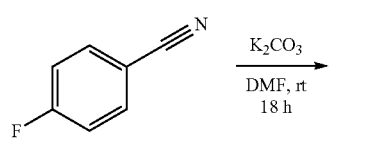

A stirred solution of 4-fluorobenzonitrile (2.0 g, 16.5 mmol) in anhydrous dimethylformamide (5 ml), morpholine (1.44 g, 16.5 mmol) and $K_2CO_3$ (2.85 g, 20.6 mmol) were added was heated for 18 h at 110° C. Water was added and formed precipitate was filtered, washed with water and hexane. Yield 2.6 g (83%). LCMS (C18 column 20×2 mm, particle size 2.5 μm, pore size 100A, water-acetonitrile+ 0.1% TFA, gradient 5 to 87% for 3 min, retention time 1.24 min). MS (ESI) m/z 189.1 [MH]+. $^1$H-NMR (400 MHz, DMSO-$d_6$): δ (ppm) 3.27 (t, 4H), 3.72 (t, 4H), 7.02 (d, 2H), 7.60 (d, 2H).

Synthesis of 4-morpholinobenzoic Acid

A stirred solution of 4-morpholin-4-yl-benzonitrile (2.6 g, 14.7 mmol) and sodium hydroxide (2.2 g, 58.8 mmol) in a mixture of water (90 ml) and MeOH (5 ml) was heated to reflux over a water bath for 5 hours. Then the solution was cooled to room temperature and acidified with aq HCl (10%). The precipitate was filtered, washed with water, dried in vacuo at 60° C. and crystallized from EtOH to give compound 2. Yield 2.0 g (70%). $^1$H-NMR (400 MHz, DMSO-$d_6$): δ (ppm) 3.12 (t, 2H), 3.24 (t, 2H), 3.73 (t, 4H), 6.96 (t, 2H), 7.77 (t, 2H), 12.31 (br.s, 1H).

Synthesis of N-methoxy-N-methyl-4-morpholinobenzamide

To a mixture of 4-morpholinobenzoic acid (1.4 g, 6.7 mmol), N,O-dimethylhydroxylamine (1.3 g, 8.7 mmol), HOBT (1.0 g, 7.7 mmol) and TEA (0.9 ml, 9 mmol) in DCM (25 ml) at 4° C. EDCl (1.4 g, 9 mmol) was added. The reaction was stirred overnight at ambient temperature. The mixture was washed with water (15 ml), aq. 1N HCl (20 ml), water (50 ml), brine (100 ml). The organic layer was dried over anhydrous $Na_2SO_4$, filtered, and then concentrated under reduced pressure. The residue was purified by column chromatography (silica gel, eluent 100% DCM to 5% MeOH) to afford the crude titular product. Yield 0.97 g (58%). LCMS (C18 column 20×2 mm, particle size 2.5 μm, pore size 100A, water-acetonitrile+0.1% TFA, gradient 5 to 87% for 3 min, retention time 1.12 min). MS (ESI) m/z 251.6 [MH]+. $^1$H-NMR (400 MHz, CDCl$_3$): δ (ppm) 3.26 (t, 4H), 3.36 (s, 3H), 3.59 (s, 3H), 3.89 (t, 4H), 6.89 (d, 2H), 7.74 (d, 2H).

Synthesis of 2-ethoxy-1-(4-morpholinophenyl)prop-2-en-1-one

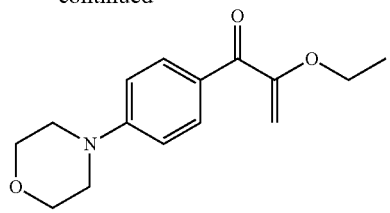

A solution of ethyl vinyl ether (0.9 g, 12.2 mmol) in dry tetrahydrofuran (25 ml) was cooled to −78° C., and tert-butyllithium (1.7M, 6.6 ml, 11.1 mmol) in pentane was added. The mixture was warmed to 0° C. over 1 h period, stirred for 45 min, and cooled down to −30° C. Then a solution of N-methoxy-N-methyl-4-morpholinobenzamide (0.93 g, 3.7 mmol) in THF (10 ml) was added, and the mixture was stirred at 0° C. for 4 h. The progress of the reaction was monitored by TLC. The mixture was poured into aq. $NH_4Cl$ (100 ml) and extracted with $Et_2O$ (3×100 ml). The combined extracts were dried over $Na_2SO_4$, filtered, and evaporated. The product was used for the next step without additional purification. Yield 0.6 g (62%). LCMS (C18 column 20×2 mm, particle size 2.5 μm, pore size 100A, water-acetonitrile+0.1% TFA, gradient 5 to 87% for 3 min, retention time 1.40 min). MS (ESI) m/z 262.0 [MH]+. $^1$H-NMR (400 MHz, $CDCl_3$): δ (ppm) 1.42 (t, 3H), 3.33 (t, 4H), 3.87 (t, 4H), 3.94 (q, 2H), 4.65 (d, 1H), 4.91 (d, 1H), 6.87 (d, 2H), 7.92 (d, 2H).

Synthesis of INT-13 ((2Z,2'E)-2,2'-(1-(4-morpholinophenyl)propane-1,2-diylidene)bis(N-ethylhydrazine-1-carbothioamide))

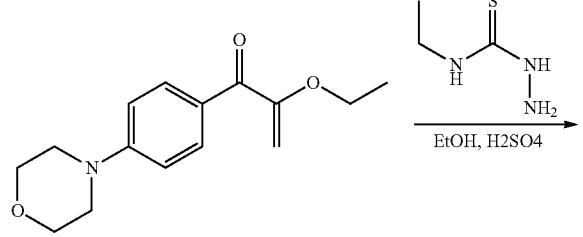

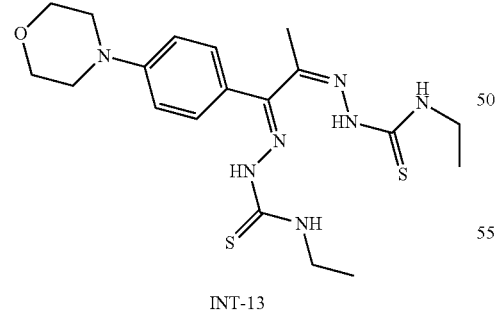

2-Ethoxy-1-(4-morpholinophenyl)prop-2-en-1-one (0.6 g, 2.3 mmol) was dissolved in EtOH (5 ml), ethyl thiosemicarbazide (0.6 g, 5.1 mmol) and 3 drops of $H_2SO_4$ were added and the reaction mixture was stirred for 4 h at reflux and for 15 h at ambient temperature. The formed precipitate was filtered, washed with EtOH, water, $Et_2O$, and dried. Yield 0.3 g (30%). LCMS (C18 column 20×2 mm, particle size 2.5 μm, pore size 100A, water-acetonitrile+0.1% TFA, gradient 5 to 87% for 3 min, retention time 1.49 min). MS (ESI) m/z 436.4 [MH]+. $^1$H-NMR (400 MHz, DMSO-$d_6$): δ (ppm) 0.93 (t, 3H), 1.15 (t, 3H), 2.33 (s, 3H), 3.19 (t, 4H), 3.34-3.38 (m, 2H), 3.56-3.63 (m, 2H), 3.75 (t, 4H), 6.97 (t, 1H), 7.12 (q, 4H), 8.70 (s, 1H), 8.74 (t, 1H), 10.75 (s, 1H).

Synthesis of Compound 13

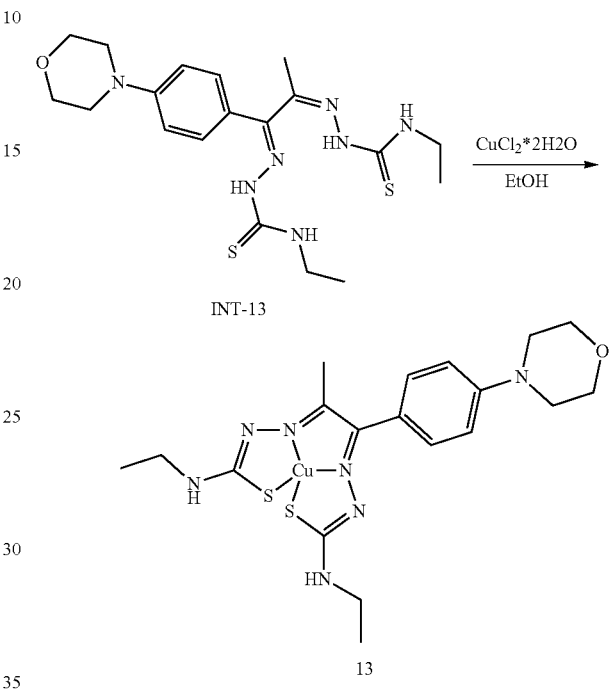

$CuCl_2\cdot 2H_2O$ (0.07 g, 0.4 mmol) was added to INT-13 (0.17 g, 0.4 mmol) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.2 g (99%). LCMS (C18 column 20×2 mm, particle size 2.5 μm, pore size 100A, water-acetonitrile+0.1% TFA, gradient 5 to 87% for 4 min, retention time 1.87). MS (ESI) m/z 497.4 [MH]+.

Scheme 6: Synthesis of Compound 16

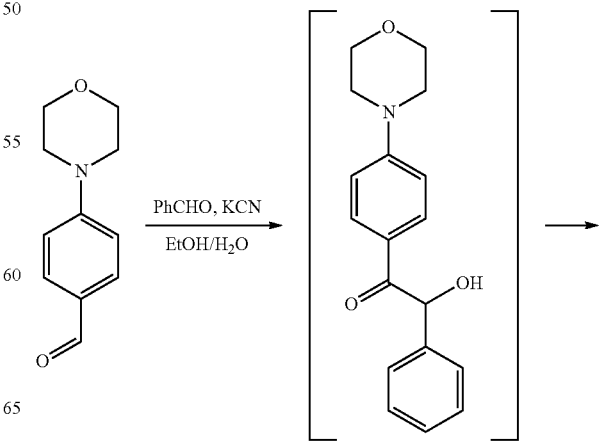

174

Synthesis of 1-(4-morpholinophenyl)-2-phenylethane-1,2-dione

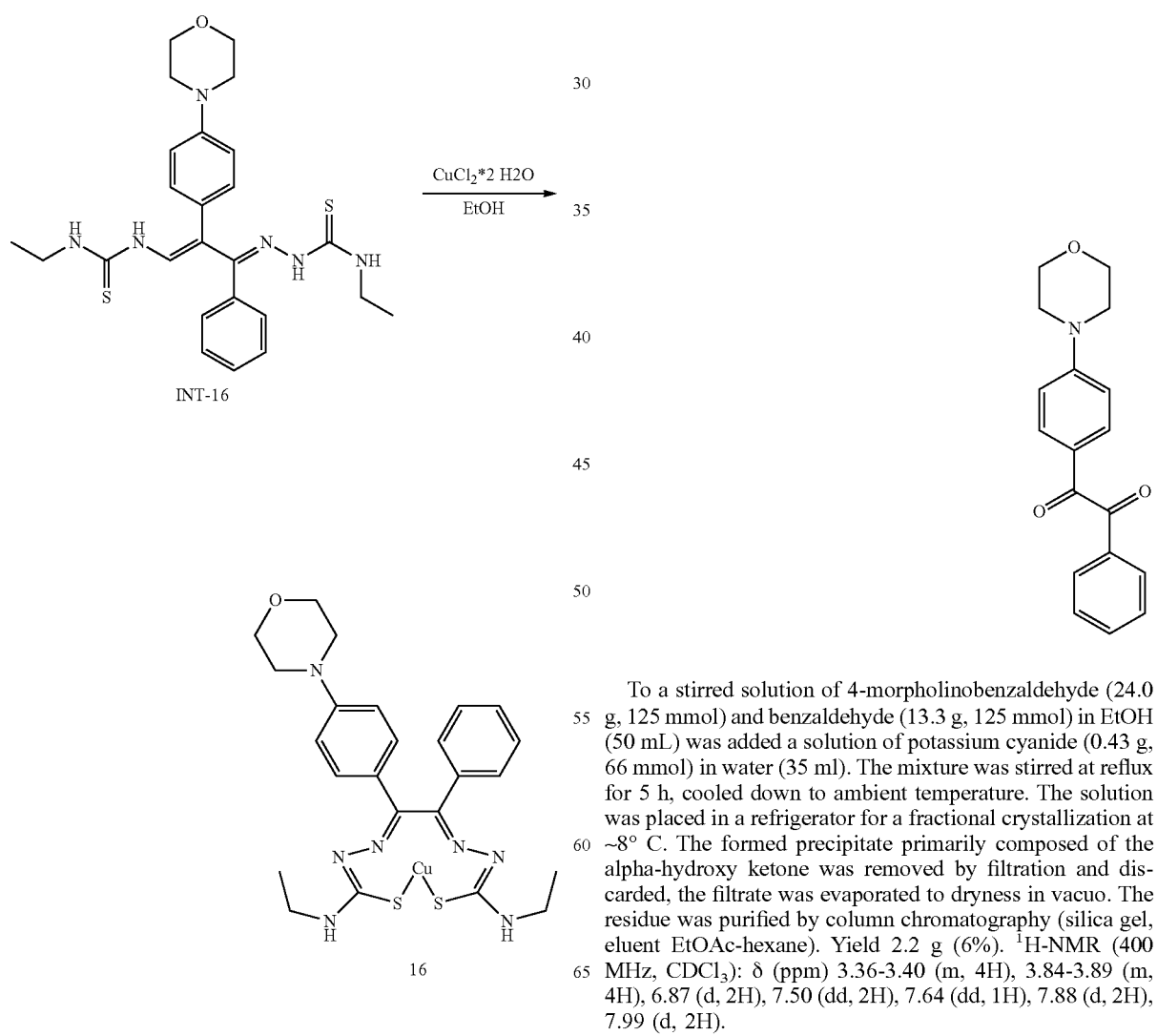

To a stirred solution of 4-morpholinobenzaldehyde (24.0 g, 125 mmol) and benzaldehyde (13.3 g, 125 mmol) in EtOH (50 mL) was added a solution of potassium cyanide (0.43 g, 66 mmol) in water (35 ml). The mixture was stirred at reflux for 5 h, cooled down to ambient temperature. The solution was placed in a refrigerator for a fractional crystallization at ~8° C. The formed precipitate primarily composed of the alpha-hydroxy ketone was removed by filtration and discarded, the filtrate was evaporated to dryness in vacuo. The residue was purified by column chromatography (silica gel, eluent EtOAc-hexane). Yield 2.2 g (6%). $^1$H-NMR (400 MHz, CDCl$_3$): δ (ppm) 3.36-3.40 (m, 4H), 3.84-3.89 (m, 4H), 6.87 (d, 2H), 7.50 (dd, 2H), 7.64 (dd, 1H), 7.88 (d, 2H), 7.99 (d, 2H).

Synthesis of INT-16 ((2E,2'E)-2,2'-(1-(4-morpholinophenyl)-2-phenylethane-1,2-diylidene)bis(N-ethylhydrazine-1-carbothioamide))

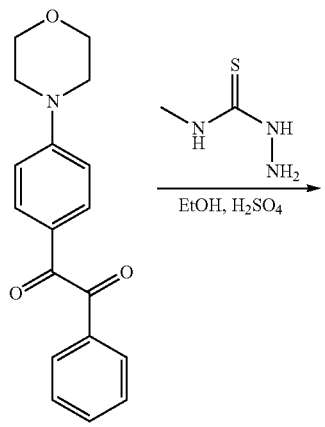

Synthesis of INT-17 ((2E,2'E)-2,2'-(1-(4-morpholinophenyl)-2-phenylethane-1,2-diylidene)bis(N-methylhydrazine-1-carbothioamide))

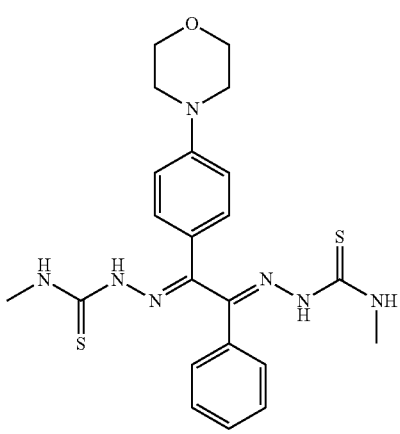

INT-17 was made using a procedure analogous to the procedure to prepare INT-16. Yield 0.31 g (36%). $^1$H-NMR (400 MHz, DMSO-d$_6$): δ (ppm) 2.99-3.06 (m, 6H), 3.17-3.20 (m, 4H), 3.70-3.74 (m, 4H), 6.94 (d, 2H), 7.42-7.47 (m, 3H), 7.55 (d, 2H), 7.70-7.74 (m, 2H), 8.84 (ddd, 2H), 9.49 (d, 2H).

Synthesis of Compound 16

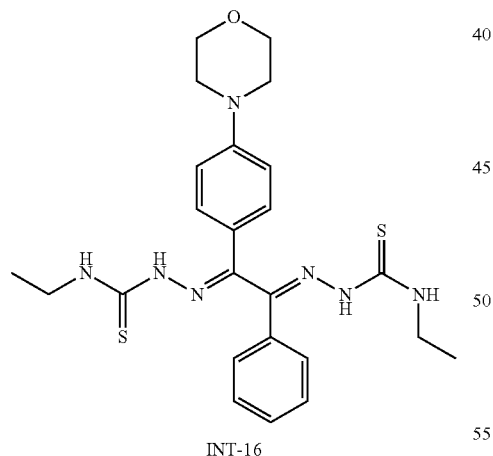

INT-16

1-(4-morpholinophenyl)-2-phenylethane-1,2-dione (0.61 g, 2.06 mmol, 1 eq) was dissolved in EtOH (15 ml), methyl thiosemicarbazide (0.45 g, 2 eq) and 3 drops of H$_2$SO$_4$ were added and the reaction mixture was stirred for 4 h at reflux and for 15 h at ambient temperature. The formed precipitate was filtered, washed with EtOH, water, Et$_2$O, and dried. Yield 0.45 g (44%). $^1$H-NMR (400 MHz, DMSO-d$_6$): δ (ppm) 1.13-1.19 (m, 6H), 3.17-3.20 (m, 4H), 3.55 (q, 4H), 3.70-3.75 (m, 4H), 6.94 (d, 2H), 7.42-7.47 (m, 3H), 7.55 (d, 2H), 7.70-7.74 (m, 2H), 8.88 (ddd, 2H), 9.49 (d, 2H).

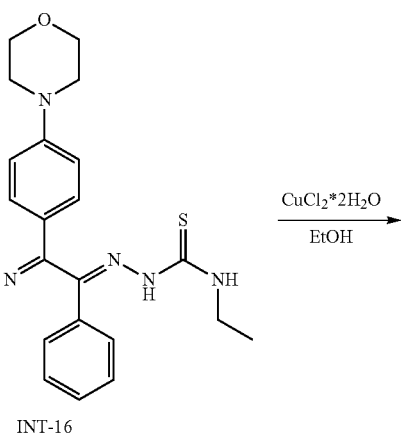

INT-16

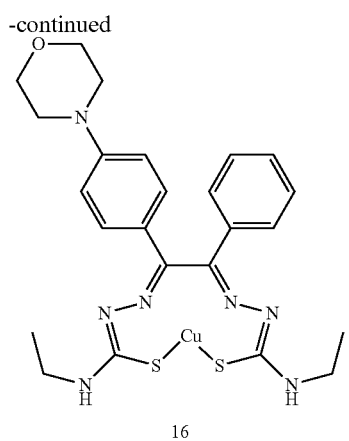

16

Cu(OAc)$_2$ 2H$_2$O (0.06 g, 1.1 eq) was added to INT-16 (0.12 g, 0.26 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.03 g (22%). LCMS (C18 column 20×2 mm, particle size 2.5 μm, pore size 100A, water-acetonitrile+0.1% TFA, gradient 5 to 87% for 4 min, retention time 2.21 min). MS (ESI) m/z 559.0 [MH]+.

Synthesis of Compound 17

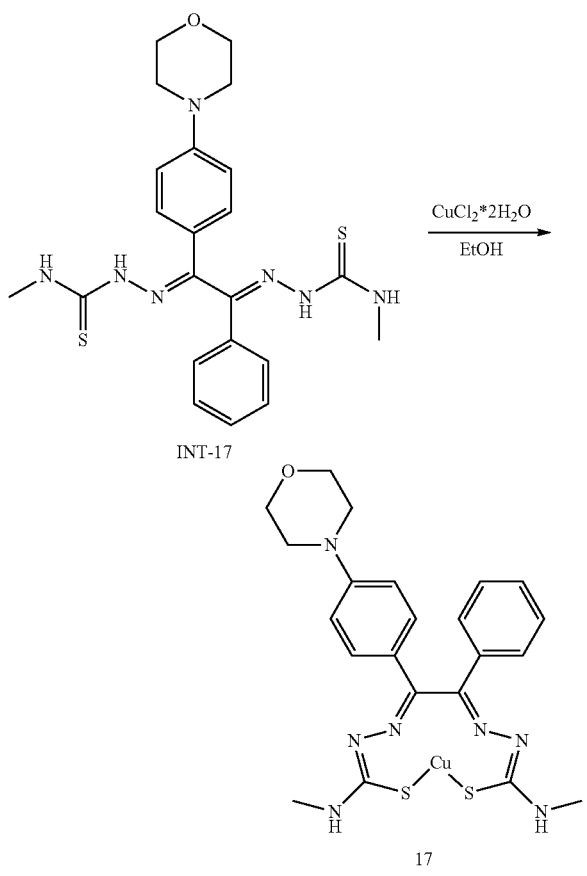

The titular compound was prepared from INT-17 according to the method to prepare compound 16. The formed complex was precipitated from the reaction mixture as a red-brown powder. The precipitate was collected by filtration, washed with water, methanol, and diethyl ether, and then dried in vacuo. Yield 0.03 g (22%). LCMS (C18 column 20×2 mm, particle size 2.5 μm, pore size 100A, water-acetonitrile+0.1% TFA, gradient 5 to 87% for 4 min, retention time 2.24 min). MS (ESI) m/z 531.2 [MH]+.

Scheme 7: Synthesis of Compound 18

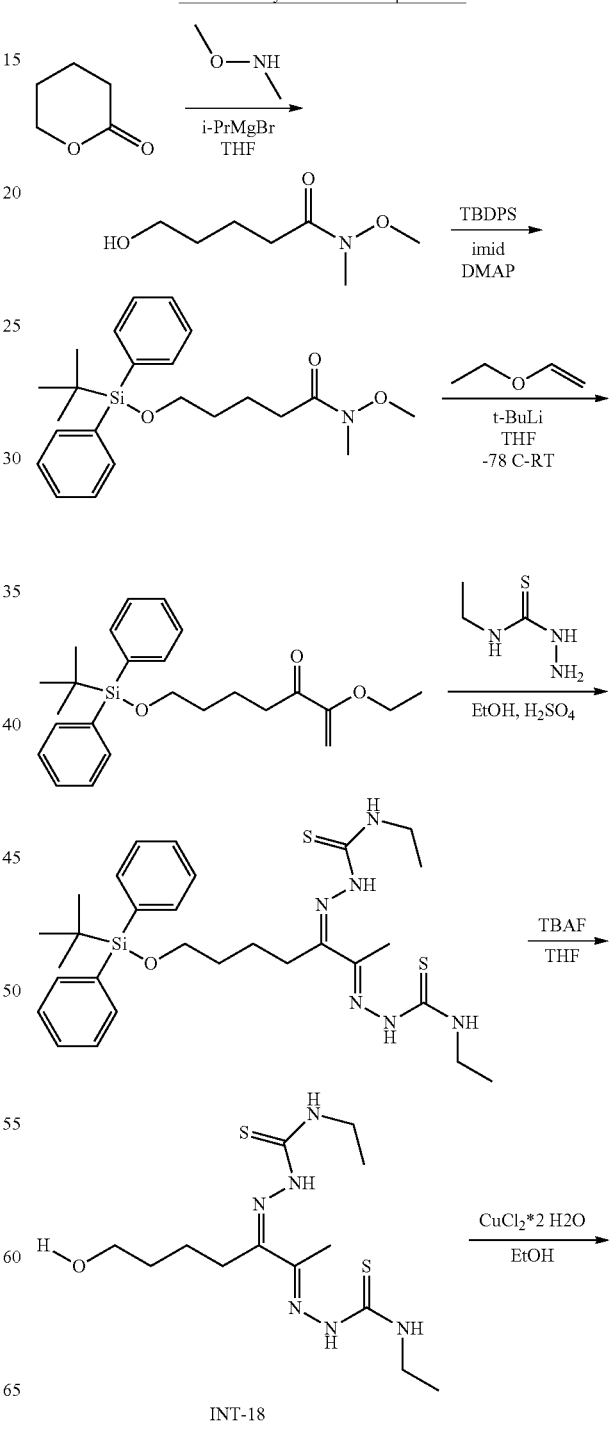

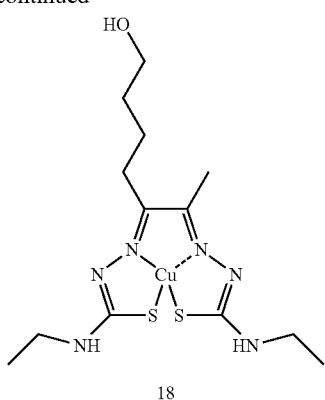

18

Synthesis of 5-hydroxy-N-methoxy-N-methylpentanamide

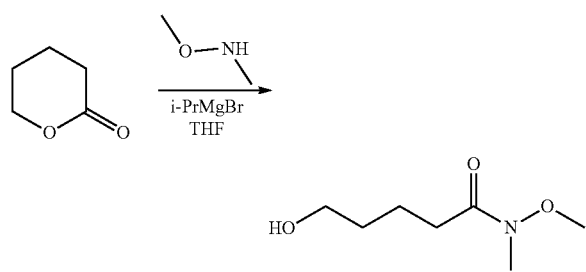

To a suspension of lactone (4 g, 40 mmol, 1 eq) and N,O-dimethylhydroxyamine hydrochloride (6.04 g, 1.55 eq) in THF (150 ml) at −20° C., 2.9 M solution of i-PrMgBr in 2-methyltetrahydrofuran (50 ml, 3.6 eq) was added dropwise over a period of 30 minutes. The mixture was stirred at −20° C. for 3 hours and quenched with 50 mL of saturated NH$_4$Cl solution. The layers were separated and the aqueous layer was extracted three times with EtOAc. The combined organic layers were washed with brine, dried over anhydrous MgSO$_4$ and concentrated in vacuo. The residue was purified by column chromatography (eluent 80/20 EtOAc/hexanes to 100% EtOAc). Yield 2.0 g (31%). NMR (400 MHz, CDCl$_3$): 1.57-1.63 (m, 2H), 1.70-1.76 (m, 2H), 2.44-2.50 (m, 2H), 3.18 (s, 3H), 3.62 (t, 2H), 3.68 (s, 2H). LCMS (C18 column 20×2 mm, particle size 2.5 μm, pore size 100A, water-acetonitrile+0.1% TFA, gradient 5 to 87% for 3 min, retention time 0.90 min), MS (ESI) m/z 162.4 [MH]+.

Synthesis of 5-((tert-butyldiphenylsilyl)oxy)-N-methoxy-N-methylpentanamide

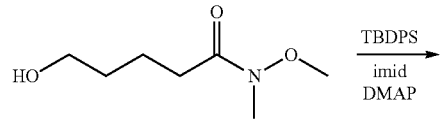

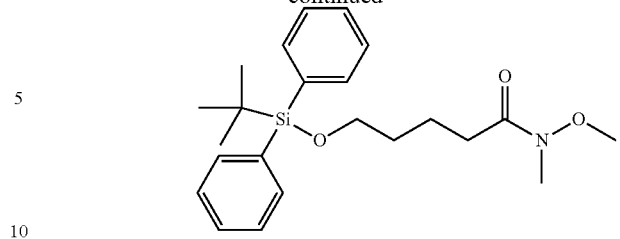

A mixture of 5-hydroxy-N-methoxy-N-methylpentanamide (2.1 g, 13 mmol, 1 eq), tert-butyldiphenylsilyl chloride (5.4 g, 5 ml, 1.5 eq), imidazole (1.6 g, 1.8 eq) and DMAP (0.16 g, 0.1 eq) in DMF (25 ml) was stirred for 15 h at ambient temperature. The reaction mixture was diluted with water (200 ml) and extracted with EtOAc (3×60 ml). Combined organic layers were dried over Na$_2$SO$_4$, filtered and solvents were evaporated. The residue was purified by column chromatography SiO$_2$/hexane, hexane:EtOAc 5:1. Yield 3 g (58.6%). NMR (400 MHz, CDCl$_3$): 1.20 (s, 9H), 1.60-1.66 (m, 2H), 1.70-1.78 (m, 2H), 2.41-2.47 (m, 2H), 3.19 (s, 3H), 3.65 (s, 3H), 3.70 (t, 2H), 7.38-7.44 (m, 6H), 7.66-7.71 (m, 4H). LCMS (C18 column 20×2 mm, particle size 2.5 μm, pore size 100A, water-acetonitrile+0.1% TFA, gradient 5 to 87% for 3 min, retention time 2.20 min), MS (ESI) m/z 400.5 [MH]+.

Synthesis of 7-((tert-butyldiphenylsilyl)oxy)-2-ethoxyhept-1-en-3-one

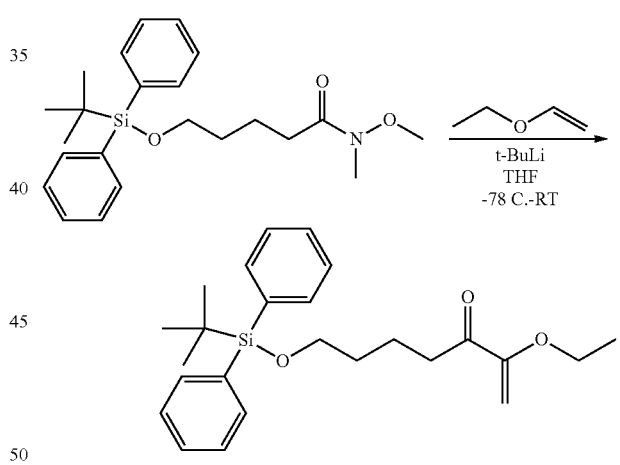

A solution of ethyl vinyl ether (1.8 g, 2.4 ml, 3.3 eq) in dry tetrahydrofuran (50 mL) was cooled to −78° C., and tert-butyllithium (1.7M, 13 ml, 3 eq) in pentane was added. The mixture was warmed to 0° C. over 1 h period, stirred for 45 min, and then cooled down to −30° C. 5-((tert-butyldiphenylsilyl)oxy)-N-methoxy-N-methylpentanamide was added (3.0 g, 7.5 mmol, 1 eq) in THF, and the mixture was stirred at 0° C. for 4 h. The progress of the reaction was monitored by TLC. The mixture was poured into aq NH$_4$Cl and extracted with Et$_2$O. The combined extracts were dried over Na$_2$SO$_4$, filtered and solvents were evaporated. The product was used for the next step without additional purification. Yield 2.5 g (81%). NMR (400 MHz, CDCl$_3$): 1.02 (s, 9H), 1.35 (t, 3H), 1.58-1.62 (m, 2H), 1.70-1.76 (m, 2H), 2.69 (t, 2H), 3.68 (t, 2H), 3.81 (q, 2H), 4.40 (d, 1H), 5.18 (d, 1H), 7.38-7.43 (m, 6H), 7.64-7.68 (m, 4H).

Synthesis of (2Z,2'E)-2,2'-(7-((tert-butyldiphenylsi-lyl)oxy)heptane-2,3-diylidene)bis(N-ethylhydrazine-1-carbothioamide)

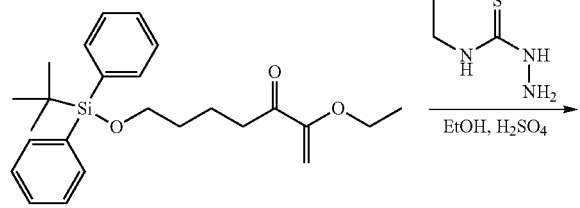

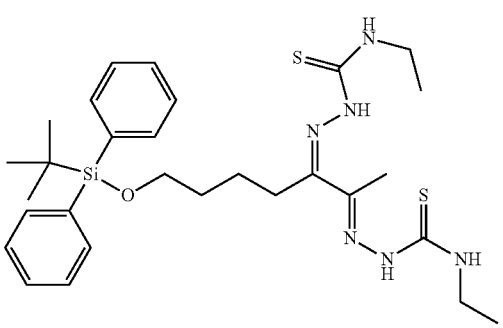

7-((tert-butyldiphenylsilyl)oxy)-2-ethoxyhept-1-en-3-one (2.0 g, 4.9 mmol, 1 eq) was dissolved in EtOH (50 ml), ethyl thiosemicarbazide (1.16 g, 2 eq) and 3 drops of H₂SO₄ were added. Reaction mixture was stirred and heated to reflux for 4 h and then maintained for 15 h at ambient temperature. The formed precipitate was filtered, washed with EtOH, water, Et₂O, and dried. Yield 1.71 g (60%). NMR (400 MHz, DMSO-d₆): 0.88 (s, 9H), 6.72 (t, 6H), 1.40-1.60 (m, 4H), 2.18 (s, 3H), 3.38-3.43 (m, 4H), 3.56-3.62 (m, 4H), 7.38-7.44 (m, 6H), 7.56-7.61 (m, 4H), 10.21-10.23 (m, 2H), 10.38-10.42 (m, 2H).

Synthesis of INT-18 ((2Z,2'E)-2,2'-(7-hydroxyhep-tane-2,3-diylidene)bis(N-ethylhydrazine-1-carbothioamide))

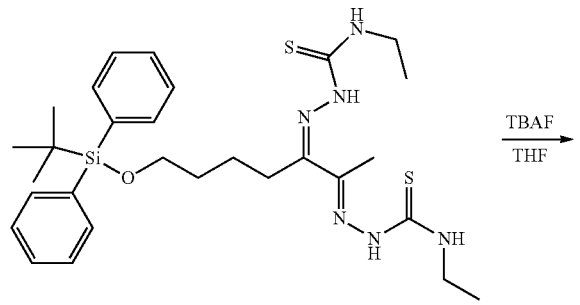

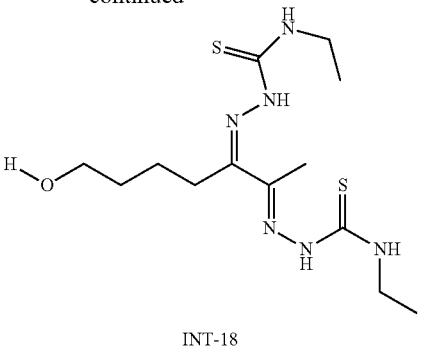

A mixture of (2Z,2'E)-2,2'-(7-((tert-butyldiphenylsilyl)oxy)heptane-2,3-diylidene)bis(N-ethylhydrazine-1-carbothioamide) (1.3 g, 2.3 mmol) and n-tetrabutylammonium fluoride trihydrate (0.88 g, 1.2 eq) in THF (25 ml) was stirred at ambient temperature for 15 h. The reaction mixture was diluted with water (150 ml) and extracted with EtOAc (3×60 ml). The organic layer was separated, dried over Na₂SO₄, filtered and solvents were evaporated. Yield 0.53 g (65%). NMR (400 MHz, DMSO-d₆): 1.10-1.16 (m, 6H), 1.38-1.48 (m, 4H), 2.19 (s, 3H), 2.84-2.87 (m, 2H), 3.41-3.47 (m, 2H), 3.58-3.62 (m, 4H), 4.50 (t, 1H), 8.26-8.38 (m, 2H), 10.20 (s, 1H), 10.41 (s, 1H).

Synthesis of Compound 18

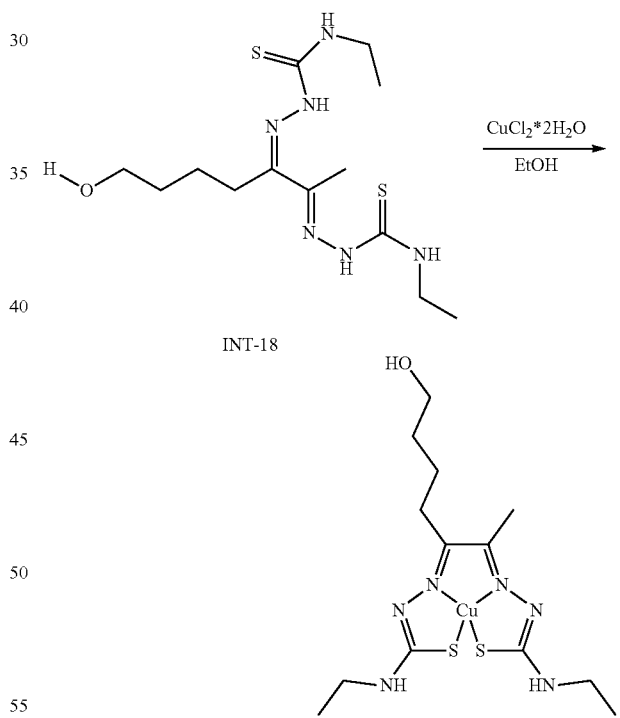

Cu(OAc)₂·2H₂O (0.12 g, 1.1 eq) was added to INT-18 (0.18 g, 0.5 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.06 g (25%). LCMS (C18 column 20×2 mm, particle size 2.5 μm, pore size 100A, water-acetonitrile+0.1% TFA, gradient 5 to 87% for 4 min, retention time 1.74 min). MS (ESI) m/z 408.5 [MH]+.

Scheme 8: Synthesis of Compound 19
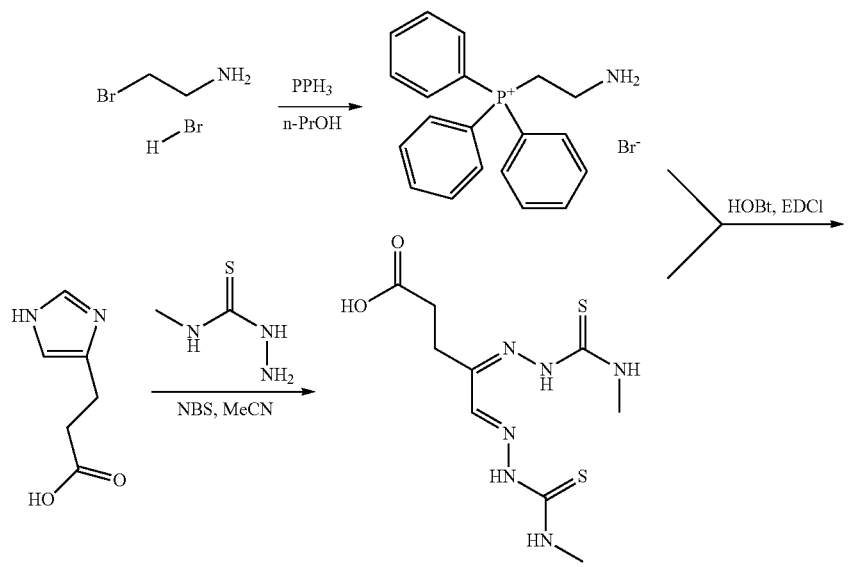
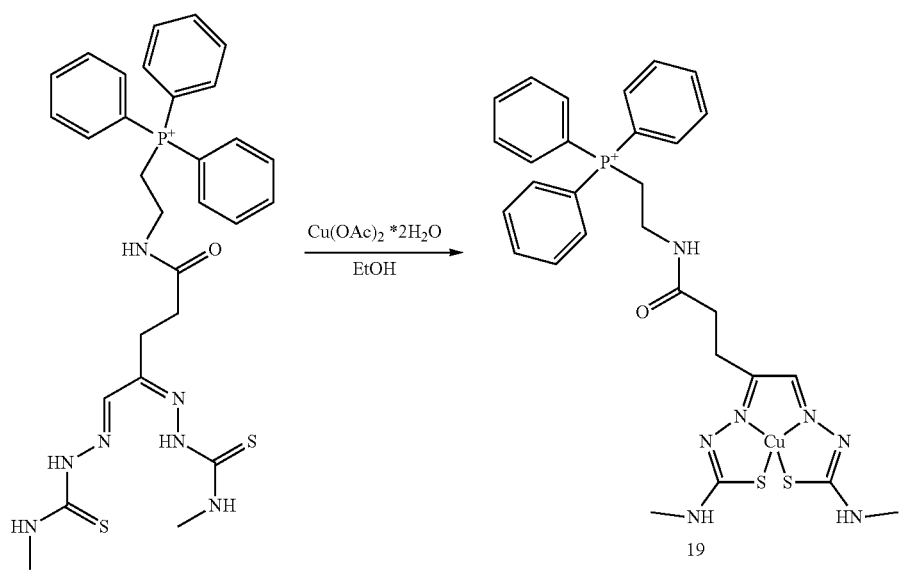

Synthesis of (2-aminoethyl)triphenylphosphonium Bromide

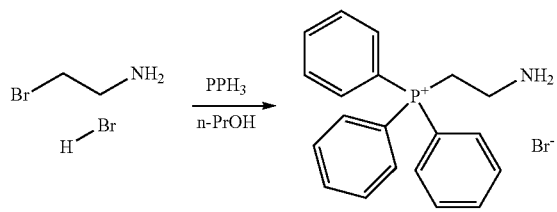

A stirred solution of triphenylphosphine (4.3 g, 16.6 mmol) and 2-bromoethylamine hydrobromide (3.4 g, 16.6 mmol) in n-propanol (100 ml) was heated to reflux for 72 hr under nitrogen atmosphere. Then the mixture was cooled to r.t., solids were filtered, washed with portions of dry ether, and dried in vacuo. The product was dissolved in 50 ml of water, insoluble solids were filtered, and filtrate was concentrated in vacuo to dryness resulting in the titular compound (6.40 g, 100%). LCMS (C18 column 20×2 mm, particle size 2.5 μm, pore size 100A, water-acetonitrile+ 0.1% TFA, gradient 5 to 87% for 3 min, retention time 1.25 min, MS (ESI) m/z 306.5 [MH]+.

Synthesis of (4Z,5E)-4,5-bis(2-(methylcarbamothioyl)hydrazineylidene)pentanoic Acid

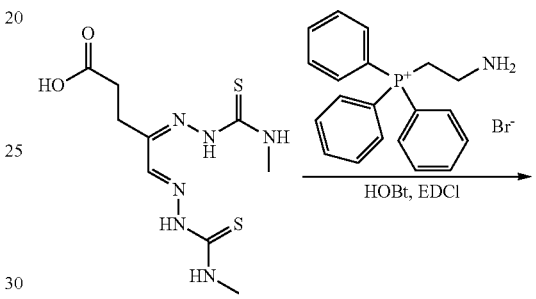

To a stirred solution of imidazole propionic acid (0.5 g, 3.6 mmol) in water (18 mL) a solution of NBS (0.63 g, 1 eq) in acetonitrile (5.5 mL) was added in a single portion. After stirring for 20 min. acetonitrile was removed in vacuo. To the reaction mixture a solution of sodium acetate trihydrate (0.7 g) and methyl thiosemicarbazide (1.12 g, 3 eq) in water (7.5 mL) was added. Crystals started forming within 5 min. The crystallization continued for 14 h at ambient temperature, the precipitate was filtered, and recrystallized from water. Yield 0.34 g (31.3%). LCMS (C18 column 20×2 mm, particle size 2.5 μm, pore size 100A, water-acetonitrile+ 0.1% TFA, gradient 5 to 87% for 3 min, retention time 1.10 min, MS (ESI) m/z 305.0 [MH]+. $^1$H-NMR (400 MHz, DMSO-$d_6$): δ (ppm) 2.41 (br.s, 2H), 2.91 (br.s, 2H), 2.99 (br.s, 6H), 7.60 (s, 1H), 8.29 (br.s, 1H), 8.54 (br.s, 1H), 10.80 (s, 1H), 11.73 (s, 1H).

Synthesis of INT-19 ((2-((4Z,5E)-4,5-bis(2-(methylcarbamothioyl)hydrazineylidene)pentanamido)ethyl)triphenylphosphonium)

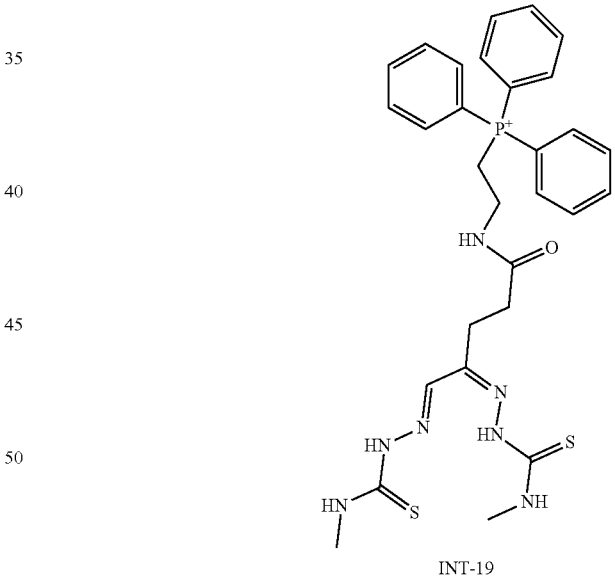

A mixture of (4Z,5E)-4,5-bis(2-(methylcarbamothioyl)hydrazineylidene)pentanoic acid (0.44 g, 1.4 mmol), (2-aminoethyl)triphenylphosphonium bromide (0.55 g, 1 eq.), EDCl (0.3 g, 1.1 eq), and HOBT (0.21 g, 1.1 eq) in DMF (15 ml) was stirred overnight at r.t. The reaction mixture was diluted with water (50 ml), extracted with dichloromethane (3×20 ml), extracts were dried over $Na_2SO_4$, filtered, and evaporated. Yield 0.2 g (23.3%). LCMS (C18 column 20×2 mm, particle size 2.5 μm, pore size 100A, water-acetonitrile+0.1% TFA, gradient 5 to 87% for 3 min, retention time 1.17 min, MS (ESI) m/z 592.8 [MH]+.

Synthesis of INT-20 ((2-((4Z,5E)-4,5-bis(2-carbamothioylhydrazineylidene)pentanamido)ethyl)triphenylphosphonium)

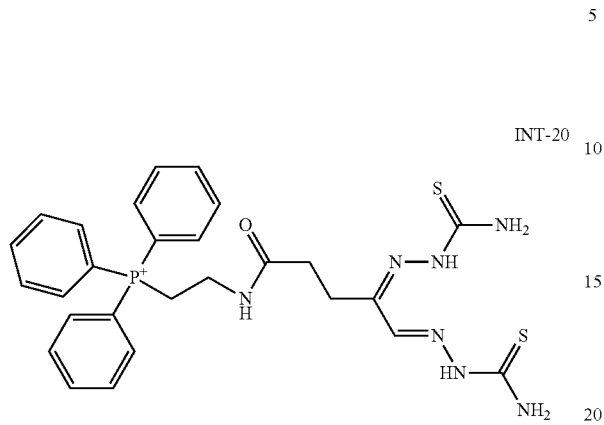

INT-20

INT-20 was made using a procedure analogous to the procedure to prepare INT-19. Yield 0.76 g (74.4%). $^1$H-NMR (400 MHz, DMSO-$d_6$): δ (ppm) 2.30-2.43 (m, 2H), 2.77-2.92 (m, 2H), 7.59 (s, 1H), 7.80 (br.s, 1H), 7.92 (br.s, 1H), 8.33 (br.s, 1H), 8.39 (br.s, 1H), 10.76 (s, 1H), 11.65 (s, 1H).

Synthesis of INT-21 ((2-((4Z,5E)-4,5-bis(2-(ethylcarbamothioyl)hydrazineylidene)pentanamido)ethyl)triphenylphosphonium)

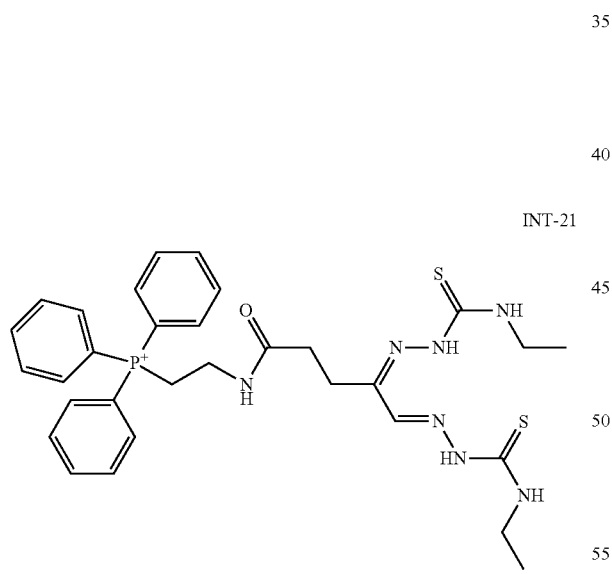

INT-21

INT-21 was made using a procedure analogous to the procedure to prepare INT-19. Yield 0.76 g (74.4%). LCMS (C18 column 20×2 mm, particle size 2.5 μm, pore size 100A, water-acetonitrile+0.1% TFA, gradient 5 to 87% for 3 min, retention time 1.33 min, MS (ESI) m/z 620.5 [MH]+. $^1$H-NMR (400 MHz, DMSO-$d_6$): δ (ppm) 1.00-1.21 (m, 6H), 2.29 (br.s, 2H), 2.87 (br.s, 2H), 3.34 (br.s, 2H), 3.49-3.55 (m, 4H), 3.65-3.77 (m, 2H), 7.58 (s, 1H), 7.77-7.96 (m, 15H), 8.41 (br.s, 1H), 8.53 (br.s, 1H), 8.60 (br.s, 1H), 10.74 (s, 1H), 11.74 (s, 1H).

Synthesis of Compound 19

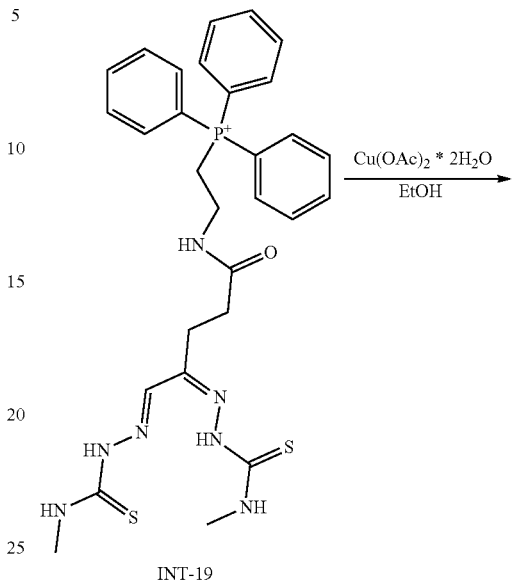

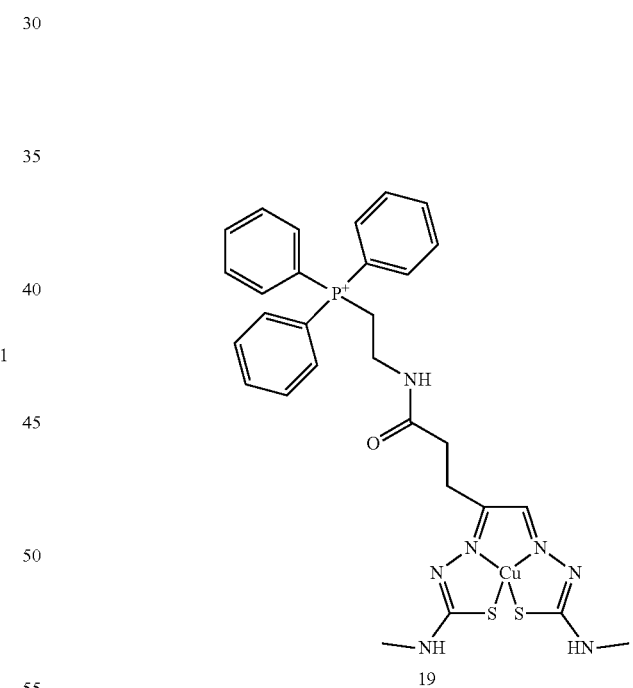

Cu(OAc)$_2$·2H$_2$O (0.025 g, 1.1 eq) was added to INT-19 (0.087 g, 0.1 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.018 g (19%). LCMS (C18 column 20×2 mm, particle size 2.5 μm, pore size 100A, water-acetonitrile+0.1% TFA, gradient 5 to 87% for 4 min, retention time 1.56 min). MS (ESI) m/z 653.3 [MH]+.

Synthesis of Compound 20

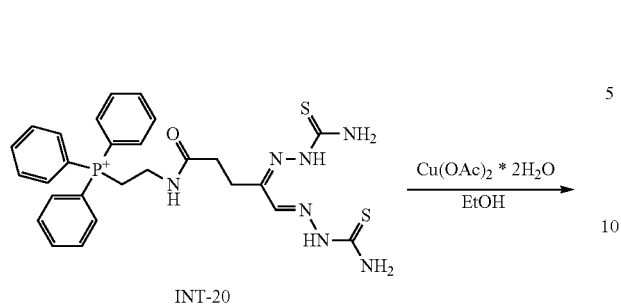

INT-20

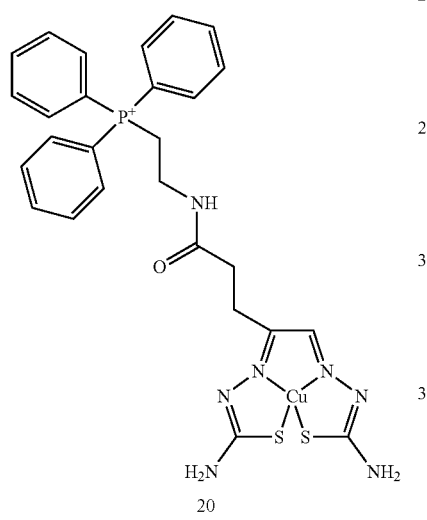

20

The titular compound was prepared from INT-20 according to the method to prepare compound 19. The product was precipitated from the reaction mixture as a red-brown powder. The precipitate was collected by filtration, washed with water, methanol, and diethyl ether, and then dried in vacuo. Yield 0.09 g (45%). LCMS (C18 column 20×2 mm, particle size 2.5 μm, pore size 100A, water-acetonitrile+0.1% TFA, gradient 5 to 87% for 4 min, retention time 1.49 min). MS (ESI) m/z 625.3 [MH]+.

Synthesis of Compound 21

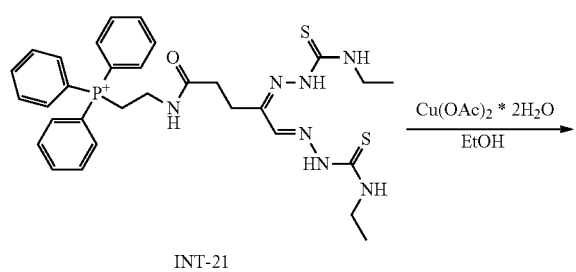

INT-21

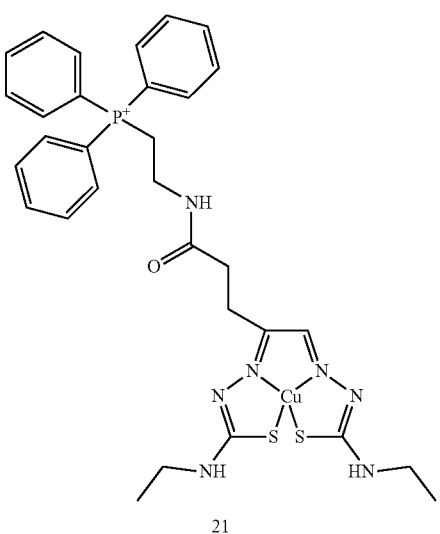

21

The titular compound was prepared from INT-21 according to the method to prepare compound 19. The product was precipitated from the reaction mixture as a red-brown powder.

The precipitate was collected by filtration, washed with water, methanol, and diethyl ether, and then dried in vacuo. Yield 0.09 g (45%). LCMS (C18 column 20×2 mm, particle size 2.5 μm, pore size 100A, water-acetonitrile+0.1% TFA, gradient 5 to 87% for 4 min, retention time 1.79 min). MS (ESI) m/z 681.2 [MH]+.

Scheme 9: Synthesis of Compound 22

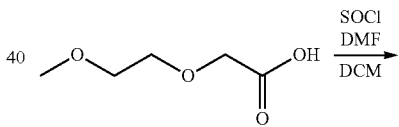

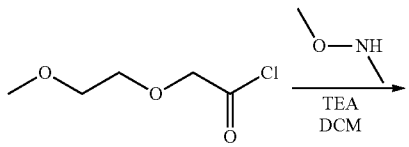

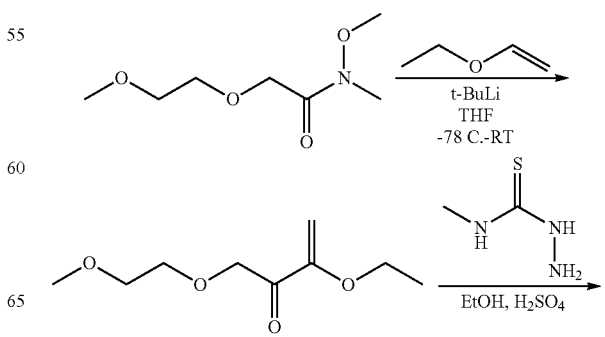

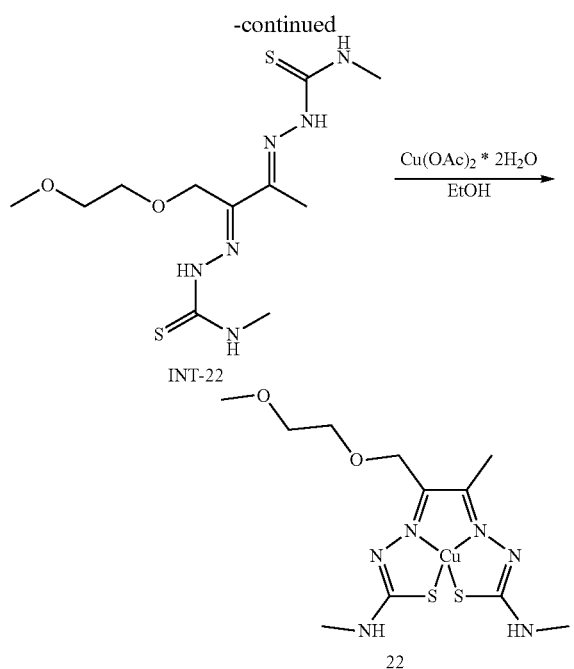

To a solution of 2-(2-methoxyethoxy)acetyl chloride (4.4 g, 29 mmol) in CH$_2$Cl$_2$ (100 mL) N,O-dimethylhydroxylamine hydrochloride was added (3.4 g, 1.2 eq) followed by Et$_3$N (11.7 g, 4 eq). The mixture was stirred at ambient temperature for 15 h, quenched with 10% aq HCl, extracted with EtOAc. The combined organic extracts were dried over Na$_2$SO$_4$, filtered and solvents were evaporated. The residue was purified on silica gel eluting with a gradient from 10% to 75% EtOAc in hexane giving compound (3) (2.7 g, 53%). NMR (400 MHz, CDCl$_3$): 3.18 (s, 3H), 3.39 (s, 3H), 3.57-3.64 (m, 2H), 3.68 (s, 3H), 3.73-3.77 (m, 2H), 4.34 (s, 2H).

Synthesis of 3-ethoxy-1-(2-methoxyethoxy)but-3-en-2-one

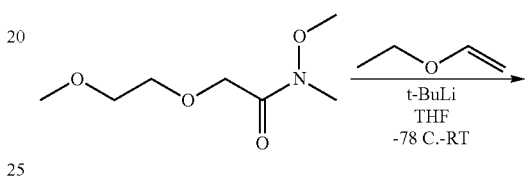

Synthesis of 2-(2-methoxyethoxy)acetyl chloride

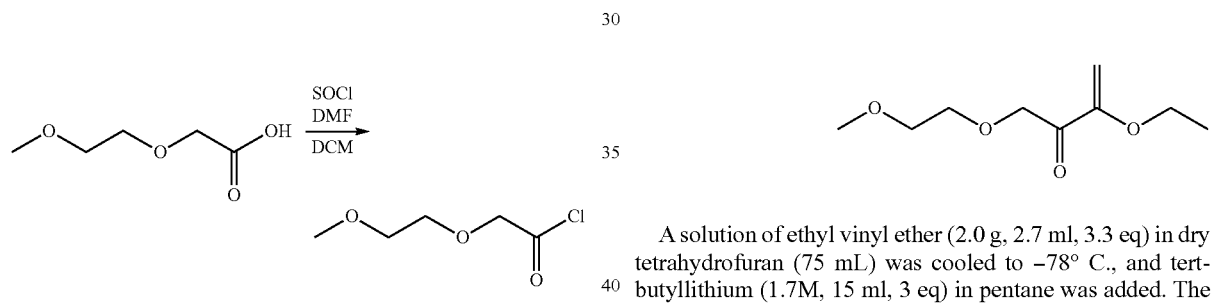

A solution of ethyl vinyl ether (2.0 g, 2.7 ml, 3.3 eq) in dry tetrahydrofuran (75 mL) was cooled to −78° C., and tert-butyllithium (1.7M, 15 ml, 3 eq) in pentane was added. The mixture was warmed to 0° C. over 1 h period, stirred for 45 min, and then cooled down to −30° C. N-methoxy-2-(2-methoxyethoxy)-N-methylacetamide was added (1.53 g, 8.6 mmol, 1 eq) in THF, and the mixture was stirred at 0° C. for 4 h. The progress of the reaction was monitored by TLC. The mixture was poured into aq NH$_4$Cl and extracted with Et$_2$O. The combined extracts were dried over Na$_2$SO$_4$, filtered and solvents were evaporated. The product was used for the next step without additional purification. Yield 0.73 g (45%) NMR (400 MHz, DMSO-d$_6$): 1.28 (t, 3H), 3.22 (s, 3H), 3.32 (s, 2H), 3.42-3.46 (m, 2H), 3.53-3.58 (m, 2H), 4.52 (s, 2H), 4.62 (d, 1H), 5.10 (d, 1H).

To a solution of acid (1) (5.0 g, 37 mmol) in CH$_2$Cl$_2$ (100 mL) few drops of DMF were added followed by SOCl$_2$ (13.3 g, 3 eq) and the mixture was stirred at ambient temperature for 15 h. The solvents were evaporated giving compound (2) (4.4 g, 78%) that was used for the next step without additional purification. NMR (400 MHz, CDCl$_3$): 3.37 (s, 3H), 3.57-3.60 (m, 2H), 3.74-3.78 (m, 2H), 4.50 (s, 2H).

Synthesis of N-methoxy-2-(2-methoxyethoxy)-N-methylacetamide

Synthesis of INT-22 ((2Z,2'E)-2,2'-(1-(2-methoxyethoxy)butane-2,3-diylidene)bis(N-methylhydrazine-1-carbothioamide))

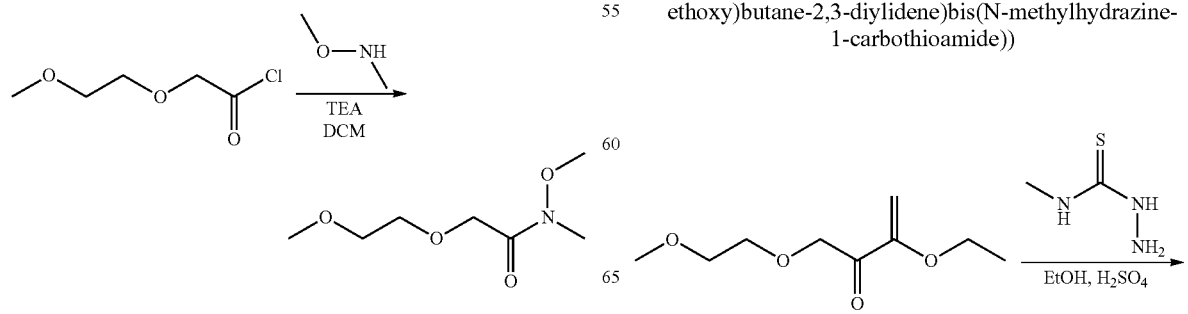

193

-continued

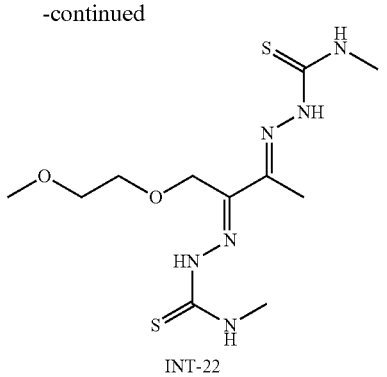

INT-22

3-ethoxy-1-(2-methoxyethoxy)but-3-en-2-one (0.73 g, 3.9 mmol, 1 eq) was dissolved in EtOH (100 ml), methyl thiosemicarbazide (0.82 g, 2 eq) and 3 drops of $H_2SO_4$ were added. Reaction mixture was stirred and heated to reflux for 4 h and then maintained for 15 h at ambient temperature. The formed precipitate was filtered, washed with EtOH, water, $Et_2O$, and dried. Yield 0.2 g (15%). NMR (400 MHz, DMSO-$d_6$): 2.20 (s, 3H), 3.02, 3.04 (m, 6H), 3.28 (s, 3H), 3.48-3.60 (m, 4H), 4.84 (s, 2H), 8.38-8.50 (m, 2H), 10.23 (s, 1H), 10.58 (s, 1H). LCMS (C18 column 20×2 mm, particle size 2.5 μm, pore size 100A, water-acetonitrile+0.1% TFA, gradient 5 to 87% for 3 min, retention time 1.34 min), MS (ESI) m/z 335.6 [MH]+.

Synthesis of Compound 22

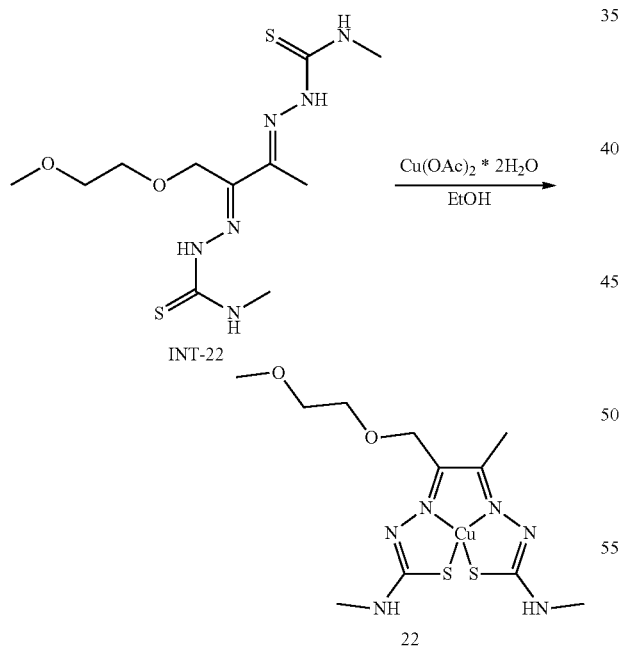

Cu(OAc)$_2$·2H$_2$O (0.16 g, 1.1 eq) was added to thiosemacarbazone 5 (0.2 g, 0.66 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.06 g (25%). LCMS (C18 column 20×2 mm,

194 particle size 2.5 μm, pore size 100A, water-acetonitrile+ 0.1% TFA, gradient 5 to 87% for 4 min, retention time 1.77 min). MS (ESI) m/z 396.3 [MH]+.

Example 2: Preparation of Compounds 23-46

Synthesis of INT-25 ((2Z,2'E)-2,2'-(1-(furan-2-yl) propane-1,2-diylidene)bis(N-methylhydrazine-1-carbothioamide))

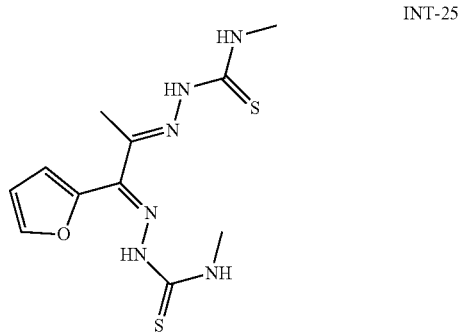 [SMILES: CNC(=S)N/N=C(/C(C)=N/NC(=S)NC)c1ccco1]

INT-25

INT-25 was made using a procedure analogous to the procedure to prepare INT-1 of Example 1. Yield 6.78 g (78%). LCMS (C18 column 20×2 mm, particle size 2.5 μm, pore size 100A, water-acetonitrile+0.1% TFA, gradient 5 to 87% for 3 min, retention time 1.34 min). MS (ESI) m/z 313.4 [MH]+. $^1$H-NMR (400 MHz, CDCl$_3$): δ (ppm) 2.25 (s, 3H), 3.20 (s, 3H), 3.28 (s, 3H), 6.62 (d, 1H), 6.84 (d, 1H), 7.31 (s, 1H), 7.33 (s, 1H), 7.53 (s, 1H), 7.71 (s, 1H), 8.79 (s, 1H), 10.52 (s, 1H).

Synthesis of INT-33 ((2E,2'E)-2,2'-(1-(2,5-dimethyl-furan-3-yl)propane-1,2-diylidene)bis(N-ethylhydra-zine-1-carbothioamide))

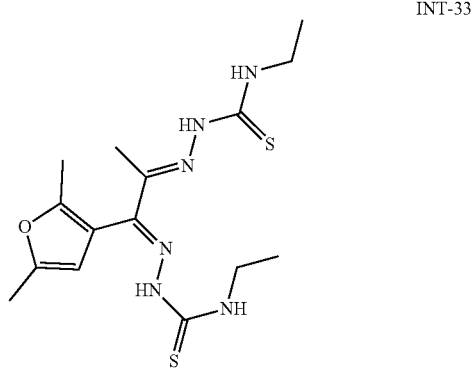 [SMILES: CCNC(=S)N/N=C(C)/C(=N/NC(=S)NCC)c1cc(C)oc1C]

INT-33

INT-33 was made using a procedure analogous to the procedure to prepare INT-1 of Example 1. Yield 1.8 g (48%). LCMS (C18 column 20×2 mm, particle size 2.5 μm, pore size 100A, water-acetonitrile+0.1% TFA, gradient 5 to 87% for 3 min, retention time 1.60 min). MS (ESI) m/z 369.5 [MH]+. $^1$H-NMR (400 MHz, DMSO-$d_6$): δ (ppm) 1.07 (t, 3H), 1.15 (t, 3H), 2.06 (s, 3H), 2.28 (s, 3H), 2.30 (s, 3H), 3.41-3.48 (m, 2H), 3.55-3.63 (m, 2H), 6.09 (s, 1H), 6.84 (d, 1H), 7.37 (t, 1H), 8.69 (t, 1H), 9.52-10.52 (m, 1H).

Synthesis of INT-41 ((2E,2'E)-2,2'-(1-(1-ethyl-1H-pyrazol-5-yl)propane-1,2-diylidene)bis(N-methylhydrazine-1-carbothioamide))

Synthesis of Compound 33

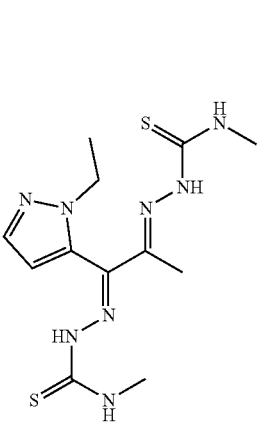

INT-41

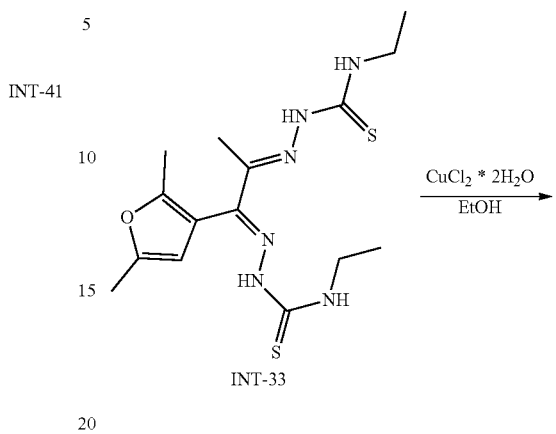

INT-33

INT-41 was made using a procedure analogous to the procedure to prepare INT-1 of Example 1. Yield 0.55 g (52.9%). LCMS (C18 column 20×2 mm, particle size 2.5 µm, pore size 100A, water-acetonitrile+0.1% TFA, gradient 5 to 87% for 3 min, retention time 0.83 min, MS (ESI) m/z 341.3 [MH]+.

Synthesis of Compound 25

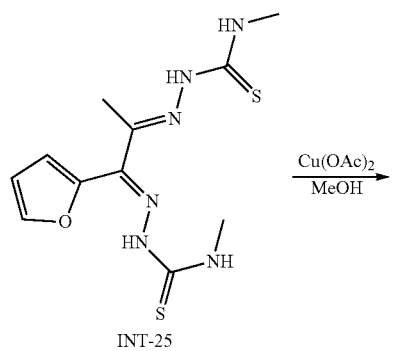

INT-25

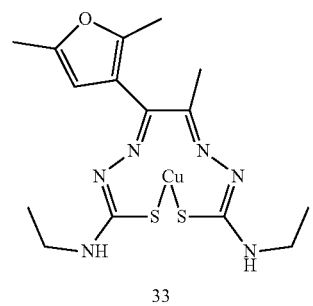

33

The titular compound was prepared from INT-33 according to the method to prepare compound 1 of Example 1. The product was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.7 g (75%). LCMS (C18 column 20×2 mm, particle size 2.5 µm, pore size 100A, water-acetonitrile+0.1% TFA, gradient 5 to 87% for 4 min, retention time 2.34 min). MS (ESI) m/z 430.5 [MH]+.

Synthesis of Compound 41

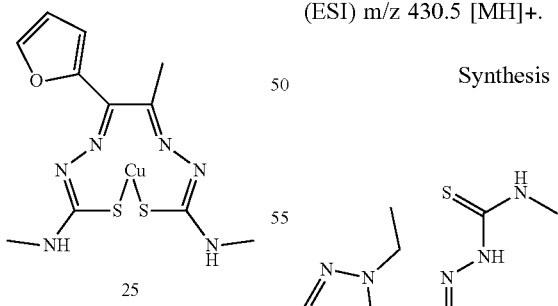

25

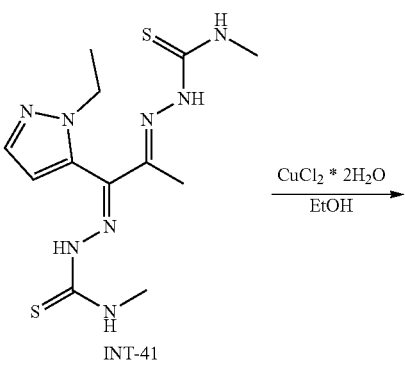

INT-41

The titular compound was prepared from INT-25 according to the method to prepare compound 1 of Example 1. Yield 6.2 g (76%). ICP/MS Sulfur: 17.36%, Copper: 16.518%. LCMS (C18 column 20×2 mm, particle size 2.5 µm, pore size 100A, water-acetonitrile+0.1% TFA, gradient 5 to 87% for 4 min, retention time 2.11 min) MS (ESI) m/z 374.1 [MH]+.

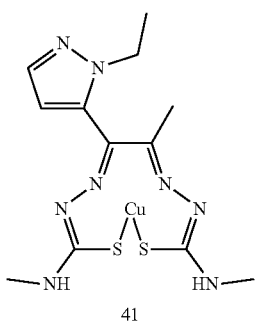

41

The titular compound was prepared from INT-41 according to the method to prepare compound 1 of Example 1. The product precipitated from the reaction mixture as a red-brown powder. The precipitate was collected by filtration, washed with water, methanol, and diethyl ether, and then dried in vacuo. Yield 0.18 g (55.7%). LCMS (C18 column 20×2 mm, particle size 2.5 μm, pore size 100A, water-acetonitrile+0.1% TFA, gradient 5 to 87% for 4 min, retention time 1.80 min). MS (ESI) m/z 401.8 [MH]+.

Scheme 10: Synthesis of Compound 23

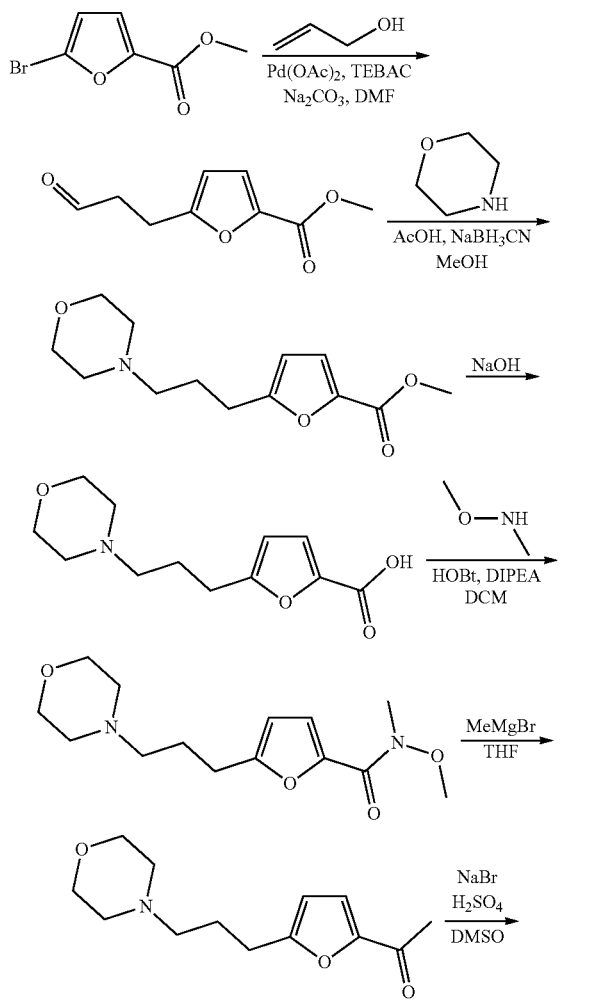

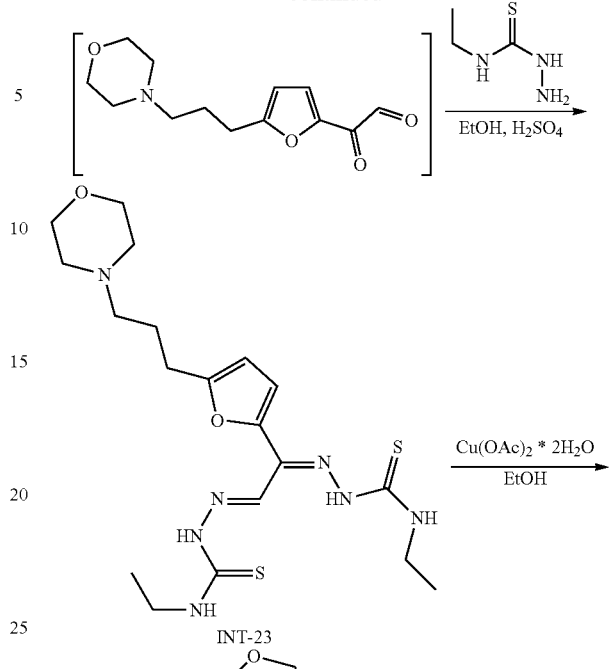

23

Synthesis of methyl 5-(3-oxopropyl)furan-2-carboxylate

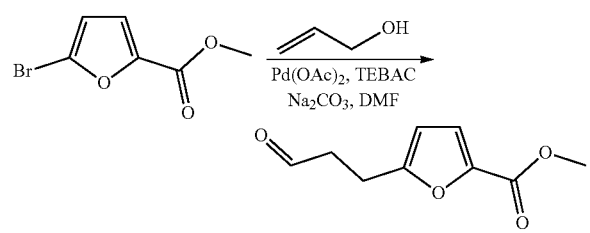

Under inert atmosphere, to a stirred solution of methyl 5-bromofuroate (5.7 g, 28 mmol, 1 eq) in DMF (550 ml) were added allyl alcohol (2.28 g, 1.4 eq), Pd(OAc)$_2$ (0.189 g, 0.03 eq), TEBAC (6.39 g, 1 eq) and Na$_2$CO$_3$ (6.85 g, 2 eq). Then the mixture was stirred at 80° C. for 2 h. Once the reaction has reached completion, the resulting mixture was filtered through Celite, concentrated at ≤40° C. in vacuo, diluted with ethyl acetate, washed with brine, concentrated in vacuo to dryness, and the residue was purified by column chromatography (ethyl acetate:hexane 1:3). Yield 2.7 g (53%). $^1$H-NMR (400 MHz, CDCl$_3$): δ (ppm) 2.89 (dd, 2H), 3.05 (dd, 2H), 3.89 (s, 3H), 6.19 (s, 1H), 7.09 (s, 1H), 9.83 (s, 1H).

Synthesis of methyl 5-(3-morpholinopropyl)furan-2-carboxylate

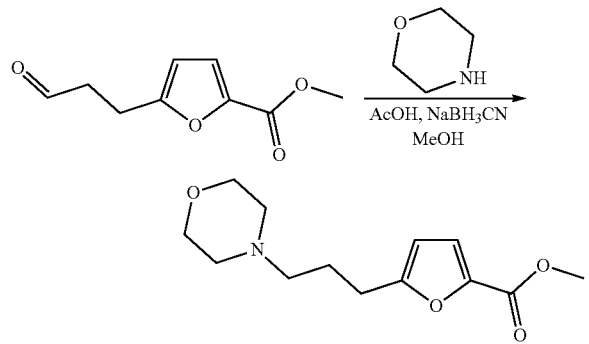

Methyl 5-(3-oxopropyl)furan-2-carboxylate (1.6 g, 9 mmol, 1 eq) was dissolved in MeOH (90 ml) and molecular sieves 3A (2.64 g) were added to the solution. After stirring for 15 min, the mixture was cooled to 0° C. To the stirred solution of aldehyde was added a solution of morpholine (1.15 g, 1.5 eq) and acetic acid (1.05 g, 2 eq) in methanol (42 ml). After stirring for 2 min, NaBH$_3$CN (1.66 g, 3 eq) was added. The resulting mixture was stirred for 14 h at 0° C. allowing to reach ambient temperature on its own accord. The reaction mixture was diluted with DCM, filtered through Celite, and filtrate was washed with aq. NaHCO$_3$. The aqueous phase was extracted with DCM twice. The organic phase was dried over Na$_2$SO$_4$, filtered, and solvents were evaporated. The residue was purified by column chromatography (SiO$_2$, eluting with EtOAc-hexane 1:5 to 1:3 to 1:1 to 100% EtOAc, and then with CH$_2$Cl$_2$-MeOH, 10:1). Yield 1.5 g (68%). LCMS (C18 column 20×2 mm, particle size 2.5 μm, pore size 100A, water-acetonitrile+0.1% TFA, gradient 5 to 87% for 3 min, retention time 0.28 min. MS (ESI) m/z 254.4 [MH]+, retention time 0.8 min. MS (ESI) m/z 254.6 [MH]+. $^1$H-NMR (400 MHz, CDCl$_3$): δ (ppm) 1.86-1.94 (m, 2H), 2.39-2.44 (m, 2H), 2.44-2.53 (m, 4H), 2.66-2.86 (m, 2H), 3.68-3.77 (m, 4H), 3.88 (s, 3H), 6.16 (d, 1H), 7.11 (d, 1H).

Synthesis of 5-(3-morpholinopropyl)furan-2-carboxylic Acid

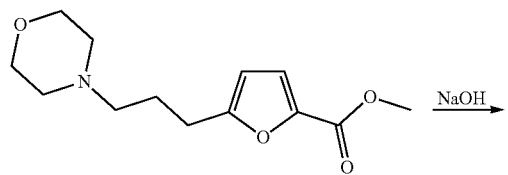

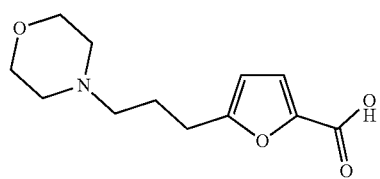

To a solution of methyl 5-(3-morpholinopropyl)furan-2-carboxylate (1.5 g, 6.0 mmol) in methanol (20 ml) was added a solution of NaOH (0.6 g, 2 eq) in water (5 ml) and the reaction mixture was stirred at room temperature overnight. Methanol was removed in vacuo, the residue was diluted with water and acidified to pH 1. The acidified solution was evaporated in vacuo to dryness and treated with isopropanol. Solid salts were filtered, and filtrate was evaporated in vacuo to dryness. Yield 1.4 g (73.5%). LCMS (C18 column 20×2 mm, particle size 2.5 μm, pore size 100A, water-acetonitrile+0.1% TFA, gradient 5 to 87% for 3 min, retention time 0.28 min. MS (ESI) m/z 240.4 [MH]+, retention time 0.67 min. MS (ESI) m/z 240.1 [MH]+. $^1$H-NMR (400 MHz, CDCl$_3$): δ (ppm) 1.98-2.15 (m, 2H), 2.68-2.80 (m, 2H), 2.91-3.17 (m, 4H), 3.37-3.49 (m, 2H), 3.75-3.99 (m, 4H), 6.41 (s, 1H), 7.14 (s, 1H), 11.26 (br.s, 1H), 12.91 (br.s, 1H).

Synthesis of N-methoxy-N-methyl-5-(3-morpholinopropyl)furan-2-carboxamide

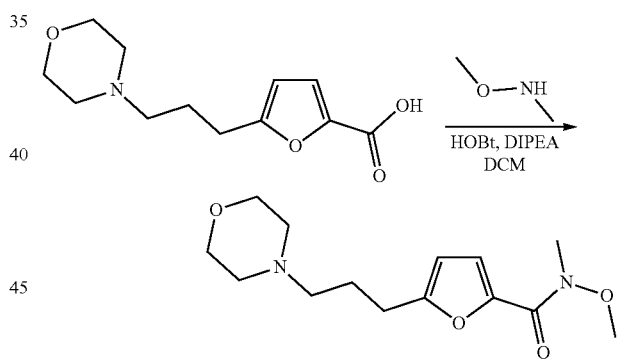

To a stirred mixture of 5-(3-morpholinopropyl)furan-2-carboxylic acid (1.2 g, 4.0 mmol, 1 eq), N,O-dimethylhydroxylamine (0.55 g, 1.3 eq), HOBt (0.65 g, 1.1 eq) and DIPEA (3 ml, 4 eq) in CH$_2$Cl$_2$ (25 ml) at 5° C. EDCl (0.83 g, 1 eq) was added. The reaction was stirred for 15 h at ambient temperature. The mixture was washed with water and brine. The organic layer was dried over anhydrous Na$_2$SO$_4$, filtered, and solvents were concentrated under reduced pressure. The product was used without further purification. Yield 0.9 g (73%). LCMS (C18 column 20×2 mm, particle size 2.5 μm, pore size 100A, water-acetonitrile+0.1% TFA, gradient 5 to 87% for 3 min, retention time 0.34 min. MS (ESI) m/z 283.6 [MH]+, retention time 0.85 min. MS (ESI) m/z 283.5 [MH]+. $^1$H-NMR (400 MHz, CDCl$_3$): δ (ppm) 1.86-1.94 (m, 2H), 2.40-2.53 (m, 6H), 2.71-2.81 (m, 2H), 3.34 (s, 3H), 3.68-3.74 (m, 4H), 3.76 (s, 3H), 6.15 (d, 1H), 7.07 (d, 1H).

Synthesis of 1-(5-(3-morpholinopropyl)furan-2-yl)ethan-1-one

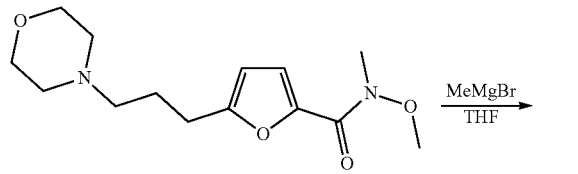

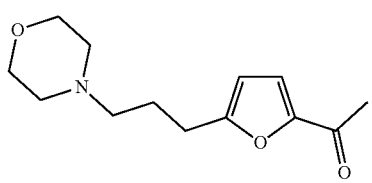

A solution of N-methoxy-N-methyl-5-(3-morpholinopropyl)furan-2-carboxamide (0.9 g, 3.0 M, 1 eq) in THF (50 ml) was cooled to 5° C. and methylmagnesium bromide solution in THF (3.4 M, 2.8 ml, 3 eq), was added. The reaction mixture was stirred at 5° C. for 2 h, poured into aq $NH_4Cl$ and extracted with $Et_2O$. The combined extracts were dried over $Na_2SO_4$, and evaporated. The titular product was used in the next step without purification. Yield 0.6 g (79%). LCMS (C18 column 20×2 mm, particle size 2.5 μm, pore size 100A, water-acetonitrile+0.1% TFA, gradient 5 to 87% for 3 min, retention time 0.3 min, MS (ESI) m/z 238.4 [MH]+, retention time 0.8 min, MS (ESI) m/z 238.4 [MH]+. $^1$H-NMR (400 MHz, $CDCl_3$): δ (ppm) 1.88-1.96 (m, 2H), 2.35-2.64 (m, 9H), 2.73-2.79 (m, 2H), 3.66-3.90 (m, 4H), 6.20 (s, 1H), 7.11 (s, 1H).

Synthesis of INT-23 ((2E,2'E)-2,2'-(1-(5-(3-morpholinopropyl)furan-2-yl)ethane-1,2-diylidene)bis(N-ethylhydrazine-1-carbothioamide))

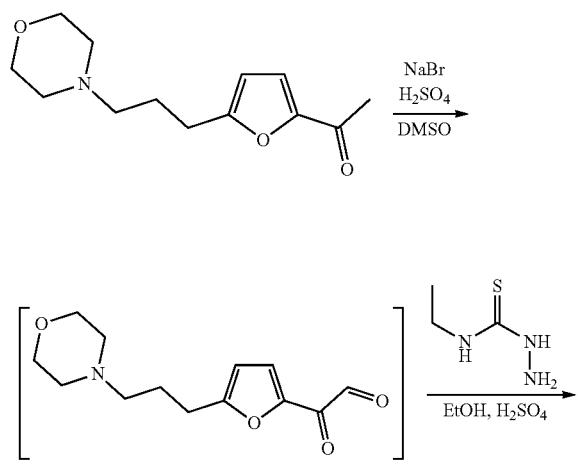

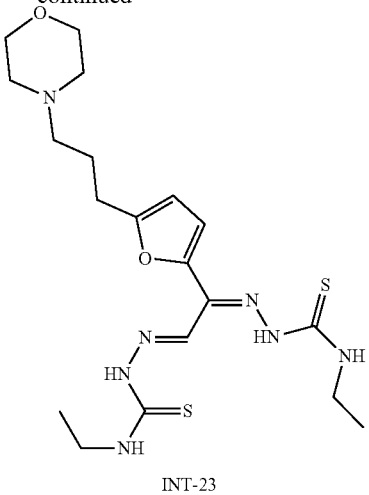

A mixture of 1-(5-(3-morpholinopropyl)furan-2-yl)ethan-1-one (0.5 g, 2.0 mmol, 1 eq), NaBr (0.11 g, 0.5 eq), and DMSO (1.1 ml) was heated to 85° C., then $H_2SO_4$ (6 drops) was added (foaming), and the reaction temperature began to rise. The reaction was heated to 110-115° C. until the formation of dimethyl sulfide has stopped, and the reaction mixture became viscous. The formed viscous substance was dissolved in EtOH and to the solution added ethyl thiosemicarbazide (0.5 g, 2 eq). The reaction mixture was refluxed for 2 hours, then cooled to room temperature, solvents were evaporated in vacuo, the residue was dissolved in water (25 ml), neutralized with aq.sat. $Na_2CO_3$ and extracted with EtOAc (3×50 ml). The organic layer was separated, dried over $Na_2SO_4$, filtered, and solvents were evaporated. The residue was treated with water. The formed precipitate was filtered and washed with EtOH to give the pure titular compound. Yield 0.2 g (21%). LCMS (C18 column 20×2 mm, particle size 2.5 μm, pore size 100A, water-acetonitrile+0.1% TFA, gradient 5 to 87% for 3 min, retention time 1.18 min, MS (ESI) m/z 454.4 [MH]+.

Synthesis of INT-27 ((2E,2'E)-2,2'-(1-(5-(3-morpholinopropyl)furan-2-yl)ethane-1,2-diylidene)bis(N-methylhydrazine-1-carbothioamide))

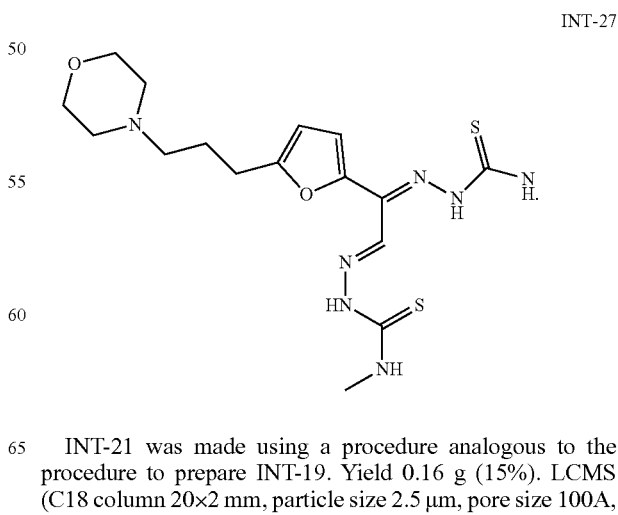

INT-21 was made using a procedure analogous to the procedure to prepare INT-19. Yield 0.16 g (15%). LCMS (C18 column 20×2 mm, particle size 2.5 μm, pore size 100A, water-acetonitrile+0.1% TFA, gradient 5 to 87% for 3 min, retention time 1.02 min, MS (ESI) m/z 426.3 [MH]+.

Synthesis of Compound 23

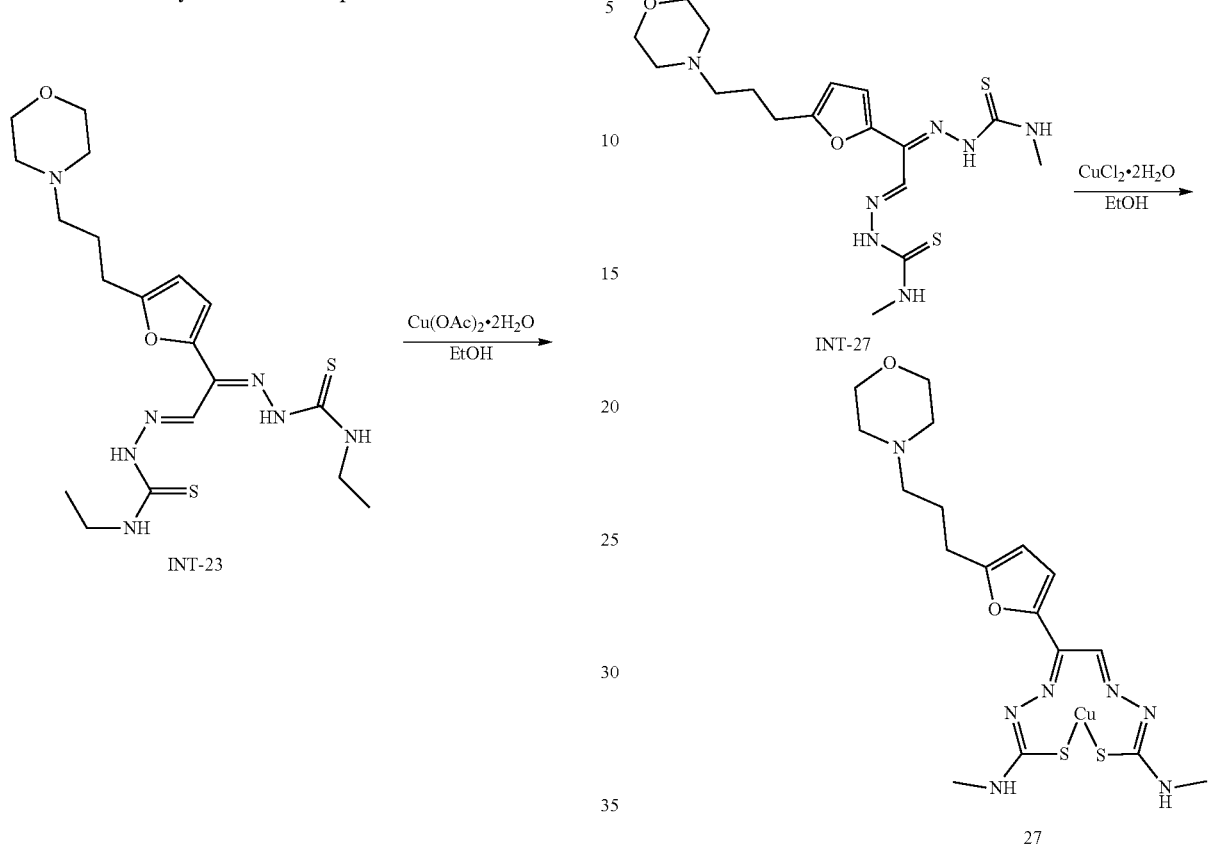

CuCl$_2$·2H$_2$O (0.034 g, 1 eq) was added to the thiosemicarbazone 6 (0.09 g, 0.2 mmol, 1 eq) in ethanol. The mixture was stirred for 15 h at ambient temperature. The formed complex was precipitated out of the mixture as a red-brown powder. The precipitate was collected by filtration, washed with water, methanol, and diethyl ether, and then dried in vacuo. Yield 0.05 g (48%). LCMS (C18 column 20×2 mm, particle size 2.5 μm, pore size 100A, water-acetonitrile+ 0.1% TFA, gradient 5 to 87% for 4 min, retention time 1.56 min). MS (ESI) m/z 515.4 [MH]+.

Synthesis of Compound 27

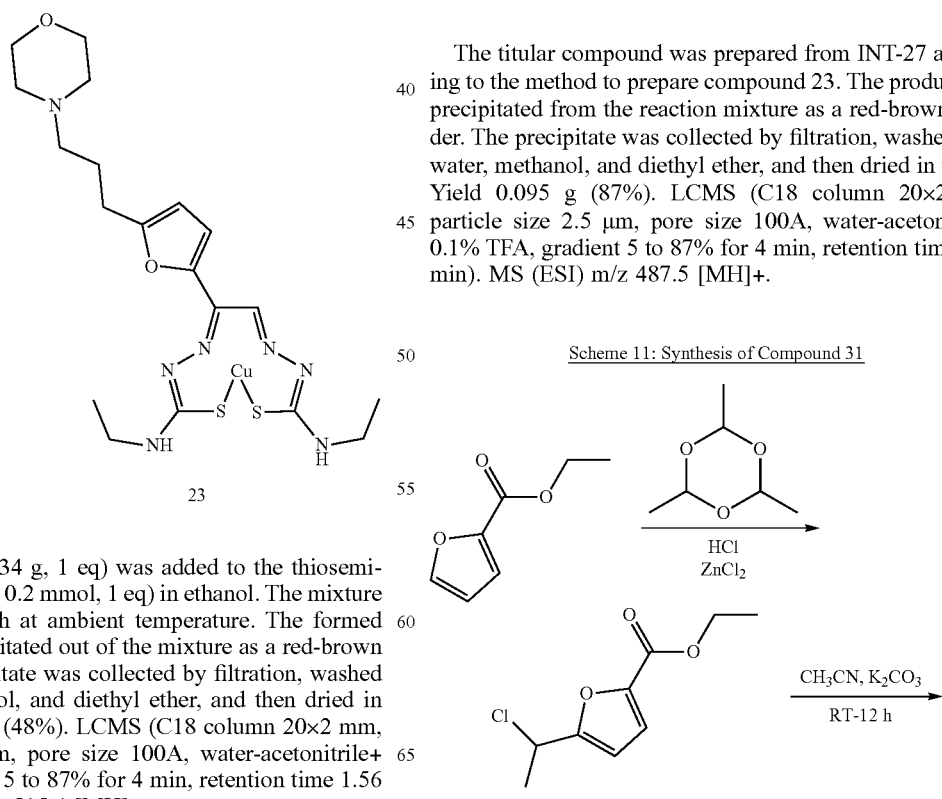

The titular compound was prepared from INT-27 according to the method to prepare compound 23. The product was precipitated from the reaction mixture as a red-brown powder. The precipitate was collected by filtration, washed with water, methanol, and diethyl ether, and then dried in vacuo. Yield 0.095 g (87%). LCMS (C18 column 20×2 mm, particle size 2.5 μm, pore size 100A, water-acetonitrile+ 0.1% TFA, gradient 5 to 87% for 4 min, retention time 1.46 min). MS (ESI) m/z 487.5 [MH]+.

Scheme 11: Synthesis of Compound 31

205
-continued

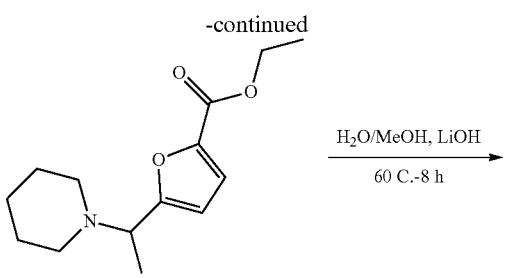

H₂O/MeOH, LiOH
60 C.-8 h →

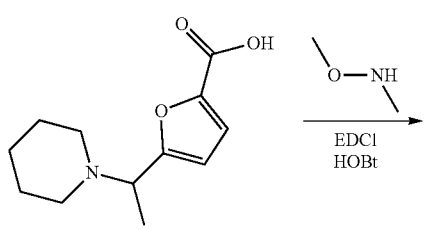

t-BuLi →

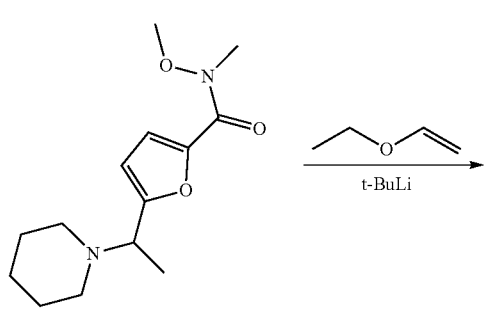

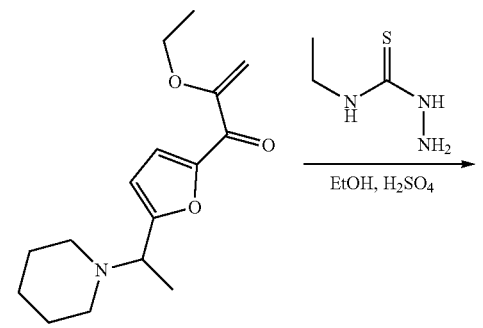

CuCl₂
EtOH →

INT-31

206
-continued

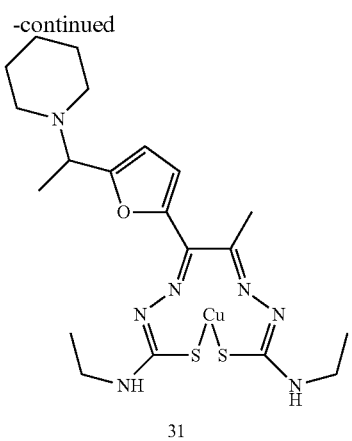

31

Synthesis of ethyl 5-(1-chloroethyl)furan-2-carboxylate

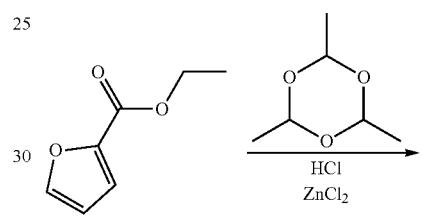

HCl
ZnCl₂ →

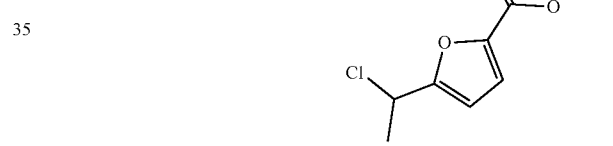

Zinc chloride (3.9 g, 28.6 mmol) was added to a solution of paraldehyde (17.3 g, 131.1 mmol) and ethyl 2-furoate (16.9 g, 120.7 mmol) in chloroform (36 mL). Hydrogen chloride was passed through the mixture during 5 h at 25-30° C. under vigorous stirring. Then, 250 mL of chloroform was added; the reaction mixture was washed with water (2×30 mL), and then dried over calcium chloride. Solvent was removed under reduced pressure, to give the target product 1 that was used for the next step without additional purification. Yield 35 g (31%). ¹H-NMR (400 MHz, CDCl₃): δ (ppm) 1.18 (d, 3H), 1.33 (t, 3H), 4.32 (q, 2H), 5.09 (q, 1H), 6.41 (d, 1H), 7.07 (d, 1H).

Synthesis of ethyl 5-(1-(piperidin-1-yl)ethyl)furan-2-carboxylate

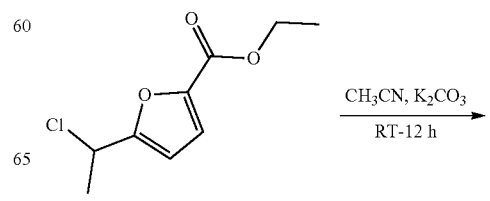

CH₃CN, K₂CO₃
RT-12 h →

-continued

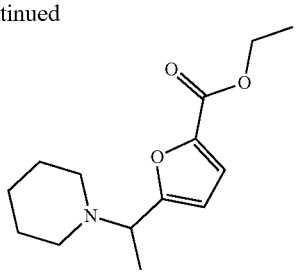

A suspension of ethyl 5-(1-chloroethyl)furan-2-carboxylate (5.0 g, 24.6 mmol), piperidine (4.2 g, 49.2 mmol), and potassium carbonate (6.8 g, 49.2 mmol) in $CH_3CN$ (100 ml) was stirred at 50° C. for 12 h. The mixture was cooled to room temperature. $CH_3CN$ was removed by evaporation, and the residue was diluted with 20 ml of aq. 2N sodium carbonate and extracted with dichloromethane. The organic phase was washed with brine, dried over $Na_2SO_4$, filtered, and evaporated to dryness. The residue was purified by column chromatography (silica gel, eluent 100% DCM to 5% MeOH) to afford the titular product that was used for the next step without additional purification. Yield 5.1 g (82%). LCMS (C18 column 20×2 mm, particle size 2.5 μm, pore size 100A, water-acetonitrile+0.1% TFA, gradient 5 to 87% for 3 min, retention time 0.90 min). MS (ESI) m/z 252.1 [MH]+. $^1$H-NMR (400 MHz, $CDCl_3$): δ (ppm) 1.36 (d, 2H), 1.38 (d, 3H), 1.44 (d, 3H), 1.58 (q, 4H), 2.35-2.41 (m, 2H), 2.48-2.53 (m, 2H), 3.81 (q, 1H), 4.35 (q, 2H), 6.29 (d, 1H), 7.17 (d, 1H).

Synthesis of
5-(1-(piperidin-1-yl)ethyl)furan-2-carboxylic Acid

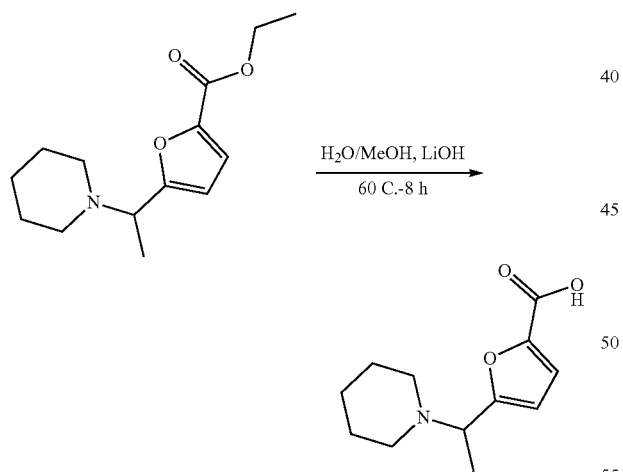

A solution of ethyl 5-(1-(piperidin-1-yl)ethyl)furan-2-carboxylate (5.1 g, 20.3 mmol) in MeOH (50 ml) was added to a 20% aqueous solution of LiOH (1.6 g, 60.9 mmol). The reaction mixture was stirred for 8 h at 60° C. Then the solvent was removed by freeze-drying, and the corresponding crude product was used for the next step without further purification. Yield 4.4 g (83%). LCMS (C18 column 20×2 mm, particle size 2.5 μm, pore size 100A, water-acetonitrile+0.1% TFA, gradient 5 to 87% for 3 min, retention time 0.65 min). MS (ESI) m/z 224.4 [MH]+. $^1$H-NMR (400 MHz, DMSO-$d_6$): δ (ppm) 1.33-1.38 (m, 2H), 1.43 (d, 3H), 1.57-1.61 (m, 4H), 2.07 (s, 1H), 2.60-2.63 (m, 2H), 4.07 (q, 2H), 4.32 (s, 1H), 6.52 (d, 1H), 7.04 (d, 1H).

Synthesis of N-methoxy-N-methyl-5-(1-(piperidin-1-yl)ethyl)furan-2-carboxamide

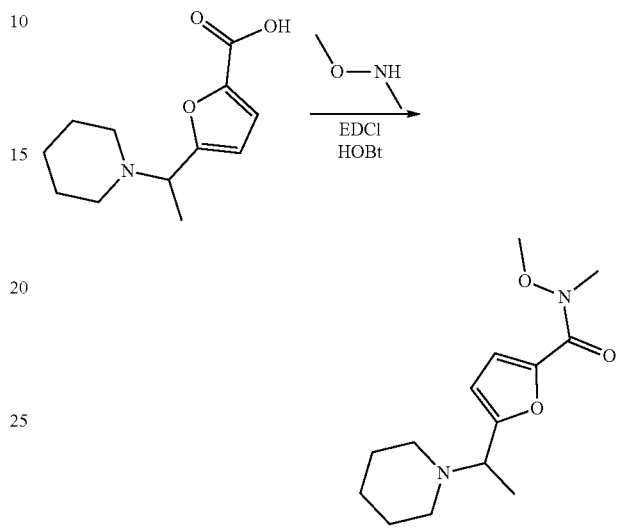

To a stirred mixture of 5-(1-(piperidin-1-yl)ethyl)furan-2-carboxylic acid (5.2 g, 20 mmol), N,O-dimethylhydroxylamine (2.3 g, 24 mmol), HOBt (3.2 g, 24 mmol) and TEA (12 ml, 90 mol) in DCM (80 ml) at 4° C. was added EDCl (4.6 g, 24 mmol) and the mixture was then stirred overnight at r.t. The mixture was washed with water (15 ml), brine (100 ml). The organic layer was dried over anhydrous $Na_2SO_4$ and then concentrated under reduced pressure. The residue was purified by column chromatography (silica gel, eluent 100% DCM to 5% MeOH) to afford crude product. Yield 2.2 g (42%). LCMS (C18 column 20×2 mm, particle size 2.5 μm, pore size 100A, water-acetonitrile+0.1% TFA, gradient 5 to 87% for 3 min, retention time 0.77 min). MS (ESI) m/z 267.5 [MH]+. $^1$H-NMR (400 MHz, $CDCl_3$): δ (ppm) 1.38 (t, 2H), 1.46 (d, 3H), 1.54-1.60 (m, 4H), 2.36-2.41 (m, 2H), 2.50-2.55 (m, 2H), 3.33 (s, 3H), 3.78 (s, 3H), 3.81-3.87 (m, 1H), 6.26 (dd, 1H), 7.23 (dd, 1H).

Synthesis of 2-ethoxy-1-(5-(1-(piperidin-1-yl)ethyl)furan-2-yl)prop-2-en-1-one

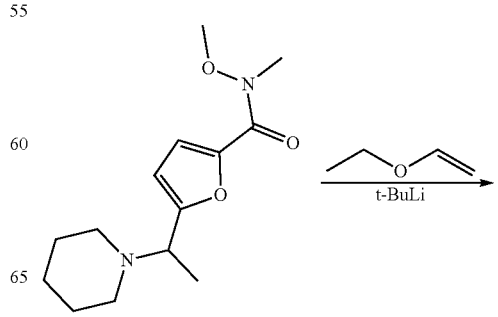

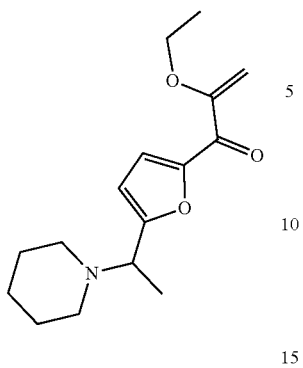

A solution of ethyl vinyl ether (1.8 g, 24.4 mmol) in tetrahydrofuran (50 ml) was cooled to −78° C., and tert-butyllithium (1.7M, 14.0 ml, 22.2 mmol) in pentane was added. The mixture was warmed to 0° C. over 1 h period, stirred for 45 min, and cooled down to −30° C. To the mixture a solution of N-methoxy-N-methyl-5-(1-(piperidin-1-yl)ethyl)furan-2-carboxamide (1.0 g, 3.7 mmol) in THF (15 ml) was added, and the mixture was stirred at 0° C. for 4 h. The progress of the reaction was monitored by TLC. The mixture was poured into aq. NH$_4$Cl (100 ml) and extracted with Et$_2$O (3×50 ml). The combined extracts were dried over Na$_2$SO$_4$. The product solution was then decanted, and the solvent was removed under reduced pressure giving the titular compound that was used for the next step without further purification. Yield 1.1 g (87%). LCMS (C18 column 20×2 mm, particle size 2.5 μm, pore size 100A, water-acetonitrile+0.1% TFA, gradient 5 to 87% for 3 min, retention time 0.97 min). MS (ESI) m/z 278.6 [MH]+. $^1$H-NMR (400 MHz, CDCl$_3$): δ (ppm) 1.38 (t, 2H), 1.46 (d, 3H), 1.47 (d, 3H), 1.55-1.63 (m, 4H), 2.38-2.44 (m, 2H), 2.51-2.56 (m, 2H), 3.81-3.87 (m, 1H), 3.93 (q, 2H), 4.58 (d, 1H), 5.33 (d, 1H), 6.31 (d, 1H), 7.47 (d, 1H).

Synthesis of INT-31 ((2Z,2'E)-2,2'-(1-(5-(1-(piperidin-1-yl)ethyl)furan-2-yl)propane-1,2-diylidene)bis(N-ethylhydrazine-1-carbothioamide))

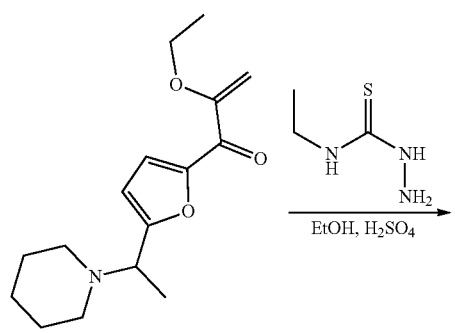

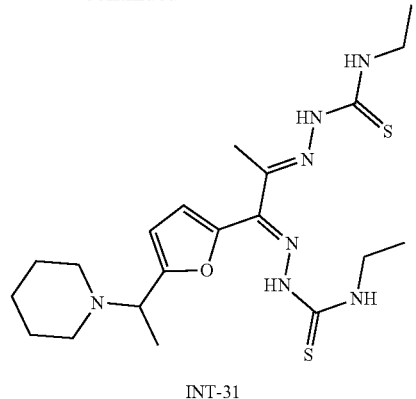

INT-31

2-Ethoxy-1-(5-(1-(piperidin-1-yl)ethyl)furan-2-yl)prop-2-en-1-one (1.1 g, 3.7 mmol) was dissolved in EtOH (30 ml), ethyl thiosemicarbazide (0.9 g, 7.4 mmol) and 3 drops of H$_2$SO$_4$ were added. The stirred reaction mixture was heated to reflux for 4 h and then maintained overnight at ambient temperature. The progress of the reaction was monitored by TLC (CCl$_4$/EtOAc 7:3). The precipitate was filtered, washed with EtOH, water, Et$_2$O, and dried. Yield 0.5 g (33%). LCMS (C18 column 20×2 mm, particle size 2.5 μm, pore size 100A, water-acetonitrile+0.1% TFA, gradient 5 to 87% for 3 min, retention time 1.17 min). MS (ESI) m/z 452.0 [MH]+. $^1$H-NMR (400 MHz, DMSO-d$_6$): δ (ppm) 1.07 (t, 3H), 1.15 (t, 3H), 1.38-1.55 (m, 3H), 1.60-1.66 (m, 4H), 1.70-1.79 (m, 4H), 2.33 (s, 3H), 3.41-3.48 (m, 2H), 3.55-3.63 (m, 2H), 4.72 (s, 1H), 6.91 (dd, 1H), 7.14 (dd, 1H), 7.73 (t, 1H), 8.73 (t, 1H), 9.08-9.78 (m, 2H), 10.48 (s, 1H), 10.55 (s, 1H).

Synthesis of INT-24 ((2E,2'E)-2,2'-(1-(5-(morpholinomethyl)furan-2-yl)propane-1,2-diylidene)bis(N-ethylhydrazine-1-carbothioamide))

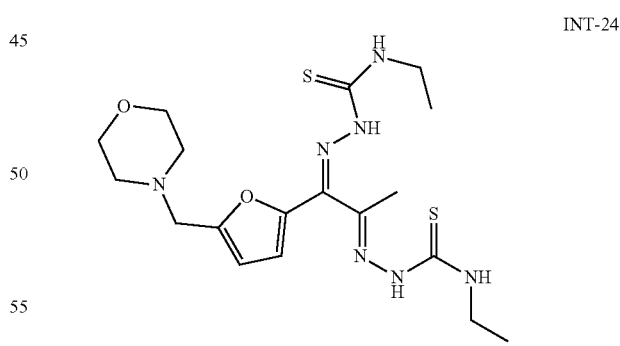

INT-24

INT-24 was made using a procedure analogous to the procedure to prepare INT-31. Yield 4.6 g (63%). LCMS (C18 column 20×2 mm, particle size 2.5 μm, pore size 100A, water-acetonitrile+0.1% TFA, gradient 5 to 87% for 3 min, retention time 1.01 min). MS (ESI) m/z 440.5 [MH]+. $^1$H-NMR (400 MHz, DMSO-d$_6$): δ (ppm) 1.10 (t, 3H), 1.16 (t, 3H), 1.39, 2.32 (s, 3H), 2.35-2.47 (m, 4H), 3.42-3.58 (m, 2H), 3.58-3.76 (m, 8H), 6.61 (s, 1H), 7.01 (s, 1H), 7.78 (br.s, 1H), 8.70 (br.s, 1H), 10.40 (s, 1H), 10.51 (s, 1H).

Synthesis of INT-32 ((2E,2'E)-2,2'-(1-(5-(morpholinomethyl)furan-2-yl)propane-1,2-diylidene)bis(N-methylhydrazine-1-carbothioamide))

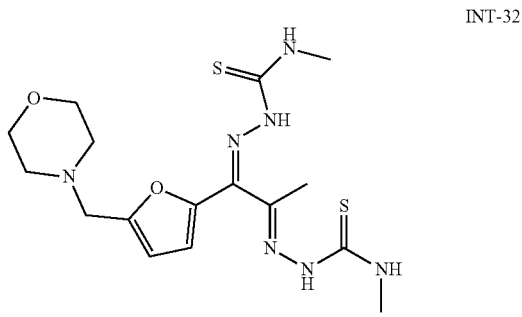 [SMILES: CNC(=S)N/N=C(C)/C(=N\NC(=S)NC)c1ccc(CN2CCOCC2)o1]

INT-32

INT-32 was made using a procedure analogous to the procedure to prepare INT-31. Yield 0.25 g (54%). LCMS (C18 column 20×2 mm, particle size 2.5 μm, pore size 100A, water-acetonitrile+0.1% TFA, gradient 5 to 87% for 3 min, retention time 1.06 min. MS (ESI) m/z 412.4 [MH]+. $^1$H-NMR (400 MHz, DMSO-d$_6$): δ (ppm) 2.33 (s, 3H), 2.92-3.00 (m, 4H), 3.03-3.10 (m, 4H), 3.12-3.45 (m, 4H), 3.70-3.82 (m, 4H), 4.5 (s, 3H), 6.9 (s, 1H), 7.07 (s, 1H), 7.71 (s, 1H), 8.67 (s, 1H), 10.39 (s, 1H), 10.54 (s, 1H).

Synthesis of INT-37 ((2E,2'E)-2,2'-(1-(5-((4-methylpiperazin-1-yl)methyl)furan-2-yl)propane-1,2-diylidene)bis(N-ethylhydrazine-1-carbothioamide))

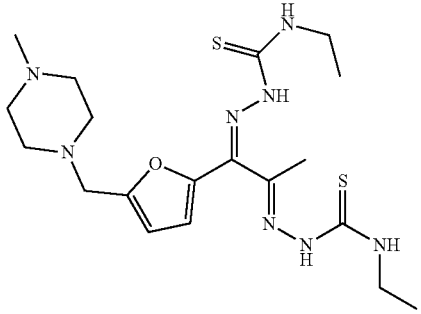

INT-37

INT-37 was made using a procedure analogous to the procedure to prepare INT-31. Yield 0.9 g (61.5%). LCMS (C18 column 20×2 mm, particle size 2.5 μm, pore size 100A, water-acetonitrile+0.1% TFA, gradient 5 to 87% for 3 min, retention time 1.06 min). MS (ESI) m/z 453.5 [MH]+. $^1$H-NMR (400 MHz, DMSO-d$_6$): δ (ppm) 1.10 (t, 3H), 1.16 (t, 3H), 1.39, 2.32 (s, 3H), 2.55-2.74 (m, 2H), 2.79-2.89 (M, 4H), 3.42-3.59 (m, 6H), 3.62 (q, 2H), 3.97 (s, 3H), 6.71 (s, 1H), 7.08 (s, 1H), 7.76 (s, 1H), 8.74 (s, 1H), 10.44 (s, 1H), 10.54 (s, 1H).

Synthesis of INT-39 ((2Z,2'E)-2,2'-(1-(5-(1-morpholinoethyl)furan-2-yl)propane-1,2-diylidene)bis(N-ethylhydrazine-1-carbothioamide))

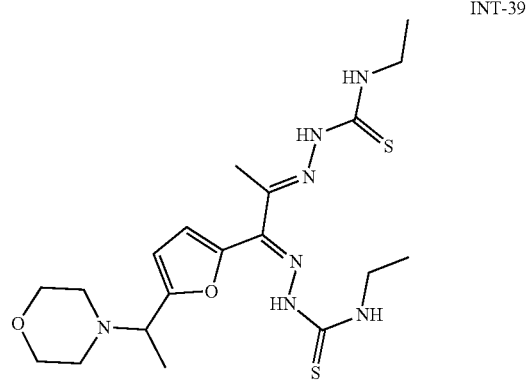 [SMILES: CCNC(=S)N/N=C(/C(C)=N/NC(=S)NCC)c1ccc(C(C)N2CCOCC2)o1]

INT-39

INT-39 was made using a procedure analogous to the procedure to prepare INT-31. Yield 0.2 g (20%). LCMS (C18 column 20×2 mm, particle size 2.5 μm, pore size 100A, water-acetonitrile+0.1% TFA, gradient 5 to 87% for 3 min, retention time 1.11 min). MS (ESI) m/z 454.3 [MH]+. $^1$H-NMR (400 MHz, DMSO-d$_6$): δ (ppm) 1.10 (t, 3H), 1.16 (t, 3H), 1.39 (dd, 3H), 2.32 (s, 3H), 2.34-2.38 (m, 2H), 2.47-2.49 (m, 2H), 3.48-3.53 (m, 2H), 3.56-3.65 (m, 4H), 3.60-3.65 (m, 2H), 3.84-3.90 (m, 1H), 6.56 (dd, 1H), 7.06 (dd, 1H), 7.87 (t, 1H), 8.70 (t, 1H), 10.47 (d, 1H), 10.59 (d, 1H).

Synthesis of Compound 31

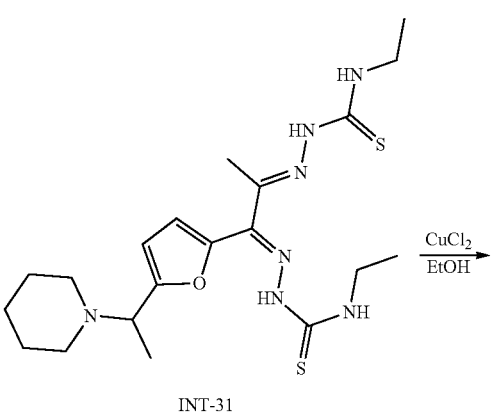

INT-31

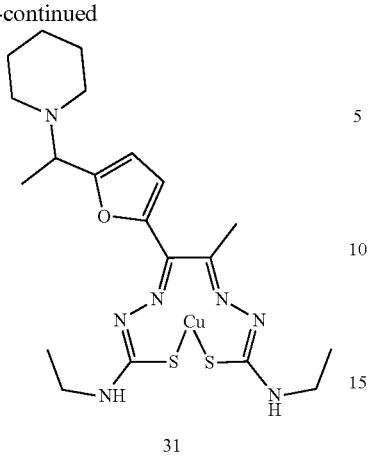

31

CuCl$_2$·2H$_2$O (0.2 g, 2.4 mmol) was added to compound 6 (0.5 g, 1.2 mmol) in 30 ml of ethanol. The mixture was stirred for 15 h at ambient temperature. The formed precipitate was collected by filtration after cooling, washed with water (2×50 ml), ethanol (2×50 ml), and copious amounts of diethyl ether (5×50 ml), and then dried in vacuo Yield 0.4 g (75%). LCMS (C18 column 20×2 mm, particle size 2.5 μm, pore size 100A, water-acetonitrile+0.1% TFA, gradient 5 to 87% for 4 min, retention time 1.66 min). MS (ESI) m/z 513.3 [MH]+.

Synthesis of Compound 24

The titular compound was prepared from INT-24 according to the method to prepare compound 31. The product precipitated out of the reaction mixture as a red-brown powder. The precipitate was collected by filtration, washed with water, methanol, and diethyl ether, and then dried in vacuo. Yield 4.7 g (92%). LCMS (C18 column 20×2 mm, particle size 2.5 μm, pore size 100A, water-acetonitrile+0.1% TFA, gradient 5 to 87% for 4 min, retention time 1.48 min). MS (ESI) m/z 501.3 [MH]+.

Synthesis of Compound 32

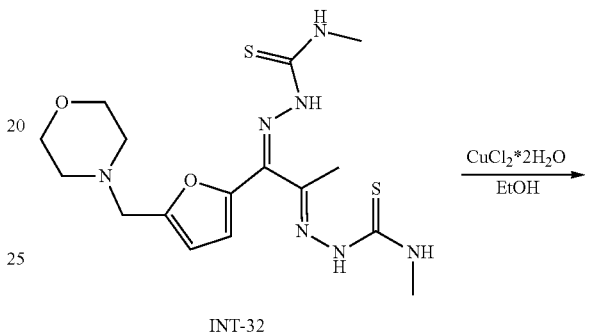

INT-32

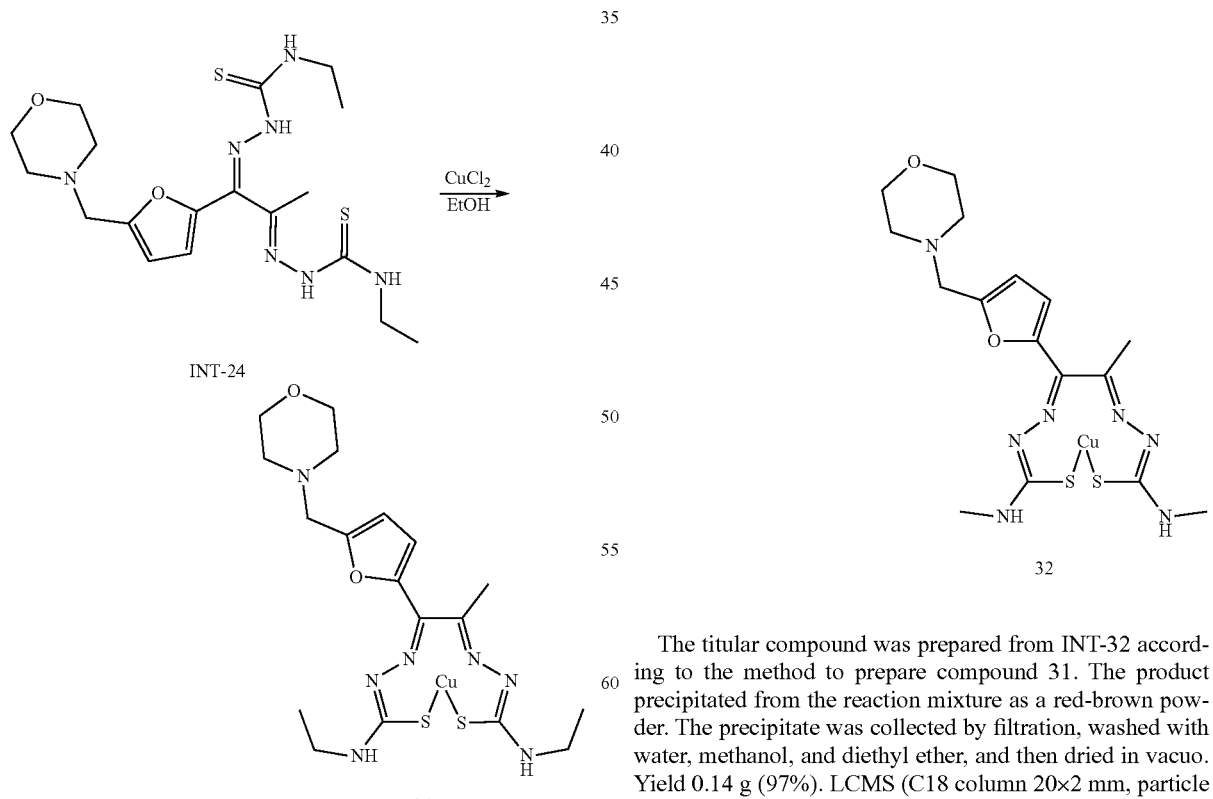

INT-24

24

32

The titular compound was prepared from INT-32 according to the method to prepare compound 31. The product precipitated from the reaction mixture as a red-brown powder. The precipitate was collected by filtration, washed with water, methanol, and diethyl ether, and then dried in vacuo. Yield 0.14 g (97%). LCMS (C18 column 20×2 mm, particle size 2.5 μm, pore size 100A, water-acetonitrile+0.1% TFA, gradient 5 to 87% for 4 min, retention time 1.38 min). MS (ESI) m/z 473.0 [MH]+.

215

Synthesis of Compound 37

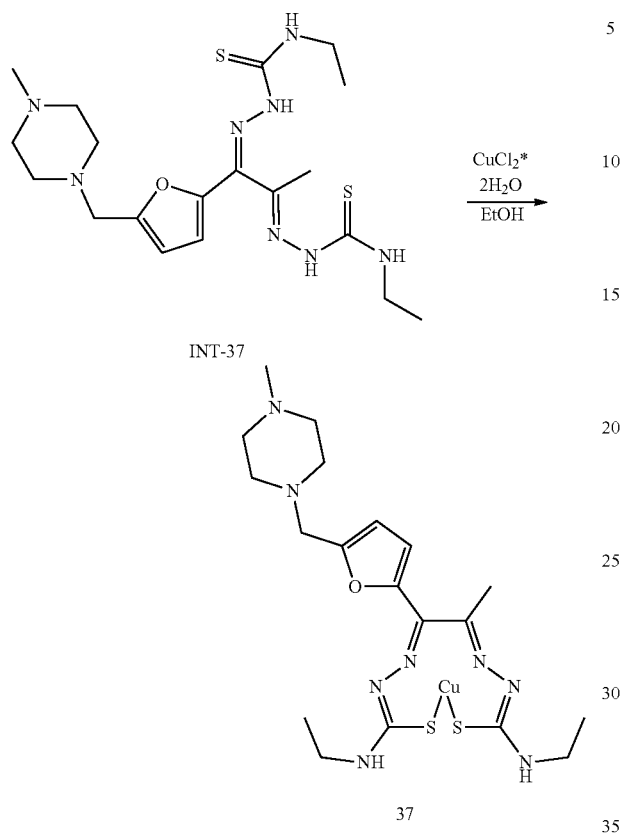

INT-37

37

The titular compound was prepared from INT-37 according to the method to prepare compound 31. The product precipitated from the reaction mixture as a red-brown powder. The precipitate was collected by filtration, washed with water, methanol, and diethyl ether, and then dried in vacuo. Yield 0.8 g (96%). LCMS (C18 column 20×2 mm, particle size 2.5 μm, pore size 100A, water-acetonitrile+0.1% TFA, gradient 5 to 87% for 4 min, retention time 1.52 min). MS (ESI) m/z 514.3 [MH]+.

Synthesis of Compound 39

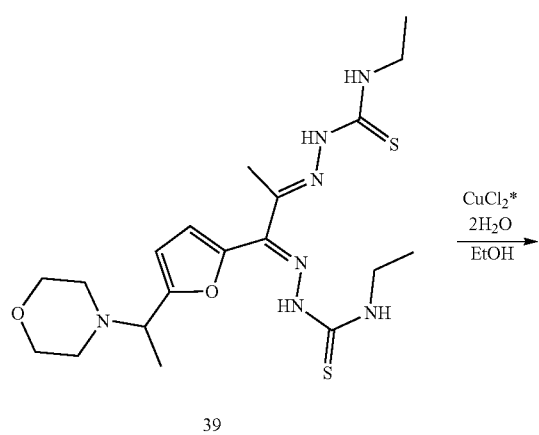

39

216

-continued

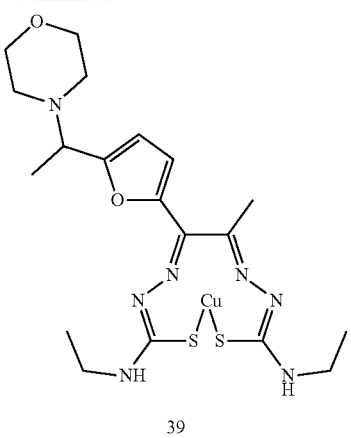

39

The titular compound was prepared from INT-39 according to the method to prepare compound 31. The product precipitated from the reaction mixture as a red-brown powder. The precipitate was collected by filtration, washed with water (2×50 ml), ethanol (2×50 ml), and copious amounts of diethyl ether (5×50 ml), and then dried in vacuo. Yield 0.15 g (86%). LCMS (C18 column 20×2 mm, particle size 2.5 μm, pore size 100A, water-acetonitrile+0.1% TFA, gradient 5 to 87% for 4 min, retention time 1.57 min). MS (ESI) m/z 515.2 [MH]+.

Scheme 12: Synthesis of Compound 26

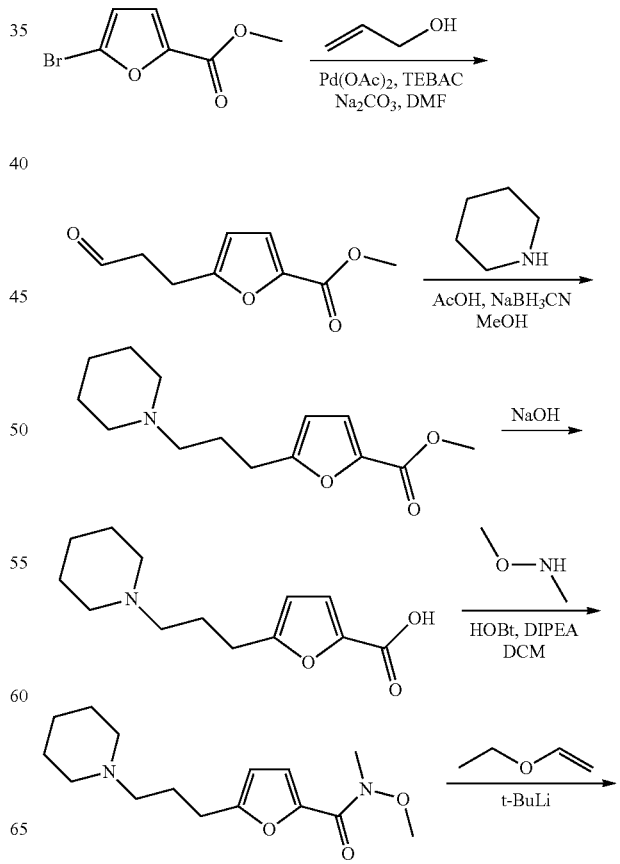

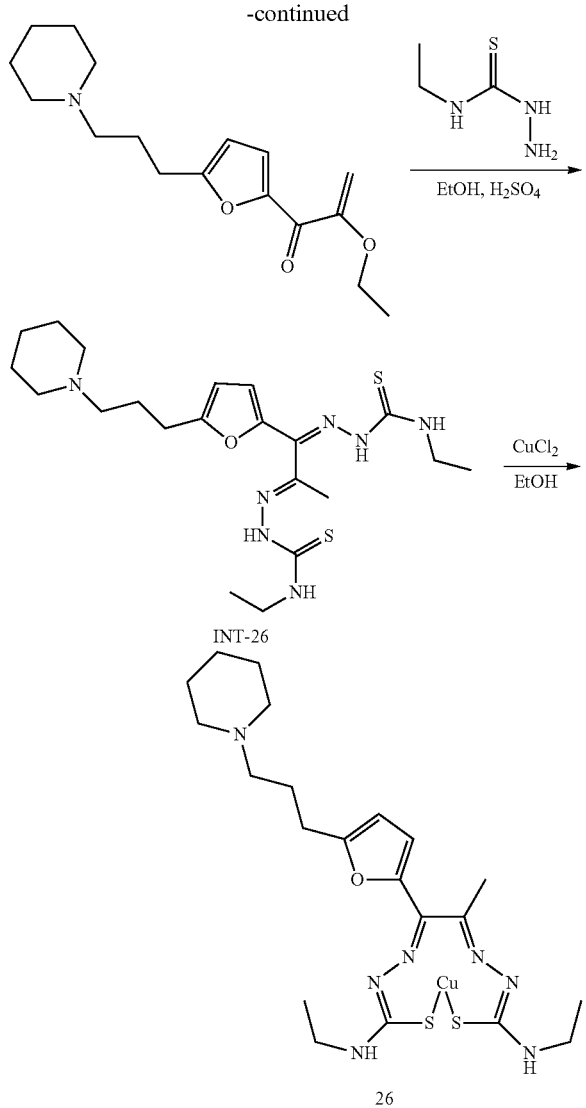

INT-26

26

Synthesis of methyl 5-(3-oxopropyl)furan-2-carboxylate

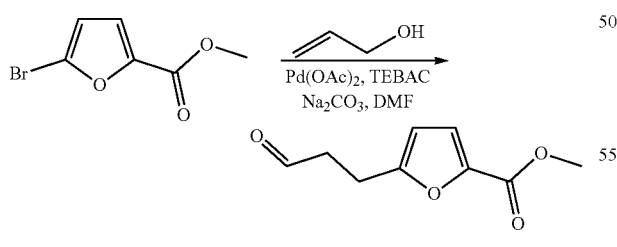

Under inert atmosphere, 5-bromo-methyl furoate (5.7 g, 28 mmol, 1 eq) was dissolved in 550 ml DMF. Allyl alcohol (2.28 g, 1.4 eq), Pd(OAc)$_2$ (0.189 g, 0.03 eq), TEBAC (6.39 g, 1 eq) and Na$_2$CO$_3$ (6.85 g, 2 eq) were added. Then the mixture was stirred at 80° C. for 2 h. Upon completion, the resulting mixture was filtered through Celite, filtrate was concentrated in vacuo at ≤40° C., diluted with ethyl acetate, washed with brine, concentrated to dryness, and the residue was purified by column chromatography (silica gel, ethyl acetate-hexane 1:3). Yield 2.7 g (53%). $^1$H-NMR (400 MHz, CDCl$_3$): δ (ppm) 2.89 (dd, 2H), 3.05 (dd, 2H), 3.89 (s, 3H), 6.19 (s, 1H), 7.09 (s, 1H), 9.83 (s, 1H).

Synthesis of methyl 5-(3-(piperidin-1-yl)propyl)furan-2-carboxylate

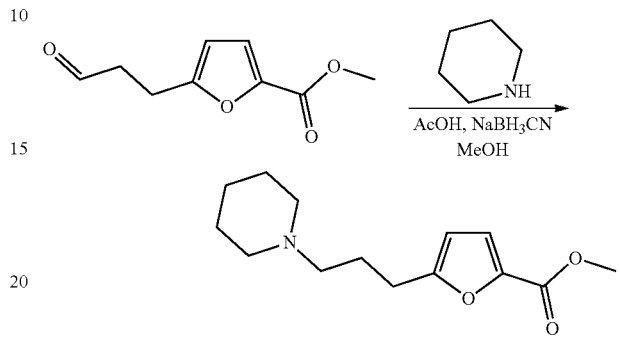

methyl 5-(3-oxopropyl)furan-2-carboxylate (2.7 g, 15 mmol, 1 eq) was dissolved in MeOH (150 ml), and molecular sieves (4.4 g) were added to the solution. After stirring for 15 min, the mixture was cooled down to 0° C. To the stirred solution of aldehyde 1 a solution of piperidine (1.9 g, 1.5 eq) and acetic acid (1.8 g, 2 eq) in methanol (70 ml) was added at 0° C. After stirring for 2 min, NaBH$_3$CN (2.8 g, 3 eq) was added. The resulting mixture was stirred for 14 h allowing to warm up from 0° C. to room temperature on its own accord. Then the reaction mixture was diluted with DCM, filtered through Celite, and filtrate was washed with aq. NaHCO$_3$. The aqueous phase was extracted with DCM twice. The organic phase was dried over Na$_2$SO$_4$, filtered, and concentrated in vacuo to dryness. The residue was purified by column chromatography (SiO$_2$, eluting first with EtOAc/hexane, gradient 1:5 to 1:3 to 1:1 to 100% EtOAc, and afterwards with CH$_2$Cl$_2$/MeOH, 10:1). Yield 1.8 g (49%). LCMS (C18 column 20×2 mm, particle size 2.5 μm, pore size 100A, water-acetonitrile+0.1% TFA, gradient 5 to 87% for 3 min, retention time 0.94 min. MS (ESI) m/z 252.4 [MH]+. $^1$H-NMR (400 MHz, CDCl$_3$): δ (ppm) 1.45-1.66 (m, 2H), 1.78-1.88 (m, 2H), 1.96-2.17 (m, 4H), 2.57-2.88 (m, 6H), 3.41-3.56 (m, 2H), 3.88 (s, 3H), 6.23 (s, 1H), 7.09 (s, 1H).

Synthesis of 5-(3-(piperidin-1-yl)propyl)furan-2-carboxylic Acid

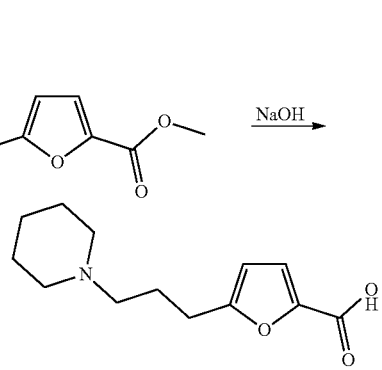

To a stirred solution of methyl 5-(3-(piperidin-1-yl)propyl)furan-2-carboxylate (1.8 g, 7.0 mmol) in methanol (20 ml) a solution of NaOH (0.73 g, 2.6 eq) in water (25 ml) was added. The reaction mixture was stirred for 15 h at ambient temperature. Methanol was removed in vacuo, the residue diluted with water and acidified to pH 1. The acidified solution was evaporated to dryness and residue was treated with isopropanol. Solid salts were filtered, and filtrate was evaporated to dryness. Yield 1.35 g (68%). LCMS (C18 column 20×2 mm, particle size 2.5 μm, pore size 100A, water-acetonitrile+0.1% TFA, gradient 5 to 87% for 3 min, retention time 0.35 min. MS (ESI) m/z 238.3 [MH]+, retention time 0.86 min. MS (ESI) m/z 238.3 [MH]+.

Synthesis of N-methoxy-N-methyl-5-(3-(piperidin-1-yl)propyl)furan-2-carboxamide

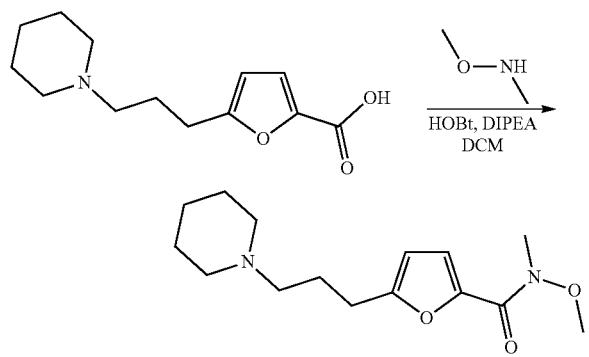

To a mixture of methyl 5-(3-(piperidin-1-yl)propyl)furan-2-carboxylate (1.35 g, 5.0M, 1 eq), N,O-dimethylhydroxylamine (0.72 g, 1.3 eq), HOBt (0.83 g, 1.1 eq), and DIPEA (3.3 ml, 4 eq) in CH$_2$Cl$_2$ (25 ml) at 5° C. EDCl (1.04 g, 1.1 eq) was added. The reaction then was stirred for 15 h at ambient temperature. The mixture was washed with water and brine. The organic layer was dried over anhydrous Na$_2$SO$_4$, filtered, and concentrated under reduced pressure. Product was used further without purification. Yield 0.4 g (29%). LCMS (C18 column 20×2 mm, particle size 2.5 μm, pore size 100A, water-acetonitrile+0.1% TFA, gradient 5 to 87% for 3 min, retention time 0.35 min. MS (ESI) m/z 281.5 [MH]+, retention time 0.93 min. MS (ESI) m/z 281.3 [MH]+. $^1$H-NMR (400 MHz, CDCl$_3$): δ (ppm) 1.38-1.48 (m, 2H), 1.55-1.64 (m, 4H), 1.86-1.97 (m, 2H), 2.31-2.48 (m, 6H), 2.69-2.81 (m, 2H), 3.34 (s, 3H), 3.76 (s, 3H), 6.14 (d, 1H), 7.07 (d, 1H).

Synthesis of 2-ethoxy-1-(5-(3-(piperidin-1-yl)propyl)furan-2-yl)prop-2-en-1-one

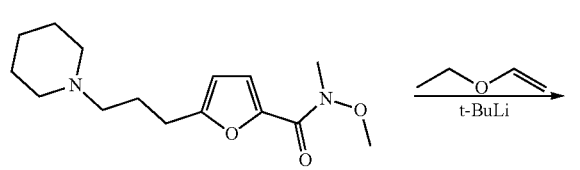

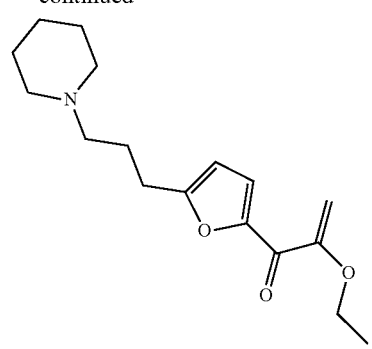

A solution of ethyl vinyl ether (0.72 g, 0.96 ml, 7 eq) in dry tetrahydrofuran (20 mL) was cooled to −78° C., and tert-butyllithium (1.7M, 5 ml, 6q) in pentane was added. The mixture was warmed to 0° C. over 1 h period, stirred for 45 min, and cooled down to −30° C. A solution of N-methoxy-N-methyl-5-(3-(piperidin-1-yl)propyl)furan-2-carboxamide (0.4 g, 1.4 mmol, 1 eq) in THF was added, and the mixture was stirred at 0° C. for 4 h. The progress of the reaction was monitored by TLC. The mixture was poured into aq NH$_4$Cl and extracted with Et$_2$O. The combined extracts were dried over Na$_2$SO$_4$, filtered, and evaporated in vacuo. The product was used for the next step without additional purification. Yield 0.39 g (93%). LCMS (C18 column 20×2 mm, particle size 2.5 μm, pore size 100A, water-acetonitrile+0.1% TFA, gradient 5 to 87% for 3 min, retention time 1.04 min. MS (ESI) m/z 292.3 [MH]+. $^1$H-NMR (400 MHz, CDCl$_3$): δ (ppm) 1.18-1.48 (m, 5H), 1.50-1.64 (m, 4H), 1.82-2.03 (m, 2H), 2.27-2.48 (m, 6H), 2.62-2.78 (m, 2H), 3.84-3.98 (m, 2H), 3.92 (q, 2H), 4.56 (s, 1H), 5.31 (s, 1H), 6.21 (d, 1H), 7.44 (d, 1H).

Synthesis of INT-26 ((2E,2'E)-2,2'-(1-(5-(3-(piperidin-1-yl)propyl)furan-2-yl)propane-1,2-diylidene)bis(N-ethylhydrazine-1-carbothioamide))

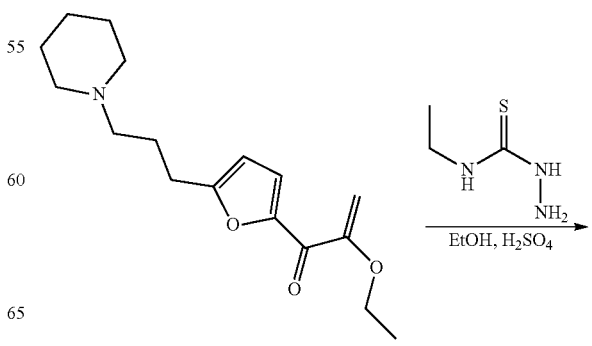

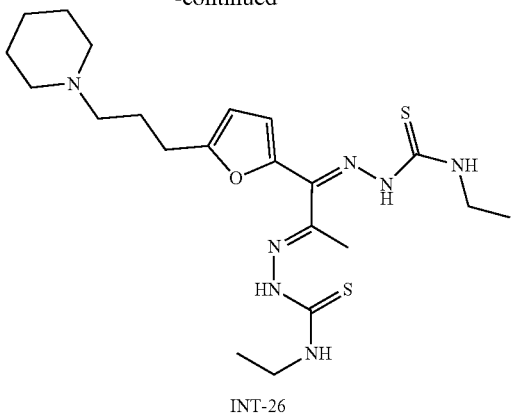

INT-26

2-ethoxy-1-(5-(3-(piperidin-1-yl)propyl)furan-2-yl)prop-2-en-1-one (0.41 g, 1.45 mmol, 1 eq) was dissolved in EtOH (10 ml), ethyl thiosemicarbazide (0.33 g, 2 eq) and 1 drop of $H_2SO_4$ were added. Reaction mixture was stirred and heated to reflux for 4 h and then maintained for 15 h at ambient temperature. The formed precipitate was filtered, washed with EtOH, water, $Et_2O$ and crystallized from EtOH. Yield 0.08 g (12%). LCMS (C18 column 20×2 mm, particle size 2.5 μm, pore size 100A, water-acetonitrile+0.1% TFA, gradient 5 to 87% for 3 min, retention time 1.21 min. MS (ESI) m/z 466.5 [MH]+. $^1$H-NMR (400 MHz, $CDCl_3$): δ (ppm) 1.11 (t, 3H), 1.16 (t, 1H), 1.53-1.91 (m, 6H), 2.05-2.15 (m, 2H), 2.32 (s, 3H), 2.77-2.89 (m, 2H), 3.05-3.19 (m, 2H), 3.35-3.45 (m, 4H), 3.53 (q, 2H), 3.62 (q, 2H), 6.49 (s, 1H), 7.05 (s, 1H), 7.78 (s, 1H), 8.72 (s, 1H), 10.48 (s, 1H), 10.52 (s, 1H).

Synthesis of INT-28 ((2Z,2'E)-2,2'-(1-(5-(3-morpholinopropyl)furan-2-yl)butane-2,3-diylidene)bis(N-ethylhydrazine-1-carbothioamide))

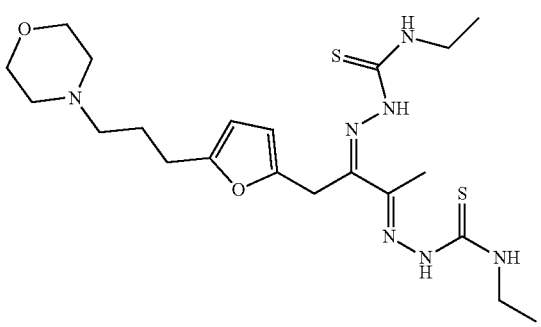

INT-28

INT-28 was made using a procedure analogous to the procedure to prepare INT-26. Yield 0.18 g (50%). LCMS (C18 column 20×2 mm, particle size 2.5 μm, pore size 100A, water-acetonitrile+0.1% TFA, gradient 5 to 87% for 3 min, retention time 1.15 min. MS (ESI) m/z 468.5 [MH]+. $^1$H-NMR (400 MHz, $CDCl_3$): δ (ppm) 1.11 (t, 3H), 1.16 (t, 1H), 2.04-2.14 (m, 2H), 2.32 (s, 3H), 2.77-2.86 (m, 2H), 3.17-3.26 (m, 2H), 3.39-3.73 (m, 10H), 3.91-4.04 (m, 2H), 6.5 (s, 1H), 7.06 (s, 1H), 7.8 (s, 1H), 8.72 (s, 1H), 10.47 (s, 1H), 10.52 (s, 1H).

Synthesis of Compound 26

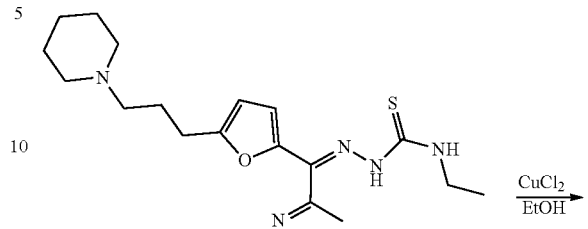

26

$CuCl_2·2H_2O$ (0.026 g, 1 eq) was added to thiosemicarbazone 6 (0.07 g, 0.15 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.054 g (68%). LCMS (C18 column 20×2 mm, particle size 2.5 μm, pore size 100A, water-acetonitrile+0.1% TFA, gradient 5 to 87% for 4 min, retention time 1.76 min). MS (ESI) m/z 527.5 [MH]+.

Synthesis of Compound 28

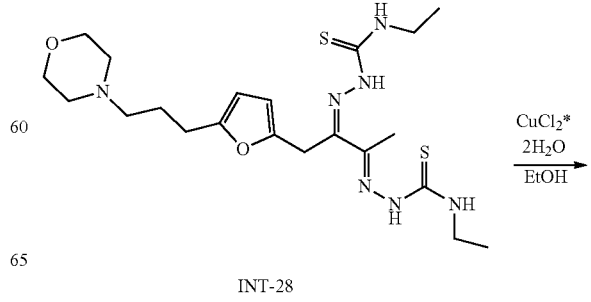

INT-28

223

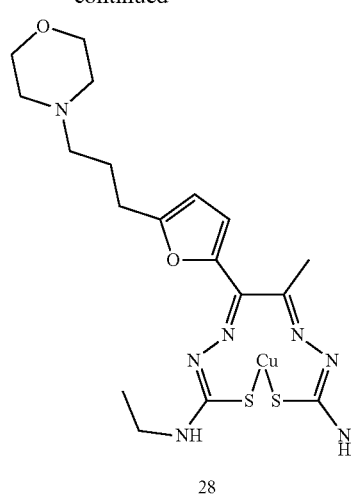

28

The titular compound was prepared from INT-28 according to the method to prepare compound 26. The product precipitated from the reaction mixture as a red-brown powder. The precipitate was collected by filtration, washed with water, methanol, and diethyl ether, and then dried in vacuo. Yield 0.14 g (85%). LCMS (C18 column 20×2 mm, particle size 2.5 μm, pore size 100A, water-acetonitrile+0.1% TFA, gradient 5 to 87% for 4 min, retention time 1.65 min). MS (ESI) m/z 529.0 [MH]+.

Scheme 13: Synthesis of Compound 29

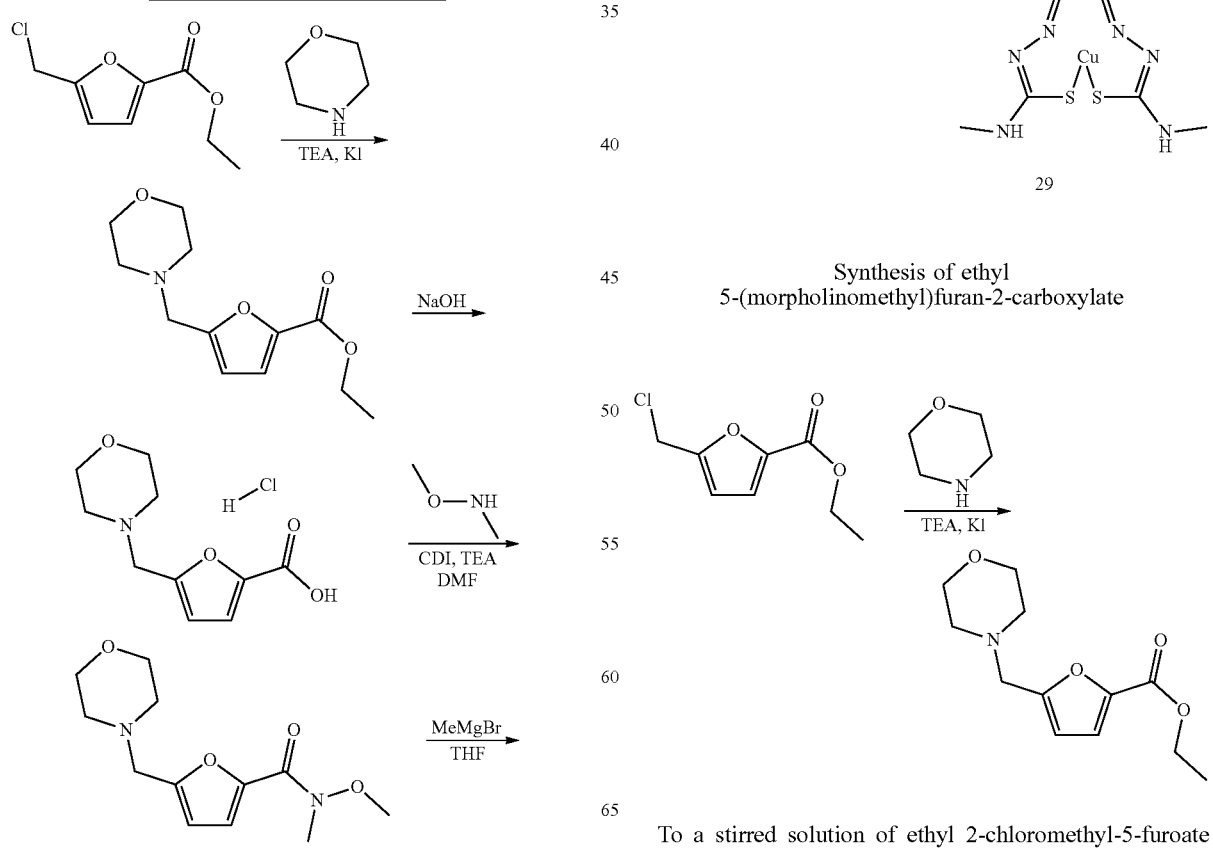

224

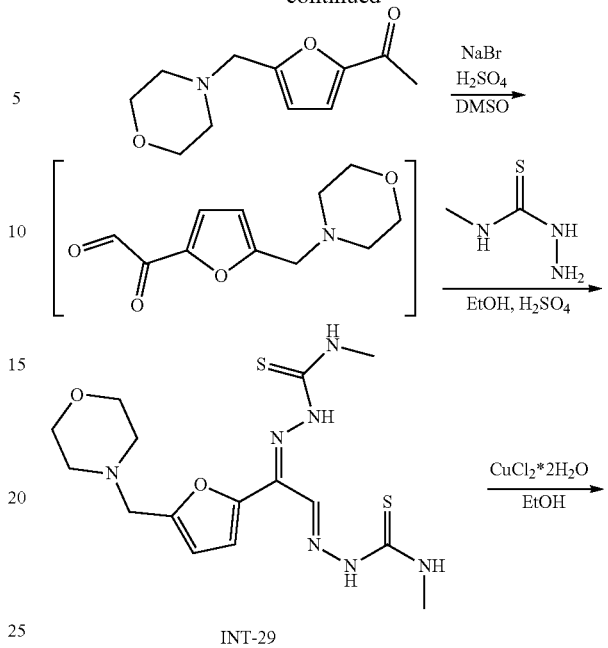

INT-29

29

Synthesis of ethyl 5-(morpholinomethyl)furan-2-carboxylate

To a stirred solution of ethyl 2-chloromethyl-5-furoate (9.6 g, 50 mmol) in CH$_2$Cl$_2$ (200 ml) were added morpholine (4.43 g, 4.4 ml, 1 eq), triethylamine (10.3 g, 14 ml, 2 eq) and KI (0.1 g). The reaction mixture was stirred for 15 h at room temperature, then washed with water (3×50 ml). The organic layer was separated, dried over Na₂SO₄, filtered, and solvents were evaporated. Yield 8 g (66%). LCMS (C18 column 20×2 mm, particle size 2.5 μm, pore size 100A, water-acetonitrile+0.1% TFA, gradient 5 to 87% for 3 min, retention time 0.82 min). MS (ESI) m/z 240.1 [MH]+. ¹H-NMR (400 MHz, CDCl₃): δ (ppm) 1.38 (t, 3H), 2.50-2.55 (m, 4H), 3.62 (s, 3H), 3.70-3.75 (m, 4H), 4.37 (q, 2H), 6.36 (d, 1H), 7.13 (d, 1H).

Synthesis of
5-(morpholinomethyl)furan-2-carboxylate
Hydrochloride

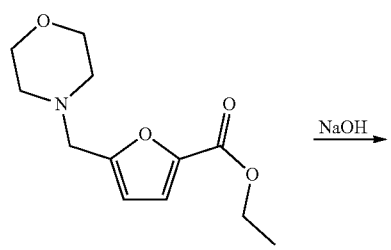

To a solution of ethyl 5-(morpholinomethyl)furan-2-carboxylate (4.6 g, 20 mmol) in methanol (100 ml) a solution of NaOH (2 g, 2 eq) in water (10 ml) was added, and the reaction mixture was stirred for 15 h at ambient temperature. Methanol was stripped off in vacuo, the residue diluted with water and acidified to pH 1. The acidified solution was evaporated to dryness and the residue was treated with isopropanol. Solid salts were filtered, and filtrate was evaporated to dryness. Yield 4.4 g (86%). LCMS (C18 column 20×2 mm, particle size 2.5 μm, pore size 100A, water-acetonitrile+0.1% TFA, gradient 5 to 87% for 3 min, retention time 0.29 min). MS (ESI) m/z 212.3 [MH]+.

Synthesis of N-methoxy-N-methyl-5-(morpholinomethyl)furan-2-carboxamide

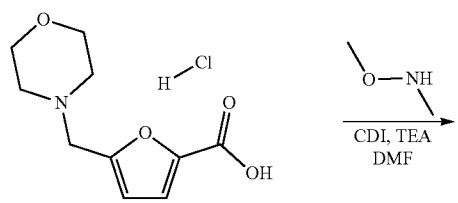

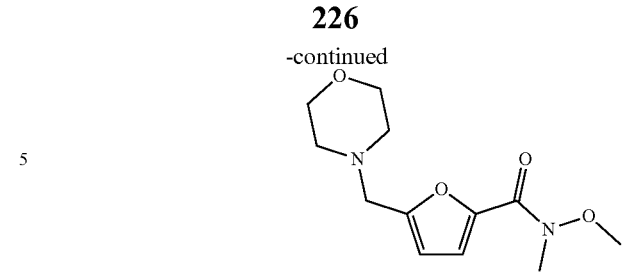

A mixture of 5-(morpholinomethyl)furan-2-carboxylate hydrochloride (7.1 g, 29 mmol) and 1,1'-carbonyldiimidazole (5.57 g, 1.2 eq) in DMF (47 mL) was stirred at 60° C. for 30 min. Then N,O-dimethylhydroxylamine (3.35 g, 1.2 eq) and triethylamine (3.2 g, 4.4 ml, 1.1 eq) were added. The mixture was stirred at 80° C. for 16 h, then the volatiles were evaporated in vacuo, and the residue was partitioned between EtOAc and H₂O. The organic layer was separated, dried over Na₂SO₄, filtered, and solvents were evaporated. Yield 7 g (96%). LCMS (C18 column 20×2 mm, particle size 2.5 μm, pore size 100A, water-acetonitrile+0.1% TFA, gradient 5 to 87% for 3 min, retention time 0.28 min. MS (ESI) m/z 255.6 [MH]+, retention time 0.78 min. MS (ESI) m/z 255.6 [MH]+. ¹H-NMR (400 MHz, CDCl₃): δ (ppm) 2.52-2.55 (m, 4H), 3.35 (s, 3H), 3.64 (s, 2H), 3.71-3.74 (m, 4H), 6.36 (d, 1H), 6.71 (d, 1H).

Synthesis of
1-(5-(morpholinomethyl)furan-2-yl)ethan-1-one

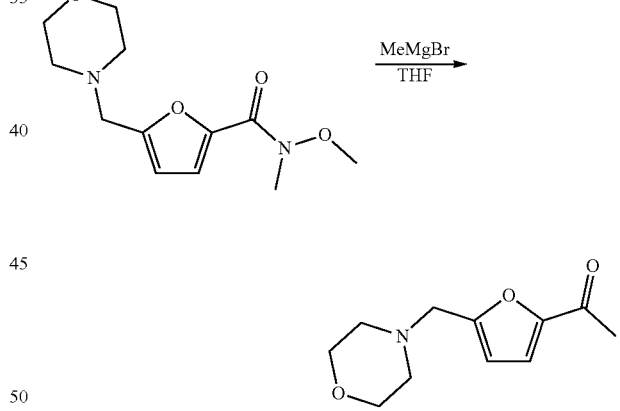

A solution of N-methoxy-N-methyl-5-(morpholinomethyl)furan-2-carboxamide (3.4 g, 13 mmol, 1 eq) in THF (150 ml) was cooled to 5° C. and methylmagnesium bromide solution in THF (1.4 M, 26 ml, 3 eq) was added. The reaction mixture was stirred at 5° C. for 2 h, poured into aq NH₄Cl and extracted with Et₂O. The combined extracts were dried over Na₂SO₄, filtered, and solvents were evaporated. Compound 3 was used for the next step without purification. Yield 2.6 g (93%). LCMS (C18 column 20×2 mm, particle size 2.5 μm, pore size 100A, water-acetonitrile+0.1% TFA, gradient 5 to 87% for 3 min, retention time 0.31 min, MS (ESI) m/z 210.1 [MH]+, retention 0.67 min, MS (ESI) m/z 210.3 [MH]+. ¹H-NMR (400 MHz, DMSO-d₆): δ (ppm) 2.34-2.45 (m, 7H), 3.49-3.63 (m, 6H), 6.54 (s, 1H), 7.46 (s, 1H).

Synthesis of INT-29 ((2E,2'E)-2,2'-(1-(5-(morpholinomethyl)furan-2-yl)ethane-1,2-diylidene)bis(N-methylhydrazine-1-carbothioamide))

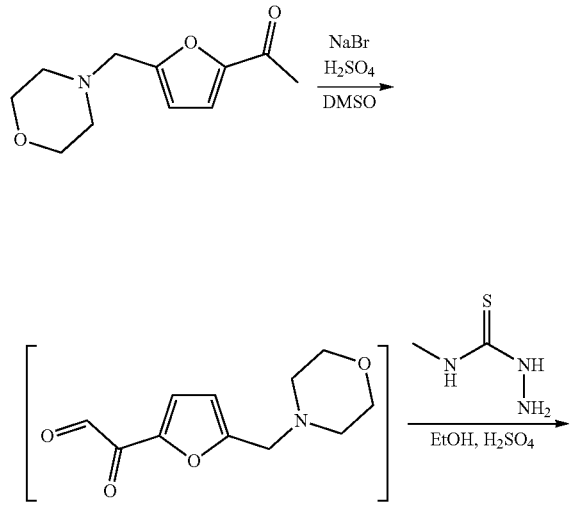

Synthesis of INT-38 ((2E,2'E)-2,2'-(1-(5-(morpholinomethyl)furan-2-yl)ethane-1,2-diylidene)bis(N-ethylhydrazine-1-carbothioamide))

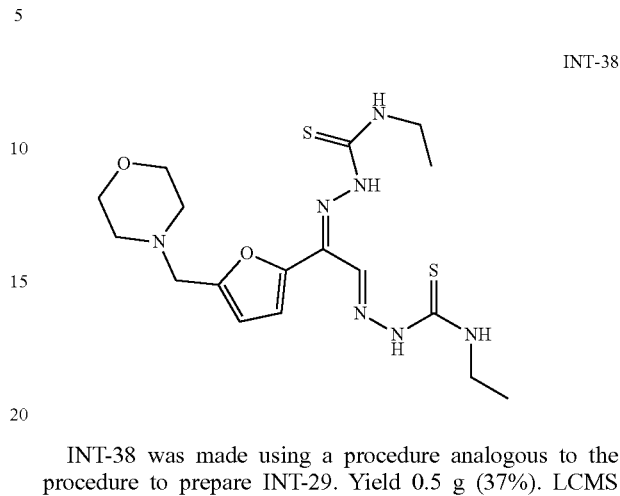

INT-38 was made using a procedure analogous to the procedure to prepare INT-29. Yield 0.5 g (37%). LCMS (C18 column 20×2 mm, particle size 2.5 μm, pore size 100A, water-acetonitrile+0.1% TFA, gradient 5 to 87% for 3 min, retention time 1.12 min, MS (ESI) m/z 426.0 [MH]+.

Synthesis of Compound 29

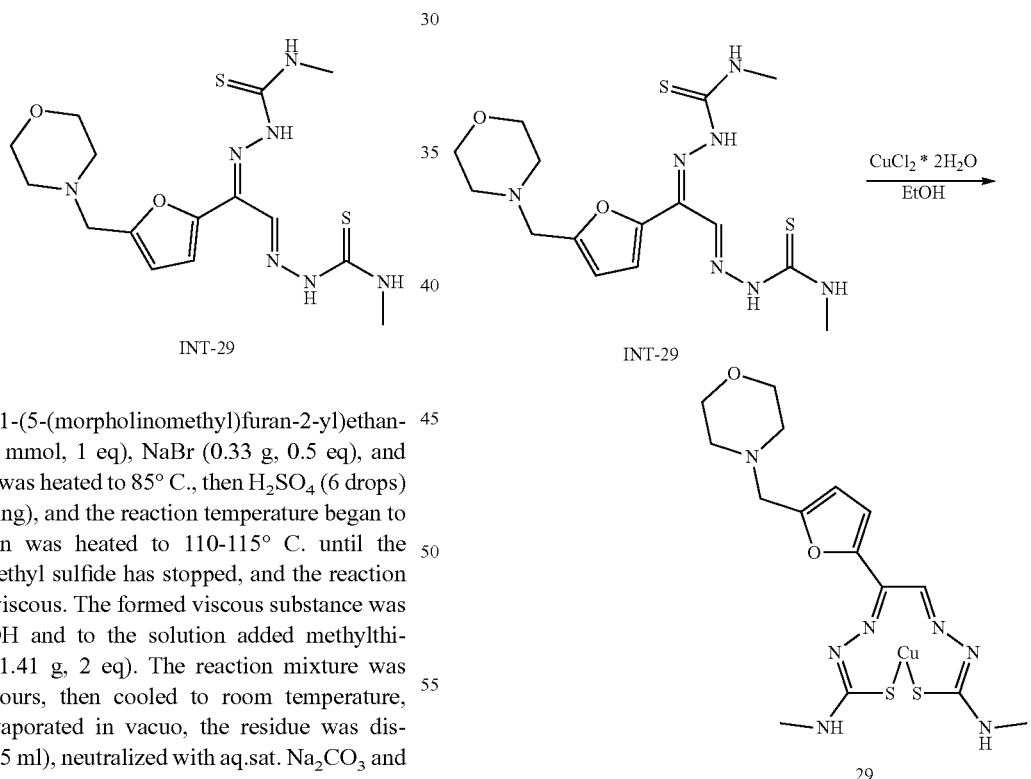

A mixture of 1-(5-(morpholinomethyl)furan-2-yl)ethan-1-one (1.4 g, 7.0 mmol, 1 eq), NaBr (0.33 g, 0.5 eq), and DMSO (3.45 ml) was heated to 85° C., then $H_2SO_4$ (6 drops) was added (foaming), and the reaction temperature began to rise. The reaction was heated to 110-115° C. until the formation of dimethyl sulfide has stopped, and the reaction mixture became viscous. The formed viscous substance was dissolved in EtOH and to the solution added methylthiosemicarbazide (1.41 g, 2 eq). The reaction mixture was refluxed for 2 hours, then cooled to room temperature, solvents were evaporated in vacuo, the residue was dissolved in water (25 ml), neutralized with aq.sat. $Na_2CO_3$ and extracted with EtOAc (3×50 ml). The organic layer was separated, dried over $Na_2SO_4$, filtered, and solvents were evaporated. The residue was treated with water. The formed precipitate was filtered and washed with EtOH to give the pure titular compound. Yield 0.7 g (26%). LCMS (C18 column 20×2 mm, particle size 2.5 μm, pore size 100A, water-acetonitrile+0.1% TFA, gradient 5 to 87% for 3 min, retention time 1.08 min, MS (ESI) m/z 398.3 [MH]+.

$CuCl_2 \cdot 2H_2O$ (0.062 g, 1 eq) was added to thiosemicarbazone 6 (0.14 g, 0.4 mmol, 1 eq) in ethanol. The mixture was stirred for 15 h at ambient temperature. The formed complex was precipitated out of the mixture as a red-brown powder. The precipitate was collected by filtration, washed with water, methanol, and diethyl ether, and then dried in vacuo. Yield 0.055 g (32%). LCMS (C18 column 20×2 mm, particle size 2.5 μm, pore size 100A, water-acetonitrile+ 0.1% TFA, gradient 5 to 87% for 4 min, retention time 1.29 min). MS (ESI) m/z 459.5 [MH]+.

Synthesis of Compound 38

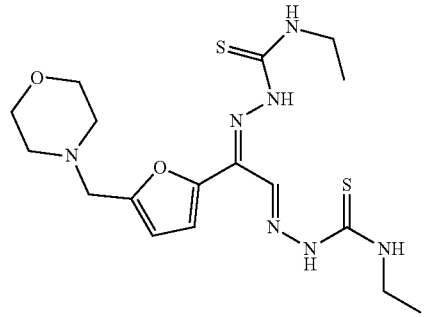
INT-29

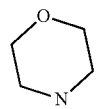

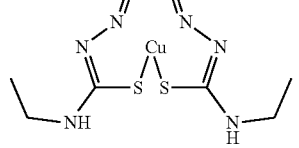
38

The titular compound was prepared from INT-36 according to the method to prepare compound 29. The product precipitated out of the reaction mixture as a red-brown powder. The precipitate was collected by filtration, washed with water, methanol, and diethyl ether, and then dried in vacuo. Yield 0.07 g (77%). LCMS (C18 column 20×2 mm, particle size 2.5 μm, pore size 100A, water-acetonitrile+ 0.1% TFA, gradient 5 to 87% for 4 min, retention time 1.47 min). MS (ESI) m/z 487.4 [MH]+.

Scheme 14: Synthesis of Compound 30

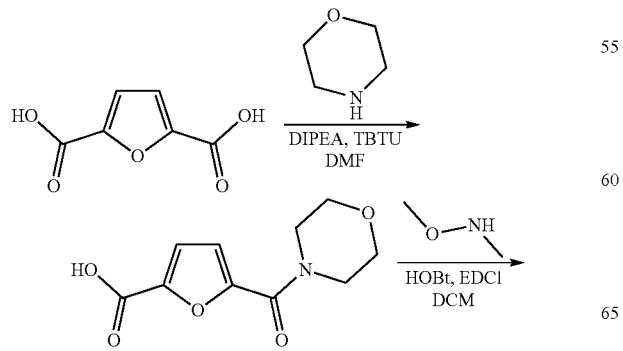

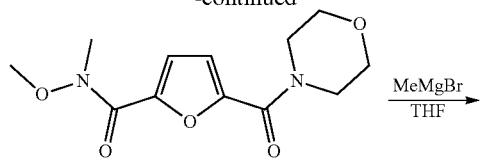

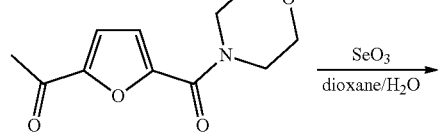

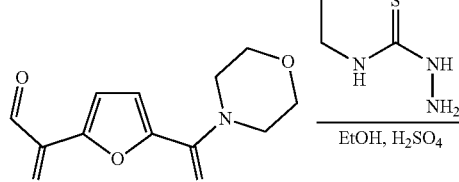

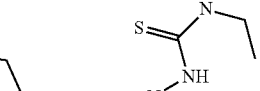
INT-30

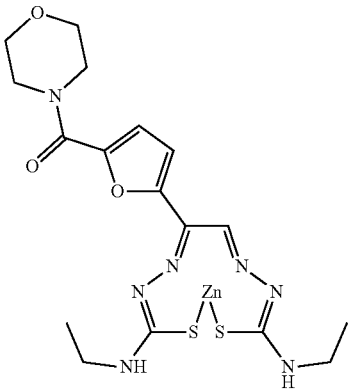
ZN-30

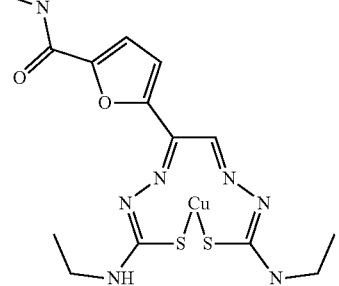
30

Synthesis of
5-(morpholine-4-carbonyl)furan-2-carboxylic Acid

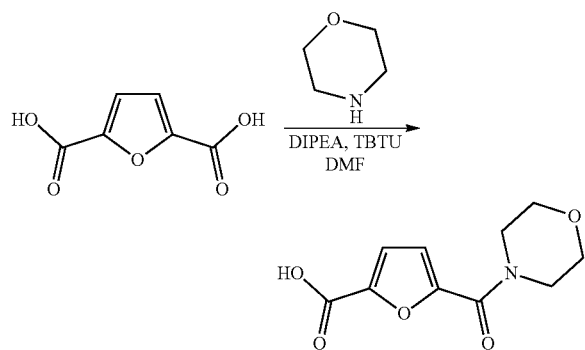

To a stirred solution of furan 2,5-dicarboxylic acid (5 g, 32 mmol, 1 eq) in DMF (100 ml) DIPEA was added (14.5 g, 19.5 ml, 3.5 eq), the reaction flask was flushed with argon, and the solution of TBTU (12.3 g, 1.2 eq) in DMF (75 ml) was added dropwise at ambient temperature over 1 h. The reaction mixture was stirred for an additional hour. Then morpholine was added in one portion and the mixture was stirred at ambient temperature for 2 h. The mixture was cooled in an ice-bath, HCl (2N, 170 ml) was added and the product was extracted with EtOAc, EtOAc was evaporated, the residue was washed with EtOH and ether. Yield 6.19 g (85%). LCMS (C18 column 20×2 mm, particle size 2.5 μm, pore size 100A, water-acetonitrile+0.1% TFA, gradient 5 to 87% for 3 min, retention time 0.33 min). MS (ESI) m/z 226.3 [MH]+, retention time 0.84 min). MS (ESI) m/z 226.3 [MH]+. $^1$H-NMR (400 MHz, DMSO-$d_6$): δ (ppm) 3.52-3.88 (m, 8H), 7.09 (d, 1H), 7.29 (d, 1H).

Synthesis of N-methoxy-N-methyl-5-(morpholine-4-carbonyl)furan-2-carboxamide

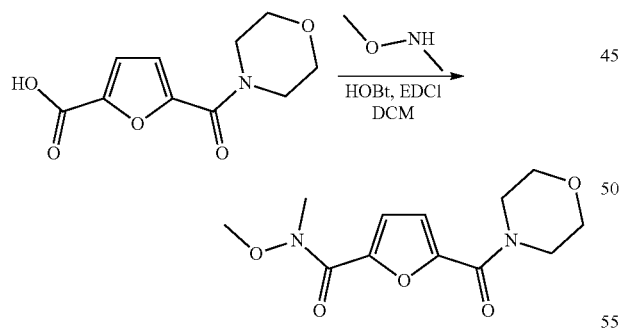

To a mixture of 5-(morpholine-4-carbonyl)furan-2-carboxylic acid (2.6 g, 11 mmol, 1 eq), N,O-dimethylhydroxylamine (1.46 g, 1.3 eq), HOBT (1.71, 1 eq) and DIPEA (2 ml) in DCM (150 ml) was added EDCl (2.21 g, 1 eq) at 4° C. and the mixture was stirred overnight at room temperature. The reaction mixture was treated with water. The solid substance insoluble in water and DCM was removed by filtration. Organic layer was separated, dried over Na$_2$SO$_4$, filtered, and solvents were evaporated. The residue was purified by column chromatography (SiO2, CH$_2$Cl$_2$ 100%). Yield 2.1 g (68%). LCMS (C18 column 20×2 mm, particle size 2.5 μm, pore size 100A, water-acetonitrile+0.1% TFA, gradient 5 to 87% for 3 min, retention time 0.95 min). MS (ESI) m/z 269.5 [MH]+. $^1$H-NMR (400 MHz, DMSO-$d_6$): δ (ppm) 3.26 (s, 3H), 3.54-3.73 (m, 8H), 3.76 (s, 3H), 7.10 (d, 1H), 7.22 (d, 1H).

Synthesis of 1-(5-(morpholine-4-carbonyl)furan-2-yl)ethan-1-one

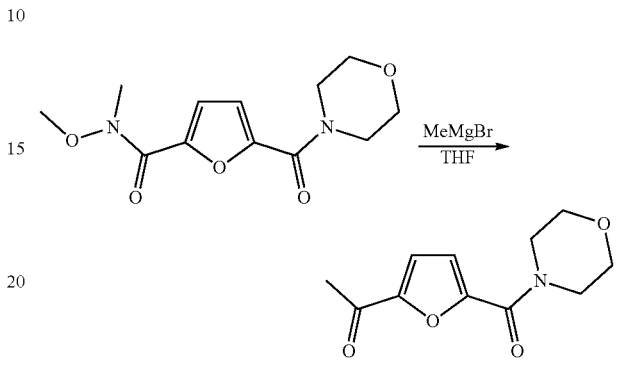

A solution of N-methoxy-N-methyl-5-(morpholine-4-carbonyl)furan-2-carboxamide (1.45 g, 5.4 mmol, 1 eq) in THF (50 ml) was cooled down to 5° C. and methylmagnesium bromide solution in THF (1.4M, 11 ml, 3 eq) was added. The reaction mixture was stirred at 5° C. for 2 h, poured into aq NH$_4$Cl and extracted with Et$_2$O. The combined extracts were dried over Na$_2$SO$_4$, filtered, and solvents were evaporated. The titular product was used for the next step without purification. Yield 0.45 g (37%). LCMS (C18 column 20×2 mm, particle size 2.5 μm, pore size 100A, water-acetonitrile+0.1% TFA, gradient 5 to 87% for 3 min, retention time 0.92 min). MS (ESI) m/z 224.4 [MH]+. $^1$H-NMR (400 MHz, DMSO-$d_6$): δ (ppm) 2.46 (s, 3H), 3.57-3.79 (m, 8H), 3.76 (s, 3H), 7.14 (d, 1H), 7.50 (d, 1H).

Synthesis of 2-(5-(morpholine-4-carbonyl)furan-2-yl)-2-oxoacetaldehyde

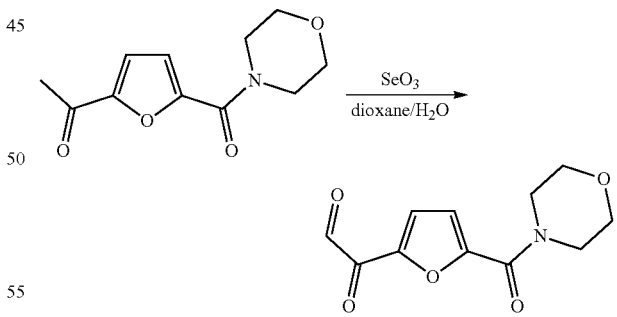

A three-necked flask was charged with SeO$_2$ (0.42 g, 1.4 eq), 1,4-dioxane (6 mL), and water (0.36 mL). The mixture was heated to 50° C. and stirred until most of SeO$_2$ was dissolved. 1-(5-(Morpholine-4-carbonyl)furan-2-yl)ethan-1-one (0.6 g, 0.003M, 1 eq) was added, and the reaction was heated to gentle reflux overnight. Selenium solids precipitated during the course of the reaction. The mixture was cooled in an ice bath and filtered through diatomaceous earth to remove the selenium. The filter cake was washed with portions of 1,4-dioxane. The filtrate was concentrated to yield 0.5 g of crude titular product, it was used for the next step without purification. Yield 0.5 g (78%). LCMS (C18 column 20×2 mm, particle size 2.5 μm, pore size 100A, water-acetonitrile+0.1% TFA, gradient 5 to 87% for 3 min, retention time 0.92 min, MS (ESI) m/z 238.1 [MH]+.

Synthesis of INT-30 ((2E,2'E)-2,2'-(1-(5-(morpholine-4-carbonyl)furan-2-yl)ethane-1,2-diylidene)bis(N-ethylhydrazine-1-carbothioamide))

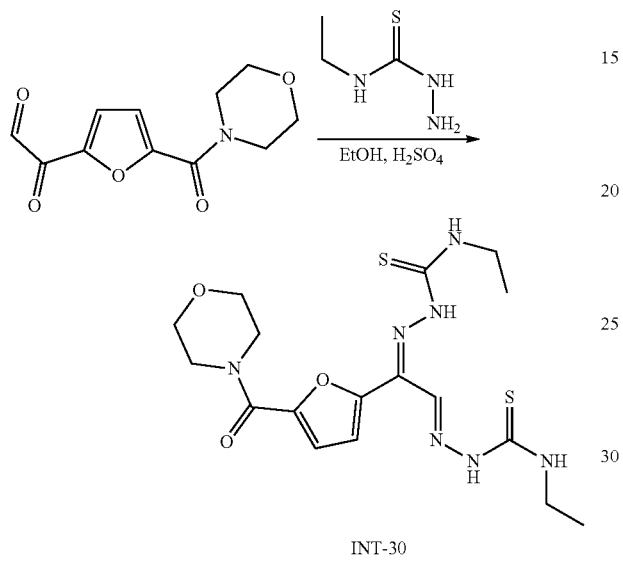

INT-30

Crude 2-(5-(morpholine-4-carbonyl)furan-2-yl)-2-oxoacetaldehyde (0.5 g, 2.0 mmol, 1 eq) was dissolved in EtOH (25 ml), ethyl thiosemicarbazide (0.5 g, 2 eq) and 2 drops of H₂SO₄ were added. Reaction mixture was stirred and heated to reflux for 4 h and then maintained for 15 h at ambient temperature. Formed precipitate was filtered, washed with EtOH, MeCN, water, Et₂O, and dried. Yield 0.25 g (27%). LCMS (C18 column 20×2 mm, particle size 2.5 μm, pore size 100A, water-acetonitrile+0.1% TFA, gradient 5 to 87% for 3 min, retention time 1.37 min, MS (ESI) m/z 440.5 [MH]+. ¹H-NMR (400 MHz, DMSO-d₆): δ (ppm) 1.00-1.26 (m, 6H), 3.43-4.09 (m, 13H), 7.19 (s, 1H), 7.24 (s, 1H), 6.06 (br.s, 1H), 8.92 (br.s, 1H), 11.98 (s, 1H), 12.29 (s, 1H).

Synthesis of Intermediate ZN-30

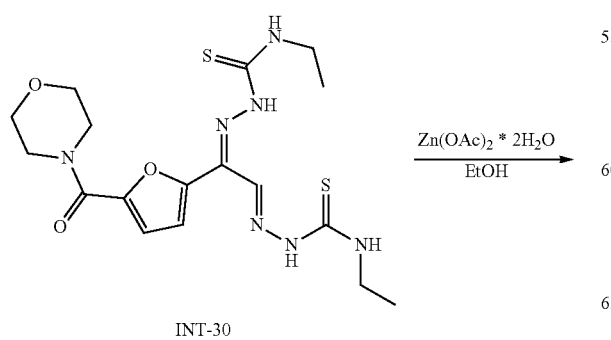

INT-30

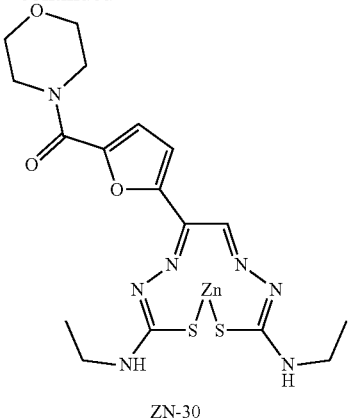

ZN-30

Zn(OAc)₂ 2H₂O (0.19 g, 1.5 eq) was added to INT-30 (0.73 g, 2.0 mmol, 1 eq) in ethanol. The mixture was refluxed for 4 h. The formed complex was precipitated from the mixture as a yellow powder. The precipitate was collected by filtration, washed with water, methanol, and diethyl ether, and then dried in vacuo. Yield 0.175 g (61%). ¹H-NMR (400 MHz, DMSO-d₆): δ (ppm) 1.11 (t, 3H), 1.19 (t, 3H), 3.36-3.85 (m, 13H), 7.11 (s, 1H), 7.15 (s, 1H), 8.20 (s, 1H), 8.43 (s, 1H).

Synthesis of Compound 30

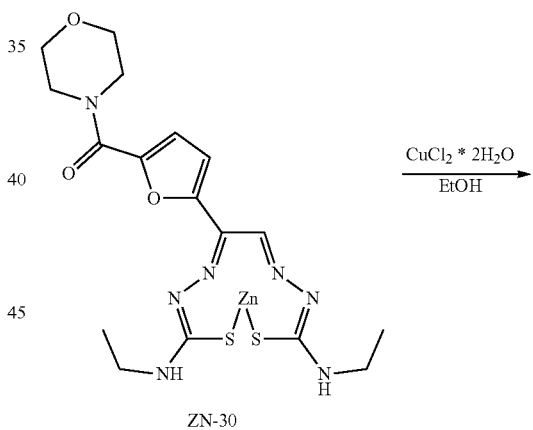

ZN-30

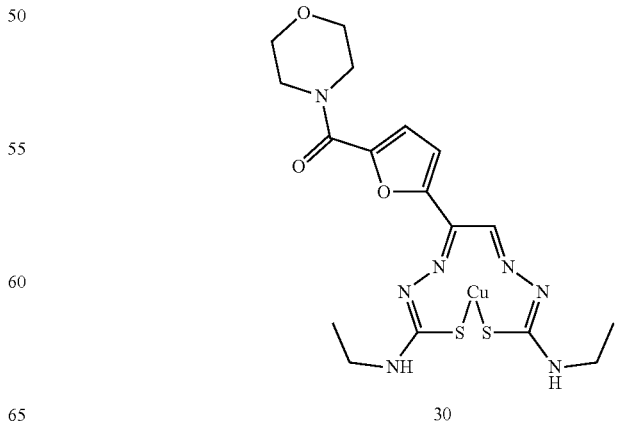

30

ZN-30 (0.175 g, 0.3 mmol, 1 eq) was dissolved in DMSO (4 ml) and a solution of CuCl$_2$ 2H$_2$O (0.076 g, 1.1 eq) in water (4 ml) was added. The mixture was stirred for 5 min, filtered and washed with water and Et$_2$O. Yield 0.08 g (46%). LCMS (C18 column 20×2 mm, particle size 2.5 μm, pore size 100A, water-acetonitrile+0.1% TFA, gradient 5 to 87% for 4 min, retention time 1.86 min). MS (ESI) m/z 501.3 [MH]+.

Scheme 15: Synthesis of Compound 34

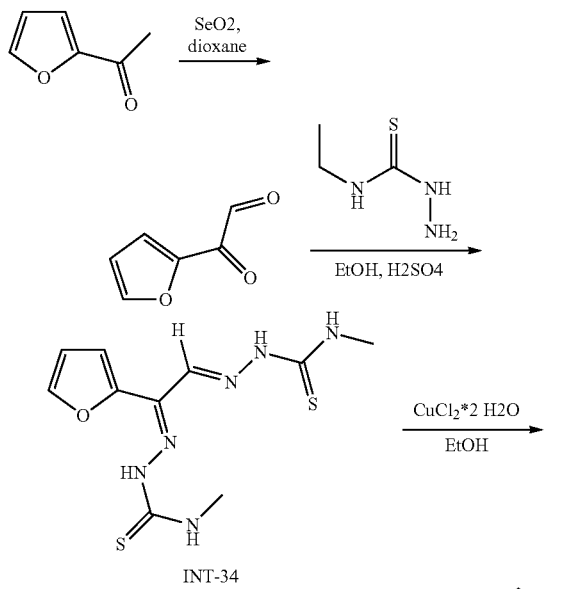

Synthesis of 2-(furan-2-yl)-2-oxoacetaldehyde

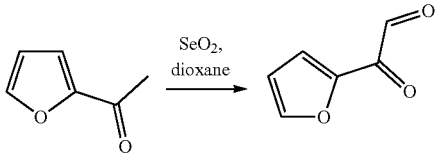

A three-necked flask was charged with SeO$_2$ (3.2 g, 28.6 mmol), 1,4-dioxane (37 ml), and water (2.5 ml). The mixture was heated to 50° C. and stirred until most of SeO$_2$ was dissolved. 1-(2-Furyl)ethanone (3 g, 27.2 mmol) was added, and the reaction was heated to gentle reflux overnight. The progress of the reaction was monitored by TLC (CCl$_4$/EtOAc 7:3). Selenium solids precipitated during the course of the reaction. The mixture was cooled over an ice bath and filtered through diatomaceous earth to remove the selenium. The filter cake was washed with portions of 1,4-dioxane. The filtrate was concentrated to give 3.0 g of crude compound 1, it was used for the next step without purification. Yield 3.0 g (88%).

Synthesis of INT-34 ((2Z,2'E)-2,2'-(1-(furan-2-yl)ethane-1,2-diylidene)bis(N-methylhydrazine-1-carbothioamide))

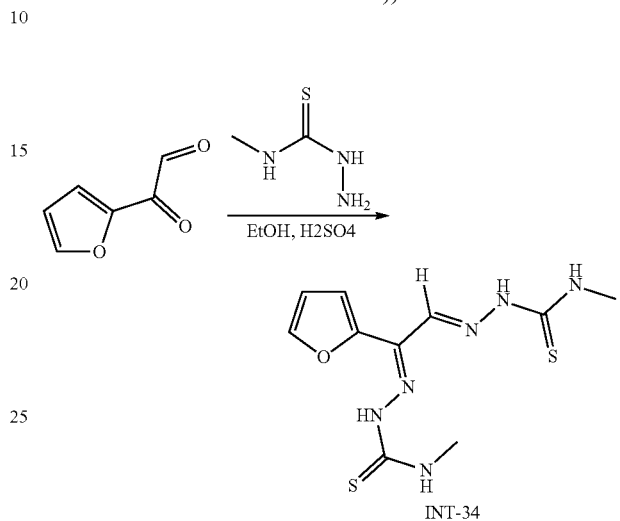

2-(Furan-2-yl)-2-oxoacetaldehyde (0.7 g, 6 mmol) was dissolved in EtOH (20 mL), methyl thiosemicarbazide (1.3 g, 12 mmol) and 3 drops of H$_2$SO$_4$ were added. Reaction mixture was stirred and heated to reflux for 4 h and then maintained for 15 h at ambient temperature. The progress of the reaction was monitored by TLC (CCl$_4$/EtOAc 7:3). The formed precipitate was filtered, washed with EtOH, water, Et$_2$O, and dried. Yield 0.57 g (32%). LCMS (C18 column 20×2 mm, particle size 2.5 μm, pore size 100A, water-acetonitrile+0.1% TFA, gradient 5 to 87% for 3 min, retention time 1.35 min). MS (ESI) m/z 299.5 [MH]+. $^1$H-NMR (400 MHz, DMSO-d$_6$): δ (ppm) 3.02 (d, 3H), 3.01 (d, 3H), 6.78 (q, 1H), 7.52 (d, 1H), 7.84 (s, 1H), 7.99-8.04 (m, 1H), 8.13 (dd, 1H), 8.88-8.92 (m, 1H), 10.81 (s, 1H), 11.79 (s, 1H).

Synthesis of INT-35 ((2Z,2'E)-2,2'-(1-(furan-2-yl)ethane-1,2-diylidene)bis(N-ethylhydrazine-1-carbothioamide)):

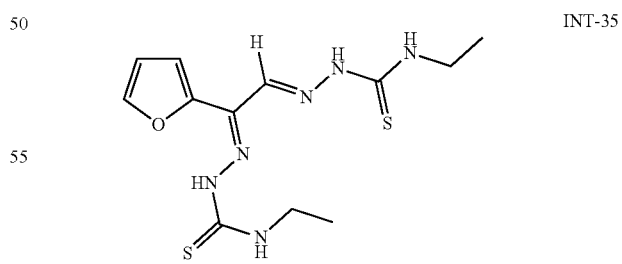

INT-35 was made using a procedure analogous to the procedure to prepare INT-34. Yield 0.47 g (24%). LCMS (C18 column 20×2 mm, particle size 2.5 μm, pore size 100A, water-acetonitrile+0.1% TFA, gradient 5 to 87% for 3 min, retention time 2.23 min). MS (ESI) m/z 327.5 [MH]+. $^1$H-NMR (400 MHz, DMSO-d$_6$): δ (ppm) 1.07 (t, 3H), 1.15 (t, 3H), 3.41-3.48 (m, 2H), 3.55-3.63 (m, 2H), 6.78 (q, 1H), 7.52 (d, 1H), 7.84 (s, 1H), 7.99-8.04 (m, 1H), 8.13 (dd, 1H), 8.88-8.92 (m, 1H), 10.81 (s, 1H), 11.79 (s, 1H).

Synthesis of INT-36 ((2Z,2'E)-2,2'-(1-(5-nitrofuran-2-yl)ethane-1,2-diylidene)bis(N-ethylhydrazine-1-carbothioamide))

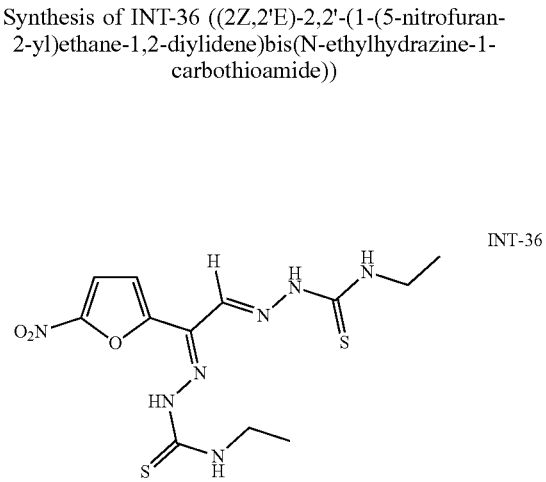

INT-36

INT-36 was made using a procedure analogous to the procedure to prepare INT-34. Yield 0.02 g (24%). LCMS (C18 column 20×2 mm, particle size 2.5 μm, pore size 100A, water-acetonitrile+0.1% TFA, gradient 5 to 87% for 10 min, retention time 8.11 min). MS (ESI) m/z 372.5 [MH]+.

Synthesis of INT-40 ((2Z,2'E)-2,2'-(1-(5-bromothiophen-2-yl)ethane-1,2-diylidene)bis(N-ethylhydrazine-1-carbothioamide))

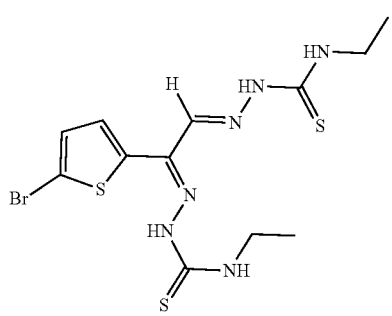

INT-40

INT-40 was made using a procedure analogous to the procedure to prepare INT-34. Yield 0.24 g (39%). LCMS (C18 column 20×2 mm, particle size 2.5 μm, pore size 100A, water-acetonitrile+0.1% TFA, gradient 5 to 87% for 3 min, retention time 1.85 min). MS (ESI) m/z 422.4 [MH]+.
$^1$H-NMR (400 MHz, DMSO-$d_6$): δ (ppm) 1.15 (t, 3H), 1.18 (t, 3H), 3.41-3.49 (m, 4H), 7.25 (d, 1H), 7.33 (d, 1H), 8.09 (t, 1H), 8.16 (s, 1H), 8.60 (t, 1H), 11.75 (s, 1H), 11.90 (s, 1H).

Synthesis of Compound 34

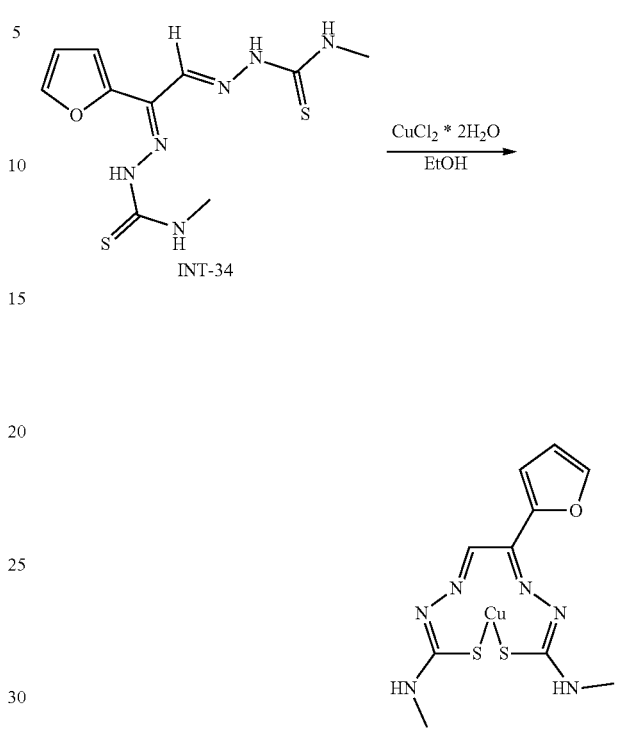

34

CuCl$_2$·2H$_2$O (0.33 g, 1.9 mmol) was added to INT-34 (0.57 g, 1.9 mmol) in 10 ml of ethanol. The mixture was stirred overnight. Complex was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.3 g (47%). LCMS (C18 column 20×2 mm, particle size 2.5 μm, pore size 100A, water-acetonitrile+0.1% TFA, gradient 5 to 87% for 3 min, retention time 1.40 min). LCMS (C18 column 20×2 mm, particle size 2.5 μm, pore size 100A, water-acetonitrile+0.1% TFA, gradient 5 to 87% for 4 min, retention time 1.83 min). MS (ESI) m/z 360.3 [MH]+.

Synthesis of Compound 35

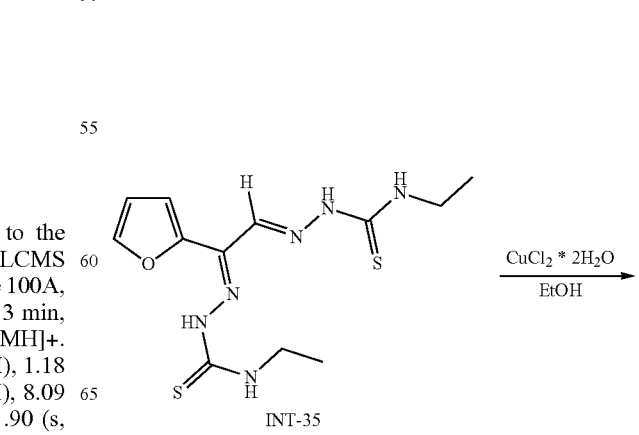

INT-35

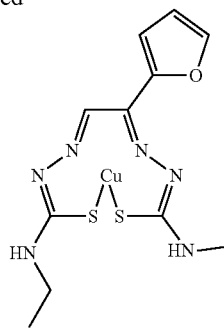

35

The titular compound was prepared from INT-35 according to the method to prepare compound 34. The product was collected by filtration after cooling, washed with water (2×50 ml), ethanol (2×50 ml), and copious amounts of diethyl ether (5×50 ml), and then dried in vacuo. Yield 0.3 g (57%). LCMS (C18 column 20×2 mm, particle size 2.5 μm, pore size 100A, water-acetonitrile+0.1% TFA, gradient 5 to 87% for 4 min, retention time 2.18 min). MS (ESI) m/z 388.5 [MH]+.

Synthesis of Compound 36

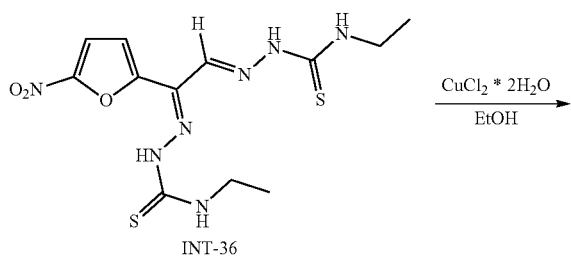

INT-36

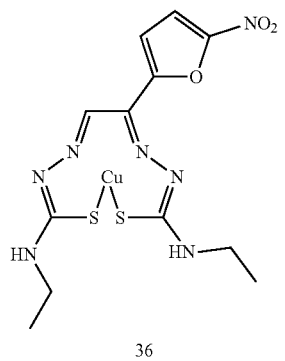

36

The titular compound was prepared from INT-36 according to the method to prepare compound 34. The product was isolated as a red-brown powder. Yield 0.026 g (40%). LCMS (C18 column 20×2 mm, particle size 2.5 μm, pore size 100A, water-acetonitrile+0.1% TFA, gradient 5 to 87% for 3 min, retention time 1.70 min). LCMS (C18 column 20×2 mm, particle size 2.5 μm, pore size 100A, water-acetonitrile+ 0.1% TFA, gradient 5 to 87% for 4 min, retention time 1.69 min). MS (ESI) m/z 433.2 [MH]+.

Synthesis of Compound 40

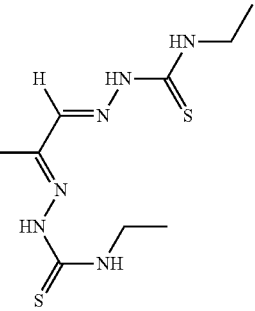

INT-40

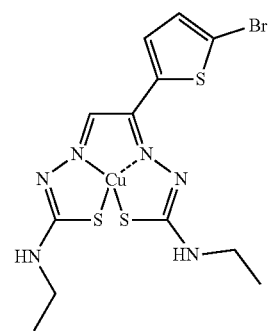

40

The titular compound was prepared from INT-40 according to the method to prepare compound 34. The product was isolated as a red-brown powder. The formed precipitate was collected by filtration after cooling, washed with water (2×50 ml), ethanol (2×50 ml), and copious amounts of diethyl ether (5×50 ml), and then dried in vacuo. Yield 0.01 g (6%). LCMS (C18 column 20×2 mm, particle size 2.5 μm, pore size 100A, water-acetonitrile+0.1% TFA, gradient 5 to 87% for 4 min, retention time 2.72 min). MS (ESI) m/z 484.1 [MH]+.

Scheme 16: Synthesis of Compound 42

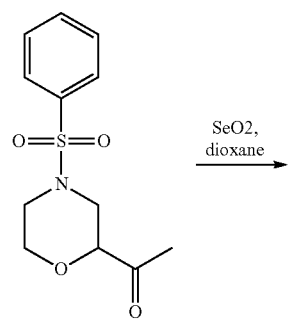

-continued

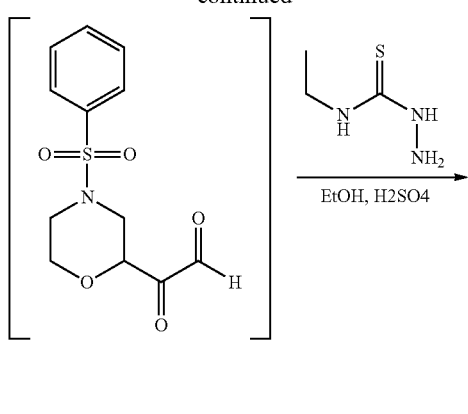

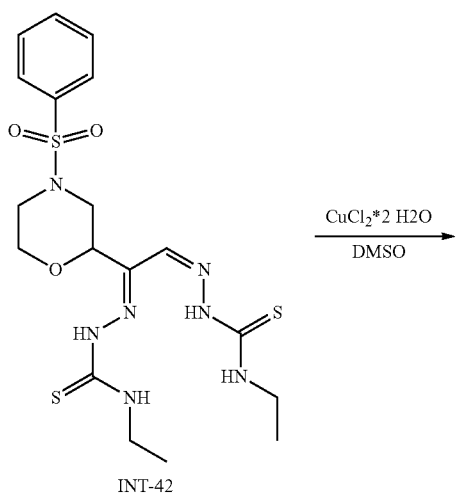

INT-42

Synthesis of 1-(4-(phenylsulfonyl)morpholin-2-yl)ethan-1-one

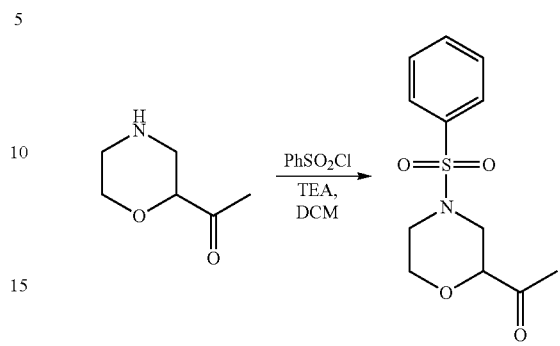

To a solution of 1-morpholin-2-yl-ethanone (0.3 g, 2.3 mmol) in DCM (50 ml) triethylamine (0.59 g, 2.5 eq) was added at 5° C. followed by benzenesulfonyl chloride (0.51 g, 1.25 eq) The mixture was stirred at ambient temperature for 15 h, acidified with aq. 10% HCl, extracted with DCM. The combined organic extracts were dried over $Na_2SO_4$, filtered, and evaporated. The residue was purified by column chromatography (silica gel, eluent 10% EtOAc in hexane). Yield 0.30 g (48%). NMR (400 MHz, $CDCl_3$): 2.20 (s, 3H), 2.22-2.28 (m, 1H), 2.46 (ddd, 1H), 3.58-3.61 (m, 1H), 3.76 (ddd, 1H), 3.90-3.95 (m, 1H), 4.00-4.09 (m, 2H), 7.54-7.60 (m, 2H), 7.63-7.67 (m, 1H), 7.77-7.80 (m, 2H).

Synthesis of INT-42 ((2Z,2'Z)-2,2'-(1-(4-(phenylsulfonyl)morpholin-2-yl)ethane-1,2-diylidene)bis(N-ethylhydrazine-1-carbothioamide))

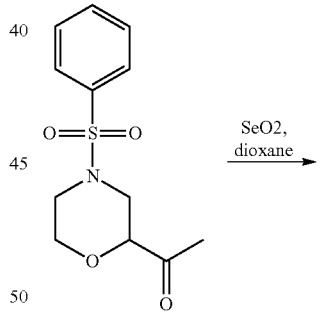

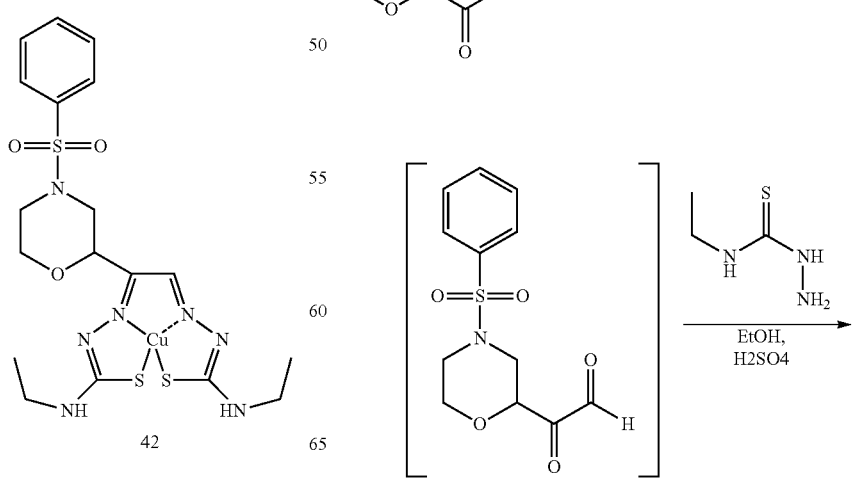

-continued

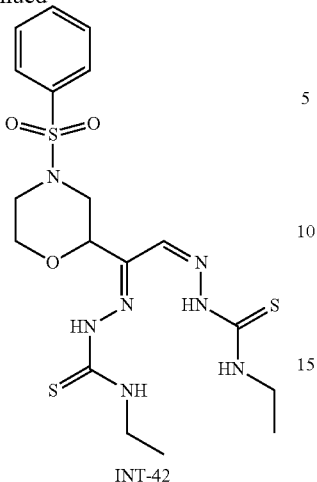

INT-42

A flask was charged with SeO$_2$ (0.14 g, 1.1 eq), 1,4-dioxane (3.5 mL), and water (0.1 mL). The mixture was warmed up to 50° C. and was stirred until most of SeO$_2$ was dissolved. 1-(4-(phenylsulfonyl)morpholin-2-yl)ethan-1-one was added, and the reaction was heated at gentle reflux for 4 h. Selenium solids were precipitated over the course of the reaction. The mixture was cooled over an ice bath and filtered through diatomaceous earth to remove the selenium. The filter cake was washed with portions of 1,4-dioxane. The filtrate was concentrated in vacuo until most of 1,4-dioxane was removed. The residue was dissolved in EtOH and filtered. To the filtrate thiosemicarbazide and 1 drop of H$_2$SO$_4$ were added and the reaction mixture was refluxed for 2 h. The precipitate was filtered. Yield 0.08 g (15%). LCMS (C18 column 20×2 mm, particle size 2.5 μm, pore size 100A, water-acetonitrile+0.1% TFA, gradient 5 to 87% for 3 min, retention time 1.62 min), MS (ESI) m/z 486.5 [MH]+.

Synthesis of Compound 42

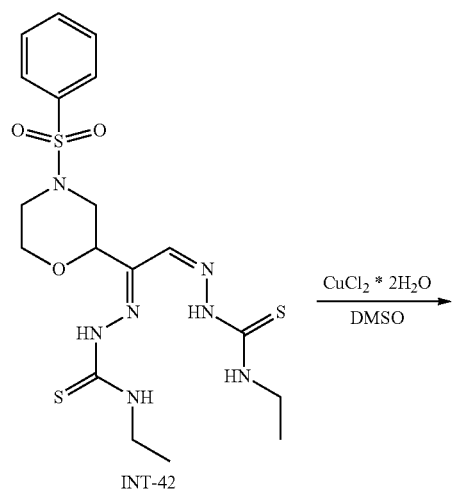

INT-42

-continued

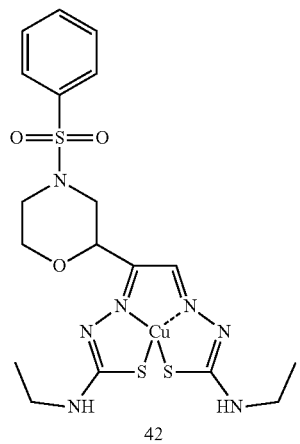

42

INT-42 (0.08 g, 0.17 mmol) was dissolved in DMSO (0.4 ml) and a solution of CuCl$_2$·2H$_2$O (28 mg, 1.0 eq) in water (0.4 ml) was added. The mixture was stirred for 5 min, filtered, and precipitate was washed with saturated solution of potassium carbonate, water and Et$_2$O. Yield 0.015 g (17%). LCMS (C18 column 20×2 mm, particle size 2.5 μm, pore size 100A, water-acetonitrile+0.1% TFA, gradient 5 to 87% for 4 min, retention time 2.27 min). MS (ESI) m/z 547.5 [MH]+.

Scheme 17 Synthesis of Compound 43

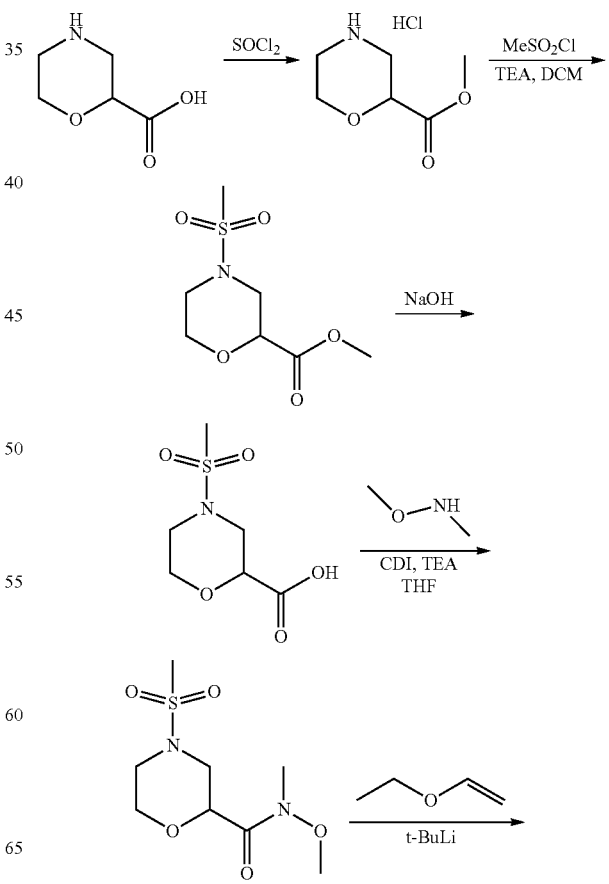

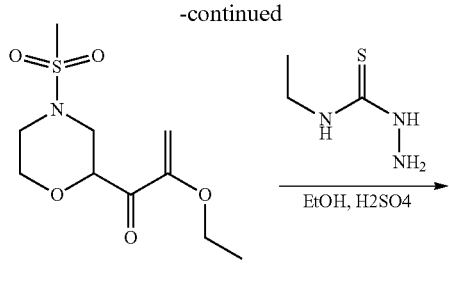

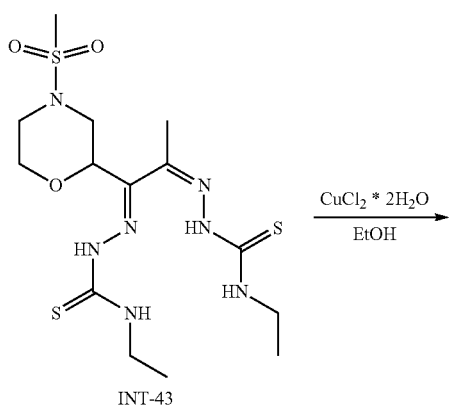

INT-43

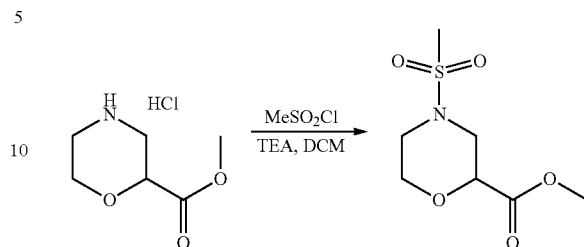

Synthesis of Methyl morpholine-2-carboxylate Hydrochloride

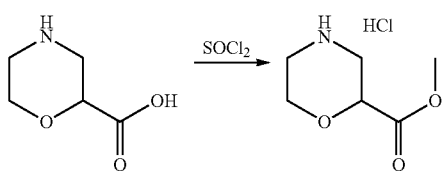

To a suspension of morpholine-2 carboxylic acid (1.94 g, 15 mmol, 1 eq) in methanol (75 ml) thionyl chloride (8.8 g, 5.4 ml, 5 eq) was added dropwise at 0-10° C. The reaction mixture was stirred at room temperature for 1 h and then heated for 4 h to reflux. The reaction mixture was evaporated. Yield 2.3 g (85.6%). NMR (400 MHz, DMSO-$d_6$): 2.78-3.15 (m, 3H), 3.25-3.35 (m, 1H), 3.69 (s, 3H), 3.69-3.81 (m, 1H), 3.95-4.05 (m, 1H), 4.60 (dd, 1H), 9.80-10.40 (m, 2H).

Synthesis of Methyl 4-(methylsulfonyl)morpholine-2-carboxylate

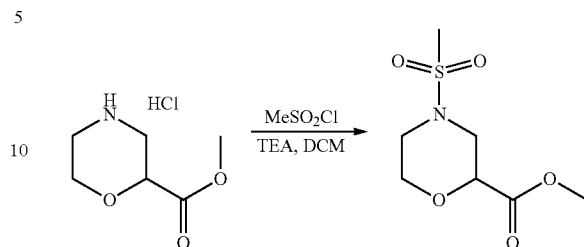

A mixture of methyl morpholine-2-carboxylate hydrochloride (2.3 g, 12.7 mmol, 1 eq), methanesulfonyl chloride (1.74 g, 1.1 ml, 1.2 eq) and triethylamine (3.2 g, 4.4 ml, 2.5 eq) in methylene chloride (100 ml) was stirred for 15 h at ambient temperature. The reaction mixture was washed with water, dried over $Na_2SO_4$, filtered, and solvents were evaporated. Yield 1.3 g (46%). NMR (400 MHz, CDCl$_3$): 2.83 (s, 3H), 2.95-3.04 (m, 2H), 3.50-3.58 (m, 1H), 3.74-3.80 (m, 1H), 3.82 (s, 3H), 3.83-3.88 (m, 1H), 4.09 (ddd, 1H), 4.27 (dd, 1H).

Synthesis of 4-(methylsulfonyl)morpholine-2-carboxylic Acid

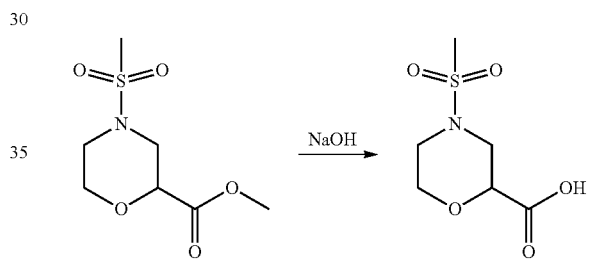

Methyl 4-(methylsulfonyl)morpholine-2-carboxylate (1.3 g, 5.8 mmol, 1 eq) was dissolved in methanol (50 ml) and a solution of NaOH (0.58 g, 2.5 eq) in water (10 ml) was added. The reaction mixture was stirred overnight at room temperature. Methanol was removed in vacuo, the residue diluted with water, acidified with conc. HCl to pH 1 and extracted with EtOAc. The organic layer was separated, dried over $Na_2SO_4$, filtered, and concentrated in vacuo. Yield 0.95 g (78%). NMR (400 MHz, DMSO-$d_6$): 2.32 (s, 3H), 2.87-2.95 (m, 1H), 3.20-3.25 (m, 2H), 3.51-3.59 (m, 2H), 3.83-3.99 (m, 2H).

Synthesis of N-methoxy-N-methyl-4-(methylsulfonyl)morpholine-2-carboxamide

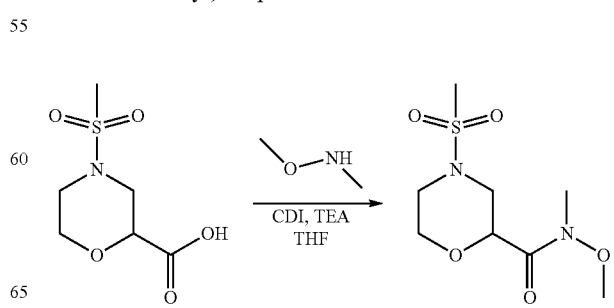

To a stirred solution of the 4-(methylsulfonyl)morpholine-2-carboxylic acid (0.97 g, 5 mmol, 1 eq) in THF (25 ml) at 0° C. carbonyldiimidazole (0.69 g, 0.5 eq) was added. Then N,O-dimethylhydroxylamine hydrochloride (0.45 g, 1 eq) and triethylamine (2.34 g, 3.2 ml, 5 eq) were added to the solution, and ice bath was removed. The reaction mixture was stirred at room temperature until disappearance of the acid, as determined using TLC. After completion, triethylamine hydrochloride was removed by filtration. Filtrate was concentrated to dryness via rotary evaporation. The residue was purified by a short-path silica gel column chromatography eluting with 20% ethyl acetate in hexane. Yield 0.26 g (22%). LCMS (C18 column 20×2 mm, particle size 2.5 μm, pore size 100A, water-acetonitrile+0.1% TFA, gradient 5 to 87% for 3 min, retention time 0.99 min), MS (ESI) m/z 253.1 [MH]+.

Synthesis of 2-ethoxy-1-(4-(methylsulfonyl)morpholin-2-yl)prop-2-en-1-one

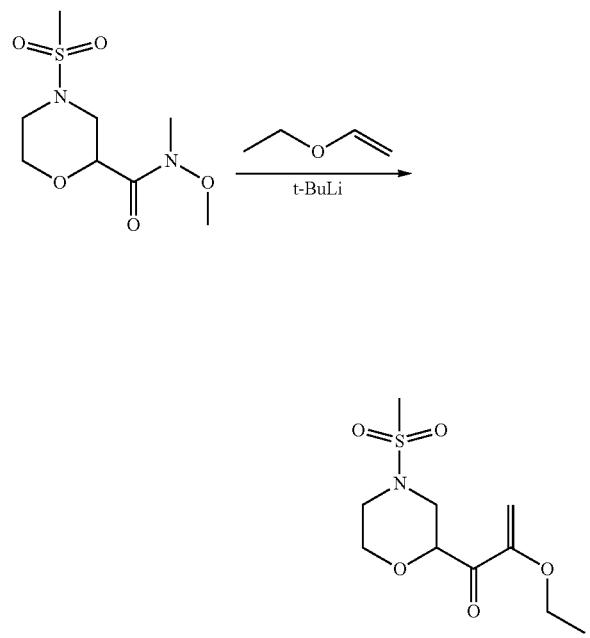

A solution of ethyl vinyl ether (0.82 g, 1 ml, 11 eq) in dry tetrahydrofuran (20 mL) was cooled to −78° C., and tert-butyllithium (1.7M, 6 ml, 9.9 eq) in pentane was added. The mixture was warmed to 0° C. over 1 h period, stirred for 45 min, and then cooled down to −30° C. Magnesium bromide etherate (2.5 g, 9.9 eq) was added. Then the mixture was warmed to 0° C. over a 15 min period and N-methoxy-N-methyl-4-(methylsulfonyl)morpholine-2-carboxamide was added (0.26 g, 1 mmol, 1 eq) in THF. The mixture was stirred at 0° C. for 4 h. The progress of the reaction was monitored by TLC. The mixture was poured into aq NH$_4$Cl and extracted with Et$_2$O. The combined extracts were dried over Na$_2$SO$_4$, filtered and solvents evaporated. The product was used for the next step without additional purification. Yield 0.17 g (62%). LCMS (C18 column 20×2 mm, particle size 2.5 μm, pore size 100A, water-acetonitrile+0.1% TFA, gradient 5 to 87% for 3 min, retention time 1.36 min), MS (ESI) m/z 527.3 [2MH]+

Synthesis of INT-43 ((2Z,2'Z)-2,2'-(1-(4-(methylsulfonyl)morpholin-2-yl)propane-1,2-diylidene)bis(N-ethylhydrazine-1-carbothioamide))

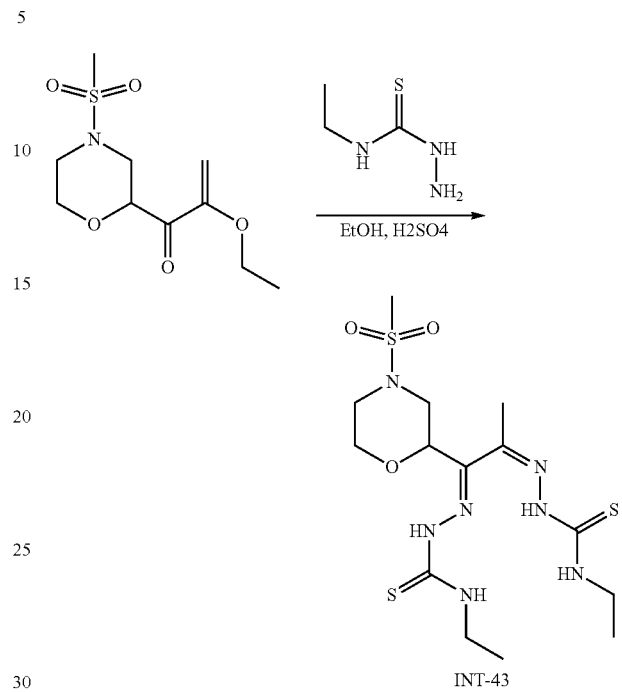

2-Ethoxy-1-(4-(methylsulfonyl)morpholin-2-yl)prop-2-en-1-one (0.16 g, 0.6 mmol, 1 eq) was dissolved in EtOH (20 ml), ethyl thiosemicarbazide (0.14 g, 2 eq) and 1 drop of H$_2$SO$_4$ were added. Reaction mixture was stirred and heated to reflux for 4 h and then maintained for 15 h at ambient temperature. The formed precipitate was filtered, washed with EtOH, water, Et$_2$O, and dried. Yield 0.15 g (55%). NMR (400 MHz, DMSO-d$_6$): 1.10-1.21 (m, 6H), 1.47-1.53 (m, 1H), 2.16-2.21 (m, 1H), 2.47-2.55 (m, 4H), 2.78-2.84 (m, 1H), 2.95 (br.d, 1H), 3.08-3.16 (m, 1H), 3.30 (s, 3H), 3.42-3.50 (m, 4H), 7.78 (br.s, 1H), 8.69 (br.s, 1H), 10.75 (s, 1H), 12.18 (s, 1H). LCMS (C18 column 20×2 mm, particle size 2.5 μm, pore size 100A, water-acetonitrile+0.1% TFA, gradient 5 to 87% for 3 min, retention time 1.47 min), MS (ESI) m/z 438.4 [MH]+.

Synthesis of Compound 43

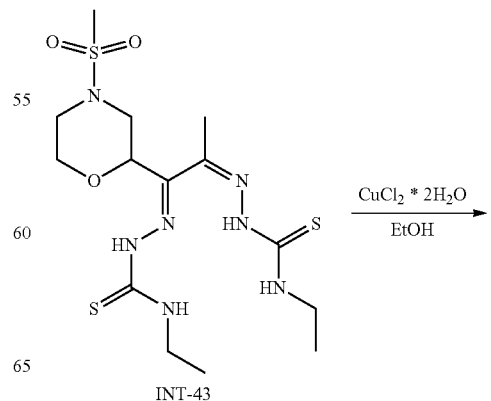

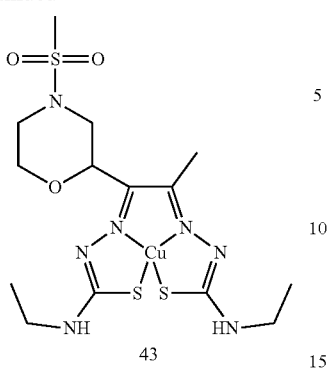

CuCl$_2$·2H$_2$O (0.058 g, 1 eq) was added to thiosemacarbazone 6 (0.15 g, 0.3 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.07 g (41%). LCMS (C18 column 20×2 mm, particle size 2.5 μm, pore size 100A, water-acetonitrile+ 0.1% TFA, gradient 5 to 87% for 4 min, retention time 2.06 min). MS (ESI) m/z 499.5 [MH]+.

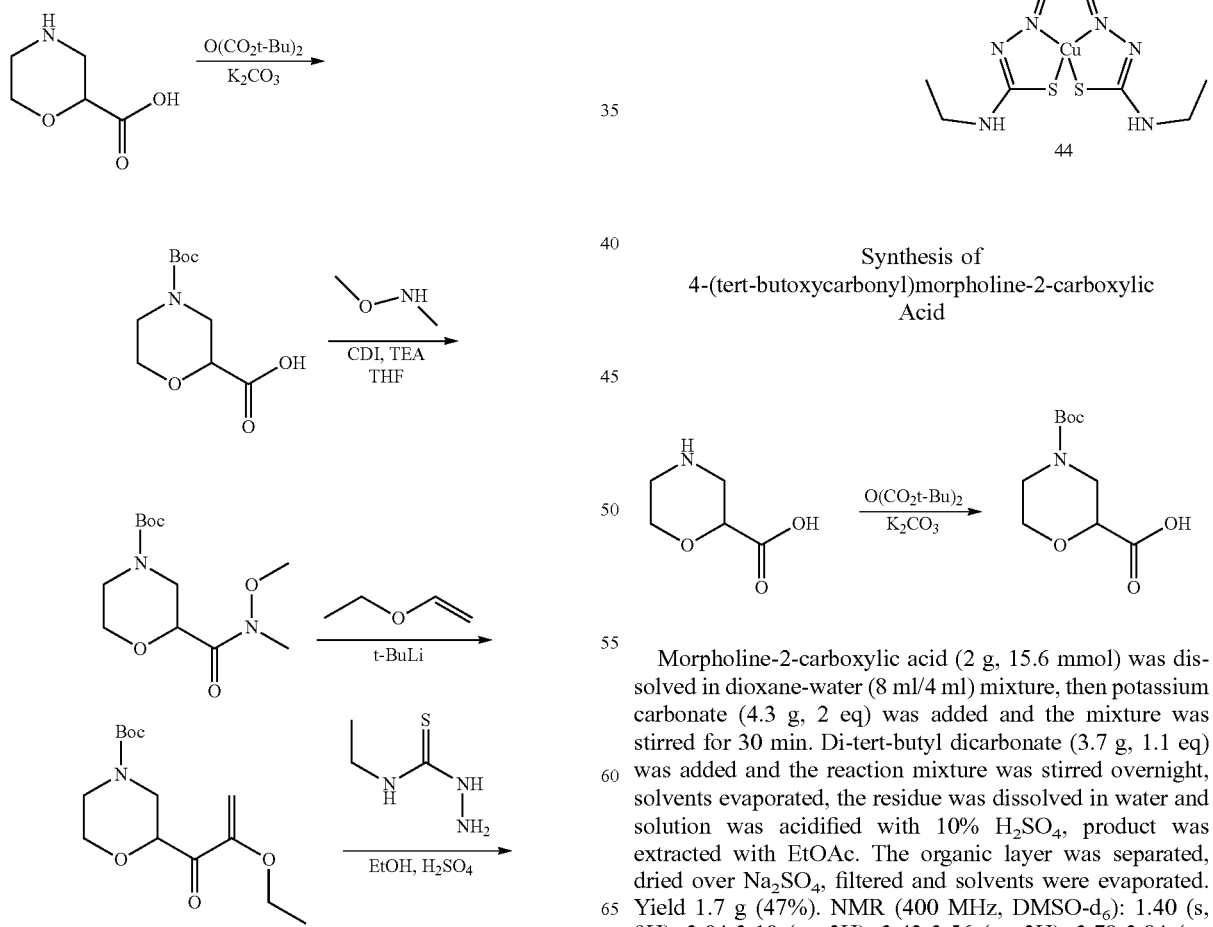

Scheme 18 Synthesis of Compound 44

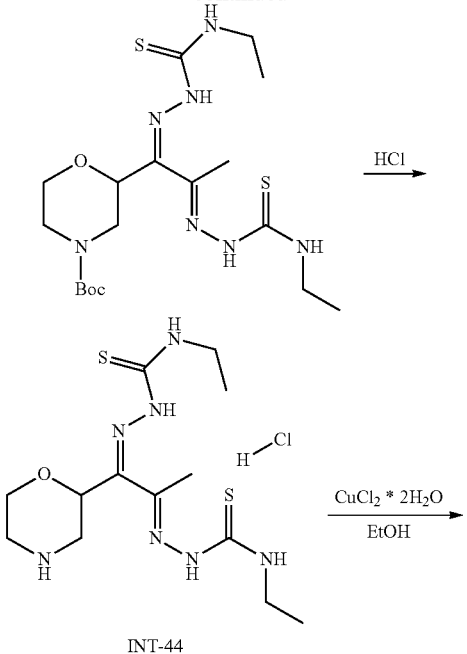

Synthesis of 4-(tert-butoxycarbonyl)morpholine-2-carboxylic Acid

Morpholine-2-carboxylic acid (2 g, 15.6 mmol) was dissolved in dioxane-water (8 ml/4 ml) mixture, then potassium carbonate (4.3 g, 2 eq) was added and the mixture was stirred for 30 min. Di-tert-butyl dicarbonate (3.7 g, 1.1 eq) was added and the reaction mixture was stirred overnight, solvents evaporated, the residue was dissolved in water and solution was acidified with 10% H$_2$SO$_4$, product was extracted with EtOAc. The organic layer was separated, dried over Na$_2$SO$_4$, filtered and solvents were evaporated. Yield 1.7 g (47%). NMR (400 MHz, DMSO-d$_6$): 1.40 (s, 9H), 3.04-3.10 (m, 2H), 3.42-3.56 (m, 2H), 3.78-3.84 (m, 2H), 4.01-4.07 (m, 1H), 12.95 (br.s, 1H).

Synthesis of tert-butyl 2-(methoxy(methyl)carbamoyl)morpholine-4-carboxylate

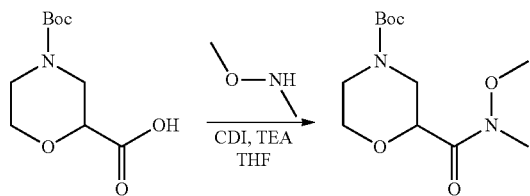

A solution of CDI in THF (7 ml) was added to a solution of 4-(tert-butoxycarbonyl)morpholine-2-carboxylic acid in THF (7 ml) at 0° C. The mixture was stirred at RT for 1 h. Then the mixture was cooled to 0° C. and a suspension of triethylamine (0.7 ml) and N,O-dimethylhydroxylamine in MeCN (10 ml) was added at 0° C., and the reaction was stirred at r.t. for 16 h. Then solvents were evaporated, the residue was dissolved in DCM, solution was washed with water, acetic acid (20% solution), and sat.NaHCO$_3$. The organic layer was separated, dried The organic layer was washed with water, separated, dried over Na$_2$SO$_4$, filtered and solvents were evaporated. The residue was purified by column chromatography SiO$_2$/hexane:EtOAc 2:1. Yield 0.78 g (73%). NMR (400 MHz, CDCl$_3$): 1.49 (s, 9H), 3.02 (br.s, 1H), 3.24 (s, 3H), 3.60 (dd, 1H), 3.75 (s, 3H), 3.90 (br.s, 1H), 4.00-4.30 (m, 2H), 4.85 (br.s, 1H).

Synthesis of tert-butyl 2-(2-ethoxyacryloyl)morpholine-4-carboxylate

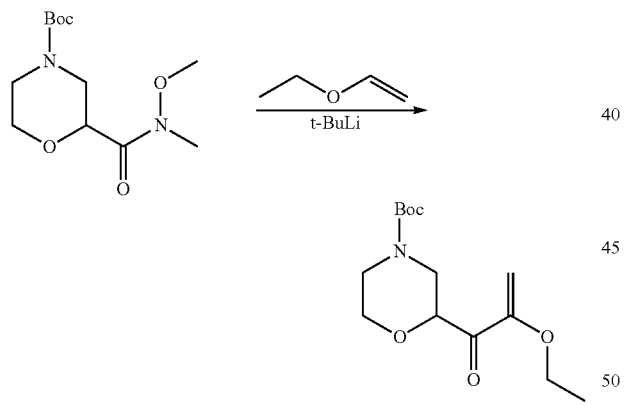

A solution of ethyl vinyl ether (2 g, 2.6 ml, 11 eq) in dry tetrahydrofuran (75 mL) was cooled to −78° C., and tert-butyllithium (1.7M, 13 ml, 8.9 eq) in pentane was added. The mixture was warmed to 0° C. over 1 h period, stirred for 45 min, and then cooled down to −30° C. Magnesium bromide etherate (5.2 g, 8.9 eq) was added. Then the mixture was warmed to 0° C. over a 15 min period and tert-butyl 2-(methoxy(methyl)carbamoyl)morpholine-4-carboxylate was added (0.7 g, 2.6 mmol, 1 eq) in THF. The mixture was stirred at 0° C. for 4 h. The progress of the reaction was monitored by TLC. The mixture was poured into aq NH$_4$Cl and extracted with Et$_2$O. The combined extracts were dried over Na$_2$SO$_4$, and evaporated. The product was used for the next step without additional purification. Yield 0.6 g (82%). LCMS (C18 column 20×2 mm, particle size 2.5 μm, pore size 100A, water-acetonitrile+0.1% TFA, gradient 5 to 87% for 3 min, retention time 1.33 min), MS (ESI) m/z 286.1 [MH]+.

Synthesis of tert-butyl 2-((6E,8E)-8-methyl-4,11-dithioxo-3,5,6,9,10,12-hexaazatetradeca-6,8-dien-7-yl)morpholine-4-carboxylate

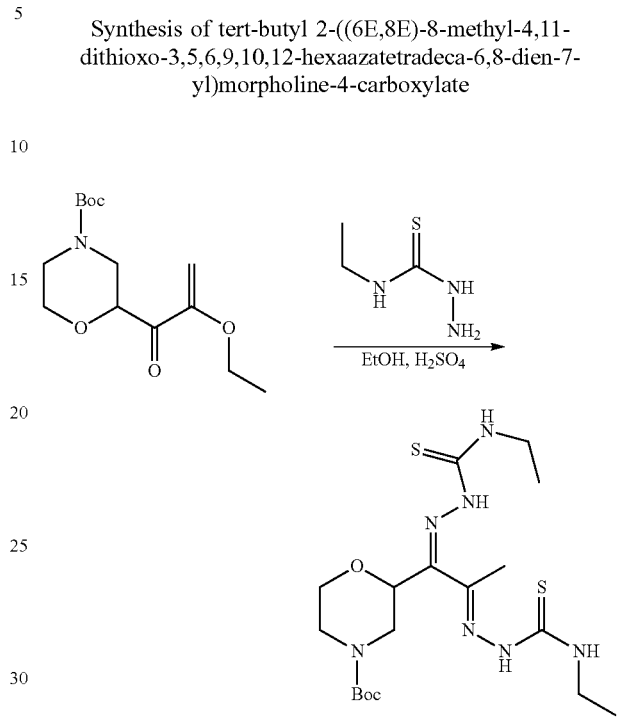

Tert-butyl 2-(2-ethoxyacryloyl)morpholine-4-carboxylate (0.39 g, 1.4 mmol, 1 eq) was dissolved in EtOH (150 ml), ethyl thiosemicarbazide (0.33 g, 2 eq) and 3 drops of H$_2$SO$_4$ were added. Reaction mixture was stirred and heated to reflux for 4 h and then maintained for 15 h at ambient temperature. The formed precipitate was filtered, washed with EtOH, water, Et$_2$O, and dried. Yield 0.23 g (37.2%). NMR (400 MHz, DMSO-d$_6$): 1.10-1.18 (m, 6H), 1.40 (br.d, 9H), 2.20 (s, 3H), 2.90-2.06 (m, 1H), 3.18 (br.s, 1H), 3.52-3.80 (m, 6H), 3.82-3.87 (m, 1H), 4.02-4.07 (m, 2H), 5.12 (br.s, 1H), 8.28 (br.s, 1H), 8.51 (t, 1H), 10.24 (s, 1H), 11.20 (br.s, 1H).

Synthesis of INT-44 (2E,2'E)-2,2'-(1-(morpholin-2-yl)propane-1,2-diylidene)bis(N-ethylhydrazine-1-carbothioamide) hydrochloride

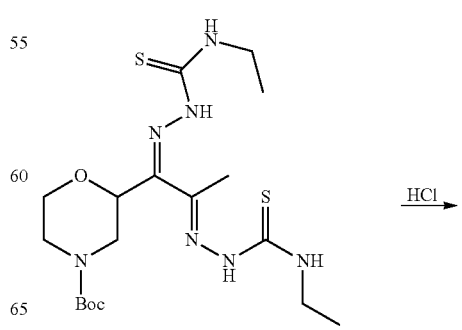

253

-continued

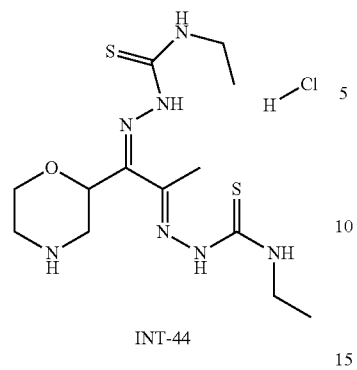

INT-44

To a solution of tert-butyl 2-((6E,8E)-8-methyl-4,11-dithioxo-3,5,6,9,10,12-hexaazatetradeca-6,8-dien-7-yl)morpholine-4-carboxylate (0.23 g, 0.5 mmol) in dioxane HCl/dioxane (3M, 6 ml) was added. The reaction mixture was stirred at room temperature overnight. Formed precipitate was filtered. Yield 0.15 g (76%). LCMS (C18 column 20×2 mm, particle size 2.5 μm, pore size 100A, water-acetonitrile+0.1% TFA, gradient 5 to 87% for 3 min, retention time 1.13 min), MS (ESI) m/z 360.4 [MH]+.

Synthesis of Compound 44

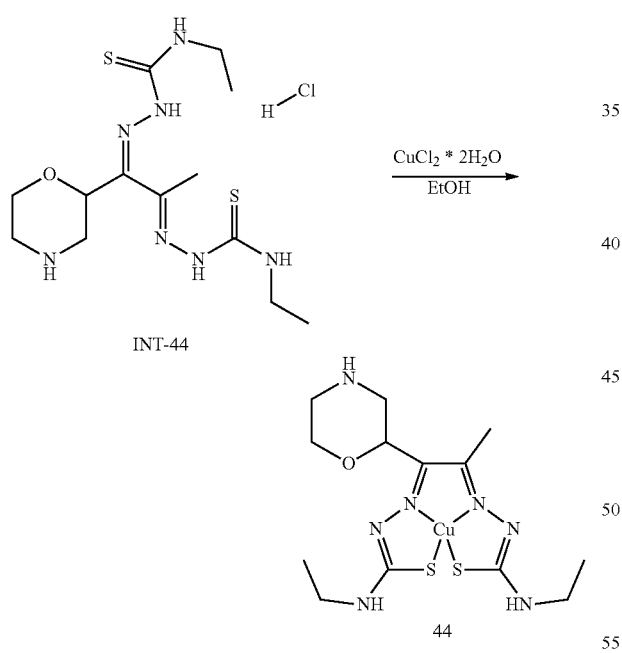

INT-44

44

CuCl$_2$·2H$_2$O (0.036 g, 1 eq) was added to INT-44 (0.1 g, 0.2 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.03 g (33%). LCMS (C18 column 20×2 mm, particle size 2.5 μm, pore size 100A, water-acetonitrile+0.1% TFA, gradient 5 to 87% for 4 min, retention time 1.47 min). MS (ESI) m/z 421.0 [MH]+.

254

Scheme 19: Synthesis of Compound 45

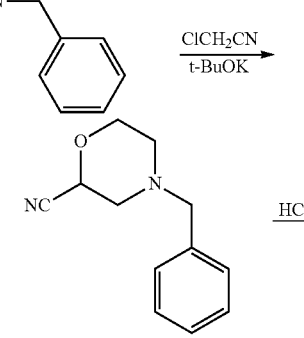

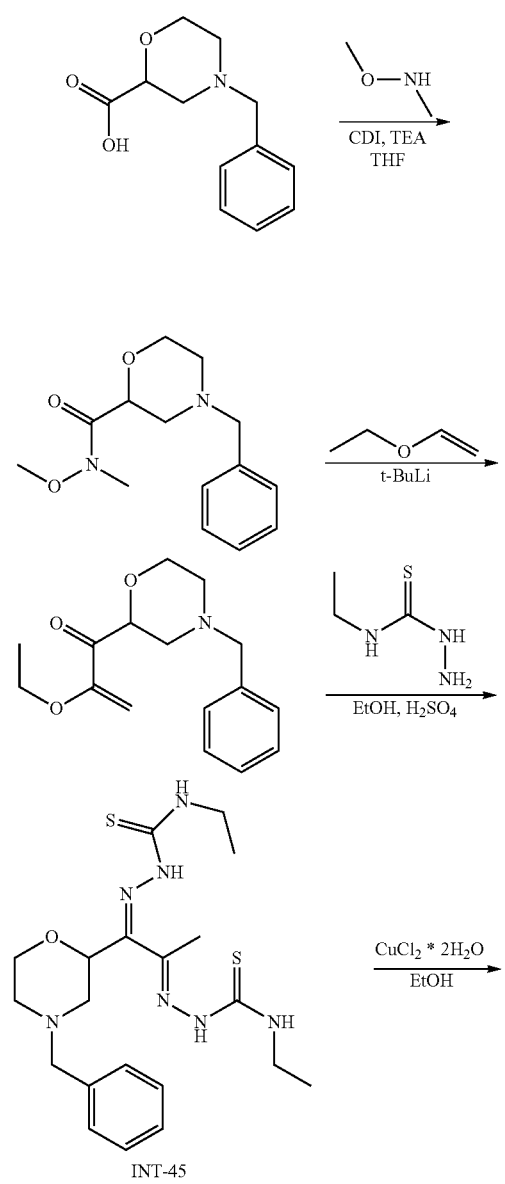

INT-45

-continued

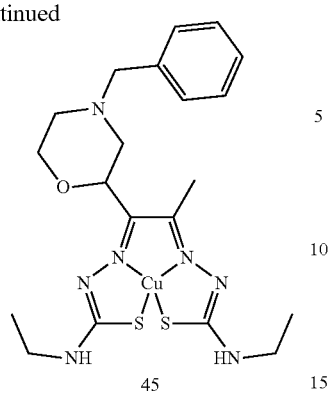

Synthesis of 4-benzylmorpholine-2-carbonitrile

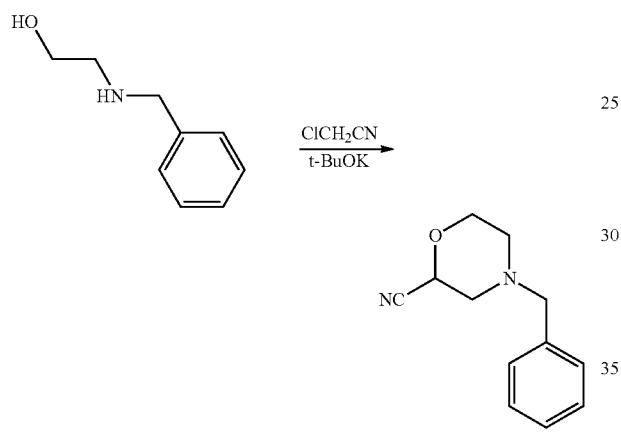

2-Chloroacetonitrile (6 g, 1.03 eq) was dissolved in toluene (16 ml). A solution of N-benzylethanolamine (10 g, 66 mmol) in toluene (5 ml) was added and the reaction mixture was stirred for 15 h at ambient temperature. Then toluene (30 ml) was added and the solution was cooled down to −5° C. Suspension of t-BuOK (7.6 g, 1.03 eq) in THF (128 ml) was slowly added and the mixture was stirred at −5° C. for 50 min. The mixture was washed with brine, dried and evaporated. The residue was purified by column chromatography (silica gel, hexane:EtOAc gradient 3:1 to 1:1. Yield 8.4 g (62.8%). LCMS (C18 column 20×2 mm, particle size 2.5 μm, pore size 100A, water-acetonitrile+0.1% TFA, gradient 5 to 87% for 3 min, retention time 1.22 min), MS (ESI) m/z 203.4 [MH]+.

Synthesis of 4-benzylmorpholine-2-carboxylic Acid

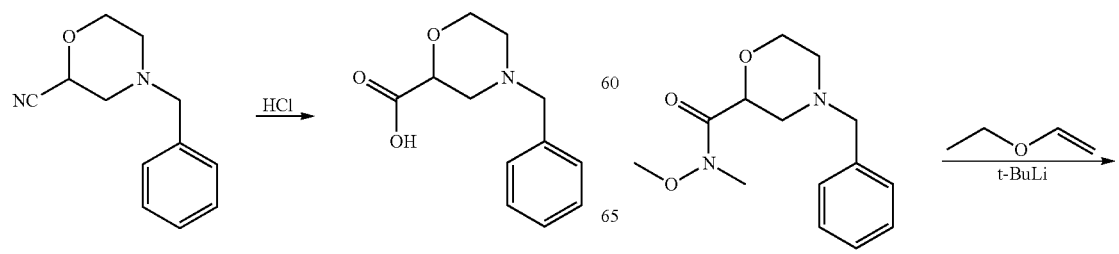

4-Benzylmorpholine-2-carbonitrile (1.6 g, 7.9 mmol, 1 eq) was dissolved in HCl (6M, 65 ml) and the reaction mixture was refluxed for 2.5 h. Then toluene (15 ml) was added and refluxing was continued for additional 3 h. The reaction mixture was evaporated to dryness. Yield 1.6 g (78.5%). LCMS (C18 column 20×2 mm, particle size 2.5 μm, pore size 100A, water-acetonitrile+0.1% TFA, gradient 5 to 87% for 3 min, retention time 0.65 min), MS (ESI) m/z 222.4 [MH]+.

Synthesis of 4-benzyl-N-methoxy-N-methylmorpholine-2-carboxamide

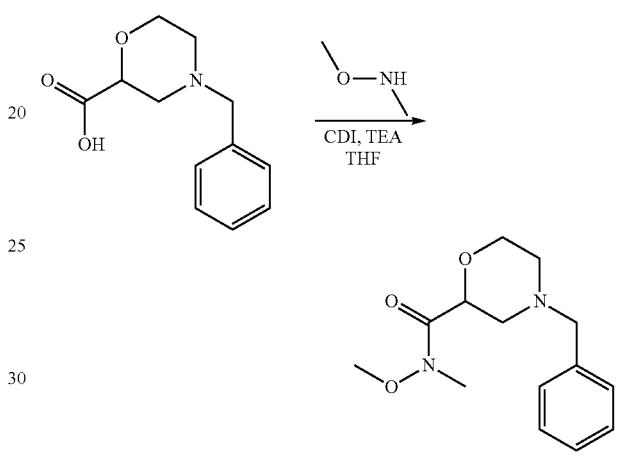

A solution of CDI (1.2 g, 1.2 eq) in THF (12 ml) was added to a solution of 4-benzylmorpholine-2-carboxylic acid (1.6 g, 6.2 mmol, 1 eq) and triethylamine (0.8 ml) in THF (12 ml) at 0° C. The mixture was stirred at room temperature for 1 h. Then the mixture was cooled to 0° C. and a suspension of triethylamine (1.2 ml) and N,O-dimethylhydroxylamine (0.73 g, 1.2 eq) in MeCN (17 ml) at 0° C. was added, and the reaction was stirred at room temperature for 16 h. Then the solvents were evaporated. The residue was dissolved in DCM, solution was washed with water, then with acetic acid (20% aq solution) and aq.sat. NaHCO$_3$. The organic layer was separated, dried over Na$_2$SO$_4$, filtered and solvents were evaporated. Yield 0.9 g (54.8%). LCMS (C18 column 20×2 mm, particle size 2.5 μm, pore size 100A, water-acetonitrile+0.1% TFA, gradient 5 to 87% for 3 min, retention time 1.00 min), MS (ESI) m/z 265.1 [MH]+.

Synthesis of 1-(4-benzylmorpholin-2-yl)-2-ethoxyprop-2-en-1-one

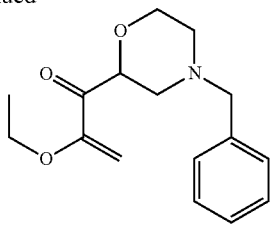

A solution of ethyl vinyl ether (0.34 g, 0.5 ml, 3.3 eq) in dry tetrahydrofuran (20 mL) was cooled to −78° C., and tert-butyllithium (1.7M, 2.4 ml, 3 eq) in pentane was added. The mixture was warmed to 0° C. over 1 h period, stirred for 45 min, and then cooled down to −30° C. 4-Benzyl-N-methoxy-N-methylmorpholine-2-carboxamide was added (3.0 g, 7.5 mmol, 1 eq) in THF, and the mixture was stirred at 0° C. for 4 h. The progress of the reaction was monitored by TLC. The mixture was poured into aq NH$_4$Cl and extracted with Et$_2$O. The combined extracts were dried over Na$_2$SO$_4$, filtered and solvents were evaporated. The product was used for the next step without additional purification. Yield 0.3 g (82%). LCMS (C18 column 20×2 mm, particle size 2.5 μm, pore size 100A, water-acetonitrile+0.1% TFA, gradient 5 to 87% for 3 min, retention time 1.03 min), MS (ESI) m/z 276.1 [MH]+.

Synthesis of INT-45 ((2E,2'E)-2,2'-(1-(4-benzylmorpholin-2-yl)propane-1,2-diylidene)bis(N-ethylhydrazine-1-carbothioamide)

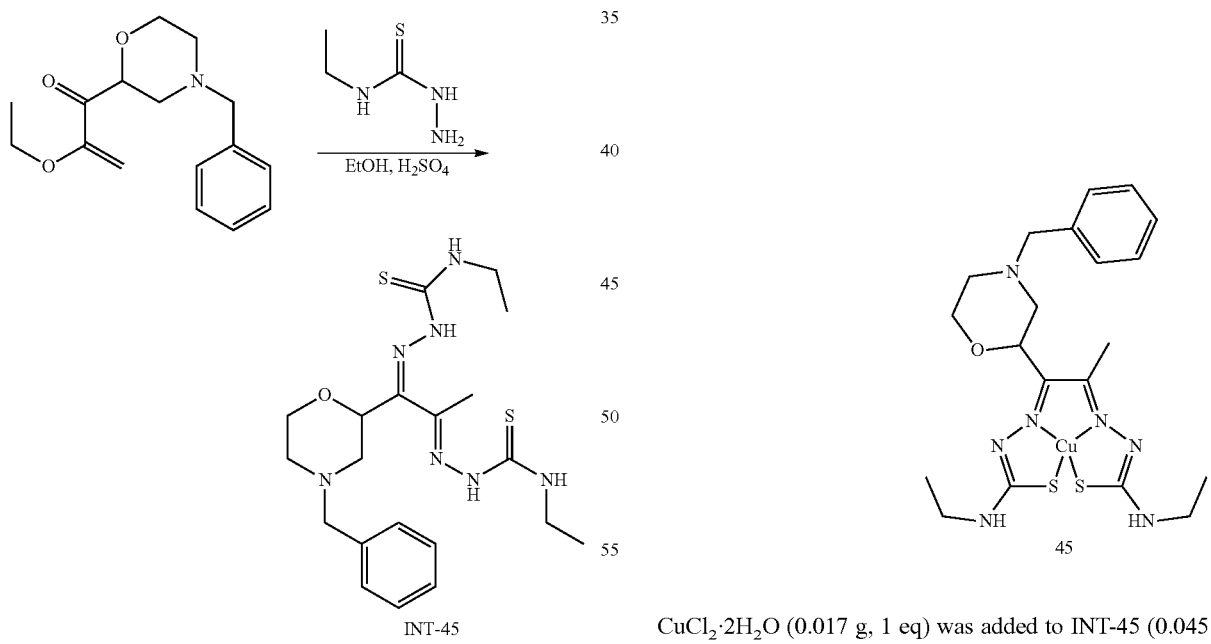

1-(4-Benzylmorpholin-2-yl)-2-ethoxyprop-2-en-1-one (0.3 g, 1 mmol, 1 eq) was dissolved in EtOH (10 ml), ethyl thiosemicarbazide (0.26 g, 2 eq) and 1 drop of H$_2$SO$_4$ were added. Reaction mixture was stirred and heated to reflux for 4 h and then maintained for 15 h at ambient temperature. The formed precipitate was filtered, washed with EtOH, water, Et$_2$O, and dried. Yield 0.08 g (16%). NMR (400 MHz, DMSO-d$_6$): 1.05 (t, 6H), 2.37 (s, 3H), 3.50-3.56 (m, 4H), 3.80 (br.s, 1H), 4.25 (br.s, 2H), 5.65 (br.s, 1H), 7.30-7.48 (m, 4H), 8.09 (br.s, 1H), 8.59 (br.s, 1H), 10.22 (s, 1H), 10.80 (br.s, 1H). LCMS (C18 column 20×2 mm, particle size 2.5 μm, pore size 100A, water-acetonitrile+0.1% TFA, gradient 5 to 87% for 3 min, retention time 1.20 min), MS (ESI) m/z 450.4 [MH]+.

Synthesis of Compound 45

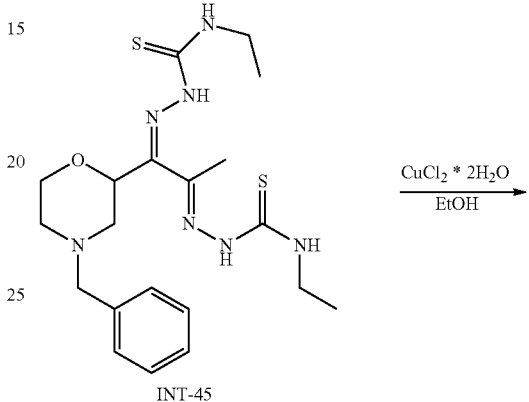

CuCl$_2$·2H$_2$O (0.017 g, 1 eq) was added to INT-45 (0.045 g, 0.1 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.035 g (68.5%). LCMS (C18 column 20×2 mm, particle size 2.5 μm, pore size 100A, water-acetonitrile+0.1% TFA, gradient 5 to 87% for 4 min, retention time 1.70 min). MS (ESI) m/z 511.3 [MH]+.

Scheme 20: Synthesis of Compound 46

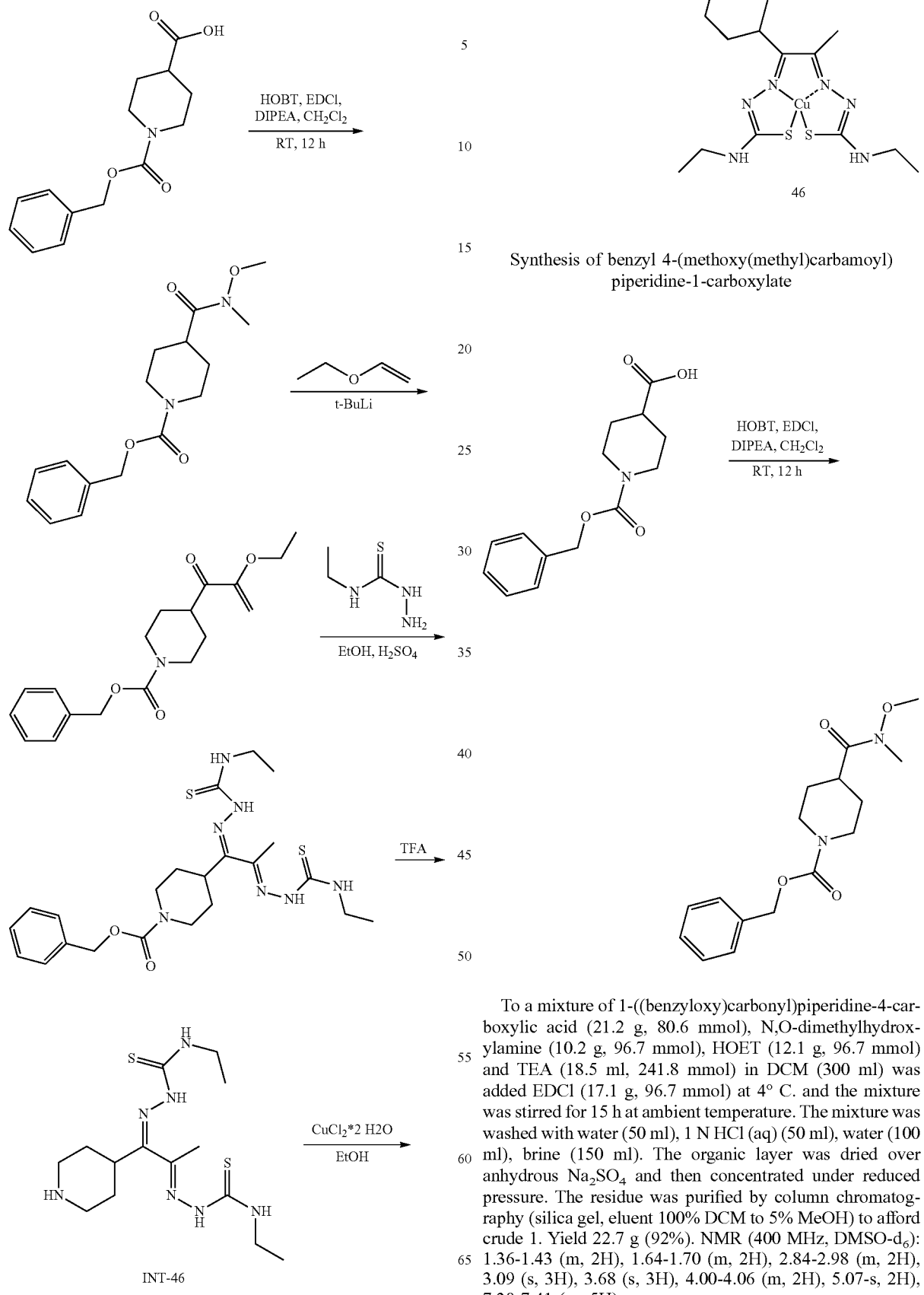

Synthesis of benzyl 4-(methoxy(methyl)carbamoyl)piperidine-1-carboxylate

To a mixture of 1-((benzyloxy)carbonyl)piperidine-4-carboxylic acid (21.2 g, 80.6 mmol), N,O-dimethylhydroxylamine (10.2 g, 96.7 mmol), HOET (12.1 g, 96.7 mmol) and TEA (18.5 ml, 241.8 mmol) in DCM (300 ml) was added EDCl (17.1 g, 96.7 mmol) at 4° C. and the mixture was stirred for 15 h at ambient temperature. The mixture was washed with water (50 ml), 1 N HCl (aq) (50 ml), water (100 ml), brine (150 ml). The organic layer was dried over anhydrous $Na_2SO_4$ and then concentrated under reduced pressure. The residue was purified by column chromatography (silica gel, eluent 100% DCM to 5% MeOH) to afford crude 1. Yield 22.7 g (92%). NMR (400 MHz, DMSO-$d_6$): 1.36-1.43 (m, 2H), 1.64-1.70 (m, 2H), 2.84-2.98 (m, 2H), 3.09 (s, 3H), 3.68 (s, 3H), 4.00-4.06 (m, 2H), 5.07-s, 2H), 7.30-7.41 (m, 5H).

Synthesis of benzyl 4-(2-ethoxyacryloyl)piperidine-1-carboxylate

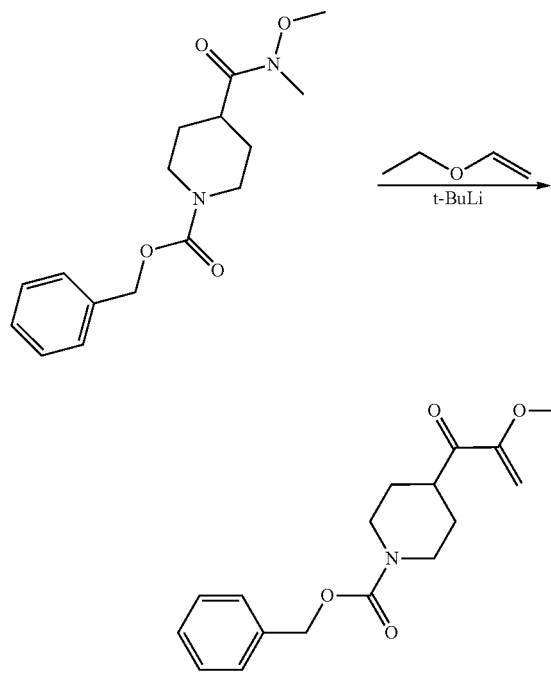

A solution of ethyl vinyl ether (2.0 g, 28.1 mmol) in dry tetrahydrofuran (45 ml) was cooled down to −78° C., and tert-butyllithium (1.7M, 15.6 ml, 25.5 mmol) in pentane was added. The mixture was warmed to 0° C. over 1 h period, stirred for 45 min, and then cooled down to −30° C. Benzyl 4-(methoxy(methyl)carbamoyl)piperidine-1-carboxylate (2.6 g, 8.5 mmol) was added in THF (15 ml), stirring at 0° C. for 4 h. The progress of the reaction was monitored by TLC. The mixture was poured into diluted $NH_4Cl$ (100 ml) and extracted with $Et_2O$ (3×100 ml). The combined extracts were dried over $Na_2SO_4$, filtered and solvents were evaporated. The product was used for the next step without additional purification. Yield 0.77 g (29%). LCMS (C18 column 20×2 mm, particle size 2.5 μm, pore size 100A, water-acetonitrile+0.1% TFA, gradient 5 to 87% for 3 min, retention time 1.58 min), MS (ESI) m/z 318.2 [MH]+.

Synthesis of benzyl 4-((6Z,8E)-8-methyl-4,11-dithioxo-3,5,6,9,10,12-hexaazatetradeca-6,8-dien-7-yl)piperidine-1-carboxylate

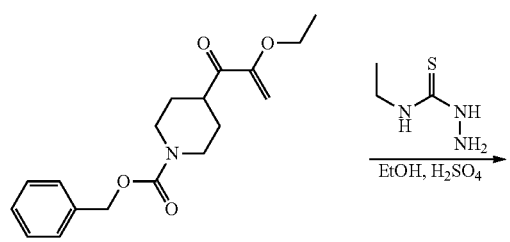

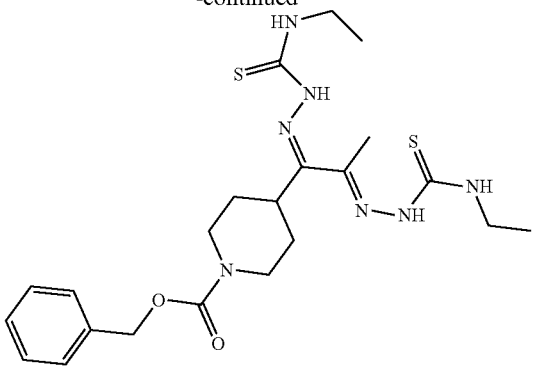

Benzyl 4-(2-ethoxyacryloyl)piperidine-1-carboxylate (1.5 g, 4.6 mmol) was dissolved in EtOH (80 ml), ethyl thiosemicarbazide (1.2 g, 10.1 mmol) and 3 drops of $H_2SO_4$ were added. Reaction mixture was stirred and heated to reflux for 4 h and then maintained for 15 h at ambient temperature. The formed precipitate was filtered, washed with EtOH, water, $Et_2O$, and dried. Yield 0.3 g (14%). LCMS (C18 column 20×2 mm, particle size 2.5 μm, pore size 100A, water-acetonitrile+0.1% TFA, gradient 5 to 87% for 3 min, retention time 1.47 min), MS (ESI) m/z 492.2 [MH]+.

Synthesis of INT-46 ((2Z,2'E)-2,2'-(1-(piperidin-4-yl)propane-1,2-diylidene)bis(N-ethylhydrazine-1-carbothioamide))

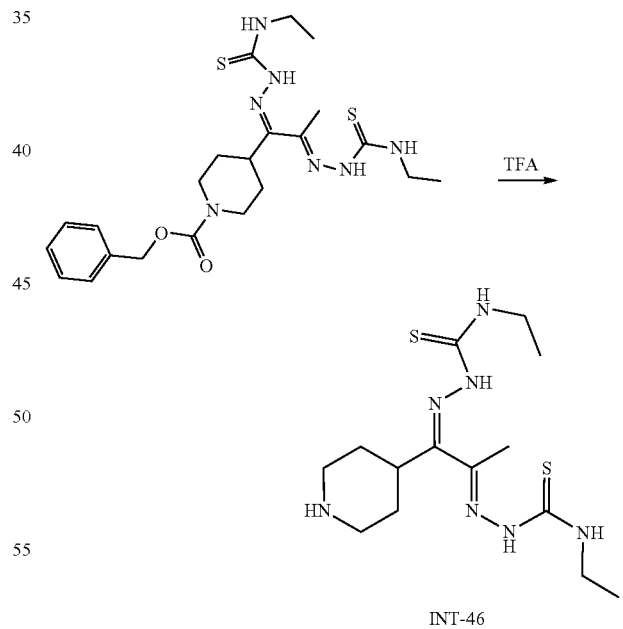

INT-46

Benzyl 4-((6Z,8E)-8-methyl-4,11-dithioxo-3,5,6,9,10,12-hexaazatetradeca-6,8-dien-7-yl)piperidine-1-carboxylate (0.35 g, 0.7 mmol) was dissolved in $CF_3COOH$ (5 ml) and solution was heated to refluxed for 2.5 h. After cooling down to ambient temperature, the reaction mixture was diluted with aq.sat. $NaHCO_3$ solution, and extracted with $CH_2Cl_2$ (3×15 ml). The organic layer was washed with water, separated, dried over $Na_2SO_4$, filtered and solvents were evaporated. The residue was purified by column chromatography (silica gel, eluent 100% DCM to 5% MeOH) to afford the crude titular product. Yield 0.25 g (98%). LCMS (C18 column 20×2 mm, particle size 2.5 μm, pore size 100A, water-acetonitrile+0.1% TFA, gradient 5 to 87% for 3 min, retention time 1.11 min), MS (ESI) m/z 358.5 [MH]+.

Synthesis of Compound 46

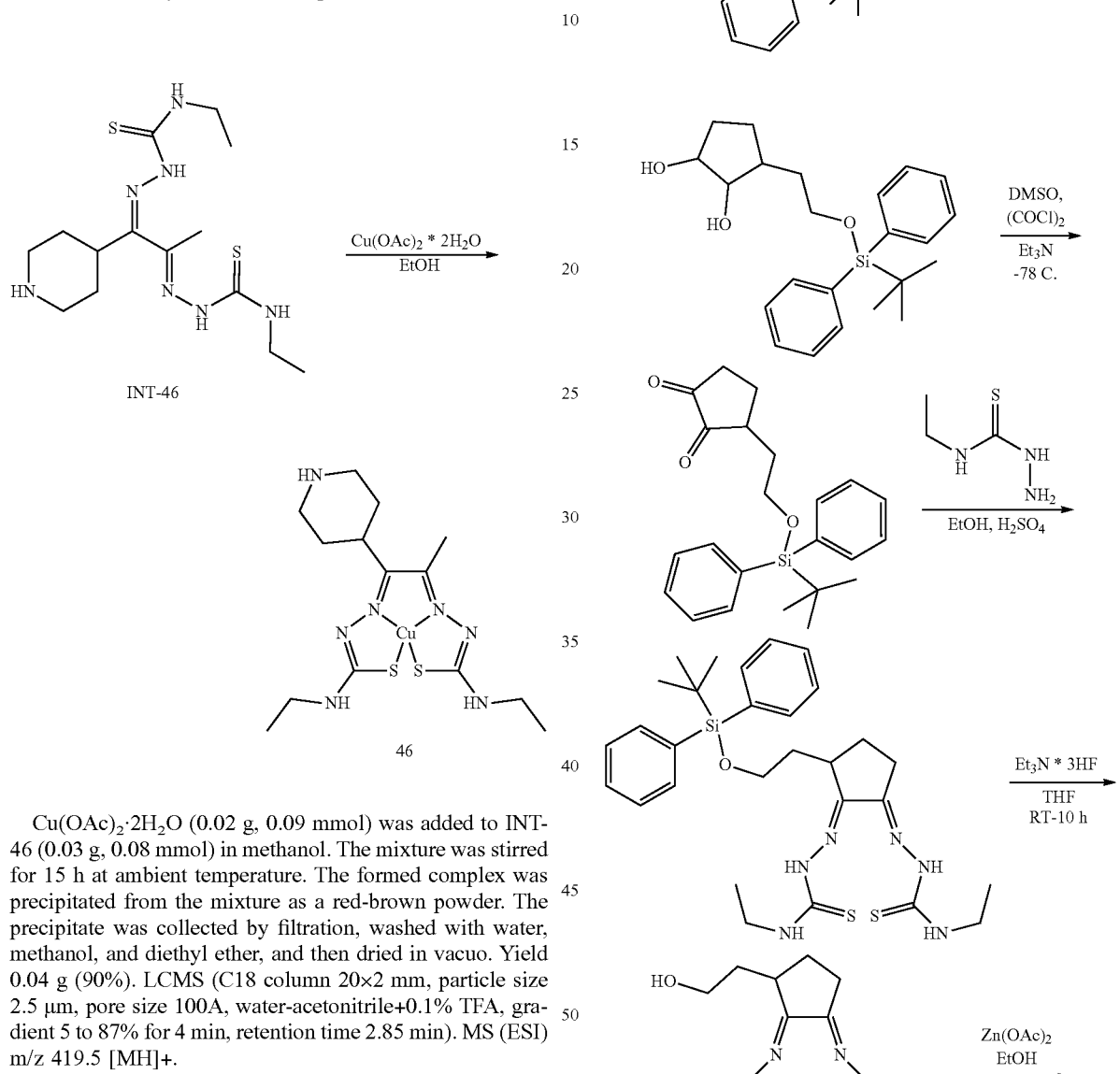

Cu(OAc)$_2$·2H$_2$O (0.02 g, 0.09 mmol) was added to INT-46 (0.03 g, 0.08 mmol) in methanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.04 g (90%). LCMS (C18 column 20×2 mm, particle size 2.5 μm, pore size 100A, water-acetonitrile+0.1% TFA, gradient 5 to 87% for 4 min, retention time 2.85 min). MS (ESI) m/z 419.5 [MH]+.

Example 3: Preparation of Compounds 47-53

Scheme 21: Synthesis of Compound 47

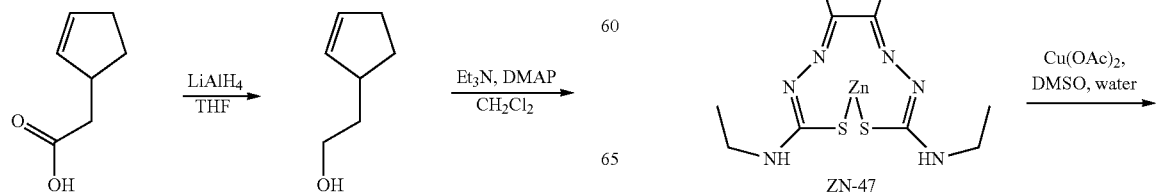

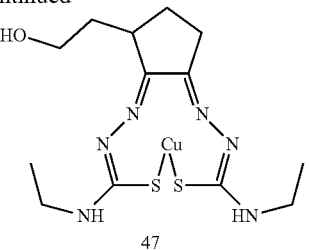

47

Synthesis of 2-(cyclopent-2-en-1-yl)ethan-1-ol

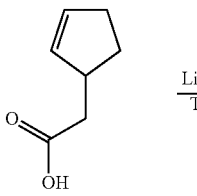 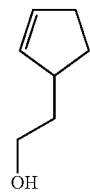

To a stirred suspension of LiAlH₄ (3.76 g, 99.0 mmol, 2.5 equiv) in THF (250 ml) a solution of cyclopent-2-eneacetic acid (5.0 g, 39.6 mmol, 1.0 equiv) in THF (50 ml) was slowly added at 0° C. The mixture was heated to reflux for 3 h, and then cooled to 0° C. The reaction was quenched with Na₂SO₄ (10%) and extracted with Et₂O (3×100 ml). The combined extracts were dried over Na₂SO₄, filtered and evaporated. The product was used for the next step without additional purification. Yield 4.06 g (91%). ¹H-NMR (400 MHz, CDCl₃): δ (ppm) 1.40-1.48 (m, 1H), 1.50-1.51 (m, 1H), 1.56-1.64 (m, 1H), 1.67-1.76 (m, 1H), 2.04-2.13 (m, 1H), 2.27-2.37 (m, 2H), 2.78 (br.s, 1H), 3.66-3.75 (m, 2H), 5.68-5.71 (m, 1H), 5.74-5.76 (m, 1H).

Synthesis of tert-butyl(2-(cyclopent-2-en-1-yl)ethoxy)diphenylsilane

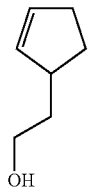 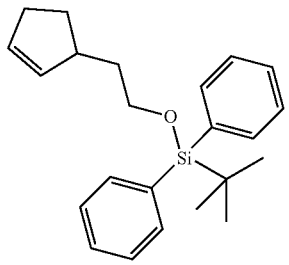

To a solution of 2-(cyclopent-2-en-1-yl)ethan-1-ol (4.05 g, 36.1 mmol) in dichloromethane (200 ml) was added tert-butyldiphenylsilyl chloride (11.9 g, 43.3 mmol), triethylamine (4.7 g, 46.9 mmol), and 4-(dimethylamino)pyridine (0.22 g, 1.8 mmol), the mixture was stirred at room temperature for 3 hours. After quenching the reaction by the addition of 1N hydrochloric acid, the mixture was extracted with dichloromethane. The organic extracts were washed with water, aq. sodium bicarbonate, and brine, dried over anhydrous sodium sulfate, filtered and then concentrated in vacuo. Flash chromatography (silica gel, hexane-ethyl acetate 50:1) of the residue gave compound 2. Yield 11.3 g (89%). ¹H-NMR (400 MHz, DMSO-d₆): δ (ppm) 0.99 (s, 9H), 1.26-1.35 (m, 1H), 1.43-1.51 (m, 1H), 1.61-1.69 (m, 1H), 1.88-1.97 (m, 1H), 2.13-2.30 (m, 2H), 2.70-2.76 (m, 1H), 3.68 (t, 2H), 5.62-5.65 (m, 1H), 5.66-5.70 (m, 1H), 7.41-7.46 (m, 6H), 7.60-7.62 (m, 4H).

Synthesis of 3-(2-((tert-butyldiphenylsilyl)oxy)ethyl)cyclopentane-1,2-diol

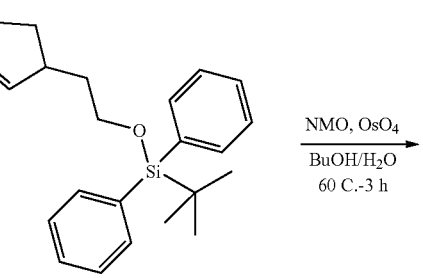

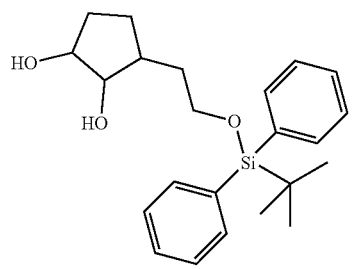

Tert-butyl(2-(cyclopent-2-en-1-yl)ethoxy)diphenylsilane (9.0 g, 25.6 mmol) was dissolved in an H₂O-tBuOH (1:3) mixture then N-methylmorpholine N-oxide (3.9 g, 33.3 mmol) and OSO₄ (0.004 g of 4% solution in water, 0.001 eq) were added. The reaction mixture was stirred at 60° C. until completion, monitoring by TLC (CHCl₃—CH₃OH 20:1), solid catalyst was filtered, rinsed with EtOAc, and the filtrate quenched with an aqueous solution of Na₂S₂O₃ (10%). The aqueous layer was extracted with EtOAc, the organic extracts combined, dried over Na₂SO₄, filtered and solvents were evaporated. The crude product was purified by flash chromatography (gradient CHCl₃-MeOH from 1:0 to 95:5), to afford diol 3. Yield 6.3 g (64%). LCMS (C18 column 20×2 mm, particle size 2.5 μm, pore size 100A, water-acetonitrile+0.1% TFA, gradient 5 to 87% for 3 min, retention time 1.99 min). MS (ESI) m/z 385.1 [MH]+. ¹H-NMR (400 MHz, DMSO-d₆): δ (ppm) 0.98 (s, 9H), 1.26-1.55 (m, 2H), 1.66-1.68 (m, 1H), 1.69-1.78 (m, 2H), 1.79-1.88 (m, 2H), 3.59-3.60 (m, 1H), 3.67 (q, 2H), 3.74-3.88 (m, 1H), 4.09 (dd, 1H), 4.32 (dd, 1H), 7.41-7.48 (m, 6H), 7.60-7.62 (m, 4H).

Synthesis of 3-(2-((tert-butyldiphenylsilyl)oxy)ethyl)cyclopentane-1,2-dione

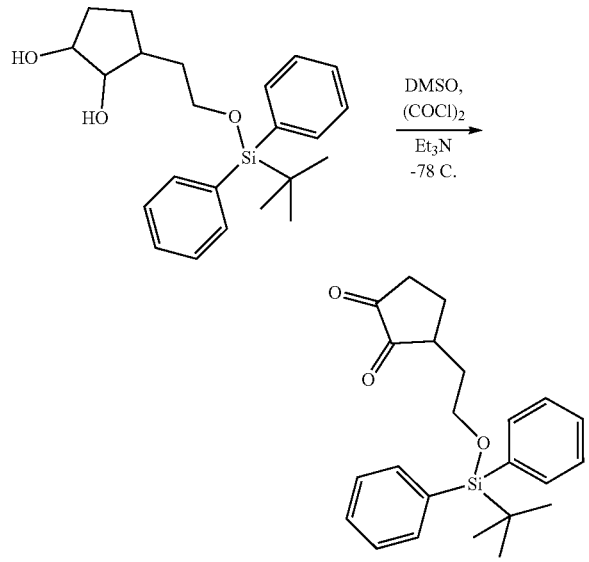

Dimethyl sulfoxide (3.6 g, 46.8 mmol) was added to a stirred solution of oxalyl chloride (2.97 g, 23.4 mmol) in dichloromethane (100 ml) at −78° C. After 15 min a solution of 3-(2-((tert-butyldiphenylsilyl)oxy)ethyl)cyclopentane-1,2-diol (3.0 g, 7.9 mmol) in dichloromethane (20 ml) was slowly added (over period of 15 min) and the resulting solution was stirred at −78° C. for 1 h. Then triethylamine (7.3 g, 70 mmol) was added, the mixture was stirred for 15 min at −78° C. and then warmed to ambient temperature. The reaction mixture was washed with water, organic layer was dried over $Na_2SO_4$, filtered, and evaporated. Yield 1.6 g (54%). LCMS (C18 column 20×2 mm, particle size 2.5 µm, pore size 100A, water-acetonitrile+0.1% TFA, gradient 5 to 87% for 3 min, retention time 2.01 min). MS (ESI) m/z 381.1 [MH]+. $^1$H-NMR (400 MHz, DMSO-$d_6$): δ (ppm) 0.97 (s, 9H), 1.90 (t, 1H), 2.27-2.35 (m, 2H), 2.46-2.51 (m, 2H), 3.52-3.46 (m, 2H), 3.63-3.86 (m, 2H), 7.41-7.48 (m, 6H), 7.60-7.62 (m, 4H).

Synthesis of (2E,2'E)-2,2'-(3-(2-((tert-butyldiphenylsilyl)oxy)ethyl)cyclopentane-1,2-diylidene)bis(N-ethylhydrazine-1-carbothioamide)

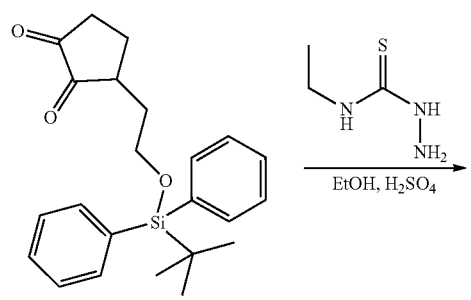

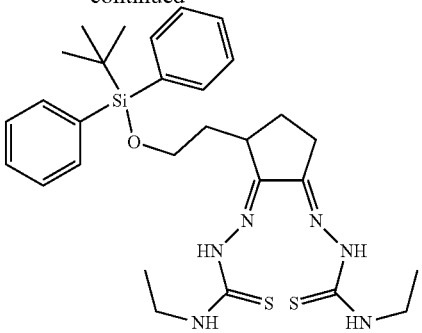

3-(2-((tert-butyldiphenylsilyl)oxy)ethyl)cyclopentane-1,2-dione (1.6 g, 4.2 mmol) was dissolved in EtOH (25 ml), ethyl thiosemicarbazide (1.02 g, 4.4 mmol) and 3 drops of $H_2SO_4$ were added and the reaction mixture was stirred for 4 h at reflux and for 15 h at ambient temperature. The formed precipitate was filtered, washed with EtOH, water, $Et_2O$, and dried to afford the product 5. Yield 1.75 g (74%). LCMS (C18 column 20×2 mm, particle size 2.5 µm, pore size 100A, water-acetonitrile+0.1% TFA, gradient 5 to 87% for 3 min, retention time 2.58 min). MS (ESI) m/z 583.3 [MH]+. $^1$H-NMR (400 MHz, DMSO-$d_6$): δ (ppm) 0.99 (s, 9H), 1.11 (t, 3H), 1.20 (t, 3H), 1.41-1.59 (m, 2H), 1.96-2.03 (m, 2H), 2.21-2.29 (m, 1H), 2.71-2.85 (m, 2H), 3.53-3.62 (m, 4H), 3.71-3.83 (m, 2H), 7.41-7.48 (m, 6H), 7.61-7.63 (m, 4H). 7.75 (t, 1H), 8.57 (t, 1H), 10.73 (s, 1H), 12.26 (s, 1H).

Synthesis of INT-47 ((2E,2'E)-2,2'-(3-(2-hydroxyethyl)cyclopentane-1,2-diylidene)bis(N-ethylhydrazine-1-carbothioamide))

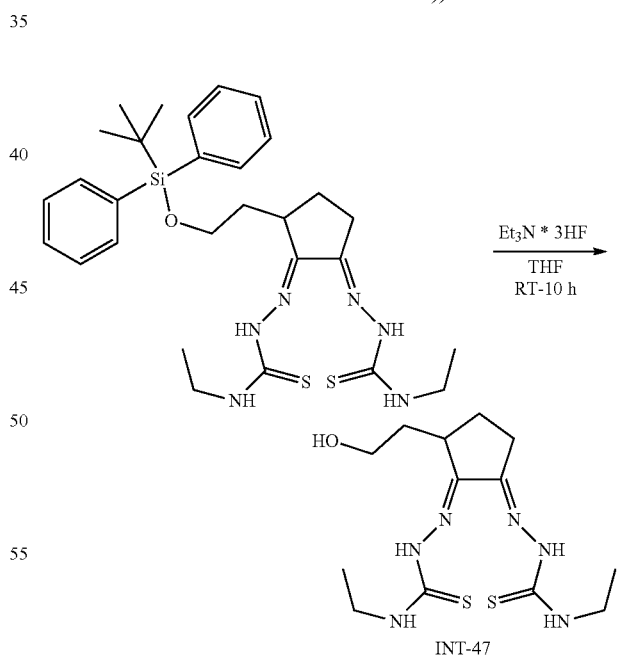

To a solution of (2E,2'E)-2,2'-(3-(2-((tert-butyldiphenylsilyl)oxy)ethyl)cyclopentane-1,2-diylidene)bis(N-ethylhydrazine-1-carbothioamide) (0.85 g, 1.46 mmol) in THF (25 ml) was added triethylamine trihydrofluoride at ambient temperature. The resulting mixture was stirred at ambient temperature for 10 h, treated with sat. aq. ammonium chloride. The solution was extracted with ether, washed with aqueous sat. aq. ammonium chloride and brine. The organic layer was dried over Na₂SO₄, filtered, and solvents were concentrated under reduced pressure providing the crude titular product. Yield 0.18 g (36%). LCMS (C18 column 20×2 mm, particle size 2.5 μm, pore size 100A, water-acetonitrile+0.1% TFA, gradient 5 to 87% for 3 min, retention time 1.30 min). MS (ESI) m/z 345.0 [MH]+. ¹H-NMR (400 MHz, DMSO-d₆): δ (ppm) 1.28 (t, 3H), 1.35 (t, 3H), 1.58-1.81 (m, 2H), 1.86-1.95 (m, 1H), 2.03-2.13 (m, 1H), 2.24-2.33 (m, 1H), 2.44-2.57 (m, 1H), 2.65-2.77 (m, 1H), 2.85-2.93 (m, 1H), 3.31-3.53 (m, 1H), 3.68-2.82 (m, 5H), 7.25-7.32 (m, 1H), 7.41-7.48 (m, 1H), 8.75 (s, 1H), 12.27 (s, 1H).

Synthesis of ZN-47

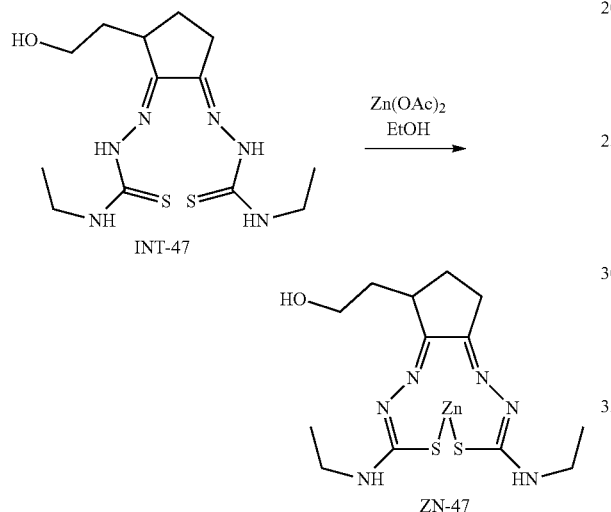

Zn(OAc)₂ 2H₂O (0.58 g, 2.7 mmol) was added to INT-47 (0.61 g, 1.8 mmol) in ethanol. The mixture was refluxed for 4 h. The formed complex was precipitated from the mixture as a yellow powder. The precipitate was collected by filtration, washed with water, methanol, and diethyl ether, and then dried in vacuo. Yield 0.72 g (99%). ¹H-NMR (400 MHz, DMSO-d₆): δ (ppm) 1.09 (t, 3H), 1.14 (t, 3H), 1.35-1.48 (m, 2H), 2.01-2.11 (m, 2H), 2.51-2.55 (m, 2H), 2.67-2.73 (m, 1H), 2.76-2.84 (m, 1H), 3.47-3.56 (m, 4H), 4.34 (t, 1H), 4.42 (t, 1H), 7.37 (br.s, 1H), 7.85 (t, 1H).

Synthesis of Compound 47

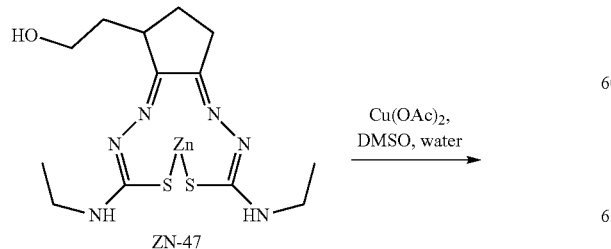

-continued

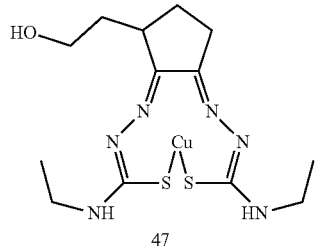

ZN-47 (0.72 g, 1.7 mmol) was dissolved in DMSO (3.6 ml) and a solution of CUCl₂ 2H₂O (0.39 g, 1.9 mmol) in water (3.6 ml) was added. The mixture was stirred for 5 min, precipitate was filtered and washed with saturated solution of potassium carbonate, water and Et₂O. Yield 0.09 g (13%). LCMS (C18 column 20×2 mm, particle size 2.5 μm, pore size 100A, water-acetonitrile+0.1% TFA, gradient 5 to 87% for 4 min, retention time 1.81 min). MS (ESI) m/z 406.5 [MH]+.

Scheme 22: Synthesis of Compound 48

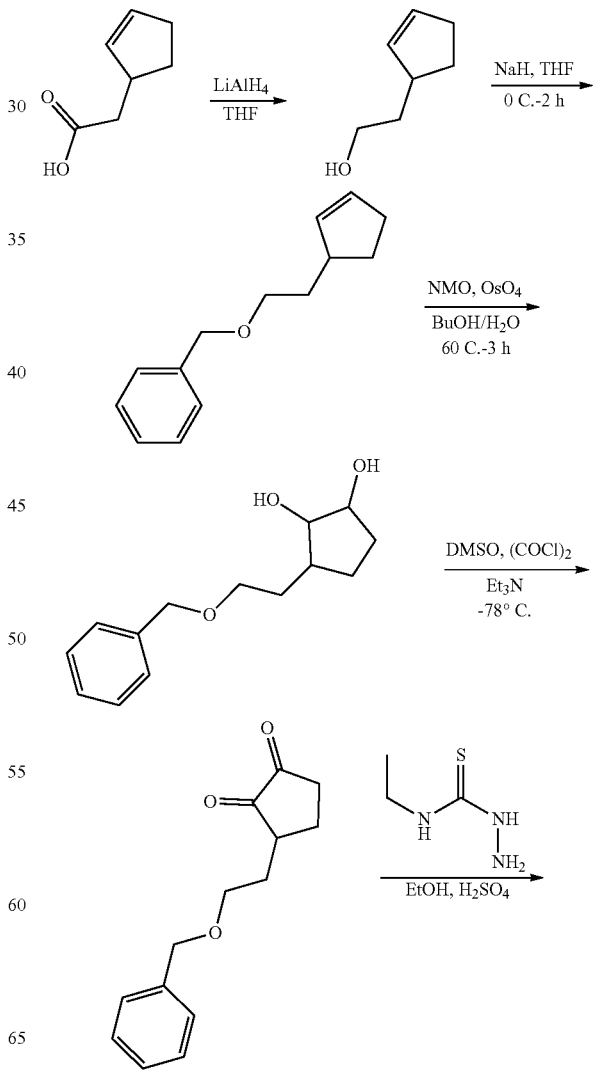

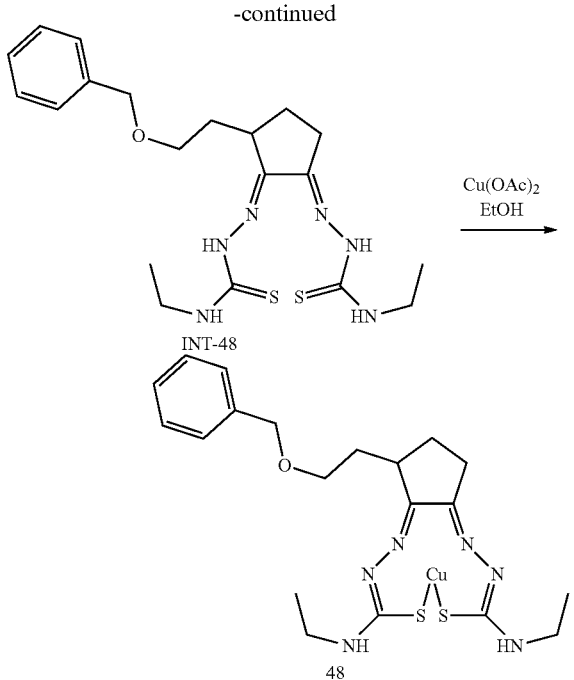

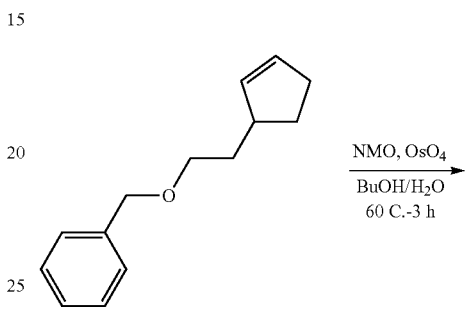

three times with Et$_2$O. The combined extracts were washed with water, brine, dried over Na$_2$SO$_4$, filtered and solvents were evaporated. The crude product was used without purification. Yield 1.8 g (99%). $^1$H-NMR (400 MHz, DMSO-d$_6$): δ (ppm) 1.33-1.41 (m, 1H), 1.46-1.55 (m, 1H), 1.61-1.69 (m, 1H), 1.93-2.02 (m, 1H), 2.14-2.33 (m, 2H), 2.70 (t, 1H), 3.47 (t, 2H), 4.45 (s, 2H), 5.70 (t, 2H), 7.25-7.32 (m, 3H), 7.34-7.45 (m, 2H).

Synthesis of 3-(2-(benzyloxy)ethyl)cyclopentane-1,2-diol

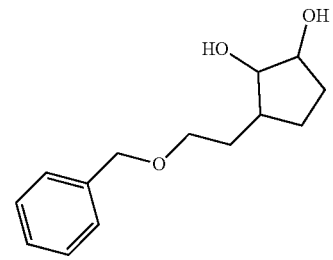

Synthesis of 2-(cyclopent-2-en-1-yl)ethan-1-ol

To a stirred suspension of LiAlH$_4$ (4.14 g, 109.0 mmol) in THF (250 ml) cooled to 0° C., a solution of cyclopent-2-eneacetic acid (5.5 g, 43.6 mmol, 1.0 equiv) in THF (50 ml) was slowly added. The mixture was heated to reflux for 3 h, and then cooled to 0° C. The reaction was quenched with Na$_2$SO$_4$ (10%) and extracted with Et$_2$O (3×100 ml). The combined extracts were dried over Na$_2$SO$_4$, filtered and evaporated. The product was used for the next step without additional purification. Yield 4.4 g (90%). $^1$H-NMR (400 MHz, CDCl$_3$): δ (ppm) 1.40-1.49 (m, 1H), 1.50-1.51 (m, 1H), 1.58-1.64 (m, 1H), 1.67-1.76 (m, 1H), 2.04-2.13 (m, 1H), 2.42-2.37 (m, 2H), 2.78 (br.s, 1H), 3.69-3.77 (m, 2H), 5.68-5.71 (m, 1H), 5.74-5.77 (m, 1H).

Synthesis of ((2-(cyclopent-2-en-1-yl)ethoxy)methyl)benzene

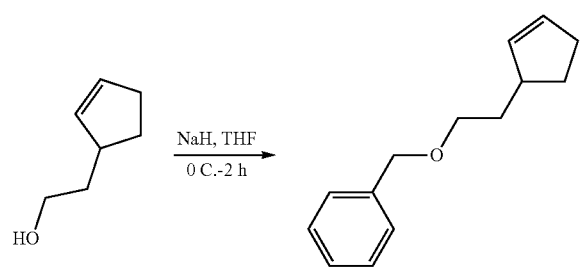 [SMILES: OCCC1C=CCC1 ; C1=CC(CCOCc2ccccc2)CC1]

To a stirred solution of 2-(cyclopent-2-en-1-yl)ethan-1-ol (1.0 g, 8.9 mmol) in DMF (12 ml) at 0° C. in one portion NaH (0.5 g, 13.5 mmol, 60-65% in mineral oil) was added. After stirring for 30 min to the solution was added benzyl chloride (2.03 g, 16.1 mmol). The reaction was stirred overnight, then quenched with water (15 ml) and extracted ((2-(cyclopent-2-en-1-yl)ethoxy)methyl)benzene (2.2 g, 11.1 mmol) was dissolved in an H2O-tBuOH mixture (1:3) then N-methylmorpholine N-oxide (1.7 g, 14.4 mmol) and OSO$_4$ (0.008 g of 4% solution in water, 0.001 eq) were added. The reaction mixture was stirred at 60° C. until completion, monitored by TLC (CHCl$_3$—CH$_3$OH 20:1), solid catalyst was filtered, rinsed with EtOAc, and the filtrate was quenched with an aqueous solution of Na$_2$S$_2$O$_3$ (10%). The aqueous layer was extracted with EtOAc, the organic extracts were combined, dried over Na$_2$SO$_4$, filtered and solvents were evaporated. The crude product purified by flash chromatography (CHCl$_3$-MeOH gradient 1:0 to 95:5), to afford the titular product. Yield 1.64 g (62%). LCMS (C18 column 20×2 mm, particle size 2.5 μm, pore size 100A, water-acetonitrile+0.1% TFA, gradient 5 to 87% for 3 min, retention time 1.20 min). MS (ESI) m/z 237.0 [MH]+. $^1$H-NMR (400 MHz, DMSO-d$_6$): δ (ppm) 0.95-1.03 (m, 1H), 1.29-1.59 (m, 2H), 1.66-1.68 (m, 1H), 1.69-1.78 (m, 2H), 1.79-1.88 (m, 1H), 3.41-3.48 (m, 2H), 3.45 (qq, 1H), 3.75-3.91 (m, 1H), 4.09 (dd, 1H), 4.32 (dd, 1H), 4.41-4.48 (m, 2H), 7.25-7.36 (m, 5H).

Synthesis of 3-(2-(benzyloxy)ethyl)cyclopentane-1,2-dione

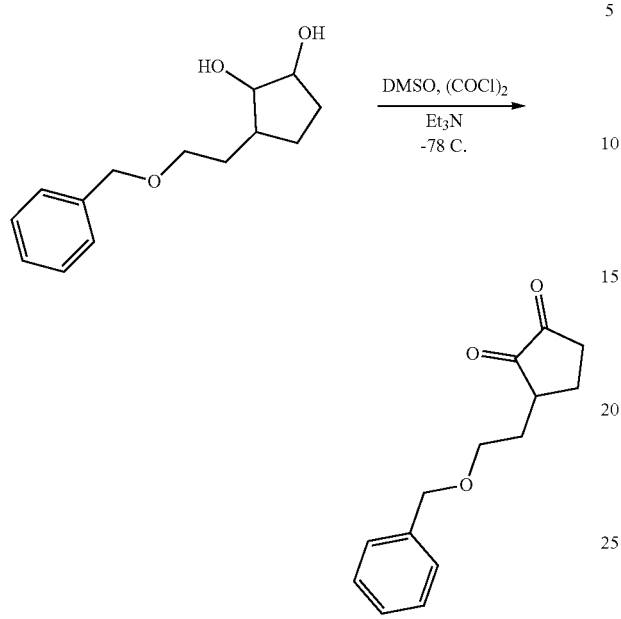

Dimethyl sulfoxide (6.1 g, 78.0 mmol) was added to a stirred solution of oxalyl chloride (4.9 g, 39.0 mmol) in dichloromethane (150 ml) at −78° C. After 15 min a solution of 3-(2-(benzyloxy)ethyl)cyclopentane-1,2-diol (3.1 g, 13.0 mmol) in dichloromethane (20 ml) was slowly added (over period of 15 min) and the resulting solution was stirred at −78° C. for 1 h. Then triethylamine (11.8 g, 117.0 mmol) was added, the mixture was stirred for 15 min at −78° C. and then warmed to ambient temperature. The reaction mixture was washed with water, organic layer was dried over $Na_2SO_4$, filtered and solvents were evaporated. Yield 2.6 g (87%). LCMS (C18 column 20×2 mm, particle size 2.5 μm, pore size 100A, water-acetonitrile+0.1% TFA, gradient 5 to 87% for 3 min, retention time 1.26 min). MS (ESI) m/z 233.1 [MH]+.

Synthesis of INT-48 ((2E,2'E)-2,2'-(3-(2-(benzyloxy)ethyl)cyclopentane-1,2-diylidene)bis(N-ethylhydrazine-1-carbothioamide))

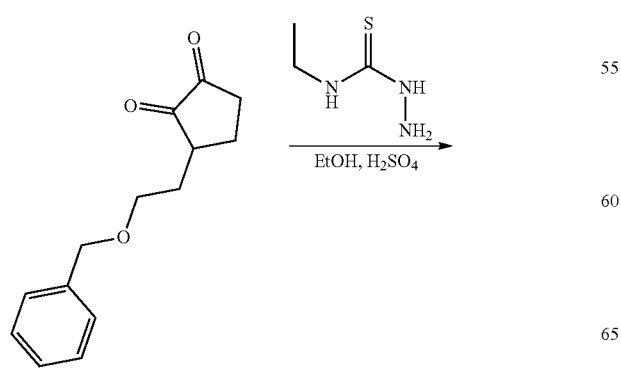

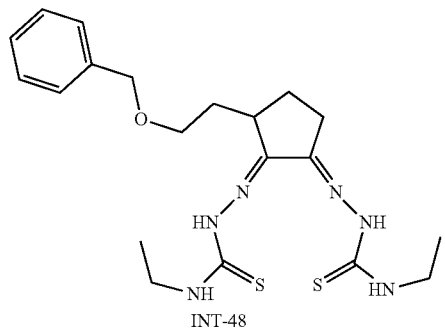

3-(2-(benzyloxy)ethyl)cyclopentane-1,2-dione (2.6 g, 11.4 mmol) was dissolved in EtOH (35 ml), ethyl thiosemicarbazide (2.86 g, 23.9 mmol) and 3 drops of $H_2SO_4$ were added and the reaction mixture was stirred for 4 h at reflux and for 15 h at ambient temperature. The formed precipitate was filtered, washed with EtOH, water, $Et_2O$, and dried to afford the product. Yield 0.40 g (9%). LCMS (C18 column 20×2 mm, particle size 2.5 μm, pore size 100A, water-acetonitrile+0.1% TFA, gradient 5 to 87% for 3 min, retention time 1.86 min). MS (ESI) m/z 435.4 [MH]+. $^1$H-NMR (400 MHz, DMSO-$d_6$): δ (ppm) 1.12 (t, 3H), 1.19 (t, 3H), 1.46-1.58 (m, 2H), 2.05-2.15 (m, 1H), 2.22-2.32 (m, 1H), 2.53-2.58 (m, 1H), 2.74-2.82 (m, 2H), 3.41-3.63 (m, 6H), 4.47 (d, 2H), 7.26-7.37 (m, 5H), 7.77 (t, 1H), 8.66 (t, 1H), 10.74 (s, 1H), 12.25 (s, 1H).

Synthesis of INT-49 ((2E,2'E)-2,2'-(3-(2-methoxyethyl)cyclopentane-1,2-diylidene)bis(N-ethylhydrazine-1-carbothioamide))

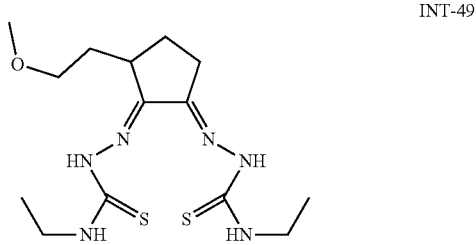 [SMILES: CCNC(=S)N/N=C1\CCC(CCOC)\C1=N/NC(=S)NCC]

INT-49 was made using a procedure analogous to the procedure to prepare INT-48. Yield 1.1 g (72%). $^1$H-NMR (400 MHz, DMSO-$d_6$): δ (ppm) 1.73 (t, 2H), 1.97-2.01 (m, 2H), 2.24-2.27 (m, 1H), 2.36-2.39 (m, 1H), 2.53-2.57 (m, 1H), 2.62-2.67 (m, 1H), 3.12 (d, 3H), 3.38-3.45 (m, 1H).

Synthesis of Compound 48

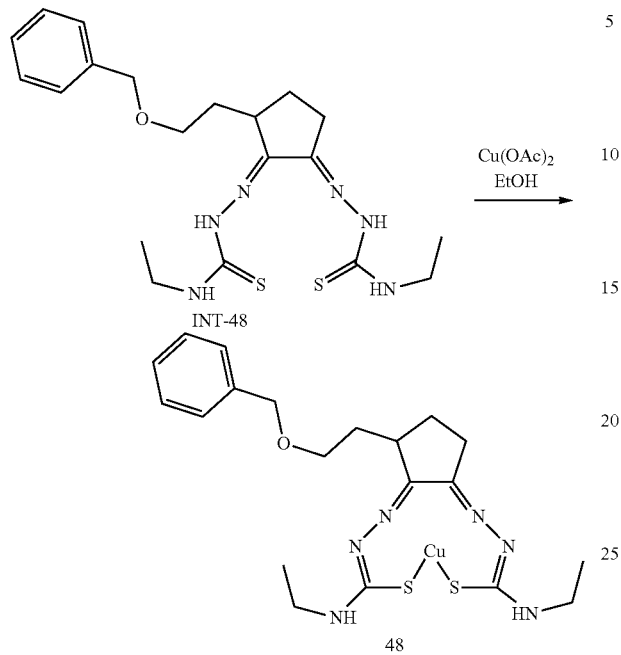

Cu(OAc)$_2$ 2H$_2$O (0.26 g, 1.12 mmol) was added to INT-48 5 (0.4 g, 0.92 mmol) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.1 g (22%). LCMS (C18 column 20×2 mm, particle size 2.5 μm, pore size 100A, water-acetonitrile+0.1% TFA, gradient 5 to 87% for 4 min, retention time 1.98 min). MS (ESI) m/z 496.5 [MH]+.

Synthesis of Compound 49

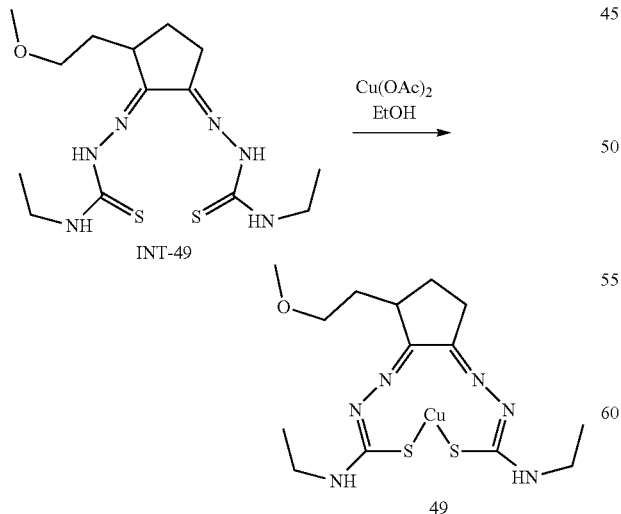

The titular compound was prepared from INT-49 according to the method to prepare compound 48. The product precipitated from the reaction mixture as a red-brown powder. The precipitate was collected by filtration, washed with water, methanol, and diethyl ether, and then dried in vacuo. Yield 0.03 g (35%). LCMS (C18 column 20×2 mm, particle size 2.5 μm, pore size 100A, water-acetonitrile+0.1% TFA, gradient 5 to 87% for 4 min, retention time 2.33 min). MS (ESI) m/z 420.5 [MH]+.

Scheme 23: Synthesis of Coumpound 50

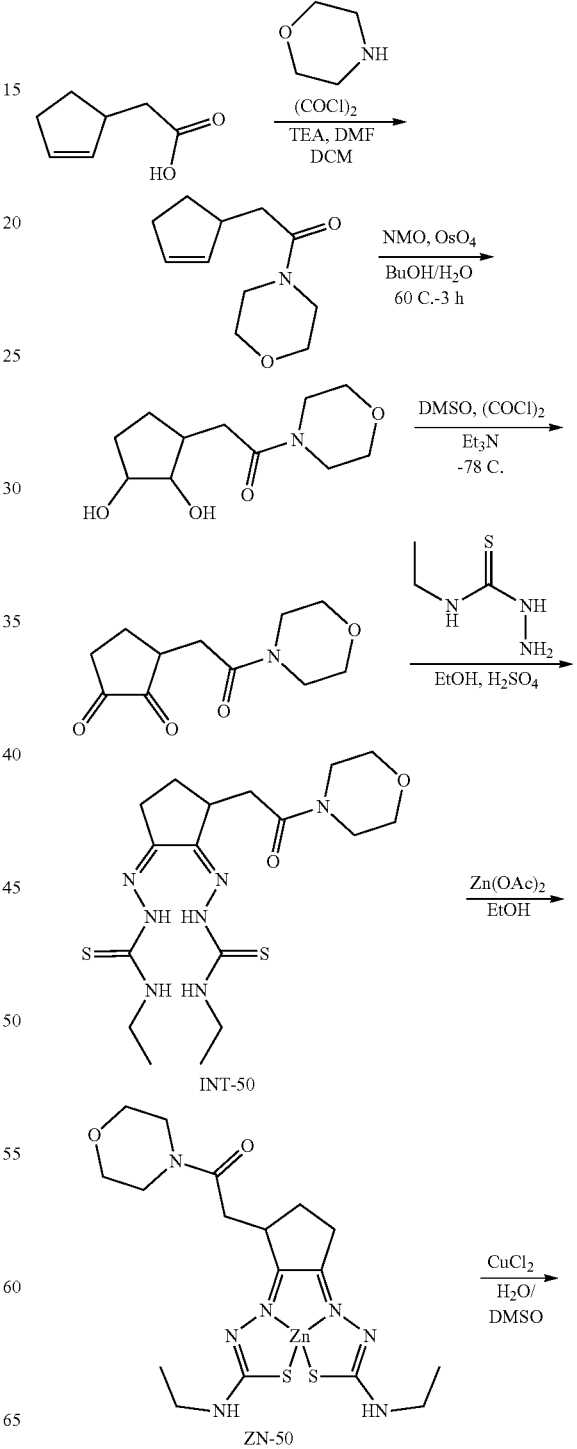

277

-continued

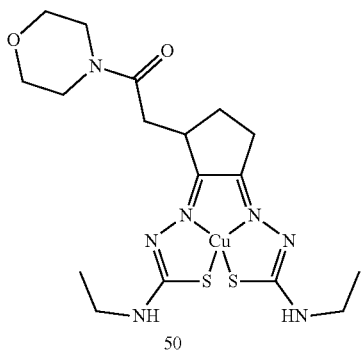

Synthesis of 2-(cyclopent-2-en-1-yl)-1-morpholinoethan-1-one

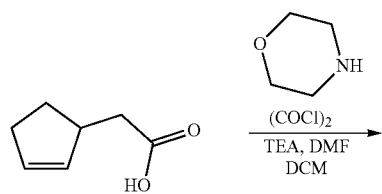

Oxalyl chloride (2.41 g, 1.2 eq) was added to a solution of 2-cyclopentene-1-acetic acid (2.0 g, 16 mmol) in dichloromethane (100 ml), 1 drop of DMF was added and the mixture was stirred at ambient temperature for 2 h. Solvents were evaporated under reduced pressure, the residue was dissolved in EtOAc, to the solution were added Et$_3$N (1.92 g, 1.2 eq) and morpholine (1.38 g, 1 eq). The reaction was stirred overnight at ambient temperature. The reaction mixture was washed with water, organic layer was dried over Na$_2$SO$_4$, filtered, and concentrated in vacuo. The residue was purified by column chromatography (SiO$_2$, CH$_2$Cl$_2$—MeOH, 10:1). Yield 2.1 g (67.8%). LCMS (C18 column 20×2 mm, particle size 2.5 µm, pore size 100A, water-acetonitrile+0.1% TFA, gradient 5 to 87% for 3 min, retention time 1.16 min, MS (ESI) m/z 196.4 [MH]+. $^1$H-NMR (400 MHz, CDCl$_3$): δ (ppm) 1.41-1.53 (m, 1H), 2.12-2.25 (m, 1H), 2.29-2.46 (m, 4H), 3.09-3.21 (m, 1H), 3.42-3.54 (m, 2H), 3.58-3.76 (m, 6H), 5.70-5.74 (m, 1H), 5.75-5.83 (m, 1H).

278

Synthesis of 2-(2,3-dihydroxycyclopentyl)-1-morpholinoethan-1-one

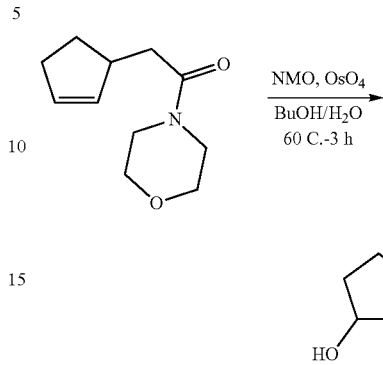

2-(Cyclopent-2-en-1-yl)-1-morpholinoethan-1-one (2.1 g, 10.7 mmol) was dissolved in an H$_2$O-tBuOH mixture (1:3) and to the stirred solution N-methylmorpholine-N-oxide (1.64 eq) and OSO$_4$ (0.035 g of 4% solution in water, 0.001 eq) were added. The reaction mixture was stirred at 60° C. for 4 h and then at ambient temperature for 15 h. The reaction was quenched with Na$_2$S$_2$O$_3$ (10%) and extracted with EtOAc, organic layer was dried over Na$_2$SO$_4$, filtered and evaporated. Yield 1.7 g (68.9%). LCMS (C18 column 20×2 mm, particle size 2.5 µm, pore size 100A, water-acetonitrile+0.1% TFA, gradient 5 to 87% for 3 min, retention time 0.83 min, MS (ESI) m/z 230.3 [MH]+.

Synthesis of 3-(2-morpholino-2-oxoethyl)cyclopentane-1,2-dione

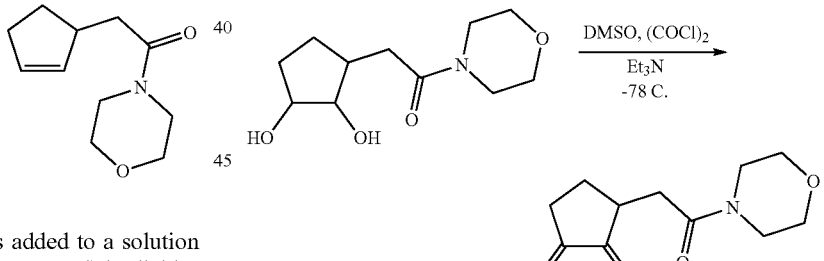

Dimethyl sulfoxide (1.5 g, 1.4 ml, 4 eq) was added to a stirred solution of oxalyl chloride (1.83 g, 1.2 ml, 3 eq) in dichloromethane (40 ml) at −78° C. After 5 min, a solution of 2-(2,3-dihydroxycyclopentyl)-1-morpholinoethan-1-one (1.1 g, 4.8 mmol, 1 eq) in dichloromethane (80 ml) was slowly added (over period of 15 min) and the resulting solution was stirred at −78° C. for 1 h. Then triethylamine (2.9 g, 4 ml, 6 eq) was added, the mixture was stirred for 15 min at −78° C. and then warmed to ambient temperature. The reaction mixture was washed with water, organic layer was dried over Na$_2$SO$_4$, filtered and evaporated. Yield 0.89 g (82.3%). LCMS (C18 column 20×2 mm, particle size 2.5 µm, pore size 100A, water-acetonitrile+0.1% TFA, gradient 5 to 87% for 3 min, retention time 0.88 min, MS (ESI) m/z 225.9 [MH]+.

Synthesis of INT-50 ((2Z,2'Z)-2,2'-(3-(2-morpholino-2-oxoethyl)cyclopentane-1,2-diylidene)bis(N-ethylhydrazine-1-carbothioamide))

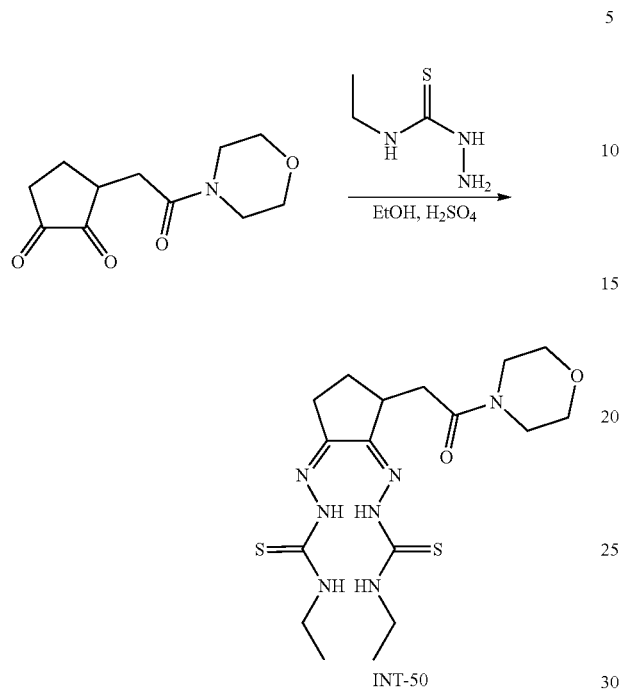

INT-50

3-(2-Morpholino-2-oxoethyl)cyclopentane-1,2-dione (0.89 g, 4 mmol, 1 eq) was dissolved in EtOH (25 ml), ethyl thiosemicarbazide (0.94 g, 2 eq) and 3 drops of $H_2SO_4$ were added and the reaction mixture was stirred for 4 h at reflux and for 15 h at ambient temperature. The formed precipitate was filtered, washed with EtOH, water and crystallized from isopropyl alcohol. Yield 0.6 g (35.5%). LCMS (C18 column 20×2 mm, particle size 2.5 μm, pore size 100A, water-acetonitrile+0.1% TFA, gradient 5 to 87% for 3 min, retention time 1.33 min, MS (ESI) m/z 428.5 [MH]+. $^1$H-NMR (400 MHz, CDCl$_3$): δ (ppm) 1.14 (t, 3H), 1.20 (t, 3H), 1.46-1.56 (m, 1H), 2.14-2.21 (m, 1H), 2.45-2.55 (m, 2H), 2.74-2.87 (m, 1H), 2.89-2.96 (m, 1H), 3.06-3.13 (m, 1H), 3.46 (br.s, 4H), 3.53-3.65 (m, 8H), 7.78 (br.s, 1H), 8.69 (br.s, 1H), 10.75 (br.s, 1H), 12.18 (s, 1H).

Synthesis of ZN-50

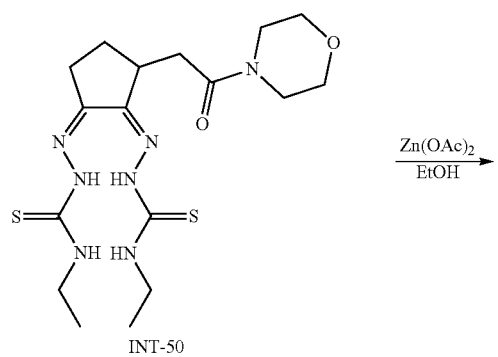

INT-50

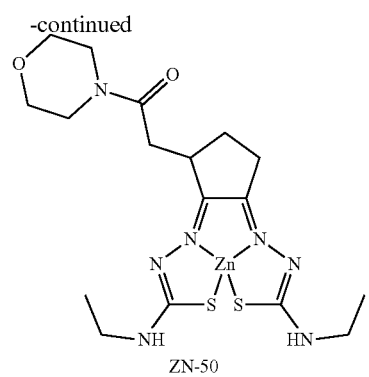

ZN-50

Zn(OAc)$_2$ 2H$_2$O (0.15 g, 1.5 eq) was added to INT-50 (0.2 g, 0.5 mmol, 1 eq) in ethanol. The mixture was refluxed for 4 h. The formed complex was precipitated out of the mixture as yellow powder. The precipitate was collected by filtration, washed with water, methanol, and diethyl ether, and then dried in vacuo. Yield 0.1 g (43.5%). $^1$H-NMR (400 MHz, CDCl$_3$): δ (ppm) 1.1 (t, 3H), 1.15 (t, 3H), 1.37-1.49 (m, 1H), 2.06-2.17 (m, 1H), 2.33-2.47 (m, 2H), 2.77-2.87 (m, 1H), 2.88-2.96 (m, 1H), 3.00-3.09 (m, 1H), 3.40-3.65 (m, 12H), 7.40 (br.s, 1H), 7.95 (br.s, 1H).

Synthesis of Compound 50

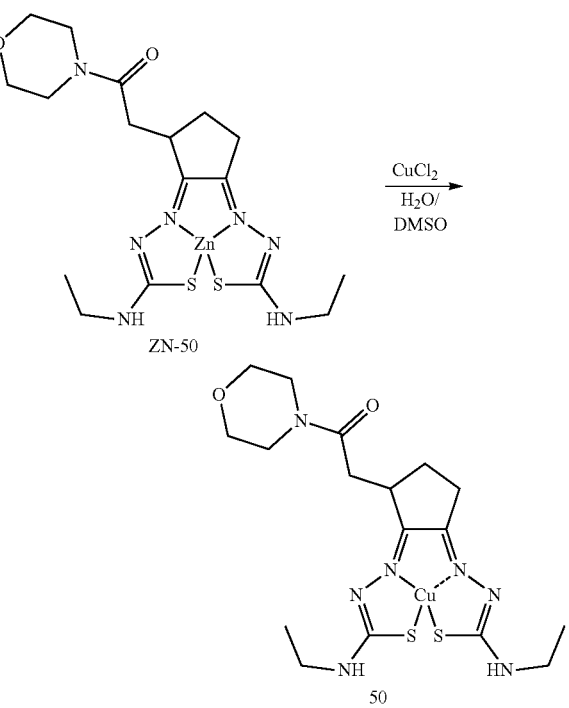

ZN-50 (0.075 g, 0.15 mmol, 1 eq) was dissolved in DMSO (1.8 ml) and a solution of CuCl$_2$ 2H$_2$O (0.034 g, 1.1 eq) in water (1.8 ml) was added. The mixture was stirred for 5 min, filtered, and precipitate was washed with saturated solution of potassium carbonate, water and Et$_2$O. Yield 0.044 g (58.8%). LCMS (C18 column 20×2 mm, particle size 2.5 μm, pore size 100A, water-acetonitrile+0.1% TFA, gradient 5 to 87% for 4 min, retention time 1.85 min). MS (ESI) m/z 489.4 [MH]+.

Scheme 24: Synthesis of Compound 51

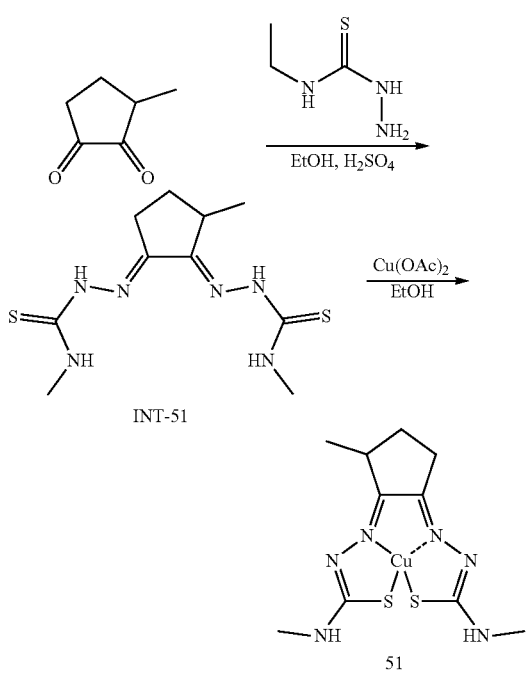

INT-51

Synthesis of INT-51 ((2E,2'E)-2,2'-(3-methylcyclopentane-1,2-diylidene)bis(N-methylhydrazine-1-carbothioamide))

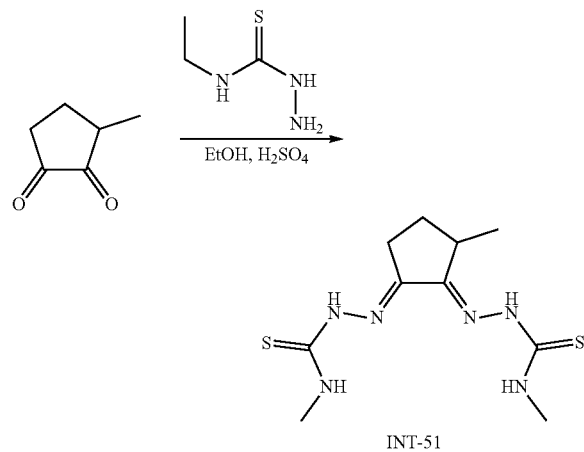

INT-51

3-Methyl-1,2-cyclopentanedione (2 g, 17.8 mmol, 1 eq) was dissolved in EtOH (100 ml), methylthiosemicarbazide (3.75 g, 2 eq) and 3 drops of $H_2SO_4$ were added and the reaction mixture was stirred for 4 h at reflux and for 15 h at ambient temperature. The formed precipitate was filtered, washed with EtOH, water, $Et_2O$, and dried. Yield 3.87 g (80%). LCMS (C18 column 20×2 mm, particle size 2.5 μm, pore size 100A, water-acetonitrile+0.1% TFA, gradient 5 to 87% for 3 min, retention time 1.34 min, MS (ESI) m/z 287.0 [MH]+. $^1$H-NMR (400 MHz, DMSO-$d_6$): δ (ppm) 1.05-1.27 (m, 9H), 1.35-1.48 (m, 1H), 2.01-2.15 (m, 1H), 2.47-2.56 (m, 1H), 2.71-2.82 (m, 2H), 3.49-3.63 (m, 4H), 7.74 (br.s, 1H), 8.65 (br.s, 1H), 10.74 (s, 1H), 12.23 (s, 1H).

Synthesis of INT-52 ((2E,2'E)-2,2'-(3-methylcyclopentane-1,2-diylidene)bis(N-ethylhydrazine-1-carbothioamide))

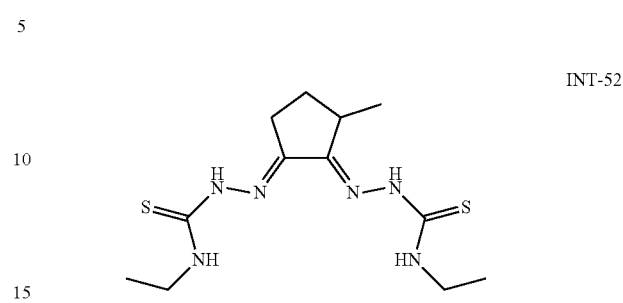

INT-52

INT-52 was made using a procedure analogous to the procedure to prepare INT-51. Yield 5 g (90.5%). LCMS (C18 column 20×2 mm, particle size 2.5 μm, pore size 100A, water-acetonitrile+0.1% TFA, gradient 5 to 87% for 3 min, retention time 1.59 min, MS (ESI) m/z 315.1 [MH]+. $^1$H-NMR (400 MHz, DMSO-$d_6$): δ (ppm) 1.16 (d, 3H), 1.36-1.47 (m, 1H), 2.09-2.16 (m, 1H), 2.45-2.65 (m, 1H), 2.69-2.82 (m, 2H), 3.02 (br.s, 6H), 7.88 (br.s, 1H), 8.60 (br.s, 1H), 10.82 (s, 1H), 12.33 (s, 1H).

Synthesis of INT-53 ((2E,2'E)-2,2'-(3-methylcyclopentane-1,2-diylidene)bis(N-(2-(diethylamino)ethyl)hydrazine-1-carbothioamide))

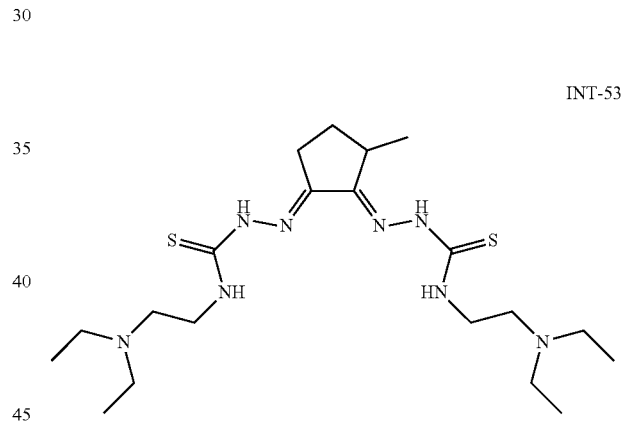

INT-53

INT-53 was made using a procedure analogous to the procedure to prepare INT-51. Yield 0.5 g (25%). $^1$H-NMR (400 MHz, DMSO-$d_6$): δ (ppm) 0.92-0.99 (m, 12H), 1.17 (d, 3H), 1.38-1.47 (m, 1H), 2.10-2.18 (m, 1H), 2.58-2.67 (m, 4H), 2.74-2.82 (m, 2H), 3.54-3.63 (m, 4H), 7.79 (br.s, 1H), 8.50 (br.s, 1H), 10.80 (s, 1H), 12.21 (s, 1H).

Synthesis of Compound 51

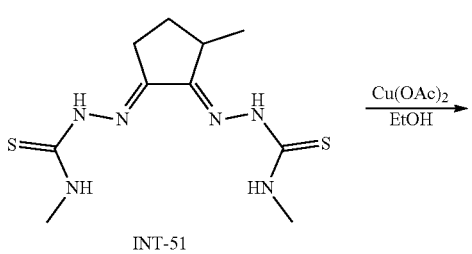

INT-51

283
-continued

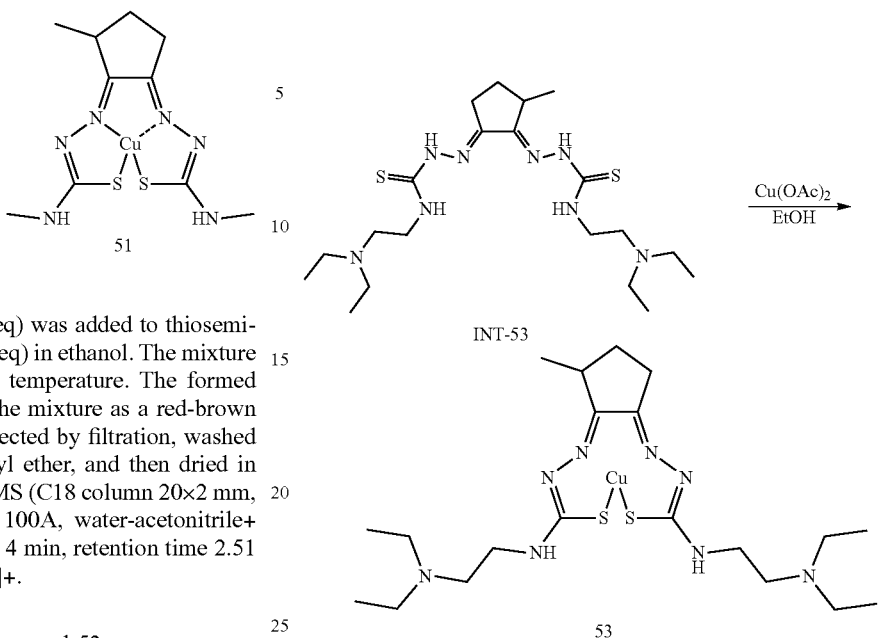

51

Cu(OAc)$_2$ 2H$_2$O (0.61 g, 1.1 eq) was added to thiosemicarbazone 1 (0.73 g, 2.5 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.46 g (51.9%). LCMS (C18 column 20×2 mm, particle size 2.5 µm, pore size 100A, water-acetonitrile+ 0.1% TFA, gradient 5 to 87% for 4 min, retention time 2.51 min). MS (ESI) m/z 348.0 [MH]+.

Synthesis of Compound 52

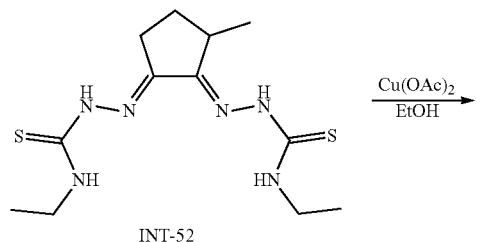

INT-52

The titular compound was prepared from INT-52 according to the method to prepare compound 51. The complex precipitated out of the reaction mixture as a red-brown powder. The precipitate was collected by filtration, washed with water, methanol, and diethyl ether, and then dried in vacuo. Yield 0.7 g (79%). LCMS (C18 column 20×2 mm, particle size 2.5 µm, pore size 100A, water-acetonitrile+ 0.1% TFA, gradient 5 to 87% for 4 min, retention time 2.62 min). MS (ESI) m/z 376.3 [MH]+.

284
Synthesis of Compound 53

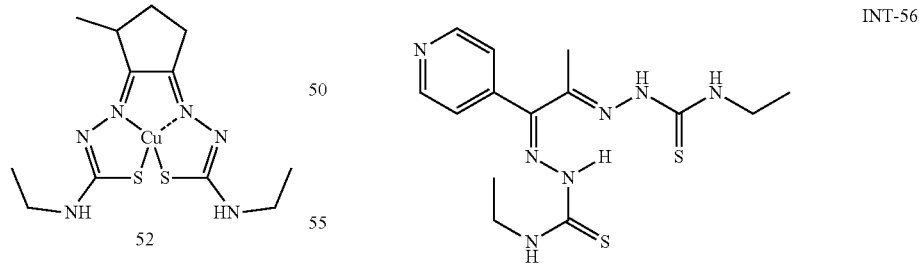

INT-53

53

The titular compound was prepared from INT-53 according to the method to prepare compound 51. The product precipitated from the reaction mixture as a red-brown powder. The precipitate was collected by filtration, washed with water, methanol, and diethyl ether, and then dried in vacuo. Yield 0.07 g (15%). LCMS (C18 column 20×2 mm, particle size 2.5 µm, pore size 100A, water-acetonitrile+0.1% TFA, gradient 5 to 87% for 4 min, retention time 1.25 min). MS (ESI) m/z 518.3 [MH]+.

Example 4: Preparation of Compounds 54-65

Synthesis of INT-56 ((2Z,2'E)-2,2'-(1-(pyridin-4-yl) propane-1,2-diylidene)bis(N-ethylhydrazine-1-carbothioamide))

INT-56

INT-55 was made using a procedure analogous to the procedure to prepare INT-1 of Example 1. Yield 0.030 g (5%). LCMS (C18 column 100×4.6 mm, 5.0 µm, pore size 100 Å, water-acetonitrile+0.1% TFA, gradient 5 to 87% for 10 min, retention time 5.01 min). MS (ESI) m/z 352.6 [MH]+. $^1$H-NMR (400 MHz, DMSO-d$_6$): δ (ppm) 0.89 (t, 3H), 1.16 (t, 3H), 2.36 (s, 3H), 3.60 (m, 4H), 6.82 (t, 1H), 7.32 (d, 2H), 7.73 (d, 1H), 8.73 (d, 2H), 9.37 (s, 1H), 10.77 (s, 1H).

Synthesis of INT-58 ((2Z,2'E)-2,2'-(1-(pyridin-2-yl)propane-1,2-diylidene)bis(N-ethylhydrazine-1-carbothioamide))

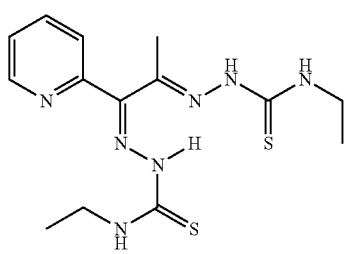

INT-58

INT-58 was made using a procedure analogous to the procedure to prepare INT-1 of Example 1. Yield 0.75 g (76.4%). $^1$H-NMR (400 MHz, DMSO D): δ (ppm) 0.99 (t, 3H), 1.16 (t, 3H), 2.38 (s, 3H), 3.36-3.46 (m, 2H), 3.56-3.66 (m, 2H), 7.36 (t, 1H), 7.55 (dd, 1H), 7.66 (d, 1H), 8.01 (t, 1H), 8.73-8.75 (m, 2H), 10.58 (s, 1H), 11.82 (s, 1H).

Synthesis of INT-62 ((2Z,2'E)-2,2'-(1-(pyridin-3-yl)propane-1,2-diylidene)bis(N-ethylhydrazine-1-carbothioamide))

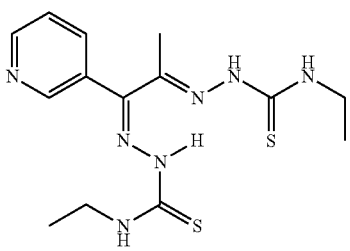

INT-62

INT-62 was made using a procedure analogous to the procedure to prepare INT-1 of Example 1. Yield 0.69 g (65%). LCMS (C18 column 100×4.6 mm, 5.0 μm, pore size 100 Å, water-acetonitrile+0.1% TFA, gradient 5 to 87% for 10 min, retention time 4.71 min). MS (ESI) m/z 352.1 [MH]+. $^1$H-NMR (400 MHz, DMSO-d$_6$): δ (ppm) 0.90 (t, 3H), 1.15 (t, 3H), 2.37 (s, 3H), 3.60 (m, 4H), 6.81 (t, 1H), 7.53 (m, 1H), 7.71 (d, 1H), 8.43 (s, 1H), 8.65-8.70 (m, 2H), 9.73 (br.s, 1H), 10.65 (br.s, 1H).

Synthesis of INT-64 ((2E,2'E)-2,2'-(1-(4-(dimethylamino)phenyl)propane-1,2-diylidene)bis(N-ethylhydrazine-1-carbothioamide))

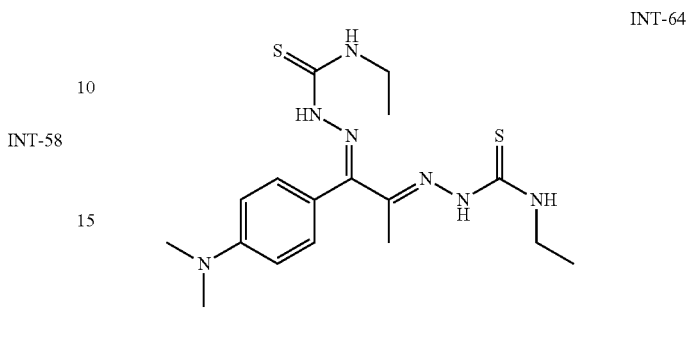

INT-64

INT-64 was made using a procedure analogous to the procedure to prepare INT-1 of Example 1. Yield 0.67 g (68.4%). LCMS (C18 column 20×2 mm, particle size 2.5 μm, pore size 100A, water-acetonitrile+0.1% TFA, gradient 5 to 87% for 3 min, retention time 1.54 min, MS (ESI) m/z 394.5 [MH]+. $^1$H-NMR (400 MHz, DMSO-d$_6$): δ (ppm) 0/94 (t, 3H), 1.15 (t, 3H), 2.33 (s, 3H), 2.87 (s, 6H), 6.85 (d, 2H), 7.02 (br.s), 7.11 (d, 2H), 8.71 (br.s, 1H), 10.72 (s, 1H).

Synthesis of Compound 56

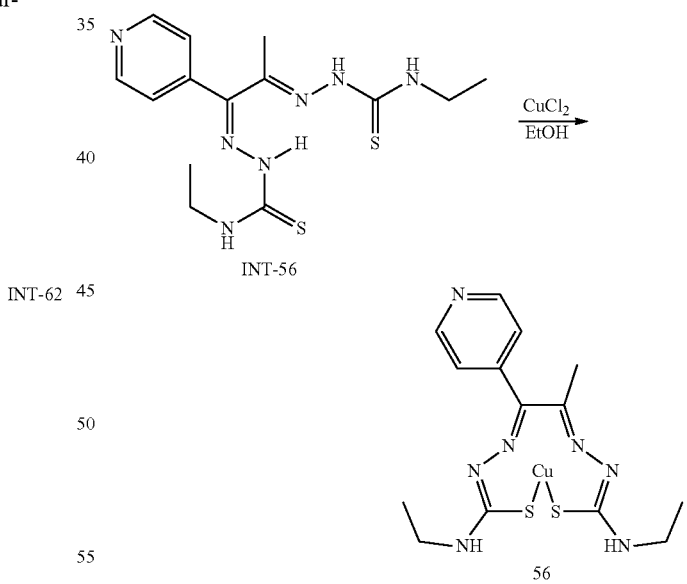

The titular compound was prepared from INT-56 according to the method to prepare compound 1 of Example 1. Complex was isolated as a red-brown powder. The product was collected by filtration after cooling, washed with water (2×15 ml), ethanol (2×15 ml), and then dried in vacuo to afford the titular product. Yield 0.010 g (28%). LCMS (C18 column 20×2 mm, 2.5 μm, pore size 100 Å, water-acetonitrile+0.1% TFA, gradient 5 to 87% for 4 min, retention time 3.41 min). MS (ESI) m/z 413.5 [MH]+.

Synthesis of Compound 58

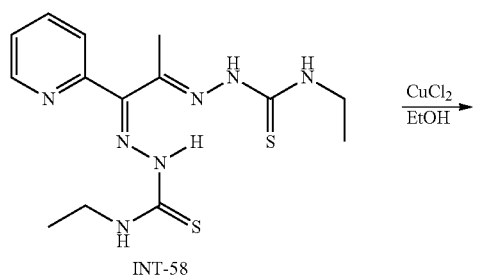

The titular compound was prepared from INT-58 according to the method to prepare compound 1 of Example 1. The product precipitated from the reaction mixture as a red-brown powder. The precipitate was collected by filtration, washed with water, methanol, diethyl ether, and then dried in vacuo. Yield 0.044 g (18.6%). LCMS (C18 column 20×2 mm, 2.5 μm, pore size 100 Å, water-acetonitrile+0.1% TFA, gradient 5 to 87% for 4 min, retention time 1.36 min). MS (ESI) m/z 413.4 [MH]+.

Synthesis of Compound 62

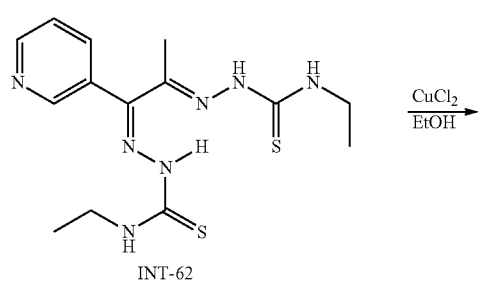

The titular compound was prepared from INT-62 according to the method to prepare compound 1 of Example 1. The product was isolated as a red-brown powder. The formed precipitate was collected by filtration after cooling, washed with water (2×15 ml), ethanol (2×15 ml), and then dried in vacuo. Yield 0.094 g (27%). LCMS (C18 column 20×2 mm, 2.5 μm, pore size 100 Å, water-acetonitrile+0.1% TFA, gradient 5 to 87% for 4 min, retention time 1.72 min). MS (ESI) m/z 413.5 [MH]+.

Synthesis of Compound 64

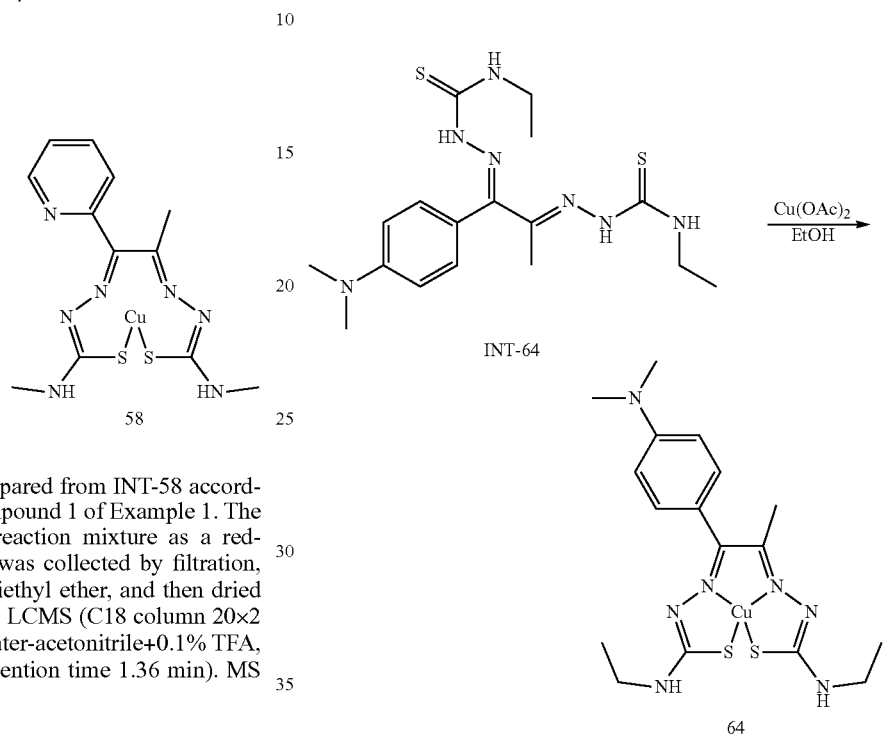

The titular compound was prepared from INT-64 according to the method to prepare compound 1 of Example 1. The product precipitated from the reaction mixture as a red-brown powder. The precipitate was collected by filtration, washed with water, methanol, and diethyl ether, and then dried in vacuo. Yield 0.037 g (18%). LCMS (C18 column 20×2 mm, particle size 2.5 μm, pore size 100A, water-acetonitrile+0.1% TFA, gradient 5 to 87% for 4 min, retention time 2.31 min). MS (ESI) m/z 455.1 [MH]+.

Synthesis of INT-63 ((2Z,2'E)-2,2'-(1-(4-(dimethylamino)phenyl)ethane-1,2-diylidene)bis(N-ethylhydrazine-1-carbothioamide))

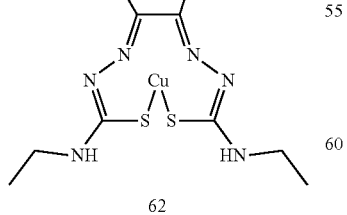

INT-63 was made using a procedure analogous to the procedure to prepare INT-34 of Example 2. Yield 0.57 g (35%). LCMS (C18 column 20×2 mm, particle size 2.5 μm, pore size 100A, water-acetonitrile+0.1% TFA, gradient 5 to 87% for 3 min, retention time 1.63 min, MS (ESI) m/z 380.5 [MH]+. $^1$H-NMR (400 MHz, DMSO-$d_6$): δ (ppm) 1.12-1.24 (m, 6H), 2.96 (s, 6H), 3.53-3.67 (m, 4H), 6.75 (d, 2H), 7.64 (d, 2H), 7.88 (br.s, 1H), 8.22 (s, 1H), 8.76 (br.s, 1H), 11.73 (s, 1H), 12.18 (s, 1H).

Synthesis of Compound 63

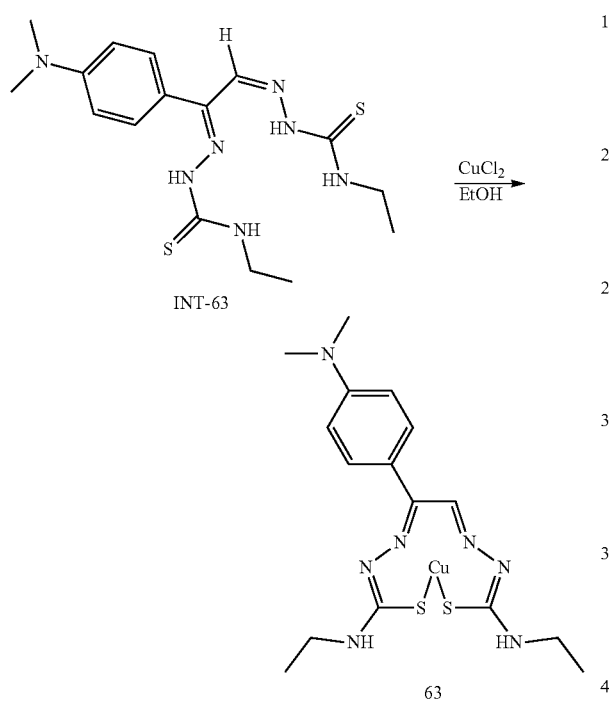

The titular compound was prepared from INT-63 according to the method to prepare compound 43 of Example 2. The product precipitated from the reaction mixture as a red-brown powder. The precipitate was collected by filtration, washed with water, methanol, and diethyl ether, and then dried in vacuo. Yield 0.075 g (47%). LCMS (C18 column 20×2 mm, particle size 2.5 μm, pore size 100A, water-acetonitrile+0.1% TFA, gradient 5 to 87% for 4 min, retention time 2.07 min). MS (ESI) m/z 441.1 [MH]+.

Synthesis of INT-55 ((2E,2'E)-2,2'-(pentane-2,3-diylidene)bis(N-(tert-butyl)hydrazine-1-carbothioamide))

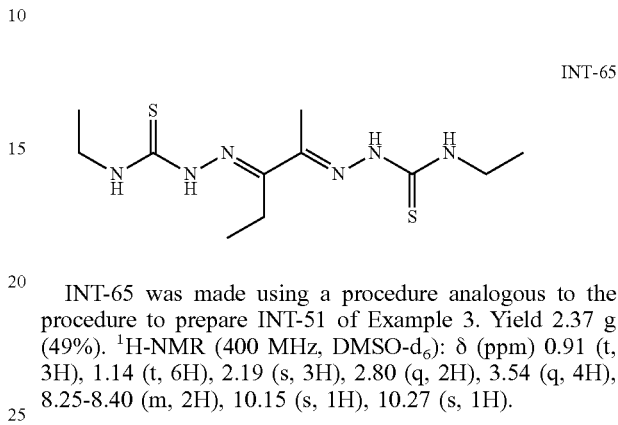

INT-55 was made using a procedure analogous to the procedure to prepare INT-51 of Example 3. Yield 1.97 g (34%). NMR (400 MHz, DMSO-$d_6$): 0.96 (s, 3H), 1.50 (s, 9H), 1.52 (s, 9H), 2.10 (s, 3H), 2.74 (q, 2H), 7.75 (s, 1H), 7.79 (s, 1H), 10.30-10.48 (m, 2H).

Synthesis of INT-65 ((2E,2'E)-2,2'-(pentane-2,3-diylidene)bis(N-ethylhydrazine-1-carbothioamide))

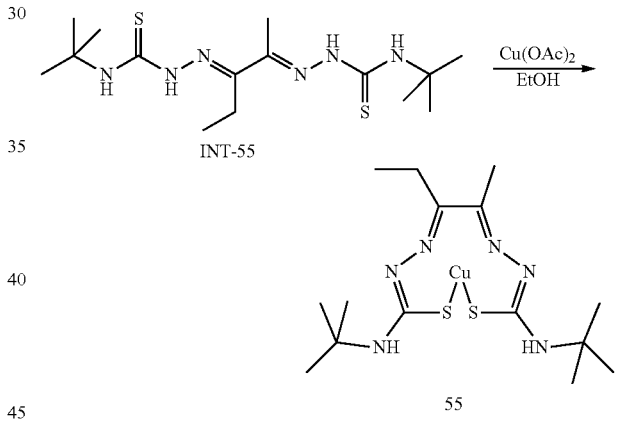

INT-65 was made using a procedure analogous to the procedure to prepare INT-51 of Example 3. Yield 2.37 g (49%). $^1$H-NMR (400 MHz, DMSO-$d_6$): δ (ppm) 0.91 (t, 3H), 1.14 (t, 6H), 2.19 (s, 3H), 2.80 (q, 2H), 3.54 (q, 4H), 8.25-8.40 (m, 2H), 10.15 (s, 1H), 10.27 (s, 1H).

Synthesis of Compound 55

The titular compound was prepared from INT-55 according to the method to prepare compound 51 of Example 3. The product precipitated from the reaction mixture as a red-brown powder. The precipitate was collected by filtration, washed with water, methanol, and diethyl ether, and then dried in vacuo. Yield 0.4 g (82%). LCMS (C18 column 20×2 mm, particle size 2.5 μm, pore size 100A, water-acetonitrile+0.1% TFA, gradient 5 to 87% for 4 min, retention time 3.41 min). MS (ESI) m/z 420.6 [MH]+.

Synthesis of Compound 65

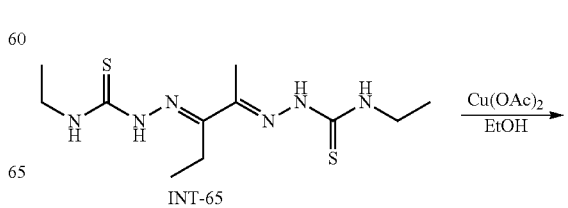

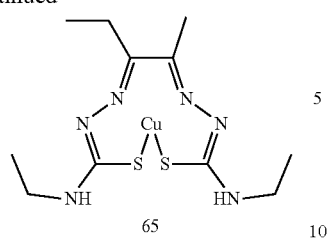

65

The titular compound was prepared from INT-65 according to the method to prepare compound 51 of Example 3. The formed complex was precipitated from the mixture as a red-brown powder. The precipitate was collected by filtration, washed with water, methanol, and diethyl ether, and then dried in vacuo. Yield 0.4 g (82%). LCMS (C18 column 20×2 mm, particle size 2.5 µm, pore size 100A, water-acetonitrile+0.1% TFA, gradient 5 to 87% for 4 min, retention time 2.68 min). MS (ESI) m/z 364.3 [MH]+.

Scheme 25: Synthesis of Compound 54

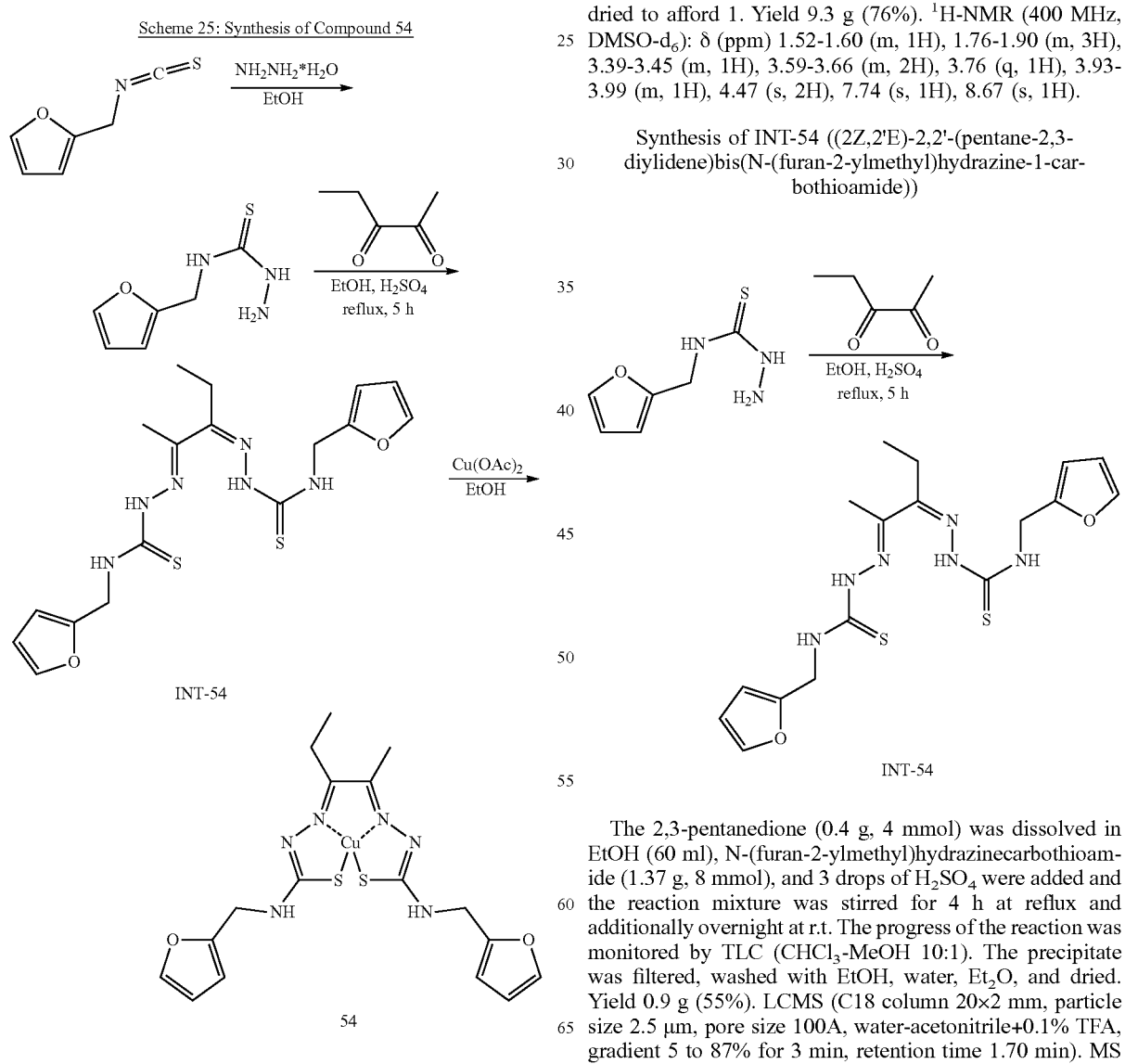

INT-54

54

Synthesis of N-(furan-2-ylmethyl)hydrazinecarbothioamide

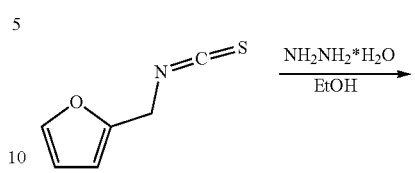

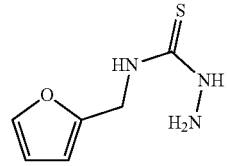

To a solution of 2-(isothiocyanatomethyl)tetrahydrofuran (10 g, 71.8 mmol) in EtOH (100 ml) was added at 0° C. hydrazine hydrate (4.5 g, 89.75 mmol) and the reaction mixture was stirred for 3 h. The formed precipitate was collected by filtration, washed with ethanol (2×150 ml), and dried to afford 1. Yield 9.3 g (76%). $^1$H-NMR (400 MHz, DMSO-$d_6$): δ (ppm) 1.52-1.60 (m, 1H), 1.76-1.90 (m, 3H), 3.39-3.45 (m, 1H), 3.59-3.66 (m, 2H), 3.76 (q, 1H), 3.93-3.99 (m, 1H), 4.47 (s, 2H), 7.74 (s, 1H), 8.67 (s, 1H).

Synthesis of INT-54 ((2Z,2'E)-2,2'-(pentane-2,3-diylidene)bis(N-(furan-2-ylmethyl)hydrazine-1-carbothioamide))

INT-54

The 2,3-pentanedione (0.4 g, 4 mmol) was dissolved in EtOH (60 ml), N-(furan-2-ylmethyl)hydrazinecarbothioamide (1.37 g, 8 mmol), and 3 drops of $H_2SO_4$ were added and the reaction mixture was stirred for 4 h at reflux and additionally overnight at r.t. The progress of the reaction was monitored by TLC (CHCl$_3$-MeOH 10:1). The precipitate was filtered, washed with EtOH, water, Et$_2$O, and dried. Yield 0.9 g (55%). LCMS (C18 column 20×2 mm, particle size 2.5 µm, pore size 100A, water-acetonitrile+0.1% TFA, gradient 5 to 87% for 3 min, retention time 1.70 min). MS (ESI) m/z 407.5 [MH]+. $^1$H-NMR (400 MHz, DMSO-$d_6$): δ

(ppm) 0.90 (t, 3H), 2.19 (s, 3H), 2.90 (q, 2H), 4.82 (d, 4H), 6.27-6.29 (m, 2H), 6.40 (s, 2H), 7.58 (s, 2H), 8.65 (t, 1H), 8.73 (t, 1H), 10.42 (s, 1H), 10.53 (s, 1H).

Synthesis of Compound 54

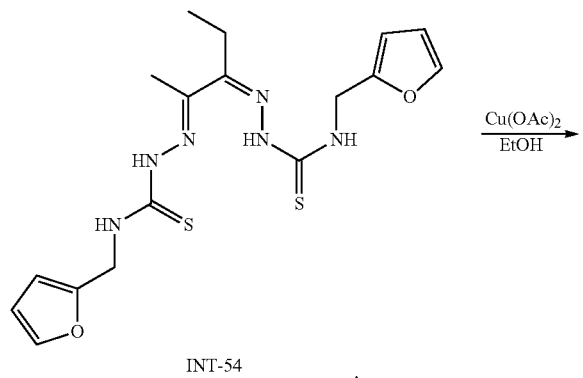

Cu(OAc)$_2$·2H$_2$O (0.12 g, 1.1 eq) was added to INT-54 (0.2 g, 0.5 mmol, 1 eq) in ethanol. The mixture was stirred for 15 h at ambient temperature. The formed complex was precipitated from the mixture as a red-brown powder. The precipitate was collected by filtration, washed with water, methanol, and diethyl ether, and then dried in vacuo. Yield 0.022 g (9.5%). LCMS (C18 column 20×2 mm, particle size 2.5 μm, pore size 100A, water-acetonitrile+0.1% TFA, gradient 5 to 87% for 4 min, retention time 2.62 min). MS (ESI) m/z 468.4 [MH]+.

Scheme 26: Synthesis of Compound 57

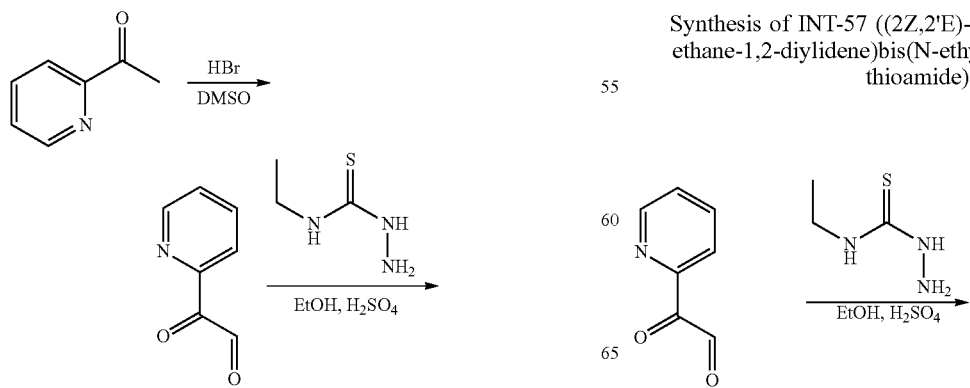

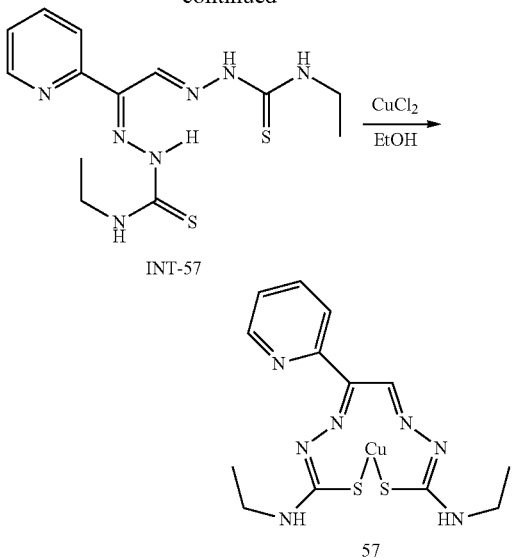

Synthesis of 2-oxo-2-(pyridin-2-yl)acetaldehyde

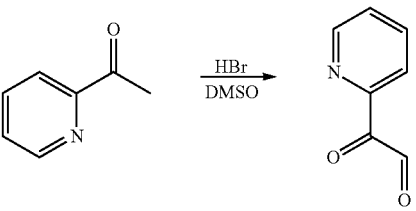

To a solution of 1-(pyridin-2-yl)ethan-1-one (10.0 g, 82.5 mmol) in DMSO (150 ml) 47% HBr (28 ml, 247.5 mmol) was added and the mixture was stirred at 60° C. overnight. The reaction was quenched with NaHCO$_3$ and diluted with water to a total volume of 1000 ml. The product was extracted with EtOAc (3×150 ml), the combined organic layers were dried over anhydrous Na$_2$SO$_4$, filtered, and solvents were removed under reduced pressure yielding crude product as a yellow oil. Yield 2.8 g (23%). LCMS (C18 column 20×2 mm, 2.5 μm, pore size 100 Å, water-acetonitrile+0.1% TFA, gradient 5 to 87% for 3 min, retention time 0.32 min). MS (ESI) m/z 136.1 [MH]+.

Synthesis of INT-57 ((2Z,2'E)-2,2'-(1-(pyridin-2-yl)ethane-1,2-diylidene)bis(N-ethylhydrazine-1-carbothioamide))

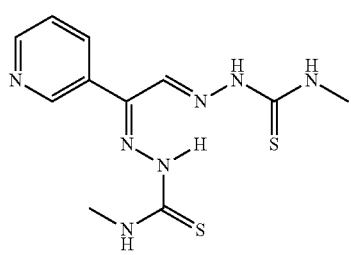

INT-57

Ethyl thiosemicarbazide (1.76 g, 14.0 mmol) and 1 drop of $H_2SO_4$ were added to a solution of 2-oxo-2-(pyridin-2-yl)acetaldehyde (1.0 g, 7.0 mmol) in EtOH (50 ml), the reaction was heated to reflux for 4 h. The precipitate was filtered, washed with EtOH, $Et_2O$ and dried. Yield 0.123 g (5.9%). LCMS (C18 column 20×2 mm, 2.5 μm, pore size 100 Å, water-acetonitrile+0.1% TFA, gradient 5 to 87% for 3 min, retention time 1.41 min). MS (ESI) m/z 338.3 [MH]+. $^1$H-NMR (400 MHz, DMSO-$d_6$): δ (ppm) 1.21 (dt, 6H), 3.56-3.70 (m, 4H), 7.42 (dd, 1H), 7.86-7.93 (m, 2H), 8.41 (d, 1H), 8.58 (d, 1H), 8.89 (s, 1H), 8.79 (s, 1H), 9.20 (t, 1H), 12.01 (s, 1H), 12.80 (s, 1H).

Synthesis of INT-59 ((2Z,2'E)-2,2'-(1-(pyridin-3-yl)ethane-1,2-diylidene)bis(N-methylhydrazine-1-carbothioamide))

INT-59

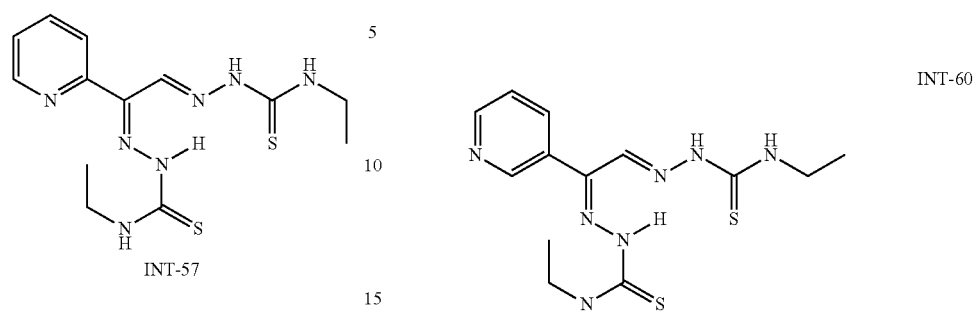

INT-59 was made using a procedure analogous to the procedure to prepare INT-57. Yield 0.53 g (19%). LCMS (C18 column 20×2 mm, 2.5 μm, pore size 100 Å, water-acetonitrile+0.1% TFA, gradient 5 to 87% for 10 min, retention time 4.49 min). MS (ESI) m/z 310.4 [MH]+. $^1$H-NMR (400 MHz, DMSO-$d_6$): δ (ppm) 3.0 (s, 3H), 3.06 (s, 3H), 7.80 (dd, 1H), 8.2 (s, 1H), 8.58 (d, 1H), 8.78 (d, 1H), 8.89 (s, 1H), 8.92-8.98 (m, 1H), 9.16 (s, 1H), 11.78 (s, 1H), 12.09 (s, 1H).

Synthesis of INT-60 ((2Z,2'E)-2,2'-(1-(pyridin-3-yl)ethane-1,2-diylidene)bis(N-ethylhydrazine-1-carbothioamide))

INT-60

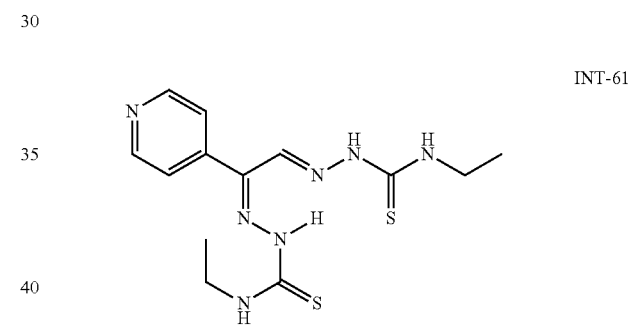

INT-60 was made using a procedure analogous to the procedure to prepare INT-57. Yield 0.90 g (30%). LCMS (C18 column 20×2 mm, 2.5 μm, pore size 100 Å, water-acetonitrile+0.1% TFA, gradient 5 to 87% for 10 min, retention time 5.26 min). MS (ESI) m/z 338.5 [MH]+. $^1$H-NMR (400 MHz, DMSO-$d_6$): δ (ppm) 1.17 (t, 6H), 3.61 (q, 4H), 7.47 (dd, 1H), 8.0 (t, 1H), 8.18 (d, 1H), 8.22 (s, 1H), 8.62 (d, 1H), 8.98-9.07 (m, 1H), 11.77 (s, 1H), 12.31 (s, 1H).

Synthesis of INT-61 ((2Z,2'E)-2,2'-(1-(pyridin-4-yl)ethane-1,2-diylidene)bis(N-ethylhydrazine-1-carbothioamide))

INT-61

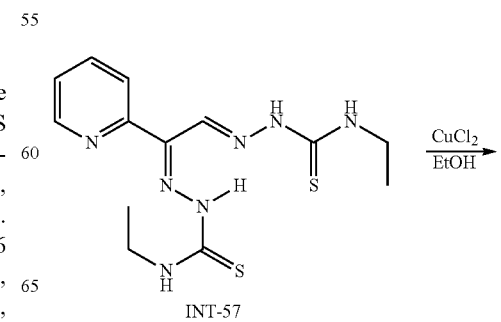

INT-61 was made using a procedure analogous to the procedure to prepare INT-57. Yield 180 mg (7%). LCMS (C18 column 20×2 mm, 2.5 μm, pore size 100 Å, water-acetonitrile+0.1% TFA, gradient 5 to 87% for 10 min, retention time 4.97 min). MS (ESI) m/z 338.5 [MH]+. $^1$H-NMR (400 MHz, DMSO-$d_6$): δ (ppm) 1.18 (t, 3H), 1.20 (t, 3H), 3.58 (q, 2H), 3.64 (q, 2H), 7.80 (d, 1H), 8.04 (t, 1H), 8.24 (s, 1H), 8.65 (d, 1H), 9.12 (t, 1H), 11.79 (s, 1H), 12.47 (s, 1H).

Synthesis of Compound 57

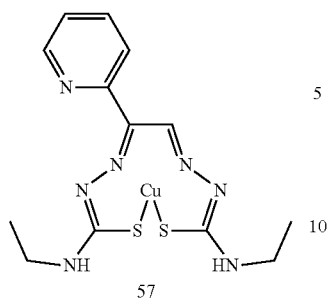

57

To a solution of INT-57 (0.123 g, 0.365 mmol) in EtOH (10 ml) a solution of CuCl$_2$·2H$_2$O (0.062 g, 0.365 mmol) in EtOH (2 ml) was added. The mixture was stirred overnight at r.t. The formed precipitate was collected by filtration, washed with water (2×10 ml), ethanol (2×10 ml), diethyl ether (5×5 ml), and dried in vacuo. Yield 0.06 g (41.4%). LCMS (C18 column 20×2 mm, 2.5 μm, pore size 100 Å, water-acetonitrile+0.1% TFA, gradient 5 to 87% for 4 min, retention time 1.39). MS (ESI) m/z 399.0 [MH]+.

Synthesis of Compound 59

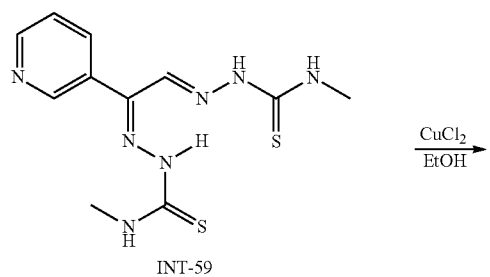

INT-59

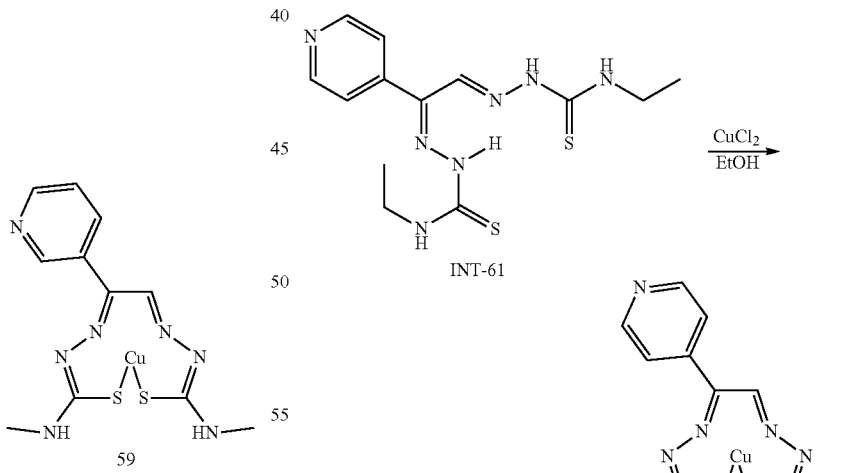

59

The titular compound was prepared from INT-59 according to the method to prepare compound 57. The titular product was collected by filtration, washed with water (2×50 ml), ethanol (2×50 ml), and diethyl ether (5×50 ml), and then dried in vacuo. Yield 230 mg (95%). LCMS (C18 column 20×2 mm, 2.5 μm, pore size 100 Å, water-acetonitrile+0.1% TFA, gradient 5 to 87% for 4 min, retention time 1.34, 1.47 min. MS (ESI) m/z 371.0 [MH]+.

Synthesis of Compound 60

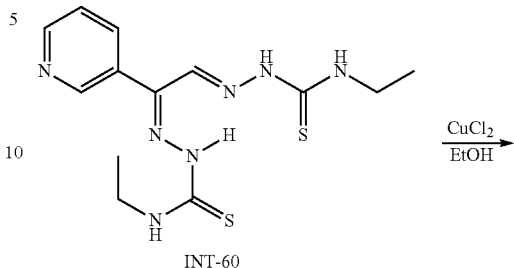

INT-60

60

The titular compound was prepared from INT-60 according to the method to prepare compound 57. The titular product was collected by filtration, washed with water (2×50 ml), ethanol (2×50 ml), and diethyl ether (5×50 ml), and then dried in vacuo. Yield 218 mg (92%). LCMS (C18 column 20×2 mm, 2.5 μm, pore size 100 Å, water-acetonitrile+0.1% TFA, gradient 5 to 87% for 4 min, retention time 1.58, 1.73 min. MS (ESI) m/z 399.0 [MH]+.

Synthesis of Compound 61

INT-61

61

The titular compound was prepared from INT-61 according to the method to prepare compound 57. The product was collected by filtration, washed with water (2×50 ml), ethanol (2×50 ml), and diethyl ether (5×50 ml), and then dried in vacuo. Yield 140 mg (66%). LCMS (C18 column 20×2 mm, 2.5 μm, pore size 100 Å, water-acetonitrile+0.1% TFA, gradient 5 to 87% for 4 min, retention time 1.48, 1.66 min. MS (ESI) m/z 399.0 [MH]+.

Example 5: Preparation of Compounds 66-78

Scheme 27: Synthesis of Compound 66

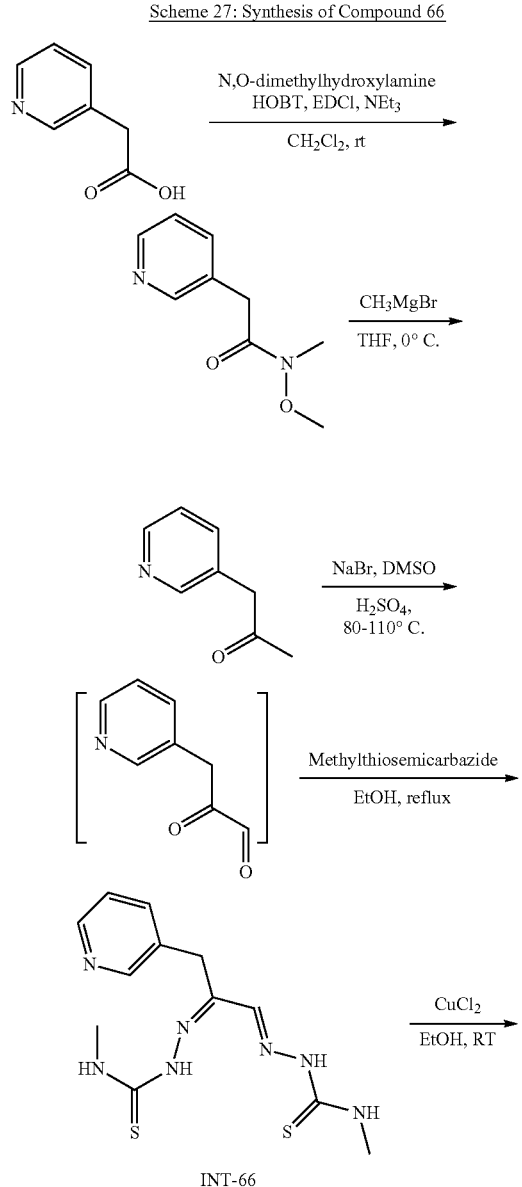

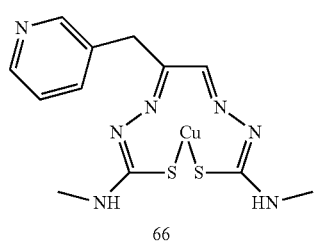

Synthesis of N-methoxy-N-methyl-2-(pyridin-3-yl)acetamide

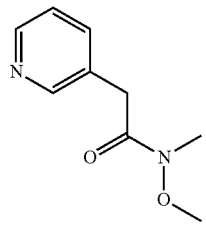

To a mixture of 3-pyridineacetic acid (25.0 g, 0.144 mol), Weinreb amine (16.8 g, 0.172 mol), HOBt (23.3 g, 0.172 mol), and triethylamine (71 ml, 0.5 mol) in DCM (400 ml) at 5° C. was added EDCl (33.2 g, 172 mol) and reaction was stirred for 15 h at ambient temperature. The mixture was washed with water (150 ml) and brine (250 ml). The organic layer was dried over anh. Na$_2$SO$_4$, filtered, and then concentrated under reduced pressure. The residue was purified by column chromatography (silica gel, eluent EtOAc-hexane, 2:1) to afford compound 1. Yield 20.0 g (77%). $^1$H-NMR (400 MHz, CDCl$_3$), δ (ppm): 8.63-8.27 (m, 2H), 7.65 (d, J=7.8 Hz, 1H), 7.28-7.03 (m, 1H), 3.76 (s, 2H), 3.67 (s, 3H), 3.19 (s, 3H).

Synthesis of 1-(pyridin-3-yl)propan-2-one

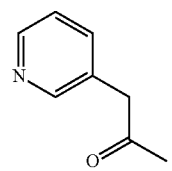

A solution of N-methoxy-N-methyl-2-(pyridin-3-yl)acetamide (9.5 g, 52.7 mmol, 1 eq) in THF (200 ml) was cooled to 5° C. and methylmagnesium bromide (1.4M in THF, 46.5 ml, 3 eq) was added. The reaction mixture was stirred at 5° C. for 2 h, poured into aq NH$_4$Cl and extracted with Et$_2$O. The combined extracts were dried over anh. Na$_2$SO$_4$ and evaporated in vacuo. Compound 2 was used for the next step without purification. Yield 6.1 g (86%). LC-MS 0.27 min, m/z 136.6 [MH]+. $^1$H-NMR (400 MHz, CDCl$_3$), δ (ppm): 8.48 (d, J=4.7 Hz, 1H), 8.41 (s, 1H), 7.50 (d, J=7.8 Hz, 1H), 7.31-7.12 (m, 1H), 3.67 (d, J=19.5 Hz, 2H), 2.18 (s, 3H).

Synthesis of INT-66 ((2Z,2'E)-2,2'-(3-(pyridin-3-yl)propane-1,2-diylidene)bis(N-methylhydrazine-1-carbothioamide))

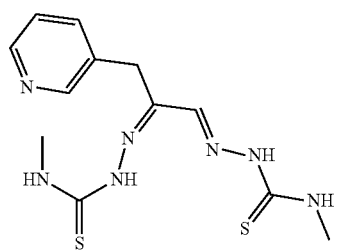 [SMILES: CNC(=S)N/N=C(\C=N\NC(=S)NC)Cc1cccnc1]

A mixture of 1-(pyridin-3-yl)propan-2-one (1.3 g, 6.9 mmol, 1 eq), NaBr (0.7 g, 1 eq) and DMSO (2 ml) was heated to 85° C. and $H_2SO_4$ (6 drops) was added (foaming, exothermic). The reaction was heated at 110-115° C. until the formation of dimethyl sulfide has stopped, and the reaction mixture became viscous. The formed viscous oil was dissolved in EtOH and methylthiosemicarbazide (2.023 g, 2 eq) was added. The reaction mixture was heated to reflux for 4 h, then stirred overnight at rt. The precipitate was collected by filtration, washed with EtOH, MeCN, water, $Et_2O$, and dried to afford the titular product. Yield 0.95 g (30%). LC-MS 0.97 min, m/z 324.6 [MH]+.

Synthesis of Compound 66

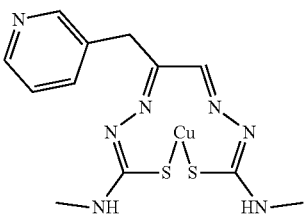

Copper(II) acetate dihydrate (0.72 g, 1.1 eq) was added to a stirred solution of INT-66 (0.12 g, 0.38 mmol, 1 eq) in ethanol. The mixture was stirred for 15 h at rt. The formed complex precipitated as a red-brown powder. The precipitate was collected by filtration, washed with water, methanol, diethyl ether, and dried in vacuo. Yield 0.14 g (99%).

Scheme 28: Synthesis of Compound 67

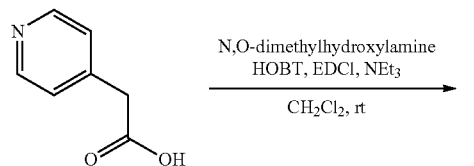

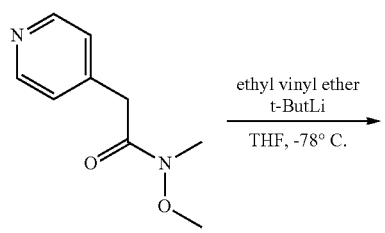

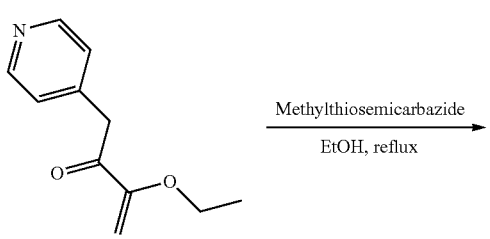

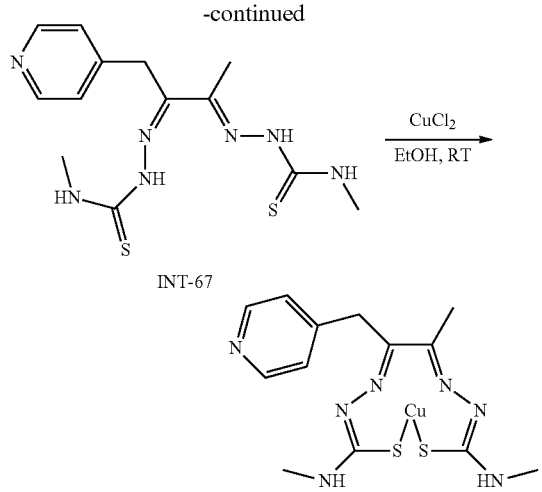

Synthesis of N-methoxy-N-methyl-2-(pyridin-4-yl)acetamide

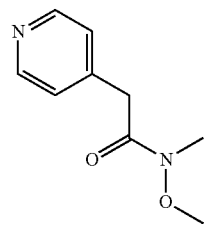

To a mixture of 4-pyridineacetic acid (4.2 g, 24.2 mmol), Weinreb amine (2.8 g, 29.0 mmol), HOBt (3.9 g, 29.0 mmol), and triethylamine (11.9 ml, 84.7 mmol) in DCM (100 ml) at 5° C. was added EDCl (5.6 g, 29.0 mmol) and reaction was stirred for 15 h at rt. The mixture was washed with water (150 ml) and brine (250 ml). The organic layer was dried over anh. $Na_2SO_4$, filtered, and then concentrated under reduced pressure. The residue was purified by column chromatography (silica gel, eluent EtOAc-hexane 2:1) to afford the titular compound. Yield 2.9 g (66%). LC-MS 0.97 min, m/z 324.6 [MH]+. $^1$H-NMR (400 MHz, $CDCl_3$), δ (ppm): 8.55 (d, J=5.3 Hz, 2H), 7.36-7.08 (m, 2H), 3.78 (s, 2H), 3.66 (s, 3H), 3.21 (s, 3H).

Synthesis of 3-ethoxy-1-(pyridin-4-yl)but-3-en-2-one

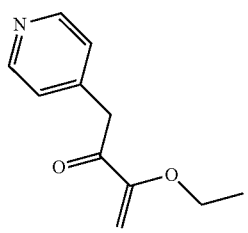

A solution of ethyl vinyl ether (4.1 ml, 41.8 mmol) in dry THF (30 ml) was cooled to −78° C., and tert-butyllithium (1.7M in pentane, 23 ml, 38.8 mmol) was added. The mixture was warmed to 0° C. over 1 h period, stirred for 45 min, and cooled down to −30° C. A solution of N-methoxy-N-methyl-2-(pyridin-4-yl)acetamide (0.7 g, 3.8 mmol) in THF (15 ml) was added, and the reaction was stirred at 0° C. for 4 h. The progress of the reaction was monitored by TLC. The mixture was poured into aq. $NH_4Cl$ (30 ml) and extracted with $Et_2O$ (3×50 ml). The combined extracts were dried over anh. $Na_2SO_4$, filtered, and evaporated in vacuo. The product was used for the next step without additional purification. Yield 0.2 g (27%). LC-MS 0.66 min, m/z 192.4 [MH]+. $^1$H-NMR (400 MHz, $CDCl_3$), δ (ppm): 8.54 (dd, J=4.4, 1.6 Hz, 2H), 7.23-7.06 (m, 2H), 5.23 (t, J=11.8 Hz, 1H), 4.42 (t, J=14.5 Hz, 1H), 3.99 (s, 2H), 3.83 (q, J=7.0 Hz, 2H), 1.40 (t, J=7.0 Hz, 3H).

Synthesis of INT-67 ((2Z,2'E)-2,2'-(1-(pyridin-4-yl)butane-2,3-diylidene)bis(N-methylhydrazine-1-carbothioamide))

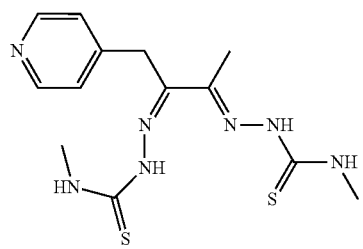 [SMILES: CNC(=S)N/N=C(Cc1ccncc1)\C(C)=N\NC(=S)NC]

3-Ethoxy-1-(pyridin-4-yl)but-3-en-2-one (0.2 g, 1.05 mmol, 1 eq) was dissolved in EtOH (20 ml), methylthiosemicarbazide (0.22 g, 2.1 mmol, 2 eq) and 3 drops of $H_2SO_4$ were added and the reaction mixture was heated to reflux for 4 h and then stirred for 15 h at rt. The formed precipitate was filtered, washed with EtOH, water, $Et_2O$, and dried. Yield 0.21 g (60.2%). LC-MS 0.91 min, m/z 338.9 [MH]+. $^1$H-NMR (400 MHz, DMSO), δ (ppm): 10.85 (s, 1H), 10.35 (s, 1H), 8.78 (d, J=6.6 Hz, 2H), 8.51 (d, J=4.6 Hz, 1H), 8.34 (d, J=4.5 Hz, 1H), 7.72 (d, J=6.5 Hz, 2H), 4.76 (s, 2H), 3.00 (dd, J=14.4, 4.6 Hz, 6H), 2.28 (s, 3H).

Synthesis of Compound 67

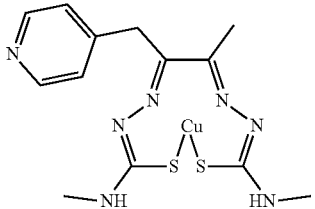

Copper(II) acetate dihydrate (0.09 g, 0.46 mmol) was added to a stirred solution of thiosemicarbazone 3 (0.15 g, 0.44 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.075 g (42.3%).

Scheme 29: Synthesis of Compound 68

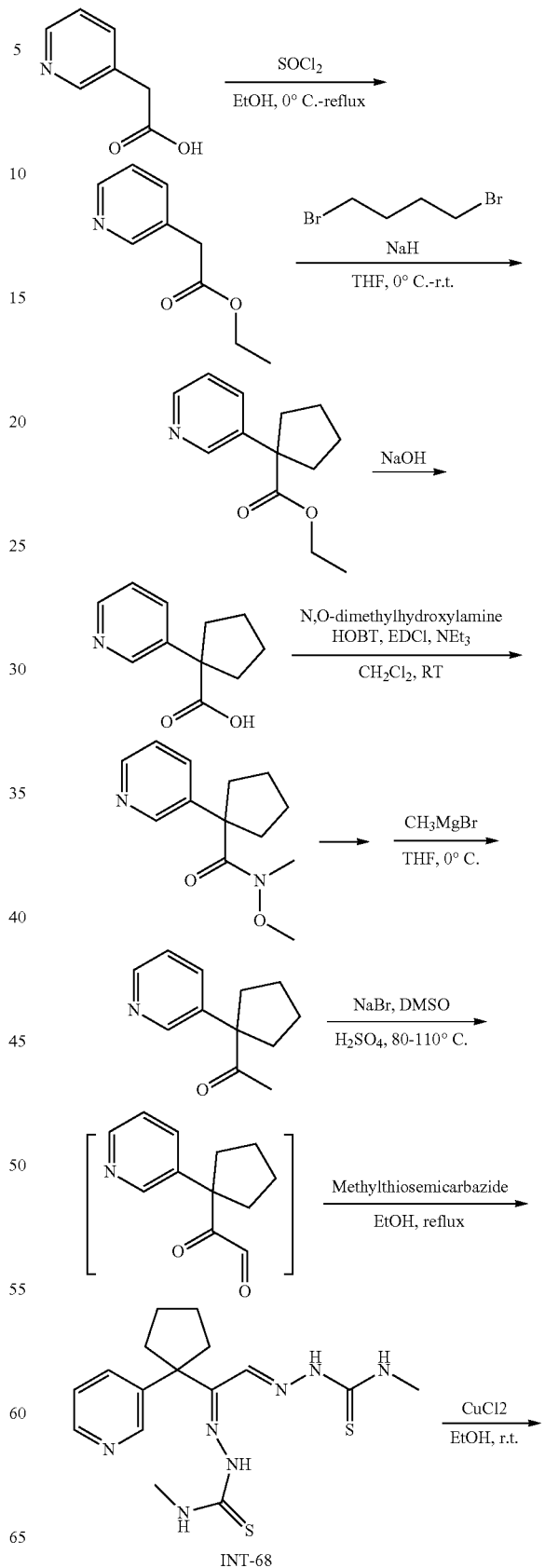

-continued

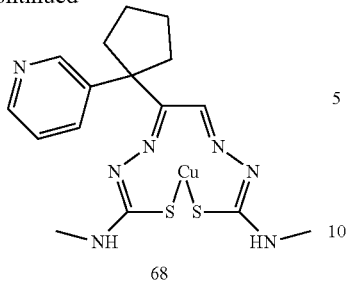
68

Synthesis of ethyl 2-(pyridin-3-yl)acetate

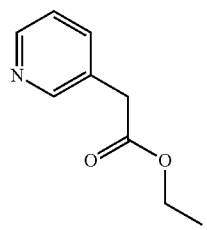

To a stirred solution of 3-pyridineacetic acid (25.0 g, 145 mmol) in EtOH (250 ml) at 0-5° C. was added SOCl$_2$ (11.6 ml, 160 m mol) in small portions over 15 min interval. After completing addition, the reaction was heated to reflux for additional 16 h, and EtOH was evaporated under reduced pressure. To the residue was added 2M aqueous Na$_2$CO$_3$ (30 ml), and the resulting mixture was extracted with EtOAc (3×400 ml). The combined organic layers were washed with brine (100 mL), dried over anh. Na$_2$SO$_4$, filtered, and concentrated in vacuo to afford compound 1 as a colorless liquid. Yield 22.3 g (93%). $^1$H-NMR (400 MHz, CDCl$_3$), δ (ppm): 1.26 (t, 3H), 3.62 (s, 2H), 4.17 (q, 2H), 7.27-7.28 (m, 1H), 7.64-7.65 (m, 1H), 8.53 (m, 2H).

Synthesis of ethyl 1-(pyridin-3-yl)cyclopentane-1-carboxylate

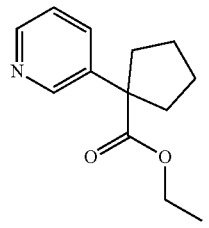 [SMILES: CCOC(=O)C1(c2cccnc2)CCCC1]

To a stirred suspension of sodium hydride (7.3 g, 181 mmol, 60% in mineral oil) in dry THF (160 ml) at 0° C. was added dropwise a solution of ethyl 2-(pyridin-3-yl)acetate (10.0 g, 60.5 mmol) in dry THF (35 ml). The reaction mixture was stirred at 0° C. until no more effervescence. Then 1,4-dibromobutane (19.6 g, 90.5 mmol) was added at 0° C. and the reaction mixture was stirred for 14 h at rt. Subsequently, the reaction mixture was quenched with aqueous saturated ammonium chloride (60 ml). The reaction mixture was extracted with EtOAc (3×40 ml). The organic phase was washed with brine (100 ml), dried over anh. Na$_2$SO$_4$, filtered, and concentrated in vacuo to dryness. Crude material (19 g) was obtained as a dark solid, and then was purified by flash chromatography (silica gel, eluent hexane/ethyl acetate from 4:1 to 1:1). Yield 9.8 g (74%). LC-MS 1.01 min, m/z 220.6 [MH]+. $^1$H-NMR (400 MHz, CDCl3), δ (ppm): 1.16 (t, 3H), 1.74-1.78 (m, 4H), 1.88-1.98 (m, 2H), 2.67-2.73 (m, 2H), 4.09 (q, 2H), 7.23-7.27 (m, 1H), 7.67-7.71 (m, 1H), 8.49 (dd, 1H), 8.65 (dd, 1H).

Synthesis of 1-(pyridin-3-yl)cyclopentane-1-carboxylic Acid

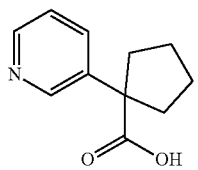 [SMILES: O=C(O)C1(c2cccnc2)CCCC1]

A solution of ethyl 1-(pyridin-3-yl)cyclopentane-1-carboxylate (8.4 g, 38.5 mmol) in MeOH (60 ml) was added to a solution of LiOH (2.5 g, 96.2 mmol) in water (10 ml). The reaction mixture was stirred at 60° C. for 8 h. Then the solvent was removed by freeze-drying, and the corresponding crude product was used for the next step without further purification. Yield 7 g (80%). LC-MS 0.82 min, m/z 192.1 [MH]+. $^1$H-NMR (400 MHz, DMSO-d$_6$), δ (ppm): 1.66-1.70 (m, 4H), 1.85-1.92 (m, 2H), 2.52-2.58 (m, 2H), 7.56 (dd, 1H), 7.98-8.02 (m, 1H), 8.58 (dd, 1H), 8.66 (d, 1H), 12.66 (br.s, 1H).

Synthesis of N-methoxy-N-methyl-1-(pyridin-3-yl) cyclopentane-1-carboxamide

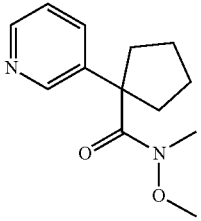 [SMILES: CON(C)C(=O)C1(c2cccnc2)CCCC1]

To a mixture of 1-(pyridin-3-yl)cyclopentane-1-carboxylic acid (5.0 g, 22.0 mmol), Weinreb amine (2.6 g, 26.4 mmol), HOBt (3.6 g, 26.4 mmol), and triethylamine (10.8 ml, 77 mmol) in DCM (150 ml) at 4° C. was added EDCl (5.1 g, 26.4 mmol) and reaction was stirred overnight at rt. Then the mixture was washed with water (100 ml) and brine (100 ml). The organic layer was dried over anh. Na$_2$SO$_4$ and then concentrated under reduced pressure. The residue was purified by column chromatography (silica gel, eluent DCM 100% to DCM/MeOH 95:5 v/v) to afford crude product. Yield 2.5 g (49%). LC-MS 0.84 min, m/z 235.3 [MH]+. $^1$H-NMR (400 MHz, CDCl$_3$), δ (ppm): 1.66-1.81 (m, 4H), 2.05-2.11 (m, 2H), 2.42-2.48 (m, 2H), 2.89 (s, 3H), 3.13 (s, 3H), 7.34 (q, 1H), 7.65 (d, 1H), 8.49 (d, 1H), 8.59 (d, 1H).

Synthesis of 1-(1-(pyridin-3-yl)cyclopentyl)ethan-1-one

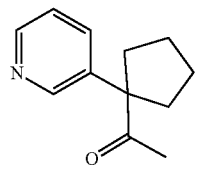

A solution of N-methoxy-N-methyl-1-(pyridin-3-yl)cyclopentane-1-carboxamide (1.27 g, 5.42 mmol, 1 eq) in THF (100 ml) was cooled to 5° C. and methylmagnesium bromide (1.4M in THF, 39.1 ml, 10 eq) was added. The reaction mixture was stirred at 5° C. for 2 h, poured into aq $NH_4Cl$ and extracted with $Et_2O$. The combined extracts were dried over anh. $Na_2SO_4$, and evaporated in vacuo. The titular product was used for the next step without purification. Yield 1 g (97%). LC-MS 1.14 min, m/z 190.6 [MH]+.

Synthesis of INT-68 ((2Z,2'E)-2,2'-(1-(1-(pyridin-3-yl)cyclopentyl)ethane-1,2-diylidene)bis(N-methylhydrazine-1-carbothioamide))

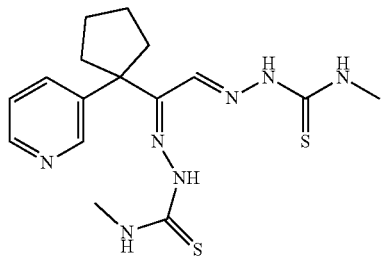 [SMILES: CNC(=S)N/N=C(\C=N\NC(=S)NC)C1(c2cccnc2)CCCC1]

Compound 6. A mixture of 1-(1-(pyridin-3-yl)cyclopentyl)ethan-1-one (1.3 g, 6.9 mmol, 1 eq), NaBr (0.7 g, 1 eq) and DMSO (2 ml) was heated to 85° C. and H2SO4 (6 drops) was added (foaming, exothermic). The reaction was heated at 110-115° C. until the formation of dimethyl sulfide has stopped, and the reaction mixture became viscous. The formed viscous oil was dissolved in EtOH and methylthiosemicarbazide (1.44 g, 2 eq) was added. The reaction mixture was heated to reflux for 4 h, then stirred overnight at rt. The precipitate was collected by filtration, washed with EtOH, MeCN, water, $Et_2O$, and dried to afford the titular product. Yield 0.5 g (19%). LC-MS 1.10 min, m/z 378.8 [MH]+. $^1$H-NMR (400 MHz, DMSO), δ (ppm): 12.05 (s, 1H), 11.51 (s, 1H), 8.57 (s, 2H), 8.44 (d, J=3.9 Hz, 1H), 7.76 (dd, J=24.5, 5.8 Hz, 2H), 7.59 (s, 1H), 7.36 (dd, J=7.7, 4.8 Hz, 1H), 3.02 (dd, J=46.9, 4.3 Hz, 6H), 2.50 (s, 2H), 2.46 (s, 2H), 2.00 (d, J=12.5 Hz, 2H), 1.64 (s, 4H).

Synthesis of Compound 68

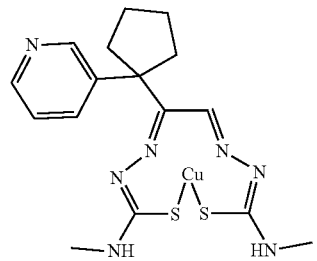

Copper(II) chloride dihydrate (0.078 g, 0.46 mmol) was added to a stirred solution of INT-68 (0.16 g, 0.42 mmol) in ethanol (30 ml). The mixture was stirred for 15 h at rt. Complex was isolated as a red-brown powder. The formed precipitate was filtered, washed with water (2×50 ml), ethanol (2×50 ml), and copious amounts of diethyl ether (5×50 ml), and then dried in vacuo. Yield 0.04 g (22%).

Scheme 30: Synthesis of Compound 69

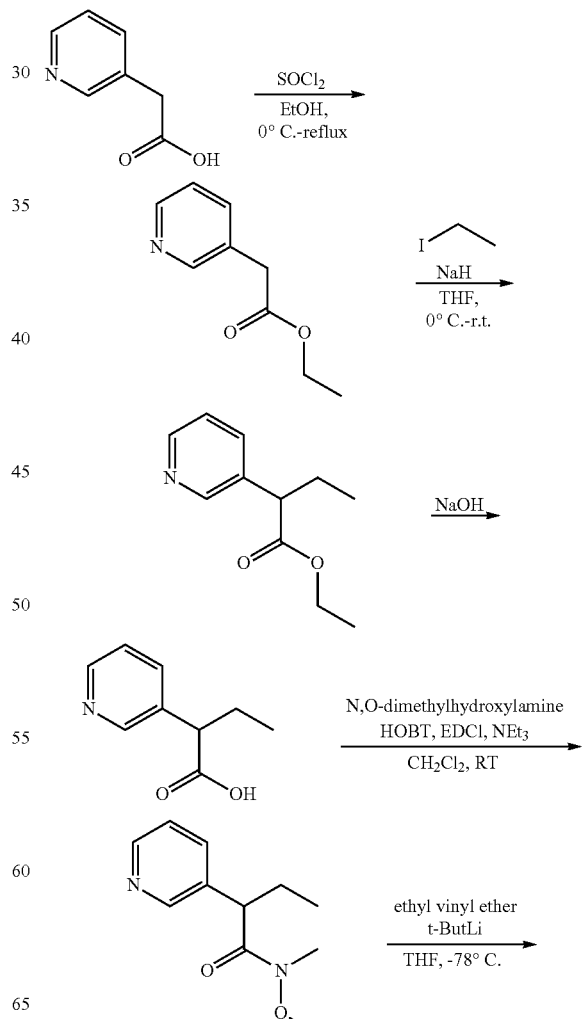

-continued

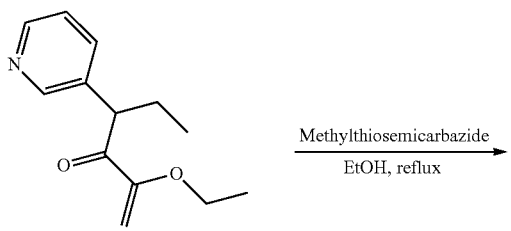

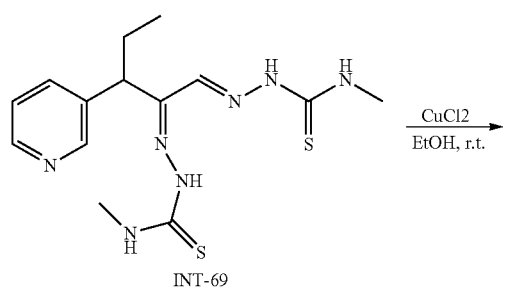

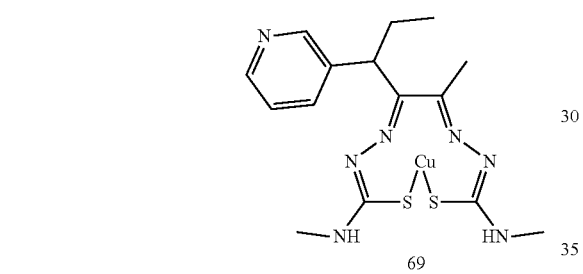

Synthesis of ethyl 2-(pyridin-3-yl)acetate

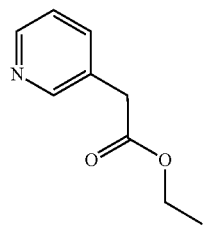

To a stirred solution of 3-pyridineacetic acid (25.0 g, 145 mmol) in EtOH (250 ml) at 0-5° C. was added SOCl$_2$ (11.6 ml, 160 m mol) over 15 min interval. After completing addition, the reaction was heated to reflux for additional 16 h, then EtOH was evaporated under reduced pressure. To the residue was added 2M aqueous Na$_2$CO$_3$ (30 ml), and the resulting mixture was extracted with EtOAc (3×400 ml). The combined organic layers were washed with brine (100 mL), dried over anh. Na$_2$SO$_4$, filtered, and concentrated in vacuo to afford the titular product as a colorless liquid. Yield 22.3 g (93%). $^1$H-NMR (400 MHz, CDCl$_3$), δ (ppm): 1.26 (t, 3H), 3.62 (s, 2H), 4.17 (q, 2H), 7.27-7.28 (m, 1H), 7.64-7.65 (m, 1H), 8.53 (m, 2H).

Synthesis of ethyl 2-(pyridin-3-yl)butanoate

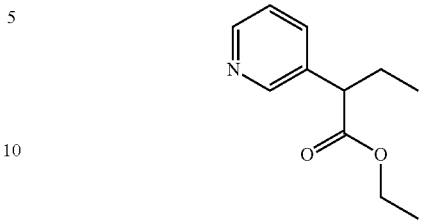

To a solution of ethyl 2-(pyridin-3-yl)acetate (10.08 g, 61 mmol) in THF (100 mL) was added sodium hydride (2.54 g, 66 mmol, 60% dispersion in mineral oil) in small portions. After stirring at rt for 10 min, iodoethane (5.1 ml, 66 mmol) was added, and the resulting mixture was stirred overnight at rt. Then the reaction mixture was quenched with aq. solution NH$_4$Cl, extracted with EtOAc, dried over anh. Na2SO4, filtered, and concentrated in vacuo resulting in compound 2 as a colorless liquid. Yield 10.6 g (86%). LC-MS 0.77 min, m/z 194.1 [MH]+. $^1$H-NMR (400 MHz, CDCl$_3$), δ (ppm): 0.91 (t, J=8 Hz, 3H), 1.22 (t, J=8 Hz, 3H), 1.74-1.85 (m, 1H), 2.07-2.18 (m, 1H), 3.46 (t, J=7.6 Hz, 1H), 4.07-4.21 (m, 2H), 7.25-7.28 (m, 1H), 7.67-7.70 (m, 1H), 8.51-8.54 (m, 2H).

Synthesis of 2-(pyridin-3-yl)butanoic Acid

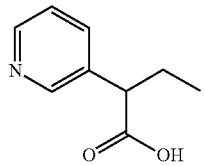

A solution of ethyl 2-(pyridin-3-yl)butanoate (10.6 g, 54.8 mmol) in MeOH (60 ml) was added to a solution of NaOH (5.5 g, 137.2 mmol) in water (22 ml). The reaction mixture was stirred for 8 h at rt. Then the solvent was removed by freeze-drying, and the corresponding crude product was used for the next step without further purification. Yield 10.3 g (93%). LC-MS 0.51 min, m/z 166.1 [MH]+. $^1$H-NMR (400 MHz, CDCl$_3$), δ (ppm): 0.81 (t, J=6.8 Hz, 3H), 1.67-1.78 (m, 1H), 1.96-2.05 (m, 1H), 2.08 (s, 1H), 3.60 (t, J=7.6 Hz, 1H), 7.53-7.56 (m, 1H), 7.92-7.95 (m, 1H), 8.56-8.61 (m, 2H).

Synthesis of N-methoxy-N-methyl-2-(pyridin-3-yl)butanamide

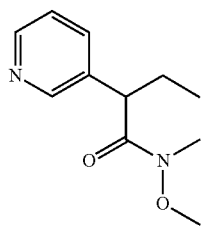

To a mixture of 2-(pyridin-3-yl)butanoic acid (10.3 g, 51.0 mmol), Weinreb amine (5.9 g, 61.2 mmol), HOBt (8.3 g, 61.2 mmol), and triethylamine (25 ml, 176 mmol) in DCM (150 ml) at 4° C. was added EDCl (11.7 g, 61.2 mmol) and reaction was stirred overnight at rt. The mixture was washed with water (100 ml) and brine (100 ml). The organic layer was dried over anh. $Na_2SO_4$ and then concentrated under reduced pressure. The residue was purified by column chromatography (silica gel, eluent DCM 100% to DCM/MeOH 95:5 v/v) to afford crude product. Yield 7.3 g (68%). LC-MS 0.76 min, m/z 208.9 [MH]+. $^1$H-NMR (400 MHz, $CDCl_3$), δ (ppm): 0.90 (t, J=7.6 Hz, 3H), 1.73-1.80 (m, 1H), 2.08-2.15 (m, 1H), 3.17 (s, 3H), 3.57 (s, 3H), 3.91-3.96 (m, 1H), 7.26-7.28 (m, 1H), 7.74-7.77 (m, 1H), 8.48-8.50 (m, 1H), 8.53 (d, J=2 Hz, 1H).

Synthesis of 2-ethoxy-4-(pyridin-3-yl)hex-1-en-3-one

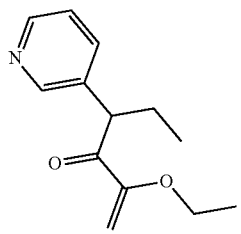 [SMILES: C=C(OCC)C(=O)C(CC)c1cccnc1]

A solution of ethyl vinyl ether (4.3 ml, 45.1 mmol) in dry tetrahydrofuran (30 ml) was cooled to −78° C., and tert-butyllithium (1.7M in pentane, 24 ml, 41 mmol) was added. The mixture was warmed to 0° C. over 1 h period, stirred for 45 min, and cooled down to −30° C. A solution of N-methoxy-N-methyl-2-(pyridin-3-yl)butanamide (1.7 g, 8.2 mmol) in THF (35 ml) was added, and the reaction was stirred at 0° C. for 4 h. The progress of the reaction was monitored by TLC. The mixture was poured into aq. $NH_4Cl$ (30 ml) and extracted with $Et_2O$ (3×50 ml). The combined extracts were dried over anh. $Na_2SO_4$, filtered, and evaporated in vacuo. The product was used for the next step without additional purification. Yield 1.15 g (64%). LC-MS 1.15 min, m/z 219.9 [MH]+. $^1$H-NMR (400 MHz, $CDCl_3$), δ (ppm): 0.86 (t, J=7.2 Hz, 3H), 1.34 (t, J=6.8 Hz, 3H), 1.68-1.79 (m, 1H), 2.04-2.15 (m, 1H), 3.62-3.70 (m, 1H), 3.74-3.82 (m, 1H), 4.27 (t, J=8 Hz, 1H), 4.35 (d, J=2 Hz, 1H), 5.20 (d, J=2.8 Hz, 1H), 7.23-7.27 (m, 1H), 7.55-7.58 (m, 1H), 8.47-8.49 (m, 1H), 8.52 (d, J=2 Hz, 1H).

Synthesis of INT-69 ((2Z,2'E)-2,2'-(3-(pyridin-3-yl)pentane-1,2-diylidene)bis(N-methylhydrazine-1-carbothioamide))

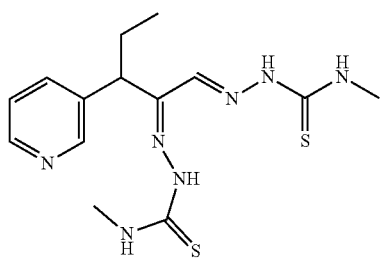 [SMILES: CCC(C(/C=N/NC(=S)NC)=N/NC(=S)NC)c1cccnc1]

Compound 6. To a stirred solution of 2-ethoxy-4-(pyridin-3-yl)hex-1-en-3-one (0.89 g, 4.05 mmol, 1 eq) in EtOH (20 ml) methyl thiosemicarbazide (0.85 g, 8.1 mmol, 2 eq) and 3 drops of $H_2SO_4$ were added and the reaction mixture was heated to reflux for 4 h, and then stirred for 15 h at rt. The formed precipitate was filtered, washed with EtOH, water, $Et_2O$, and dried. Yield 0.67 g (45%). LC-MS 1.01 min, m/z 366.3 [MH]+.

Synthesis of Compound 69

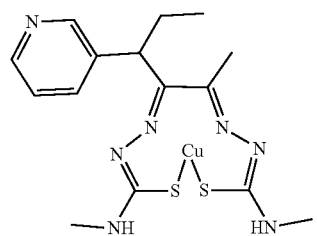

Copper(II) chloride dihydrate (0.12 g, 0.73 mmol) was added to a stirred solution of INT-69 (0.24 g, 0.67 mmol) in ethanol (30 ml). The mixture was stirred overnight at rt. Complex was isolated as a red-brown powder. The formed precipitate was filtered, washed with water (2×50 ml), ethanol (2×50 ml), and copious amounts of diethyl ether (5×50 ml), and then dried in vacuo. Yield 0.13 g (45%).

Scheme 30: Synthesis of Compound 70

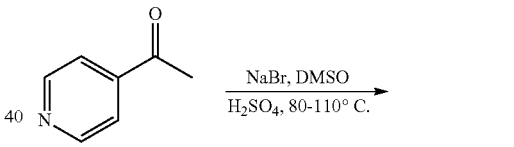

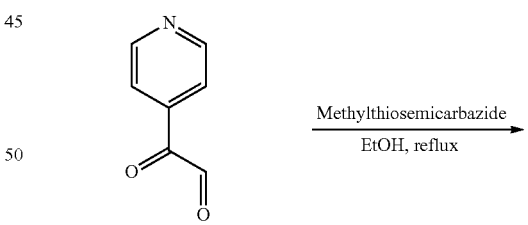

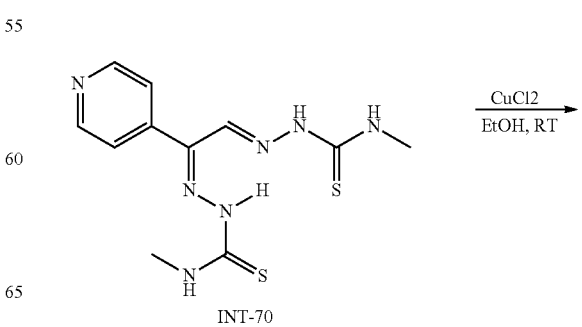

INT-70

314

Synthesis of Compound 70

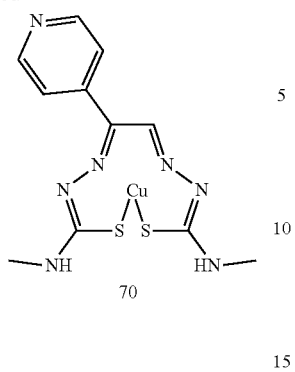

To a solution of INT-70 (70 mg, 0.2 mmol) in EtOH (10 ml) was added a solution of copper(II) chloride dihydrate (42 mg, 0.22 mmol) in EtOH (2 ml). The mixture was stirred overnight at rt. The formed precipitate was collected by filtration, washed with water (2×5 ml), ethanol (2×5 ml), diethyl ether (5×5 ml), and then dried in vacuo to give the product as a dry powder. Yield 42 mg (50%).

Scheme 32: Synthesis of Compound 71

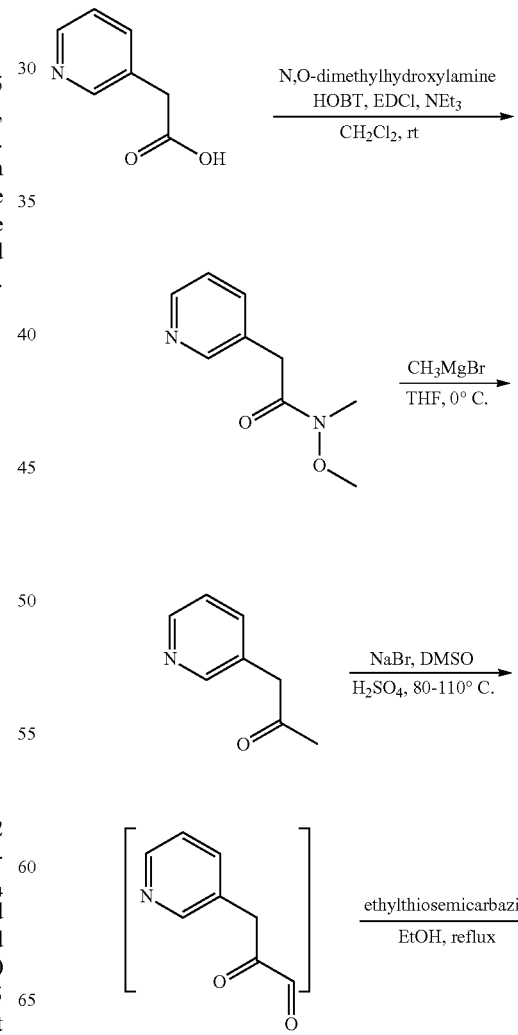

313
-continued

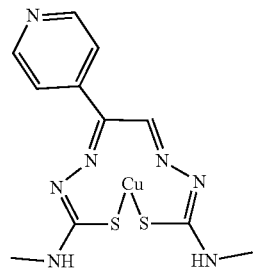

70

Synthesis of 2-oxo-2-(pyridin-4-yl)acetaldehyde

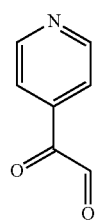

To a solution of 1-pyridin-4-ylethanone (10.0 g, 82.5 mmol) in DMSO (100 ml) was added conc. HBr (28 ml, 247.5 mmol) and the mixture was stirred at 50° C. overnight. The reaction mixture was quenched with NaHCO$_3$ then diluted with water to a total volume of 1000 ml. The obtained solution was extracted with EtOAc (3×150 ml), the combined organic layers were dried over anh. Na$_2$SO$_4$ and evaporated in vacuo to give the product 1 as a yellow oil. Yield 2.0 g (18%). LC-MS 0.35 min, m/z 136.1 [MH]+.

Synthesis of INT-70 ((2Z,2'E)-2,2'-(1-(pyridin-4-yl)ethane-1,2-diylidene)bis(N-methylhydrazine-1-carbothioamide))

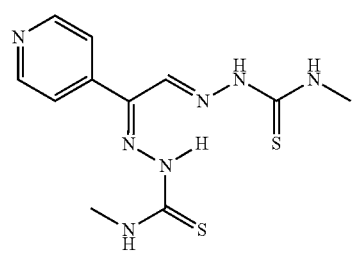 [SMILES: CNC(=S)N/N=C(\C=N\NC(=S)NC)c1ccncc1]

To a solution of 2-oxo-2-(pyridin-4-yl)acetaldehyde (1.2 g, 8.9 mmol) in EtOH (100 ml) was added methyl thiosemicarbazide (1.87 g, 19.8 mmol) followed by 2 drops of H$_2$SO$_4$ then the reaction mixture was heated to reflux for 4 h and stirred overnight at rt. The precipitate was filtered, washed with EtOH, Et$_2$O, and dried to afford compound 2. Yield 70 mg (4%). LC-MS (reverse phase C18 column 20×2 mm, 2.5 μm, pore size 100 Å, water-acetonitrile+0.1% TFA, gradient 5 to 87% over 10 min) 4.27 min, (ESI) m/z 310.1 [MH]+.

-continued

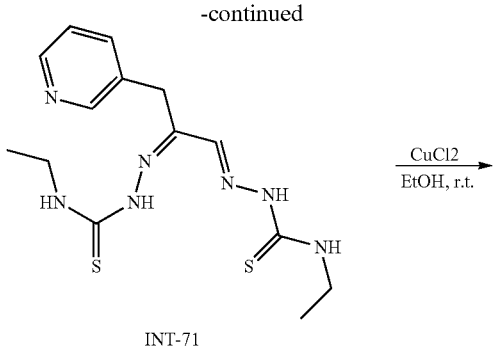

INT-71

Synthesis of 1-(pyridin-3-yl)propan-2-one

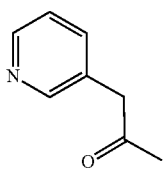

A solution of N-methoxy-N-methyl-2-(pyridin-3-yl)acetamide (9.5 g, 52.7 mmol, 1 eq) in THF (200 ml) was cooled to 5° C. and methylmagnesium bromide (1.4M in THF, 46.5 ml, 3 eq) was added. The reaction mixture was stirred at 5° C. for 2 h, poured into aq NH₄Cl and extracted with Et₂O. The combined extracts were dried over anh. Na₂SO₄, and evaporated in vacuo. The titular product was used for the next step without purification. Yield 6.1 g (86%). LC-MS 0.27 min, m/z 136.6 [MH]+. ¹H-NMR (400 MHz, CDCl₃), δ (ppm): 8.48 (d, J=4.7 Hz, 1H), 8.41 (s, 1H), 7.50 (d, J=7.8 Hz, 1H), 7.31-7.12 (m, 1H), 3.67 (d, J=19.5 Hz, 2H), 2.18 (s, 3H).

Synthesis of INT-71 ((2Z,2'E)-2,2'-(3-(pyridin-3-yl) propane-1,2-diylidene)bis(N-ethylhydrazine-1-carbothioamide))

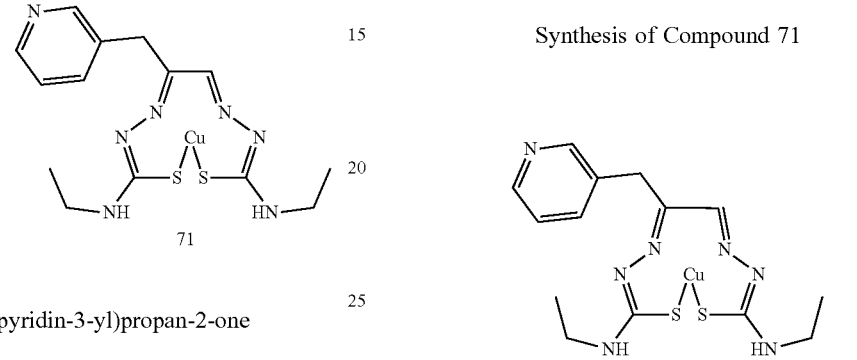

A mixture of 1-(pyridin-3-yl)propan-2-one (1.5 g, 11.1 mmol, 1 eq), NaBr (1.14 g, 1 eq) and DMSO (2 ml) was heated to 85° C. and H₂SO₄ (6 drops) was added (foaming, exothermic). The reaction was heated at 110-115° C. until the formation of dimethyl sulfide has stopped, and the reaction mixture became viscous. The formed viscous oil was dissolved in EtOH and ethylthiosemicarbazide (2.64 g, 2 eq) was added. The reaction mixture was heated to reflux for 4 h, then stirred overnight at rt. The precipitate was collected by filtration, washed with EtOH, MeCN, water, Et₂O, and dried to afford the titular product. Yield 0.175 g (4.5%). LC-MS 1.19 min, m/z 352.8 [MH]+.

Synthesis of Compound 71

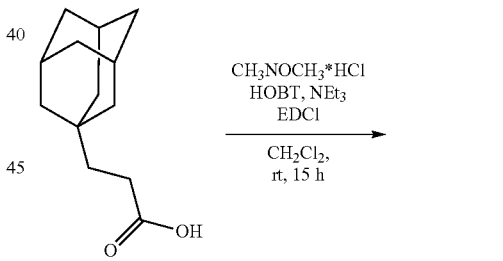

Copper(II) acetate dihydrate (0.055 g, 1 eq) was added to a stirred solution of INT-71 (0.175 g, 0.5 mmol, 1 eq) in ethanol. The mixture was stirred for 15 h at rt. The formed complex precipitated as a red-brown powder. The precipitate was collected by filtration, washed with water, methanol, diethyl ether, and dried in vacuo. Yield 0.14 g (69%).

Scheme 33: Synthesis of Compound 72

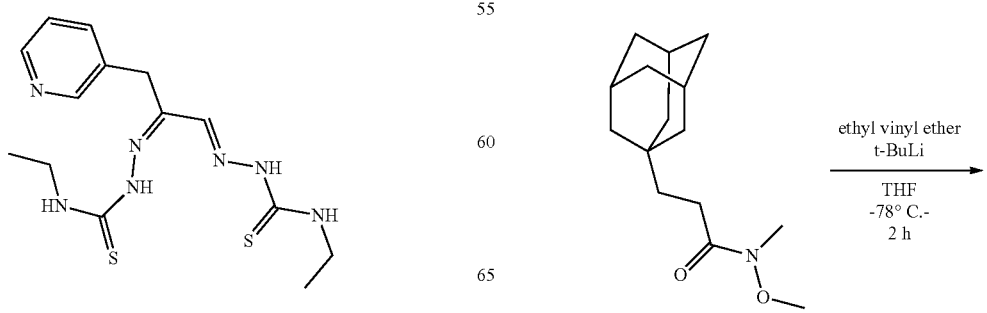

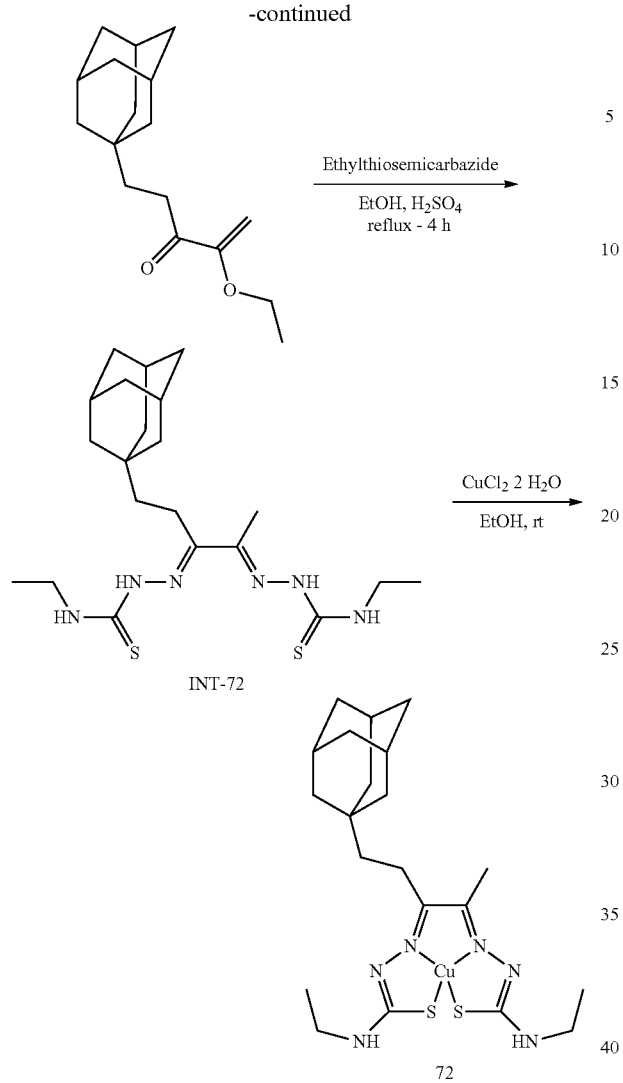

chromatography (silica gel, eluent CCl$_4$ 100% then CCl$_4$/EtOAc 8:2). Yield 3.5 g (58%). LC-MS 1.88 min, m/z 252.4 [MH]+. $^1$H-NMR (400 MHz, CDCl$_3$), δ (ppm): 3.71 (d, J=1.6 Hz, 3H), 3.19 (s, 3H), 2.42-2.31 (m, 2H), 1.97 (s, 3H), 1.72 (d, J=11.9 Hz, 3H), 1.68-1.58 (m, 4H), 1.50 (s, 6H), 1.43 (dd, J=9.8, 7.1 Hz, 2H).

Synthesis of 5-((3r,5r,7r)-adamantan-1-yl)-2-ethoxy-pent-1-en-3-one

A solution of ethyl vinyl ether (2.01 g, 2.7 ml, 3.3 eq) in dry THF (150 ml) was cooled to −78° C., and tert-butyl-lithium (1.7M in pentane, 16 ml, 3 eq) was added. The mixture was warmed to 0° C. over 1 h period, stirred for 45 min, and then cooled down to −30° C. A solution of 3-((3r,5r,7r)-adamantan-1-yl)-N-methoxy-N-methylpropanamide (2.12 g, 8.4 mmol) in THF (15 ml) was added and stirring continued at 0° C. for 4 h. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used for the next step without additional purification. Yield 2.2 g (99.9%). $^1$H-NMR (400 MHz, CDCl$_3$), δ (ppm): 5.18 (s, 1H), 4.36 (d, J=33.6 Hz, 1H), 3.82 (q, J=6.9 Hz, 2H), 2.64 (dd, J=20.9, 13.1 Hz, 2H), 1.97 (s, 4H), 1.79-1.53 (m, 8H), 1.56-1.15 (m, 13H).

Synthesis of INT-72 ((2E,2'E)-2,2'-(5-((3r,5r,7r)-adamantan-1-yl)pentane-2,3-diylidene)bis(N-ethyl-hydrazine-1-carbothioamide)

Synthesis of 3-((3r,5r,7r)-adamantan-1-yl)-N-methoxy-N-methylpropanamide

To a stirred mixture of 3-((3r,5r,7r)-adamantan-1-yl)propanoic acid (5 g, 24 mmol), N,O-dimethylhydroxylamine (2.81 g, 1.2 eq), HOBt (3.89 g, 1.2 eq), and triethylamine (8.5 ml, 6.11 g, 2.5 eq) in DCM (50 ml) at 5° C. was added EDCl (5.52 g, 1.2 eq) and reaction was stirred for 15 h at rt. The mixture was washed with water and brine. The organic layer was dried over anh. Na$_2$SO$_4$ and then concentrated under reduced pressure. The product was purified by column 5-((3r,5r,7r)-adamantan-1-yl)-2-ethoxypent-1-en-3-one (2.21 g, 8.4 mmol) was dissolved in EtOH (60 ml), ethyl-thiosemicarbazide (2.01 g, 2 eq) and 3 drops of H$_2$SO$_4$ were added. The stirred reaction mixture was heated to reflux for 4 h and then maintained for 15 h at rt. The formed precipitate was filtered, washed with EtOH, aq.sat. Na$_2$CO$_3$, water, Et$_2$O, and dried. Yield 2.2 g (59.6%). LC-MS 2.17 min, m/z 437.5 [MH]+.

Synthesis of Compound 72

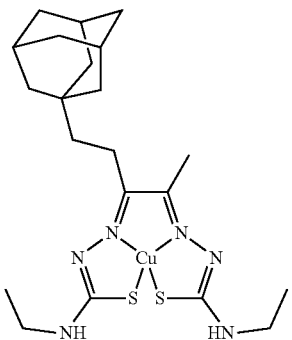

Copper(II) chloride dihydrate (0.23 g, 1 eq) was added to a stirred solution of INT-72 (0.59 g) in ethanol. The mixture was stirred for 15 h at rt. The formed complex precipitated as a red-brown powder. The precipitate was collected by filtration, washed with water, diethyl ether, and dried. Yield 0.61 g (90.8%).

Scheme 34: Synthesis of Compound 73

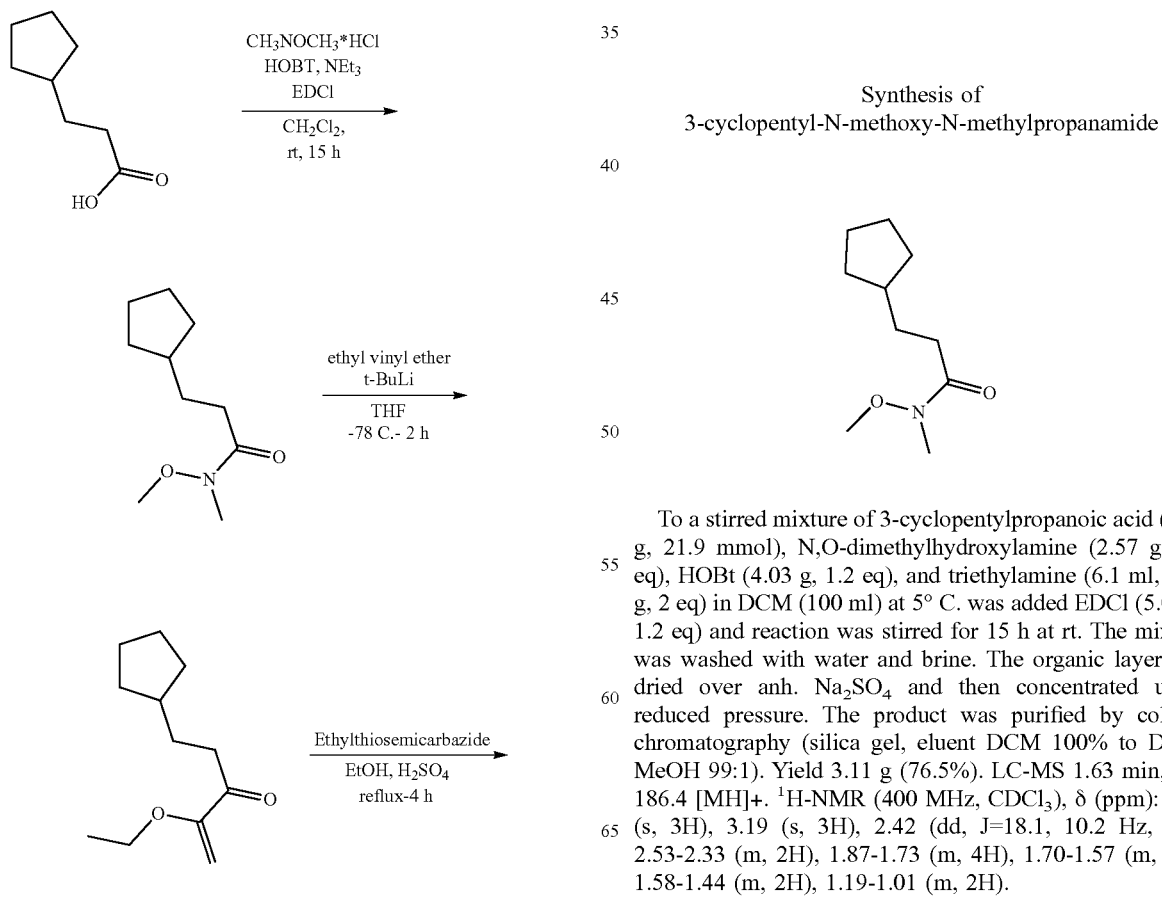

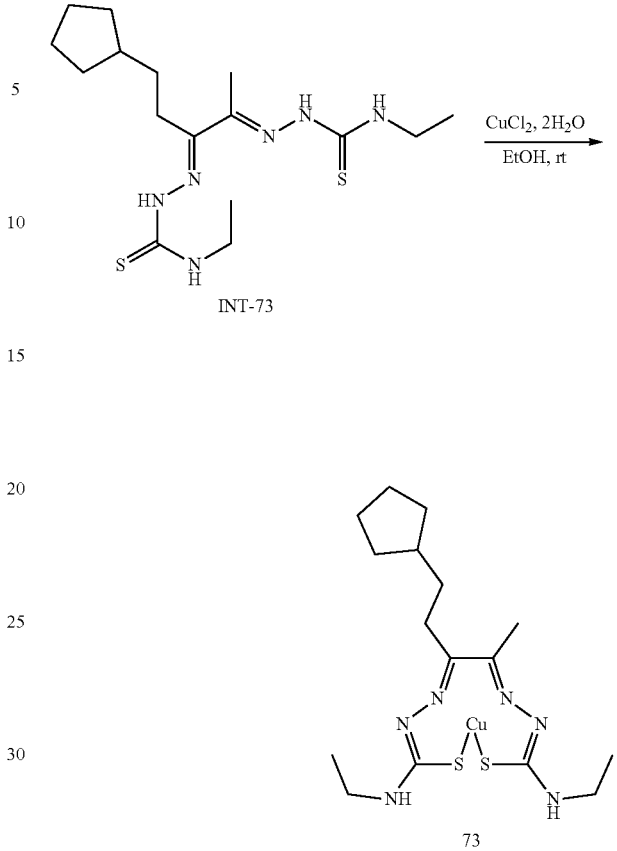

Synthesis of 3-cyclopentyl-N-methoxy-N-methylpropanamide

To a stirred mixture of 3-cyclopentylpropanoic acid (3.12 g, 21.9 mmol), N,O-dimethylhydroxylamine (2.57 g, 1.2 eq), HOBt (4.03 g, 1.2 eq), and triethylamine (6.1 ml, 4.43 g, 2 eq) in DCM (100 ml) at 5° C. was added EDCl (5.05 g, 1.2 eq) and reaction was stirred for 15 h at rt. The mixture was washed with water and brine. The organic layer was dried over anh. Na$_2$SO$_4$ and then concentrated under reduced pressure. The product was purified by column chromatography (silica gel, eluent DCM 100% to DCM/MeOH 99:1). Yield 3.11 g (76.5%). LC-MS 1.63 min, m/z 186.4 [MH]+. $^1$H-NMR (400 MHz, CDCl$_3$), δ (ppm): 3.69 (s, 3H), 3.19 (s, 3H), 2.42 (dd, J=18.1, 10.2 Hz, 2H), 2.53-2.33 (m, 2H), 1.87-1.73 (m, 4H), 1.70-1.57 (m, 5H), 1.58-1.44 (m, 2H), 1.19-1.01 (m, 2H).

321
Synthesis of 5-cyclopentyl-2-ethoxypent-1-en-3-one

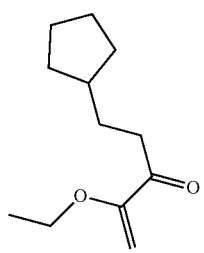

A solution of ethyl vinyl ether (3.85 g, 5.1 ml, 6.6 eq) in dry THF (100 ml) was cooled to −78° C., and tert-butyl-lithium (1.7M in pentane, 28 ml, 6 eq) was added. The mixture was warmed to 0° C. over 1 h period, stirred for 45 min, and then cooled down to −30° C. A solution of 3-cyclopentyl-N-methoxy-N-methylpropanamide (1.5 g, 8 mmol) in THF (15 ml) was added and stirring continued at 0° C. for 4 h. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used for the next step without additional purification. Yield 1.05 g (99.0%). LC-MS 0.91 min, m/z 180.9 [MH]+.

Synthesis of INT-73 ((2E,2'E)-2,2'-(5-cyclopentyl-pentane-2,3-diylidene)bis(N-ethylhydrazine-1-carbo-thioamide))

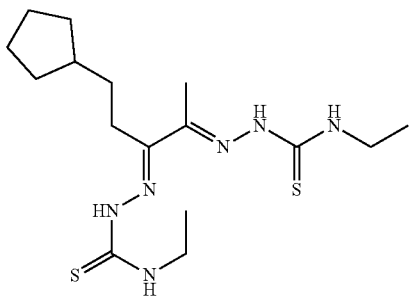 [SMILES: CCNC(=S)N/N=C(C)/C(CCC1CCCC1)=N/NC(=S)NCC]

5-cyclopentyl-2-ethoxypent-1-en-3-one (1.05 g, 8 mmol) was dissolved in EtOH (25 ml), ethylthiosemicarbazide (1.93 g, 2 eq) and 3 drops of H$_2$SO$_4$ were added. The stirred reaction mixture was heated to reflux for 4 h and then maintained for 15 h at rt. The formed precipitate was filtered, washed with EtOH, aq.sat. Na$_2$CO$_3$, water, Et$_2$O, and dried. Yield 2 g (68%). LC-MS 1.83 min, m/z 371.5 [MH]+.

322
Synthesis of Compound 73

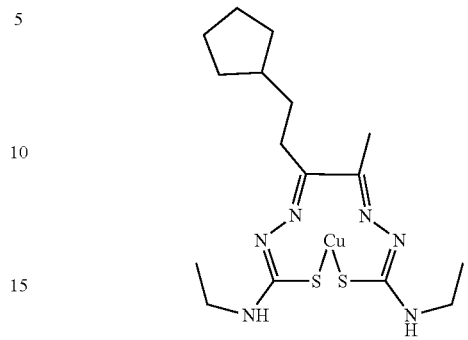

Copper(II) chloride dihydrate (0.23 g, 1 eq) was added to a stirred solution of INT-73 (0.5 g, 1.3 mmol) in ethanol. The mixture was stirred for 15 h at rt. The formed complex precipitated as a red-brown powder. The precipitate was collected by filtration, washed with water, diethyl ether, and dried. Yield 0.5 g (88.7%).

Scheme 35: Synthesis of Compound 74

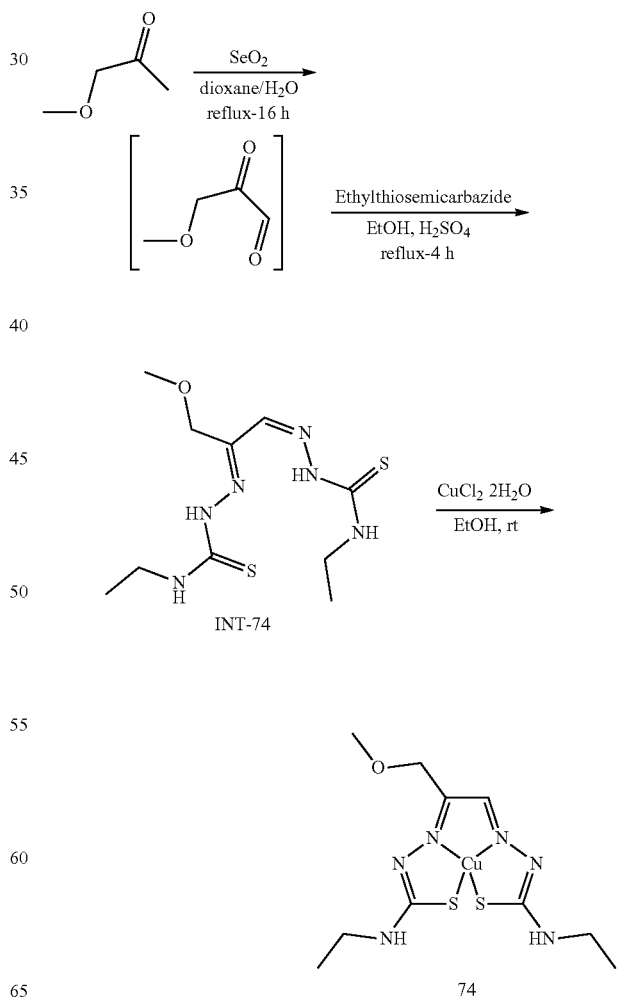

Synthesis of INT-74 ((2Z,2'Z)-2,2'-(3-methoxypropane-1,2-diylidene)bis(N-ethylhydrazine-1-carbothioamide))

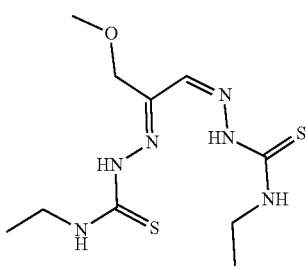 [SMILES: CCNC(=S)N/N=C\C(COC)=N\NC(=S)NCC]

A three-necked flask was charged with SeO$_2$ (3.6 g, 1.05 eq), 1,4-dioxane (70 mL), and water (14 mL). The mixture was heated to 50° C. and stirred until most of SeO$_2$ dissolves. 1-methoxypropan-2-one (2.72 g, 30.9 mmol) was added, and the reaction was heated to gentle reflux overnight. Selenium solids precipitated during the course of the reaction. The mixture was cooled in an ice bath and filtered through diatomaceous earth to remove selenium. The filter cake was washed with portions of 1,4-dioxane. The filtrate was evaporated to dryness and dissolved in EtOH (100 ml). Ethylthiosemicarbazide (7.35 g, 2 eq) and 3 drops of H$_2$SO$_4$ were added. The stirred reaction mixture was heated to reflux for 4 h. Formed precipitate was filtered, washed with EtOH, aq.sat. Na$_2$CO$_3$, water, Et$_2$O, and dried. Yield 2.4 g (25.5%). LC-MS 1.37 min, m/z 305.5 [MH]+.

Synthesis of Compound 74

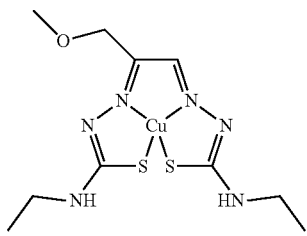

Copper(II) chloride dihydrate (0.1 g, 1 eq) was added to a stirred solution of INT-74 (0.184 g, 0.6 mmol) in ethanol. The mixture was stirred for 15 h at rt. The formed complex precipitated as a red-brown powder. The precipitate was collected by filtration, washed with water, diethyl ether, and dried. Yield 0.1 g (45.2%).

Scheme 36: Synthesis of Compound 75

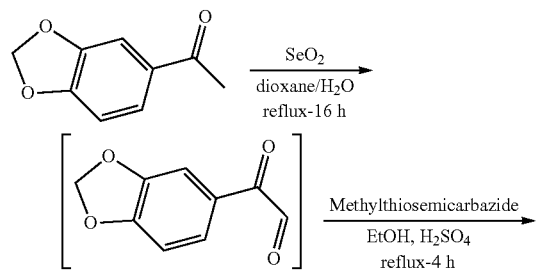

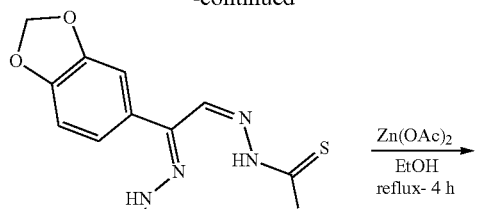

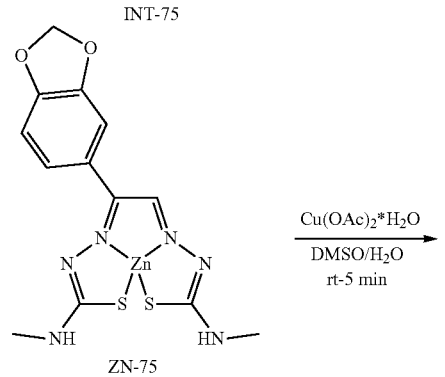

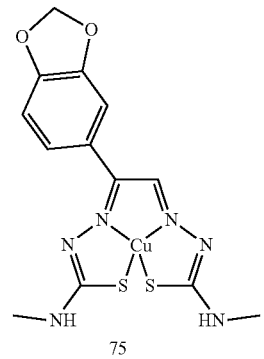

Synthesis of INT-75 ((2Z,2'E)-2,2'-(1-(benzo[d][1,3]dioxol-5-yl)ethane-1,2-diylidene)bis(N-methylhydrazine-1-carbothioamide))

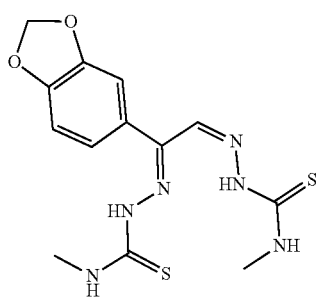

A three-necked flask was charged with SeO$_2$ (2.12 g, 1.05 eq), 1,4-dioxane (41 mL), and water (9 mL). The mixture was heated to 50° C. and stirred until most of SeO$_2$ dissolves. 1-(benzo[d][1,3]dioxol-5-yl)ethan-1-one (2.72 g, 30.9 mmol) was added, and the reaction was heated to gentle reflux overnight. Selenium solids precipitated during the course of the reaction. The mixture was cooled in an ice bath and filtered through diatomaceous earth to remove selenium. The filter cake was washed with portions of 1,4-dioxane. The filtrate was evaporated to dryness and dissolved in EtOH (100 ml). Methylthiosemicarbazide (3.84 g, 2 eq) and 3 drops of H₂SO₄ were added. The stirred reaction mixture was heated to reflux for 4 h. Formed precipitate was filtered, washed with EtOH, aq.sat. Na₂CO₃, water, Et₂O, and dried. Yield 2.16 g (33.5%). LC-MS 1.53 min, m/z 353.3 [MH]+. ¹H-NMR (400 MHz, DMSO-d6), δ (ppm): 12.13 (s, 1H), 11.71 (s, 1H), 8.82 (d, J=4.3 Hz, 1H), 8.21-8.04 (m, 2H), 7.60 (d, J=1.5 Hz, 1H), 7.18 (d, J=8.2 Hz, 1H), 6.98 (d, J=8.2 Hz, 1H), 6.08 (s, 2H), 3.04 (dd, J=15.0, 4.5 Hz, 6H).

Synthesis of ZN-75

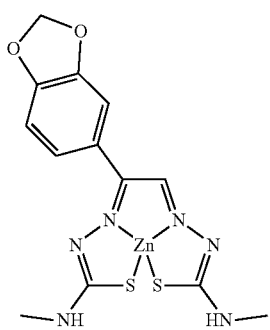

Zinc acetate (0.28 g, 1.5 eq) was added to INT-75 (0.36 g, 1 mmol) in ethanol. The mixture was heated to reflux for 4 h. The formed complex precipitated as a yellow powder. The precipitate was collected by filtration, washed with water, methanol, diethyl ether, and dried in vacuo. Yield 0.33 g (76.8%).

Synthesis of Compound 75

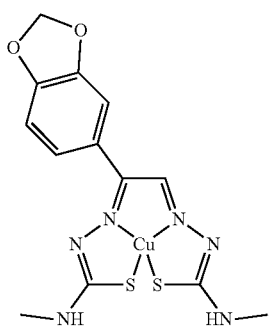

ZN-75 (0.32 g, 0.8 mmol) was dissolved in DMSO (9 ml) and a solution of Cu(OAc)₂*H₂O (0.17 g, 1.1 eq) in water (9 ml) was added. The mixture was stirred for 5 min, filtered, and precipitate was washed with saturated solution of potassium carbonate, water, and Et₂O. Yield 0.15 g (48.5%).

Scheme 37: Synthesis of Compound 76

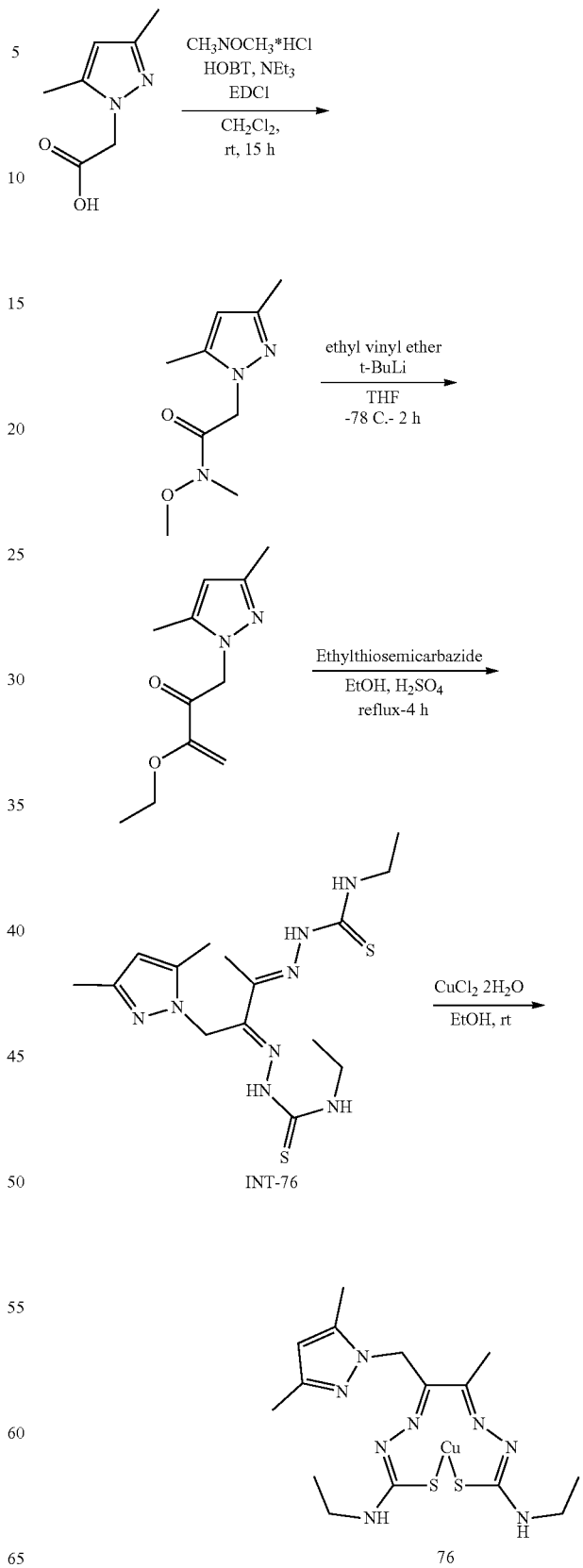

Synthesis of 2-(3,5-dimethyl-1H-pyrazol-1-yl)-N-methoxy-N-methylacetamide

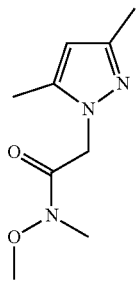

To a stirred mixture of 2-(3,5-dimethyl-1H-pyrazol-1-yl)acetic acid (1.95 g, 12.6 mmol), N,O-dimethylhydroxylamine (1.48 g, 1.2 eq), HOBt (2.32 g, 1.2 eq), and triethylamine (3.5 ml, 2.54 g, 2 eq) in DCM (80 ml) at 5° C. was added EDCl (2.9 g, 1.2 eq) and reaction was stirred for 15 h at rt. The mixture was washed with water and brine. The organic layer was dried over anh. $Na_2SO_4$ and then concentrated under reduced pressure. The product was used further without additional purification. Yield 1.7 g (68.1%). LC-MS 0.88 min, m/z 198.3 [MH]+. $^1$H-NMR (400 MHz, $CDCl_3$), δ (ppm): 5.88 (s, 1H), 4.98 (s, 2H), 3.79 (s, 3H), 3.22 (s, 3H), 2.23 (d, J=6.6 Hz, 6H).

Synthesis of 1-(3,5-dimethyl-1H-pyrazol-1-yl)-3-ethoxybut-3-en-2-one

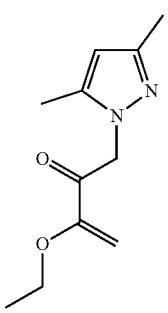

A solution of ethyl vinyl ether (6.83 g, 9 ml, 11 eq) in dry THF (150 ml) was cooled to −78° C., and tert-butyllithium (1.7M in pentane, 50 ml, 10 eq) was added. The mixture was warmed to 0° C. over 1 h period, stirred for 45 min, and then cooled down to −30° C. A solution of 2-(3,5-dimethyl-1H-pyrazol-1-yl)-N-methoxy-N-methylacetamide (1.7 g, 8.6 mmol) in THF (20 ml) was added and stirring continued at 0° C. for 4 h. The mixture was poured into aq. $NH_4Cl$ (100 ml) and extracted with $Et_2O$ (3×100 ml). The combined extracts were dried over anh. $Na_2SO_4$, filtered, and solvents were evaporated in vacuo. The product was used for the next step without additional purification. Yield 0.4 g (22.2%). LC-MS 1.15 min, m/z 209.1 [MH]+.

Synthesis of INT-76 ((2E,2'E)-2,2'-(1-(3,5-dimethyl-1H-pyrazol-1-yl)butane-2,3-diylidene)bis(N-ethyl-hydrazine-1-carbothioamide))

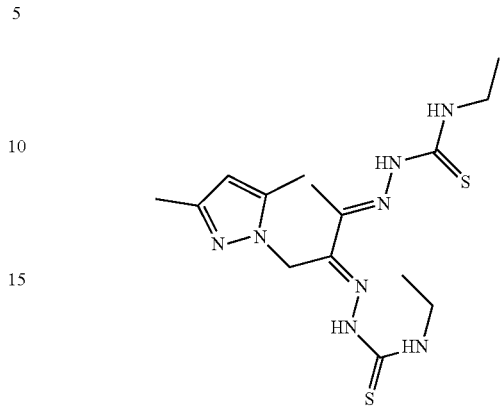

1-(3,5-dimethyl-1H-pyrazol-1-yl)-3-ethoxybut-3-en-2-one (0.4 g, 1.9 mmol) was dissolved in EtOH (15 ml), ethylthiosemicarbazide (0.46 g, 2 eq) and 1 drop of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.05 g (6.8%). LC-MS 1.62 min, m/z 383.5 [MH]+.

Synthesis of Compound 76

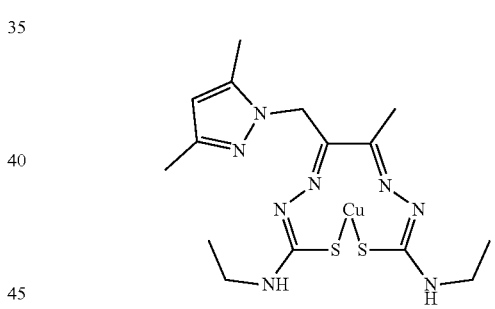

Copper(II) chloride dihydrate (0.23 g, 1 eq) was added to a stirred solution of INT-76 (0.5 g, 1.3 mmol) in ethanol. The mixture was stirred for 15 h at rt. The formed complex precipitated as a red-brown powder. The precipitate was collected by filtration, washed with water, diethyl ether, and dried. Yield 0.5 g (88.7%).

Scheme 38: Synthesis of Compound 77

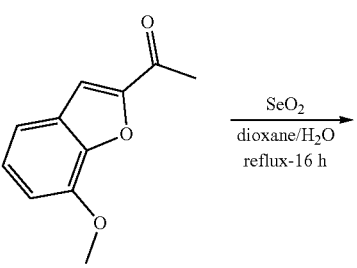

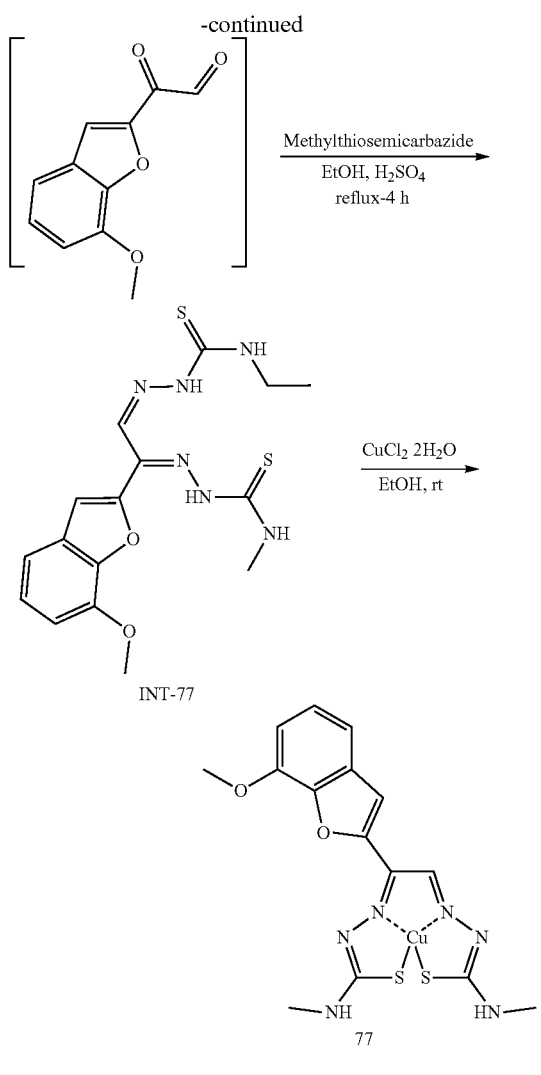

INT-77

Synthesis of INT 77 ((2Z,2'Z)-2,2'-(1-(7-methoxy-benzofuran-2-yl)ethane-1,2-diylidene)bis(N-methyl-hydrazine-1-carbothioamide))

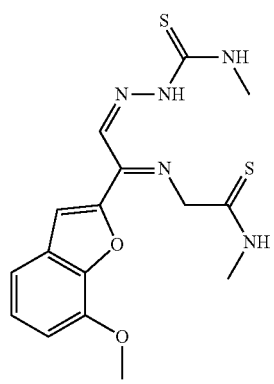 [SMILES: CNC(=S)C/N=C(/C=N\NC(=S)NC)c1cc2cccc(OC)c2o1]

A three-necked flask was charged with SeO$_2$ (1.84 g, 1.05 eq), 1,4-dioxane (36 mL), and water (8 mL). The mixture was heated to 50° C. and stirred until most of SeO$_2$ dissolves. 1-(7-methoxybenzofuran-2-yl)ethan-1-one (3 g, 15.8 mmol) was added, and the reaction was heated to gentle reflux overnight. Selenium solids precipitated during the course of the reaction. The mixture was cooled in an ice bath and filtered through diatomaceous earth to remove selenium. The filter cake was washed with portions of 1,4-dioxane. The filtrate was evaporated to dryness and dissolved in EtOH (100 ml). Methylthiosemicarbazide (3.32 g, 2 eq) and 3 drops of H$_2$SO$_4$ were added. The stirred reaction mixture was heated to reflux for 4 h. Formed precipitate was filtered, washed with EtOH, aq.sat. Na$_2$CO$_3$, water, Et$_2$O, and dried. Yield 2.15 g (36%). LC-MS 1.63 min, m/z 379.3 [MH]+.

Synthesis of Compound 77

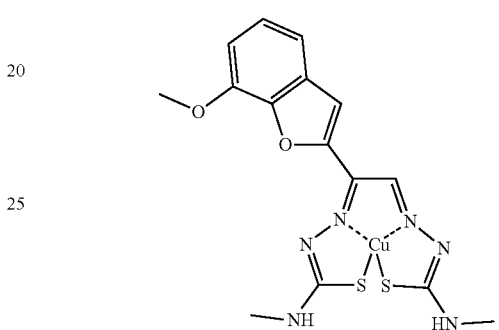

Copper(II) chloride dihydrate (0.15 g, 1 eq) was added to a stirred solution of INT-77 (0.34 g, 0.89 mmol) in ethanol. The mixture was stirred for 15 h at rt. The formed complex precipitated as a red-brown powder. The precipitate was collected by filtration, washed with water, diethyl ether, and dried. Yield 0.34 g (86.8%).

Scheme 39: Synthesis of Compound 78

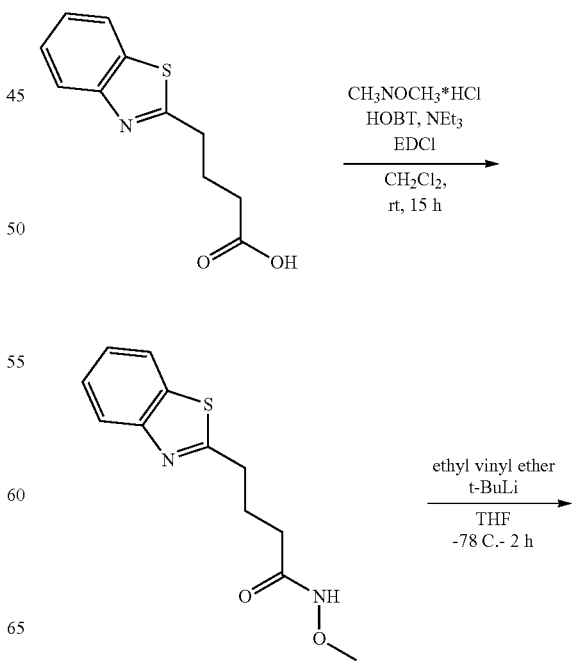

-continued

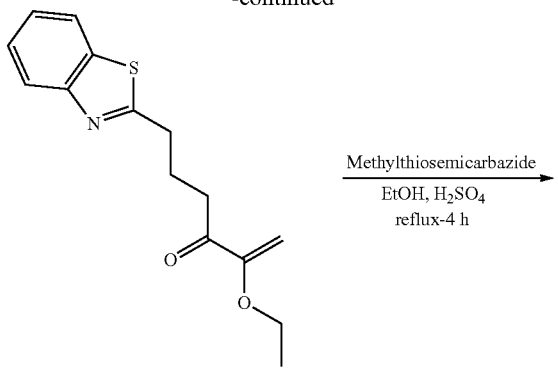

Methylthiosemicarbazide
EtOH, H₂SO₄
reflux-4 h

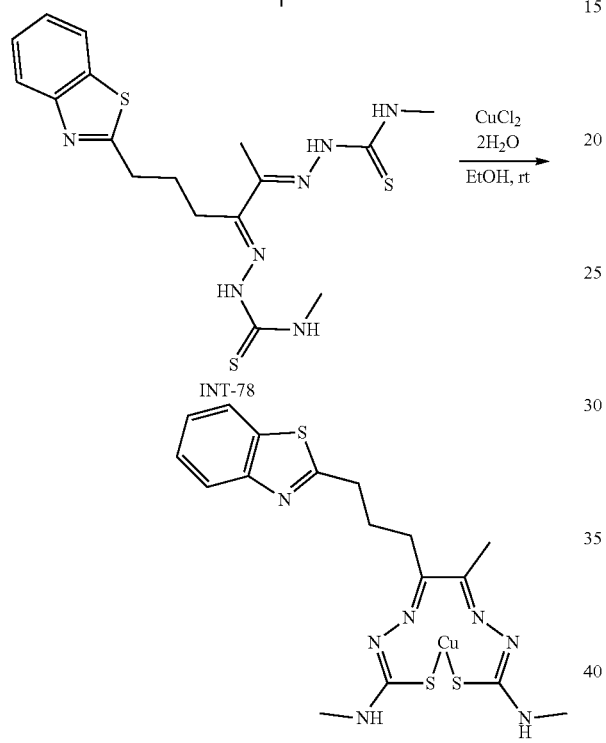

Synthesis of 4-(benzo[d]thiazol-2-yl)-N-methoxybutanamide

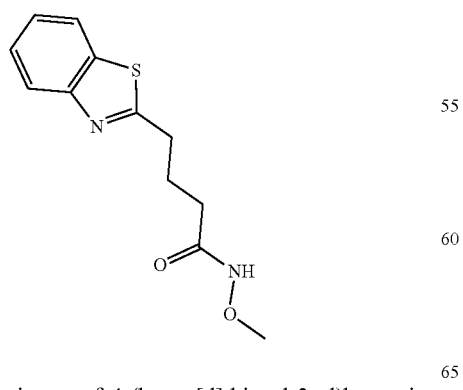

To a stirred mixture of 4-(benzo[d]thiazol-2-yl)butanoic acid (1.22 g, 5.5 mmol), N,O-dimethylhydroxylamine (0.65 g, 1.2 eq), HOBt (0.89 g, 1.2 eq), and triethylamine (2 ml, 1.44 g, 2.5 eq) in DCM (50 ml) at 5° C. was added EDCl (1.27 g, 1.2 eq) and reaction was stirred for 15 h at rt. The mixture was washed with water and brine. The organic layer was dried over anh. Na₂SO₄ and then concentrated under reduced pressure. The product was used further without additional purification. Yield 1.46 g (99.9%). LC-MS 1.3 min, m/z 265.1 [MH]+. ¹H-NMR (400 MHz, CDCl₃), δ (ppm): 7.92 (dd, J=46.1, 8.1 Hz, 2H), 7.41 (dt, J=15.2, 7.3 Hz, 2H), 3.66 (s, 3H), 3.33-3.11 (m, 5H), 2.60 (t, J=7.1 Hz, 2H), 2.25 (p, J=7.3 Hz, 2H).

Synthesis of 6-(benzo[d]thiazol-2-yl)-2-ethoxyhex-1-en-3-one

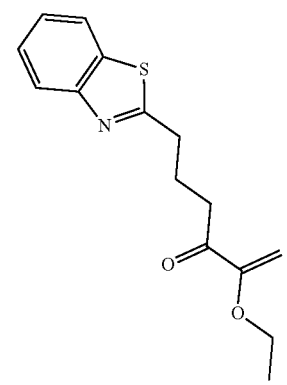 [SMILES: C=C(OCC)C(=O)CCCc1nc2ccccc2s1]

A solution of ethyl vinyl ether (1.2 g, 1.6 ml, 5.5 eq) in dry THF (40 ml) was cooled to −78° C., and tert-butyllithium (1.7M in pentane, 9.4 ml, 5 eq) was added. The mixture was warmed to 0° C. over 1 h period, stirred for 45 min, and then cooled down to −30° C. A solution of 4-(benzo[d]thiazol-2-yl)-N-methoxybutanamide (0.8 g, 3 mmol) in THF (5 ml) was added and stirring continued at 0° C. for 4 h. The mixture was poured into aq. NH₄Cl (15 ml) and extracted with Et₂O (3×25 ml). The combined extracts were dried over anh. Na₂SO₄, filtered, and solvents were evaporated in vacuo. The product was used for the next step without additional purification. Yield 0.83 g (99.6%). LC-MS 1.62 min, m/z 276.3 [MH]+.

Synthesis of INT-78 ((2E,2'E)-2,2'-(6-(benzo[d]thiazol-2-yl)hexane-2,3-diylidene)bis(N-methylhydrazine-1-carbothioamide))

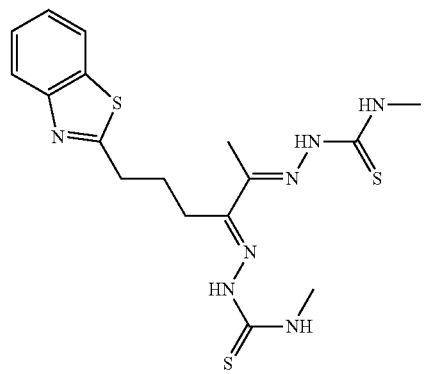 [SMILES: CNC(=S)N/N=C(C)/C(CCCc1nc2ccccc2s1)=N/NC(=S)NC]

6-(benzo[d]thiazol-2-yl)-2-ethoxyhex-1-en-3-one (086 g, 3.1 mmol) was dissolved in EtOH (30 ml), methylthiosemicarbazide (0.66 g, 2 eq) and 1 drop of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.79 g (60.1%). LC-MS 1.57 min, m/z 422.3 [MH]+. $^1$H-NMR (400 MHz, DMSO-d6), δ (ppm): 10.61 (s, 1H), 10.24 (s, 1H), 8.40 (d, J=4.4 Hz, 1H), 8.23 (d, J=4.5 Hz, 1H), 8.07 (dd, J=25.5, 8.0 Hz, 2H), 7.44 (dt, J=33.7, 7.7 Hz, 2H), 3.21 (t, J=7.2 Hz, 2H), 3.14-2.92 (m, 8H), 2.21 (s, 3H), 1.89 (d, J=7.3 Hz, 2H).

Synthesis of Compound 78

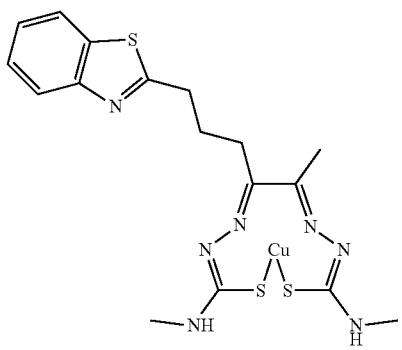

Copper(II) chloride dihydrate (0.32 g, 1 eq) was added to a stirred solution of INT-78 (0.79 g, 1.3 mmol) in ethanol. The mixture was stirred for 15 h at rt. The formed complex precipitated as a red-brown powder. The precipitate was collected by filtration, washed with water, diethyl ether, and dried. Yield 0.66 g (73.2%).

Example 6: Preparation of Compounds 79-127

Scheme 40: Synthesis of Compound 79

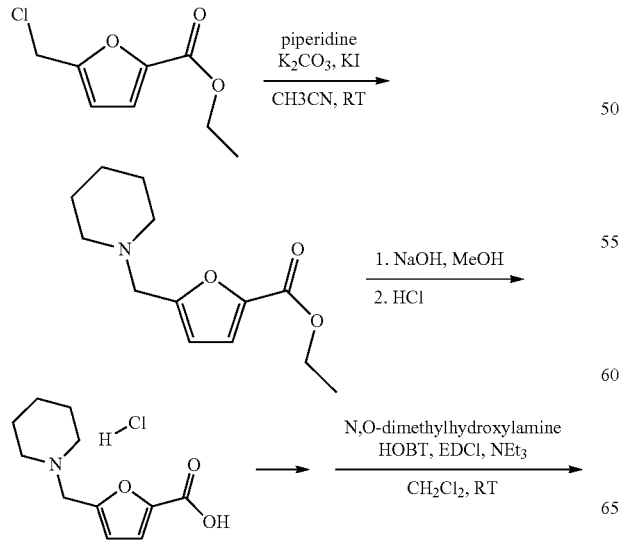

Synthesis of ethyl 5-(piperidin-1-ylmethyl)furan-2-carboxylate

To a solution of ethyl 5-(chloromethyl)furan-2-carboxylate (5 g, 27 mmol) in $CH_3CN$ (150 ml) were added piperidine (2.56 g, 1 eq), potassium carbonate (7.33 g, 2 eq), and potassium iodide (1.3 g, 0.3 eq). The reaction mixture was stirred overnight at rt. Solids were filtered and filtrate was concentrated in vacuo. The residue was dissolved in DCM and washed with water (3×50 ml). Organic layer was separated, dried over anh. Na$_2$SO$_4$, filtered, and solvents were evaporated in vacuo. Yield 3.6 g (57%). LC-MS 0.87 min, m/z 238.3 [MH]+. $^1$H-NMR (400 MHz, DMSO-d6), δ (ppm): 7.22 (d, J=3.4 Hz, 1H), 6.48 (d, J=3.4 Hz, 1H), 4.26 (q, J=7.1 Hz, 2H), 3.50 (s, 2H), 2.34 (s, 4H), 1.56-1.42 (m, 4H), 1.40-1.22 (m, 5H).

Synthesis of
5-(piperidin-1-ylmethyl)furan-2-carboxylic Acid

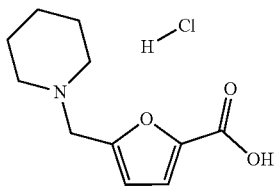

To a solution of ethyl 5-(piperidin-1-ylmethyl)furan-2-carboxylate (3.6 g, 15 mmol) in methanol (80 ml), a solution of NaOH (1.52 g, 2.5 eq) in water (10 ml) was added, and the reaction mixture was stirred for 15 h at rt. Methanol was removed in vacuo, the residue was diluted with water and acidified to pH 1. The acidified solution was evaporated to dryness and treated with acetonitrile. Solids were filtered, and filtrate was evaporated in vacuo to dryness. Yield 2.94 g (79%). LC-MS 0.61 min, m/z 210.4 [MH]+. $^1$H NMR (400 MHz, DMSO-d6), δ (ppm): 13.31 (br.s, 1H), δ 10.96 (br.s, 1H), 7.26 (s, 1H), δ 6.92 (s, 1H), 4.40 (s, 1H), 3.14-3.41 (br.s, 2H), 2.76-3.10 (br.s, 2H), 1.34-1.91 (m, 6H).

Synthesis of N-methoxy-N-methyl-5-(piperidin-1-ylmethyl)furan-2-carboxamide

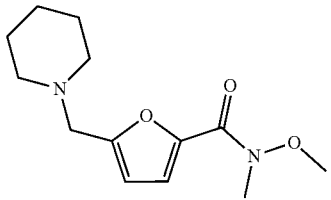 [SMILES: CON(C)C(=O)c1ccc(CN2CCCCC2)o1]

To a stirred mixture of 5-(piperidin-1-ylmethyl)furan-2-carboxylic acid (2.94 g, 12 mmol), N,O-dimethylhydroxylamine (1.4 g, 1.2 eq), HOBt (2.2 g, 1.2 eq), and triethylamine (6.7 ml, 4.84 g, 4 eq) in DCM (100 ml) at 5° C. was added EDCl (2.75 g, 1.2 eq) and reaction was stirred for 15 h at rt. The mixture was washed with water and brine. The organic layer was dried over anh. Na$_2$SO$_4$ and then concentrated under reduced pressure. Product was used without further purification. Yield 2.2 g (73%). LC-MS 0.76 min, m/z 253.4 [MH]+. $^1$H-NMR (400 MHz, CDCl$_3$), δ (ppm): 7.09 (d, J=3.4 Hz, 1H), 6.36 (d, J=3.4 Hz, 1H), 3.77 (s, 3H), 3.66 (s, 2H), 3.34 (s, 3H), 2.42 (d, J=68.1 Hz, 4H), 1.61 (dt, J=11.1, 5.6 Hz, 4H), 1.42 (d, J=5.4 Hz, 2H).

Synthesis of 1-(5-(piperidin-1-ylmethyl)furan-2-yl)ethan-1-one

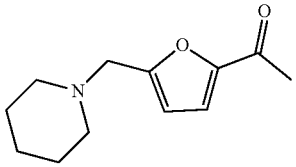

A solution of N-methoxy-N-methyl-5-(piperidin-1-ylmethyl)furan-2-carboxamide (2.2 g, 8.7 mmol) in THF (100 ml) was cooled to 5° C. and methylmagnesium bromide (1.4M in THF, 19 ml, 3 eq) was added. The reaction mixture was stirred at 5° C. for 2 h, poured into aq NH$_4$Cl and extracted with Et$_2$O. The combined extracts were dried over anh. Na$_2$SO$_4$, filtered, and solvents were evaporated in vacuo. Compound 5 was used for the next step without purification. Yield 1.7 g (94.6%). LC-MS 0.74 min, m/z 208.1 [MH]+. $^1$H-NMR (400 MHz, CDCl$_3$), δ (ppm): 7.14 (d, J=3.5 Hz, 1H), δ 6.37 (d, J=3.4 Hz, 1H), δ 3.61 (s, 2H), δ 2.47 (s, 7H), δ 1.60 (dt, J=11.0, 5.6 Hz, 4H), δ 1.48-1.39 (m, 2H).

Synthesis of INT-79 ((2E,2'E)-2,2'-(1-(5-(piperidin-1-ylmethyl)furan-2-yl)ethane-1,2-diylidene)bis(N-methylhydrazine-1-carbothioamide))

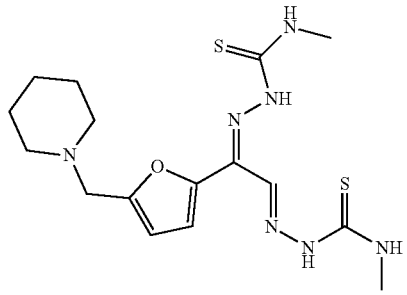 [SMILES: CNC(=S)N/N=C/C(=N\NC(=S)NC)c1ccc(CN2CCCCC2)o1]

A mixture of 1-(5-(piperidin-1-ylmethyl)furan-2-yl)ethan-1-one (1.15 g, 5.5 mmol), NaBr (0.57 g, 1 eq), and DMSO (3 ml) was heated to 85° C., then H$_2$SO$_4$ (6 drops) was added (foaming, exothermic). The reaction was heated to 110-115° C. until the formation of dimethyl sulfide has stopped, and the reaction mixture became viscous. The formed viscous substance was dissolved in EtOH, solids were filtered and methylthiosemicarbazide (1.16 g, 2 eq) was added to the filtrate. The reaction mixture was heated to reflux for 2 h, then cooled to rt, solvents were evaporated in vacuo, the residue was dissolved in water (25 ml), neutralized with aq.sat. K$_2$CO$_3$ and extracted with EtOAc (3×50 ml). The organic layer was separated, dried over anh. Na$_2$SO$_4$, filtered, and solvents were evaporated in vacuo. The residue was treated with water. The formed precipitate was filtered and washed with EtOH to give pure titular product. Yield 1.16 g (52.8%). LC-MS 1.08 min, m/z 396.1 [MH]+. $^1$H-NMR (400 MHz, DMSO-d6), δ (ppm): 11.67 (s, 1H), 8.75 (s, 1H), 7.19 (s, 1H), 6.93 (d, J=3.1 Hz, 1H), 6.44 (d, J=2.9 Hz, 1H), 6.13 (s, 1H), 5.37 (s, 1H), 3.45 (d, J=22.7 Hz, 2H), 3.33 (m, 3H), 2.76 (d, J=4.2 Hz, 3H), 2.35 (s, 4H), 1.41-1.55 (m, 6H).

Synthesis of Compound 79

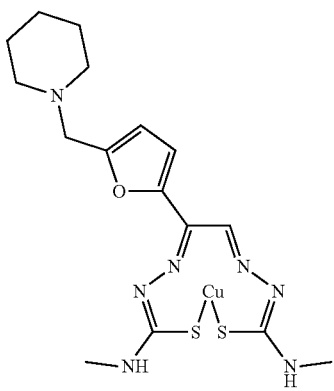

Copper(II) chloride dihydrate (0.08 g, 1 eq) was added to a stirred solution of INT-79 (0.186 g, 0.47 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.1 g (46.5%).

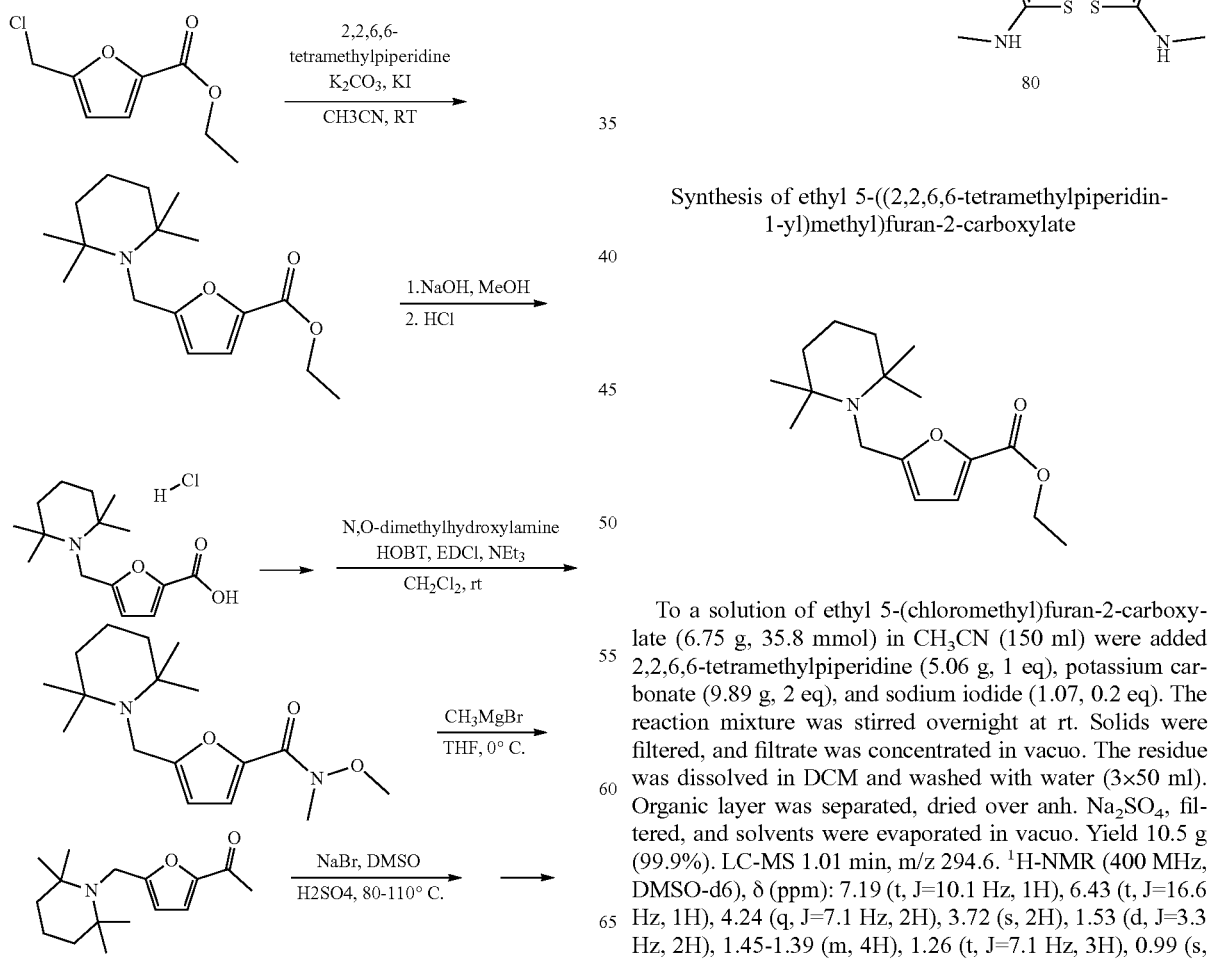

Synthesis of ethyl 5-((2,2,6,6-tetramethylpiperidin-1-yl)methyl)furan-2-carboxylate To a solution of ethyl 5-(chloromethyl)furan-2-carboxylate (6.75 g, 35.8 mmol) in $CH_3CN$ (150 ml) were added 2,2,6,6-tetramethylpiperidine (5.06 g, 1 eq), potassium carbonate (9.89 g, 2 eq), and sodium iodide (1.07, 0.2 eq). The reaction mixture was stirred overnight at rt. Solids were filtered, and filtrate was concentrated in vacuo. The residue was dissolved in DCM and washed with water (3×50 ml). Organic layer was separated, dried over anh. $Na_2SO_4$, filtered, and solvents were evaporated in vacuo. Yield 10.5 g (99.9%). LC-MS 1.01 min, m/z 294.6. $^1$H-NMR (400 MHz, DMSO-d6), δ (ppm): 7.19 (t, J=10.1 Hz, 1H), 6.43 (t, J=16.6 Hz, 1H), 4.24 (q, J=7.1 Hz, 2H), 3.72 (s, 2H), 1.53 (d, J=3.3 Hz, 2H), 1.45-1.39 (m, 4H), 1.26 (t, J=7.1 Hz, 3H), 0.99 (s, 12H).

Synthesis of 5-((2,2,6,6-tetramethylpiperidin-1-yl)methyl)furan-2-carboxylic Acid

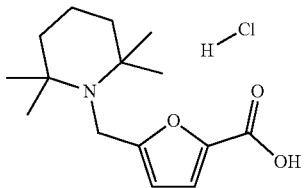

To a solution of ethyl 5-((2,2,6,6-tetramethylpiperidin-1-yl)methyl)furan-2-carboxylate (10.5 g, 354.8 mmol) in methanol (200 ml) was added a solution of NaOH (3.58 g, 2.5 eq) in water (20 ml) and the reaction mixture was stirred overnight at rt. Methanol was removed in vacuo, the residue was diluted with water and acidified with conc. HCl to pH 1. The acidified solution was evaporated to dryness and treated with acetonitrile. Solids were filtered and filtrate was evaporated in vacuo to dryness. Yield 10.8 g (99.8%). LC-MS 0.88 min, m/z 266.5 [MH]+.

Synthesis of N-methoxy-N-methyl-5-((2,2,6,6-tetramethylpiperidin-1-yl)methyl)furan-2-carboxamide

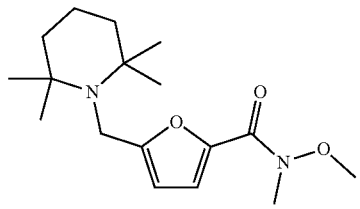

To a stirred mixture of 5-((2,2,6,6-tetramethylpiperidin-1-yl)methyl)furan-2-carboxylic acid (10.8 g, 35.8 mmol), N,O-dimethylhydroxylamine (4.18 g, 1.2 eq), HOBt (5.8 g, 1.2 eq), and triethylamine (18 ml, 12.94 g, 3.5 eq) in DCM (200 ml) at 5° C. was added EDCl (8.38 g, 1.2 eq) and reaction was stirred for 15 h at rt. The mixture was washed with water and brine. The organic layer was dried over anh. Na$_2$SO$_4$ and then concentrated under reduced pressure. Product was purified by column chromatography (SiO$_2$, eluent CCl$_4$/EtOAc from 8:2 to 7:3, then CHCl$_3$/MeOH from 99:1 to 98:2). Yield 7.42 g (75.9%). LC-MS 0.74 min, m/z 269.5 [MH]+. $^1$H-NMR (400 MHz, CDCl$_3$), δ (ppm): 7.08 (d, J=3.4 Hz, 1H), 6.33 (s, 1H), 3.76 (s, 3H), 3.71 (m, 6H), 3.33 (s, 3H), 3.16-2.98 (m, 2H), 1.02 (d, J=6.5 Hz, 12H).

Synthesis of 1-(5-((2,2,6,6-tetramethylpiperidin-1-yl)methyl)furan-2-yl)ethan-1-one

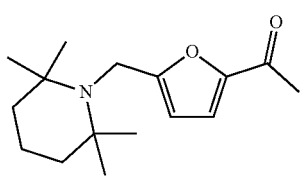 [SMILES: CC(=O)c1ccc(CN2C(C)(C)CCCC2(C)C)o1]

A solution of N-methoxy-N-methyl-5-((2,2,6,6-tetramethylpiperidin-1-yl)methyl)furan-2-carboxamide (6 g, 19.4 mmol) in THF (120 ml) was cooled to 5° C. and methylmagnesium bromide (3.4M in THF/toluene, 17 ml, 3 eq) was added. The reaction mixture was stirred at 5° C. for 2 h, poured into aq NH$_4$Cl and extracted with Et$_2$O. The combined extracts were dried over anh. Na$_2$SO$_4$, filtered, and solvents were evaporated in vacuo. Compound 5 was used for the next step without purification. Yield 4.2 g (82%). LCMS 0.67 min, m/z 264.6 [MH]+. $^1$H-NMR (400 MHz, CDCl$_3$), δ (ppm): 7.12 (d, J=3.3 Hz, 1H), 6.52-6.35 (m, 1H), 3.77 (s, 2H), 2.43 (d, J=0.9 Hz, 3H), 1.63-1.55 (m, 2H), 1.48 (dd, J=15.2, 10.0 Hz, 4H), 1.03 (t, J=2.1 Hz, 12H).

Synthesis of INT-80 ((2E,2'E)-2,2'-(1-(5-((2,2,6,6-tetramethylpiperidin-1-yl)methyl)furan-2-yl)ethane-1,2-diylidene)bis(N-methylhydrazine-1-carbothioamide))

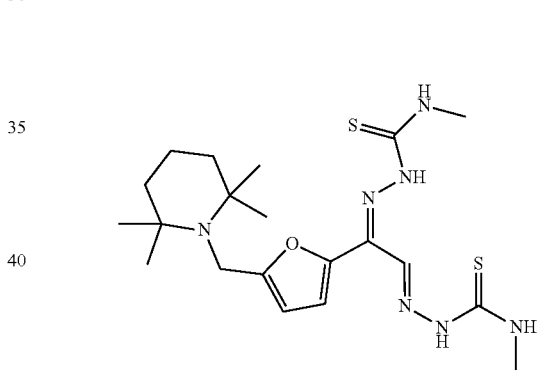

A mixture of 1-(5-((2,2,6,6-tetramethylpiperidin-1-yl)methyl)furan-2-yl)ethan-1-one (0.93 g, 3.5 mmol), NaBr (0.36 g, 1 eq), and DMSO (1.8 ml) was heated to 85° C., then H$_2$SO$_4$ (6 drops) was added (foaming, exothermic). The reaction was heated to 110-115° C. until the formation of dimethyl sulfide has stopped, and the reaction mixture became viscous. The formed viscous substance was dissolved in EtOH, solids were filtered and methylthiosemicarbazide (1.16 g, 2 eq) was added to the filtrate. The reaction mixture was heated to reflux for 2 h, then cooled to rt, solvents were evaporated in vacuo, the residue was dissolved in water (25 ml), neutralized with aq.sat. K$_2$CO$_3$ and extracted with EtOAc (3×60 ml). The organic layer was separated, dried over anh. Na$_2$SO$_4$, filtered, and solvents were evaporated in vacuo. The residue was treated with water. The formed precipitate was filtered and washed with EtOH to give pure titular product. Yield 1.05 g (65.8%). LC-MS 1.17 min, m/z 452.3 [MH]+.

Synthesis of Compound 80

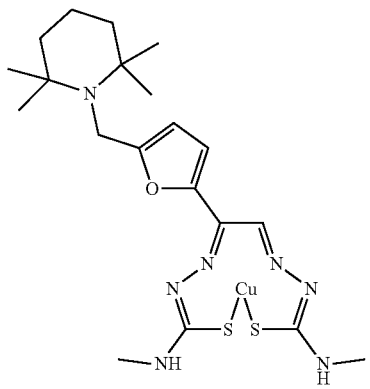

Copper(II) chloride dihydrate (0.036 g, 1 eq) was added to a stirred solution of INT-80 (0.099 g, 4.7 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.08 g (71.2%).

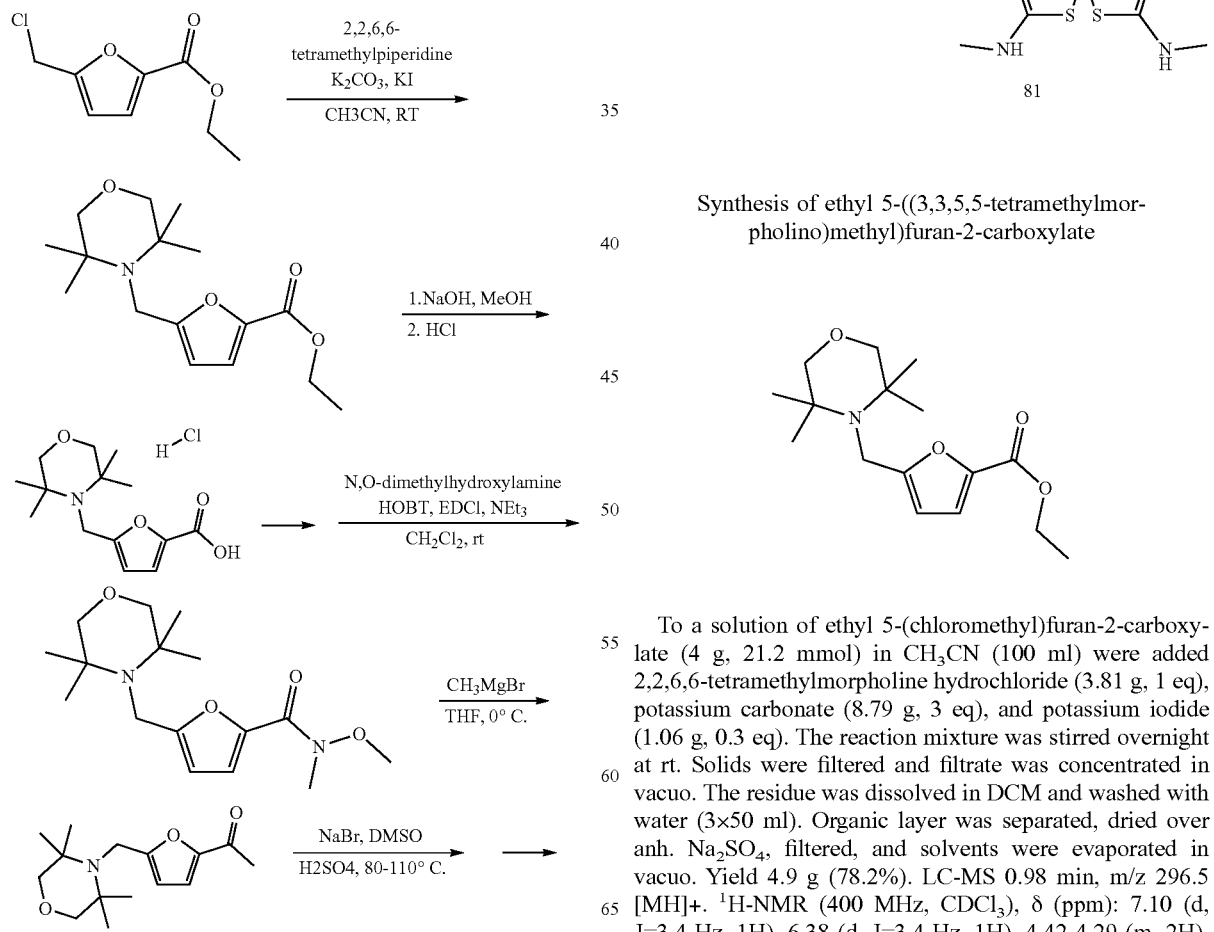

Synthesis of ethyl 5-((3,3,5,5-tetramethylmorpholino)methyl)furan-2-carboxylate To a solution of ethyl 5-(chloromethyl)furan-2-carboxylate (4 g, 21.2 mmol) in $CH_3CN$ (100 ml) were added 2,2,6,6-tetramethylmorpholine hydrochloride (3.81 g, 1 eq), potassium carbonate (8.79 g, 3 eq), and potassium iodide (1.06 g, 0.3 eq). The reaction mixture was stirred overnight at rt. Solids were filtered and filtrate was concentrated in vacuo. The residue was dissolved in DCM and washed with water (3×50 ml). Organic layer was separated, dried over anh. $Na_2SO_4$, filtered, and solvents were evaporated in vacuo. Yield 4.9 g (78.2%). LC-MS 0.98 min, m/z 296.5 [MH]+. $^1$H-NMR (400 MHz, $CDCl_3$), δ (ppm): 7.10 (d, J=3.4 Hz, 1H), 6.38 (d, J=3.4 Hz, 1H), 4.42-4.29 (m, 2H), 3.77 (s, 2H), 3.43 (s, 4H), 1.44-1.35 (m, 3H), 1.03 (s, 12H).

Synthesis of 5-((3,3,5,5-tetramethylmorpholino)methyl)furan-2-carboxylic Acid

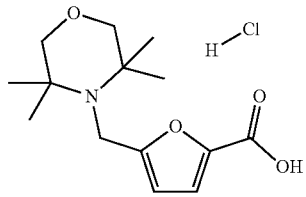

To a solution of ethyl 5-((3,3,5,5-tetramethylmorpholino)methyl)furan-2-carboxylate (4.9 g, 16.6 mmol) in methanol (100 ml) was added a solution of NaOH (1.66 g, 2.5 eq) in water (10 ml) and the reaction mixture was stirred overnight at rt. Methanol was removed in vacuo, the residue was diluted with water and acidified with conc. HCl to pH 1. The acidified solution was evaporated to dryness and treated with acetonitrile. Solids were filtered and filtrate was evaporated in vacuo to dryness. Yield 3.91 g (77.6%). LC-MS 0.74 min, m/z 268.6 [MH]+.

Synthesis of N-methoxy-N-methyl-5-((3,3,5,5-tetramethylmorpholino)methyl)furan-2-carboxamide

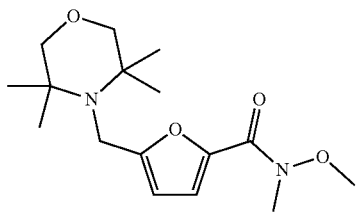

To a stirred mixture of 5-((3,3,5,5-tetramethylmorpholino)methyl)furan-2-carboxylic acid (3.91 g, 12.9 mmol), N,O-dimethylhydroxylamine (1.51 g, 1.2 eq), HOBt (2.36 g, 1.2 eq), and triethylamine (7.2 ml, 5.2 g, 4 eq) in DCM (100 ml) at 5° C. was added EDCl (2.96 g, 1.2 eq) and reaction was stirred for 15 h at rt. The mixture was washed with water and brine. The organic layer was dried over anh. Na$_2$SO$_4$ and then concentrated under reduced pressure. Product was purified by column chromatography (SiO$_2$, eluent CCl$_4$/EtOAc from 8:2 to 2:1). Yield 2.3 g (57.6%). LC-MS 0.78 min, m/z 311.5 [MH]+. $^1$H-NMR (400 MHz, DMSO-d6), δ (ppm): 7.08 (d, J=3.1 Hz, 1H), 6.41 (s, 1H), 3.73 (s, 5H), 3.31 (d, J=2.6 Hz, 6H), 3.21 (s, 3H), 0.98 (s, 12H).

Synthesis of 1-(5-((3,3,5,5-tetramethylmorpholino)methyl)furan-2-yl)ethan-1-one

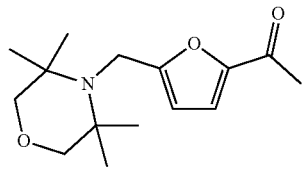 [SMILES: CC(=O)c1ccc(CN2C(C)(C)COCC2(C)C)o1]

A solution of N-methoxy-N-methyl-5-((3,3,5,5-tetramethylmorpholino)methyl)furan-2-carboxamide (1.3 g, 4.2 mmol) in THF (50 ml) was cooled to 5° C. and methylmagnesium bromide (1.4M in THF, 9 ml, 3 eq) was added. The reaction mixture was stirred at 5° C. for 2 h, poured into aq NH$_4$Cl and extracted with Et$_2$O. The combined extracts were dried over anh. Na$_2$SO$_4$, filtered, and solvents were evaporated in vacuo. Compound 5 was used for the next step without purification. Yield 1.0 g (90%). LC-MS 0.80 min, m/z 266.3 [MH]+. $^1$H-NMR (400 MHz, DMSO-d6), δ (ppm): 7.35 (d, J=3.2 Hz, 1H), 6.48 (s, 1H), 3.74 (s, 2H), 3.31 (s, 6H), 2.35 (s, 3H), 0.97 (s, 12H).

Synthesis of INT-81 ((2E,2'E)-2,2'-(1-(5-((3,3,5,5-tetramethylmorpholino)methyl)furan-2-yl)ethane-1,2-diylidene)bis(N-methylhydrazine-1-carbothioamide))

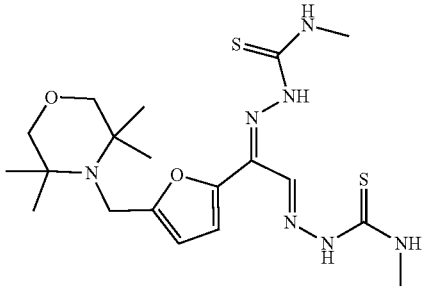

A mixture of 1-(5-((3,3,5,5-tetramethylmorpholino)methyl)furan-2-yl)ethan-1-one (0.48 g, 1.8 mmol), NaBr (0.19 g, 1 eq), and DMSO (1 ml) was heated to 85° C., then H$_2$SO$_4$ (3 drops) was added (foaming, exothermic). The reaction was heated to 110-115° C. until the formation of dimethyl sulfide has stopped, and the reaction mixture became viscous. The formed viscous substance was dissolved in EtOH, solids were filtered and methylthiosemicarbazide (1.16 g, 2 eq) was added to the filtrate. The reaction mixture was heated to reflux for 2 h, then cooled to rt, solvents were evaporated in vacuo, the residue was dissolved in water (25 ml), neutralized with aq.sat. K$_2$CO$_3$ and extracted with EtOAc (3×60 ml). The organic layer was separated, dried over anh. Na$_2$SO$_4$, filtered, and solvents were evaporated in vacuo. The residue was treated with water. The formed precipitate was filtered and washed with EtOH to give pure titular product. Yield 0.28 g (34%). LC-MS 1.05 min, m/z 454.4 [MH]+.

Synthesis of Compound 81

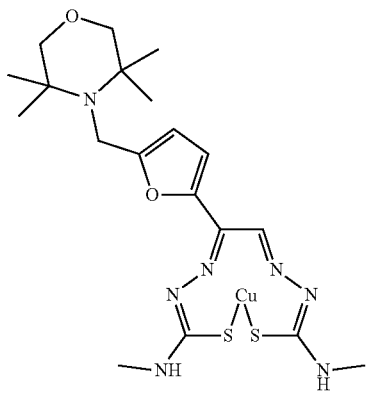

Copper(II) chloride dihydrate (0.053, 1 eq) was added to a stirred solution of INT-81 (0.14 g, 0.3 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.15 g (94.2%).

Scheme 43: Synthesis of Compound 82

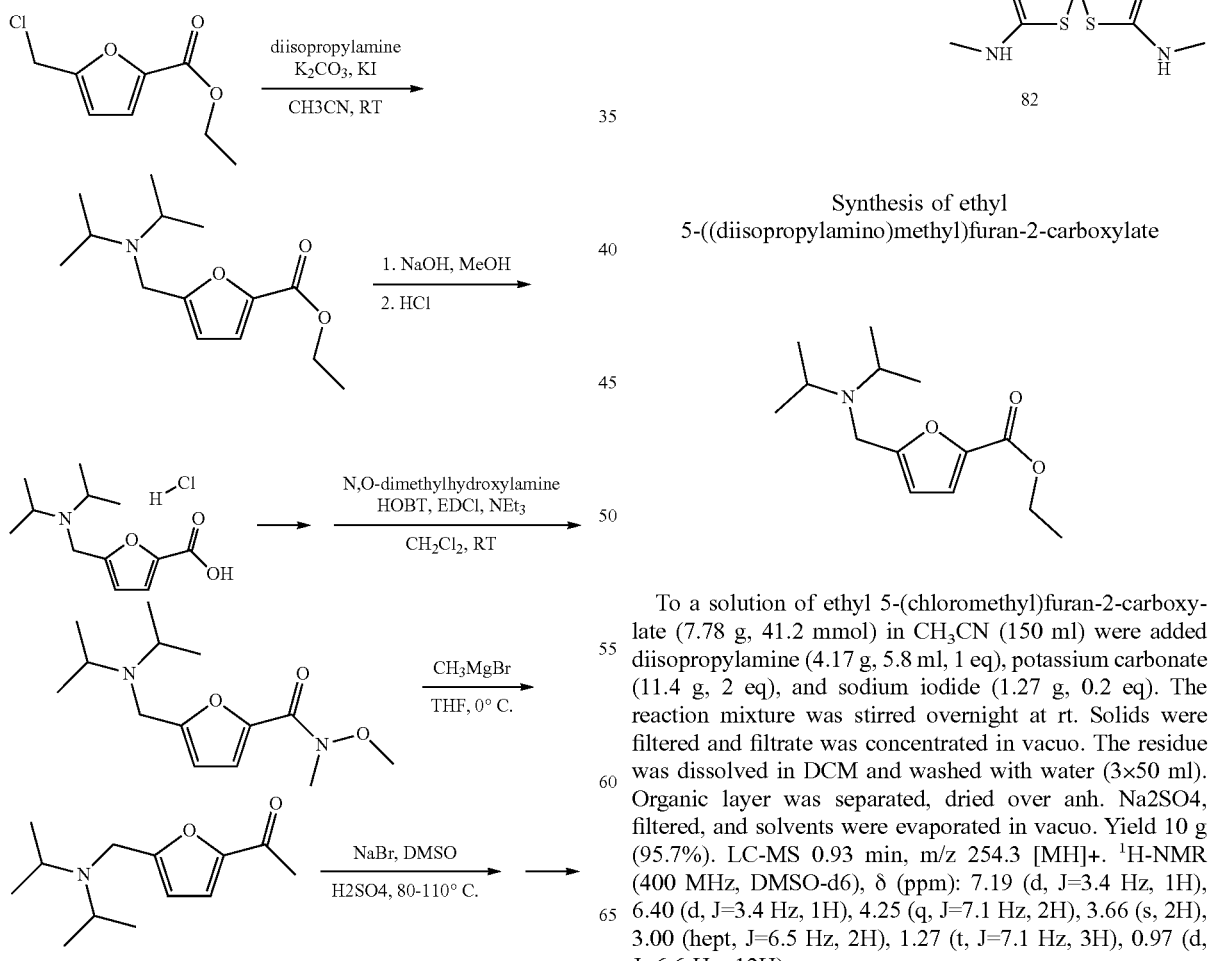

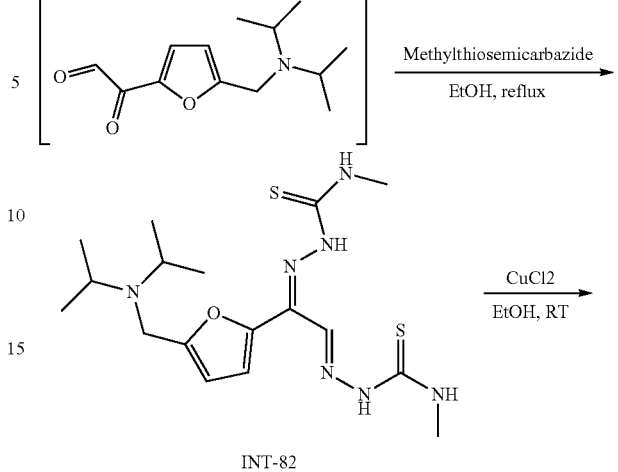

INT-82

82

Synthesis of ethyl 5-((diisopropylamino)methyl)furan-2-carboxylate

To a solution of ethyl 5-(chloromethyl)furan-2-carboxylate (7.78 g, 41.2 mmol) in CH$_3$CN (150 ml) were added diisopropylamine (4.17 g, 5.8 ml, 1 eq), potassium carbonate (11.4 g, 2 eq), and sodium iodide (1.27 g, 0.2 eq). The reaction mixture was stirred overnight at rt. Solids were filtered and filtrate was concentrated in vacuo. The residue was dissolved in DCM and washed with water (3×50 ml). Organic layer was separated, dried over anh. Na2SO4, filtered, and solvents were evaporated in vacuo. Yield 10 g (95.7%). LC-MS 0.93 min, m/z 254.3 [MH]+. $^1$H-NMR (400 MHz, DMSO-d6), δ (ppm): 7.19 (d, J=3.4 Hz, 1H), 6.40 (d, J=3.4 Hz, 1H), 4.25 (q, J=7.1 Hz, 2H), 3.66 (s, 2H), 3.00 (hept, J=6.5 Hz, 2H), 1.27 (t, J=7.1 Hz, 3H), 0.97 (d, J=6.6 Hz, 12H).

Synthesis of 5-((diisopropylamino)methyl)furan-2-carboxylic Acid

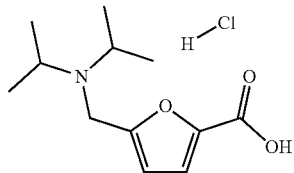

To a solution of ethyl 5-((diisopropylamino)methyl)furan-2-carboxylate (10 g, 39.5 mmol) in methanol (65 ml) was added a solution of NaOH (1.66 g, 2.5 eq) in water (20 ml) and the reaction mixture was stirred overnight at rt. Methanol was removed in vacuo, the residue was diluted with water and acidified with conc. HCl to pH 1. The acidified solution was evaporated to dryness and treated with acetonitrile. Solids were filtered, and filtrate was evaporated in vacuo to dryness. Yield 9.53 g (92.2%). LC-MS 0.6 min, m/z 226.5 [MH]+.

Synthesis of 5-((diisopropylamino)methyl)-N-methoxy-N-methylfuran-2-carboxamide

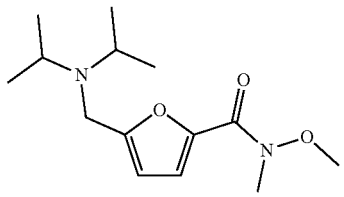 [SMILES: CON(C)C(=O)c1ccc(CN(C(C)C)C(C)C)o1]

To a stirred mixture of 5-((diisopropylamino)methyl)furan-2-carboxylic acid (9.53 g, 36.4 mmol), N,O-dimethylhydroxylamine (4.26 g, 1.2 eq), HOBt (5.9 g, 1.2 eq) and triethylamine (18 ml, 12.94 g, 3.5 eq) in DCM (100 ml) at 5° C. was added EDCl (2.96 g, 1.2 eq) and reaction was stirred for 15 h at rt. The mixture was washed with water and brine. The organic layer was dried over anh. Na$_2$SO$_4$ and then concentrated under reduced pressure. Product was purified by column chromatography (SiO$_2$, eluent CCl$_4$/EtOAc from 8:2 to 2:1). Yield 2.3 g (57.6%). LC-MS 0.78 min, m/z 311.5 [MH]+. $^1$H-NMR (400 MHz, CDCl$_3$), δ (ppm): 7.08 (d, J=3.4 Hz, 1H), 6.33 (s, 1H), 3.76 (s, 3H), 3.71 (s, 2H), 3.33 (s, 3H), 3.18-2.94 (m, 2H), 1.02 (d, J=6.5 Hz, 12H).

Synthesis of 1-(5-((diisopropylamino)methyl)furan-2-yl)ethan-1-one

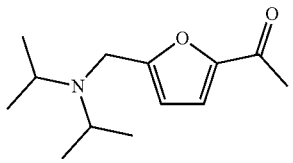 [SMILES: CC(=O)c1ccc(CN(C(C)C)C(C)C)o1]

A solution of 5-((diisopropylamino)methyl)-N-methoxy-N-methylfuran-2-carboxamide (2.68 g, 10 mmol) in THF (75 ml) was cooled to 5° C. and methylmagnesium bromide (1.4 M in THF, 22 ml, 3 eq) was added. The reaction mixture was stirred at 5° C. for 2 h, poured into aq NH$_4$Cl and extracted with Et$_2$O. The combined extracts were dried over anh. Na$_2$SO$_4$, filtered, and solvents were evaporated in vacuo. Compound 5 was used for the next step without purification. Yield 2.0 g (89.7%). LC-MS 0.87 min, m/z 224.4 [MH]+. $^1$H-NMR (400 MHz, DMSO-d$_6$), δ (ppm): 7.13 (d, J=3.5 Hz, 1H), 6.38 (s, 1H), 3.70 (s, 2H), 3.08 (dt, J=12.7, 6.2 Hz, 2H), 2.44 (s, 3H), 1.04 (d, J=6.5 Hz, 12H).

Synthesis of INT 82 ((2E,2'E)-2,2'-(1-(5-((diisopropylamino)methyl)furan-2-yl)ethane-1,2-diylidene)bis(N-methylhydrazine-1-carbothioamide))

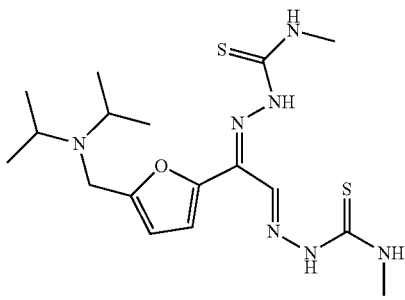 [SMILES: CNC(=S)N/N=C/C(=N\NC(=S)NC)c1ccc(CN(C(C)C)C(C)C)o1]

A mixture of 1-(5-((diisopropylamino)methyl)furan-2-yl)ethan-1-one (1.0 g, 4.5 mmol), NaBr (0.46 g, 1 eq), and DMSO (2.5 ml) was heated to 85° C., then H$_2$SO$_4$ (3 drops) was added (foaming, exothermic). The reaction was heated to 110-115° C. until the formation of dimethyl sulfide has stopped, and the reaction mixture became viscous. The formed viscous substance was dissolved in EtOH, solids were filtered and methylthiosemicarbazide (0.94 g, 2 eq) was added to the filtrate. The reaction mixture was heated to reflux for 2 h, then cooled to rt, solvents were evaporated in vacuo, the residue was dissolved in water (25 ml), neutralized with aq.sat. K$_2$CO$_3$ and extracted with EtOAc (3×60 ml). The organic layer was separated, dried over anh. Na$_2$SO$_4$, filtered, and solvents were evaporated in vacuo. The residue was treated with water. The formed precipitate was filtered and washed with EtOH to give pure titular compound. Yield 0.4 g (21.7%). LC-MS 1.12 min, m/z 412.3 [MH]+.

Synthesis of Compound 82

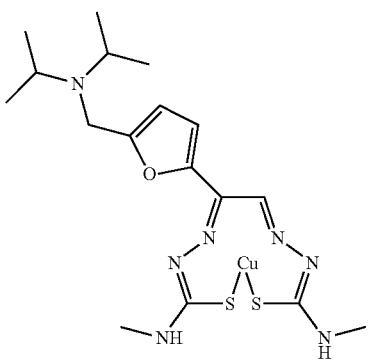

Copper(II) chloride dihydrate (0.041, 1 eq) was added to a stirred solution of INT-82 (0.1 g, 0.24 mmol) in ethanol. The mixture was stirred for 15 h at ambient temperature. The formed complex precipitated as a red-brown powder. The precipitate was collected by filtration, washed with water, methanol, diethyl ether, and dried in vacuo. Yield 0.066 g (57.3%).

Scheme 44: Synthesis of Compound 83

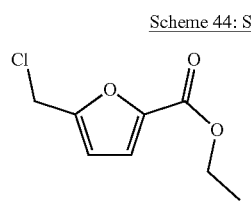

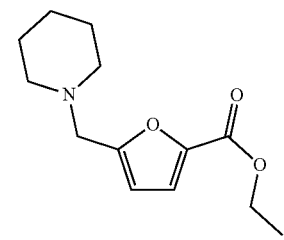

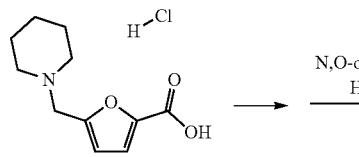

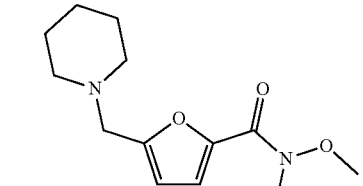

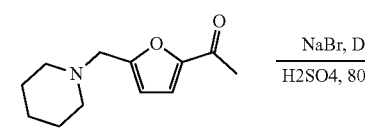

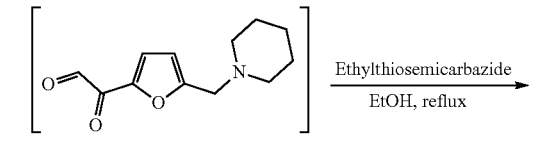

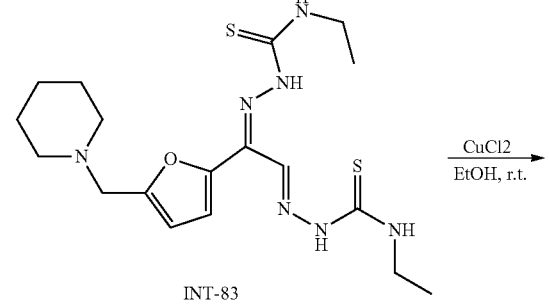

INT-83

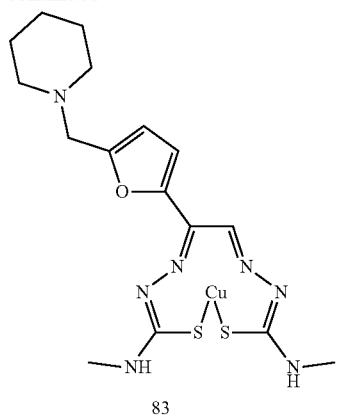

83

Synthesis of INT-83 ((2E,2'E)-2,2'-(1-(5-(piperidin-1-ylmethyl)furan-2-yl)ethane-1,2-diylidene)bis(N-ethylhydrazine-1-carbothioamide))

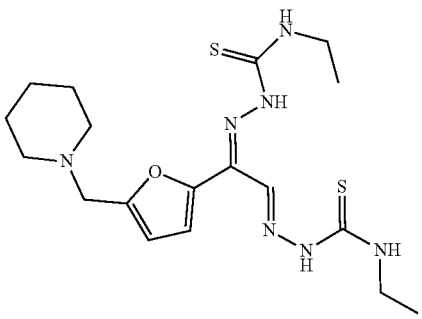 [SMILES: CCNC(=S)N/N=C/C(=N\NC(=S)NCC)c1ccc(CN2CCCCC2)o1]

A mixture of 1-(5-(piperidin-1-ylmethyl)furan-2-yl)ethan-1-one (1.2 g, 5.8 mmol), NaBr (0.6 g, 1 eq), and DMSO (3 ml) was heated to 85° C., then $H_2SO_4$ (3 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (1.16 g, 2 eq) was added to the filtrate. The reaction mixture was heated to reflux for 2 h, then cooled to rt, solvents were evaporated in vacuo, the residue was dissolved in water (25 ml), neutralized with aq.sat. $K_2CO_3$ and extracted with EtOAc (3×50 ml). The organic layer was separated, dried over anh. $Na_2SO_4$, filtered, and solvents were evaporated in vacuo. The residue was treated with water. The formed precipitate was filtered and washed with EtOH to give pure titular product. Yield 0.85 g (34.7%). LC-MS 1.2 min, m/z 424.5 [MH]+.

351
Synthesis of Compound 83

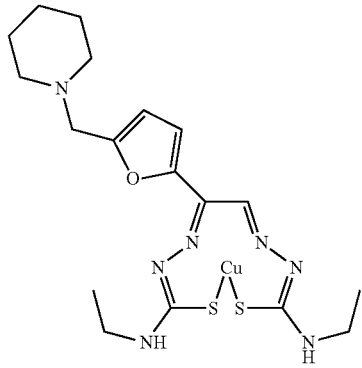

Copper(II) chloride dihydrate (0.043 g, 1 eq) was added to a stirred solution of INT-83 (0.107 g, 0.25 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.082 g (66.8%).

Scheme 45: Synthesis of Compound 84

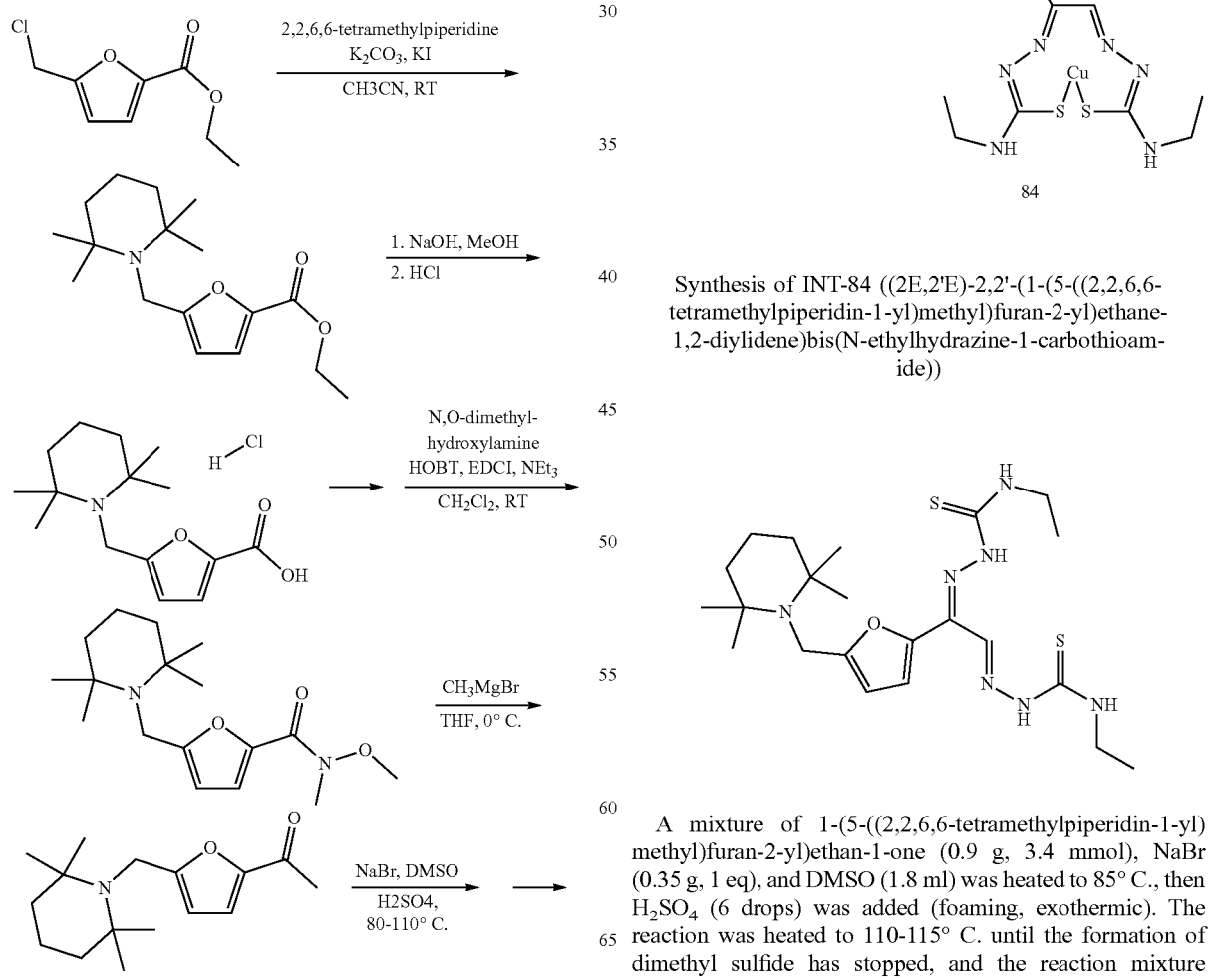

352

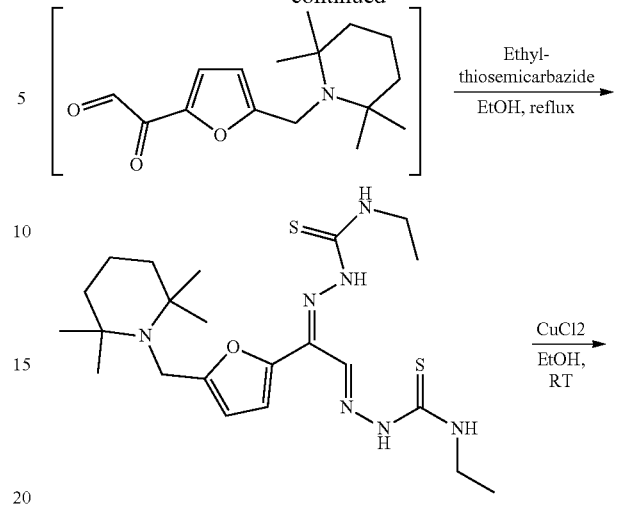

INT-84

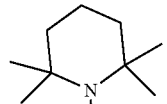

84

Synthesis of INT-84 ((2E,2'E)-2,2'-(1-(5-((2,2,6,6-tetramethylpiperidin-1-yl)methyl)furan-2-yl)ethane-1,2-diylidene)bis(N-ethylhydrazine-1-carbothioamide))

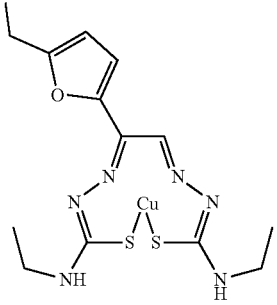

A mixture of 1-(5-((2,2,6,6-tetramethylpiperidin-1-yl)methyl)furan-2-yl)ethan-1-one (0.9 g, 3.4 mmol), NaBr (0.35 g, 1 eq), and DMSO (1.8 ml) was heated to 85° C., then $H_2SO_4$ (6 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (1.16 g, 2 eq) was added to the filtrate. The reaction mixture was heated to reflux for 2 h, then cooled to rt, solvents were evaporated in vacuo, the residue was dissolved in water (25 ml), neutralized with aq.sat. $K_2CO_3$ and extracted with EtOAc (3×60 ml). The organic layer was separated, dried over anh. $Na_2SO_4$, filtered, and solvents were evaporated in vacuo. The residue was treated with water. The formed precipitate was filtered and washed with EtOH to give pure titular product. Yield 0.6 g (36.6%). LC-MS 1.19 min, m/z 480.6 [MH]+.

Synthesis of Compound 84

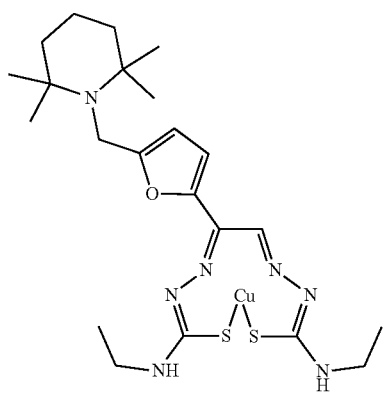

Copper(II) chloride dihydrate (0.068 g, 1 eq) was added to a stirred solution of INT-84 (0.192 g, 4.7 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.08 g (37%).

Scheme 46: Synthesis of Compound 85

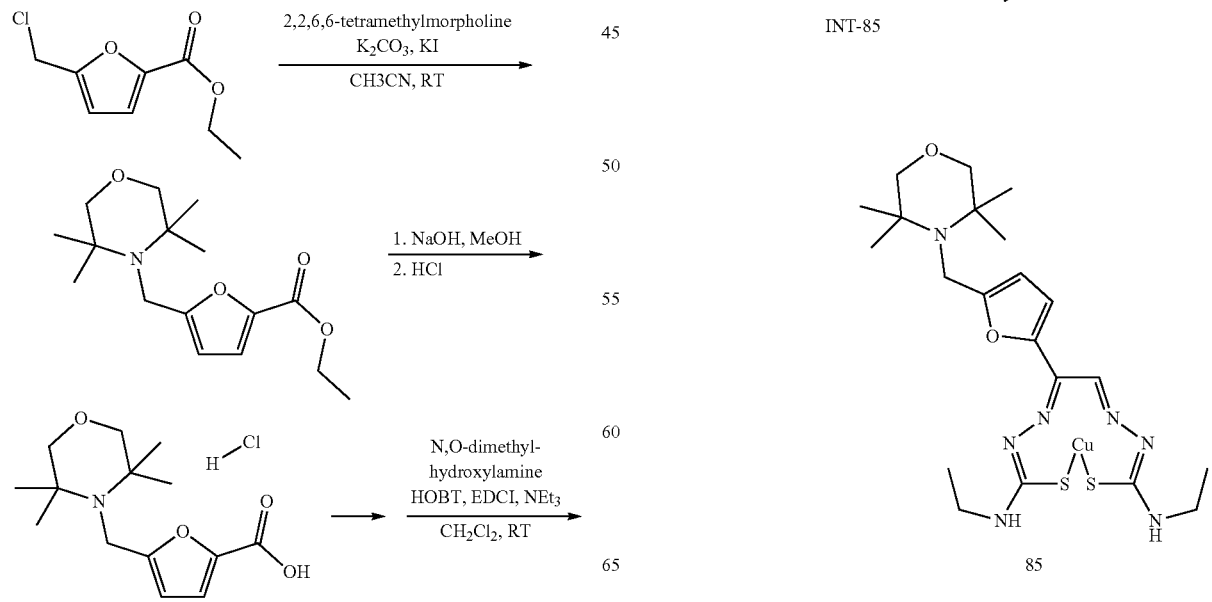

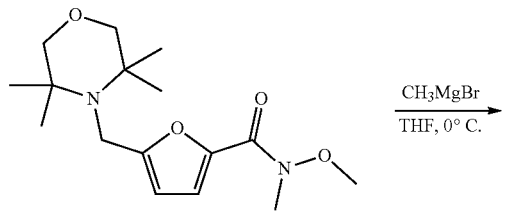

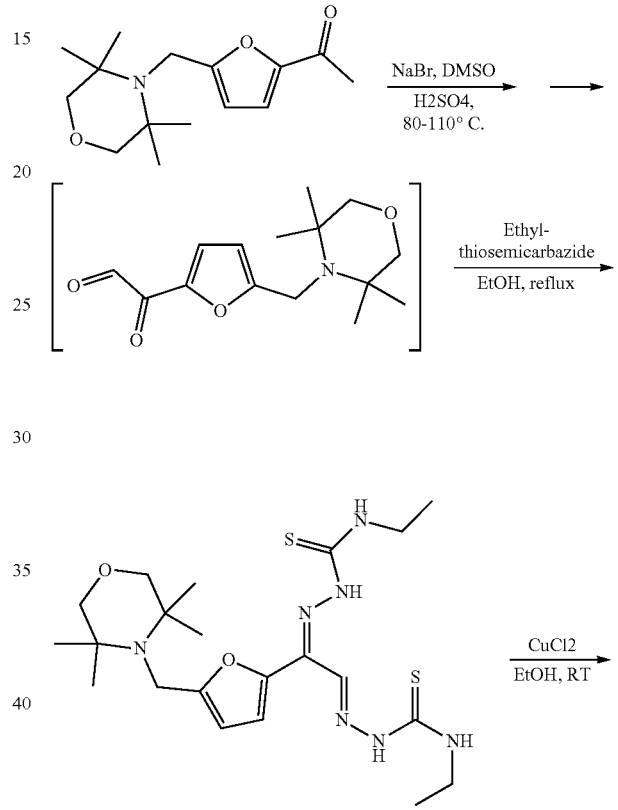

Synthesis of INT-85 ((2E,2'E)-2,2'-(1-(5-((3,3,5,5-tetramethylmorpholino)methyl)furan-2-yl)ethane-1,2-diylidene)bis(N-ethylhydrazine-1-carbothioamide))

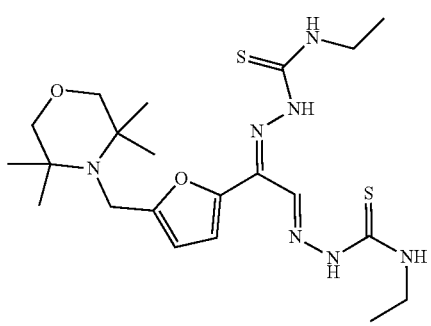 [SMILES: CCNC(=S)N/N=C/C(=N\NC(=S)NCC)c1ccc(CN2C(C)(C)COCC2(C)C)o1]

A mixture of 1-(5-((3,3,5,5-tetramethylmorpholino)methyl)furan-2-yl)ethan-1-one (0.4 g, 1.5 mmol), NaBr (0.16 g, 1 eq), and DMSO (1 ml) was heated to 85° C., then H₂SO₄ (3 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (0.36 g, 2 eq) was added to the filtrate. The reaction mixture was heated to reflux for 2 h, then cooled to rt, solvents were evaporated in vacuo, the residue was dissolved in water (25 ml), neutralized with aq.sat. K₂CO₃ and extracted with EtOAc (3×60 ml). The organic layer was separated, dried over anh. Na₂SO₄, filtered, and solvents were evaporated. The residue was treated with water. The formed precipitate was filtered and washed with EtOH to give pure titular product. Yield 0.24 g (32.4%). LC-MS 1.25 min, m/z 482.5 [MH]+.

Synthesis of Compound 85

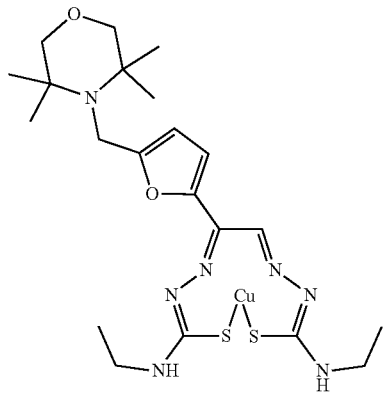

Copper(II) chloride dihydrate (0.053, 1 eq) was added to a stirred solution of INT-85 (0.15 g, 0.3 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.11 g (65.1%).

Scheme 47: Synthesis of Compound 86

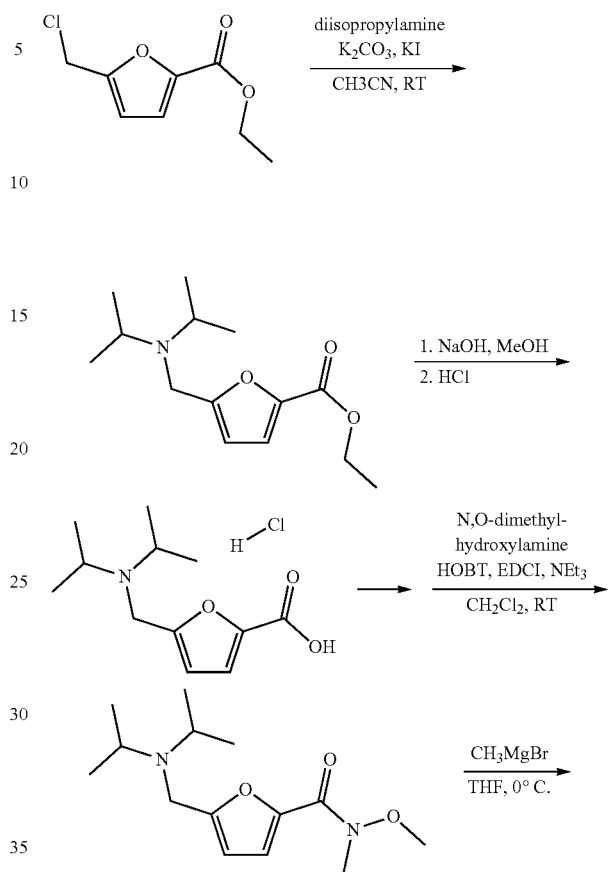

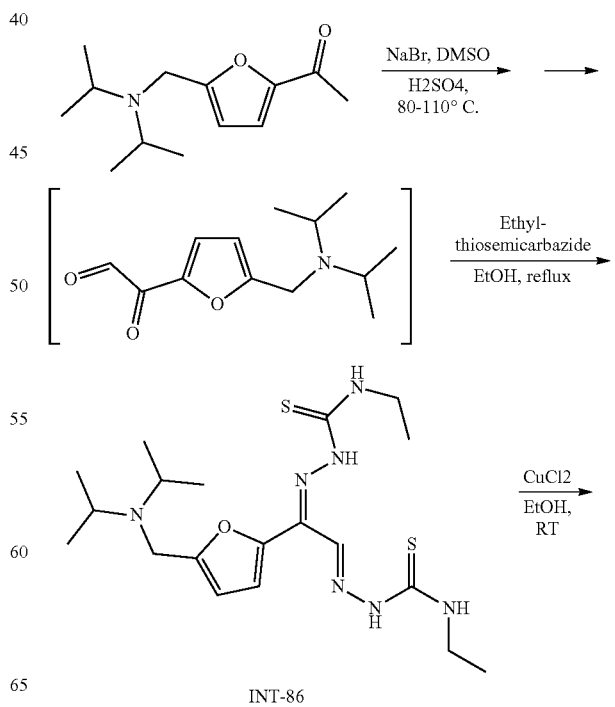

INT-86

357
-continued

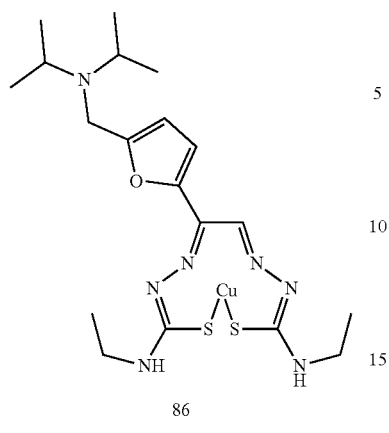

86

Synthesis of INT-86 ((2E,2'E)-2,2'-(1-(5-(((diisopropylamino)methyl)furan-2-yl)ethane-1,2-diylidene) bis(N-ethylhydrazine-1-carbothioamide))

A mixture of 1-(5-(((diisopropylamino)methyl)furan-2-yl)ethan-1-one (1.0 g, 4.5 mmol), NaBr (0.46 g, 1 eq), and DMSO (2.5 ml) was heated to 85° C., then H₂SO₄ (3 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (1.07 g, 2 eq) was added to the filtrate. The reaction mixture was heated to reflux for 2 h, then cooled to room temperature, solvents were evaporated in vacuo, the residue was dissolved in water (25 ml), neutralized with aq.sat. K₂CO₃ and extracted with EtOAc (3×60 ml). The organic layer was separated, dried over anh. Na₂SO₄, filtered, and solvents were evaporated in vacuo. The residue was treated with water. The formed precipitate was filtered and washed with EtOH to give pure titular product. Yield 0.5 g (25.4%). LC-MS 1.18 min, m/z 440.7 [MH]+.

358

Synthesis of Compound 86

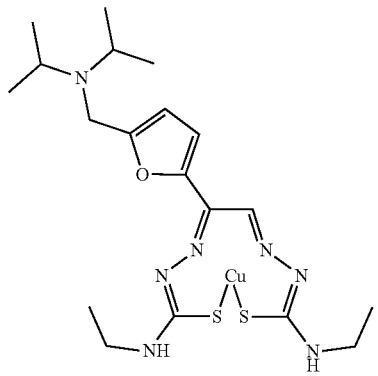

Copper(II) chloride dihydrate (0.049, 1 eq) was added to a stirred solution of INT-86 (0.126 g, 0.29 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.063 g (43.8%).

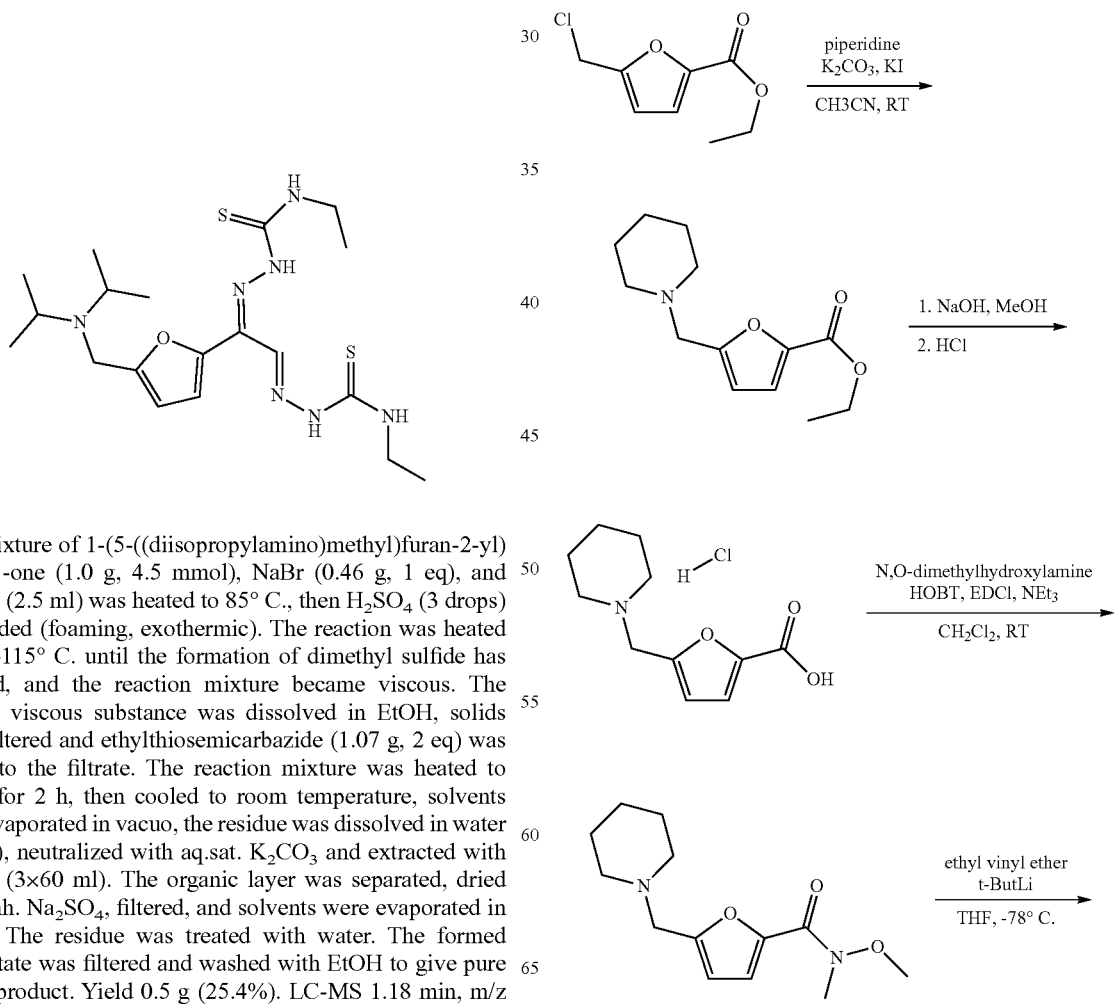

Scheme 48: Synthesis of Compound 87

359

-continued

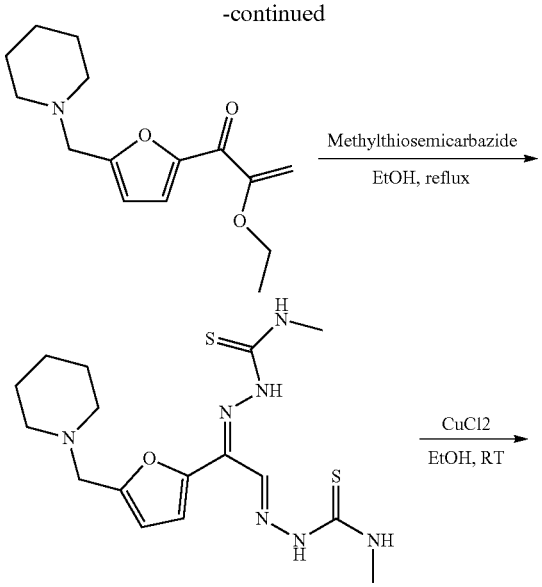

INT-87

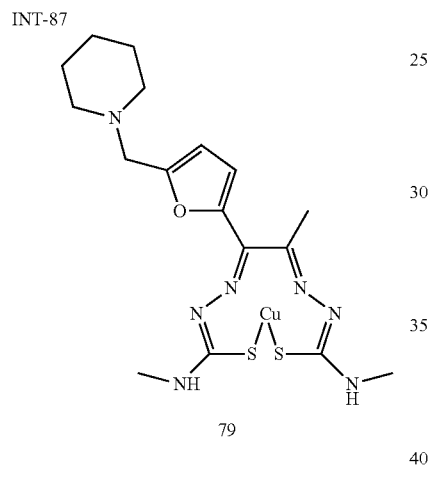

79

Synthesis of 2-ethoxy-1-(5-(piperidin-1-ylmethyl)furan-2-yl)prop-2-en-1-one

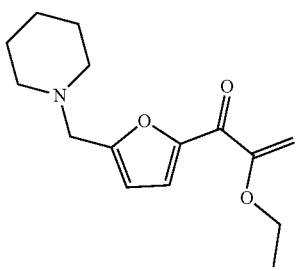 [SMILES: C=C(OCC)C(=O)c1ccc(CN2CCCCC2)o1]

A solution of ethyl vinyl ether (3.93 g, 5.2 ml, 5.5 eq) in dry THF (100 mL) was cooled to −78° C., and tert-butyl-lithium (1.7M in pentane, 31 ml, 5 eq) was added. The mixture was warmed to 0° C. over 1 h period, stirred for 45 min, and cooled down to −30° C. A solution of N-methoxy-N-methyl-5-(piperidin-1-ylmethyl)furan-2-carboxamide (2.5 g, 9.9 mmol, 1 eq) in THF was added, and then the reaction was stirred at 0° C. for 4 h. The progress of the reaction was monitored by TLC. The mixture was poured

360 into aq NH$_4$Cl and extracted with Et$_2$O. The combined extracts were dried over anh. Na$_2$SO$_4$, filtered, and solvents were evaporated in vacuo. The product was used for the next step without additional purification. Yield 2.3 g (88%). LC-MS 1.00 min, m/z 264.1 [MH]+.

Synthesis of INT-87 ((2E,2'E)-2,2'-(1-(5-(piperidin-1-ylmethyl)furan-2-yl)propane-1,2-diylidene)bis(N-methylhydrazine-1-carbothioamide))

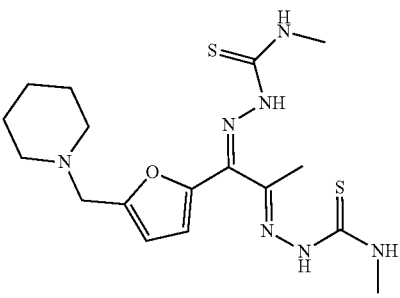 [SMILES: CNC(=S)N/N=C(C)/C(=N\NC(=S)NC)c1ccc(CN2CCCCC2)o1]

2-ethoxy-1-(5-(piperidin-1-ylmethyl)furan-2-yl)prop-2-en-1-one (1.15 g, 4.4 mmol, 1 eq) was dissolved in EtOH (10 ml), methylthiosemicarbazide (0.918 g, 2 eq) and 3 drops of H$_2$SO$_4$ were added. The stirred reaction mixture was heated for 4 h to reflux and then maintained for 15 h at rt. The formed precipitate was filtered, washed with EtOH, water, Et$_2$O, and dried. Yield 1.1 g (61.5%). LC-MS 1.04 min, m/z 410.4 [MH]+.

Synthesis of Compound 87

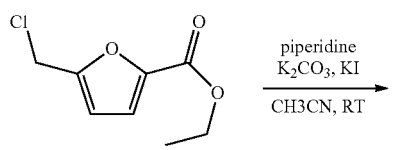

Copper(II) chloride dihydrate (0.183 g, 1.1 eq) was added to INT-87 (0.4 g, 9.8 mmol, 1 eq) in ethanol. The mixture was stirred for 15 h at rt. The formed complex precipitated as a red-brown powder. The precipitate was collected by filtration, washed with water, methanol, diethyl ether, and dried. Yield 0.16 g (34.8%).

Scheme 49: Synthesis of Compound 88

361

-continued

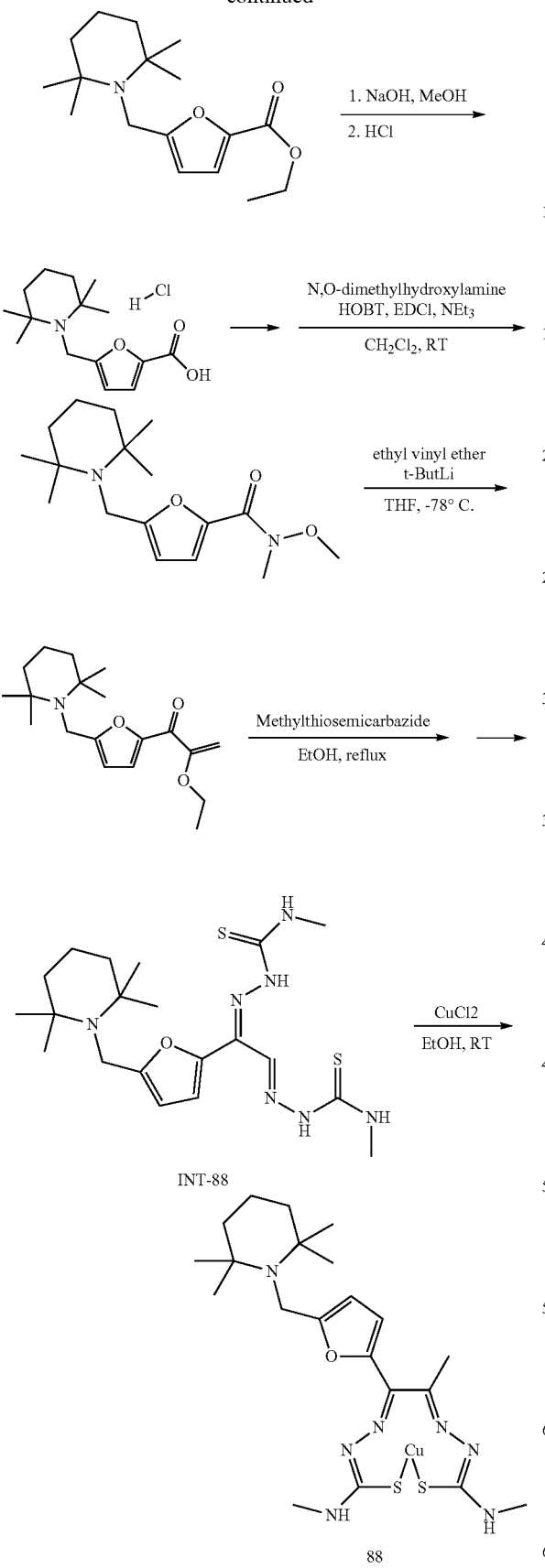

INT-88

88

362

Synthesis of 2-ethoxy-1-(5-((2,2,6,6-tetramethylpiperidin-1-yl)methyl)furan-2-yl)prop-2-en-1-one

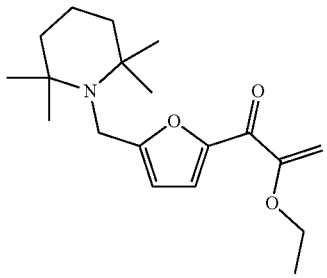 [SMILES: C=C(OCC)C(=O)c1ccc(CN2C(C)(C)CCCC2(C)C)o1]

A solution of ethyl vinyl ether (3.65 g, 4.85 ml, 6.6 eq) in dry THF (80 mL) was cooled to −78° C., and tert-butyllithium (1.6 M in pentane, 28 ml, 6 eq) was added. The mixture was warmed to 0° C. over 1 h period, stirred for 45 min, and cooled down to −30° C. A solution of N-methoxy-N-methyl-5-((2,2,6,6-tetramethylpiperidin-1-yl)methyl)furan-2-carboxamide (2.06 g, 7.7 mmol) in THF was added, and the mixture was stirred for 4 h at 0° C. The progress of the reaction was monitored by TLC (hexane/EtOAc 10:1). The mixture was poured into aq NH$_4$Cl and extracted with Et$_2$O. The combined extracts were dried over anh. Na$_2$SO$_4$, filtered, and evaporated. The product was used for the next step without additional purification. Yield 2.09 g (97.5%). LC-MS 0.87 min, m/z 280.7 [MH]+.

Synthesis of INT-88 ((2E,2'E)-2,2'-(1-(5-((2,2,6,6-tetramethylpiperidin-1-yl)methyl)furan-2-yl)propane-1,2-diylidene)bis(N-methylhydrazine-1-carbothioamide))

2-ethoxy-1-(5-((2,2,6,6-tetramethylpiperidin-1-yl)methyl)furan-2-yl)prop-2-en-1-one (1 g, 3.6 mmol) was dissolved in EtOH (50 ml), methylthiosemicarbazide (0.75 g, 2 eq) and 3 drops of H$_2$SO$_4$ were added. The stirred reaction mixture was heated to reflux for 4 h and then maintained for 15 h at rt. The formed precipitate was filtered, washed with EtOH, potassium carbonate solution, water, Et$_2$O, and dried. Yield 0.56 g (36.7%). LC-MS 1.08 min, m/z 426.3 [MH]+.

Synthesis of Compound 88

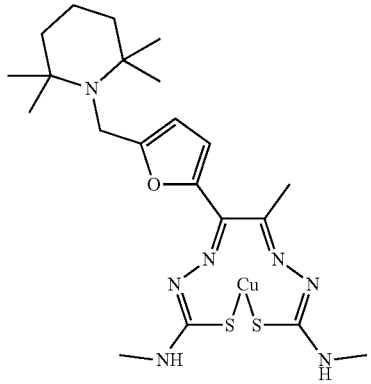

Copper(II) chloride dihydrate (0.049 g, 1 eq) was added to INT-88 (0.126 g, 0.3 mmol, 1 eq) in ethanol. The mixture was stirred for 15 h at rt. The formed complex precipitated as a red-brown powder. The precipitate was collected by filtration, washed with water, methanol, diethyl ether, and dried. Yield 0.063 g (43.8%).

Scheme 50: Synthesis of Compound 89

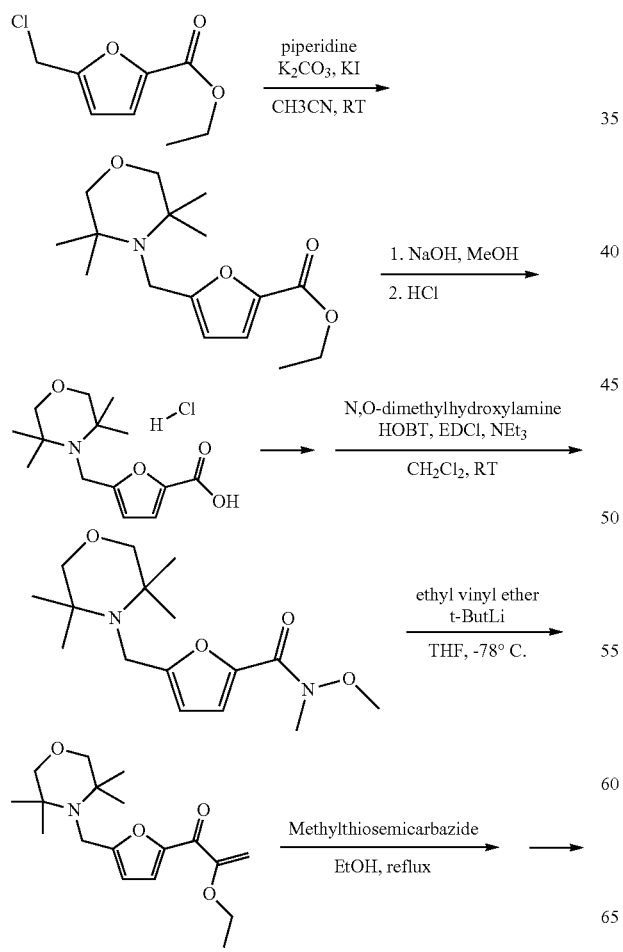

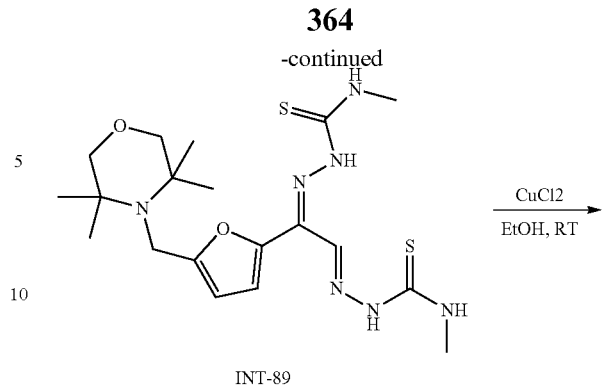

INT-89

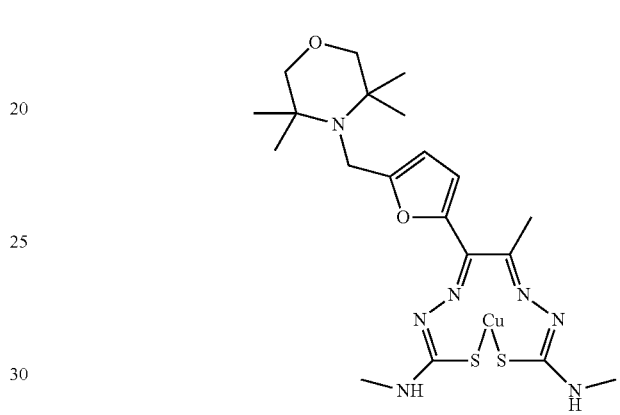

89

Synthesis of 2-ethoxy-1-(5-((3,3,5,5-tetramethyl-morpholino)methyl)furan-2-yl)prop-2-en-1-one

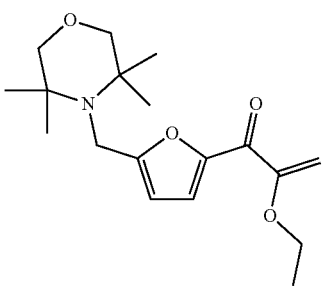 [SMILES: C=C(OCC)C(=O)c1ccc(CN2C(C)(C)COCC2(C)C)o1]

A solution of ethyl vinyl ether (1.53 g, 2.03 ml, 6.6 eq) in dry THF (25 mL) was cooled to −78° C., and tert-butyl-lithium (1.6M in pentane, 12 ml, 6 eq) was added. The mixture was warmed to 0° C. over 1 h period, stirred for 45 min, and cooled down to −30° C. A solution of N-methoxy-N-methyl-5-((3,3,5,5-tetramethylmorpholino)methyl)furan-2-carboxamide (2 g, 6.4 mmol) in THF was added, and the mixture was stirred for 4 h at 0° C. The progress of the reaction was monitored by TLC (hexane/EtOAc 10:1). The mixture was poured into aq NH$_4$Cl and extracted with Et$_2$O. The combined extracts were dried over anh. Na$_2$SO$_4$, filtered, and evaporated in vacuo. The product was used for the next step without additional purification. Yield 1 g (96.5%). LC-MS 1.05 min, m/z 322.8 [MH]+.

Synthesis of INT-89 ((2E,2'E)-2,2'-(1-(5-((3,3,5,5-tetramethylmorpholino)methyl)furan-2-yl)propane-1,2-diylidene)bis(N-methylhydrazine-1-carbothioamide))

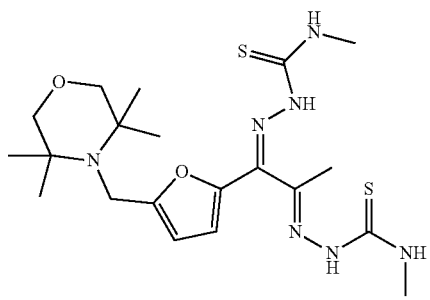

2-ethoxy-1-(5-((3,3,5,5-tetramethylmorpholino)methyl)furan-2-yl)prop-2-en-1-one (0.5 g, 1.6 mmol) was dissolved in EtOH (15 ml), methylthiosemicarbazide (0.33 g, 2 eq) and 3 drops of $H_2SO_4$ were added. The stirred reaction mixture was heated to reflux for 4 h and then maintained for 15 h at rt. The formed precipitate was filtered, washed with EtOH, potassium carbonate solution, water, $Et_2O$, and dried. Yield 0.28 g (38.5%). LC-MS 1.09 min, m/z 468.8 [MH]+.

Synthesis of Compound 89

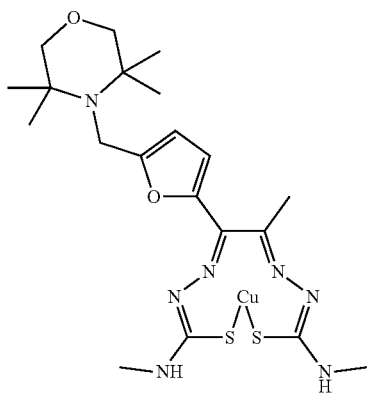

Copper(II) chloride dihydrate (0.05 g, 1 eq) was added to INT-89 (0.137 g, 0.3 mmol 1 eq) in ethanol. The mixture was stirred for 15 h at rt. The formed complex precipitated as a red-brown powder. The precipitate was collected by filtration, washed with water, methanol, diethyl ether, and dried. Yield 0.135 g (89.7%).

Scheme 51: Synthesis of Compound 90

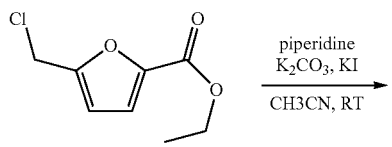

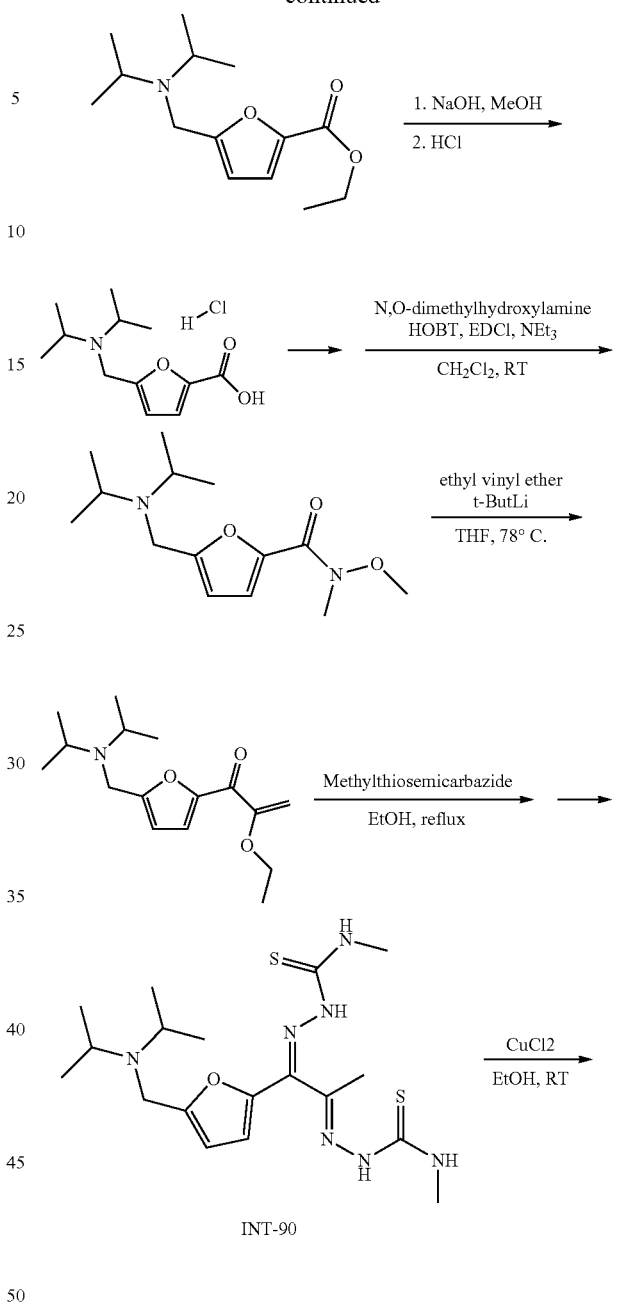

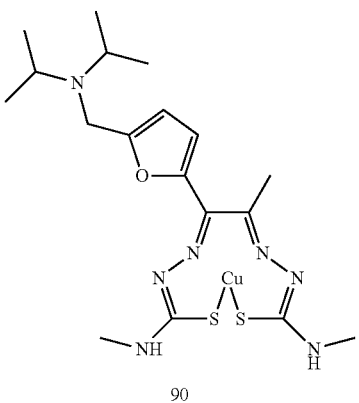

90

367
Synthesis of 1-(5-(((diisopropylamino)methyl)furan-2-yl)-2-ethoxyprop-2-en-1-one

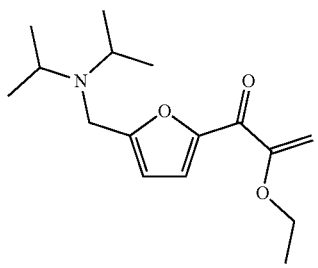 [SMILES: C=C(OCC)C(=O)c1ccc(CN(C(C)C)C(C)C)o1]

A solution of ethyl vinyl ether (1.53 g, 2.03 ml, 6.6 eq) in dry THF (25 mL) was cooled to −78° C., and tert-butyllithium (1.6M in pentane, 12 ml, 6 eq) was added. The mixture was warmed to 0° C. over 1 h period, stirred for 45 min, and cooled down to −30° C. A solution of 5-((diisopropylamino)methyl)-N-methoxy-N-methylfuran-2-carboxamide (2 g, 6.4 mmol) in THF was added and mixture was stirred for 4 h at 0° C. The progress of the reaction was monitored by TLC (hexane/EtOAc 10:1). The mixture was poured into aq NH$_4$Cl and extracted with Et$_2$O. The combined extracts were dried over anh. Na$_2$SO$_4$, filtered, and evaporated in vacuo. The product was used for the next step without additional purification. Yield 1 g (96.5%). LC-MS 1.05 min, m/z 322.8 [MH]+.

Synthesis of INT-90 ((2E,2'E)-2,2'-(1-(5-(((diisopropylamino)methyl)furan-2-yl)propane-1,2-diylidene)bis(N-methylhydrazine-1-carbothioamide))

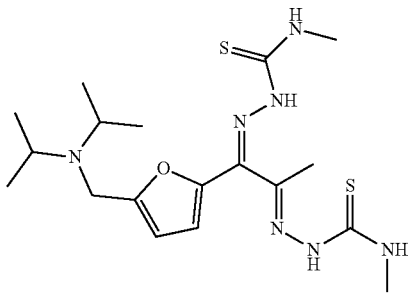 [SMILES: CNC(=S)N/N=C(C)/C(=N\NC(=S)NC)c1ccc(CN(C(C)C)C(C)C)o1]

1-(5-(((diisopropylamino)methyl)furan-2-yl)-2-ethoxyprop-2-en-1-one (1 g, 3.6 mmol) was dissolved in EtOH (25 ml), methylthiosemicarbazide (0.37 g, 2 eq) and 3 drops of H$_2$SO$_4$ were added. The stirred reaction mixture was heated to reflux for 4 h and then maintained for 15 h at rt. The formed precipitate was filtered, washed with EtOH, potassium carbonate solution, water, Et$_2$O, and dried. Yield 0.56 g (36.7%). LC-MS 1.1 min, m/z 426.4 [MH]+.

368
Synthesis of Compound 90

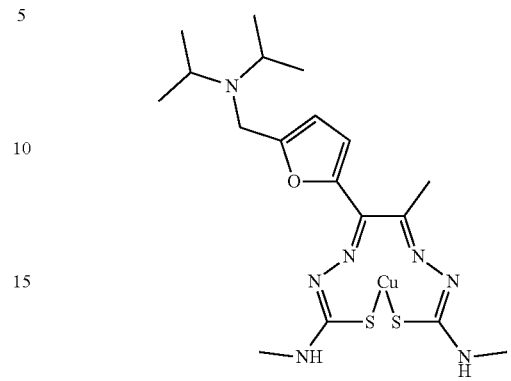

Copper(II) chloride dihydrate (0.04 g, 1 eq) was added to INT-90 (0.1 g, 2.4 mmol 1 eq) in ethanol. The mixture was stirred for 15 h at rt. The formed complex precipitated as a red-brown powder. The precipitate was collected by filtration, washed with water, methanol, and diethyl ether, and dried. Yield 0.025 g (21.7%)

Scheme 52: Synthesis of Compound 91

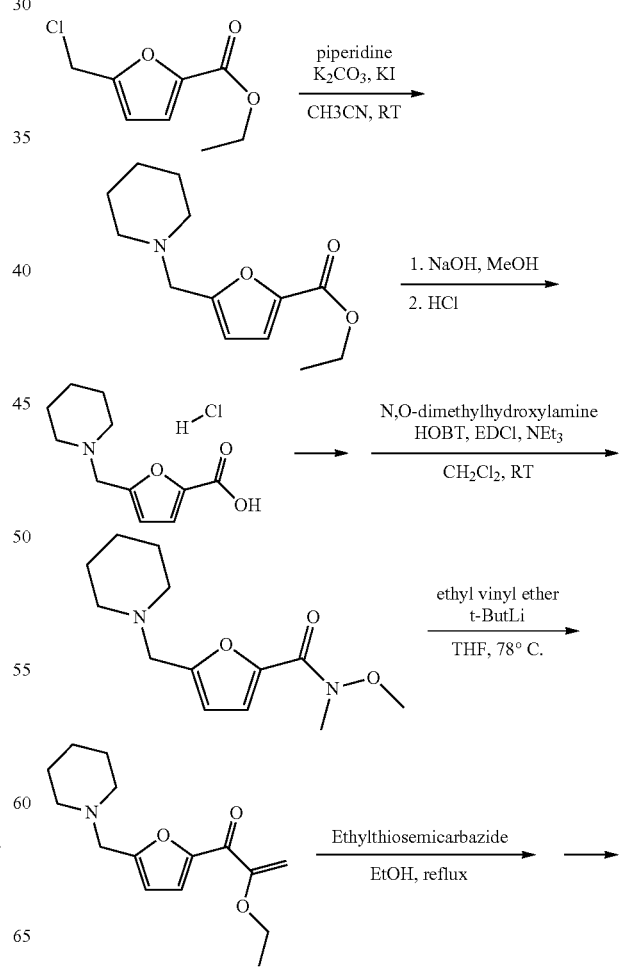

370

Synthesis of Compound 91

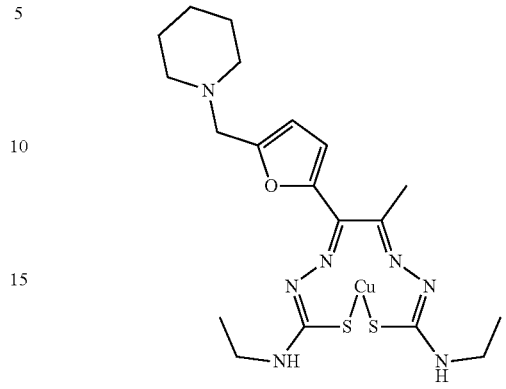

Copper(II) chloride dihydrate (0.214 g, 1.1 eq) was added to INT-91 (0.5 g, 11.4 mmol, 1 eq) in ethanol. The mixture was stirred for 15 h at rt. The formed complex precipitated as a red-brown powder. The precipitate was collected by filtration, washed with water, methanol, diethyl ether, and dried. Yield 0.51 g (89.9%).

Scheme 53: Synthesis of Compound 92

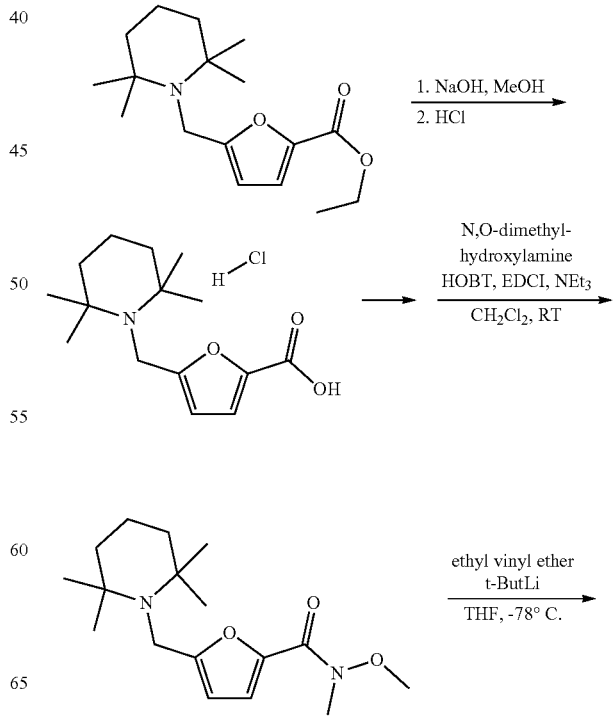

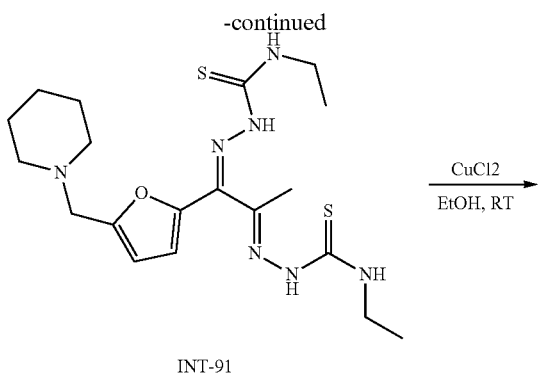

INT-91

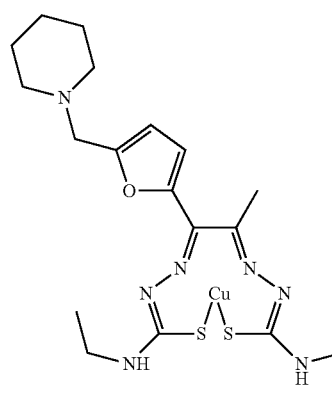

91

Synthesis of INT-91 ((2E,2'E)-2,2'-(1-(5-(piperidin-1-ylmethyl)furan-2-yl)propane-1,2-diylidene)bis(N-ethylhydrazine-1-carbothioamide))

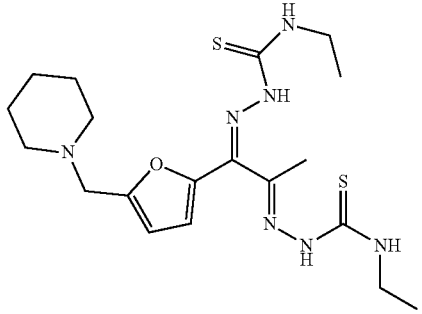 [SMILES: CCNC(=S)N/N=C(C)/C(=N\NC(=S)NCC)c1ccc(CN2CCCCC2)o1]

2-ethoxy-1-(5-(piperidin-1-ylmethyl)furan-2-yl)prop-2-en-1-one (1.15 g, 4.4 mmol, 1 eq) was dissolved in EtOH (10 ml), ethyl thiosemicarbazide (1.04 g, 2 eq) and 3 drops of $H_2SO_4$ were added. The stirred reaction mixture was heated to reflux for 4 h and then maintained for 15 h at rt. The formed precipitate was filtered, washed with EtOH, water, $Et_2O$, and dried. Yield 0.5 g (26.1%). LC-MS 1.27 min, m/z 438.5 [MH]+.

-continued

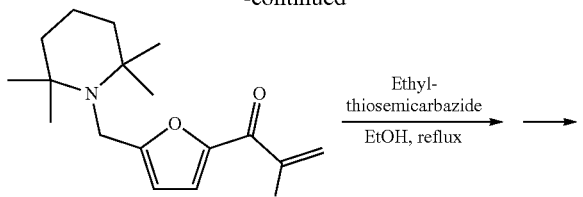

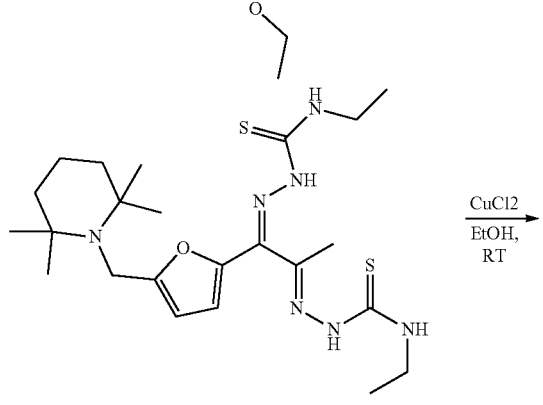

INT-92

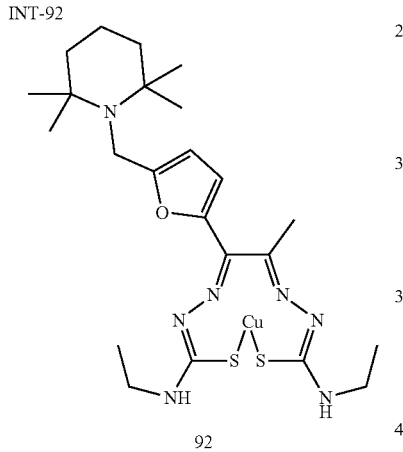

92

Synthesis of INT-92 ((2E,2'E)-2,2'-(1-(5-((2,2,6,6-tetramethylpiperidin-1-yl)methyl)furan-2-yl)propane-1,2-diylidene)bis(N-ethylhydrazine-1-carbothioamide))

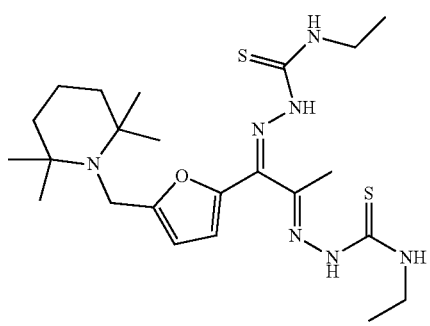 [SMILES: CCNC(=S)N/N=C(C)/C(=N\NC(=S)NCC)c1ccc(CN2C(C)(C)CCCC2(C)C)o1]

2-ethoxy-1-(5-((2,2,6,6-tetramethylpiperidin-1-yl)methyl)furan-2-yl)prop-2-en-1-one (1 g, 3.1 mmol) was dissolved in EtOH (50 ml), ethyl thiosemicarbazide (0.75 g, 2 eq) and 3 drops of $H_2SO_4$ were added. The stirred reaction mixture was heated to reflux for 4 h and then maintained for 15 h at rt. The formed precipitate was filtered, washed with EtOH, potassium carbonate solution, water, $Et_2O$, and dried. Yield 0.80 g (51.9%). LC-MS 1.19 min, m/z 494.7 [MH]+.

Synthesis of Compound 92

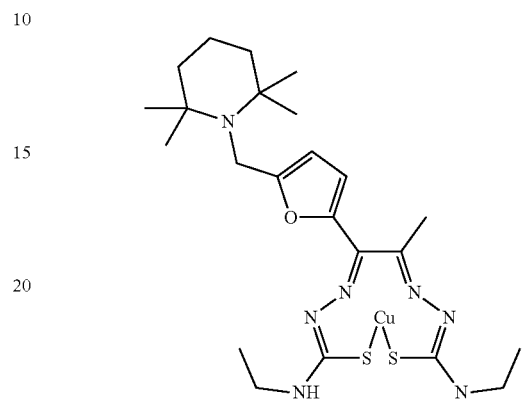

Copper(II) chloride dihydrate (0.24 g, 1 eq) was added to INT-92 (0.083 g, 1 eq) in ethanol. The mixture was stirred for 15 h at rt. The formed complex precipitated as a red-brown powder. The precipitate was collected by filtration, washed with water, methanol, diethyl ether, and dried. Yield 0.23 g (85.2%)

Scheme 54: Synthesis of Compound 93

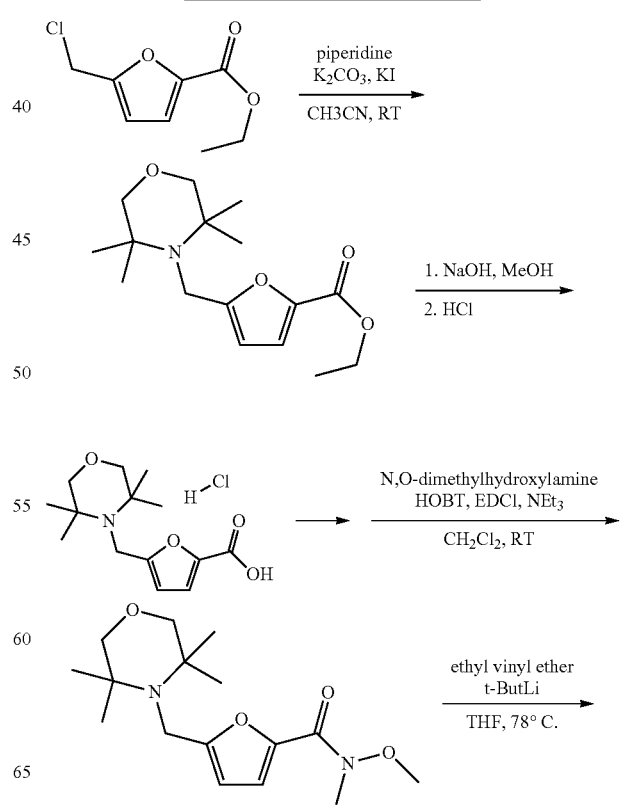

-continued

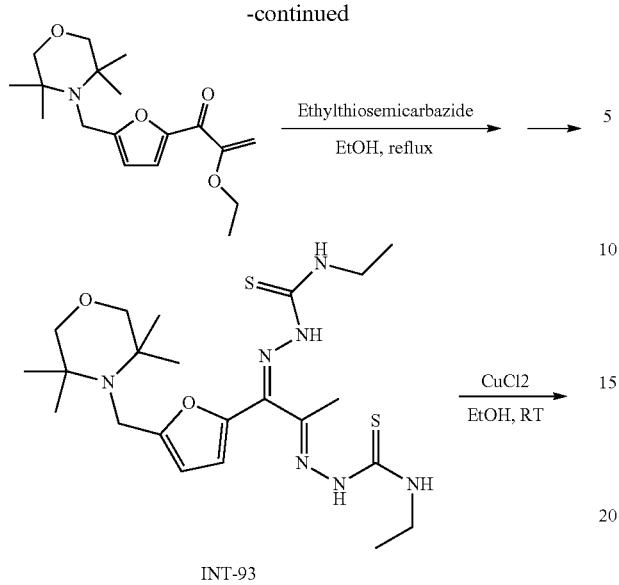

INT-93

Synthesis of INT-92 ((2E,2'E)-2,2'-(1-(5-((3,3,5,5-tetramethylmorpholino)methyl)furan-2-yl)propane-2-diylidene)bis(1N-ethylhydrazine-1-carbothioamide))

2-ethoxy-1-(5-((3,3,5,5-tetramethyl morpholino)methyl) furan-2-yl)prop-2-en-1-one (0.5 g, 1.6 mmol) was dissolved in EtOH (15 ml), ethylthiosemicarbazide (0.37 g, 2 eq) and 3 drops of $H_2SO_4$ were added. The stirred reaction mixture was heated to reflux for 4 h and then maintained for 15 h at rt. The formed precipitate was filtered, washed with EtOH, potassium carbonate solution, water, $Et_2O$, and dried. Yield 0.24 g (31.1%). LC-MS 1.26 min m/z 496.6 [MH]+.

Synthesis of Compound 93

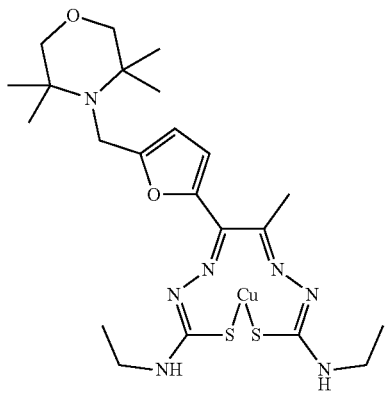

Copper(II) chloride dihydrate (0.04 g, 1 eq) was added to INT-93 (0.130 g, 0.3 mmol, 1 eq) in ethanol. The mixture was stirred for 15 h at rt. The formed complex precipitated as a red-brown powder. The precipitate was collected by filtration, washed with water, methanol, diethyl ether, and dried. Yield 0.14 g (98.7%).

Scheme 55: Synthesis of Compound 94

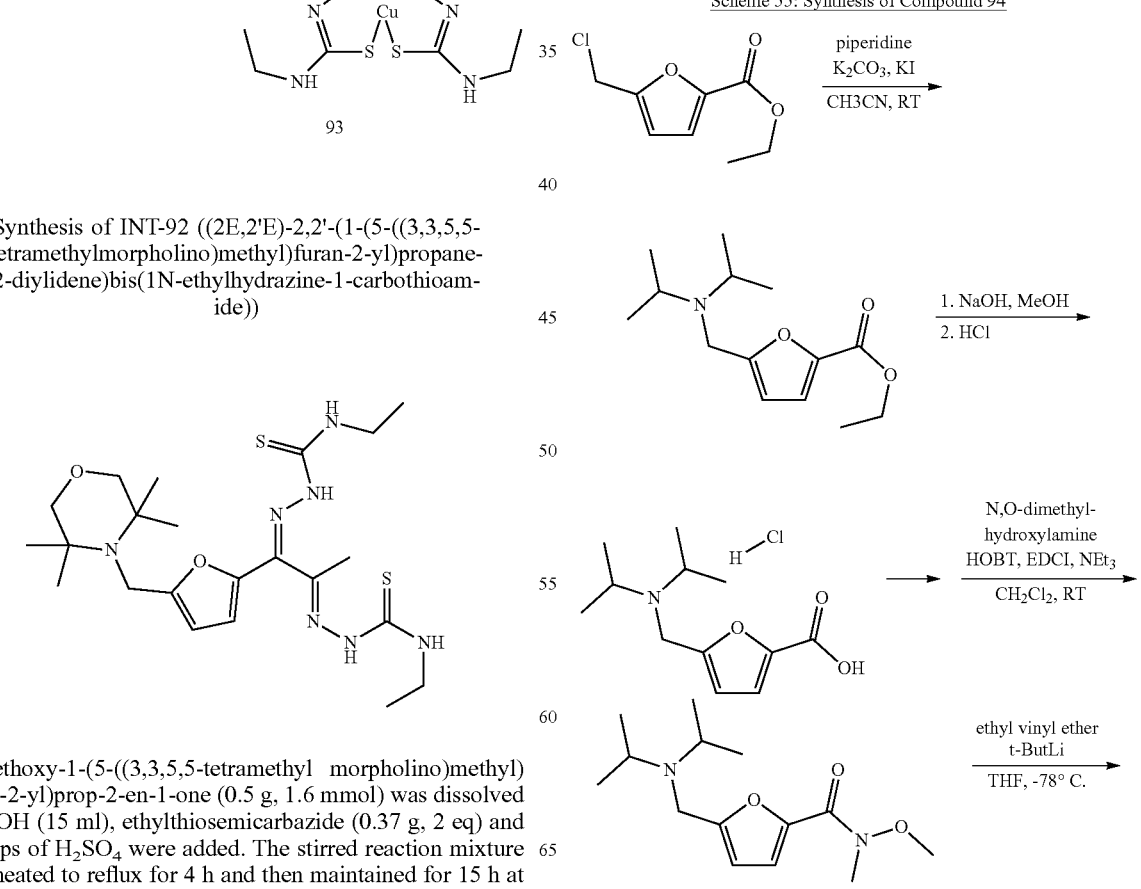

-continued

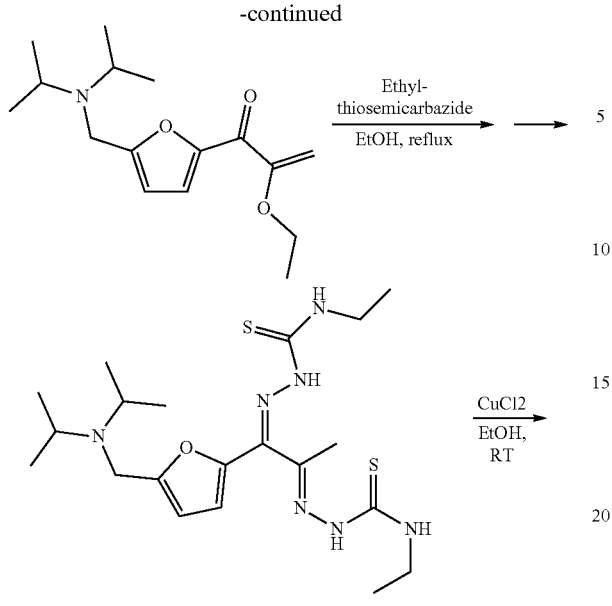

INT-94

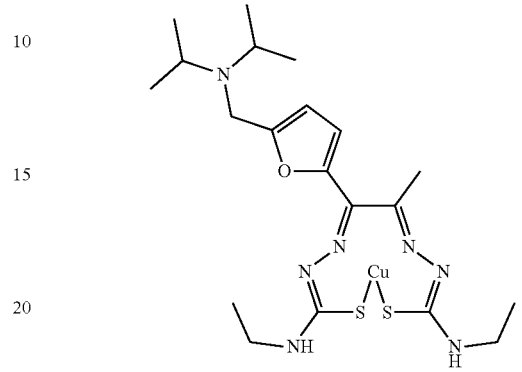

94

Synthesis of INT-94 ((2E,2'E)-2,2'-(1-(5-(((diisopropylamino)methyl)furan-2-yl)propane-1,2-diylidene) bis(N-ethylhydrazine-1-carbothioamide))

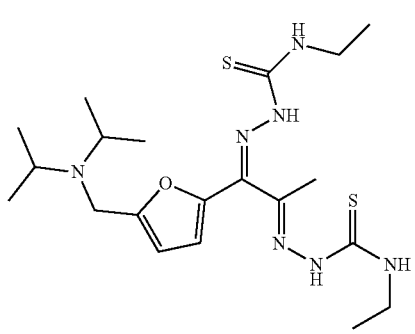 [SMILES: CCNC(=S)N/N=C(C)/C(=N\NC(=S)NCC)c1ccc(CN(C(C)C)C(C)C)o1]

1-(5-(((diisopropylamino)methyl)furan-2-yl)-2-ethoxy-prop-2-en-1-one (1 g, 3.6 mmol) was dissolved in EtOH (25 ml), ethyl thiosemicarbazide (0.85 g, 2 eq) and 3 drops of $H_2SO_4$ were added. The stirred reaction mixture was heated to reflux for 4 h and then maintained for 15 h at rt. The formed precipitate was filtered, washed with EtOH, potassium carbonate solution, water, $Et_2O$, and dried. Yield 0.8 g (49.3%). LC-MS 1.23 min, m/z 454.5 [MH]+.

Synthesis of Compound 94

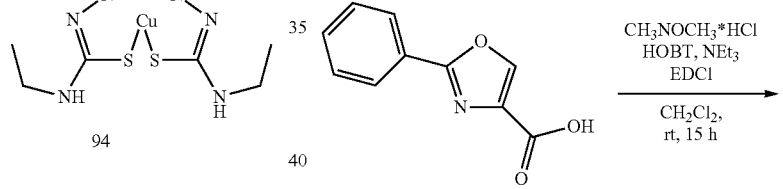

Copper(II) chloride dihydrate (0.05 g, 1 eq) was added to INT-94 (0.126 g, 0.3 mmol 1 eq) in ethanol. The mixture was stirred for 15 h at rt. The formed complex precipitated as a red-brown powder. The precipitate was collected by filtration, washed with water, methanol, diethyl ether, and dried. Yield 0.063 g (43.8%).

Scheme 56: Synthesis of Compound 95

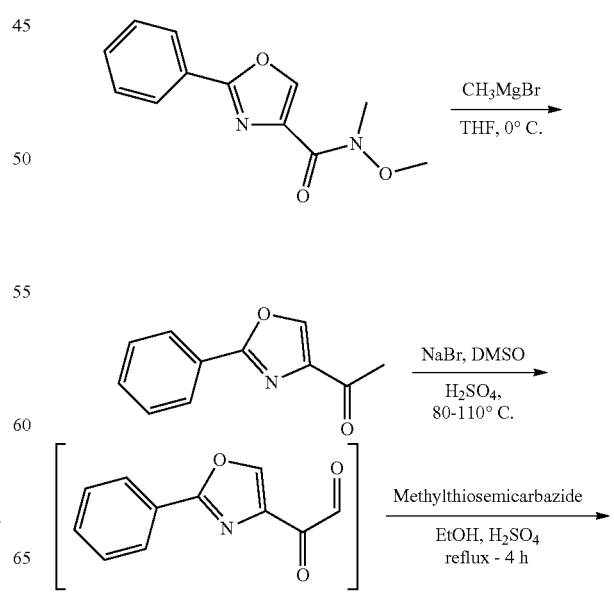

-continued

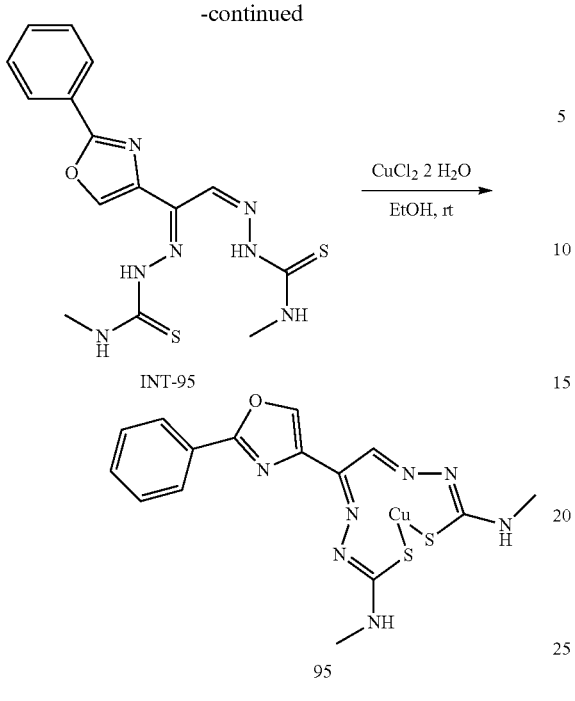

INT-95

95

Synthesis of N-methoxy-N-methyl-2-phenyloxazole-4-carboxamide

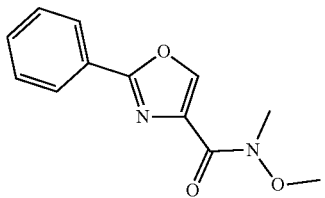 [SMILES: CON(C)C(=O)c1coc(-c2ccccc2)n1]

To a stirred mixture of 2-phenyloxazole-4-carboxylic acid (3.8 g, 20 mmol), N,O-dimethylhydroxylamine (2.35 g, 1.2 eq), HOBt (3.69 g, 1.2 eq), and triethylamine (6.02 g, 8.9 ml, 3 eq) in DCM (150 ml) at 5° C. was added EDCl (4.62 g, 1.2 eq) and reaction was stirred for 15 h at rt. The mixture was washed with water and brine. The organic layer was dried over anh. $Na_2SO_4$ and then concentrated under reduced pressure. Product was used without further purification. Yield 2.46 g (52.7%). LC-MS 1.2 min, m/z 233.1 [MH]+.

Synthesis of 1-(2-phenyloxazol-4-yl)ethan-1-one

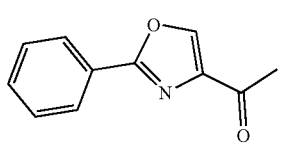

A solution of N-methoxy-N-methyl-2-phenyloxazole-4-carboxamide (1.49 g, 6.4 mmol) in THF (40 ml) was cooled to 5° C. and methylmagnesium bromide (1.4M in THF, 14 ml, 3 eq) was added. The reaction mixture was stirred at 5° C. for 2 h, poured into aq $NH_4Cl$ and extracted with $Et_2O$. The combined extracts were dried over anh. $Na_2SO_4$, filtered, and solvents were evaporated in vacuo. Compound 5 was used for the next step without purification. Yield 0.8 g (66.6%). LC-MS 1.44 min, m/z 188.4 [MH]+. $^1$H-NMR (400 MHz, $CDCl_3$), δ (ppm): 8.31-8.10 (m, 2H), 7.89 (s, 1H), 7.57-7.42 (m, 3H), 2.68 (s, 3H).

Synthesis of INT-95 ((2Z,2'E)-2,2'-(1-(2-phenyloxazol-4-yl)ethane-1,2-diylidene)bis(N-methylhydrazine-1-carbothioamide))

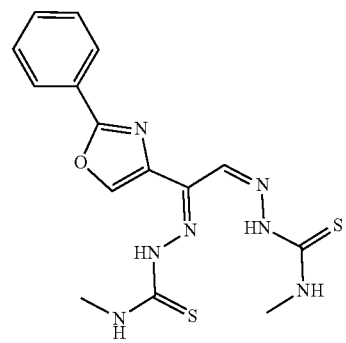 [SMILES: CNC(=S)N/N=C\C(=N\NC(=S)NC)c1coc(-c2ccccc2)n1]

A three-necked flask was charged with $SeO_2$ (0.26 g, 1.1 eq), 1,4-dioxane (7 mL), and water (0.2 mL). The mixture was heated to 50° C. and stirred until most of $SeO_2$ was dissolved. 1-(2-phenyloxazol-4-yl)ethan-1-one (0.4 g, 2.1 mmol) was added, and the reaction was heated to gentle reflux overnight. Selenium solids precipitated during the course of the reaction. The mixture was cooled in an ice bath and filtered through diatomaceous earth to remove selenium. The filter cake was washed with portions of 1,4-dioxane. The filtrate was evaporated to dryness and dissolved in EtOH (20 ml). Methylthiosemicarbazide (0.45 g, 2 eq) and 3 drops of $H_2SO_4$ were added. The stirred reaction was heated to reflux for 4 h. Formed precipitate was filtered, washed with EtOH, aq.sat. $Na_2CO_3$, water, $Et_2O$, and dried. Yield 0.13 g (16.2%). LC-MS 1.37 min, m/z 376.5 [MH]+. $^1$H-NMR (400 MHz, DMSO-d6), δ (ppm): 11.67 (s, 1H), 10.85 (s, 1H), 8.89 (d, J=4.5 Hz, 1H), 8.76 (s, 1H), 7.80 (s, 1H), 7.56-7.32 (m, 5H), 6.88 (d, J=4.7 Hz, 1H), 3.00 (t, J=16.0 Hz, 3H), 2.70 (d, J=4.6 Hz, 3H).

Synthesis of Compound 95

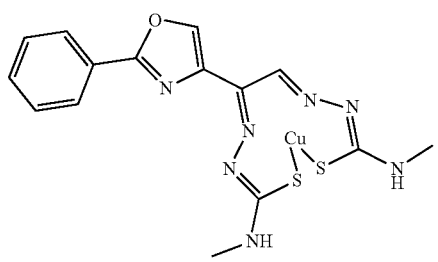

Copper(II) chloride dihydrate (0.06 g, 1 eq) was added to a stirred solution of INT-95 (0.13 g, 0.34 mmol) in ethanol. The mixture was stirred for 15 h at rt. The formed complex precipitated as a red-brown powder. The precipitate was collected by filtration, washed with water, diethyl ether, and dried. Yield 0.065 g (43%).

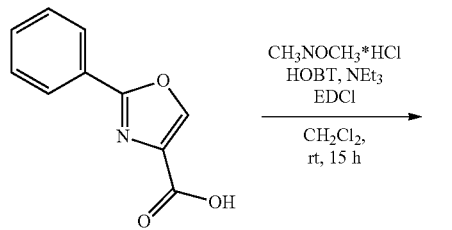

Scheme 57: Synthesis of Compound 96

Synthesis of INT-96 ((2Z,2'E)-2,2'-(1-(2-phenyloxazol-4-yl)ethane-1,2-diylidene)bis(N-ethylhydrazine-1-carbothioamide))

A three-necked flask was charged with $SeO_2$ (0.55 g, 1.2 eq), 1,4-dioxane (14 mL), and water (0.4 mL). The mixture was heated to 50° C. and stirred until most of $SeO_2$ dissolves. 1-(2-phenyloxazol-4-yl)ethan-1-one (0.78 g, 4.2 mmol) was added, and the reaction was heated to gentle reflux overnight. Selenium solids precipitated during the course of the reaction. The mixture was cooled in an ice bath and filtered through diatomaceous earth to remove selenium. The filter cake was washed with portions of 1,4-dioxane. The filtrate was evaporated to dryness and dissolved in EtOH (40 ml). Ethylthiosemicarbazide (0.99 g, 2 eq) and 3 drops of $H_2SO_4$ were added. The stirred reaction mixture was heated to reflux for 4 h. The formed precipitate was filtered, washed with EtOH, aq.sat. $Na_2CO_3$, water, $Et_2O$, and dried. Yield 0.19 g (11.3%). LC-MS 1.51 min, m/z 404.6 [MH]+. $^1$H-NMR (400 MHz, DMSO-d6), δ (ppm): 11.65 (s, 1H), 10.76 (s, 1H), 8.93 (t, J=5.7 Hz, 1H), 8.77 (s, 1H), 7.82 (s, 1H), 7.60-7.30 (m, 5H), 6.87 (t, J=5.9 Hz, 1H), 3.67-3.53 (m, 2H), 3.29-3.19 (m, 2H), 1.16 (t, J=7.1 Hz, 3H), 0.88 (t, J=7.1 Hz, 3H).

Synthesis of Compound 96

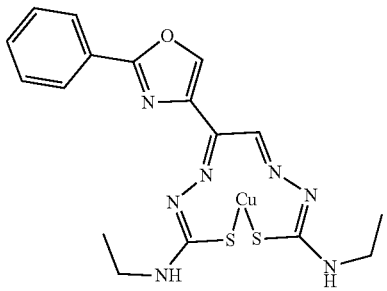

Copper(II) chloride dihydrate (0.077 g, 1 eq) was added to a stirred solution of INT-96 (0.18 g, 0.45 mmol) in ethanol. The mixture was stirred for 15 h at rt. The formed complex precipitated as a red-brown powder. The precipitate was collected by filtration, washed with water, diethyl ether, and dried Yield 0.11 g (52.2%).

Scheme 58: Synthesis of Compound 97

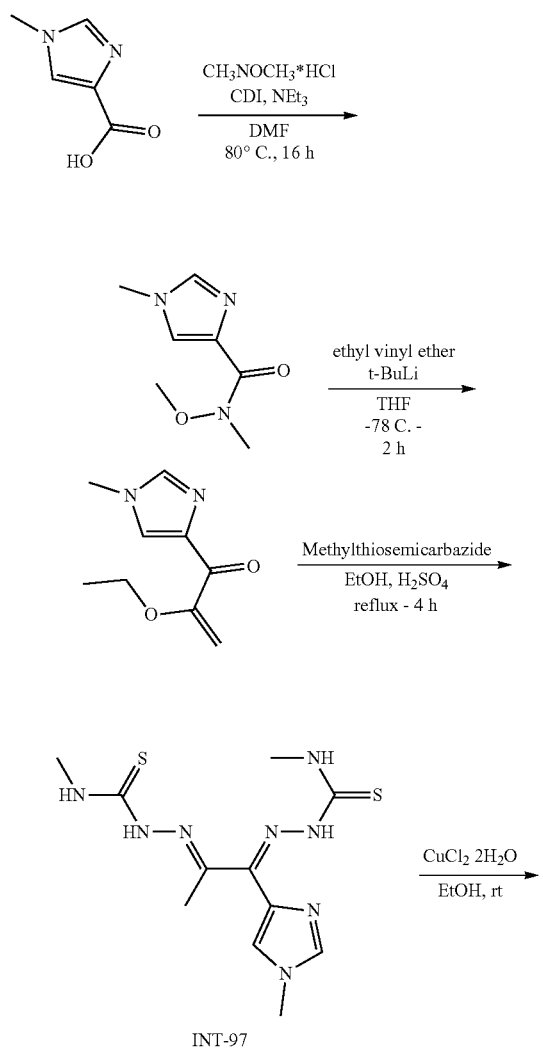

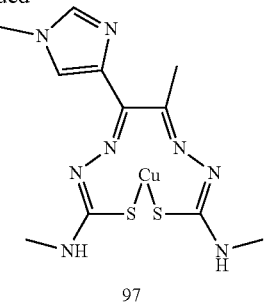

97

Synthesis of N-methoxy-N,1-dimethyl-1H-imidazole-4-carboxamide

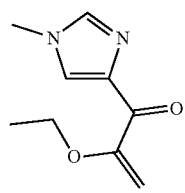

A mixture of 1-methyl-1H-imidazole-4-carboxylic acid (2.7 g, 22 mmol) and 1,1'-carbonyldiimidazole (4.21 g, 1.2 eq) in DMF (100 mL) was stirred at 60° C. for 30 min. Then N,O-dimethylhydroxylamine (2.11 g, 1 eq) and triethylamine (2.41 g, 3.3 ml, 1.1 eq) were added. The mixture was stirred at 80° C. for 16 h, then the volatiles were evaporated in vacuo, and the residue was partitioned between EtOAc and $H_2O$. The organic layer was separated, dried over anh. $Na_2SO_4$, filtered, and solvents were evaporated in vacuo. The residue was purified by column chromatography (silica gel, eluent DCM 100% to DCM/MeOH 98:2 v/v). Yield 1.24 g (33.9%). LC-MS 0.64 min, m/z 170.3 [MH]+. $^1$H-NMR (400 MHz, CDCl$_3$), δ (ppm): 7.51 (d, J=20.8 Hz, 1H), 7.45 (s, 1H), 3.73 (t, J=12.7 Hz, 6H), 3.46 (d, J=11.0 Hz, 3H).

Synthesis of 2-ethoxy-1-(1-methyl-1H-imidazol-4-yl)prop-2-en-1-one

A solution of ethyl vinyl ether (3.4 g, 4.5 ml, 6.6 eq) in dry THF (100 ml) was cooled to −78° C., and tert-butyllithium (1.7M in pentane, 24 ml, 6 eq) was added. The mixture was warmed to 0° C. over 1 h period, stirred for 45 min, and then cooled down to −30° C. A solution of N-methoxy-N,1-dimethyl-1H-imidazole-4-carboxamide (1.2 g, 7 mmol) in THF (15 ml) was added, and stirring continued at 0° C. for 4 h. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used in the next step without additional purification. Yield 1 g (78.2%). LC-MS 0.76 min, m/z 181.1 [MH]+.

Synthesis of INT-97 ((2E,2'E)-2,2'-(1-(1-methyl-1H-imidazol-4-yl)propane-1,2-diylidene)bis(N-methyl-hydrazine-1-carbothioamide))

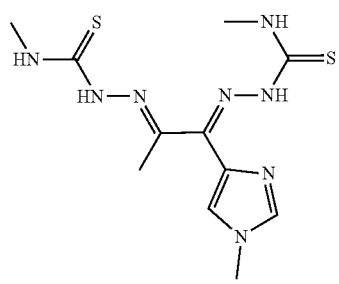 [SMILES: CNC(=S)N/N=C(C)/C(=N/NC(=S)NC)c1cn(C)cn1]

2-ethoxy-1-(1-methyl-1H-imidazol-4-yl)prop-2-en-1-one (0.5 g, 2.7 mmol) was dissolved in EtOH (15 ml), methyl-thiosemicarbazide (0.58 g, 2 eq) and 2 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.17 g (18.8%). LC-MS 1.11 min, m/z 327.4 [MH]+.

Synthesis of Compound 97

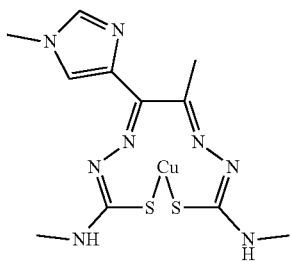

Copper(II) chloride dihydrate (0.1 g, 1 eq) was added to a stirred solution of INT-97 (0.17 g, 0.52 mmol) in ethanol. The mixture was stirred for 15 h at rt. The formed complex precipitated as a red-brown powder. The precipitate was collected by filtration, washed with water, diethyl ether, and dried. Yield 0.043 g (21.3%).

Scheme 59: Synthesis of Compound 98

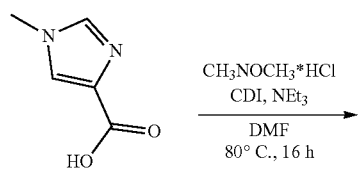

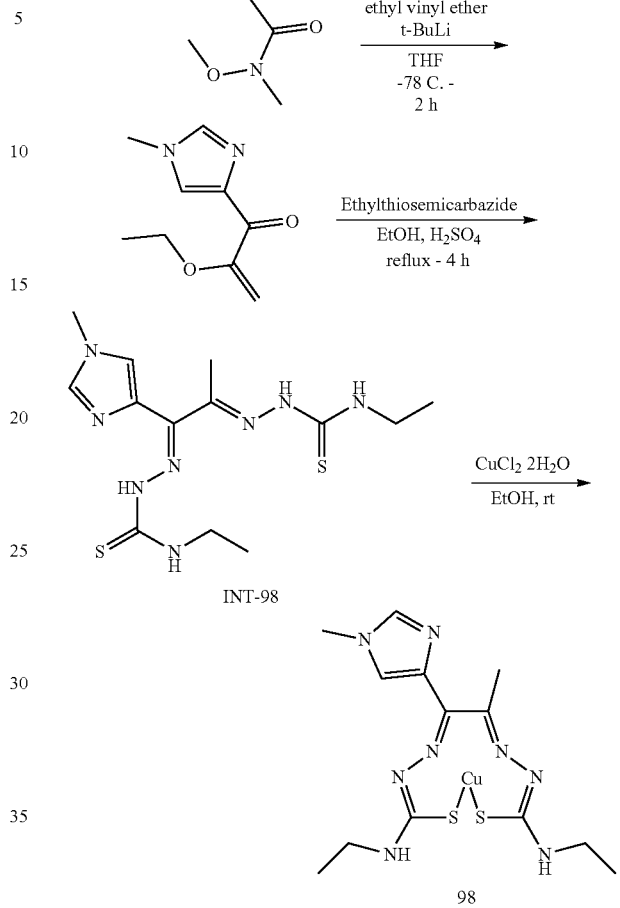

Synthesis of INT-98 ((2E,2'E)-2,2'-(1-(1-methyl-1H-imidazol-4-yl)propane-1,2-diylidene)bis(N-ethylhydrazine-1-carbothioamide))

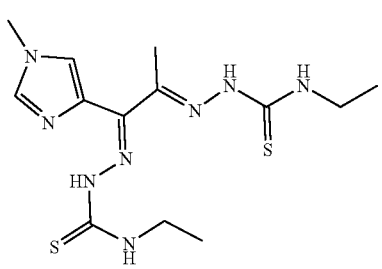 [SMILES: CCNC(=S)N/N=C(C)/C(=N/NC(=S)NCC)c1cn(C)cn1]

2-ethoxy-1-(1-methyl-1H-imidazol-4-yl)prop-2-en-1-one (0.5 g, 2.7 mmol) was dissolved in EtOH (15 ml), ethylthiosemicarbazide (0.66 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.134 g (13.6%). LC-MS 1.32 min, m/z 355.6 [MH]+.

Synthesis of Compound 98

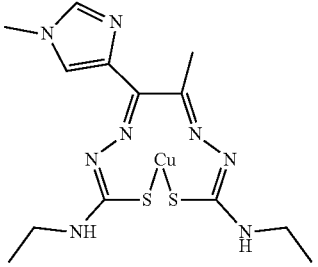

Copper(II) chloride dihydrate (0.065 g, 1 eq) was added to a stirred solution of INT-98 (0.115 g, 0.32 mmol) in ethanol. The mixture was stirred for 15 h at rt. The formed complex precipitated as a red-brown powder. The precipitate was collected by filtration, washed with water, diethyl ether, and dried. Yield 0.072 g (53.4%).

Scheme 60: Synthesis of Compound 99

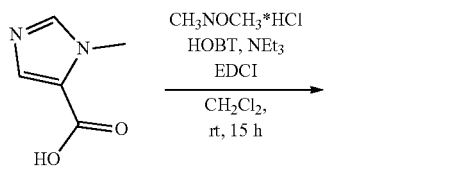

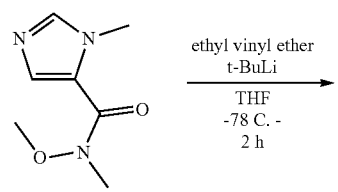

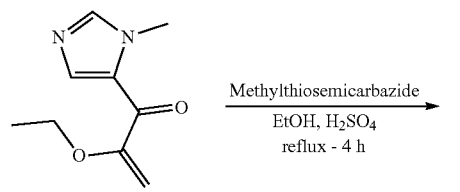

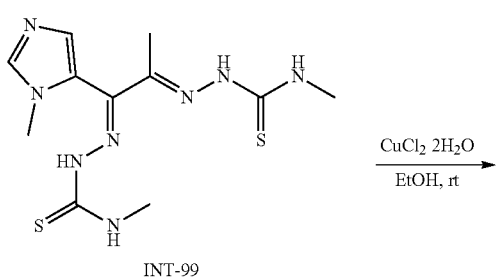

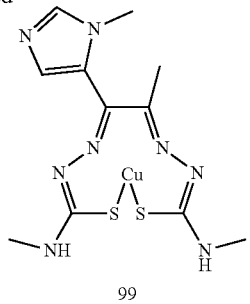

99

Synthesis of N-methoxy-N,1-dimethyl-1H-imidazole-5-carboxamide

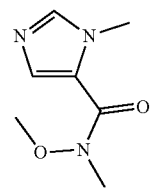

To a stirred mixture of 1-methyl-1H-imidazole-5-carboxylic acid (1.07 g, 8.4 mmol), N,O-dimethylhydroxylamine (0.99 g, 1.2 eq), HOBt (1.56 g, 1.2 eq), and triethylamine (2.2 ml, 1.6 g, 2 eq) in DCM (50 ml) at 5° C. was added EDCl (1.85 g, 1.2 eq) and reaction was stirred for 15 h at rt. The mixture was washed with water and brine. The organic layer was dried over anh. Na$_2$SO$_4$ and then concentrated under reduced pressure. The product was purified by column chromatography (silica gel, eluent 100% DCM to DCM/MeOH 99:1). Yield 0.6 g (41.8%). LC-MS 0.38 min, m/z 169.9 [MH]+. $^1$H-NMR (400 MHz, CDCl$_3$), δ (ppm): 7.75 (s, 1H), 7.55 (d, J=19.3 Hz, 1H), 3.96-3.89 (m, 3H), 3.78-3.64 (m, 3H), 3.38-3.28 (m, 3H).

Synthesis of 2-ethoxy-1-(1-methyl-1H-imidazol-5-yl)prop-2-en-1-one

A solution of ethyl vinyl ether (1.57 g, 2.1 ml, 6.6 eq) in dry THF (20 ml) was cooled to −78° C., and tert-butyllithium (1.7M in pentane, 12 ml, 6 eq) was added. The mixture was warmed to 0° C. over 1 h period, stirred for 45 min, and then cooled down to −30° C. A solution of N-methoxy-N,1-dimethyl-1H-imidazole-5-carboxamide (0.56 g, 7 mmol) in THF (15 ml) was added, and stirring continued at 0° C. for 4 h. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used for the next step without additional purification. Yield 0.5 g (83.8%). LC-MS 0.91 min, m/z 180.9 [MH]+.

Synthesis of INT-99 ((2E,2'E)-2,2'-(1-(1-methyl-1H-imidazol-5-yl)propane-1,2-diylidene)bis(N-methyl-hydrazine-1-carbothioamide))

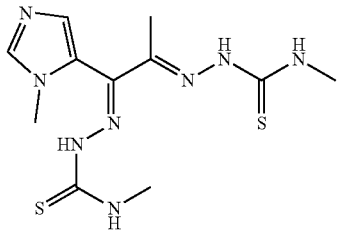 [SMILES: CNC(=S)N/N=C(C)/C(=N/NC(=S)NC)c1cncn1C]

2-ethoxy-1-(1-methyl-1H-imidazol-5-yl)prop-2-en-1-one (0.25 g, 1.4 mmol) was dissolved in EtOH (15 ml), methylthiosemicarbazide (0.29 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.073 g (16.1%). LC-MS 0.91 min, m/z 327.1 [MH]+.

Synthesis of Compound 99

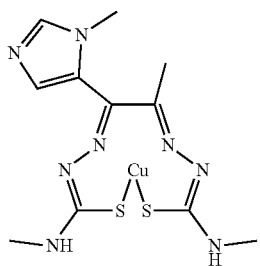

Copper(II) chloride dihydrate (0.038 g, 1 eq) was added to a stirred solution of INT-99 (0.073 g, 0.22 mmol) in ethanol. The mixture was stirred for 15 h at rt. The formed complex precipitated as a red-brown powder. The precipitate was collected by filtration, washed with water, diethyl ether, and dried. Yield 0.07 g (80.5%).

Scheme 61: Synthesis of Compound 100

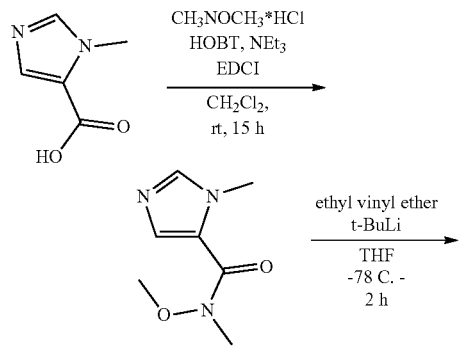

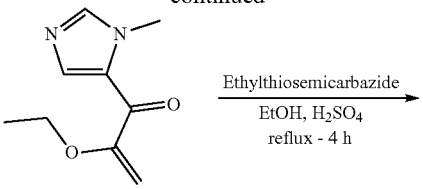

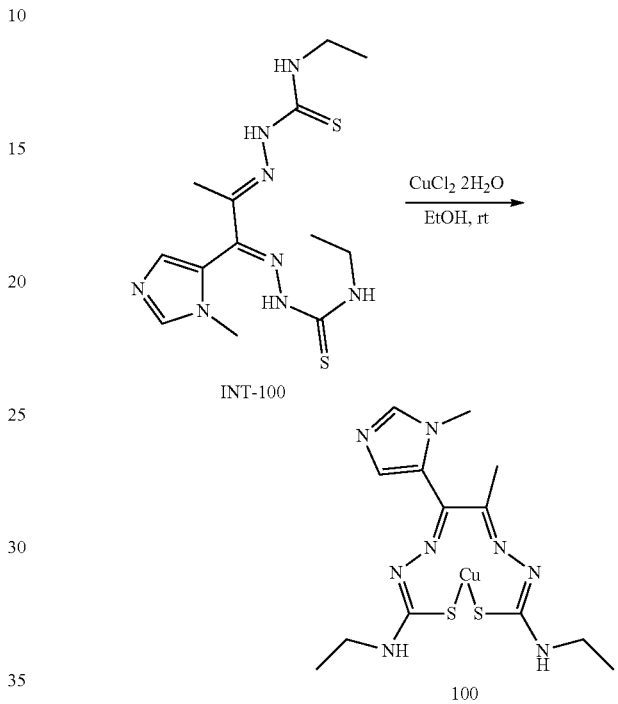

Synthesis of INT-100 ((2E,2'E)-2,2'-(1-(1-methyl-1H-imidazol-5-yl)propane-1,2-diylidene)bis(N-ethylhydrazine-1-carbothioamide))

2-ethoxy-1-(1-methyl-1H-imidazol-5-yl)prop-2-en-1-one (0.25 g, 1.4 mmol) was dissolved in EtOH (15 ml), ethylthiosemicarbazide (0.33 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.13 g (26.4%). LC-MS 1.04 min, m/z 355.5 [MH]+.

Synthesis of Compound 100

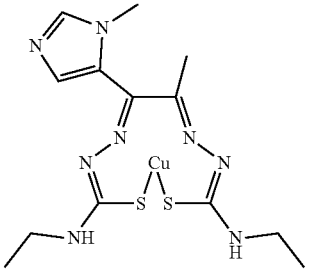

Copper(II) chloride dihydrate (0.062 g, 1 eq) was added to a stirred solution of INT-100 (0.13 g, 0.36 mmol) in ethanol. The mixture was stirred for 15 h at rt. The formed complex precipitated as a red-brown powder. The precipitate was collected by filtration, washed with water, diethyl ether, and dried. Yield 0.073 g (47.8%).

Scheme 62: Synthesis of Compound 101

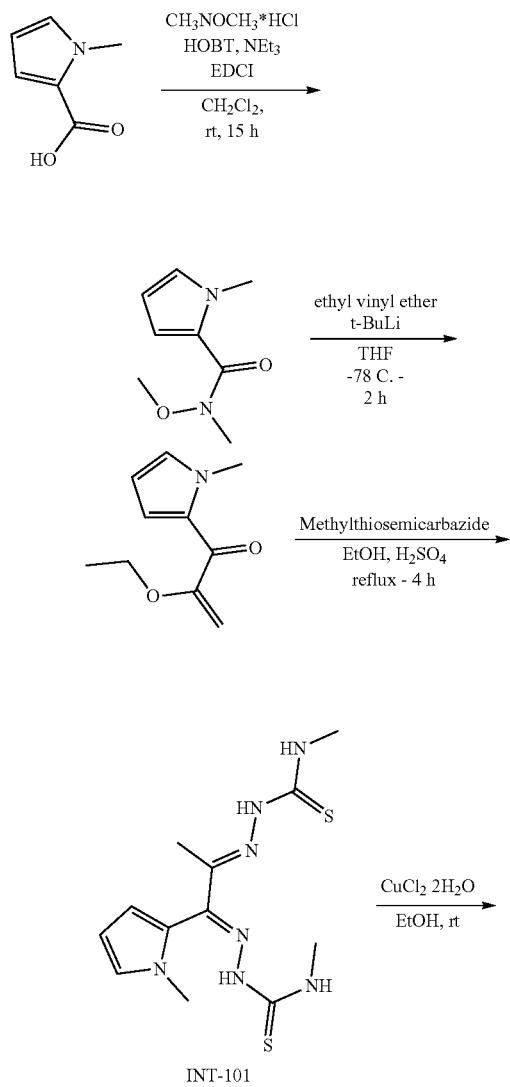

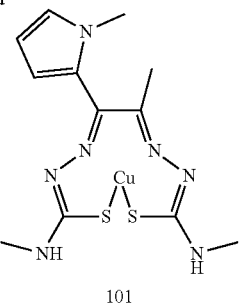

101

Synthesis of N-methoxy-N,1-dimethyl-1H-pyrrole-2-carboxamide

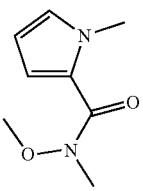

To a stirred mixture of 1-methyl-1H-pyrrole-2-carboxylic acid (5.4 g, 43.1 mmol), N,O-dimethylhydroxylamine (5.05 g, 1.2 eq), HOBt (7.93 g, 1.2 eq) and Triethylamine (12 ml, 8.7 g, 2 eq) in DCM (200 ml) at 5° C. was added EDCI (9.93 g, 1.2 eq) and reaction was stirred for 15 h at rt. The mixture was washed with water and brine. The organic layer was dried over anh. $Na_2SO_4$ and then concentrated under reduced pressure. Product was used without further purification. Yield 6.5 g (80.5%). LC-MS 0.38 min, m/z 169.9 [MH]+. $^1$H-NMR (400 MHz, $CDCl_3$), δ (ppm): 6.93 (dd, J=4.0, 1.7 Hz, 1H), 6.86-6.60 (m, 1H), 6.13 (dd, J=4.0, 2.6 Hz, 1H), 3.92 (s, 3H), 3.71 (s, 3H), 3.34 (s, 3H).

Synthesis of 2-ethoxy-1-(1-methyl-1H-pyrrol-2-yl)prop-2-en-1-one

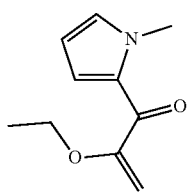

A solution of ethyl vinyl ether (4.53 g, 6 ml, 6.6 eq) in dry THF (80 ml) was cooled to −78° C., and tert-butyllithium (1.7M in pentane, 33 ml, 6 eq) was added. The mixture was warmed to 0° C. over 1 h period, stirred for 45 min, and then cooled down to −30° C. A solution of N-methoxy-N,1-dimethyl-1H-pyrrole-2-carboxamide (1.6 g, 9.5 mmol) in THF (25 ml) was added and stirring continued at 0° C. for 4 h. The mixture was poured into aq. $NH_4Cl$ (100 ml) and extracted with $Et_2O$ (3×100 ml). The combined extracts were dried over anh. $Na_2SO_4$, filtered, and solvents were evaporated in vacuo. The product was used for the next step without additional purification. Yield 1.64 g (96.2%).

Synthesis of INT-101 ((2E,2'E)-2,2'-(1-(1-methyl-1H-pyrrol-2-yl)propane-1,2-diylidene)bis(N-methyl-hydrazine-1-carbothioamide))

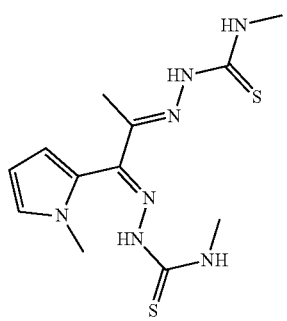 [SMILES: CNC(=S)N/N=C(C)/C(=N/NC(=S)NC)c1cccn1C]

2-ethoxy-1-(1-methyl-1H-pyrrol-2-yl)prop-2-en-1-one (0.82 g, 4.6 mmol) was dissolved in EtOH (15 ml), methylthiosemicarbazide (0.96 g, 2 eq) and 3 drops of $H_2SO_4$ were added. The stirred reaction mixture was heated to reflux for 4 h and then maintained for 15 h at rt. The solvent was evaporated in vacuo. The residue was dissolved in EtOAc and washed with aq.sat. $NaHCO_3$, water, dried with anh. $Na_2SO_4$, and concentrated under reduced pressure. The residue was purified by column chromatography (silica gel, eluent $CCl_4$/EtOAc 7:3). Yield 0.22 g (14.5%). LC-MS 1.34 min, m/z 326.5 [MH]+.

Synthesis of Compound 101

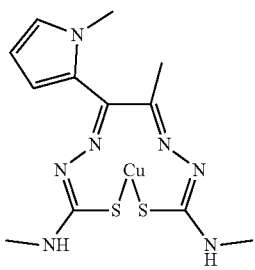

Copper(II) chloride dihydrate (0.12 g, 1 eq) was added to a stirred solution of INT-101 (0.22 g, 0.66 mmol) in ethanol. The mixture was stirred for 15 h at rt. The formed complex precipitated as a red-brown powder. The precipitate was collected by filtration, washed with water, diethyl ether, and dried. Yield 0.22 g (84.1%).

Scheme 63: Synthesis of Compound 102

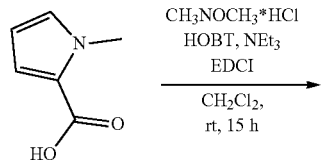

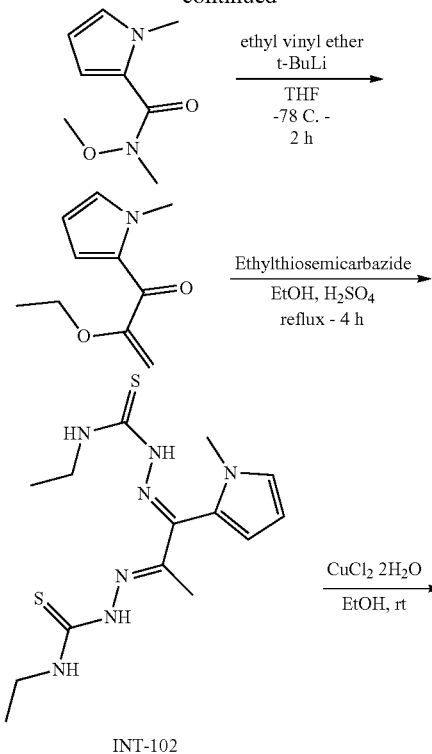

INT-102

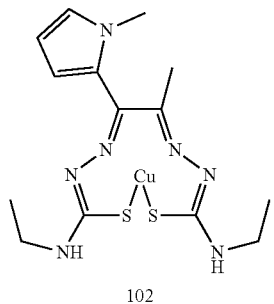

102

Synthesis of INT-102 ((2E,2'E)-2,2'-(1-(1-methyl-1H-pyrrol-2-yl)propane-1,2-diylidene)bis(N-ethyl-hydrazine-1-carbothioamide))

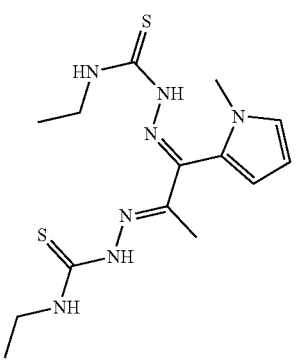 [SMILES: CCNC(=S)N/N=C(C)/C(=N/NC(=S)NCC)c1cccn1C]

2-ethoxy-1-(1-methyl-1H-pyrrol-2-yl)prop-2-en-1-one (0.82 g, 4.6 mmol) was dissolved in EtOH (15 ml), ethylthiosemicarbazide (1.1 g, 2 eq) and 3 drops of $H_2SO_4$ were added. The stirred reaction mixture was heated to reflux for 4 h and then maintained for 15 h at rt. The solvent was evaporated in vacuo. The residue was dissolved in EtOAc and washed with aq.sat. NaHCO₃, water, dried with anh. Na₂SO₄ and concentrated under reduced pressure. The residue was purified by column chromatography (silica gel, eluent CCl₄/EtOAc 7:3). Yield 0.13 g (8.03%). LC-MS 1.56 min, m/z 354.3 [MH]+.

Synthesis of Compound 102

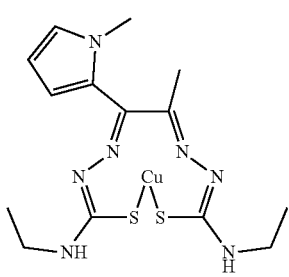

Copper(II) chloride dihydrate (0.06 g, 1 eq) was added to a stirred solution of INT-102 (0.13 g, 0.37 mmol) in ethanol. The mixture was stirred for 15 h at rt. The formed complex precipitated as a red-brown powder; precipitate was collected by filtration, washed with water, diethyl ether, and dried. Yield 0.13 g (91%).

Scheme 64: Synthesis of Compound 103

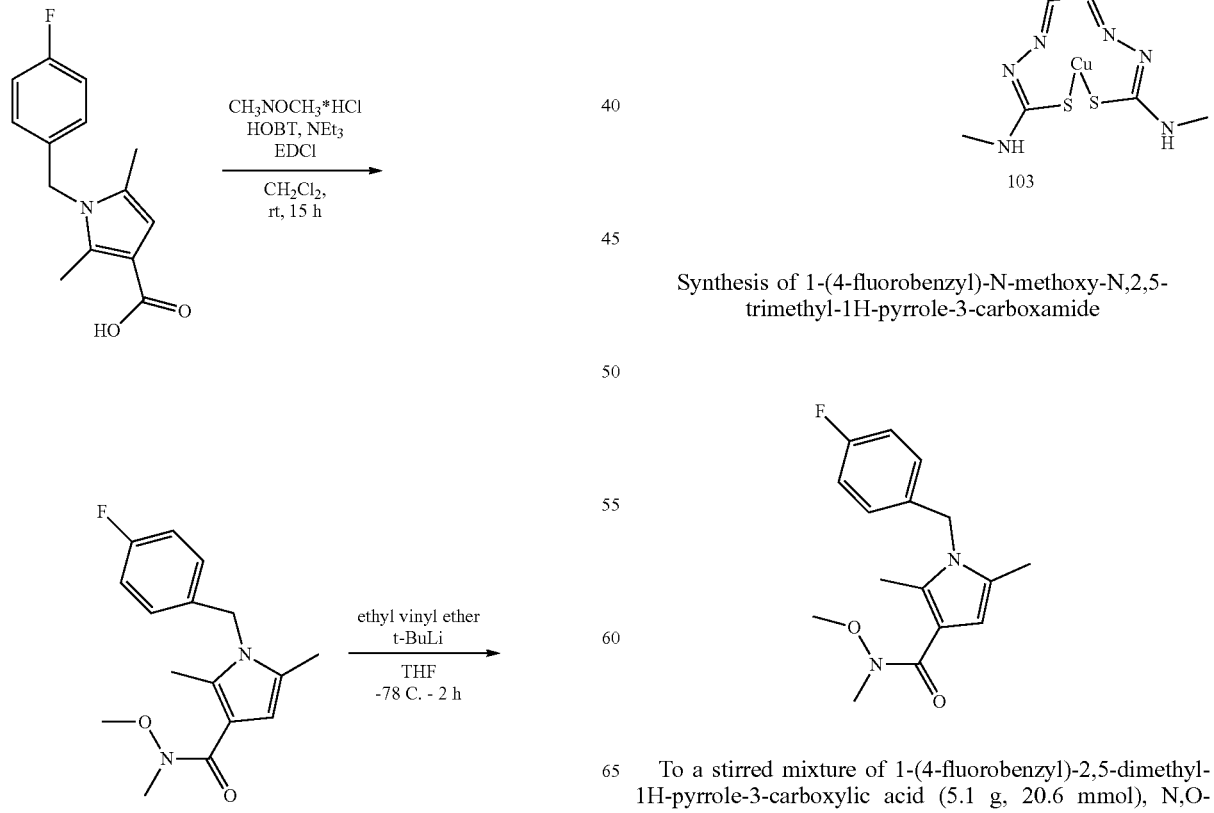

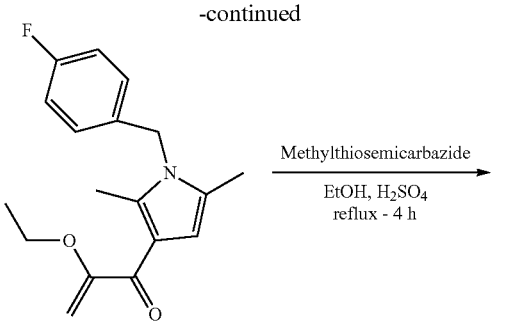

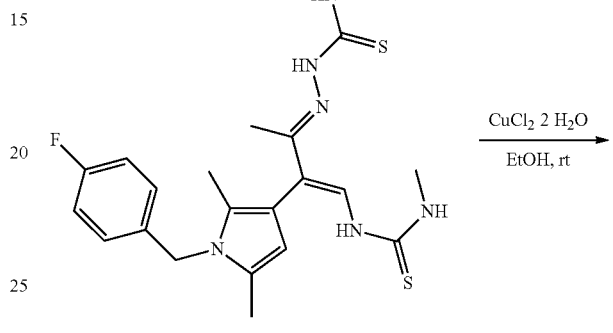

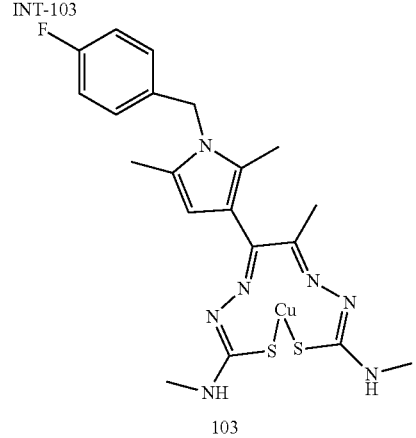

Synthesis of 1-(4-fluorobenzyl)-N-methoxy-N,2,5-trimethyl-1H-pyrrole-3-carboxamide

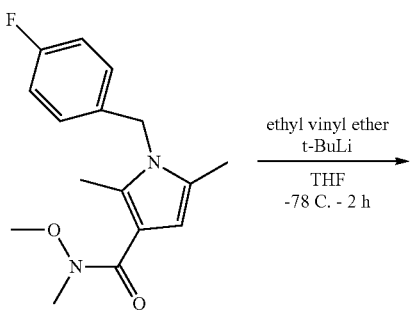

To a stirred mixture of 1-(4-fluorobenzyl)-2,5-dimethyl-1H-pyrrole-3-carboxylic acid (5.1 g, 20.6 mmol), N,O-dimethylhydroxylamine (2.41 g, 1.2 eq), HOBt (3.8 g, 1.2 eq), and triethylamine (5.7 ml, 6.3 g, 2 eq) in DCM (200 ml) at 5° C. was added EDCl (4.74 g, 1.2 eq) and reaction was then stirred for 15 h at rt. The mixture was washed with water and brine. The organic layer was dried over anh. Na$_2$SO$_4$ and then concentrated under reduced pressure. The residue was purified by column chromatography (silica gel, eluent hexane/EtOAc 2:1). Yield 2.8 g (46.8%). LC-MS 1.51 min, m/z 291.3 [MH]+. $^1$H-NMR (400 MHz, CDCl$_3$), δ (ppm): 6.99 (d, J=6.3 Hz, 2H), 6.87 (s, 2H), 6.32 (s, 1H), 5.01 (s, 2H), 3.80-3.61 (m, 3H), 3.46-3.13 (m, 3H), 2.41 (s, 3H), 2.13 (s, 3H).

Synthesis of 2-ethoxy-1-(1-(4-fluorobenzyl)-2,5-dimethyl-1H-pyrrol-3-yl)prop-2-en-1-one

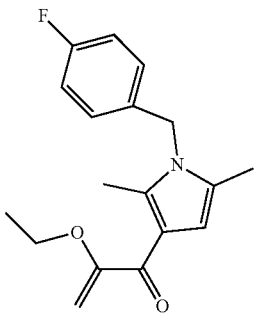 [SMILES: C=C(OCC)C(=O)c1cc(C)n(Cc2ccc(F)cc2)c1C]

A solution of ethyl vinyl ether (1.97 g, 2.61 ml, 6.6 eq) in dry THF (50 ml) was cooled to −78° C., and tert-butyl-lithium (1.7M in pentane, 14 ml, 6 eq) was added. The mixture was warmed to 0° C. over 1 h period, stirred for 45 min, and then cooled down to −30° C. A solution of 1-(4-fluorobenzyl)-N-methoxy-N,2,5-trimethyl-1H-pyrrole-3-carboxamide (1.2 g, 4.1 mmol) in THF (25 ml) was added and stirring continued for 4 h at 0° C. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used for the next step without additional purification. Yield 1.2 g (96.3%). LC-MS 1.70 min, m/z 302.3 [MH]+.

Synthesis of INT-103 ((2E,2'E)-2,2'-(1-(1-(4-fluorobenzyl)-2,5-dimethyl-1H-pyrrol-3-yl)propane-1,2-diylidene)bis(N-methylhydrazine-1-carbothioamide))

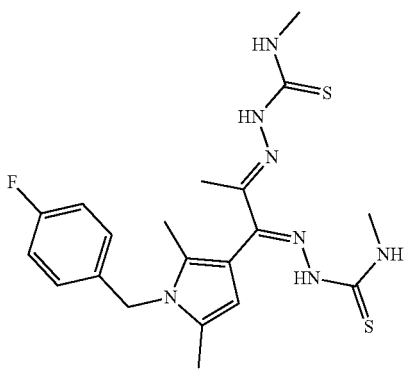 [SMILES: CNC(=S)N/N=C(C)/C(=N/NC(=S)NC)c1cc(C)n(Cc2ccc(F)cc2)c1C]

2-ethoxy-1-(1-(4-fluorobenzyl)-2,5-dimethyl-1H-pyrrol-3-yl)prop-2-en-1-one (0.6 g, 2 mmol) was dissolved in EtOH (15 ml), methylthiosemicarbazide (0.42 g, 2 eq) and 3 drops of H$_2$SO$_4$ were added. The stirred reaction mixture was heated to reflux for 4 h and then maintained for 15 h at rt. The formed precipitate was filtered, washed with EtOH, aq.sat. Na$_2$CO$_3$, water, Et$_2$O, and dried. Yield 0.32 g (35.9%). LC-MS 1.68 min, m/z 448.1 [MH]+. $^1$H-NMR (400 MHz, DMSO-d6), δ (ppm): 10.58 (s, 1H), 8.99 (s, 1H), 8.62 (d, J=4.4 Hz, 1H), 7.37 (d, J=4.5 Hz, 1H), 7.17 (t, J=8.8 Hz, 2H), 7.07-6.83 (m, 2H), 5.86 (s, 1H), 5.16 (s, 2H), 3.03 (d, J=4.5 Hz, 3H), 2.86 (d, J=4.7 Hz, 3H), 2.32 (s, 3H), 2.16 (s, 3H), 1.87 (s, 3H).

Synthesis of Compound 103

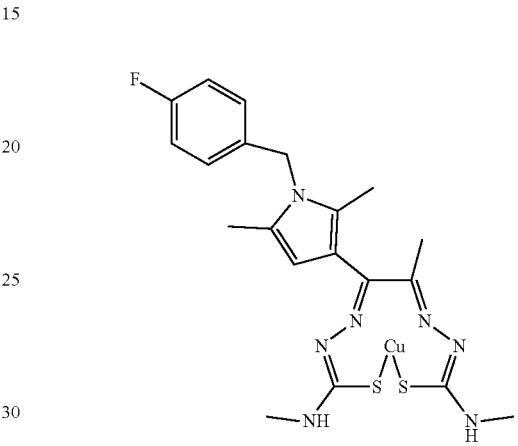

Copper(II) chloride dihydrate (0.12 g, 1 eq) was added to a stirred solution of INT-103 (0.32 g, 0.7 mmol) in ethanol. The mixture was stirred for 15 h at rt. The formed complex precipitated as a red-brown powder. The precipitate was collected by filtration, washed with water, diethyl ether, and dried. Yield 0.31 g (86.5%).

Scheme 65: Synthesis of Compound 104

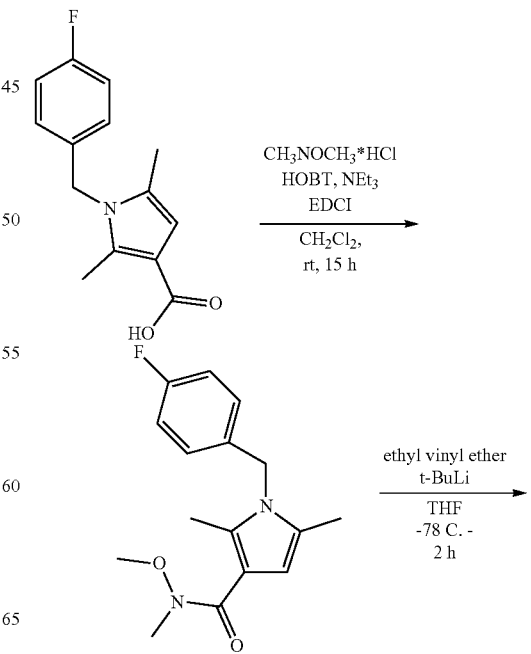

-continued

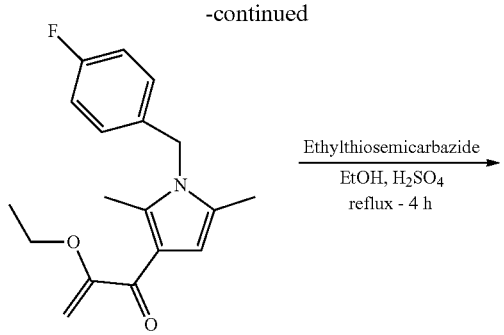
Ethylthiosemicarbazide
EtOH, H₂SO₄
reflux - 4 h

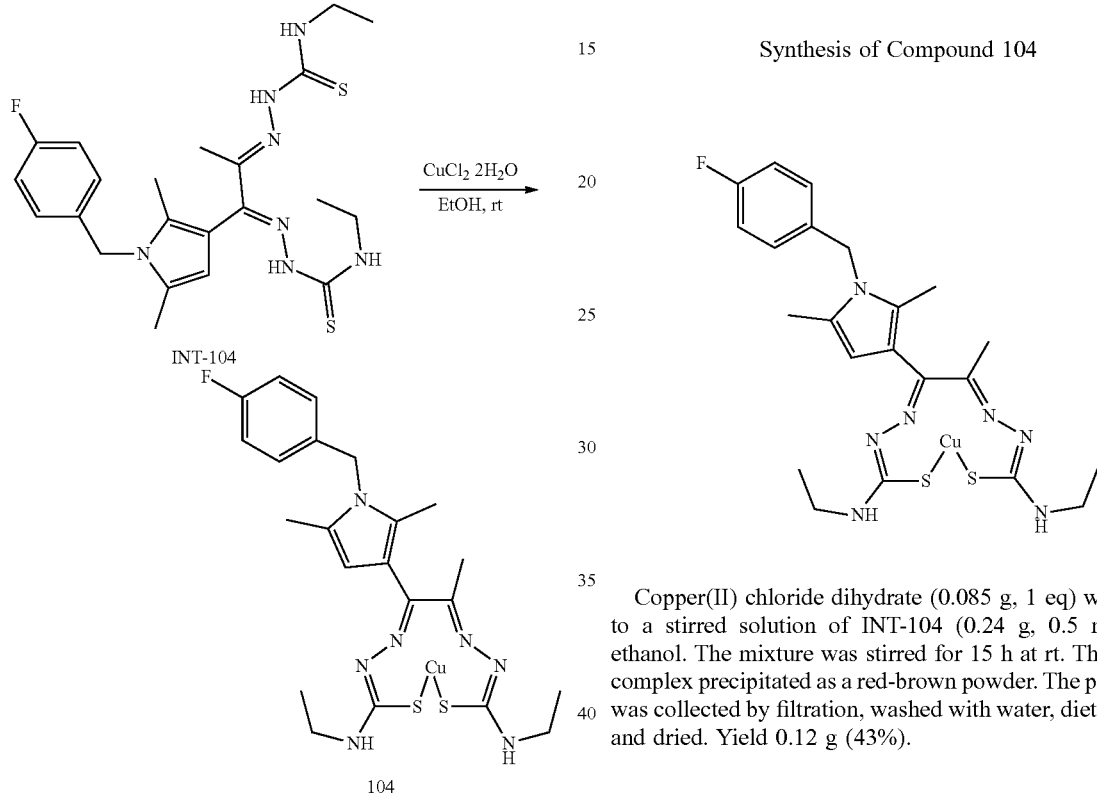

INT-104

CuCl₂ 2H₂O
EtOH, rt

104

Synthesis of INT-104 ((2E,2'E)-2,2'-(1-(1-(4-fluorobenzyl)-2,5-dimethyl-1H-pyrrol-3-yl)propane-1,2-diylidene)bis(N-ethylhydrazine-1-carbothioamide))

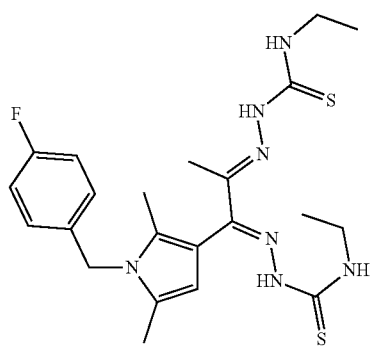 [SMILES: CCNC(=S)N/N=C(C)/C(=N/NC(=S)NCC)c1cc(C)n(Cc2ccc(F)cc2)c1C]

2-ethoxy-1-(1-(4-fluorobenzyl)-2,5-dimethyl-1H-pyrrol-3-yl)prop-2-en-1-one (0.6 g, 2 mmol) was dissolved in EtOH (15 ml), ethylthiosemicarbazide (0.47 g, 2 eq) and 3 drops of H₂SO₄ were added. The stirred reaction mixture was heated to reflux for 4 h and then maintained for 15 h at rt. The formed precipitate was filtered, washed with EtOH, aq.sat. Na₂CO₃, water, Et₂O, and dried. Yield 0.24 g (25.3%). LC-MS 1.83 min, m/z 476.5 [MH]+. $^1$H-NMR (400 MHz, DMSO-d6), δ (ppm): 10.58-10.25 (m, 1H), 8.90 (s, 1H), 8.67 (t, J=5.9 Hz, 1H), 7.37 (s, 1H), 7.17 (t, J=8.8 Hz, 2H), 7.07-6.87 (m, 2H), 5.87 (s, 1H), 5.16 (s, 2H), 3.67-3.54 (m, 2H), 3.40 (dd, J=13.5, 7.0 Hz, 2H), 2.32 (s, 3H), 2.12 (d, J=20.2 Hz, 3H), 1.89 (s, 3H), 1.15 (t, J=7.1 Hz, 3H), 0.92 (t, J=7.2 Hz, 3H).

Synthesis of Compound 104

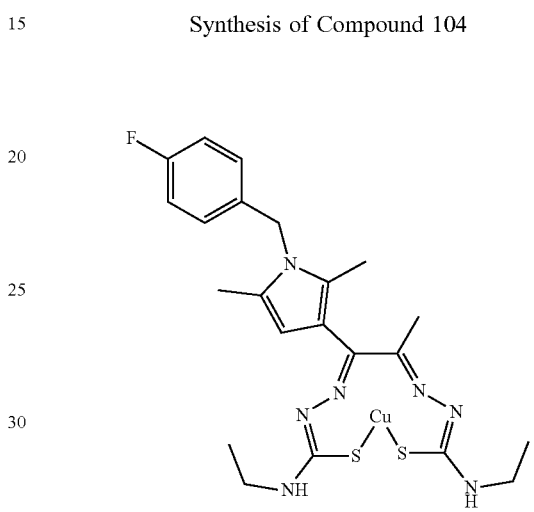

Copper(II) chloride dihydrate (0.085 g, 1 eq) was added to a stirred solution of INT-104 (0.24 g, 0.5 mmol) in ethanol. The mixture was stirred for 15 h at rt. The formed complex precipitated as a red-brown powder. The precipitate was collected by filtration, washed with water, diethyl ether, and dried. Yield 0.12 g (43%).

Scheme 66: Synthesis of Compound 105

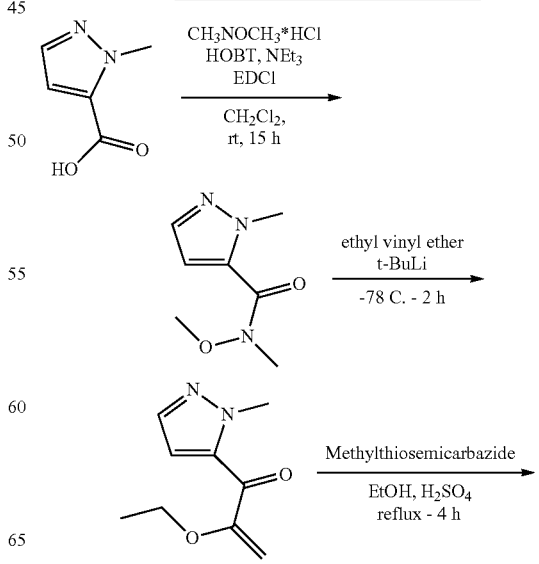

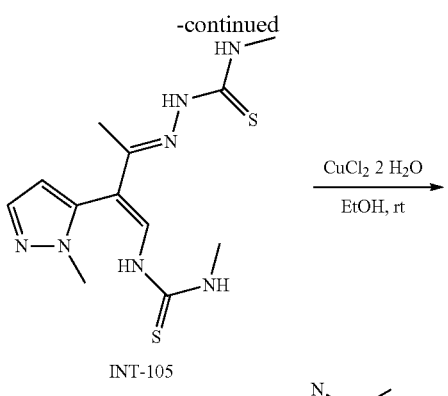

INT-105

CuCl₂ 2 H₂O
———————→
EtOH, rt

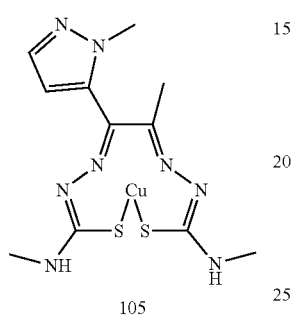

105

Synthesis of N-methoxy-N,1-dimethyl-1H-pyrazole-5-carboxamide

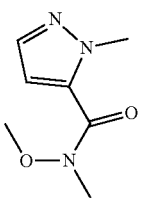

To a stirred mixture of 1-methyl-1H-pyrazole-5-carboxylic acid (4 87 g, 38.6 mmol), N,O-dimethylhydroxylamine (4.52 g, 1.2 eq), HOBt (6.26 g, 1.2 eq), and triethylamine (13.6 ml, 9.88 g, 2.5 eq) in DCM (200 ml) at 5° C. was added EDCl (8.88 g, 1.2 eq) and reaction was then stirred for 15 h at rt. The mixture was washed with water and brine. The organic layer was dried over anh. Na₂SO₄ and then concentrated under reduced pressure. The product was used without further purification. Yield 6.45 g (98.7%). LC-MS 0.86 min, m/z 170.4 [MH]+. ¹H-NMR (400 MHz, CDCl₃), δ (ppm): 7.47 (d, J=2.0 Hz, 1H), 6.76 (d, J=2.0 Hz, 1H), 4.12 (s, 3H), 3.67 (d, J=11.4 Hz, 3H), 3.35 (s, 3H).

Synthesis of 2-ethoxy-1-(1-methyl-1H-pyrazol-5-yl)prop-2-en-1-one

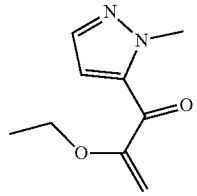

A solution of ethyl vinyl ether (2.25 g, 3 ml, 3.3 eq) in dry THF (100 ml) was cooled to −78° C., and tert-butyllithium (1.7M in pentane, 17.5 ml, 3 eq) was added. The mixture was warmed to 0° C. over 1 h period, stirred for 45 min, and then cooled down to −30° C. A solution of N-methoxy-N,1-dimethyl-1H-pyrazole-5-carboxamide (1.6 g, 9.5 mmol) in THF (25 ml) was added and stirring continued at 0° C. for 4 h. The mixture was poured into aq. NH₄Cl (100 ml) and extracted with Et₂O (3×100 ml). The combined extracts were dried over anh. Na₂SO₄, filtered, and solvents were evaporated in vacuo. The product was used for the next step without additional purification. Yield 1.7 g (99%). LC-MS 1.29 min, m/z 181.1 [MH]+.

Synthesis of INT-105 ((2E,2'E)-2,2'-(1-(1-methyl-1H-pyrazol-5-yl)propane-1,2-diylidene)bis(N-methylhydrazine-1-carbothioamide))

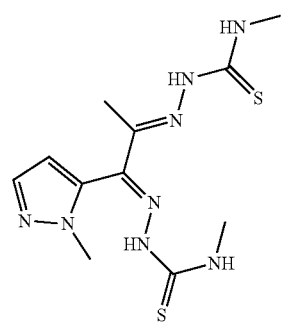 [SMILES: CNC(=S)N/N=C(C)/C(=N/NC(=S)NC)c1ccnn1C]

2-ethoxy-1-(1-methyl-1H-pyrazol-5-yl)prop-2-en-1-one (1.7 g, 9.5 mmol) was dissolved in EtOH (50 ml), methylthiosemicarbazide (2 g, 2 eq) and 3 drops of H₂SO₄ were added. The stirred reaction mixture was heated to reflux for 4 h and then maintained for 15 h at rt. The formed precipitate was filtered, washed with EtOH, aq.sat. Na₂CO₃, water, Et₂O, and dried. Yield 1.81 g (58.6%). LC-MS 1.17 min, m/z 327.5 [MH]+. ¹H-NMR (400 MHz, DMSO-d6), δ (ppm): 10.70 (s, 1H), 9.43 (s, 1H), 8.75 (d, J=4.5 Hz, 1H), 7.61 (d, J=1.9 Hz, 1H), 7.09 (d, J=4.6 Hz, 1H), 6.41 (d, J=1.9 Hz, 1H), 3.57 (s, 3H), 3.02 (t, J=11.5 Hz, 3H), 2.89 (t, J=4.7 Hz, 3H), 2.37 (s, 3H).

Synthesis of Compound 105

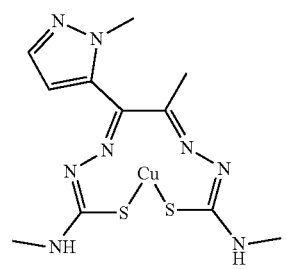

Copper(II) chloride dihydrate (0.19 g, 1 eq) was added to a stirred solution of INT-105 (0.36 g, 1.1 mmol) in ethanol. The mixture was stirred for 15 h at rt. The formed complex precipitated as a red-brown powder. The precipitate was collected by filtration, washed with water, diethyl ether, and dried. Yield 0.38 g (87%).

Scheme 67: Synthesis of Compound 106

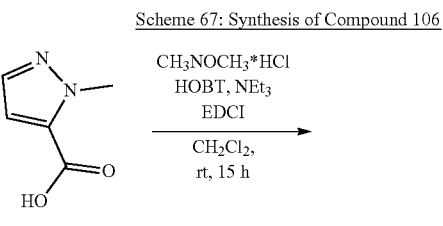

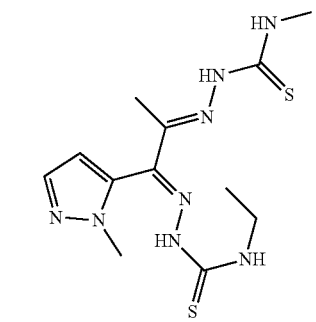 [SMILES: CCNC(=S)N/N=C(/C(C)=N/NC(=S)NC)c1ccnn1C]

Synthesis of INT-106 ((2E,2'E)-2,2'-(1-(1-methyl-1H-pyrazol-5-yl)propane-1,2-diylidene)bis(N-ethyl-hydrazine-1-carbothioamide))

2-ethoxy-1-(1-methyl-1H-pyrazol-5-yl)prop-2-en-1-one (2.3 g, 12.9 mmol) was dissolved in EtOH (75 ml), methylthiosemicarbazide (2 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 1.81 g (58.6%). LC-MS 1.34 min, m/z 355.4 [MH]+. $^1$H-NMR (400 MHz, DMSO-d6), δ (ppm): 10.82 (s, 1H), 9.50 (s, 1H), 8.78 (s, 1H), 7.82-7.43 (m, 1H), 6.94 (s, 1H), 6.58-6.13 (m, 1H), 3.74-3.53 (m, 5H), 3.45-3.27 (m, 2H), 2.44-2.03 (m, 3H), 1.34-1.05 (m, 3H), 1.07-0.78 (m, 3H).

Synthesis of Compound 106

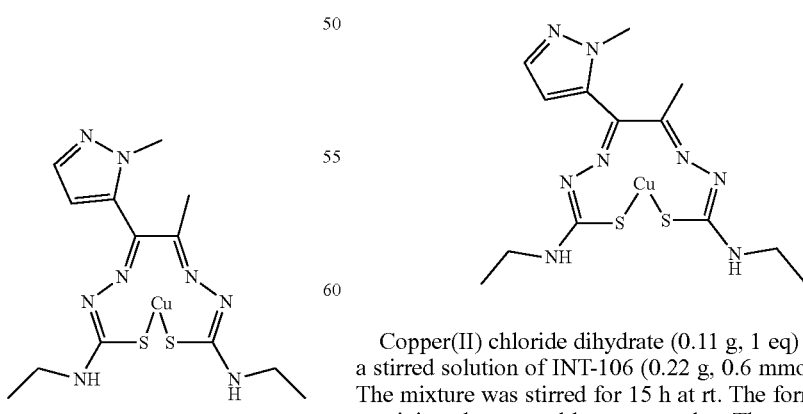

Copper(II) chloride dihydrate (0.11 g, 1 eq) was added to a stirred solution of INT-106 (0.22 g, 0.6 mmol) in ethanol. The mixture was stirred for 15 h at rt. The formed complex precipitated as a red-brown powder. The precipitate was collected by filtration, washed with water, diethyl ether, and dried. Yield 0.12 g (44.9%)

Scheme 68: Synthesis of Compound 107

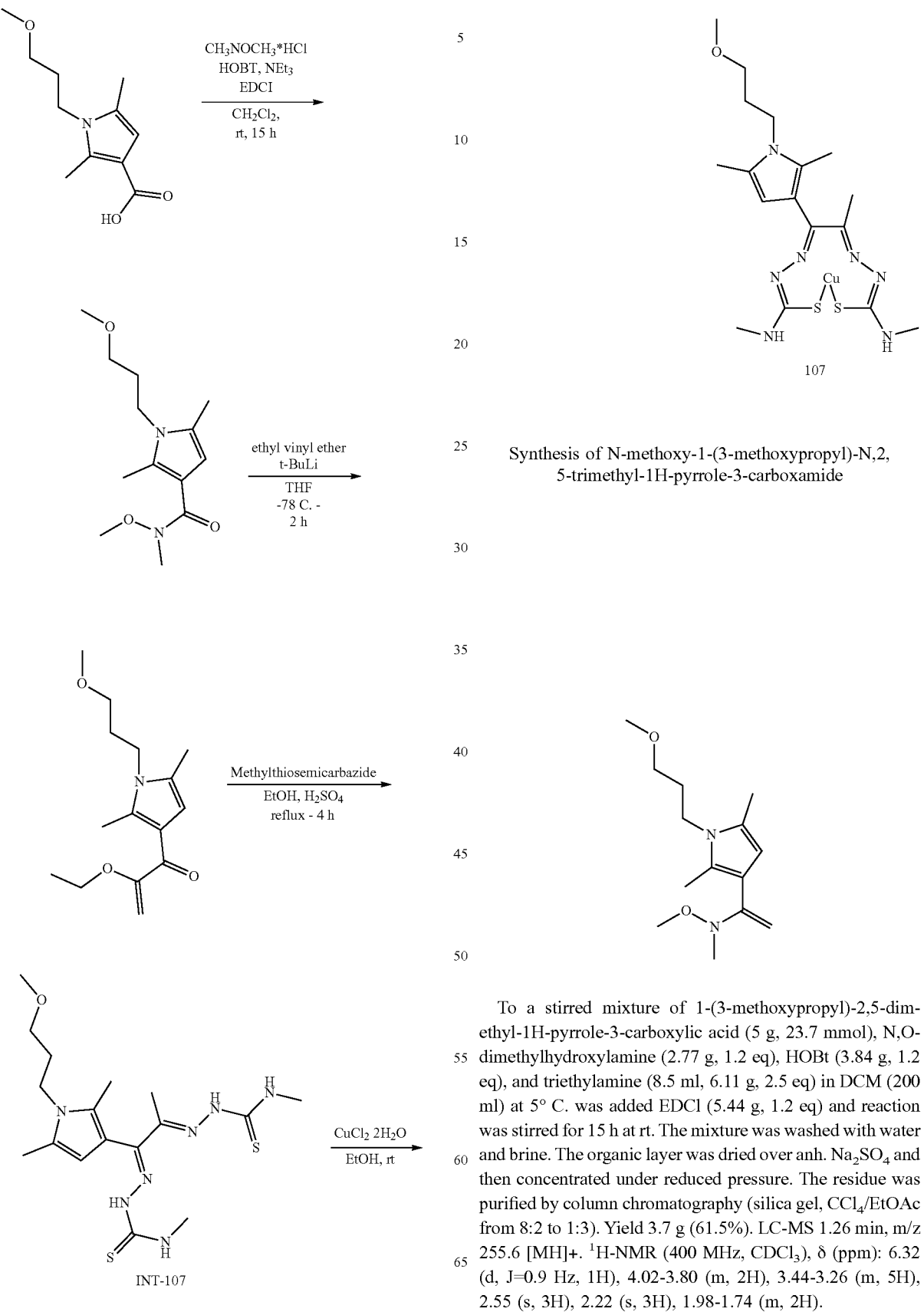

Synthesis of N-methoxy-1-(3-methoxypropyl)-N,2,5-trimethyl-1H-pyrrole-3-carboxamide To a stirred mixture of 1-(3-methoxypropyl)-2,5-dimethyl-1H-pyrrole-3-carboxylic acid (5 g, 23.7 mmol), N,O-dimethylhydroxylamine (2.77 g, 1.2 eq), HOBt (3.84 g, 1.2 eq), and triethylamine (8.5 ml, 6.11 g, 2.5 eq) in DCM (200 ml) at 5° C. was added EDCl (5.44 g, 1.2 eq) and reaction was stirred for 15 h at rt. The mixture was washed with water and brine. The organic layer was dried over anh. Na$_2$SO$_4$ and then concentrated under reduced pressure. The residue was purified by column chromatography (silica gel, CCl$_4$/EtOAc from 8:2 to 1:3). Yield 3.7 g (61.5%). LC-MS 1.26 min, m/z 255.6 [MH]+. $^1$H-NMR (400 MHz, CDCl$_3$), δ (ppm): 6.32 (d, J=0.9 Hz, 1H), 4.02-3.80 (m, 2H), 3.44-3.26 (m, 5H), 2.55 (s, 3H), 2.22 (s, 3H), 1.98-1.74 (m, 2H).

Synthesis of 2-ethoxy-1-(1-(3-methoxypropyl)-2,5-dimethyl-1H-pyrrol-3-yl)prop-2-en-1-one

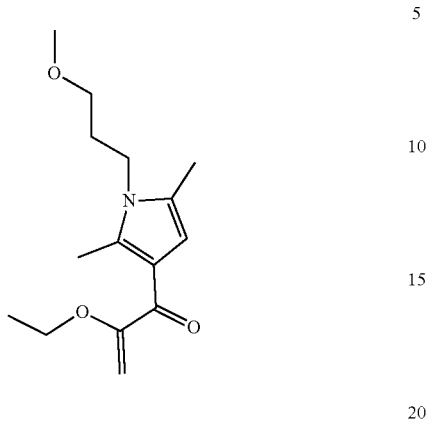

A solution of ethyl vinyl ether (1.68 g, 2.2 ml, 3.3 eq) in dry THF (100 ml) was cooled to −78° C., and tert-butyllithium (1.7M in pentane, 13.2 ml, 3 eq) was added. The mixture was warmed to 0° C. over 1 h period, stirred for 45 min, and then cooled down to −30° C. A solution of N-methoxy-1-(3-methoxypropyl)-N,2,5-trimethyl-1H-pyrrole-3-carboxamide (1.8 g, 7 mmol) in THF (25 ml) was added and stirring continued for 4 h at 0° C. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used for the next step without additional purification. Yield 1.74 g (92%). LC-MS 1.51 min, m/z 266.4 [MH]+.

Synthesis of INT-107 ((2E,2'E)-2,2'-(1-(1-(3-methoxypropyl)-2,5-dimethyl-1H-pyrrol-3-yl)propane-1,2-diylidene)bis(N-methylhydrazine-1-carbothioamide))

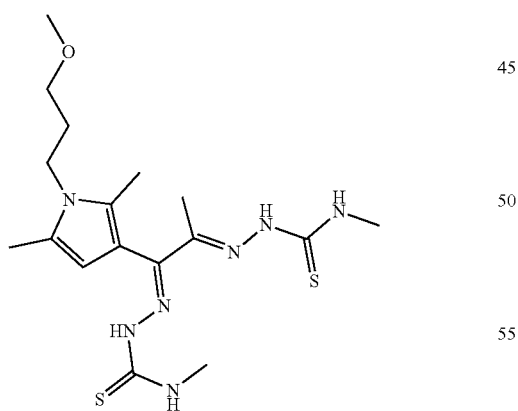

2-ethoxy-1-(1-(3-methoxypropyl)-2,5-dimethyl-1H-pyrrol-3-yl)prop-2-en-1-one (0.85 g, 3.2 mmol) was dissolved in EtOH (50 ml), methylthiosemicarbazide (0.67 g, 2 eq) and 3 drops of H$_2$SO$_4$ were added. The stirred reaction mixture was heated to reflux for 4 h and then maintained for 15 h at rt. The formed precipitate was filtered, washed with EtOH, aq.sat. Na$_2$CO$_3$, water, Et$_2$O, and dried. Yield 0.5 g (37.5%). LC-MS 1.78 min, m/z 412.5 [MH]+.

Synthesis of Compound 107

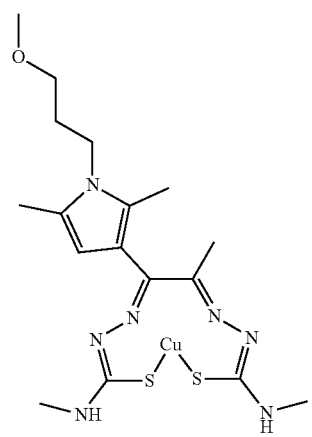

Copper(II) chloride dihydrate (0.06 g, 1 eq) was added to a stirred solution of INT-107 (0.155 g, 0.4 mmol) in ethanol. The mixture was stirred for 15 h at rt. The formed complex precipitated as a red-brown powder. The precipitate was collected by filtration, washed with water, diethyl ether, and dried. Yield 0.037 g (20.7%).

Scheme 69: Synthesis of Compound 108

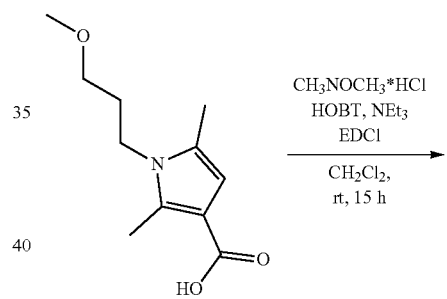

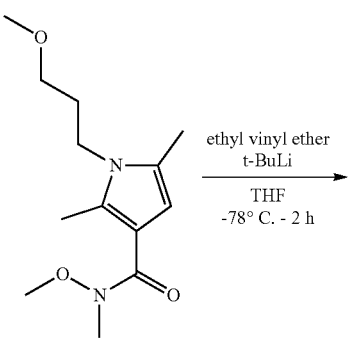

407
-continued

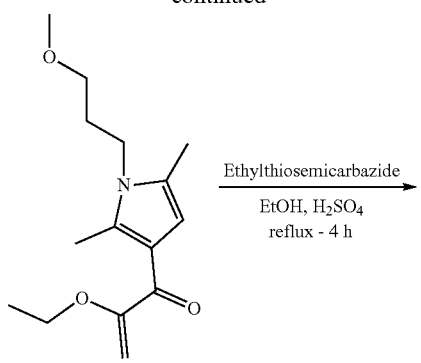

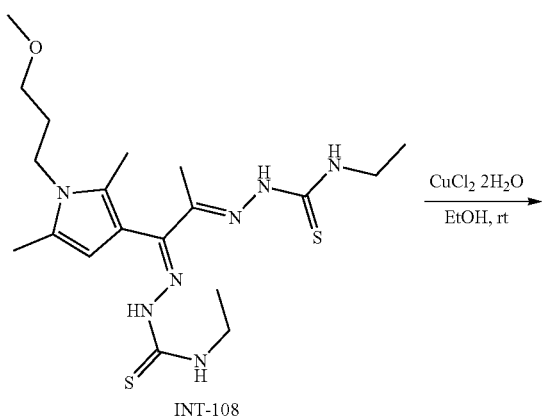

INT-108

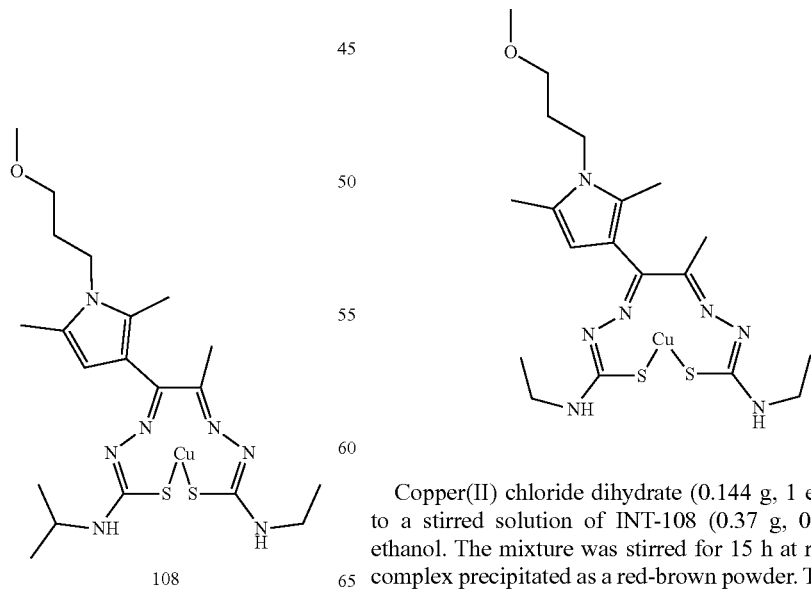

108

408

Synthesis of INT-108 ((2E,2'E)-2,2'-(1-(1-(3-methoxypropyl)-2,5-dimethyl-1H-pyrrol-3-yl)propane-1,2-diylidene)bis(N-ethylhydrazine-1-carbothioamide))

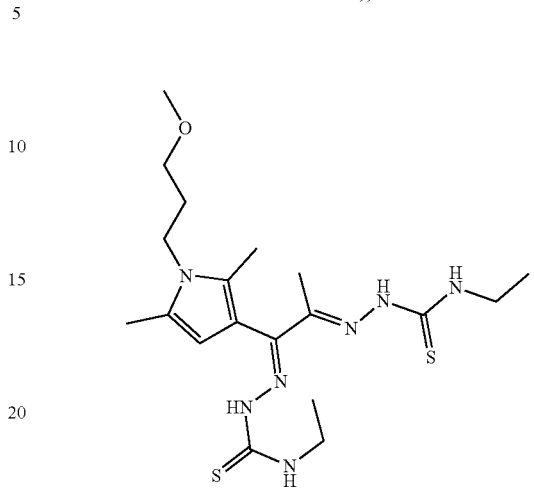

2-ethoxy-1-(1-(3-methoxypropyl)-2,5-dimethyl-1H-pyrrol-3-yl)prop-2-en-1-one (0.9 g, 3.4 mmol) was dissolved in EtOH (50 ml), ethylthiosemicarbazide (0.81 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.37 g (24.8%). LC-MS 1.71 min, m/z 440.5 [MH]+.

Synthesis of Compound 108

Copper(II) chloride dihydrate (0.144 g, 1 eq) was added to a stirred solution of INT-108 (0.37 g, 0.84 mmol) in ethanol. The mixture was stirred for 15 h at rt. The formed complex precipitated as a red-brown powder. The precipitate was collected by filtration, washed with water, diethyl ether, and dried. Yield 0.26 g (60.9%).

Scheme 70: Synthesis of Compound 109

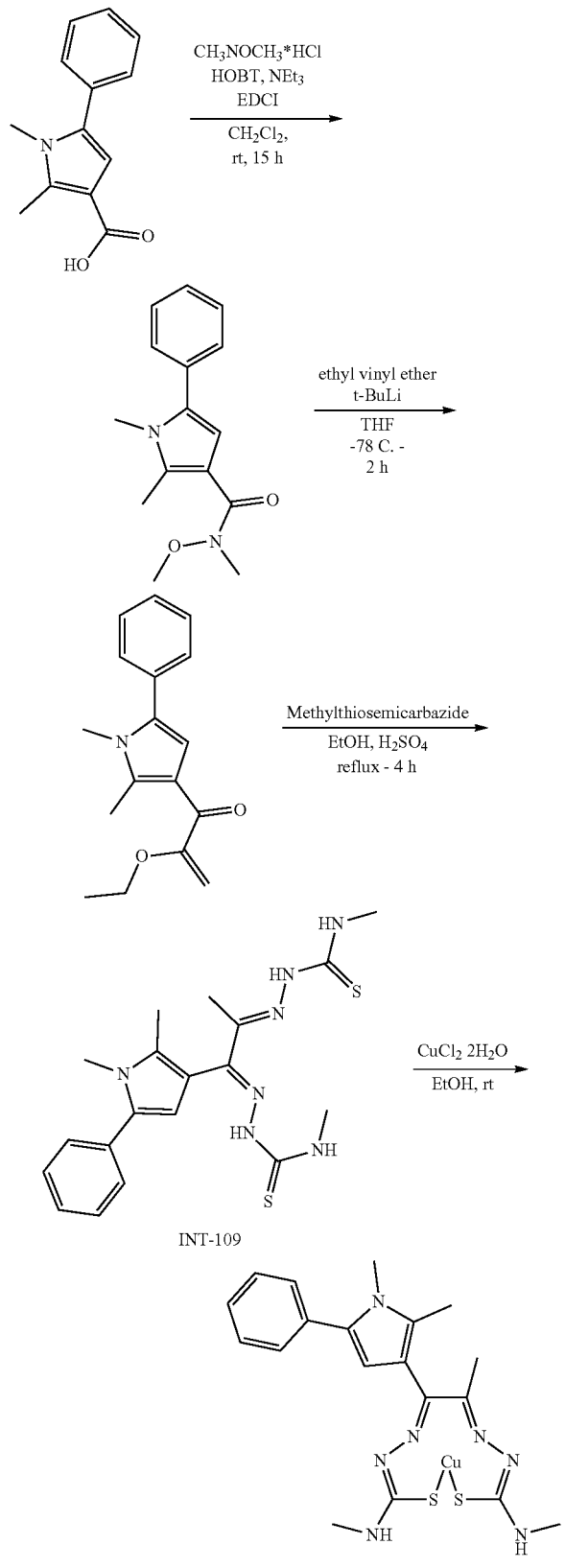

INT-109

109

Synthesis of N-methoxy-N,1,2-trimethyl-5-phenyl-1H-pyrrole-3-carboxamide

To a stirred mixture of 1,2-dimethyl-5-phenyl-1H-pyrrole-3-carboxylic acid (3.28 g, 15.2 mmol), N,O-dimethylhydroxylamine (1.78 g, 1.2 eq), HOBt (2.47 g, 1.2 eq), and triethylamine (5.5 ml, 3.95 g, 2.5 eq) in DCM (200 ml) at 5° C. was added EDCl (3.5 g, 1.2 eq) and reaction was stirred for 15 h at rt. The mixture was washed with water and brine. The organic layer was dried over anh. $Na_2SO_4$ and then concentrated under reduced pressure. The residue was purified by column chromatography (silica gel, $CCl_4$/EtOAc from 9:1 to 1:3). Yield 3.5 g (88.9%). LC-MS 1.44 min, m/z 259.4 [MH]+. $^1$H-NMR (400 MHz, $CDCl_3$), δ (ppm): δ 7.51-7.23 (m, 5H), 6.64-6.46 (m, 1H), 3.70 (ddd, J=6.1, 3.1, 1.4 Hz, 3H), 3.58-3.45 (m, 3H), 3.34 (ddd, J=6.0, 3.1, 1.4 Hz, 3H), 2.64-2.48 (m, 3H).

Synthesis of 1-(1,2-dimethyl-5-phenyl-1H-pyrrol-3-yl)-2-ethoxyprop-2-en-1-one A solution of ethyl vinyl ether (3.22 g, 4.3 ml, 3.3 eq) in dry THF (130 ml) was cooled to −78° C., and tert-butyllithium (1.7M in pentane, 25 ml, 3 eq) was added. The mixture was warmed to 0° C. over 1 h period, stirred for 45 min, and then cooled down to −30° C. A solution of N-methoxy-N,1,2-trimethyl-5-phenyl-1H-pyrrole-3-carboxamide (3.5 g, 13.5 mmol) in THF (25 ml) was added and stirring continued at 0° C. for 4 h. The mixture was poured into aq. $NH_4Cl$ (100 ml) and extracted with $Et_2O$ (3×100 ml). The combined extracts were dried over anh. $Na_2SO_4$, filtered, and solvents were evaporated in vacuo. The product was used for the next step without additional purification. Yield 3.45 g (94.5%). LC-MS 1.71 min, m/z 270.6 [MH]+.

Synthesis of INT-109 ((2E,2'E)-2,2'-(1-(1,2-dimethyl-5-phenyl-1H-pyrrol-3-yl)propane-1,2-diylidene)bis(N-methylhydrazine-1-carbothioamide))

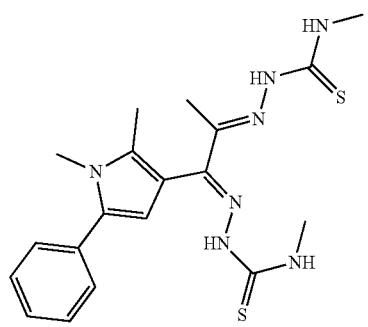 [SMILES: CNC(=S)N/N=C(C)/C(=N/NC(=S)NC)c1cc(-c2ccccc2)n(C)c1C]

1-(1,2-dimethyl-5-phenyl-1H-pyrrol-3-yl)-2-ethoxyprop-2-en-1-one (1.75 g, 6.5 mmol) was dissolved in EtOH (50 ml), methylthiosemicarbazide (1.37 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.91 g (33.6%). LC-MS 1.65 min, m/z 416.6 [MH]+. $^1$H-NMR (400 MHz, DMSO-d6), δ (ppm): 10.58 (s, 1H), 9.07 (s, 1H), 8.64 (d, J=4.6 Hz, 1H), 7.67-7.11 (m, 6H), 6.17 (s, 1H), 3.57 (s, 3H), 3.04 (d, J=4.5 Hz, 3H), 2.94 (d, J=4.7 Hz, 3H), 2.34 (s, 3H), 2.08 (d, J=20.8 Hz, 3H).

Synthesis of Compound 109

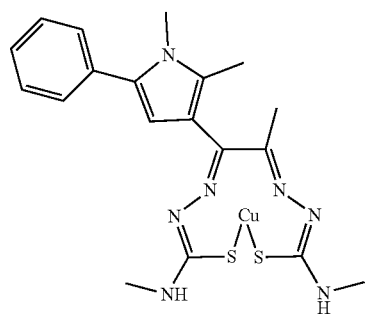

Copper(II) chloride dihydrate (0.082 g, 1 eq) was added to a stirred solution of INT-109 (0.2 g, 0.48 mmol) in ethanol. The mixture was stirred for 15 h at rt. The formed complex precipitated as a red-brown powder. The precipitate was collected by filtration, washed with water, diethyl ether, and dried. Yield 0.2 g (87.7%).

Scheme 71: Synthesis of Compound 110

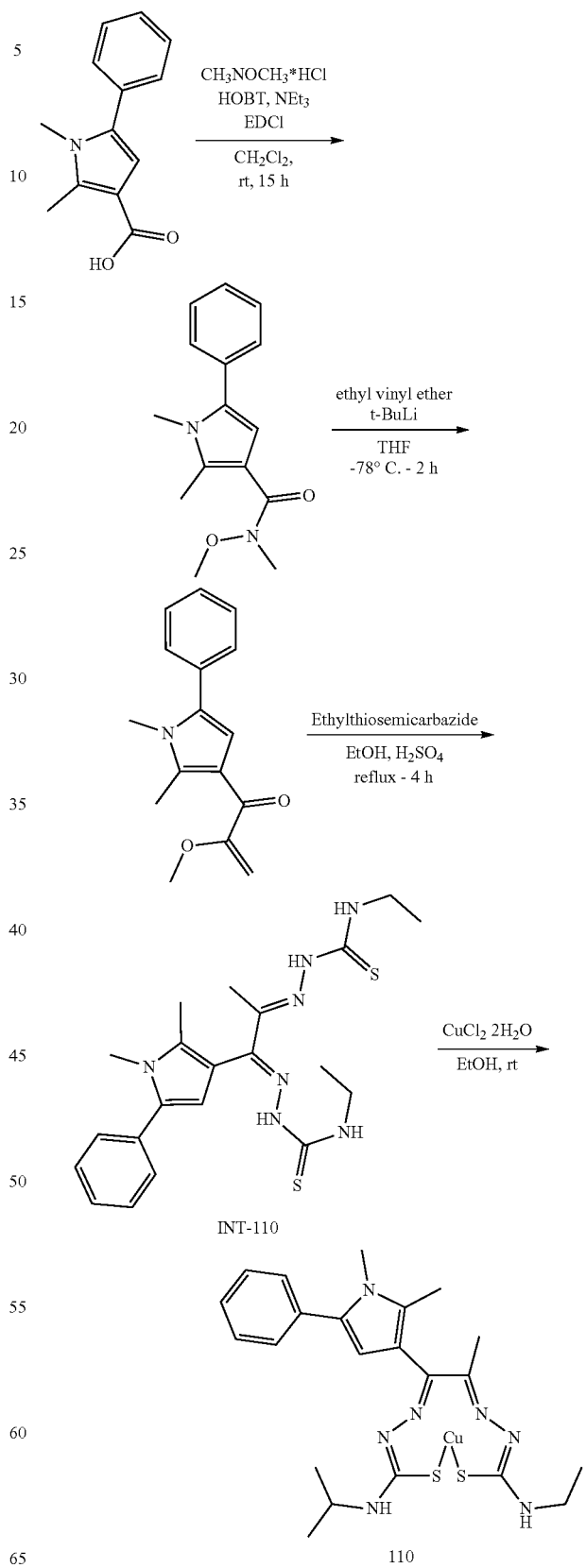

Synthesis of INT-110 ((2E,2'E)-2,2'-(1-(1,2-dimethyl-5-phenyl-1H-pyrrol-3-yl)propane-1,2-diylidene)bis(N-ethylhydrazine-1-carbothioamide))

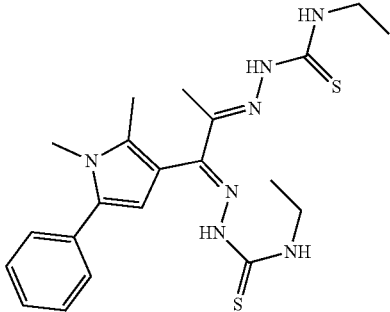 [SMILES: CCNC(=S)N/N=C(C)/C(=N/NC(=S)NCC)c1cc(-c2ccccc2)n(C)c1C]

1-(1,2-dimethyl-5-phenyl-1H-pyrrol-3-yl)-2-ethoxyprop-2-en-1-one (1.7 g, 6.3 mmol) was dissolved in EtOH (50 ml), ethylthiosemicarbazide (1.5 g, 2 eq) and 3 drops of H$_2$SO$_4$ were added. The stirred reaction mixture was heated to reflux for 4 h and then maintained for 15 h at rt. The formed precipitate was filtered, washed with EtOH, aq.sat. Na$_2$CO$_3$, water, Et$_2$O, and dried. Yield 1.03 g (36.8%). LC-MS 1.85 min, m/z 444.9 [MH]+. $^1$H-NMR (400 MHz, DMSO-d6), δ (ppm): 10.64 (s, 1H), 9.01 (s, 1H), 8.69 (t, J=5.7 Hz, 1H), 7.59-7.13 (m, 6H), 6.16 (s, 1H), 3.73-3.52 (m, 5H), 3.49-3.33 (m, 2H), 2.34 (s, 3H), 2.05 (s, 3H), 1.24-1.09 (m, 3H), 0.88 (t, J=7.2 Hz, 3H).

Synthesis of Compound 110

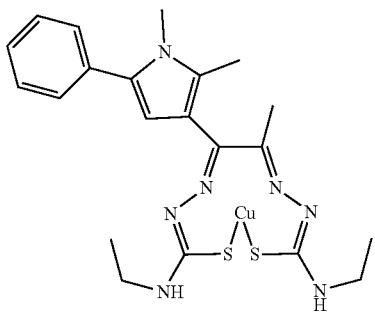

Copper(II) chloride dihydrate (0.077 g, 1 eq) was added to a stirred solution of INT-110 (0.2 g, 0.45 mmol) in ethanol. The mixture was stirred for 15 h at rt. The formed complex precipitated as a red-brown powder. The precipitate was collected by filtration, washed with water, diethyl ether, and dried. Yield 0.15 g (66.3%).

Scheme 72: Synthesis of Compound 111

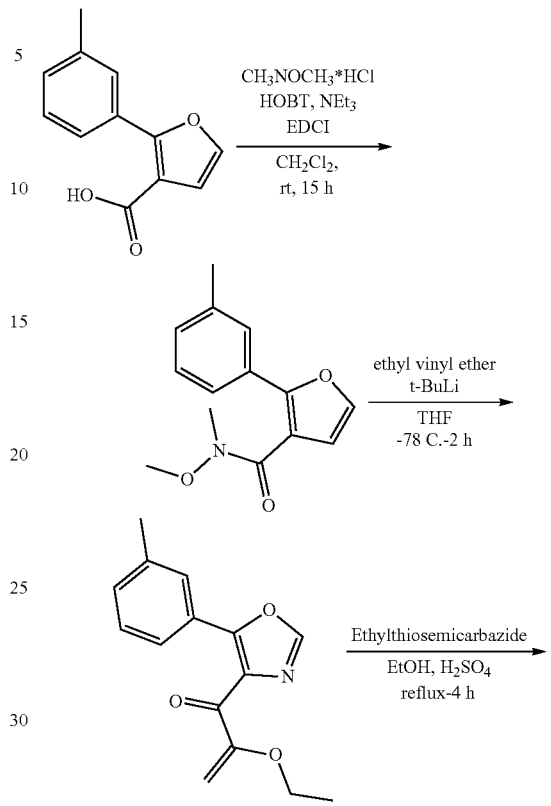

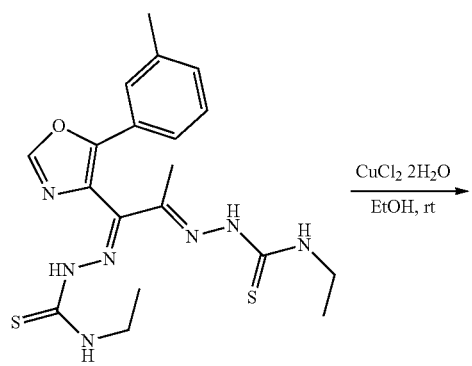

INT-111

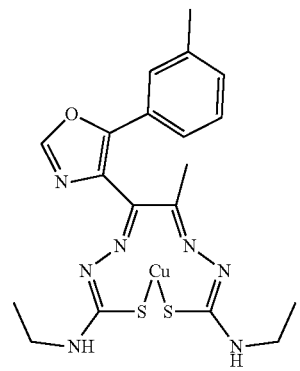

111

Synthesis of N-methoxy-N-methyl-5-(m-tolyl)oxazole-4-carboxamide

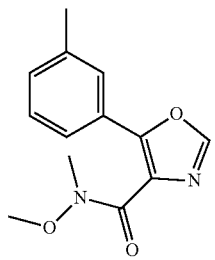 [SMILES: CON(C)C(=O)c1ncoc1-c1cccc(C)c1]

To a stirred mixture of 5-(m-tolyl)oxazole-4-carboxylic acid (2.02 g, 9.9 mmol), N,O-dimethylhydroxylamine (1.16 g, 1.2 eq), HOBt (1.83 g, 1.2 eq), and triethylamine (2.7 ml, 1.96 g, 2 eq) in DCM (50 ml) at 5° C. was added EDCl (2.28 g, 1.2 eq) and reaction was stirred for 15 h at rt. The mixture was washed with water and brine. The organic layer was dried over anh. Na$_2$SO$_4$ and then concentrated under reduced pressure. The residue was purified by column chromatography (silica gel, eluent hexane/EtOAc 3:1). Yield 1.92 g (78.4%). LC-MS 1.24 min, m/z 247.4 [MH]+. $^1$H-NMR (400 MHz, CDCl$_3$), δ (ppm): 7.89 (s, 1H), 7.65 (d, J=6.4 Hz, 2H), 7.33 (t, J=8.0 Hz, 1H), 7.22 (d, J=7.4 Hz, 1H), 3.76 (s, 3H), 3.39 (s, 3H), 2.41 (s, 3H).

Synthesis of 2-ethoxy-1-(5-(m-tolyl)oxazol-4-yl)prop-2-en-1-one

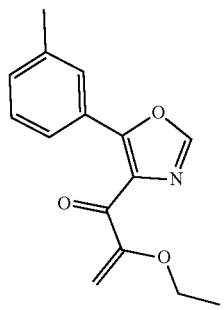 [SMILES: C=C(OCC)C(=O)c1ncoc1-c1cccc(C)c1]

A solution of ethyl vinyl ether (3.7 g, 4.9 ml, 6.6 eq) in dry THF (100 ml) was cooled to −78° C., and tert-butyllithium (1.7M in pentane, 27 ml, 6 eq) was added. The mixture was warmed to 0° C. over 1 h period, stirred for 45 min, and then cooled down to −30° C. A solution of compound 2 (1.92 g, 7.8 mmol) in THF (15 ml) was added and stirring continued at 0° C. for 4 h. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used for the next step without additional purification. Yield 1.98 g (99%). LC-MS 0.64 min, m/z 431.5 [MH]+.

Synthesis of INT-111 ((2E,2'E)-2,2'-(1-(5-(m-tolyl)oxazol-4-yl)propane-1,2-diylidene)bis(N-ethylhydrazine-1-carbothioamide))

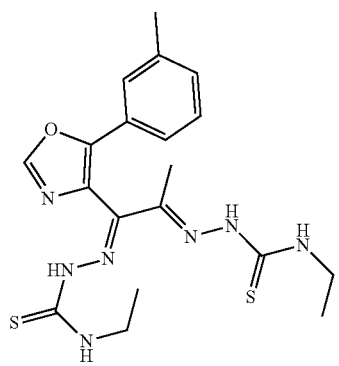 [SMILES: CCNC(=S)N/N=C(C)/C(=N/NC(=S)NCC)c1ncoc1-c1cccc(C)c1]

2-ethoxy-1-(5-(m-tolyl)oxazol-4-yl)prop-2-en-1-one (0.98 g, 7.7 mmol) was dissolved in EtOH (15 ml), ethylthiosemicarbazide (1.86 g, 2 eq) and 3 drops of H$_2$SO$_4$ were added. The stirred reaction mixture was heated to reflux for 4 h and then maintained for 15 h at rt. The formed precipitate was filtered, washed with EtOH, aq.sat. Na$_2$CO$_3$, water, Et$_2$O, and dried. Yield 0.8 g (23%). LC-MS 1.68 min), m/z 432.5 [MH]+.

Synthesis of Compound 111

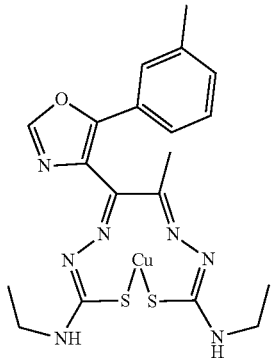

Copper(II) chloride dihydrate (0.071 g, 1 eq) was added to a stirred solution of INT-111 (0.18 g, 0.42 mmol) in ethanol. The mixture was stirred for 15 h at rt. The formed complex precipitated as a red-brown powder. The precipitate was collected by filtration, washed with water, diethyl ether, and dried. Yield 0.153 g (78.9%).

Scheme 73: Synthesis of Compound 112

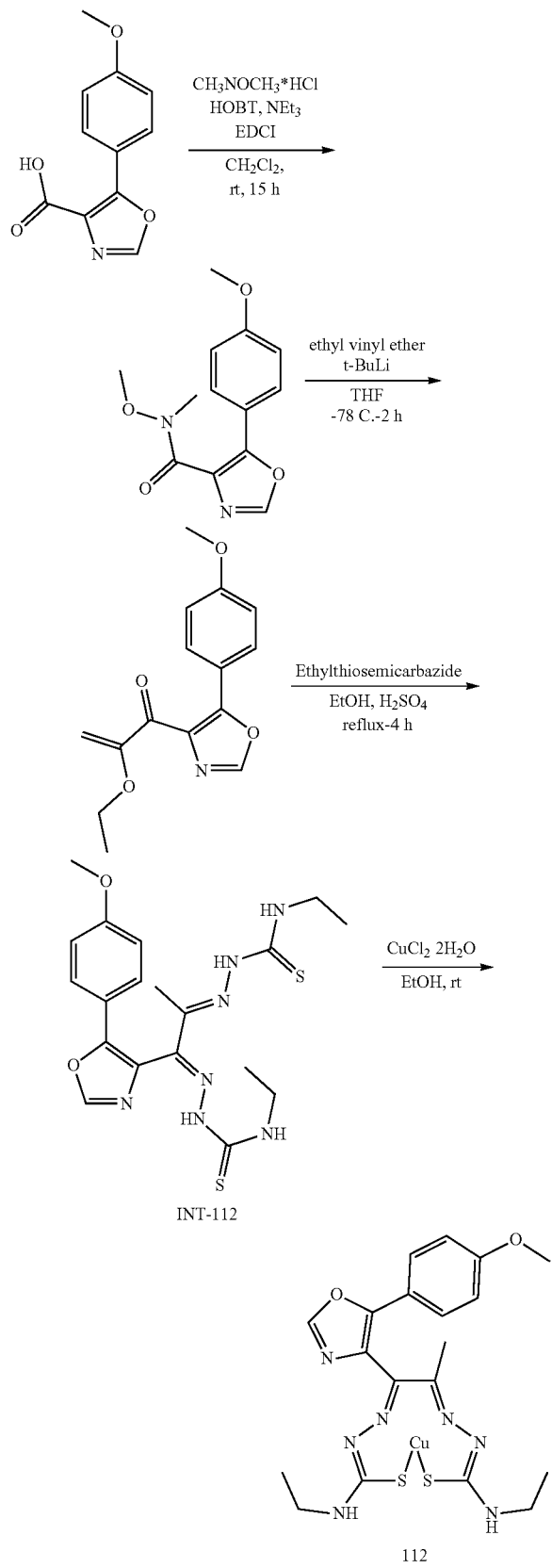

Synthesis of N-methoxy-5-(4-methoxyphenyl)-N-methyloxazole-4-carboxamide

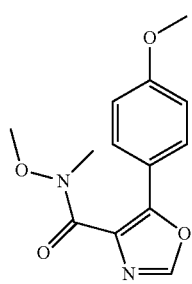

To a stirred mixture of 5-(4-methoxyphenyl)oxazole-4-carboxylic acid (4 g, 18.2 mmol), N,O-dimethylhydroxylamine (2.14 g, 1.2 eq), HOBt (3.35 g, 1.2 eq), and triethylamine (5 ml, 3.6 g, 2 eq) in DCM (100 ml) at 5° C. was added EDCl (2.28 g, 1.2 eq) and reaction was stirred for 15 h at rt. The mixture was washed with water and brine. The organic layer was dried over anh. $Na_2SO_4$ and then concentrated under reduced pressure. The residue was purified by column chromatography (silica gel, eluent hexane/EtOAc 2:1). Yield 4 g (83.6%). LC-MS 1.23 min, m/z 263.4 [MH]+. $^1$H-NMR (400 MHz, $CDCl_3$), δ (ppm): 8.00-7.68 (m, 3H), 7.05-6.86 (m, 2H), 3.86 (s, 3H), 3.78 (s, 3H), 3.39 (s, 3H).

Synthesis of 2-ethoxy-1-(5-(4-methoxyphenyl)oxazol-4-yl)prop-2-en-1-one

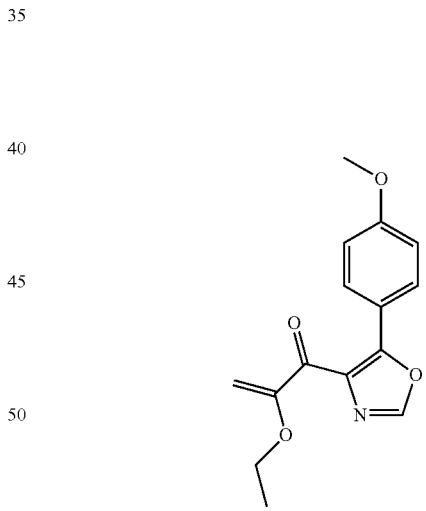

A solution of ethyl vinyl ether (3.7 g, 4.9 ml, 6.6 eq) in dry THF (100 ml) was cooled to −78° C., and tert-butyllithium (1.7M in pentane, 27 ml, 6 eq) was added. The mixture was warmed to 0° C. over 1 h period, stirred for 45 min, and then cooled down to −30° C. A solution of N-methoxy-5-(4-methoxyphenyl)-N-methyloxazole-4-carboxamide (1.92 g, 7.8 mmol) in THF (15 ml) was added and stirring continued at 0° C. for 4 h. The mixture was poured into aq. $NH_4Cl$ (100 ml) and extracted with $Et_2O$ (3×100 ml). The combined extracts were dried over anh. $Na_2SO_4$, filtered, and solvents were evaporated in vacuo. The product was used for the next step without additional purification. Yield 1.98 g (99%).

Synthesis of INT-112 ((2E,2'E)-2,2'-(1-(5-(4-methoxyphenyl)oxazol-4-yl)propane-1,2-diylidene)bis(N-ethylhydrazine-1-carbothioamide))

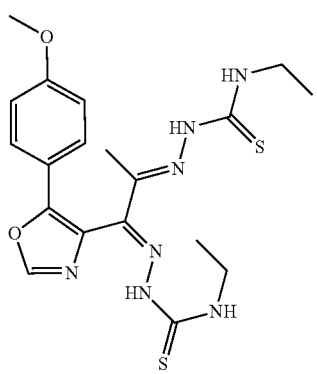 [SMILES: CCNC(=S)N/N=C(C)/C(=N/NC(=S)NCC)c1ncoc1-c1ccc(OC)cc1]

2-ethoxy-1-(5-(4-methoxyphenyl)oxazol-4-yl)prop-2-en-1-one (0.98 g, 7.7 mmol) was dissolved in EtOH (15 ml), ethylthiosemicarbazide (1.86 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.8 g (23%). LC-MS 1.68 min), m/z 432.5 [MH]+.

Synthesis of Compound 112

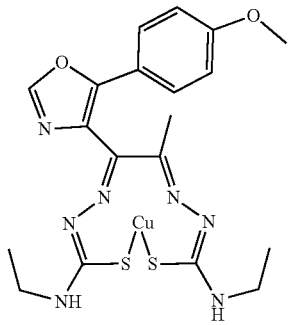

Copper(II) chloride dihydrate (0.071 g, 1 eq) was added to a stirred solution of INT-112 (0.18 g, 0.42 mmol) in ethanol. The mixture was stirred for 15 h at rt. The formed complex precipitated as a red-brown powder. The precipitate was collected by filtration, washed with water, diethyl ether, and dried. Yield 0.153 g (78.9%).

Scheme 74: Synthesis of Compound 113

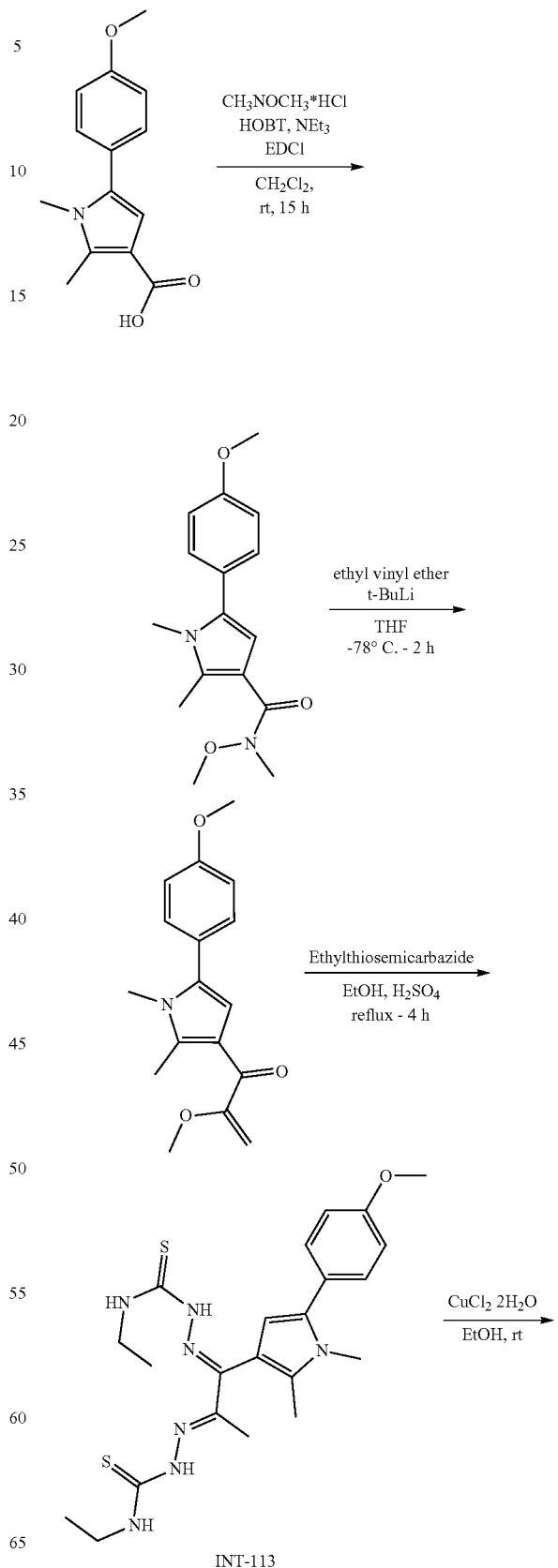

421

-continued

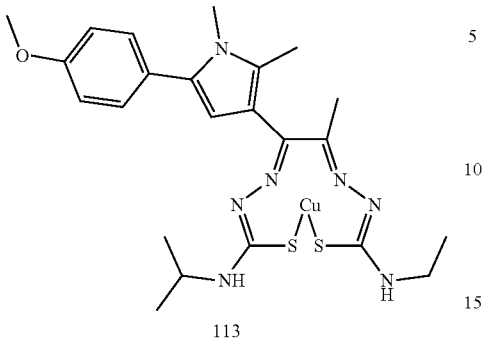

113

Synthesis of N-methoxy-5-(4-methoxyphenyl)-N,1,2-trimethyl-1H-pyrrole-3-carboxamide

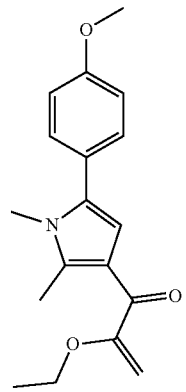 [SMILES: C=C(OCC)C(=O)c1cc(-c2ccc(OC)cc2)n(C)c1C]

To a stirred mixture of 5-(4-methoxyphenyl)-1,2-dimethyl-1H-pyrrole-3-carboxylic acid (3 g, 12.2 mmol), N,O-dimethylhydroxylamine (1.43 g, 1.2 eq), HOBt (1.98 g, 1.2 eq), and triethylamine (4.3 ml, 3.09 g, 2.5 eq) in DCM (100 ml) at 5° C. was added EDCl (2.81 g, 1.2 eq) and reaction was stirred for 15 h at rt. The mixture was washed with water and brine. The organic layer was dried over anh. $Na_2SO_4$ and then concentrated under reduced pressure. The residue was purified by column chromatography (silica gel, eluent $CCl_4$/EtOAc from 8:2 to 1:3). Yield 2.1 g (59.5%). LC-MS 1.4 min, m/z 289.4 [MH]+. $^1$H-NMR (400 MHz, $CDCl_3$), δ (ppm): 7.41-7.17 (m, 2H), 6.96 (d, J=8.7 Hz, 2H), 6.49 (s, 1H), 3.86 (s, 2H), 3.70 (s, 2H), 3.48 (s, 2H), 3.34 (s, 2H), 2.56 (s, 2H).

422

Synthesis of 2-ethoxy-1-(5-(4-methoxyphenyl)-1,2-dimethyl-1H-pyrrol-3-yl)prop-2-en-1-one A solution of ethyl vinyl ether (1.73 g, 2.3 ml, 3.3 eq) in dry THF (130 ml) was cooled to −78° C., and tert-butyl-lithium (1.7M in pentane, 14 ml, 6 eq) was added. The mixture was warmed to 0° C. over 1 h period, stirred for 45 min, and then cooled down to −30° C. A solution of N-methoxy-5-(4-methoxyphenyl)-N,1,2-trimethyl-1H-pyrrole-3-carboxamide (2.1 g, 7.3 mmol) in THF (15 ml) was added and stirring continued at 0° C. for 4 h. The mixture was poured into aq. $NH_4Cl$ (100 ml) and extracted with $Et_2O$ (3×100 ml). The combined extracts were dried over anh. $Na_2SO_4$, filtered, and solvents were evaporated in vacuo. The product was used for the next step without additional purification. Yield 2.12 g (97.2%). LC-MS 1.68 min, m/z 300.4 [MH]+.

Synthesis of INT-113 ((2E,2'E)-2,2'-(1-(5-(4-methoxyphenyl)-1,2-dimethyl-1H-pyrrol-3-yl)propane-1,2-diylidene)bis(N-ethylhydrazine-1-carbothioamide))

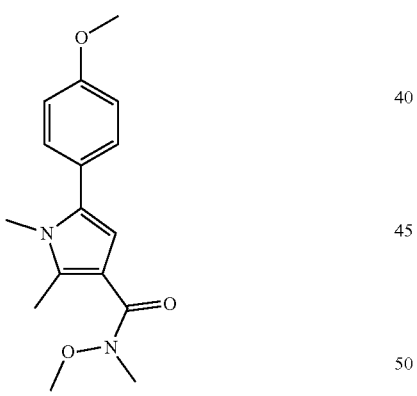

2-ethoxy-1-(5-(4-methoxyphenyl)-1,2-dimethyl-1H-pyrrol-3-yl)prop-2-en-1-one (1.9 g, 6.3 mmol) was dissolved in EtOH (50 ml), ethylthiosemicarbazide (1.851 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.8 g (23%). LC-MS 1.82 min, m/z 474.5 [MH]+.

423
Synthesis of Compound 113

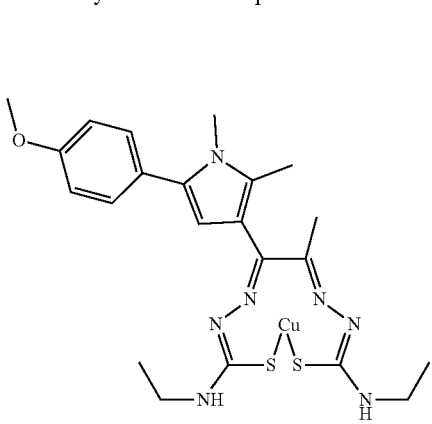

Copper(II) chloride dihydrate (0.091 g, 1 eq) was added to a stirred solution of INT-113 (0.25 g, 0.5 mmol) in ethanol. The mixture was stirred for 15 h at rt. The formed complex precipitated as a red-brown powder. The precipitate was collected by filtration, washed with water, diethyl ether, and dried. Yield 0.12 g (42.5%).

Scheme 75: Synthesis of Compound 114

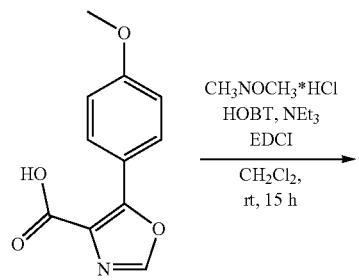

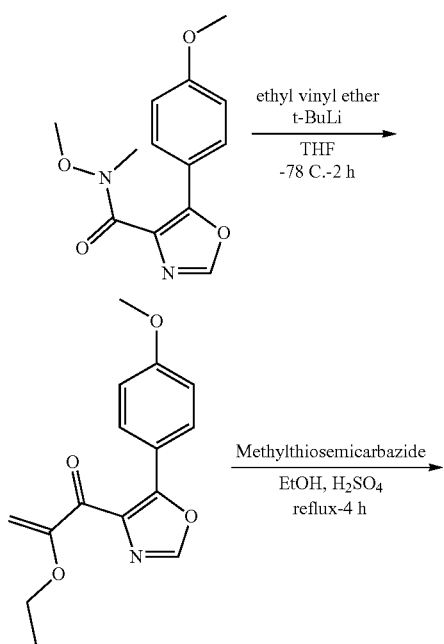

424
-continued

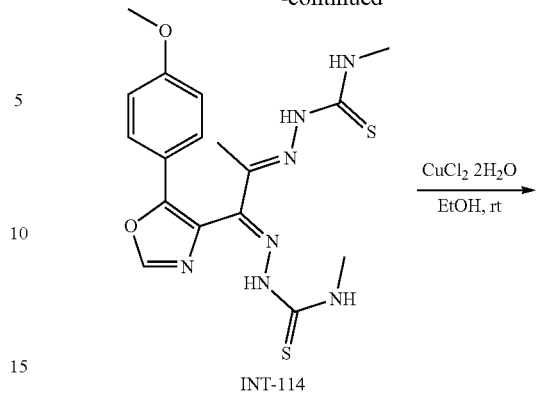

INT-114

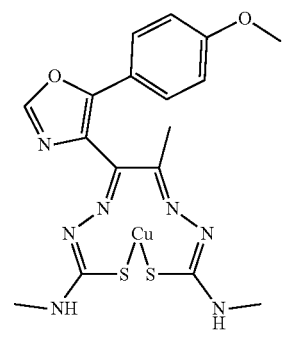

114

Synthesis of INT-114 ((2E,2'E)-2,2'-(1-(5-(4-methoxyphenyl)oxazol-4-yl)propane-1,2-diylidene)bis(N-methylhydrazine-1-carbothioamide))

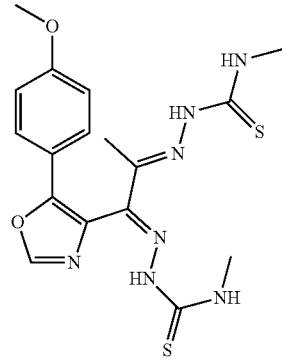 [SMILES: CNC(=S)N/N=C(C)/C(=N/NC(=S)NC)c1ncoc1-c1ccc(OC)cc1]

2-ethoxy-1-(5-(4-methoxyphenyl)oxazol-4-yl)prop-2-en-1-one (0.78 g, 2.85 mmol) was dissolved in EtOH (15 ml), methylthiosemicarbazide (0.6 g, 2 eq) and 3 drops of $H_2SO_4$ were added. The stirred reaction mixture was heated to reflux for 4 h and then maintained for 15 h at rt. The formed precipitate was filtered, washed with EtOH, aq.sat. $Na_2CO_3$, water, $Et_2O$, and dried. Yield 0.2 g (216.7%). LC-MS 1.42 min, m/z 420.3 [MH]+.

Synthesis of Compound 114

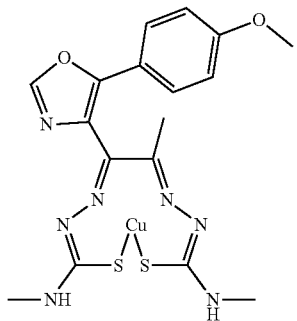

Copper(II) chloride dihydrate (0.081 g, 1 eq) was added to a stirred solution of INT-114 (0.2 g, 0.48 mmol) in ethanol. The mixture was stirred for 15 h at rt. The formed complex precipitated as a red-brown powder. The precipitate was collected by filtration, washed with water, diethyl ether, and dried. Yield 0.188 g (81.9%).

Scheme 76: Synthesis of Compound 115

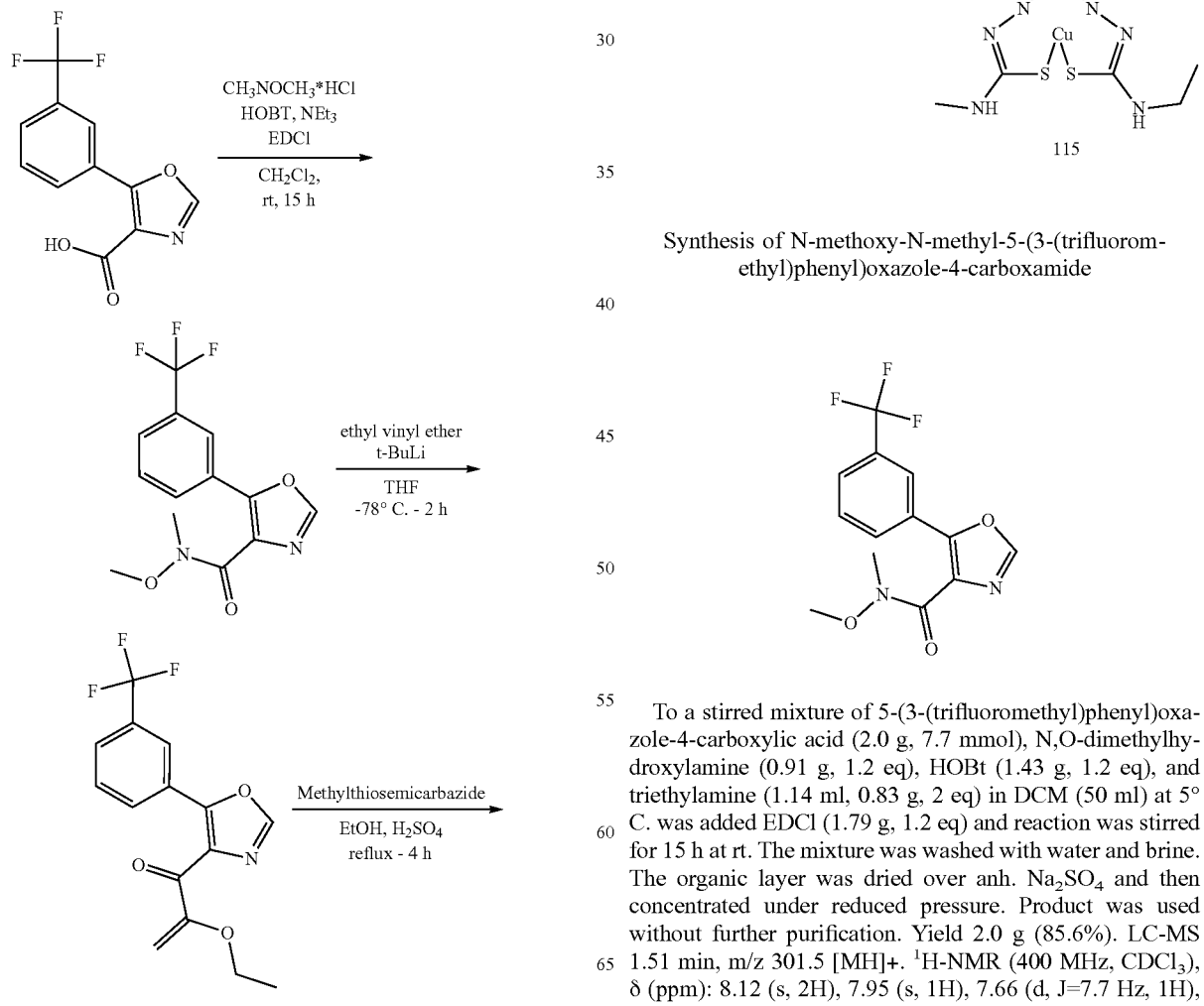

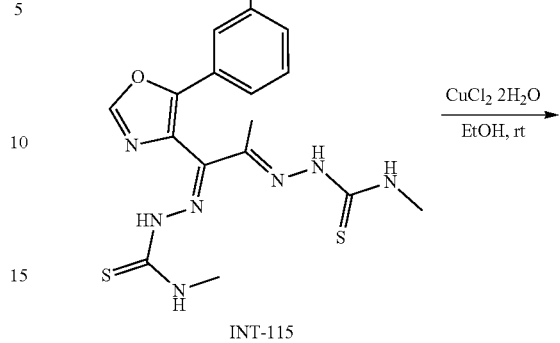

Synthesis of N-methoxy-N-methyl-5-(3-(trifluoromethyl)phenyl)oxazole-4-carboxamide To a stirred mixture of 5-(3-(trifluoromethyl)phenyl)oxazole-4-carboxylic acid (2.0 g, 7.7 mmol), N,O-dimethylhydroxylamine (0.91 g, 1.2 eq), HOBt (1.43 g, 1.2 eq), and triethylamine (1.14 ml, 0.83 g, 2 eq) in DCM (50 ml) at 5° C. was added EDCl (1.79 g, 1.2 eq) and reaction was stirred for 15 h at rt. The mixture was washed with water and brine. The organic layer was dried over anh. $Na_2SO_4$ and then concentrated under reduced pressure. Product was used without further purification. Yield 2.0 g (85.6%). LC-MS 1.51 min, m/z 301.5 [MH]+. $^1$H-NMR (400 MHz, $CDCl_3$), δ (ppm): 8.12 (s, 2H), 7.95 (s, 1H), 7.66 (d, J=7.7 Hz, 1H), 7.57 (t, J=7.9 Hz, 1H), 3.79 (s, 3H), 3.41 (s, 3H).

Synthesis of 2-ethoxy-1-(5-(3-(trifluoromethyl)phenyl)oxazol-4-yl)prop-2-en-1-one

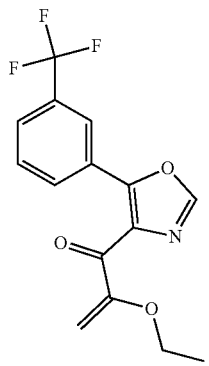 [SMILES: C=C(OCC)C(=O)c1ncoc1-c1cccc(C(F)(F)F)c1]

A solution of ethyl vinyl ether (1.08 g, 1.4 ml, 6.6 eq) in dry THF (20 ml) was cooled to −78° C., and tert-butyllithium (1.7M in pentane, 8 ml, 6 eq) was added. The mixture was warmed to 0° C. over 1 h period, stirred for 45 min, and then cooled down to −30° C. A solution of N-methoxy-N-methyl-5-(3-(trifluoromethyl)phenyl)oxazole-4-carboxamide (0.68 g, 2.3 mmol) in THF (15 ml) was added and stirring continued at 0° C. for 4 h. The mixture was poured into aq. NH₄Cl (100 ml) and extracted with Et₂O (3×100 ml). The combined extracts were dried over anh. Na₂SO₄, filtered, and solvents were evaporated in vacuo. The product was used for the next step without additional purification. Yield 0.7 g (100%). LC-MS 0.64 min, m/z 431.5 [MH]+.

Synthesis of INT-115 ((2E,2'E)-2,2'-(1-(5-(3-(trifluoromethyl)phenyl)oxazol-4-yl)propane-1,2-diylidene)bis(N-methylhydrazine-1-carbothioamide))

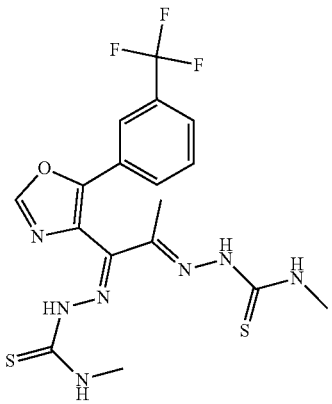 [SMILES: CNC(=S)N/N=C(C)/C(=N/NC(=S)NC)c1ncoc1-c1cccc(C(F)(F)F)c1]

2-ethoxy-1-(5-(3-(trifluoromethyl)phenyl)oxazol-4-yl)prop-2-en-1-one (0.7 g, 2.2 mmol) was dissolved in EtOH (25 ml), methylthiosemicarbazide (0.48 g, 2 eq) and 3 drops of H₂SO₄ were added. The stirred reaction mixture was heated to reflux for 4 h and then maintained for 15 h at rt. The solvent was evaporated in vacuo. The residue was dissolved in EtOAc and washed with aq.sat. NaHCO₃, water, dried with anh. Na₂SO₄ and concentrated under reduced pressure. The residue was purified by column chromatography (silica gel, eluent CCl₄/EtOAc 7:3). Yield 0.12 g (11.6%). LC-MS 1.56 min, m/z 458.5 [MH]+.

Synthesis of Compound 115

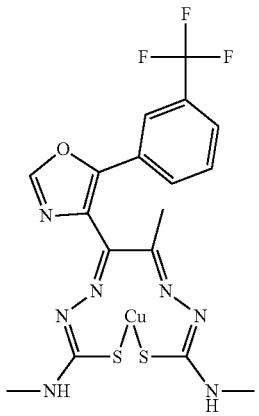

Copper(II) chloride dihydrate (0.039 g, 1 eq) was added to a stirred solution of INT-115 (0.1 g, 0.23 mmol) in ethanol. The mixture was stirred for 15 h at rt. The formed complex precipitated as a red-brown powder. The precipitate was collected by filtration, washed with water, diethyl ether, and dried. Yield 0.1 g (89.6%).

Scheme 77: Synthesis of Compound 116

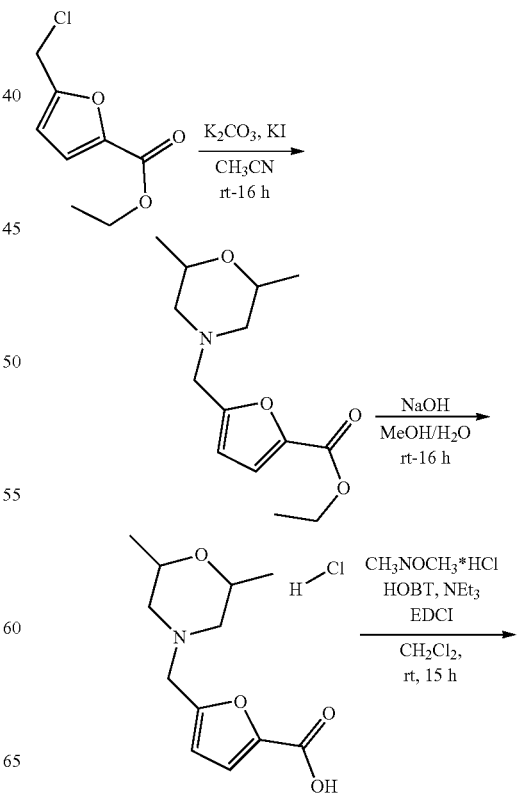

-continued

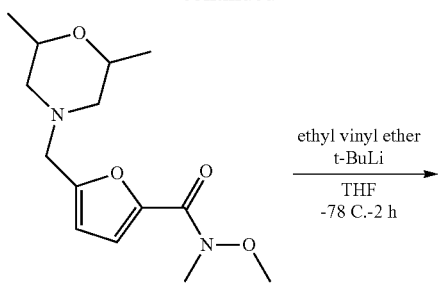

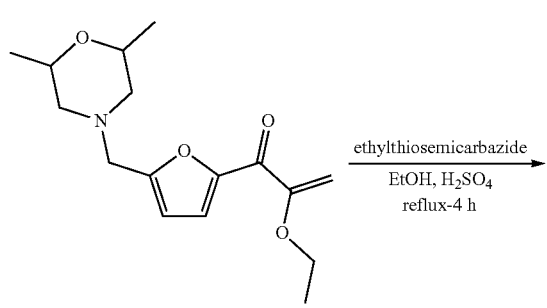

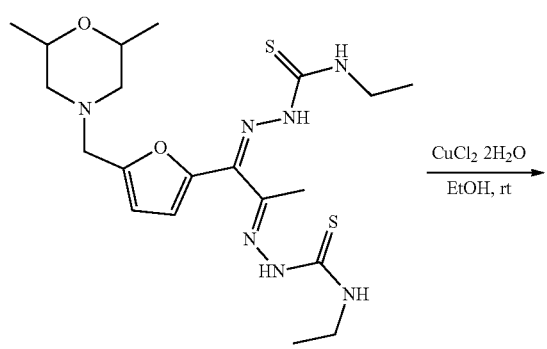

INT-116

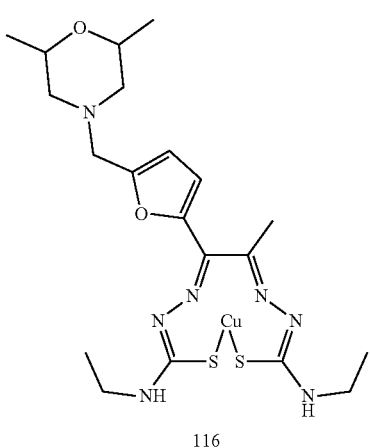

116

Synthesis of ethyl 5-((2,6-dimethylmorpholino)methyl)furan-2-carboxylate

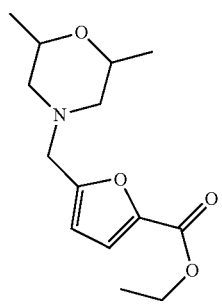 [SMILES: CCOC(=O)c1ccc(CN2CC(C)OC(C)C2)o1]

To a solution of ethyl 5-(chloromethyl)furan-2-carboxylate (3 g, 15.9 mmol) in CH₃CN (100 ml) were added 2,6-dimethylmorpholine (1.92 g, 1.05 eq), potassium carbonate (4.4 g, 2 eq), and sodium iodide (0.48 g, 0.2 eq). The reaction mixture was stirred overnight at rt. Solids were filtered and filtrate was concentrated in vacuo. The residue was dissolved in DCM and washed with water (3×50 ml). Organic layer was separated, dried over anh. Na₂SO₄, filtered, and solvents were evaporated in vacuo. The product was used without further purification. Yield 4.2 g (98.8%). LC-MS 0.88 min, m/z 268.3 [MH]+.

Synthesis of 5-((2,6-dimethylmorpholino)methyl)furan-2-carboxylic Acid

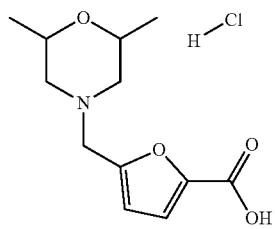

To a solution of ethyl 5-((2,6-dimethylmorpholino)methyl)furan-2-carboxylate (4.25 g, 15.9 mmol mmol) in methanol (100 ml) was added a solution of NaOH (3.58 g, 2.5 eq) in water (10 ml) and the reaction mixture was stirred overnight at rt. Methanol was removed in vacuo, the residue was diluted with water and acidified with conc. HCl to pH 1. The acidified solution was evaporated to dryness and treated with acetonitrile. Solids were filtered, and filtrate was evaporated in vacuo to dryness. Yield 4.38 g (99.9%). LC-MS 0.6 min, m/z 240.3 [MH]+.

Synthesis of 5-((2,6-dimethylmorpholino)methyl)-N-methoxy-N-methylfuran-2-carboxamide

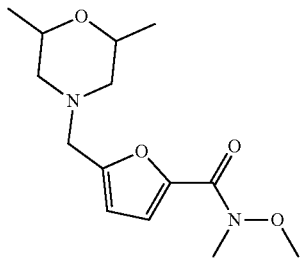

To a stirred mixture of 5-((2,6-dimethylmorpholino)methyl)furan-2-carboxylic acid (4.38 g, 15.9 mmol), N,O-dimethylhydroxylamine (1.86 g, 1.2 eq), HOBt (2.57 g, 1.2 eq), and triethylamine (8 ml, 5.75 g, 3.5 eq) in DCM (100 ml) at 5° C. was added EDCl (3.65 g, 1.2 eq) and reaction was stirred for 15 h at rt. The mixture was washed with water and brine. The organic layer was dried over anh. $Na_2SO_4$ and then concentrated under reduced pressure. Product was purified by column chromatography ($SiO_2$, eluent $CCl_4$/EtOAc from 8:2 to 7:3, then $CHCl_3$/MeOH from 99:1 to 98:2). Yield 2.1 g (46.8%). LC-MS 0.69 min, m/z 283.5 [MH]+. $^1$H-NMR (400 MHz, $CDCl_3$), δ (ppm): 7.11 (d, J=3.4 Hz, 1H), 6.36 (d, J=3.4 Hz, 1H), 3.78 (s, 3H), 3.69 (ddd, J=12.5, 8.3, 4.1 Hz, 2H), 3.64 (d, J=15.3 Hz, 2H), 3.35 (s, 3H), 2.75 (d, J=10.4 Hz, 2H), 1.86 (t, J=10.7 Hz, 2H), 1.15 (d, J=6.3 Hz, 6H).

Synthesis of 1-(5-((2,6-dimethylmorpholino)methyl)furan-2-yl)-2-ethoxyprop-2-en-1-one

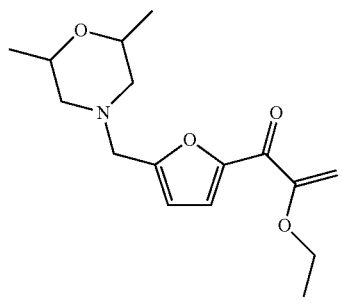 [SMILES: C=C(OCC)C(=O)c1ccc(CN2CC(C)OC(C)C2)o1]

A solution of ethyl vinyl ether (1.77 g, 2.35 ml, 3.3 eq) in dry THF (130 mL) was cooled to −78° C., and tert-butyl-lithium (1.6M in pentane, 14 ml, 3 eq) was added. The mixture was warmed to 0° C. over 1 h period, stirred for 45 min, and cooled down to −30° C. A solution of 5-((2,6-dimethylmorpholino)methyl)-N-methoxy-N-methylfuran-2-carboxamide (2.1 g, 7.4 mmol) in THF was added, and the mixture was stirred at 0° C. for 4 h. The progress of the reaction was monitored by TLC (hexane/EtOAc 10:1). The mixture was poured into aq $NH_4Cl$ and extracted with $Et_2O$. The combined extracts were dried over anh. $Na_2SO_4$, filtered, and evaporated in vacuo. The product was used for the next step without additional purification. Yield 2.1 g (96.2%). LC-MS 1.00 min, m/z 294.4 [MH]+.

Synthesis of INT-116 ((2E,2'E)-2,2'-(1-(5-((2,6-dimethylmorpholino)methyl)furan-2-yl)propane-1,2-diylidene)bis(N-ethylhydrazine-1-carbothioamide))

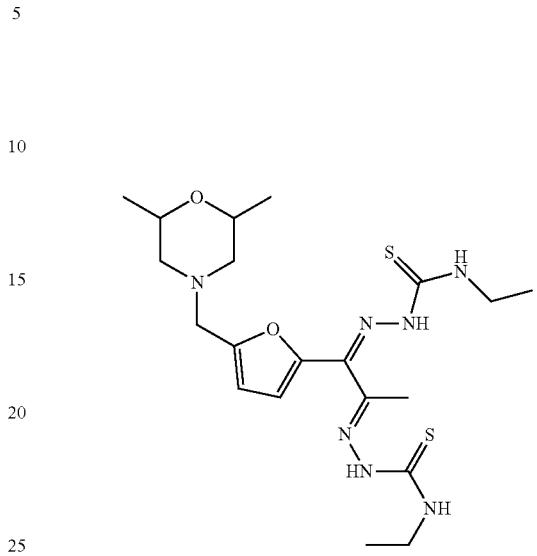

1-(5-((2,6-dimethylmorpholino)methyl)furan-2-yl)-2-ethoxyprop-2-en-1-one (2.12 g, 7.2 mmol) was dissolved in EtOH (150 ml), ethylthiosemicarbazide (1.72 g, 2 eq) and 3 drops of $H_2SO_4$ were added. The stirred reaction mixture was heated to reflux for 4 h and then maintained for 15 h at rt. The formed precipitate was filtered, washed with EtOH, potassium carbonate solution, water, $Et_2O$ and dried. Yield 1.17 g (34.6%). LC-MS 1.20 min, m/z 468.3 [MH]+.

Synthesis of Compound 116

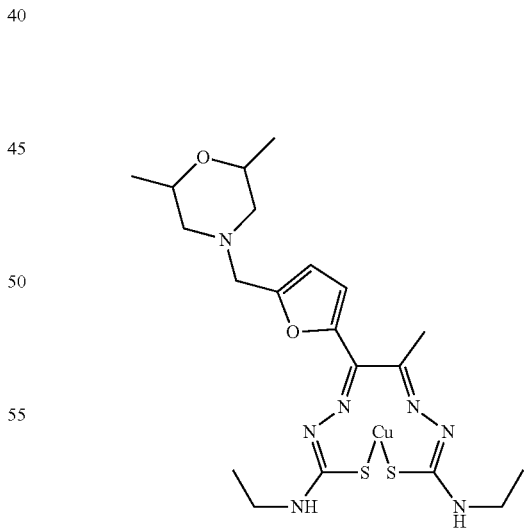

Copper(II) chloride dihydrate (0.15 g, 1 eq) was added to INT-116 (0.41 g, 8.7 mmol, 1 eq) in ethanol. The mixture was stirred for 15 h at rt. The formed complex precipitated from the mixture as a red-brown powder. The precipitate was collected by filtration, washed with water, methanol, diethyl ether, and dried. Yield 0.46 g (98.9%)

Scheme 78: Synthesis of Compound 117
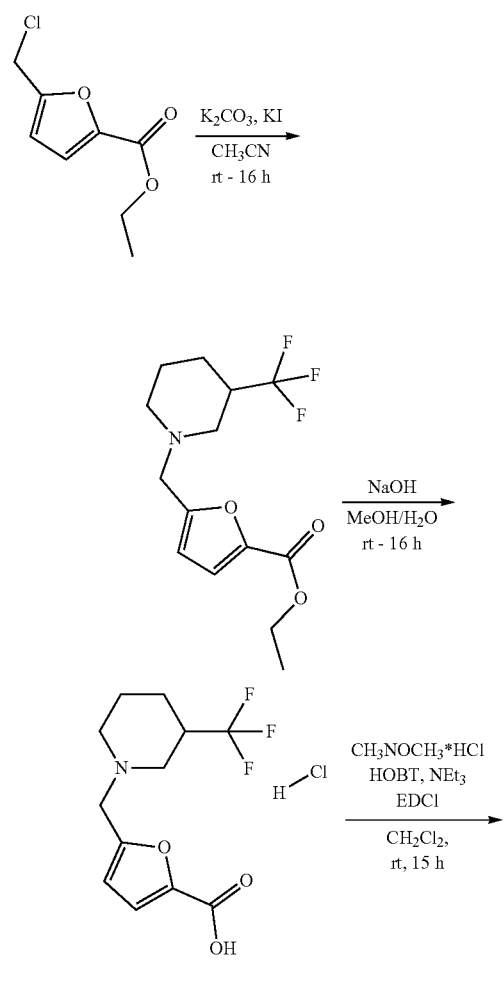
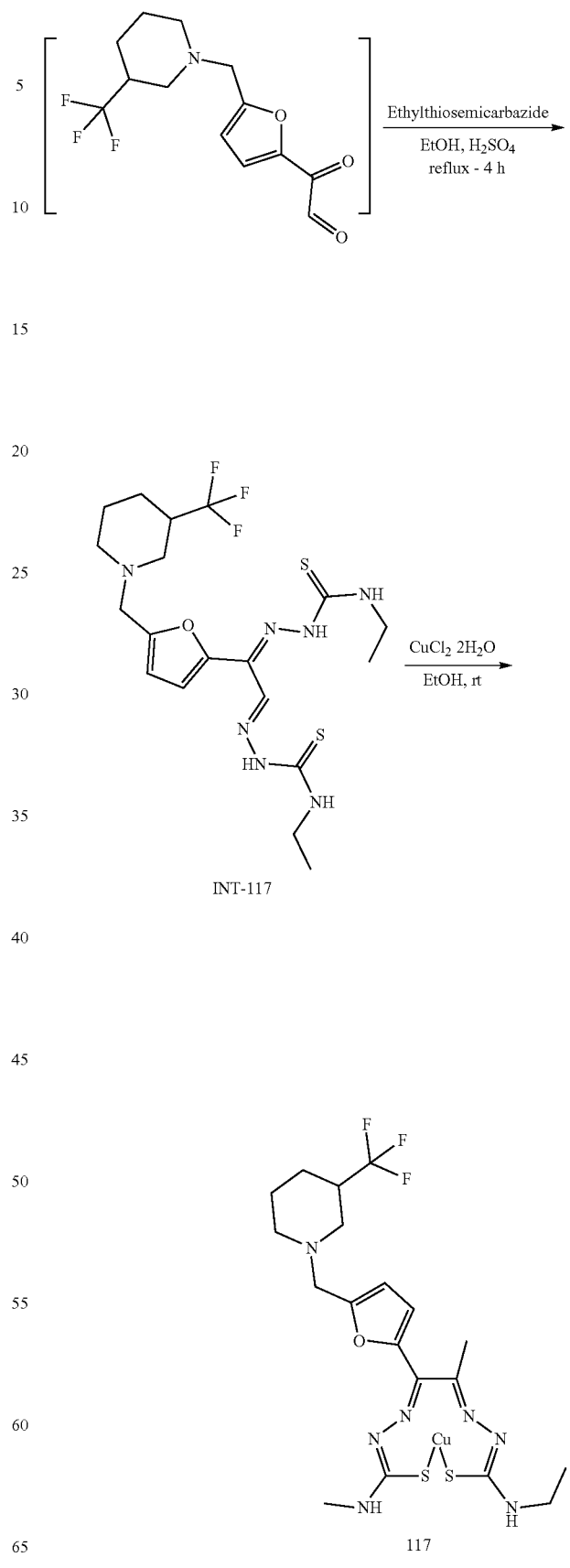
INT-117
117

435

Synthesis of ethyl 5-((3-(trifluoromethyl)piperidin-1-yl)methyl)furan-2-carboxylate

To a solution of ethyl 5-(chloromethyl)furan-2-carboxylate (2.5 g, 13.2 mmol) in CH₃CN (100 ml) were added 3-(trifluoroethyl)piperidine (2.03 g, 1 eq), potassium carbonate (5.5 g, 3 eq), and potassium iodide (0.66 g, 0.3 eq). The reaction mixture was stirred overnight rt. Solids were filtered and filtrate was concentrated in vacuo. The residue was dissolved in DCM and washed with water (3×50 ml). Organic layer was separated, dried over anh. Na₂SO₄, filtered, and solvents were evaporated in vacuo. The product was used without purification. Yield 3.9 g (96.3%). LC-MS 1.00 min m/z 306.3 [MH]+.

Synthesis of 5-((3-(trifluoromethyl)piperidin-1-yl)methyl)furan-2-carboxylic Acid

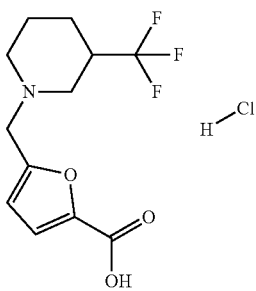 [SMILES: O=C(O)c1ccc(CN2CCCC(C(F)(F)F)C2)o1 ; Cl]

To a solution of ethyl 5-((3-(trifluoromethyl)piperidin-1-yl)methyl)furan-2-carboxylate (3.9 g, 12.7 mmol) in methanol (80 ml), a solution of NaOH (1.27 g, 2.5 eq) in water (10 ml) was added, and the reaction mixture was stirred for 15 h at rt. Methanol was removed in vacuo, the residue was diluted with water and acidified to pH 1. The acidified solution was evaporated to dryness and treated with acetonitrile. Solid salts were filtered, and filtrate was evaporated in vacuo to dryness. Yield 3.88 g (96.8%). LC-MS 0.7 min, m/z 278.5 [MH]+.

436

Synthesis of N-methoxy-N-methyl-5-((3-(trifluoromethyl)piperidin-1-yl)methyl)furan-2-carboxamide

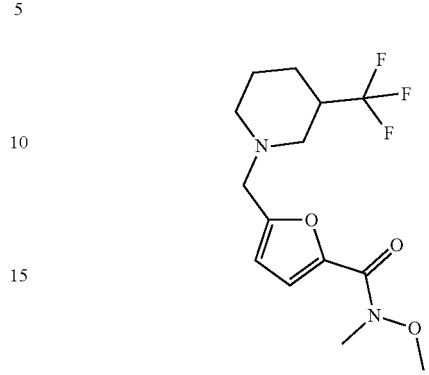

To a stirred mixture of 5-((3-(trifluoromethyl)piperidin-1-yl)methyl)furan-2-carboxylic acid (3.88 g, 12.4 mmol), N,O-dimethylhydroxylamine (1.45 g, 1.2 eq), HOBt (2.23 g, 1.2 eq), and triethylamine (6.9 ml, 5 g, 4 eq) in DCM (100 ml) at 5° C. was added EDCl (2.85 g, 1.2 eq) and reaction was stirred for 15 h at rt. The mixture was washed with water and brine. The organic layer was dried over anh. Na₂SO₄ and then concentrated under reduced pressure. The residue was purified by column chromatography (silica gel, eluent CCl₄/EtOAc 1:1). Yield 2.91 g (73.5%). LC-MS 0.93 min, m/z 321.4 [MH]+. ¹H-NMR (400 MHz, CDCl₃), δ (ppm): 7.11 (d, J=3.4 Hz, 1H), 6.34 (d, J=3.3 Hz, 1H), 3.78 (s, 3H), 3.68 (s, 2H), 3.35 (s, 3H), 3.07 (d, J=10.7 Hz, 1H), 2.92 (d, J=11.3 Hz, 1H), 2.50-2.23 (m, 1H), 2.15-1.99 (m, 2H), 1.94 (d, J=12.2 Hz, 1H), 1.75 (d, J=19.3 Hz, 1H), 1.59 (q, J=13.1 Hz, 1H).

Synthesis of 1-(5-((3-(trifluoromethyl)piperidin-1-yl)methyl)furan-2-yl)ethan-1-one

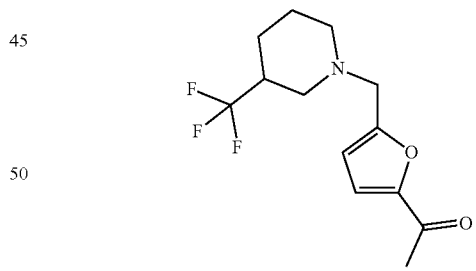

A solution of N-methoxy-N-methyl-5-((3-(trifluoromethyl)piperidin-1-yl)methyl)furan-2-carboxamide (1.75 g, 5.4 mmol) in THF (50 ml) was cooled to 5° C. and methylmagnesium bromide (3.4M in THF, 4.8 ml, 3 eq) was added. The reaction mixture was stirred at 5° C. for 2 h, poured into aq. NH₄Cl and extracted with Et₂O. The combined extracts were dried over anh. Na₂SO₄, filtered, and solvents were evaporated in vacuo. Compound 5 was used for the next step without purification. Yield 1.25 g (83.1%). LC-MS 0.84 min, m/z 376/3 [MH]+. ¹H-NMR (400 MHz, CDCl₃), δ (ppm): 7.14 (d, J=3.5 Hz, 1H), 6.37 (d, J=3.5 Hz, 1H), 3.67 (d, J=14.9 Hz, 2H), 3.12-3.02 (m, 1H), 2.90 (d, J=11.1 Hz, 1H), 2.47 (s, 3H), 2.40-2.26 (m, 1H), 2.13-2.01 (m, 2H), 1.77 (d, J=13.3 Hz, 1H), 1.69-1.53 (m, 1H), 1.35-1.16 (m, 1H).

Synthesis of INT-117 ((2E,2'E)-2,2'-(1-(5-((3-(trifluoromethyl)piperidin-1-yl)methyl)furan-2-yl)ethane-1,2-diylidene)bis(N-ethylhydrazine-1-carbothioamide))

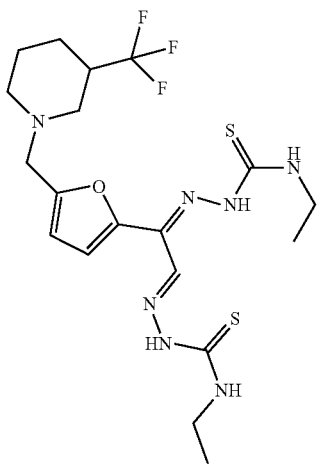 [SMILES: CCNC(=S)N/N=C/C(=N\NC(=S)NCC)c1ccc(CN2CCCC(C(F)(F)F)C2)o1]

A mixture of 1-(5-((3-(trifluoromethyl)piperidin-1-yl)methyl)furan-2-yl)ethan-1-one (1.25 g, 4.5 mmol), NaBr (0.47 g, 1 eq), and DMSO (2.5 ml) was heated to 85° C., then H₂SO₄ (6 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (1.08 g, 2 eq) was added to the filtrate. The reaction mixture was refluxed for 2 hours, then cooled to room temperature. Formed precipitate was filtered, washed with EtOH, aq.sat. K₂CO₃, water, Et₂O, and dried. Yield 0.54 g (24.2%). LC-MS 1.30 min, m/z 492.3 [MH]+.

Synthesis of Compound 117

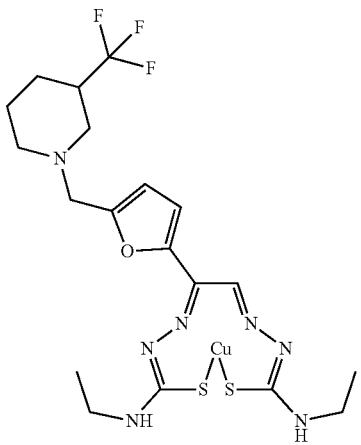

Copper(II) chloride dihydrate (0.19 g, 1 eq) was added to a stirred solution of INT-117 (0.54 g, 1.1 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.4 g (67.2%).

Scheme 79: Synthesis of Compound 118

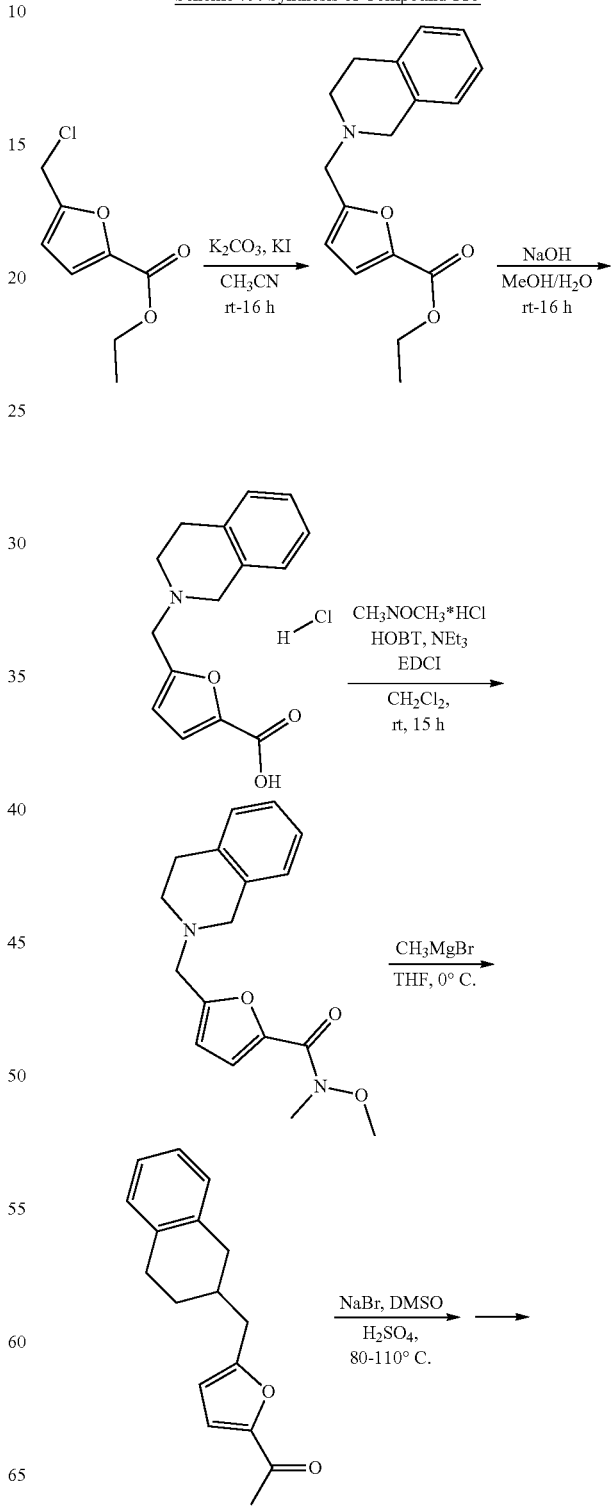

439
-continued

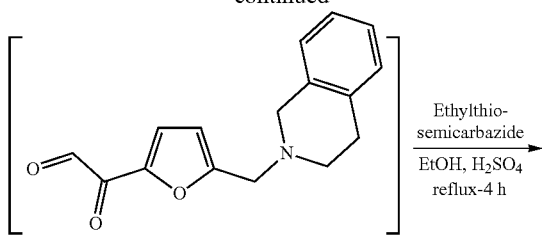

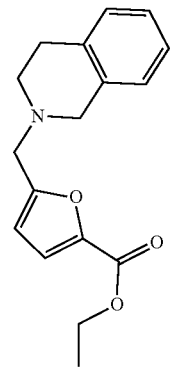 [SMILES: CCOC(=O)c1ccc(CN2CCc3ccccc3C2)o1]

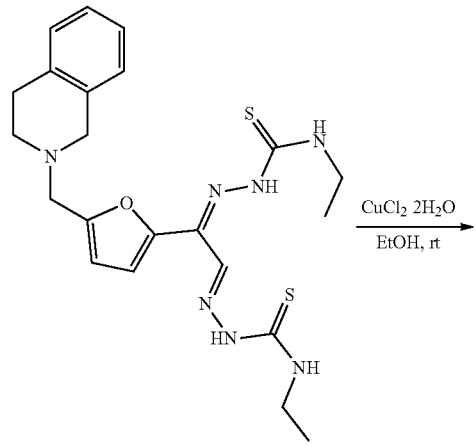

INT-118

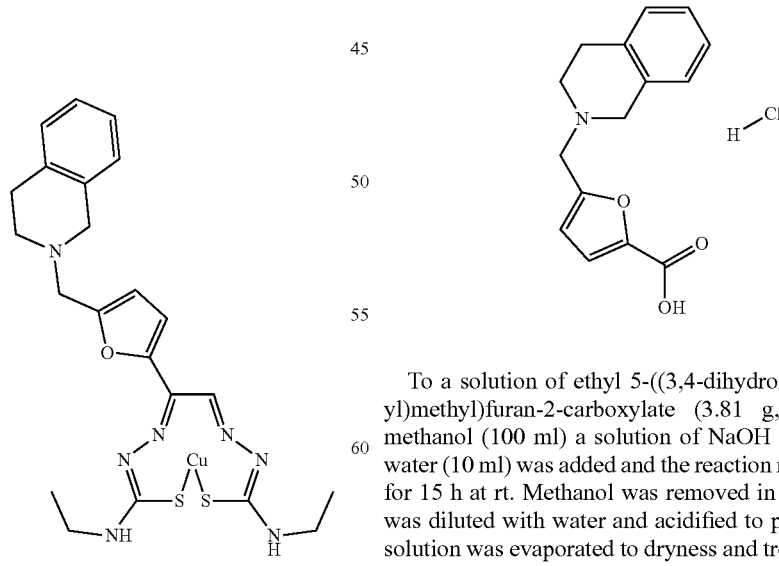

118

440

Synthesis of ethyl 5-((3,4-dihydroisoquinolin-2 (1H)-yl)methyl)furan-2-carboxylate To a solution of ethyl 5-(chloromethyl)furan-2-carboxylate (2.96 g, 15.7 mmol) in CH$_3$CN (100 ml) were added 1,2,3,4-tetrahydroisoquinoline (2.09 g, 1 eq), potassium carbonate (6.51 g, 3 eq), and potassium iodide (0.78 g, 0.3 eq). The reaction mixture was stirred overnight at rt. Solids were filtered and filtrate was concentrated in vacuo. The residue was dissolved in DCM and washed with water (3×50 ml). Organic layer was separated, dried over anh. Na$_2$SO$_4$, filtered, and solvents were evaporated in vacuo. The residue was purified by column chromatography (silica gel, eluent hexane/EtOAc 10:1). Yield 3.81 g (85.08%). LC-MS 1.07 min, m/z 286.4 [MH]+. $^1$H-NMR (400 MHz, DMSO-d6), δ (ppm): 7.25 (d, J=2.4 Hz, 1H), 7.09 (s, 3H), 7.02 (s, 1H), 6.58 (s, 1H), 4.26 (dt, J=9.3, 4.7 Hz, 2H), 3.74 (s, 2H), 3.57 (s, 2H), 2.81 (s, 2H), 2.72 (s, 2H), 1.35-1.19 (m, 3H).

Synthesis of 5-((3,4-dihydroisoquinolin-2(1H)-yl) methyl)furan-2-carboxylic Acid To a solution of ethyl 5-((3,4-dihydroisoquinolin-2(1H)-yl)methyl)furan-2-carboxylate (3.81 g, 13.3 mmol) in methanol (100 ml) a solution of NaOH (1.33 g, 2.5 eq) in water (10 ml) was added and the reaction mixture was stirred for 15 h at rt. Methanol was removed in vacuo, the residue was diluted with water and acidified to pH 1. The acidified solution was evaporated to dryness and treated with acetonitrile. Solids were filtered, and filtrate was evaporated in vacuo to dryness. Yield 3.9 g (99.4%). LC-MS 0.76 min and 0.86 min, m/z 258.0 [MH]+.

441

Synthesis of 5-((3,4-dihydroisoquinolin-2(1H)-yl) methyl)-N-methoxy-N-methylfuran-2-carboxamide

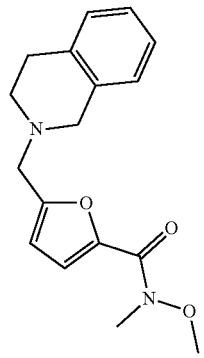 [SMILES: CON(C)C(=O)c1ccc(CN2CCc3ccccc3C2)o1]

To a stirred mixture of 5-((3,4-dihydroisoquinolin-2(1H)-yl)methyl)furan-2-carboxylic acid (3.9 g, 13.3 mmol), N,O-dimethylhydroxylamine (1.55 g, 1.2 eq), HOBt (2.44 g, 1.2 eq), and triethylamine (7.4 ml, 537 g, 4 eq) in DCM (100 ml) at 5° C. was added EDCl (3.05 g, 1.2 eq) and reaction was stirred for 15 h at rt. The mixture was washed with water and brine. The organic layer was dried over anh. $Na_2SO_4$ and then concentrated under reduced pressure. Yield 2.42 g (60.7%). LC-MS 0.90 min, m/z 301.4 [MH]+. $^1$H-NMR (400 MHz, $CDCl_3$), δ (ppm): 7.28 (s, 1H), 7.12 (m, 3H), 7.02 (s, 1H), 6.43 (s, 1H), 3.85 (s, 2H), 3.78 (s, 3H), 3.74 (s, 2H), 3.36 (s, 3H), 2.93 (s, 2H), 2.85 (s, 2H).

Synthesis of 1-(5-((3,4-dihydroisoquinolin-2(1H)-yl)methyl)furan-2-yl)ethan-1-one

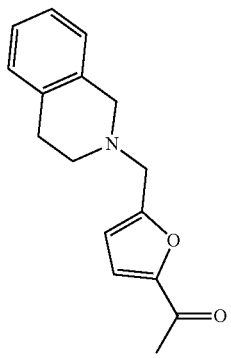 [SMILES: CC(=O)c1ccc(CN2CCc3ccccc3C2)o1]

A solution of 5-((3,4-dihydroisoquinolin-2(1H)-yl)methyl)-N-methoxy-N-methylfuran-2-carboxamide (2.42 g, 8 mmol) in THF (75 ml) was cooled to 5° C. and methylmagnesium bromide (3.4M in 2-methylTHF, 7 ml, 3 eq) was added. The reaction mixture was stirred at 5° C. for 2 h, poured into aq $NH_4Cl$ and extracted with $Et_2O$. The combined extracts were dried over anh. $Na_2SO_4$, filtered, and solvents were evaporated in vacuo. Compound 5 was used for the next step without purification. Yield 1.72 g (83.6%). LC-MS 0.46 min, m/z 256.5 [MH]+. $^1$H-NMR (400 MHz, $CDCl_3$), δ (ppm): 7.17 (t, J=5.2 Hz, 1H), 7.15-7.08 (m, 3H), 7.02 (d, J=5.5 Hz, 1H), 6.46 (d, J=3.5 Hz, 1H), 3.83 (s, 2H), 3.73 (s, 2H), 2.94 (t, J=5.8 Hz, 2H), 2.84 (t, J=5.8 Hz, 2H), 2.48 (s, 3H).

442

Synthesis of (2E,2'E)-2,2'-(1-(5-((3,4-dihydroisoquinolin-2(1H)-yl)methyl)furan-2-yl)ethane-1,2-diylidene)bis(N-ethylhydrazine-1-carbothioamide)

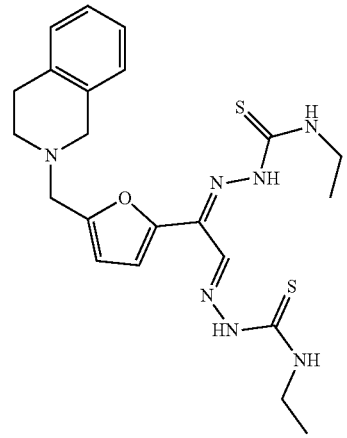 [SMILES: CCNC(=S)N/N=C/C(=N\NC(=S)NCC)c1ccc(CN2CCc3ccccc3C2)o1]

A mixture of 1-(5-((3,4-dihydroisoquinolin-2(1H)-yl) methyl)furan-2-yl)ethan-1-one (0.89 g, 3.5 mmol), NaBr (0.36 g, 1 eq), and DMSO (2 ml) was heated to 85° C., then $H_2SO_4$ (3 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (0.83 g, 2 eq) was added to the filtrate. The reaction mixture was refluxed for 2 h, then cooled to rt. Formed precipitate was filtered, washed with EtOH, aq.sat. $K_2CO_3$, water, $Et_2O$, and dried. Yield 0.52 g (31.6%). LC-MS 1.34 min, m/z 472.4 [MH]+.

Synthesis of Compound 118

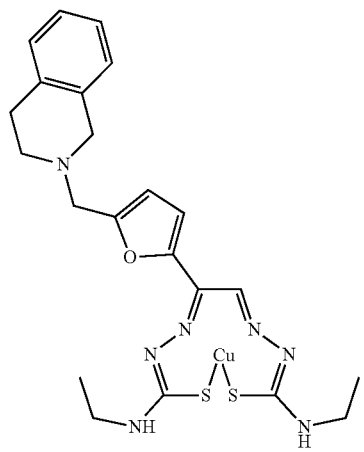

Copper(II) chloride dihydrate (0.19 g, 1 eq) was added to a stirred solution of INT-118 (0.18 g, 0.4 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.053 g (26%).

Scheme 80: Synthesis of Compound 119
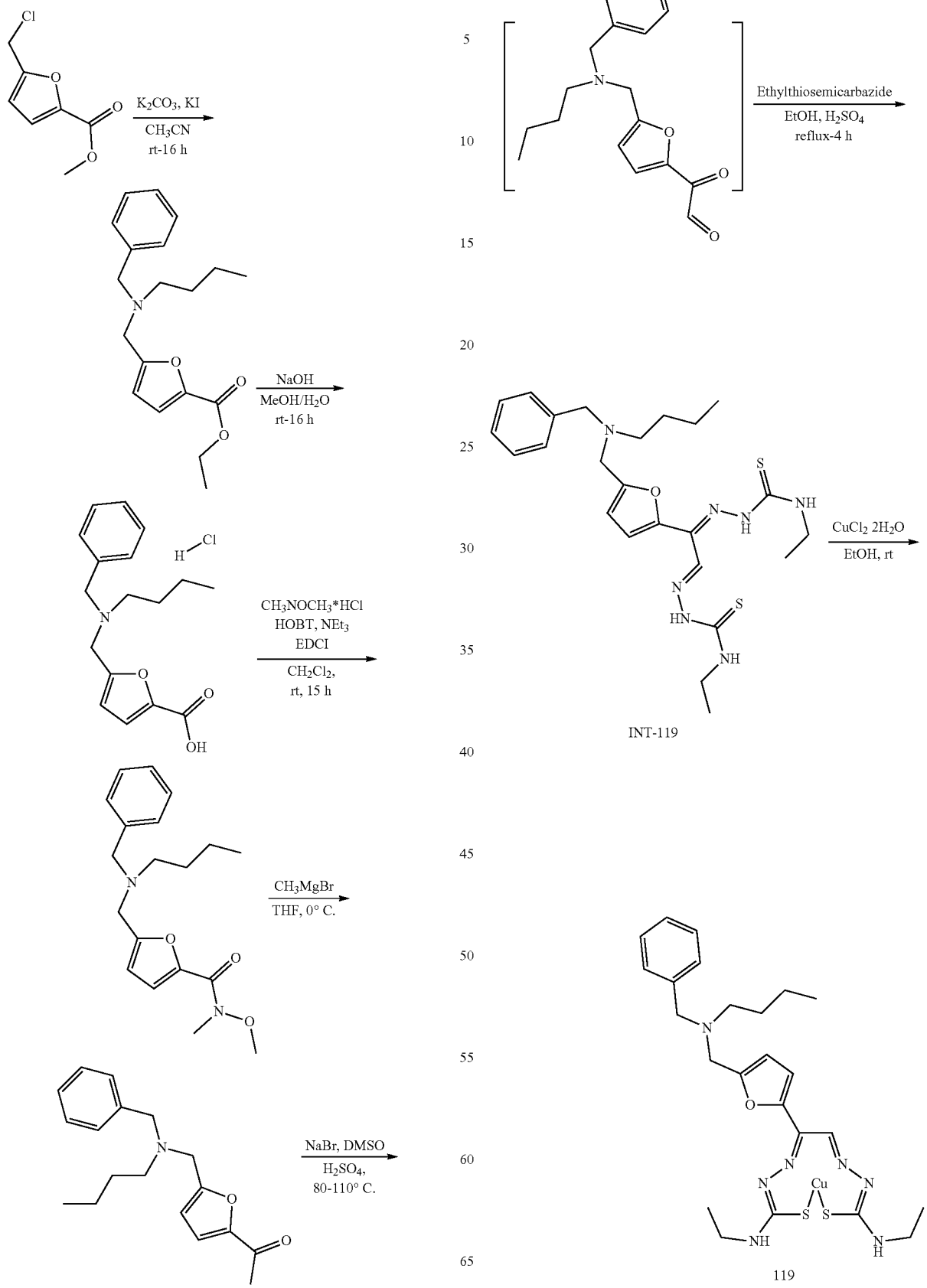

445

Synthesis of ethyl 5-((benzyl(butyl)amino)methyl)furan-2-carboxylate

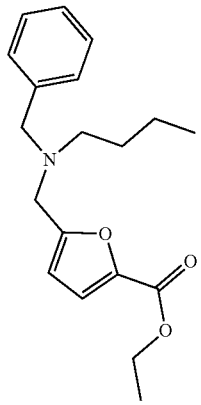 [SMILES: CCCCN(Cc1ccccc1)Cc1ccc(C(=O)OCC)o1]

To a solution of methyl 5-(chloromethyl)furan-2-carboxylate (3.0 g, 15.9 mmol) in CH₃CN (200 ml) were added N-benzylbutylamine (2.73 g, 1.05 eq), potassium carbonate (4.4 g, 2 eq), and potassium iodide (0.48 g, 0.2 eq). The reaction mixture was stirred overnight at rt. Solids were filtered and filtrate was concentrated in vacuo. The residue was dissolved in DCM and washed with water (3×75 ml). Organic layer was separated, dried over anh. Na₂SO₄, filtered, and solvents were evaporated in vacuo. The product was used without further purification. Yield 5 g (99.7%). LC-MS 1.16 min, m/z 316.3 [MH]+. ¹H-NMR (400 MHz, CDCl₃), δ (ppm): δ 7.48-7.24 (m, 5H), 7.13 (d, J=3.4 Hz, 1H), 6.33 (d, J=3.2 Hz, 1H), 4.37 (q, J=7.1 Hz, 2H), 3.69 (s, 2H), 3.62 (s, 2H), 2.49 (t, J=7.2 Hz, 2H), 1.54 (dd, J=19.9, 12.2 Hz, 2H), 1.42-1.26 (m, 5H), 0.89 (t, J=7.3 Hz, 3H).

Synthesis of 5-((benzyl(butyl)amino)methyl)furan-2-carboxylic Acid

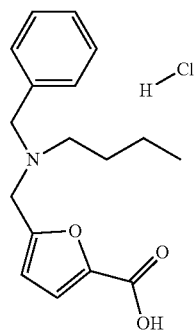

To a solution of ethyl 5-((benzyl(butyl)amino)methyl) furan-2-carboxylate (5 g, 15.9 mmol) in methanol (30 ml) a solution of NaOH (1.33 g, 2.5 eq) in water (10 ml) was added and the reaction mixture was stirred for 15 h at rt. Methanol was removed in vacuo, the residue was diluted with water and acidified to pH 1. The acidified solution was evaporated to dryness and treated with acetonitrile. Solids were filtered, and filtrate was evaporated in vacuo to dryness. Yield 5.14 g (99.9%). LC-MS 0.9 min, m/z 288.4 [MH]+.

446

Synthesis of 5-((benzyl(butyl)amino)methyl)-N-methoxy-N-methylfuran-2-carboxamide

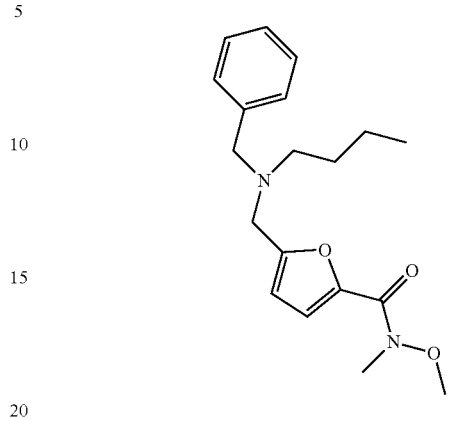

To a stirred mixture of 5-((benzyl(butyl)amino)methyl) furan-2-carboxylic acid (5 g, 15.4 mmol), N,O-dimethylhydroxylamine (1.8 g, 1.2 eq), HOBt (2.5 g, 1.2 eq), and triethylamine (7.8 ml, 5.6 g, 3.5 eq) in DCM (100 ml) at 5° C. was added EDCl (3.55 g, 1.2 eq) and reaction was stirred for 15 h at rt. The mixture was washed with water and brine. The organic layer was dried over anh. Na₂SO₄ and then concentrated under reduced pressure. Yield 4 g (78.4%). LC-MS 1.06 min, m/z 331.4 [MH]+. ¹H-NMR (400 MHz, DMSO-d6), δ (ppm): 7.37-7.28 (m, 4H), 7.23 (t, J=6.6 Hz, 1H), 7.12 (d, J=3.4 Hz, 1H), 6.48 (d, J=3.4 Hz, 1H), 3.73 (s, 3H), 3.64 (s, 2H), 3.32 (s, 2H), 3.20 (d, J=18.8 Hz, 3H), 2.38 (t, J=7.1 Hz, 2H), 1.53-1.37 (m, 2H), 1.32-1.18 (m, 2H), 0.80 (t, J=7.3 Hz, 3H).

Synthesis of 1-(5-((benzyl(butyl)amino)methyl) furan-2-yl)ethan-1-one

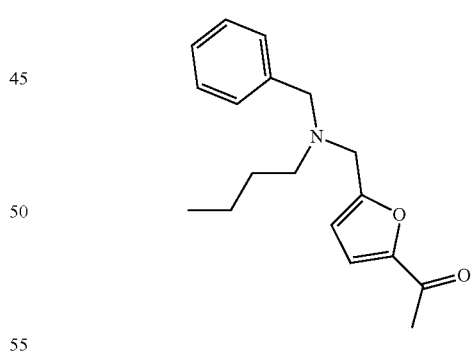

A solution of 5-((benzyl(butyl)amino)methyl)-N-methoxy-N-methylfuran-2-carboxamide (3 g, 9.1 mmol) in THF (200 ml) was cooled to 5° C. and methylmagnesium bromide (3.4M in 2-methylTHF, 8 ml, 3 eq) was added. The reaction mixture was stirred at 5° C. for 2 h, poured into aq NH₄Cl and extracted with Et₂O. The combined extracts were dried over anh. Na₂SO₄, filtered, and solvents were evaporated in vacuo. Compound 5 was used for the next step without purification. Yield 2.45 g (94.6%). LC-MS 1.04 min, m/z 286.5 [MH]+. ¹H-NMR (400 MHz, CDCl₃), δ (ppm): 7.45-7.19 (m, 5H), 7.14 (d, J=3.4 Hz, 1H), 6.36 (d, J=3.3 Hz, 1H), 3.68 (d, J=16.3 Hz, 2H), 3.63 (s, 2H), 2.64-2.45 (m, 5H), 1.59-1.48 (m, 2H), 1.32 (dt, J=25.1, 8.9 Hz, 2H), 0.89 (t, J=7.3 Hz, 3H).

Synthesis of INT-119 ((2E,2'E)-2,2'-(1-(5-((benzyl (butyl)amino)methyl)furan-2-yl)ethane-1,2-diylidene)bis(N-ethylhydrazine-1-carbothioamide))

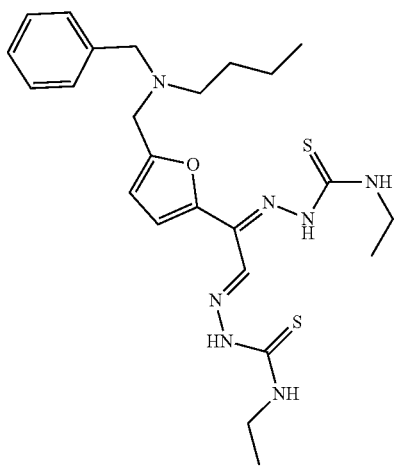 [SMILES: CCCCN(Cc1ccccc1)Cc1ccc(C(/C=N/NC(=S)NCC)=N/NC(=S)NCC)o1]

A mixture of 1-(5-((benzyl(butyl)amino)methyl)furan-2-yl)ethan-1-one (1 g, 3.5 mmol), NaBr (0.36 g, 1 eq), and DMSO (2 ml) was heated to 85° C., then H$_2$SO$_4$ (3 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (0.83 g, 2 eq) was added to the filtrate. The reaction mixture was refluxed for 2 h then cooled to room temperature. Formed precipitate was filtered, washed with EtOH, aq.sat. K$_2$CO$_3$, water, Et$_2$O, and dried. Yield 0.51 g (29%). LC-MS 1.41 min, m/z 502.5 [MH]+.

Synthesis of Compound 119

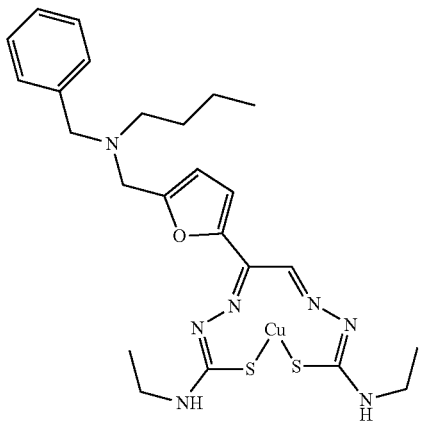

Copper(II) chloride dihydrate (0.088 g, 1 eq) was added to a stirred solution of INT-119 (0.26 g, 0.5 mmol) in ethanol. The mixture was stirred for 15 h at rt. The formed complex precipitated as a red-brown powder. The precipitate was collected by filtration, washed with water, methanol, diethyl ether, and dried in vacuo. Yield 0.25 g (84.7%).

Scheme 81: Synthesis of Compound 120

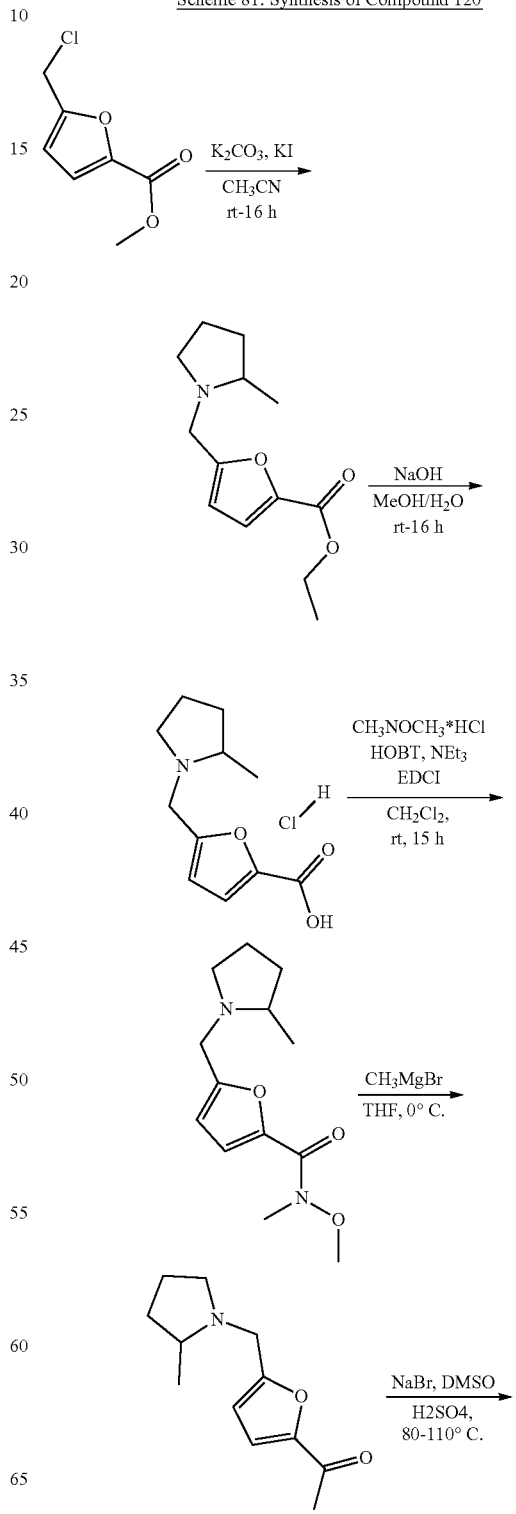

-continued

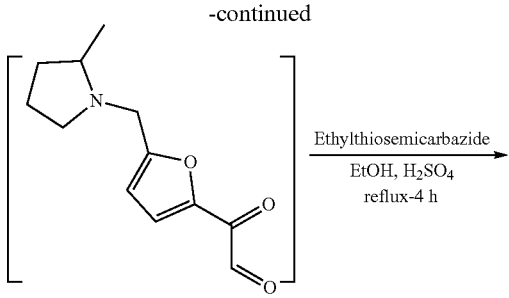

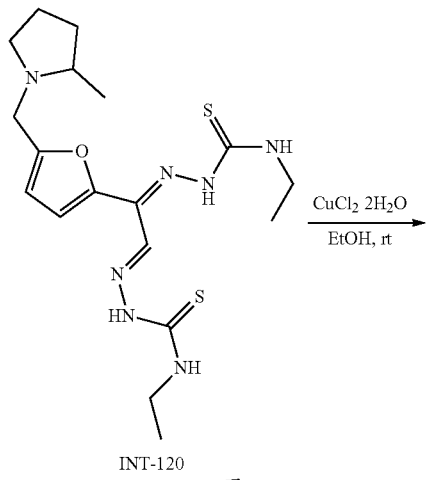

INT-120

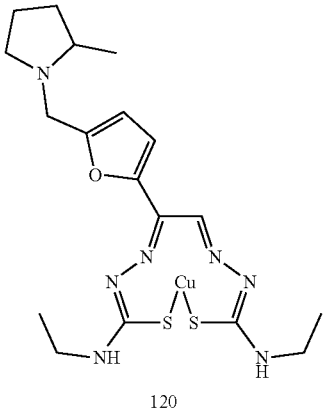

120

Synthesis of ethyl 5-((2-methylpyrrolidin-1-yl)methyl)furan-2-carboxylate

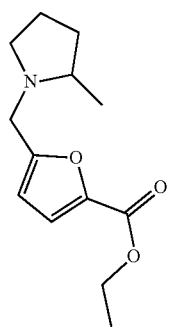 [SMILES: CCOC(=O)c1ccc(CN2CCCC2C)o1]

To a solution of methyl 5-(chloromethyl)furan-2-carboxylate (3.11 g, 16.5 mmol) in CH₃CN (100 ml) were added 2-methylpyrrolidine (1.4 g, 1 eq), potassium carbonate (6.84 g, 3 eq), and potassium iodide (0.82 g, 0.3 eq). The reaction mixture was stirred overnight at rt. Solids were filtered and filtrate was concentrated in vacuo. The residue was dissolved in DCM and washed with water (3×50 ml). Organic layer was separated, dried over anh. Na₂SO₄, filtered, and solvents were evaporated in vacuo. The residue was purified by column chromatography (silica gel, eluent hexane/EtOAc 10:1). Yield 3.84 g (98.1%). LC-MS 0.95 min, m/z 238.1 [MH]+. ¹H-NMR (400 MHz, CDCl₃), δ (ppm): 7.11 (d, J=3.4 Hz, 1H), 6.31 (d, J=3.4 Hz, 1H), 4.34 (q, J=7.1 Hz, 2H), 3.96 (d, J=14.6 Hz, 1H), 3.47 (d, J=14.6 Hz, 1H), 3.06 (td, J=8.8, 2.7 Hz, 1H), 2.50-2.36 (m, 1H), 2.30 (q, J=8.9 Hz, 1H), 1.99-1.86 (m, 1H), 1.79 (dd, J=5.1, 3.0 Hz, 1H), 1.85-1.57 (m, 2H), 1.45 (m, 1H), 1.31-1.20 (m, 1H), 1.14 (d, J=6.0 Hz, 3H).

Synthesis of 5-((2-methylpyrrolidin-1-yl)methyl)furan-2-carboxylic Acid

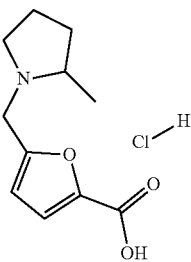

To a solution of ethyl 5-((2-methylpyrrolidin-1-yl)methyl)furan-2-carboxylate (3.84 g, 16.2 mmol) in methanol (100 ml) a solution of NaOH (1.62 g, 2.5 eq) in water (10 ml) was added and the reaction mixture was stirred for 15 h at rt. Methanol was removed in vacuo, the residue was diluted with water and acidified to pH 1. The acidified solution was evaporated to dryness and treated with acetonitrile. Solids were filtered, and filtrate was evaporated in vacuo to dryness. Yield 3.09 g (77.7%). LC-MS 0.63 min, m/z 210.4 [MH]+.

Synthesis of N-methoxy-N-methyl-5-((2-methylpyrrolidin-1-yl)methyl)furan-2-carboxamide

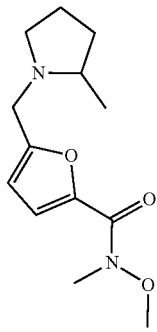 [SMILES: CON(C)C(=O)c1ccc(CN2CCCC2C)o1]

To a stirred mixture of 5-((2-methylpyrrolidin-1-yl)methyl)furan-2-carboxylic acid (3.09 g, 12.6 mmol), N,O-dimethylhydroxylamine (1.47 g, 1.2 eq), HOBt (2.31 g, 1.2 eq), and triethylamine (5.3 ml, 3.85 g, 3 eq) in DCM (100 ml) at 5° C. was added EDCl (2.89 g, 1.2 eq) and reaction was stirred for 15h at rt. The mixture was washed with water and brine. The organic layer was dried over anh. Na$_2$SO$_4$ and then concentrated under reduced pressure. The residue was purified by column chromatography (silica gel, eluent hexane/EtOAc 1:1). Yield 2.41 g (76%). LC-MS 0.73 min, m/z 253.4 [MH]+. Yield 2.42 g (60.7%). $^1$H NMR (400 MHz, DMSO-d6) δ 9.02 (d, J=3.4 Hz, 1H), 8.27 (d, J=3.4 Hz, 1H), 5.90 (t, J=13.1 Hz, 1H), 5.69 (s, 3H), 5.48 (t, J=13.0 Hz, 1H), 5.27 (s, 3H), 5.02 (td, J=9.0, 2.7 Hz, 1H), 4.45-4.34 (m, 1H), 4.28 (q, J=8.9 Hz, 1H), 3.90-3.78 (m, 1H), 3.78-3.64 (m, 1H), 3.63-3.51 (m, 1H), 3.44-3.30 (m, 1H), 3.08 (d, J=6.0 Hz, 3H).

Synthesis of 1-(5-((2-methylpyrrolidin-1-yl)methyl)furan-2-yl)ethan-1-one

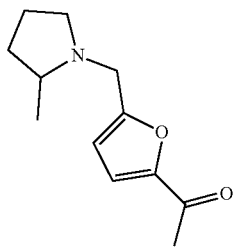

A solution of N-methoxy-N-methyl-5-((2-methylpyrrolidin-1-yl)methyl)furan-2-carboxamide (2.41 g, 9.5 mmol) in THF (75 ml) was cooled to 5° C. and methylmagnesium bromide (3.4M in 2-methylTHF, 8.5 ml, 3 eq) was added. The reaction mixture was stirred at 5° C. for 2 h, poured into aq NH$_4$Cl and extracted with Et$_2$O. The combined extracts were dried over anh. Na$_2$SO$_4$, filtered, and solvents were evaporated in vacuo. Compound 5 was used for the next step without purification. Yield 1.35 g (68.1%). LC-MS 0.68 min, m/z 207.9 [MH]+. $^1$H-NMR (400 MHz, CDCl$_3$), δ (ppm): 7.14 (d, J=3.5 Hz, 1H), 6.38 (d, J=3.2 Hz, 1H), 3.98 (d, J=14.7 Hz, 1H), 3.51 (d, J=14.8 Hz, 1H), 3.10 (t, J=7.3 Hz, 1H), 2.47 (s, 4H), 2.34 (dd, J=17.8, 9.1 Hz, 1H), 1.94 (dt, J=12.3, 9.8 Hz, 1H), 1.78 (d, J=8.5 Hz, 1H), 1.72-1.62 (m, 1H), 1.46 (dd, J=23.5, 14.0 Hz, 1H), 1.16 (d, J=6.0 Hz, 3H).

Synthesis of INT-120 ((2E,2'E)-2,2'-(1-(5-((2-methylpyrrolidin-1-yl)methyl)furan-2-yl)ethane-1,2-diylidene)bis(N-ethylhydrazine-1-carbothioamide))

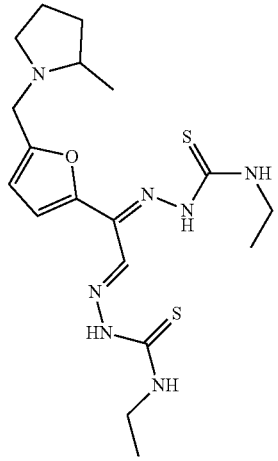 [SMILES: CCNC(=S)N/N=C/C(=N\NC(=S)NCC)c1ccc(CN2CCCC2C)o1]

A mixture of 1-(5-((2-methylpyrrolidin-1-yl)methyl)furan-2-yl)ethan-1-one (0.75 g, 3.6 mmol), NaBr (0.37 g, 1 eq), and DMSO (2 ml) was heated to 85° C., then H$_2$SO$_4$ (2 drops) was added (foaming, exothermic). The reaction was heated to 110-115° C. until the formation of dimethyl sulfide has stopped, and the reaction mixture became viscous. The formed viscous substance was dissolved in EtOH, solids were filtered and ethylthiosemicarbazide (0.86 g, 2 eq) was added to the filtrate. The reaction mixture was refluxed for 2 h, then cooled to rt. Formed precipitate was filtered, washed with EtOH, aq.sat. K$_2$CO$_3$, water, Et$_2$O, and dried. Yield 0.5 g (32.6%). LC-MS 1.21 min, m/z 424.4 [MH]+.

Synthesis of Compound 120

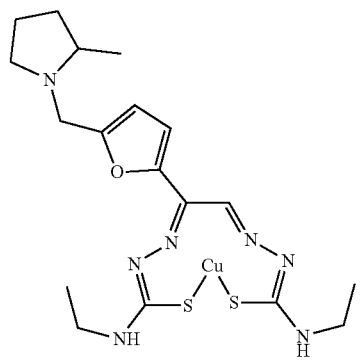

Copper(II) chloride dihydrate (0.12 g, 1 eq) was added to a stirred solution of INT-120 (0.3 g, 0.7 mmol) in ethanol. The mixture was stirred for 15h at rt. The formed complex precipitated as a red-brown powder. The precipitate was collected by filtration, washed with water, methanol, diethyl ether, and dried in vacuo. Yield 0.3 g (92.7%).

Scheme 82: Synthesis of Compound 121

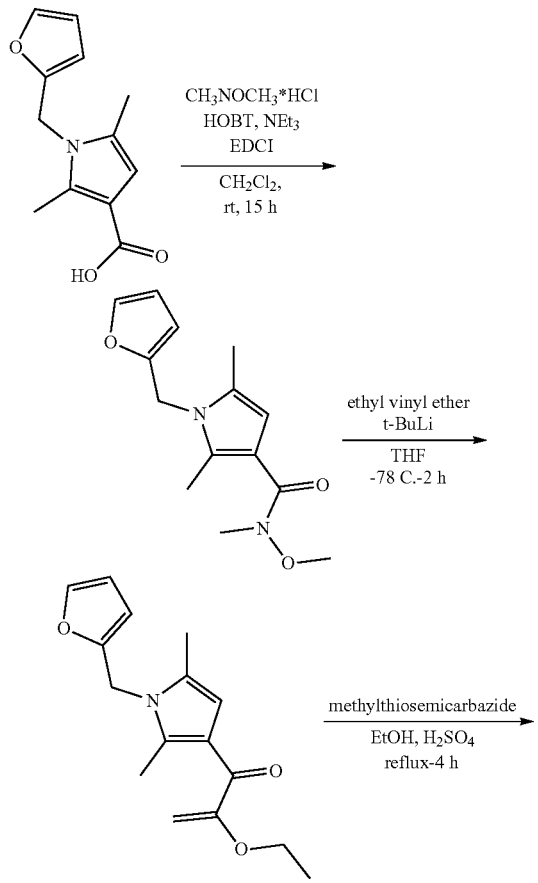

INT-121

121

Synthesis of 1-(furan-2-ylmethyl)-N-methoxy-N,2,5-trimethyl-1H-pyrrole-3-carboxamide

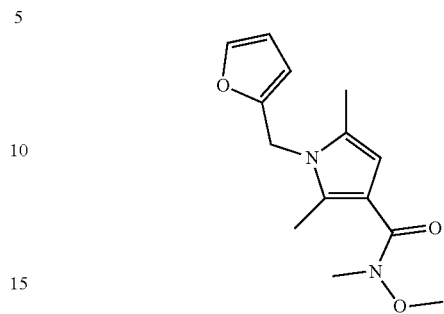

To a stirred mixture of 1-(furan-2-ylmethyl)-2,5-dimethyl-1H-pyrrole-3-carboxylic acid (3.27 g, 14.9 mmol), N,O-dimethylhydroxylamine (1.74 g, 1.2 eq), HOBt (2.42 g, 1.2 eq), and triethylamine (5.3 ml, 3.81 g, 2.5 eq) in DCM (50 ml) at 5° C. was added EDCl (3.43 g, 1.2 eq) and reaction was stirred for 15h at rt. The mixture was washed with water and brine. The organic layer was dried over anh. $Na_2SO_4$ and then concentrated under reduced pressure. The product was purified by column chromatography (silica gel, eluent DCM 100% then DCM/EtOAc 8:2). Yield 2.8 g (71.6%). $^1$H-NMR (400 MHz, $CDCl_3$), δ (ppm): 7.35 (s, 1H), 6.35-6.28 (m, 1H), 6.24 (s, 1H), 6.05 (d, J=3.2 Hz, 1H), 4.94 (s, 2H), 3.67 (s, 3H), 3.30 (s, 3H), 2.53 (s, 3H), 2.27 (s, 3H).

Synthesis of 2-ethoxy-1-(1-(furan-2-ylmethyl)-2,5-dimethyl-1H-pyrrol-3-yl)prop-2-en-1-one

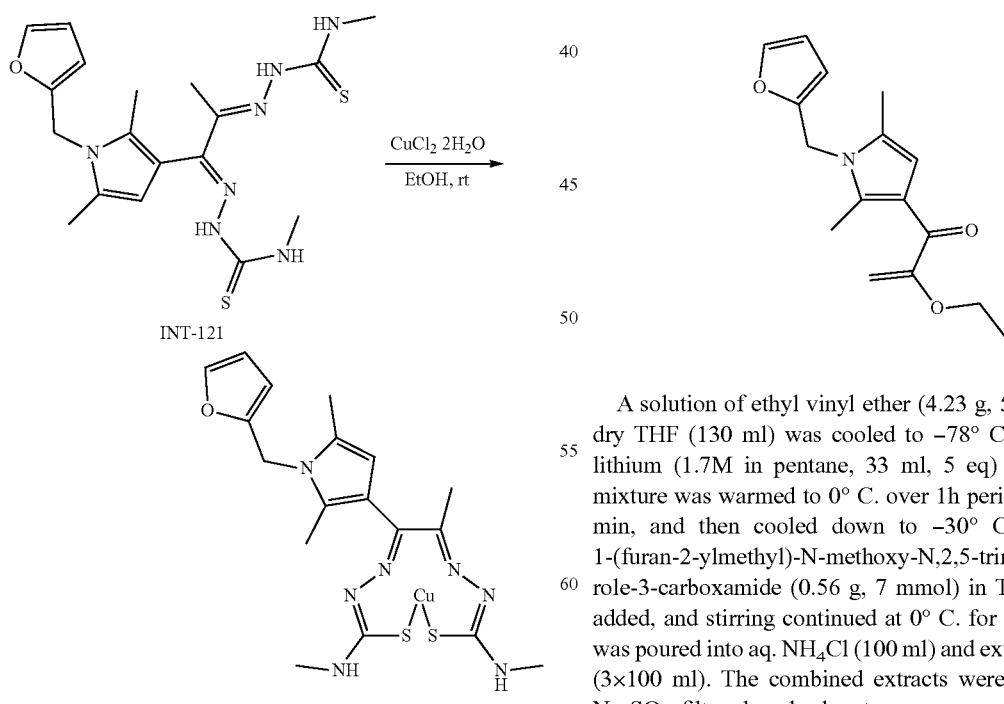

A solution of ethyl vinyl ether (4.23 g, 5.6 ml, 5.5 eq) in dry THF (130 ml) was cooled to −78° C., and tert-butyl-lithium (1.7M in pentane, 33 ml, 5 eq) was added. The mixture was warmed to 0° C. over 1h period, stirred for 45 min, and then cooled down to −30° C. A solution of 1-(furan-2-ylmethyl)-N-methoxy-N,2,5-trimethyl-1H-pyrrole-3-carboxamide (0.56 g, 7 mmol) in THF (15 ml) was added, and stirring continued at 0° C. for 4 h. The mixture was poured into aq. $NH_4Cl$ (100 ml) and extracted with $Et_2O$ (3×100 ml). The combined extracts were dried over anh. $Na_2SO_4$, filtered, and solvents were evaporated. The product was used for the next step without additional purification. Yield 1.6 g (99.8%). LC-MS 1.56 min, m/z 274.5 [MH]+.

455

Synthesis of INT-121 ((2E,2'E)-2,2'-(1-(1-(furan-2-ylmethyl)-2,5-dimethyl-1H-pyrrol-3-yl)propane-1,2-diylidene)bis(N-methylhydrazine-1-carbothioamide))

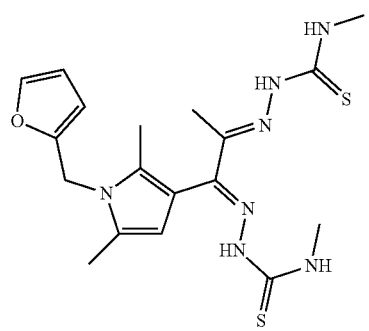 [SMILES: CNC(=S)N/N=C(C)/C(=N/NC(=S)NC)c1cc(C)n(Cc2ccco2)c1C]

2-ethoxy-1-(1-(furan-2-ylmethyl)-2,5-dimethyl-1H-pyrrol-3-yl)prop-2-en-1-one (2.91 g, 10.6 mmol) was dissolved in EtOH (150 ml), methylthiosemicarbazide (2.24 g, 2 eq) and 3 drops of $H_2SO_4$ were added. The stirred reaction mixture was heated to reflux for 4h and then maintained for 15h at rt. The formed precipitate was filtered, washed with EtOH, aq.sat. $Na_2CO_3$, water, $Et_2O$, and dried. Yield 1.6 g (35.8%). LC-MS 1.63 min, m/z 420.5 [MH]+.

Synthesis of Compound 121

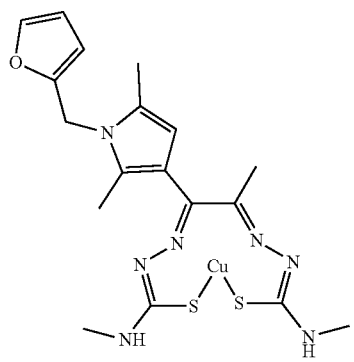

Copper(II) chloride dihydrate (0.31 g, 1 eq) was added to a stirred solution of INT-121 (0.75 g, 1 mmol) in ethanol. The mixture was stirred for 15h at rt. The formed complex precipitated as a red-brown powder. The precipitate was collected by filtration, washed with water, diethyl ether, and dried. Yield 0.6 g (68.9%).

Scheme 83: Synthesis of Compound 122

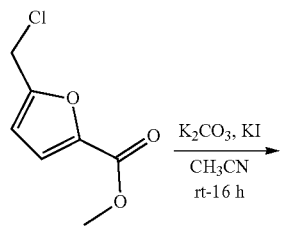

-continued

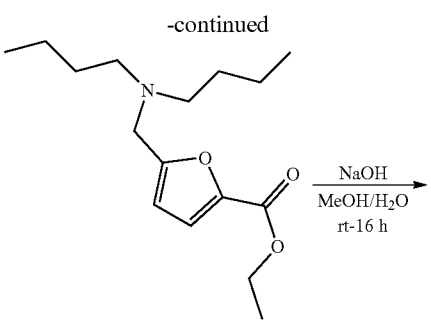

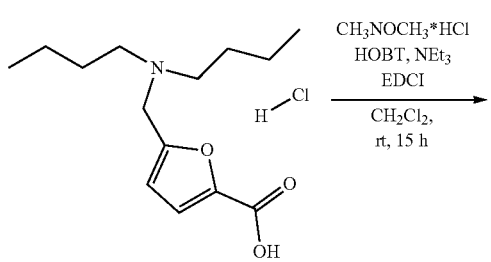

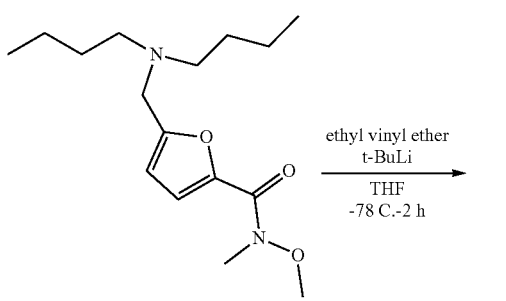

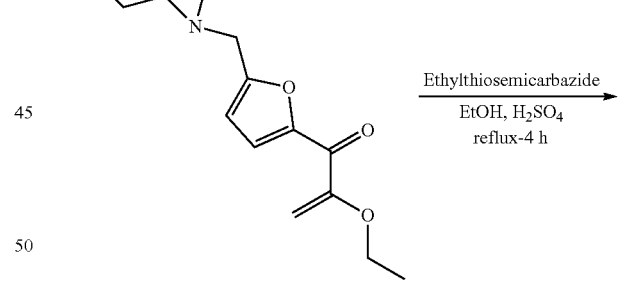

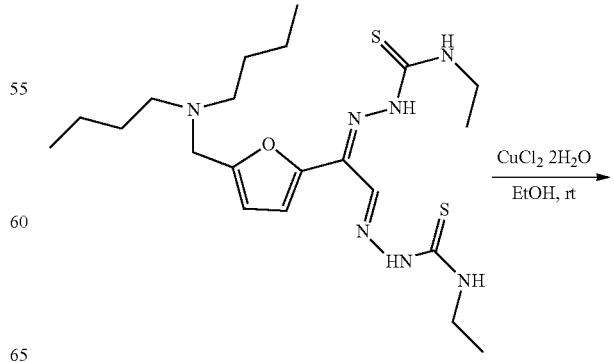

INT-122

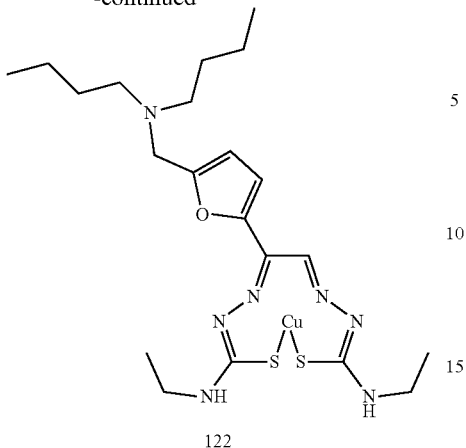

122

Synthesis of ethyl 5-((dibutylamino)methyl)furan-2-carboxylate

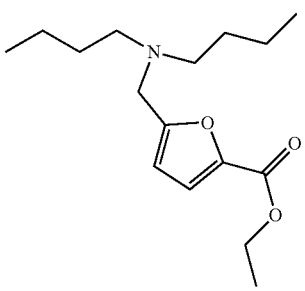 [SMILES: CCCCN(CCCC)Cc1ccc(C(=O)OCC)o1]

To a solution of methyl 5-(chloromethyl)furan-2-carboxylate (4 g, 21.2 mmol) in $CH_3CN$ (200 ml) were added di-butylamine (2.88 g, 1.05 eq), potassium carbonate (5.86 g, 2 eq), and potassium iodide (0.63 g, 0.2 eq). The reaction mixture was stirred overnight at rt. Solids were filtered and filtrate was concentrated in vacuo. The residue was dissolved in DCM and washed with water (3×100 ml). Organic layer was separated, dried over $Na_2SO_4$, filtered, and solvents were evaporated. The product was used without purification. Yield 5.9 g (98.9%). LC-MS 1.08 min, m/z 282.5 [MH]+. $^1$H-NMR (400 MHz, $CDCl_3$), δ (ppm): 7.12 (d, J=3.3 Hz, 1H), 6.30 (d, J=3.4 Hz, 1H), 4.47-4.25 (m, 2H), 3.71 (d, J=12.0 Hz, 2H), 2.54-2.31 (m, 4H), 1.53-1.20 (m, 12H), 0.90 (t, J=7.3 Hz, 6H).

Synthesis of 5-((dibutylamino)methyl)furan-2-carboxylic Acid

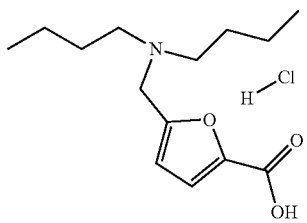

To a solution of ethyl 5-((dibutylamino)methyl)furan-2-carboxylate (5.9 g, 21 mmol) in methanol (50 ml) a solution of NaOH (2.1 g, 2.5 eq) in water (10 ml) was added and the reaction mixture was stirred for 15h at rt. Methanol was removed in vacuo, the residue was diluted with water and acidified to pH 1. The acidified solution was evaporated to dryness and treated with acetonitrile. Solids were filtered and filtrate was evaporated in vacuo to dryness. Yield 6.07 g (99.9%). LC-MS 1.09 min, m/z 254.9 [MH]+.

Synthesis of 5-((dibutylamino)methyl)-N-methoxy-N-methylfuran-2-carboxamide

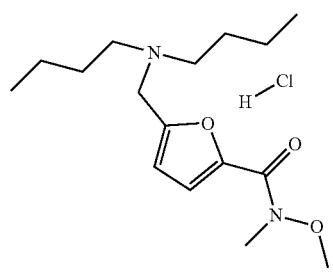

To a stirred mixture of 5-((dibutylamino)methyl)furan-2-carboxylic acid (6.07 g, 21 mmol), N,O-dimethylhydroxylamine (2.45 g, 1.2 eq), HOBt (3.4 g, 1.2 eq), and triethylamine (10.3 ml, 7.4 g, 3.5 eq) in DCM (100 ml) at 5° C. was added EDCl (4.81 g, 1.2 eq) and reaction was stirred for 15h at rt. The mixture was washed with water and brine. The organic layer was dried over anh. $Na_2SO_4$ and then concentrated under reduced pressure. The product was purified by column chromatography (silica gel, eluent DCM 100% then DCM/MeOH 96:4). Yield 4.28 g (69%). LC-MS 0.93 min, m/z 297.6 [MH]+. $^1$H-NMR (400 MHz, $CDCl_3$), δ (ppm): 7.10 (d, J=3.4 Hz, 1H), 6.31 (d, J=3.3 Hz, 1H), 3.77 (s, 3H), 3.72 (s, 2H), 3.34 (s, 3H), 2.53-2.40 (m, 4H), 1.46 (dt, J=14.9, 7.4 Hz, 4H), 1.30 (dt, J=14.7, 7.3 Hz, 4H), 0.90 (t, J=7.3 Hz, 6H).

Synthesis of 1-(5-((dibutylamino)methyl)furan-2-yl)-2-ethoxyprop-2-en-1-one

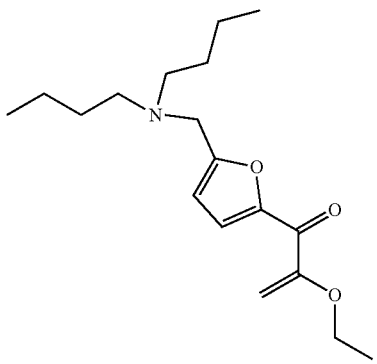 [SMILES: C=C(OCC)C(=O)c1ccc(CN(CCCC)CCCC)o1]

A solution of ethyl vinyl ether (2.68 g, 3.55 ml, 5.5 eq) in dry THF (130 mL) was cooled to −78° C., and tert-butyl-lithium (1.6M in pentane, 21 ml, 5 eq) was added. The mixture was warmed to 0° C. over 1h period, stirred for 45 min, and cooled down to −30° C. A solution of 5-((dibutylamino)methyl)-N-methoxy-N-methylfuran-2-carboxamide (2.1 g, 7.4 mmol) in THF was added and the mixture was stirred at 0° C. for 4 h. The progress of the reaction was monitored by TLC (hexane/EtOAc 10:1). The mixture was poured into aq NH₄Cl and extracted with Et₂O. The combined extracts were dried over anh. Na₂SO₄, filtered, and evaporated in vacuo. The product was used for the next step without additional purification. Yield 2.07 g (99.8%). LC-MS 1.19 min, m/z 308.6 [MH]+.

Synthesis of INT-122 ((2E,2'E)-2,2'-(1-(5-((dibutylamino)methyl)furan-2-yl)ethane-1,2-diylidene)bis(N-ethylhydrazine-1-carbothioamide))

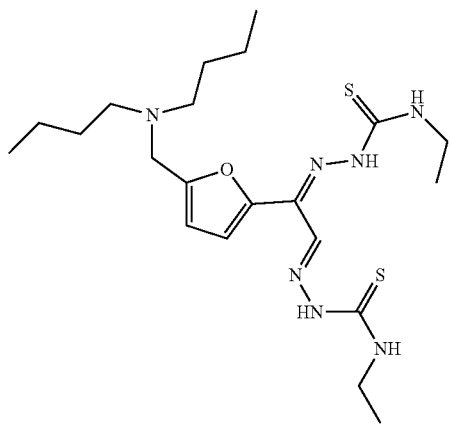 [SMILES: CCCCN(CCCC)Cc1ccc(C(/C=N/NC(=S)NCC)=N/NC(=S)NCC)o1]

1-(5-((dibutylamino)methyl)furan-2-yl)-2-ethoxyprop-2-en-1-one (2.07 g, 6.7 mmol) was dissolved in EtOH (150 ml), ethylthiosemicarbazide (1.6 g, 2 eq) and 3 drops of H₂SO₄ were added. The stirred reaction mixture was heated to reflux for 4h and then maintained for 15h at rt. The formed precipitate was filtered, washed with EtOH, potassium carbonate solution, water, Et₂O, and dried. Yield 0.79 g (24.3%). LC-MS 1.32 min, m/z 482.4 [MH]+.

Synthesis of Compound 122

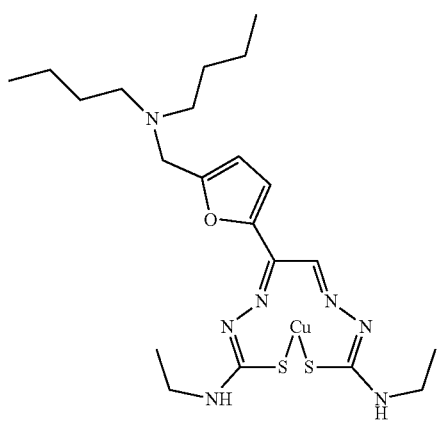

Copper(II) chloride dihydrate (0.18 g, 1 eq) was added to INT-122 (0.51 g, 1 mmol) in ethanol. The mixture was stirred for 15 h at rt. The formed complex precipitated as a red-brown powder. The precipitate was collected by filtration, washed with water, methanol, diethyl ether, and dried. Yield 0.41 g (71.3%).

Scheme 84: Synthesis of Compound 123

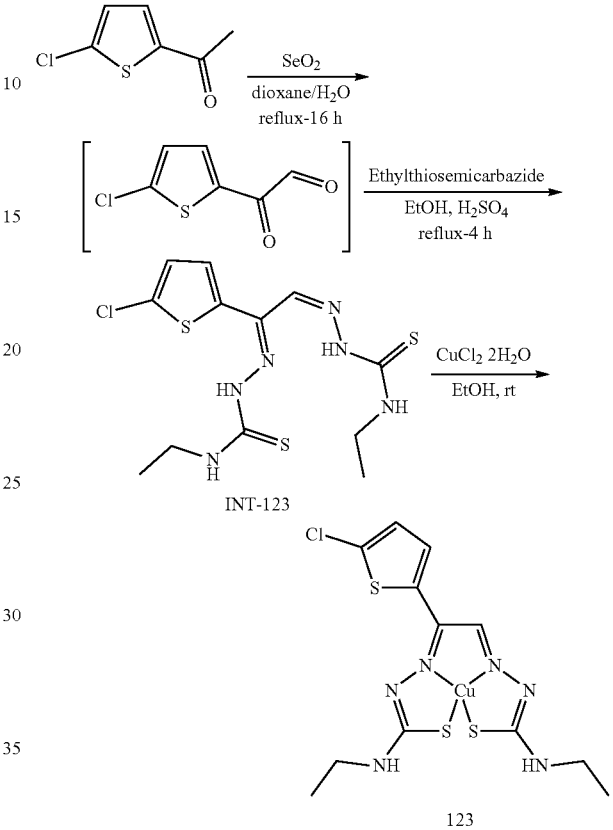

Synthesis of INT-123 ((2Z,2'Z)-2,2'-(1-(5-chlorothiophen-2-yl)ethane-1,2-diylidene)bis(N-ethylhydrazine-1-carbothioamide))

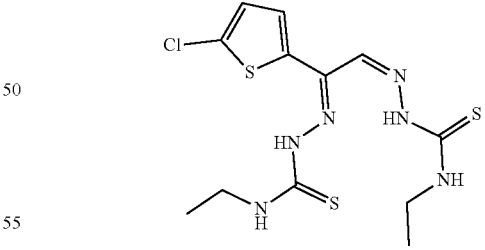

A three-necked flask was charged with SeO₂ (0.76 g, 1.05 eq), 1,4-dioxane (14 mL), and water (2.5 mL). The mixture was heated to 50° C. and stirred until most of SeO₂ dissolves. 1-(5-chlorothiophen-2-yl)ethan-1-one (1 g, 6.2 mmol) was added, and the reaction was heated to gentle reflux overnight. Selenium solids precipitated during the course of the reaction. The mixture was cooled in an ice bath and filtered through diatomaceous earth to remove selenium. The filter cake was washed with portions of 1,4-dioxane. The filtrate was evaporated to dryness and dissolved in EtOH (50 ml). Ethylthiosemicarbazide (1.48 g, 2 eq) and 3 drops of $H_2SO_4$ were added. The stirred reaction mixture was heated to reflux for 4h. Formed precipitate was filtered, washed with EtOH, aq.sat. $Na_2CO_3$, water, $Et_2O$, and dried. The product was crystallized from acetonitrile. Yield 1.3 g (55.8%). LC-MS 1.78 min, m/z 377.4 [MH]+.

Synthesis of Compound 123

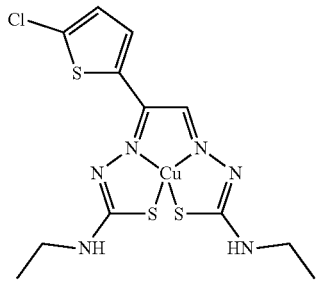

Copper(II) chloride dihydrate (0.095 g, 1 eq) was added to a stirred solution of INT-123 (0.21 g, 0.6 mmol) in ethanol. The mixture was stirred for 15h at rt. The formed complex precipitated as a red-brown powder. The precipitate was collected by filtration, washed with water, diethyl ether, and dried. Yield 0.24 g (98.7%).

Scheme 85: Synthesis of Compound 124

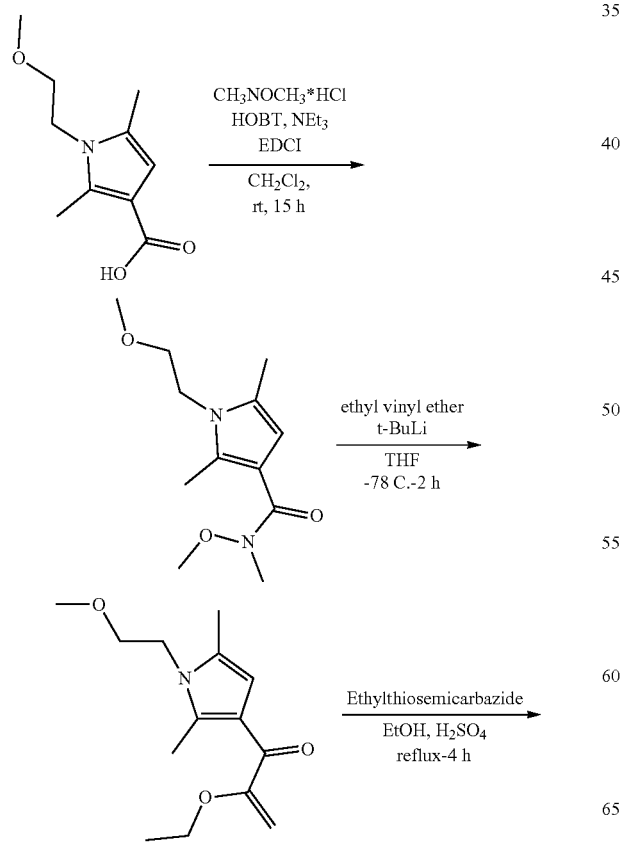

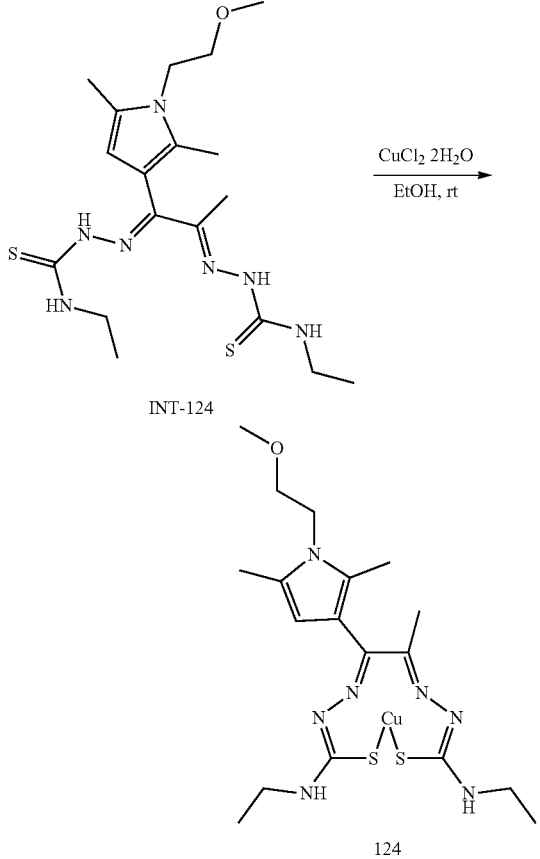

Synthesis of N-methoxy-1-(2-methoxyethyl)-N,2,5-trimethyl-1H-pyrrole-3-carboxamide

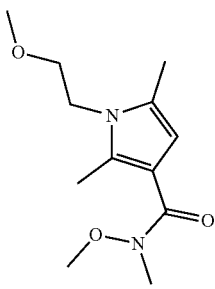 [SMILES: COCCn1c(C)cc(C(=O)N(C)OC)c1C]

To a stirred mixture of 1-(2-methoxyethyl)-2,5-dimethyl-1H-pyrrole-3-carboxylic acid (2.69 g, 13.6 mmol), N,O-dimethylhydroxylamine (1.6 g, 1.2 eq), HOBt (2.5 g, 1.2 eq), and triethylamine (3.8 ml, 2.76 g, 2 eq) in DCM (100 ml) at 5° C. was added EDCl (3.14 g, 1.2 eq) and reaction was stirred for 15h at rt. The mixture was washed with water and brine. The organic layer was dried over anh. $Na_2SO_4$ and then concentrated under reduced pressure. The product was used further without additional purification. Yield 2.33 g (71.1%). LC-MS 1.15 min, m/z 241.4. [MH]+. $^1$H-NMR (400 MHz, $CDCl_3$), δ (ppm): 6.19 (s, 1H), 3.96 (q, J=6.4 Hz, 2H), 3.66 (t, J=3.3 Hz, 3H), 3.58-3.44 (m, 2H), 3.36-3.21 (m, 6H), 2.47 (s, 3H), 2.22 (s, 3H).

463

Synthesis of 2-ethoxy-1-(1-(2-methoxyethyl)-2,5-dimethyl-1H-pyrrol-3-yl)prop-2-en-1-one

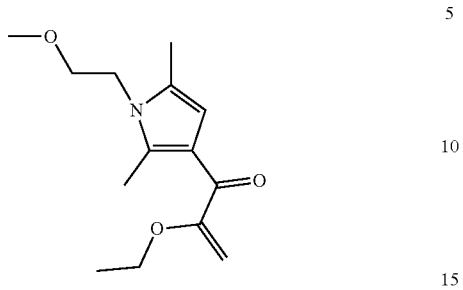

A solution of ethyl vinyl ether (2.01 g, 2.7 ml, 6.7 eq) in dry THF (50 ml) was cooled to −78° C., and tert-butyl-lithium (1.7M in pentane, 15 ml, 6 eq) was added. The mixture was warmed to 0° C. over 1h period, stirred for 45 min, and then cooled down to −30° C. A solution of N-methoxy-1-(2-methoxyethyl)-N,2,5-trimethyl-1H-pyrrole-3-carboxamide (1 g, 4.1 mmol) in THF (15 ml) was added and stirring continued at 0° C. for 4 h. The mixture was poured into aq. NH$_4$Cl (50 ml) and extracted with Et$_2$O (3×50 ml). The combined extracts were dried over anh. Na$_2$SO$_4$, filtered, and solvents were evaporated in vacuo. The product was used for the next step without additional purification. Yield 1.02 g (98%). LC-MS 1.41 min, m/z 252.4 [MH]+.

Synthesis of INT-124 ((2E,2′E)-2,2′-(1-(1-(2-methoxyethyl)-2,5-dimethyl-1H-pyrrol-3-yl)propane-1,2-diylidene)bis(N-ethylhydrazine-1-carbothioamide))

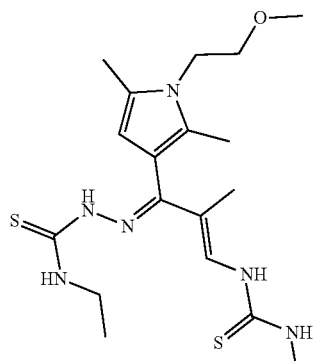

2-ethoxy-1-(1-(2-methoxyethyl)-2,5-dimethyl-1H-pyrrol-3-yl)prop-2-en-1-one (1.02 g, 4 mmol) was dissolved in EtOH (25 ml), ethylthiosemicarbazide (0.99 g, 2 eq) and 3 drops of H$_2$SO$_4$ were added. The stirred reaction mixture was heated to reflux for 4h and then maintained for 15h at rt. The formed precipitate was filtered, washed with EtOH, aq.sat. Na$_2$CO$_3$, water, Et$_2$O, and dried. Yield 0.48 g (27%). LC-MS 1.63 min, m/z 426.0 [MH]+.

464

Synthesis of Compound 124

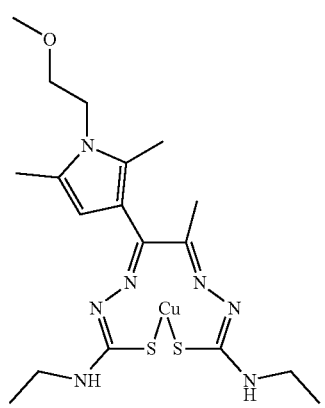

Copper(II) chloride dihydrate (0.23 g, 1 eq) was added to a stirred solution of INT-124 (0.5 g, 1.3 mmol) in ethanol. The mixture was stirred for 15h at rt. The formed complex precipitated as a red-brown powder. The precipitate was collected by filtration, washed with water, diethyl ether, and dried. Yield 0.5 g (88.7%).

Scheme 86: Synthesis of Compound 125

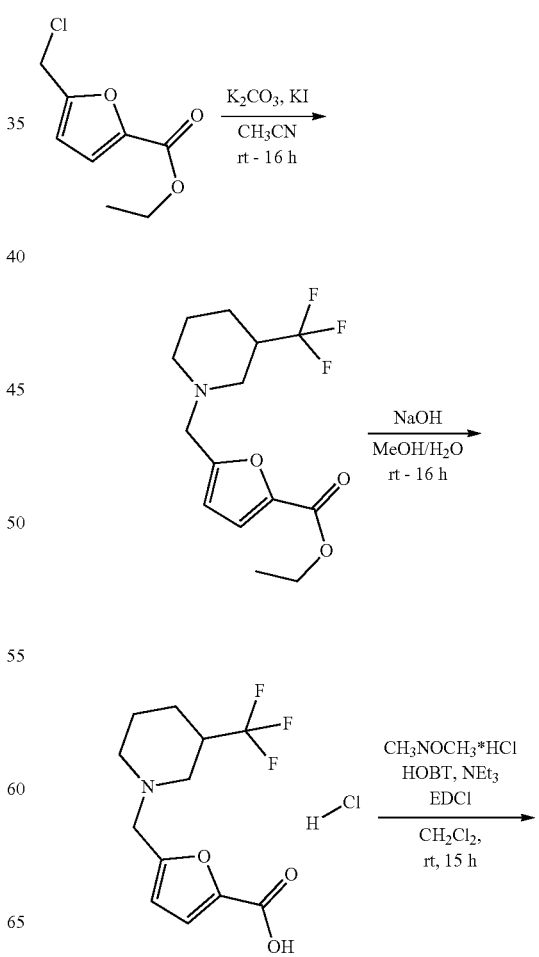

465

-continued

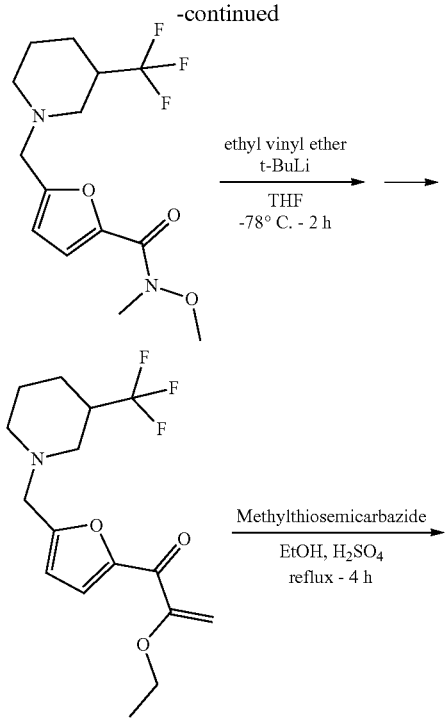

INT-125

466

Synthesis of ethyl 5-((3-(trifluoromethyl)piperidin-1-yl)methyl)furan-2-carboxylate

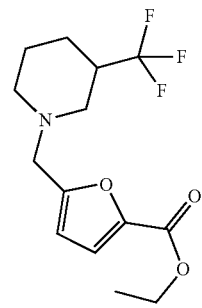 [SMILES: CCOC(=O)c1ccc(CN2CCCC(C(F)(F)F)C2)o1]

To a solution of ethyl 5-(chloromethyl)furan-2-carboxylate (2.5 g, 13.2 mmol) in $CH_3CN$ (100 ml) were added 3-(trifluoroethyl)piperidine (2.03 g, 1 eq), potassium carbonate (5.5 g, 3 eq), and potassium iodide (0.66 g, 0.3 eq). The reaction mixture was stirred overnight at rt. Solids were filtered and filtrate was concentrated in vacuo. The residue was dissolved in DCM and washed with water (3×50 ml). Organic layer was separated, dried over anh. $Na_2SO_4$, filtered, and solvents were evaporated in vacuo. Yield 3.9 g (96.3%). LC-MS 1.00 min, m/z 306.3 [MH]+.

Synthesis of 5-((3-(trifluoromethyl)piperidin-1-yl)methyl)furan-2-carboxylic Acid

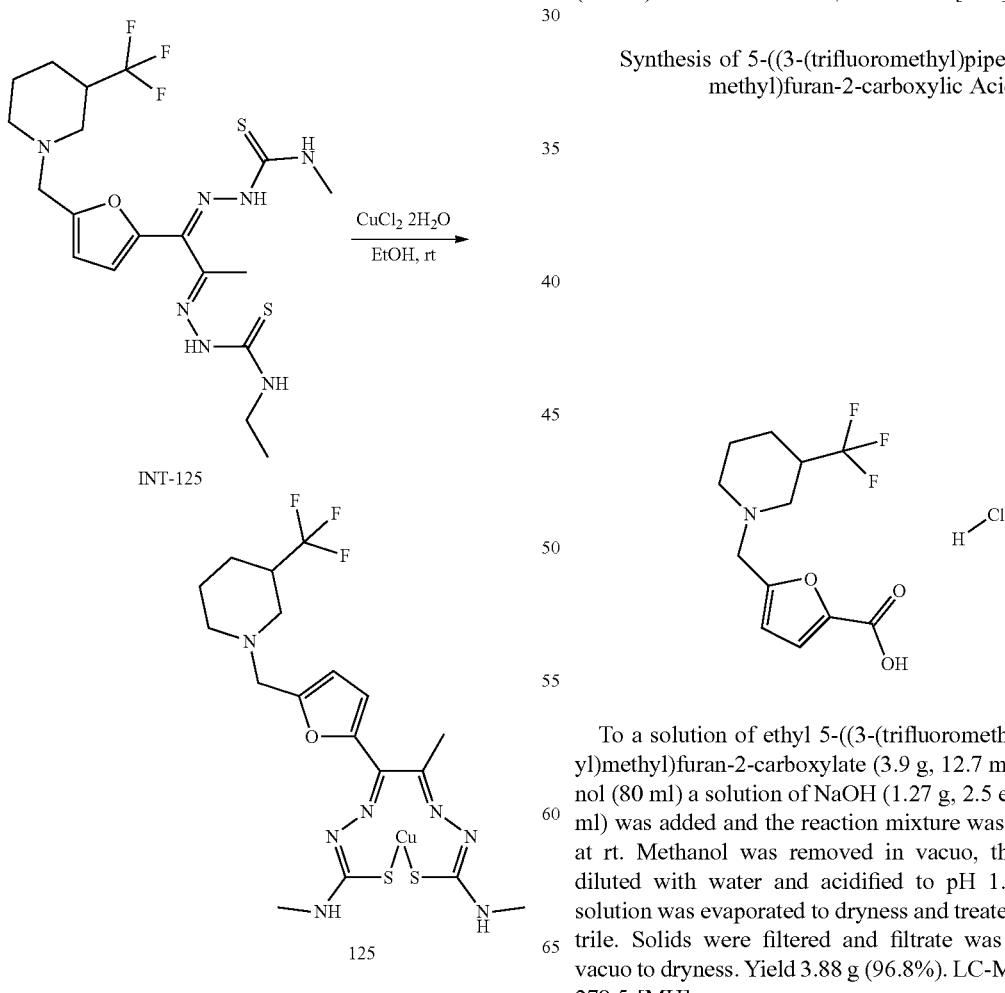

To a solution of ethyl 5-((3-(trifluoromethyl)piperidin-1-yl)methyl)furan-2-carboxylate (3.9 g, 12.7 mmol) in methanol (80 ml) a solution of NaOH (1.27 g, 2.5 eq) in water (10 ml) was added and the reaction mixture was stirred for 15h at rt. Methanol was removed in vacuo, the residue was diluted with water and acidified to pH 1. The acidified solution was evaporated to dryness and treated with acetonitrile. Solids were filtered and filtrate was evaporated in vacuo to dryness. Yield 3.88 g (96.8%). LC-MS 0.7 min, m/z 278.5 [MH]+.

Synthesis of N-methoxy-N-methyl-5-((3-(trifluoromethyl)piperidin-1-yl)methyl)furan-2-carboxamide

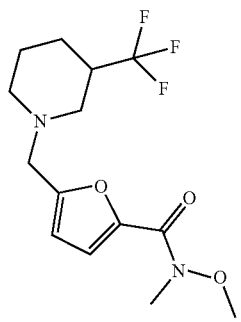 [SMILES: CON(C)C(=O)c1ccc(CN2CCCC(C(F)(F)F)C2)o1]

To a stirred mixture of 5-((3-(trifluoromethyl)piperidin-1-yl)methyl)furan-2-carboxylic acid (3.88 g, 12.4 mmol), N,O-dimethylhydroxylamine (1.45 g, 1.2 eq), HOBt (2.23 g, 1.2 eq), and triethylamine (6.9 ml, 5 g, 4 eq) in DCM (100 ml) at 5° C. was added EDCl (2.85 g, 1.2 eq) and reaction was stirred for 15h at rt. The mixture was washed with water and brine. The organic layer was dried over anh. Na$_2$SO$_4$ and then concentrated under reduced pressure. The residue was purified by column chromatography (silica gel, eluent CCl$_4$/EtOAc 1:1). Yield 2.91 g (73.5%). LC-MS 0.93 min, m/z 321.4 [MH]+. $^1$H NMR (400 MHz, CDCl$_3$), δ (ppm): 7.11 (d, J=3.4 Hz, 1H), 6.34 (d, J=3.3 Hz, 1H), 3.78 (s, 3H), 3.68 (s, 2H), 3.35 (s, 3H), 3.07 (d, J=10.7 Hz, 1H), 2.92 (d, J=11.3 Hz, 1H), 2.50-2.23 (m, 1H), 2.15-1.99 (m, 2H), 1.94 (d, J=12.2 Hz, 1H), 1.75 (d, J=19.3 Hz, 1H), 1.59 (q, J=13.1 Hz, 1H).

Synthesis of 2-ethoxy-1-(5-((3-(trifluoromethyl)piperidin-1-yl)methyl)furan-2-yl)prop-2-en-1-one

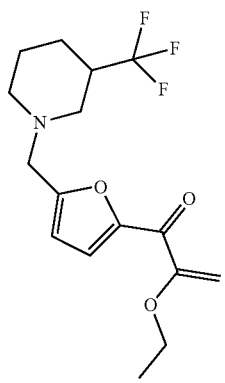 [SMILES: C=C(OCC)C(=O)c1ccc(CN2CCCC(C(F)(F)F)C2)o1]

A solution of ethyl vinyl ether (1.66 g, 2.2 ml, 6.7 eq) in dry THF (80 mL) was cooled to −78° C., and tert-butyllithium (1.7M in pentane, 12 ml, 6 eq) was added. The mixture was warmed to 0° C. over 1h period, stirred for 45 min, and cooled down to −30° C. A solution of N-methoxy-N-methyl-5-((3-(trifluoromethyl)piperidin-1-yl)methyl)furan-2-carboxamide (1.1 g, 3.4 mmol) in THF was added, and then the reaction was stirred at 0° C. for 4 h. The progress of the reaction was monitored by TLC. The mixture was poured into aq NH$_4$Cl and extracted with Et$_2$O. The combined extracts were dried over anh. Na$_2$SO$_4$, filtered, and solvents were evaporated in vacuo. The product was used for the next step without additional purification. Yield 1.13 g (99%). LC-MS 1.1 min, m/z 332.6 [MH]+.

Synthesis of INT-125 ((2E,2'E)-2,2'-(1-(5-((3-(trifluoromethyl)piperidin-1-yl)methyl)furan-2-yl)propane-1,2-diylidene)bis(N-methylhydrazine-1-carbothioamide))

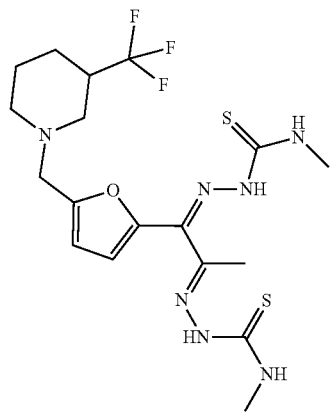 [SMILES: CNC(=S)N/N=C(C)/C(=N\NC(=S)NC)c1ccc(CN2CCCC(C(F)(F)F)C2)o1]

2-ethoxy-1-(5-((3-(trifluoromethyl)piperidin-1-yl)methyl)furan-2-yl)prop-2-en-1-one (1.13 g, 3.3 mmol, 1 eq) was dissolved in EtOH (50 ml), methylthiosemicarbazide (0.72 g, 2 eq) and 3 drops of H$_2$SO$_4$ were added. The stirred reaction mixture was heated to reflux for 4h and then maintained for 15h at rt. The formed precipitate was filtered, washed with EtOH, water, Et$_2$O, and dried. The product was purified by column chromatography (silica gel, eluent CCl$_4$/EtOAc 1:1) Yield 0.22 g (13.2%). LC-MS 1.15 min, m/z 478.5 [MH]+.

Synthesis of Compound 125

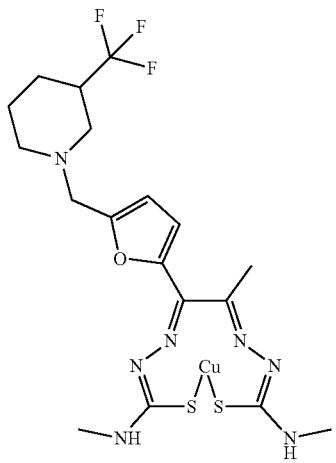

Copper(II) chloride dihydrate (0.183 g, 1.1 eq) was added to INT-125 (0.4 g, 9.8 mmol, 1 eq) in ethanol. The mixture was stirred for 15h at rt. The formed complex precipitated as a red-brown powder. The precipitate was collected by filtration, washed with water, methanol, diethyl ether, and dried. Yield 0.16 g (34.8%).

Scheme 87: Synthesis of Compound 126

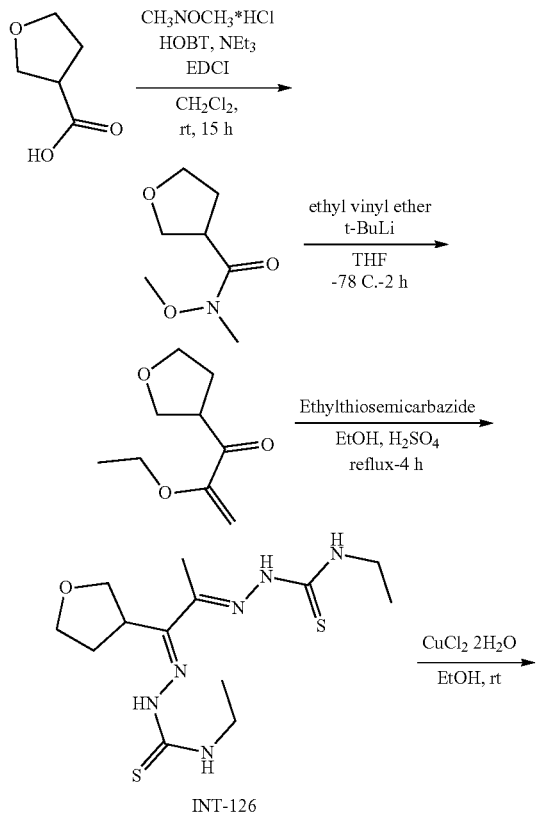

INT-126

126

Synthesis of N-methoxy-N-methyltetrahydrofuran-3-carboxamide

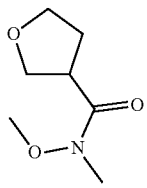

To a stirred mixture of tetrahydrofuran-3-carboxylic acid (3.71 g, 31.9 mmol), N,O-dimethylhydroxylamine (3.74 g, 1.2 eq), HOBt (5.87 g, 1.2 eq), and triethylamine (8.9 ml, 6.46 g, 2 eq) in DCM (100 ml) at 5° C. was added EDCl (7.35 g, 1.2 eq) and reaction was stirred for 15h at rt. The mixture was washed with water and brine. The organic layer was dried over anh. Na$_2$SO$_4$ and then concentrated under reduced pressure. The product was purified by column chromatography (silica gel, eluent DCM 100% then DCM/EtOAc 8:2). Yield 3.06 g (60.1%). $^1$H-NMR (400 MHz, CDCl$_3$), δ (ppm): 4.01 (t, J=8.3 Hz, 1H), 3.89-3.73 (m, 3H), 3.68 (d, J=1.0 Hz, 3H), 3.38 (dd, J=17.7, 10.3 Hz, 1H), 3.18 (d, J=11.2 Hz, 3H), 2.25-2.14 (m, 1H), 2.10-1.97 (m, 1H).

Synthesis of 2-ethoxy-1-(tetrahydrofuran-3-yl)prop-2-en-1-one

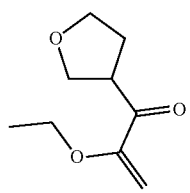

A solution of ethyl vinyl ether (4.48 g, 6 ml, 6.6 eq) in dry THF (1000 ml) was cooled to −78° C., and tert-butyllithium (1.7M in pentane, 33 ml, 6 eq) was added. The mixture was warmed to 0° C. over 1h period, stirred for 45 min, and then cooled down to −30° C. A solution of N-methoxy-N-methyltetrahydrofuran-3-carboxamide (0.56 g, 7 mmol) in THF (15 ml) was added, and stirring continued at 0° C. for 4 h. The mixture was poured into aq. NH$_4$Cl (100 ml) and extracted with Et$_2$O (3×100 ml). The combined extracts were dried over anh. Na$_2$SO$_4$, filtered, and solvents were evaporated in vacuo. The product was used for the next step without additional purification. Yield 1.6 g (99.8%). LC-MS 0.91 min, m/z 180.9 [MH]+.

Synthesis of INT-126 ((2E,2'E)-2,2'-(1-(tetrahydrofuran-3-yl)propane-1,2-diylidene)bis(N-ethylhydrazine-1-carbothioamide))

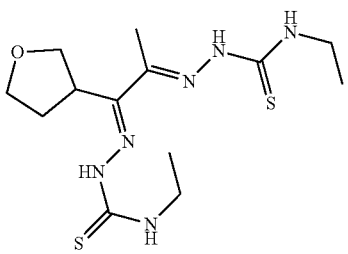 [SMILES: CCNC(=S)N/N=C(C)/C(=N/NC(=S)NCC)C1CCOC1]

2-ethoxy-1-(tetrahydrofuran-3-yl)prop-2-en-1-one (1.6 g, 9.4 mmol) was dissolved in EtOH (15 ml), ethylthiosemicarbazide (0.33 g, 2 eq) and 3 drops of H$_2$SO$_4$ were added. The stirred reaction mixture was heated to reflux for 4h and then maintained for 15h at rt. The formed precipitate was filtered, washed with EtOH, aq.sat. Na$_2$CO$_3$, water, Et$_2$O, and dried. The product was purified by crystallization from CH$_3$CN. Yield 0.13 g (26.4%). LC-MS 1.25 min, m/z 317.3 [MH]+.

Synthesis of Compound 126
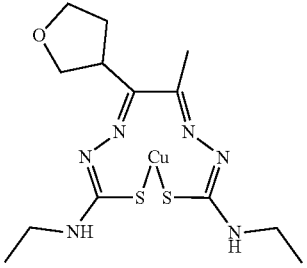
Copper(II) chloride dihydrate (0.17 g, 1 eq) was added to a stirred solution of INT-126 (0.32 g, 1 mmol) in ethanol. The mixture was stirred for 15h at rt. The formed complex precipitated as a red-brown powder. The precipitate was collected by filtration, washed with water, diethyl ether, and dried. Yield 0.34 g (88.7%).
Scheme 88: Synthesis of Compound 127
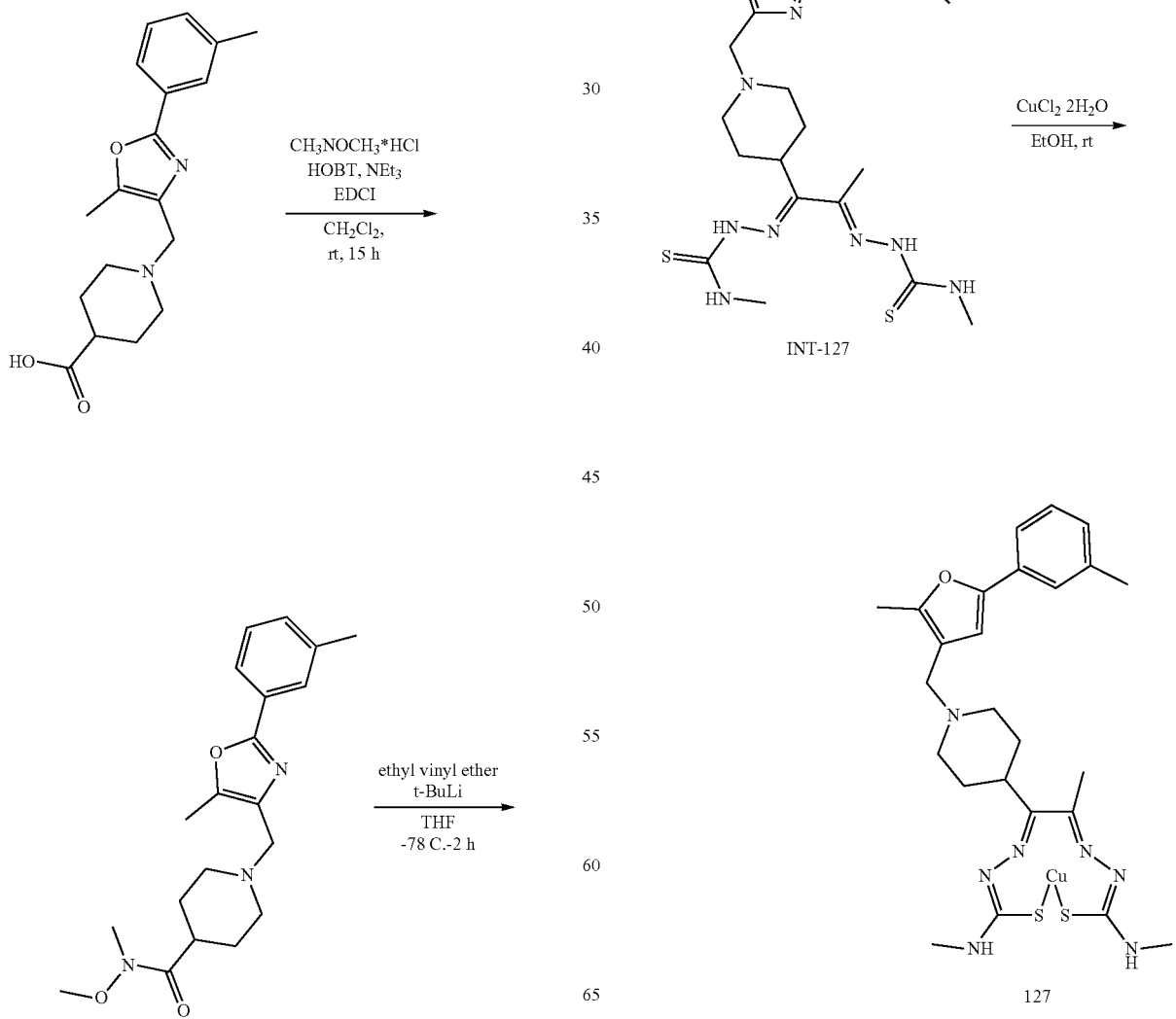
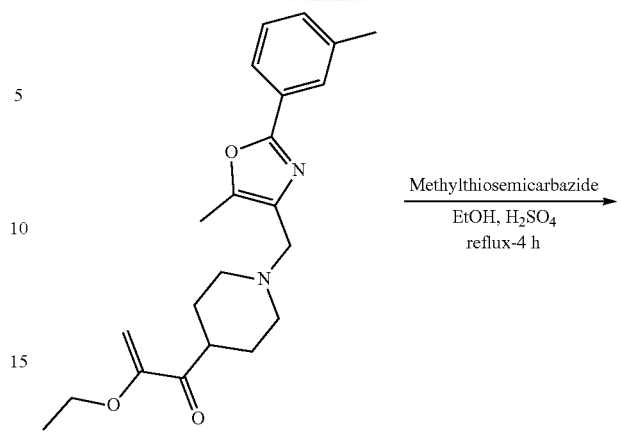

Synthesis of N-methoxy-N-methyl-1-((5-methyl-2-(m-tolyl)oxazol-4-yl)methyl)piperidine-4-carboxamide

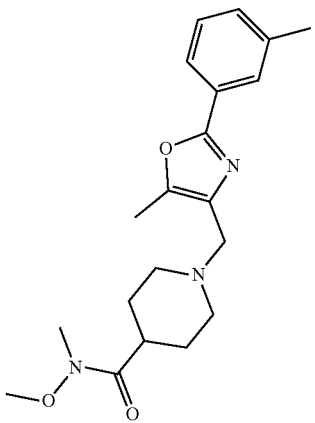

To a stirred mixture of 1-((5-methyl-2-(m-tolyl)oxazol-4-yl)methyl)piperidine-4-carboxylic acid (5.1 g, 16.2 mmol), N,O-dimethylhydroxylamine (1.9 g, 1.2 eq), HOBt (2.63 g, 1.2 eq), and triethylamine (5.6 ml, 4.03 g, 2.5 eq) in DCM (50 ml) at 5° C. was added EDCl (3.73 g, 1.2 eq) and reaction was stirred for 15h at rt. The mixture was washed with water and brine. The organic layer was dried over anh. $Na_2SO_4$ and then concentrated under reduced pressure. Product was purified by column chromatography ($SiO_2$, eluent DCM 100% then DCM/MeOH 96:4). Yield 2.3 g (39.7%). LC-MS 1.16 min, m/z 358.5 [MH]+. $^1$H-NMR (400 MHz, $CDCl_3$), δ (ppm): 7.87 (s, 1H), 7.81 (d, J=7.7 Hz, 1H), 7.32 (t, J=7.7 Hz, 1H), 7.22 (d, J=7.6 Hz, 1H), 3.70 (s, 3H), 3.51 (s, 2H), 3.18 (s, 3H), 3.06 (d, J=11.1 Hz, 2H), 2.67 (s, 1H), 2.40 (d, J=1.1 Hz, 6H), 2.15 (s, 2H), 1.89 (dd, J=22.2, 10.5 Hz, 2H), 1.78 (s, 2H).

Synthesis of 2-ethoxy-1-(1-((5-methyl-2-(m-tolyl)oxazol-4-yl)methyl)piperidin-4-yl)prop-2-en-1-one

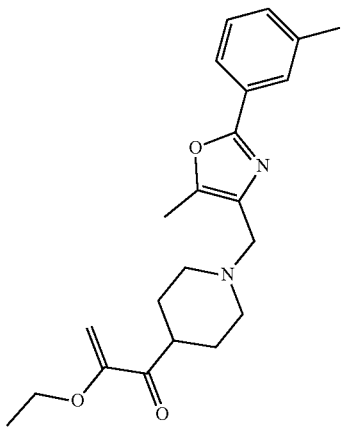 [SMILES: C=C(OCC)C(=O)C1CCN(Cc2nc(-c3cccc(C)c3)oc2C)CC1]

A solution of ethyl vinyl ether (2.55 g, 3.4 ml, 5.5 eq) in dry THF (130 ml) was cooled to −78° C., and tert-butyllithium (1.7M in pentane, 20 ml, 5 eq) was added. The mixture was warmed to 0° C. over 1h period, stirred for 45 min, and then cooled down to −30° C. A solution of N-methoxy-N-methyl-1-((5-methyl-2-(m-tolyl)oxazol-4-yl)methyl)piperidine-4-carboxamide (2.3 g, 6.4 mmol) in THF (15 ml) was added and stirring continued at 0° C. for 4 h. The mixture was poured into aq. $NH_4Cl$ (100 ml) and extracted with $Et_2O$ (3×100 ml). The combined extracts were dried over anh. $Na_2SO_4$, filtered, and solvents were evaporated in vacuo. The product was used for the next step without additional purification. Yield 2.37 g (100%). LC-MS 1.25 min, m/z 369.4 [MH]+.

Synthesis of INT-127 ((2E,2'E)-2,2'-(1-(1-((5-methyl-2-(m-tolyl)oxazol-4-yl)methyl)piperidin-4-yl)propane-1,2-diylidene)bis(N-methylhydrazine-1-carbothioamide))

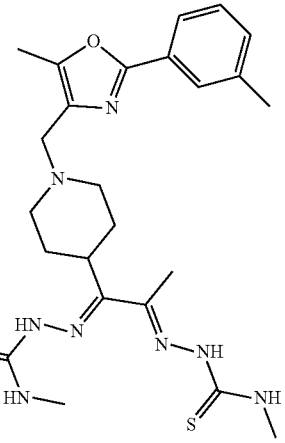

2-ethoxy-1-(1-((5-methyl-2-(m-tolyl)oxazol-4-yl)methyl)piperidin-4-yl)prop-2-en-1-one (2.37 g, 2.2 mmol) was dissolved in EtOH (150 ml), methylthiosemicarbazide (1.35 g, 2 eq) and 3 drops of $H_2SO_4$ were added. The stirred reaction mixture was heated to reflux for 4h and then maintained for 15h at rt. The solvent was evaporated in vacuo. The residue was dissolved in EtOAc and washed with aq.sat. $NaHCO_3$, water, dried over anh. $Na_2SO_4$ and concentrated under reduced pressure. The residue was purified by column chromatography (silica gel, eluent DCM/MeOH 96:4). Yield 0.44 g (13.3%). LC-MS 1.31 min, m/z 515.3 [MH]+.

Synthesis of Compound 127

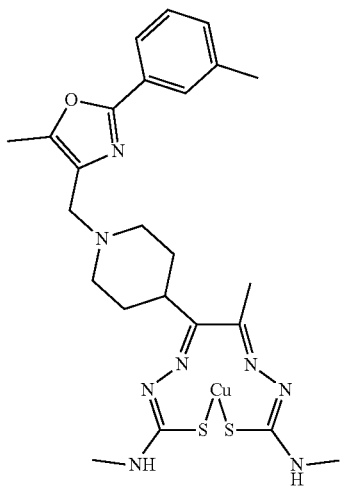

Copper(II) chloride dihydrate (0.024 g, 1 eq) was added to a stirred solution of INT-127 (0.073 g, 0.14 mmol) in ethanol. The mixture was stirred for 15h at rt. The formed complex precipitated as a red-brown powder. The precipitate was collected by filtration, washed with water, diethyl ether, and dried. Yield 0.057 g (69.7%).

Example 7: Efficacy of Copper Compounds in SOD1$^{G93A}$ Mice

The SOD1$^{G93A}$ transgenic mouse model of ALS has been the most widely used animal model since the 1990s. The mouse was genetically engineered to overexpress a mutant form of the human Cu/Zn superoxide dismutase 1 (SOD1) gene harboring an ALS-associated glycine to alanine mutation at amino acid position 93 (G93A). These mice replicate many of the features of ALS, such as motor neuron loss, muscle wasting, progressive paralysis and decreased survival. Additionally, the SOD1$^{G93A}$ mouse model has shown to be ideal for drug screening because of early onset of the disease and moderate progression.

The mice were treated with vehicle, 10 mg/kg or 30 mg/kg CuATSM or one of the derivatives: Compound 25 (2% DMSO, 10% KolliphorHS15), Compound 9 (0.5% methylcellulose), Compound 24 (0.5% methylcellulose, 0.4% TWEEN-80), and Compound 37 (0.5% methylcellulose, 0.4% TWEEN-80). Measurements were taken to assess compound muscle action potential (CMAP), neuroscore, and disease onset and survival.

Methods:

Neuroscore

Neuroscore is a neurological scoring system based on visual observations of the hindlimb designed to assess the neuromuscular function of SOD1$^{G93A}$ mice. The hindlimb is observed due to this being the earliest reported neurological sign of disease in SOD1$^{G93A}$ mice. This method provides an unbiased assessment of onset of paresis (slight or partial paralysis) and the progression and severity of the paralysis. This method has also proven to be sensitive enough to identify drug-induced changes in disease progression. Neuroscore is assigned on a 0-4 scale corresponding to the following observations: NS0=the hindlimbs present with a normal splay; NS1=hindlimbs present with an abnormal splay; NS2=the hindlimbs show signs of paresis or are partially paralyzed; NS3=rigid paralysis in the hindlimbs; NS4=the mouse is unable to right itself up. These measurements were used in the current study to assess disease onset.

Disease Onset and Survival

It has been shown that SOD1$^{G93A}$ mice have significantly shortened lifespans compared to wild-type mice. The onset of disease in the SOD1$^{G93A}$ mice typically happens around age day 90-100, with mice eventually succumbing to the disease around age day 120-130. For comparison, a wild-type mouse of the same background may live up to 2 years. The onset of the disease in the current study was defined as the time to observe a neuroscore of NS2 in the mouse, while a neuroscore of a NS4 was considered to be the humane end-point. Reported p-values to illustrate statistical significant represent a log-rank test.

Compound Muscle Action Potential (CMAP)

Compound muscle action potential (CMAP) is an electrophysiological technique that assesses the functional integrity of motor axons. Male SOD1$^{G93A}$ mice were treated with vehicle (control), 10 mg/kg, or 30 mg/kg every day for five weeks starting at about age day 50 via oral gavage. The response was measured in the innervated tibialis anterior (TA) muscle using an implanted recording electrode. To establish baseline CMAP measurements, the mice were were anesthetized, and the sciatic nerve was stimulated using implanted microelectrodes which provided small electrical currents prior to treatment with the compound or vehicle. Mice were then randomized into each treatment cohort. After daily dosing and at the end of the experiment, CMAP data was recorded and compared to the baseline measurements to calculate change from baseline and % of baseline. Data was calculated and represented as a mean±SEM, and statistics were calculated with a one-way ANOVA with Dunnett's Multiple Comparison Test vs. control mice; * p<0.05, ** p<0.01.

Results:

CuATSM

CuATSM has been used in clinical studies as an experimental treatment for ALS, but suffers from certain drawbacks that can limit its use as a therapeutic agent. CuATSM has been shown to possess a high affinity for copper, potentially causing this agent to be an inefficient delivery vehicle to bypass the distribution system that naturally limits copper transport into the central nervous system. Further, CuATSM has a compact, symmetric structure, which contributes to another limitation associated with this compound: its compact structure allows the ATSM ligand component to rapidly form extremely stable crystals, which causes several challenges in making and formulating this compound, hindering its ability to serve as suitable pharmacological agent.

Figure 1B:
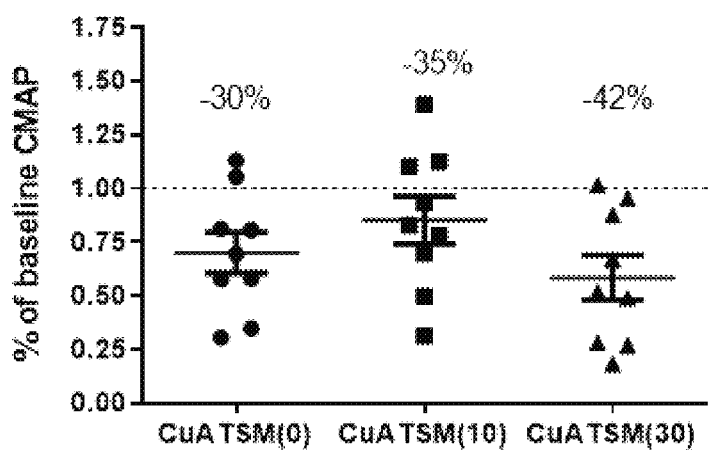
FIG. 1B is the percent of baseline of the same cohort after CuATSM or vehicle dosing.

Male SOD1$^{G93A}$ mice were treated with 10 mg/kg (n=9) or 30 mg/kg CuATSM (n=8) or vehicle (0.5% methylcellulose, 0.4% TWEEN-80, 0.9% normal saline; n=9). Changes from baseline CMAP values were observed for each cohort of mice. After four weeks of daily dosing with CuATSM or vehicle, no differences in the changes from baseline (FIG. 1A) or percent of baseline CMAP (FIG. 1B) values were observed between the different cohorts.

Compound 25

Figure 2A:
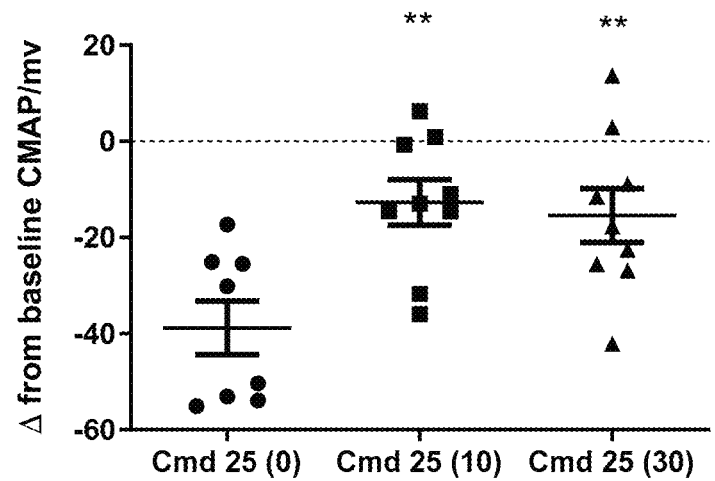
FIG. 2A illustrates the CMAP change from baseline after administering 10 mg/kg or 30 mg/kg Compound 25 or vehicle (control) to male SOD1$^{G93A}$ mice daily for five weeks.
Figure 2B:
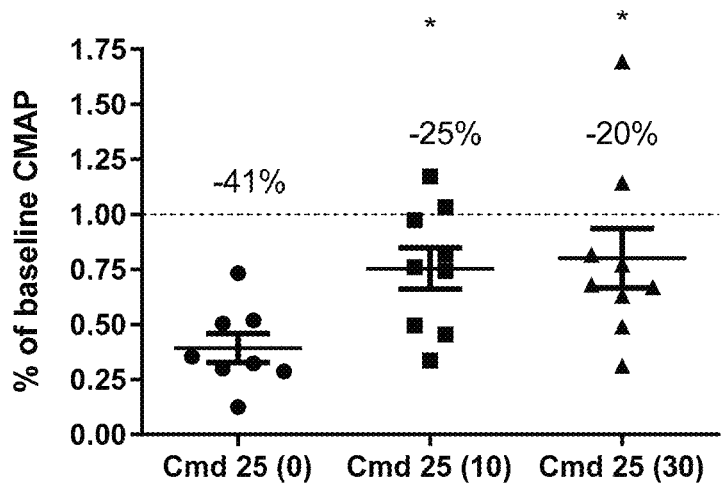
FIG. 2B illustrates the percent of baseline of the same cohort after Compound 25 or vehicle dosing.

SOD1G93A mice treated with 10 mg/kg (n=9) or 30 mg/kg (n=9) of Compound 25 or vehicle (2% DMSO, 10% KolliphorHS15; n=8) daily for 15 days. Treatments were performed daily starting at about age 50 by oral gavage. Compound muscle action potential (CMAP) was recorded for each cohort of mice, as a change from baseline after five weeks of dosing. The mice administered either 10 mg/kg or 30 mg/kg Compound 25 exhibited significant change in CMAP measurements from baseline compared to control mice (FIG. 2A). FIG. 2B illustrates CMAP data as a percentage of baseline after 5 weeks of dosing. The mice who received 10 mg/kg or 30 mg/kg Compound 25 demonstrated significantly less change than the mice receiving vehicle.

Figure 3A:
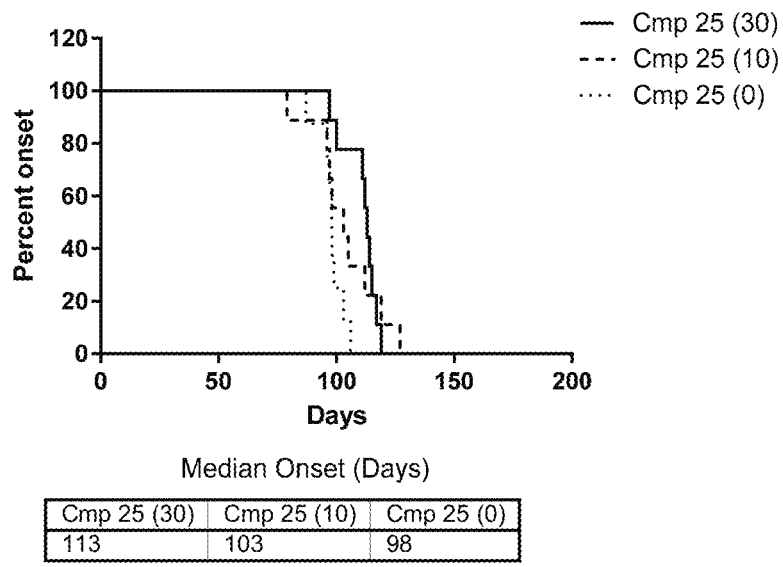
FIG. 3A compares disease onset of vehicle-treated male SOD1$^{G93A}$ mice, mice treated with 10 mg/kg Compound 25, or 30 mg/kg Compound 25.

It was found that chronic daily dosing produced several beneficial effects which included a delayed disease onset (FIG. 3A) as measured by the onset of paresis and the neuroscore. Disease onset seen in mice receiving Compound 25 was more delayed compared to mice receiving vehicle, with mice receiving 30 mg/kg displaying significantly delayed onset (113 days) compared to the mice receiving 10 mg/kg (103 days) and the control mice receiving vehicle (98 days).

Figure 3B:
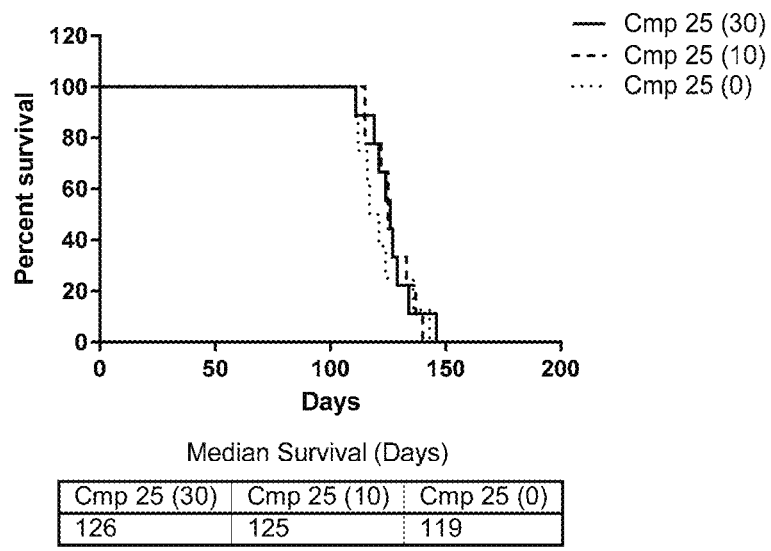
FIG. 3B compares survival of vehicle-treated male SOD1$^{G93A}$ mice, mice treated with 10 mg/kg Compound 25, or 30 mg/kg Compound 25.

Survival was also observed based on the neuroscore testing, and once a mouse reached a neuroscore of NS4, it was determined the mouse had reached a humane end-point, and survival was recorded. Treatment with Compound 25 extended median survival by 7 days (126 days) for mice receiving 30 mg/kg and 6 days (125 days) for mice receiving 10 mg/kg, compared to the mice receiving vehicle (119 days) (FIG. 3B).

Figure 4A:
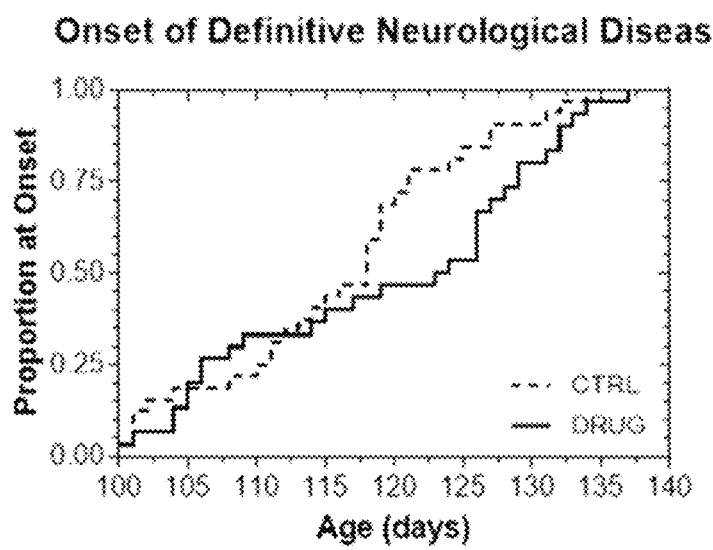
FIGS. 4A, 4B, 4C, and 4D demonstrate the benefits of chronic daily dosing of 30 mg/kg Compound 25 in a litter-matched and gender-balanced survival efficacy study compared to mice treated with vehicle.
Figure 4B:
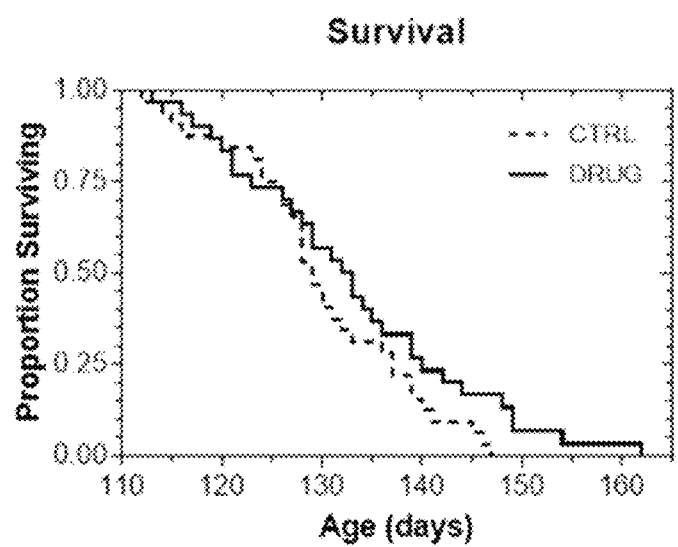
Figure 4C:
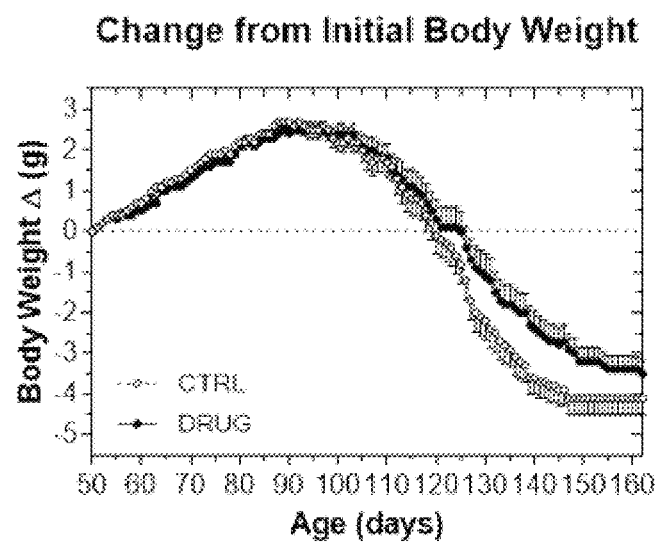
Figure 4D:
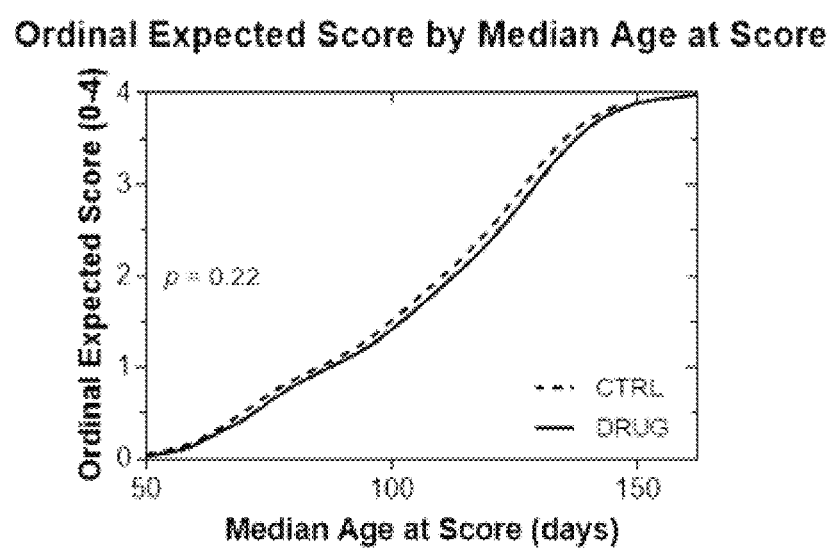

Due to the significant improvement of the mice that received Compound 25, additional measurements were observed in mice that were chronically dosed daily with 30 mg/kg of Compound 25 and compared to control mice. Overall, Compound 25 displayed benefits in a survival efficacy study based on the onset of definitive neurological disease measured as a proportion at onset (FIG. 4A), proportion of the cohort surviving as a function of age (FIG. 4B), change in body weight (FIG. 4C), and ordinal expected score by median age at the time the mice reached a neurological score of NS4 (FIG. 4D).

Compound 9

Figure 5A:
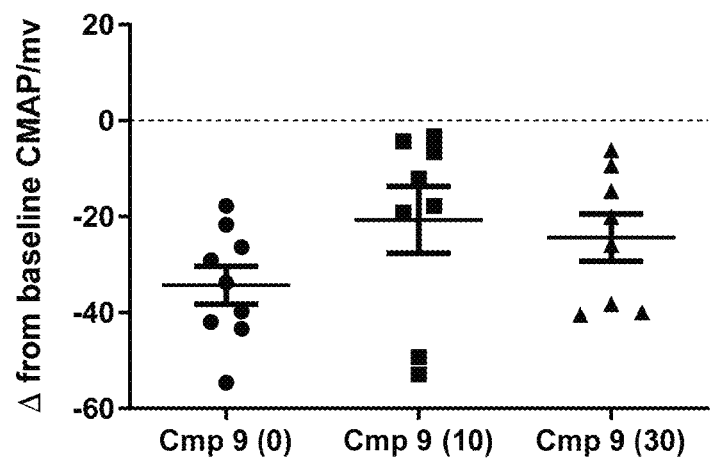
FIG. 5A illustrates CMAP change from baseline after administering 10 mg/kg or 30 mg/kg Compound 9 to male SOD1$^{G93A}$ mice compared to control mice after dosing daily for four weeks.
Figure 5B:
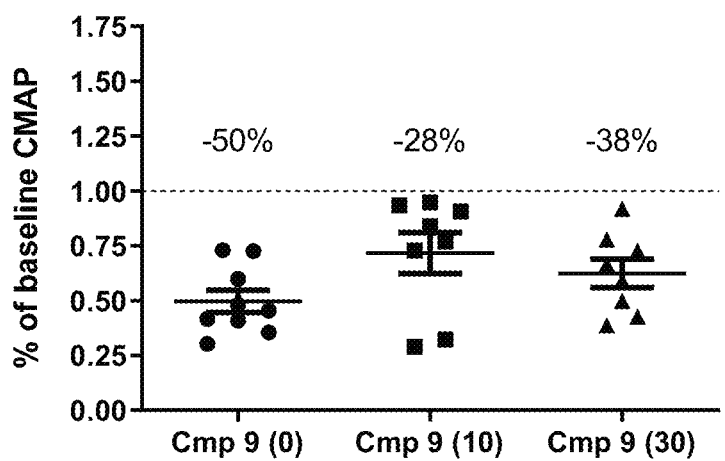
FIG. 5B is the percent of baseline of the same cohort after Compound 9 or vehicle dosing.
Figure 6A:
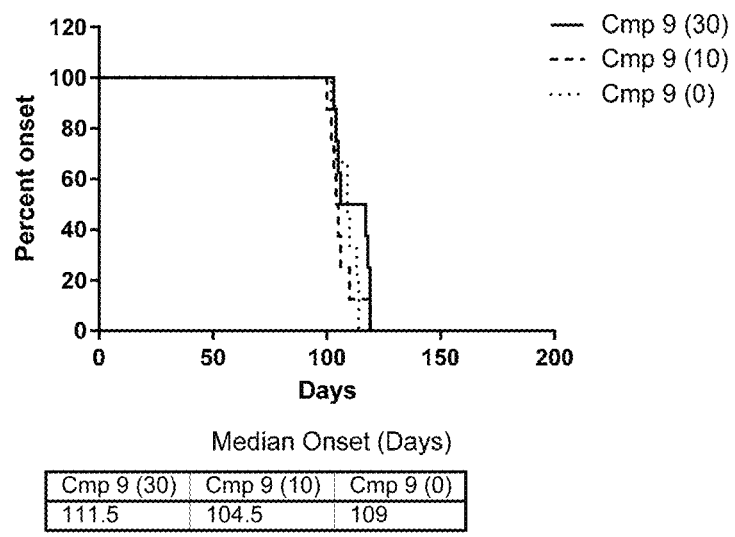
FIG. 6A compares disease onset of vehicle-treated male SOD1$^{G93A}$ mice, mice treated with 10 mg/kg Compound 9, or 30 mg/kg Compound 25.
Figure 6B:
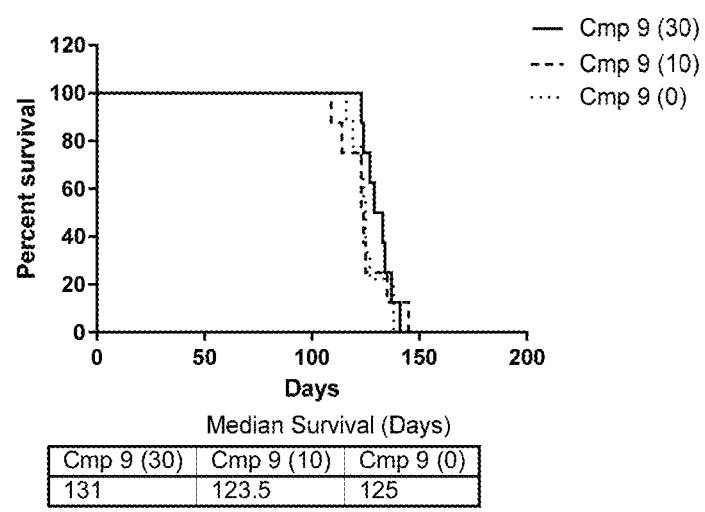
FIG. 6B compares survival of vehicle-treated male SOD1$^{G93A}$ mice, mice treated with 10 mg/kg Compound 9, or 30 mg/kg Compound 9.

Like Compound 25, male SOD1$^{G93A}$ mice were dosed with 10 mg/kg (n=8) or 30 mg/kg (n=8) of Compound 9, or vehicle (0.5% methylcellulose; n=9). Treatment began around age Day 50 via oral gavage and were administered to the mice daily. CMAP values were recorded for the cohorts after four weeks of dosing with Compound 9 or vehicle, and are illustrated as either change from baseline (FIG. 5A) or % of baseline (FIG. 5B). Disease onset (FIG. 6A) and survival (FIG. 6B), and there was no significant difference observed between the mice given either dose of Compound 9 or vehicle. Overall, Compound 9 did not significantly affect disease onset or survival in SOD1G93A mice.

Compound 24

Figure 7A:
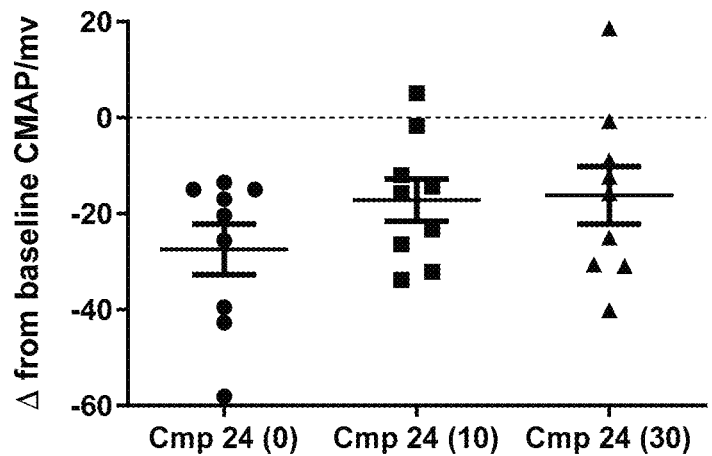
FIG. 7A illustrates the CMAP change from baseline after administering 10 mg/kg or 30 mg/kg Compound 24 or vehicle (control) to male SOD1$^{G93A}$ mice daily for three weeks.
Figure 7B:
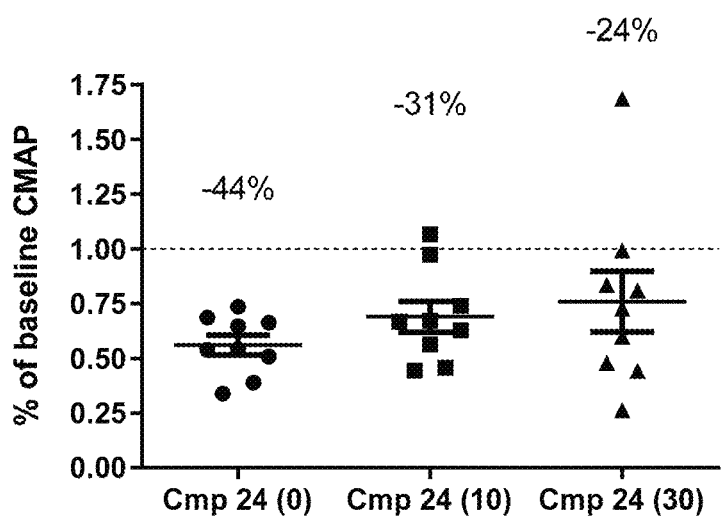
FIG. 7B illustrates the percent of baseline of the same cohort after Compound 24 or vehicle dosing.

Male SOD1$^{G93A}$ mice were dosed with 10 mg/kg (n=9) or 30 mg/kg (n=9) Compound 24, or vehicle (0.5% methylcellulose, 0.4% TWEEN-80; n=9) daily starting around age Day 50 via oral gavage. CMAP values were recorded for the cohorts after five weeks of dosing with Compound 24 or with the vehicle. CMAP data is illustrated as either change from the baseline (FIG. 7A) or % of baseline (FIG. 7B). Mice treated with Compound 24 at either dose did not significantly improve CMAP values over the control mice.

Figure 8A:
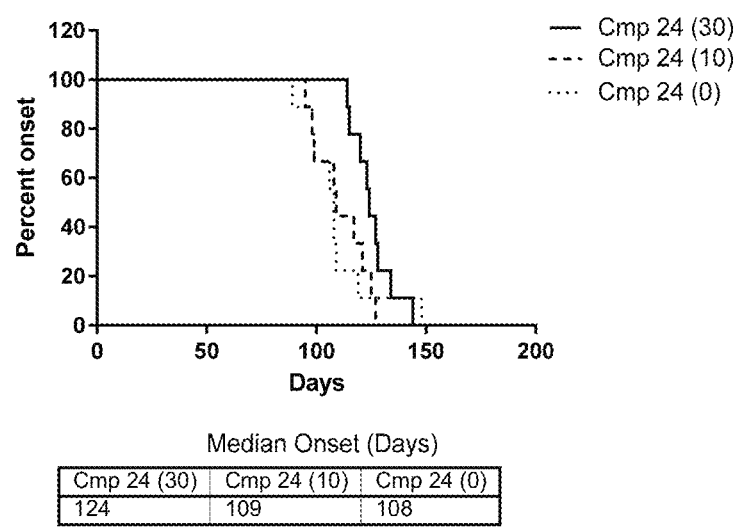
FIG. 8A compares disease onset of vehicle-treated male SOD1$^{G93A}$ mice, mice treated with 10 mg/kg Compound 24, or 30 mg/kg Compound 24.
Figure 8B:
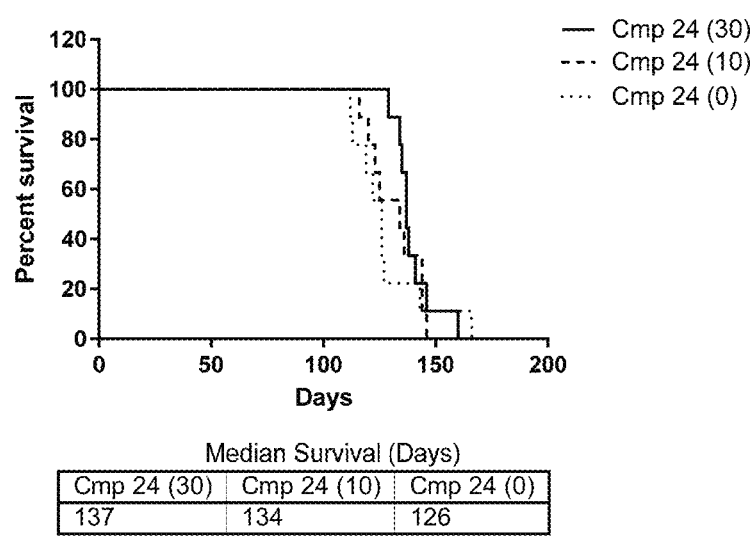
FIG. 8B compares survival of vehicle-treated male SOD1$^{G93A}$ mice, mice treated with 10 mg/kg Compound 24, or 30 mg/kg Compound 24.

Despite no significant improvement in CMAP values, mice administered 30 mg/kg Compound 24 daily experienced a significant delay in disease onset (FIG. 8A) and survival (FIG. 8B). Mice treated with 30 mg/kg of the compound saw an improvement of median disease onset by 16 days over the control (disease onset at day 124). The same mice saw extended survival by 11 days, with median survival at 137 days as compared to 126 days observed in the control mice.

Compound 37

Figure 9A:
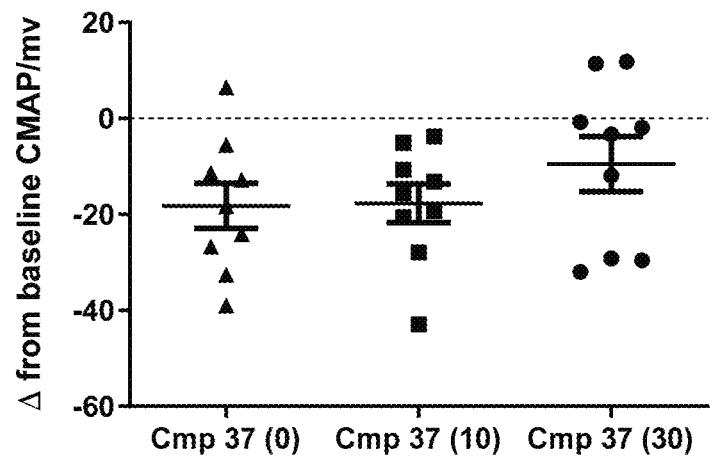
FIG. 9A illustrates the CMAP change from baseline after administering 10 mg/kg or 30 mg/kg Compound 37 or vehicle (control) to male SOD1$^{G93A}$ mice daily for four weeks.
Figure 9B:
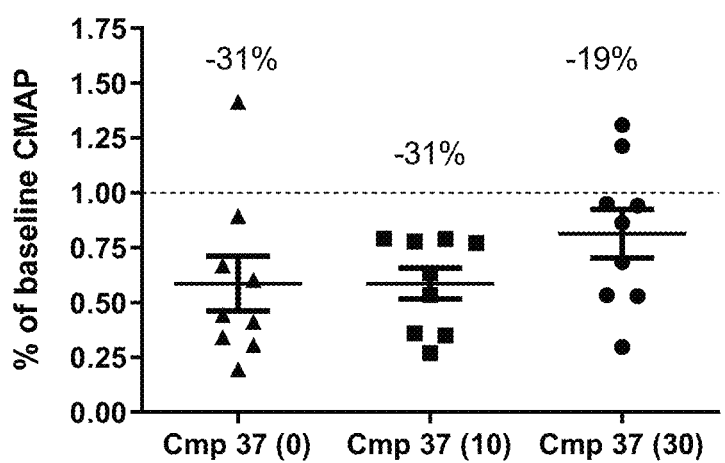
FIG. 9B illustrates the percent of baseline of the same cohort after Compound 37 or vehicle dosing.

Male SOD1$^{G93A}$ mice were dosed with 10 mg/kg (n=9) or 30 mg/kg (n=9) Compound 37, or with vehicle as a control (0.5% methylcellulose, 0.4% TWEEN-80; n=9) daily starting around age Day 50 via oral gavage. CMAP values were measured after four weeks of dosing. CMAP data is illustrated as either change from baseline (FIG. 9A) or % of baseline (FIG. 9B). Treatment with Compound 37 did not attenuate the CMAP decline in ALS mice.

Figure 10A:
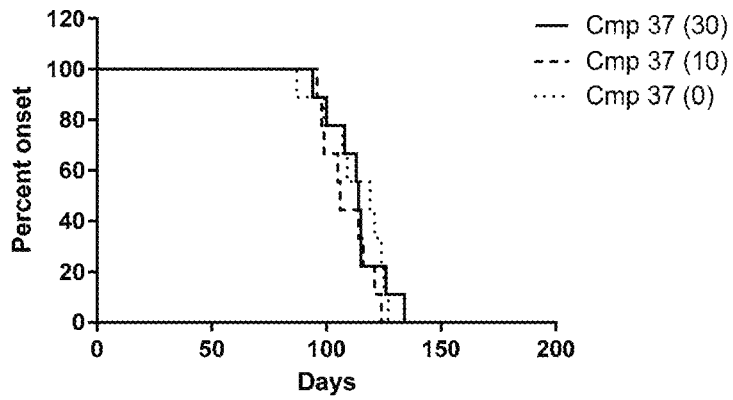
FIG. 10A compares disease onset of vehicle-treated male SOD1$^{G93A}$ mice, mice treated with 10 mg/kg Compound 37, or 30 mg/kg Compound 37.
Figure 10B:
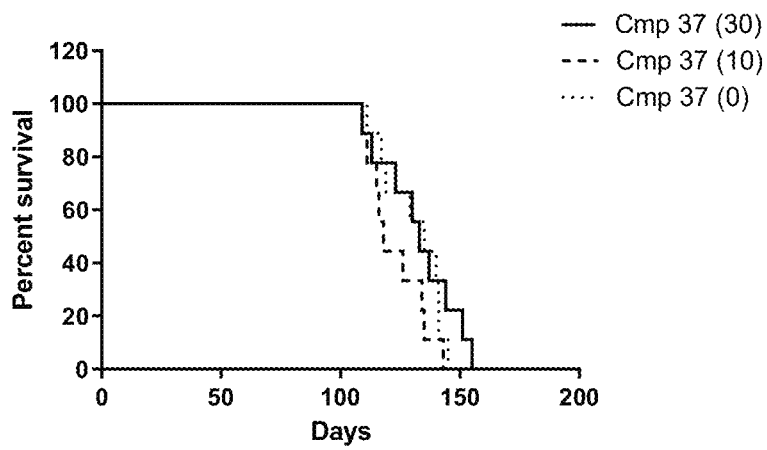
FIG. 10B compares survival of vehicle-treated male SOD1G93A mice, mice treated with 10 mg/kg Compound 37, or 30 mg/kg Compound 37.
Figure 11A:
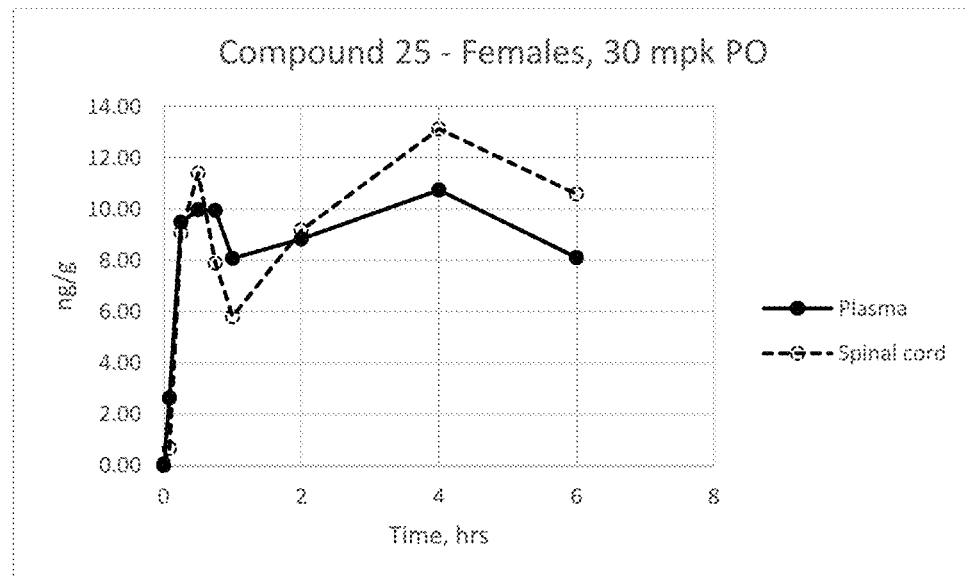
FIG. 11A depicts plasma and spinal cord concentrations of Compound 25 in female mice during the hours following administration.
Figure 11B:
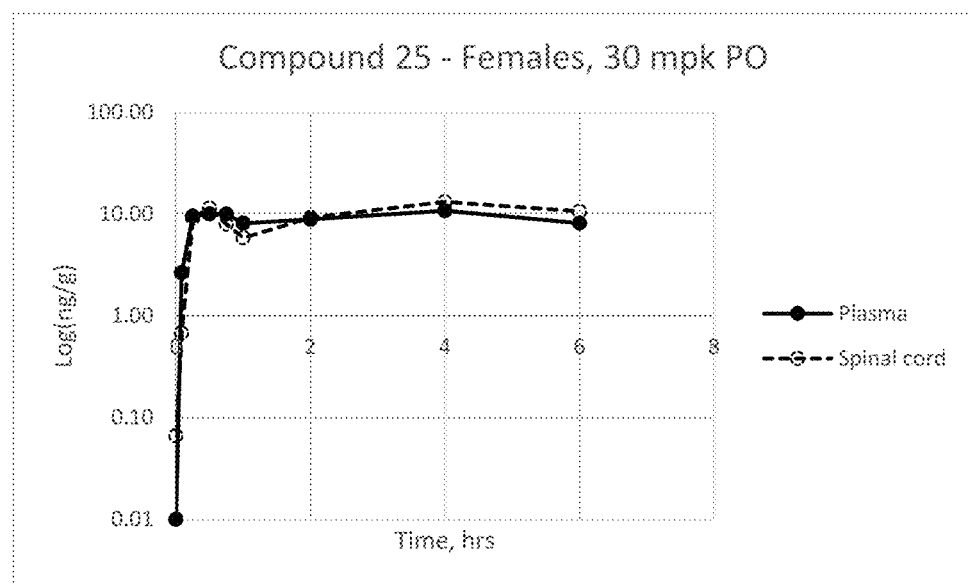
FIG. 11B is a logarithmic depiction of the data in FIG. 11A.
Figure 12A:
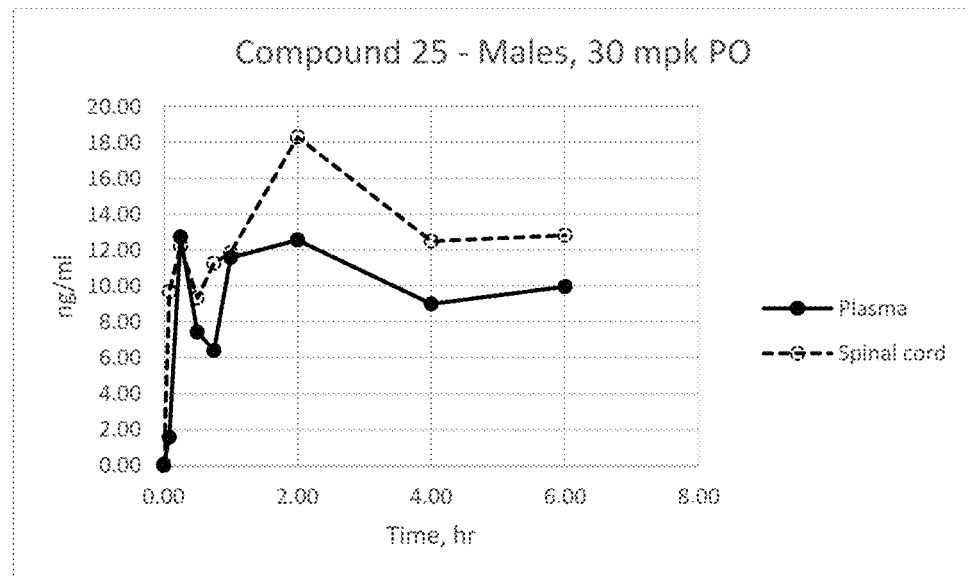
FIG. 12A depicts plasma and spinal cord concentrations of Compound 25 in male mice during the hours following administration.
Figure 12B:
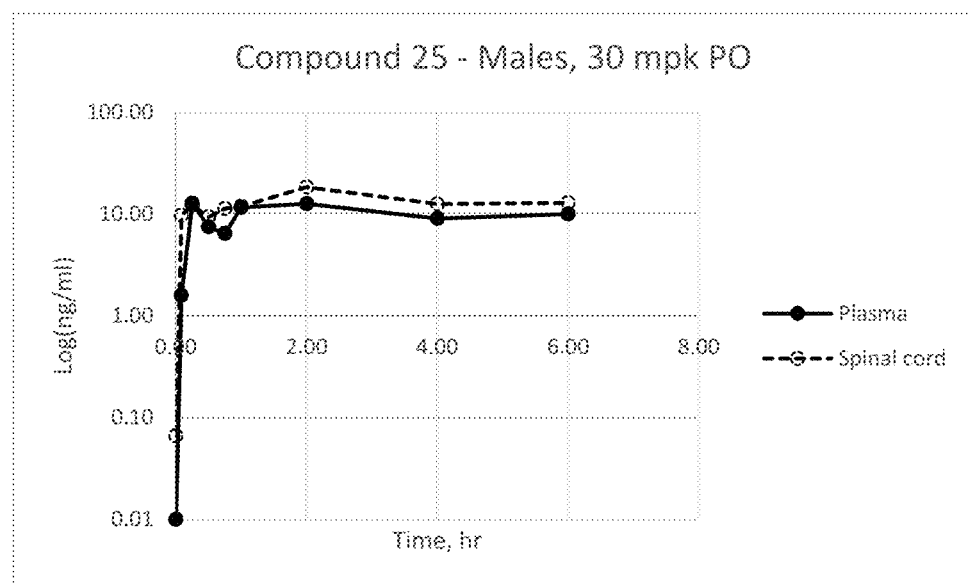
FIG. 12B is a logarithmic depiction of the data in FIG. 12A.
Figure 13A:
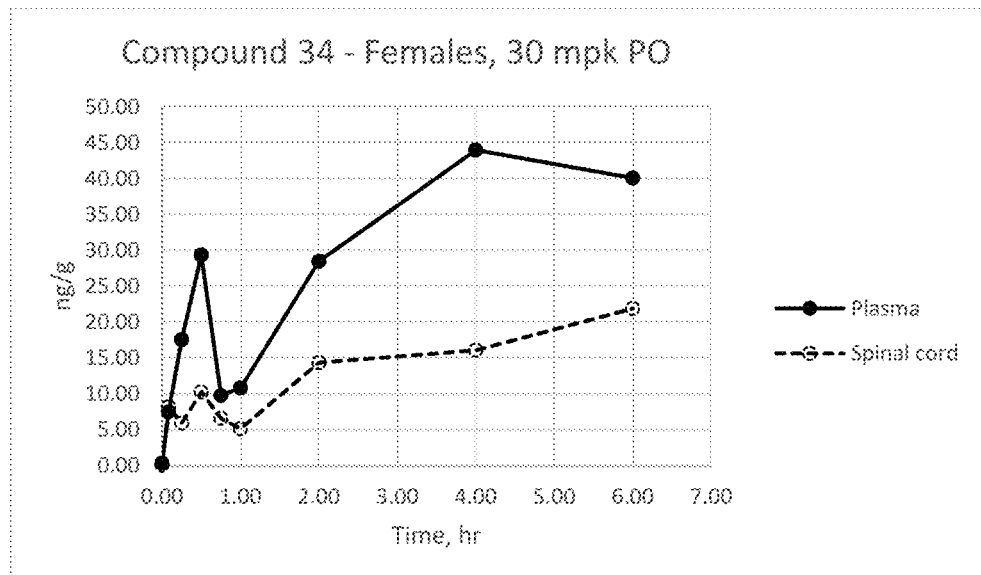
FIG. 13A depicts plasma and spinal cord concentrations of Compound 34 in female mice during the hours following administration.
Figure 13B:
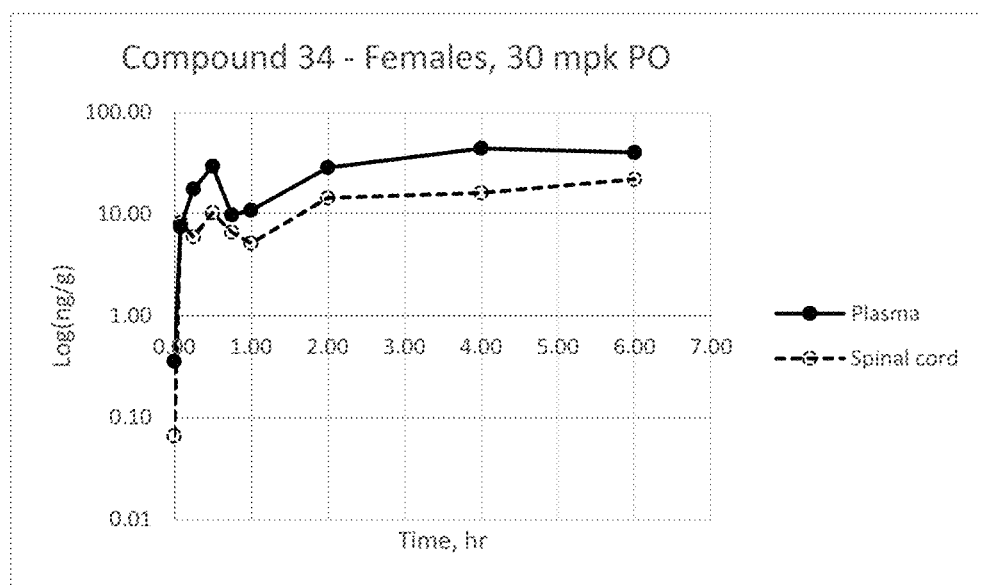
FIG. 13B is a logarithmic depiction of the data in FIG. 13A.
Figure 14A:
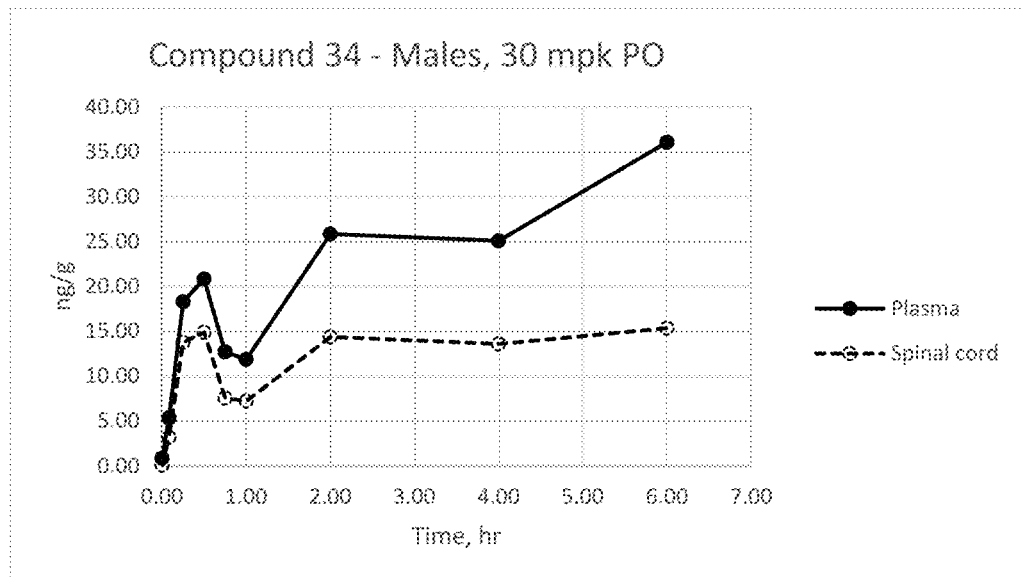
FIG. 14A depicts plasma and spinal cord concentrations of Compound 34 in male mice during the hours following administration.
Figure 14B:
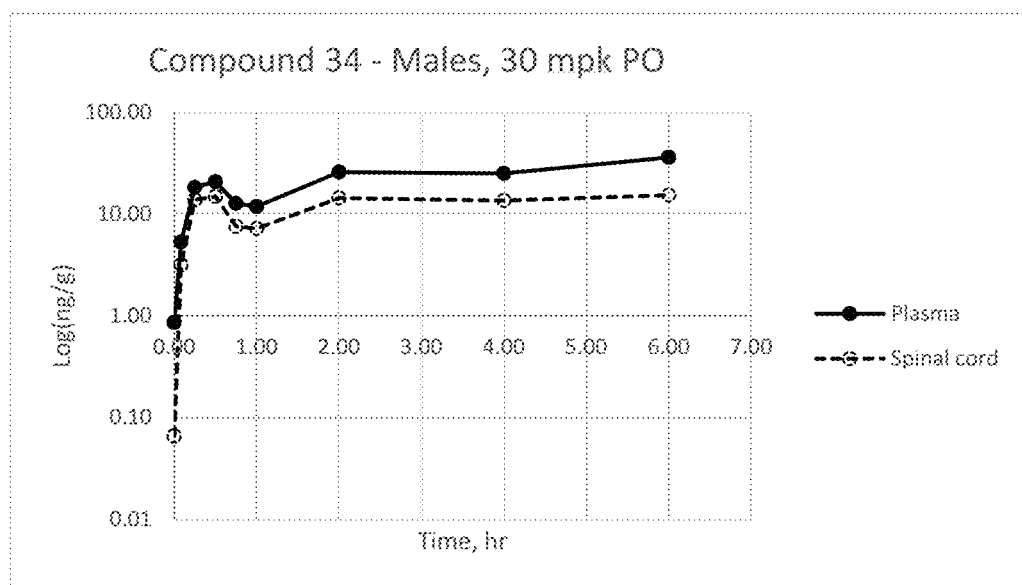
FIG. 14B is a logarithmic depiction of the data in FIG. 14A.
Figure 15A:
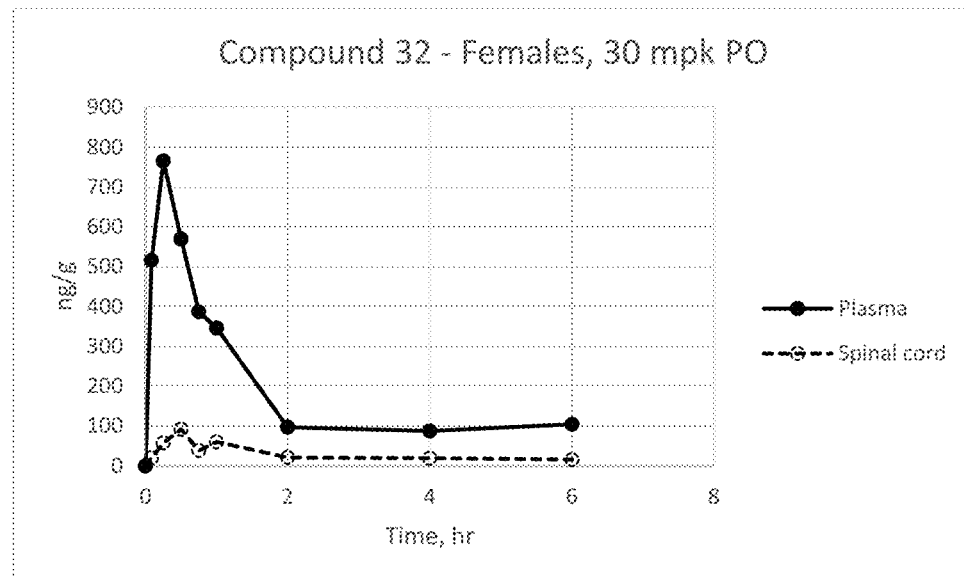
FIG. 15A depicts plasma and spinal cord concentrations of Compound 32 in female mice during the hours following administration.
Figure 15B:
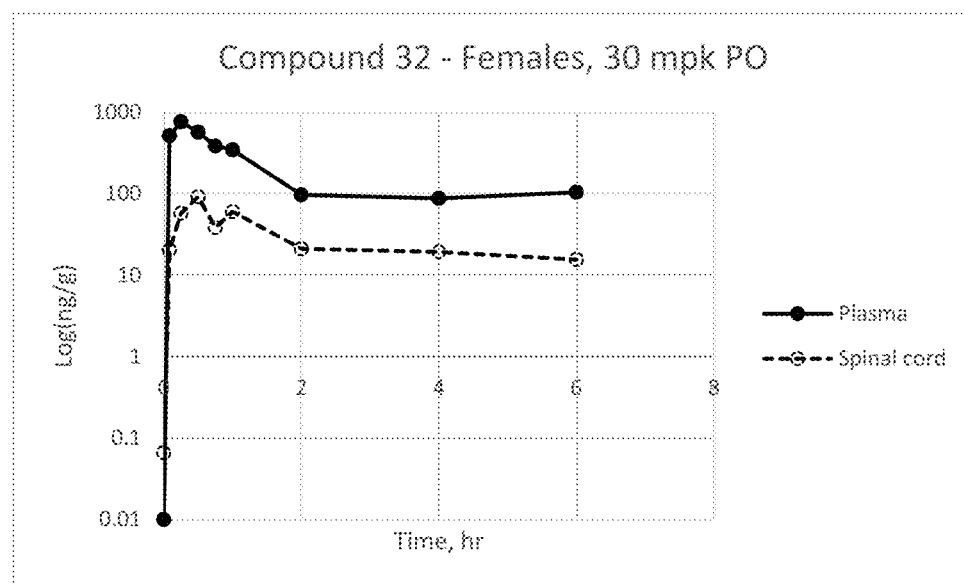
FIG. 15B is a logarithmic depiction of the data in FIG. 15A.
Figure 16A:
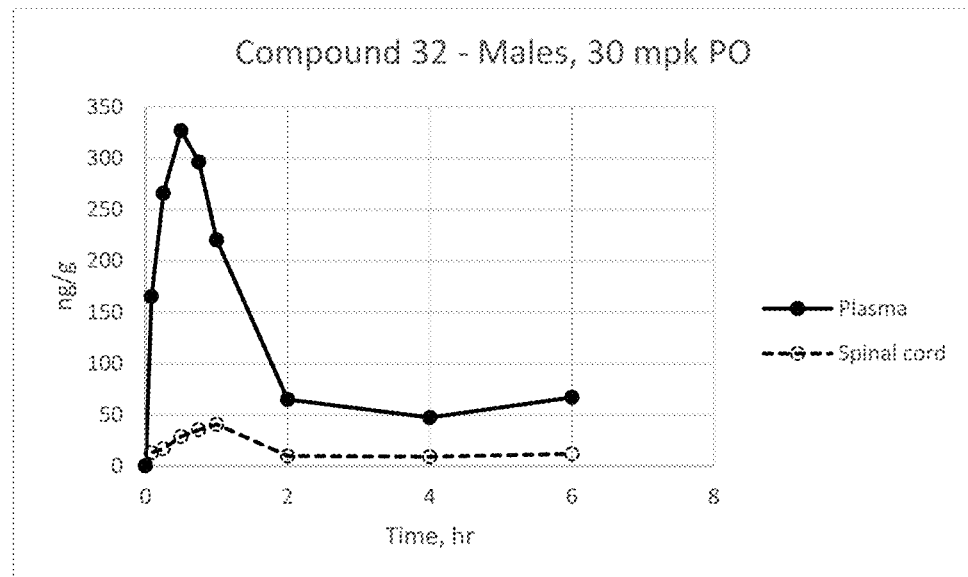
FIG. 16A depicts plasma and spinal cord concentrations of Compound 32 in male mice during the hours following administration.
Figure 16B:
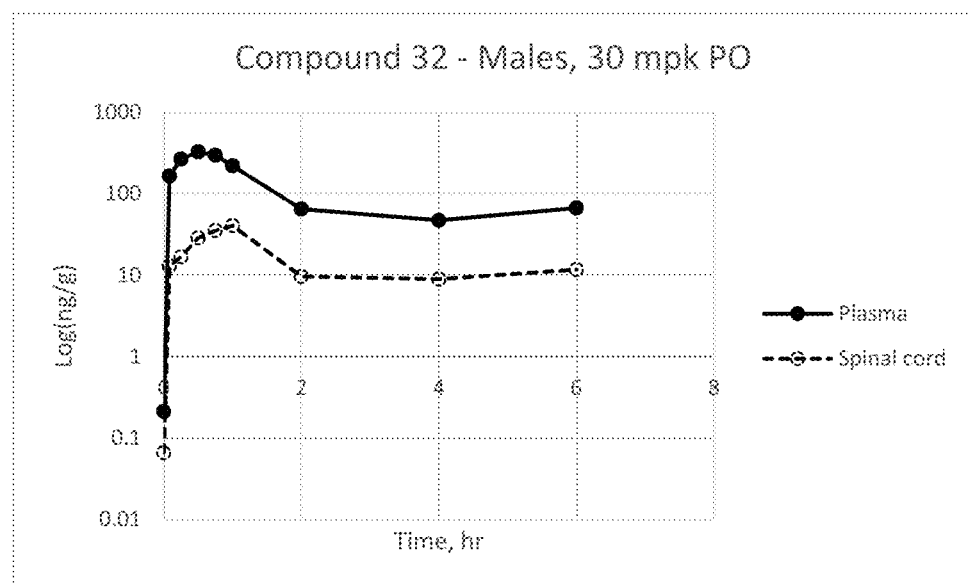
FIG. 16B is a logarithmic depiction of the data in FIG. 16A.
Figure 17A:
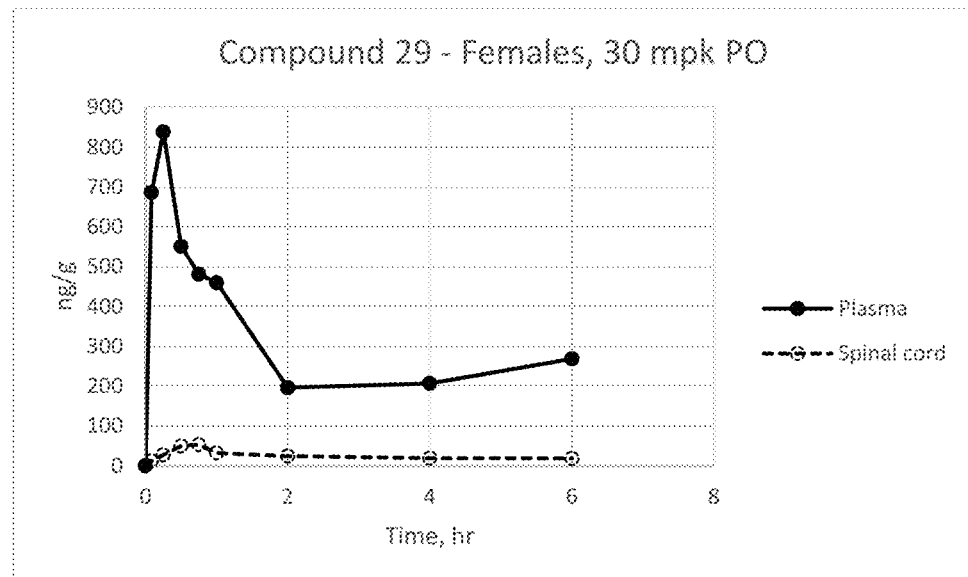
FIG. 17A depicts plasma and spinal cord concentrations of Compound 29 in female mice during the hours following administration.
Figure 17B:
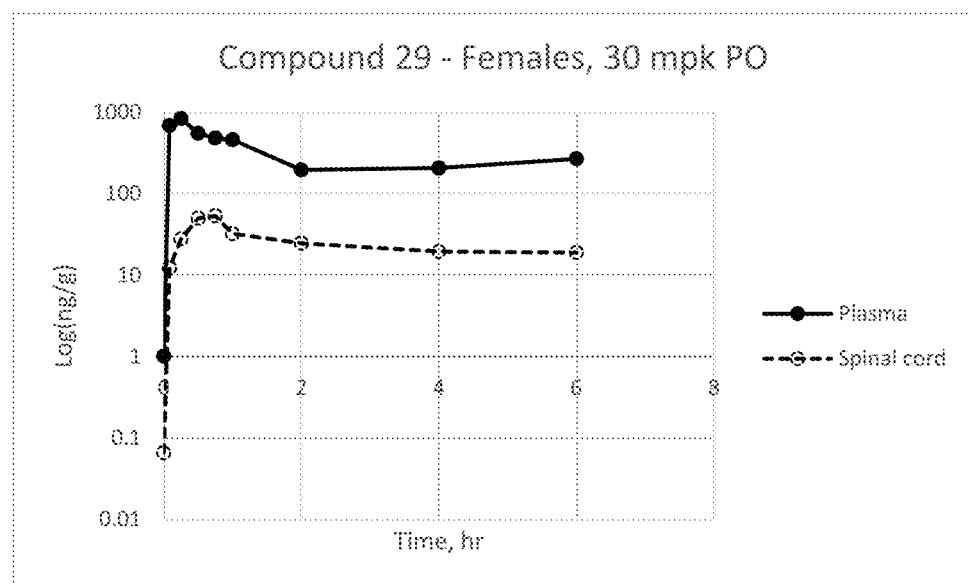
FIG. 17B is a logarithmic depiction of the data in FIG. 17A.
Figure 18A:
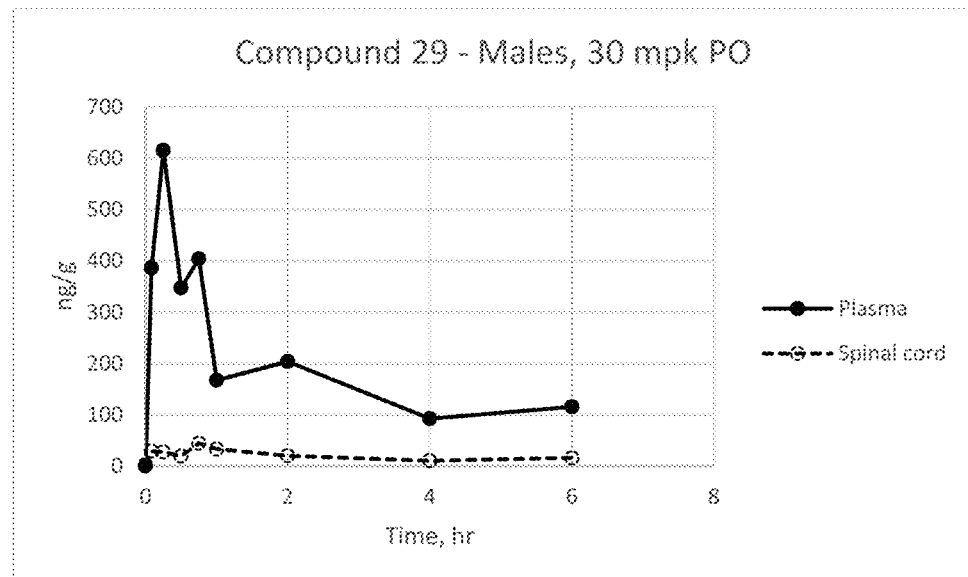
FIG. 18A depicts plasma and spinal cord concentrations of Compound 29 in male mice during the hours following administration.
Figure 18B:
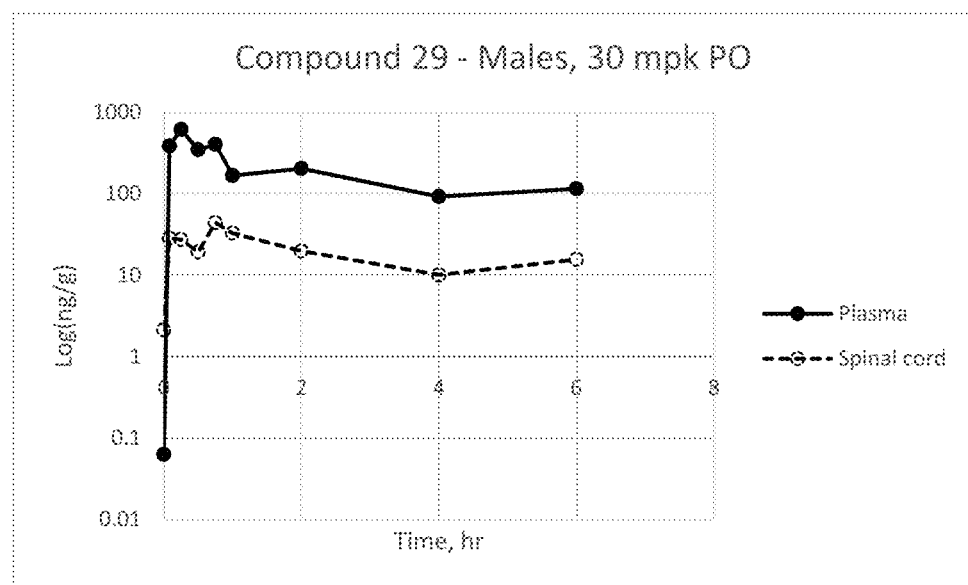
FIG. 18B is a logarithmic depiction of the data in FIG. 18A.
Figure 19A:
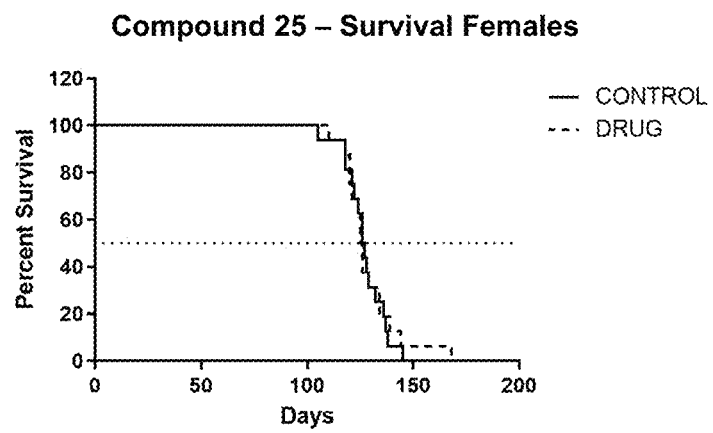
FIG. 19A illustrates the survival of female SOD1$^{G93A}$ mice treated with Compound 25 as compared to control.
Figure 19B:
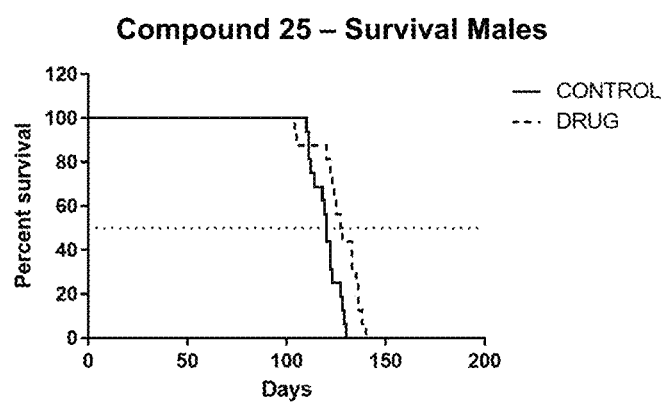
FIG. 19B illustrates the survival of male SOD1$^{G93A}$ mice treated with Compound 25 as compared to control.
Figure 20A:
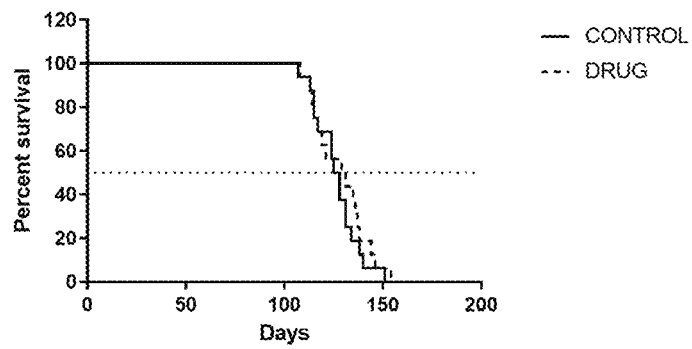
FIG. 20A illustrates the survival of female SOD1$^{G93A}$ mice treated with Compound 34 as compared to control.
Figure 20B:
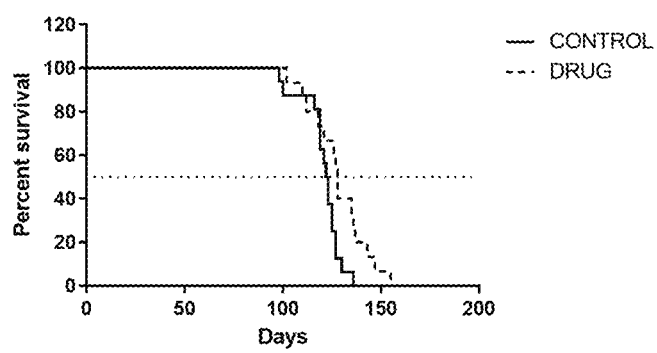
FIG. 20B illustrates the survival of male SOD1$^{G93A}$ mice treated with Compound 34 as compared to control.
Figure 21A:
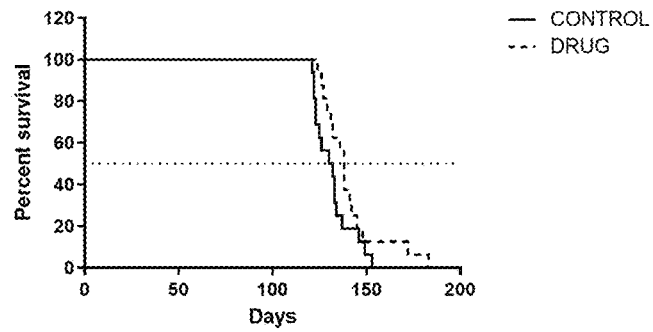
FIG. 21A illustrates the survival of female SOD1$^{G93A}$ mice treated with Compound 32 as compared to control.
Figure 21B:
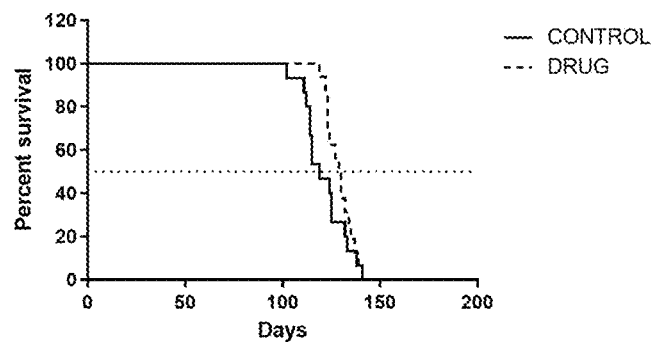
FIG. 21B illustrates the survival of male SOD1$^{G93A}$ mice treated with Compound 32 as compared to control.

Similarly, when disease onset (FIG. 10A) and survival (FIG. 10B) were measured in mice treated with Compound 37 at either dose of 10 mg/kg or 30 mg/kg, neither dose significantly affected either parameters over mice treated with vehicle.

Example 8: In Vitro Activity of Cu Complexes

In vitro activity of the ligands and their Cu and Zn complexes was determined as their ability to promote viability of human neurogenic cells in a cell-based assay. Cells were treated with the compounds added to the culture medium for 7 days. Cell viability was determined at the end of the treatment period using the CellTiter Blue® cell viability assay (Promega). The corresponding EC$_{50}$ values were calculated using nonlinear regression fitting of the standard variable slope dose response model provided in the GraphPad Prizm software.

Activity ranges of compounds of the disclosure are provided in Table 1 according to the following key:
A: EC$_{50}$ between 0.5 nM and 10 nM;
B: EC$_{50}$ between 11 nM and 25 nM;
C: EC$_{50}$ between 26 nM and 50 nM:
D: EC$_{50}$ between 51 nM and 100 nM; and
E: EC$_{50}$ between 101 nM and 500 nM.

TABLE 1

| Cpd # | Structure | Activity |
| --- | --- | --- |
| Cu-ATSM | [Cu complex structure] | D |

TABLE 1-continued

| Cpd # | Structure | Activity |
|---|---|---|
| Cu-PTSM | 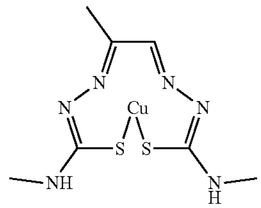 | A |
| 1 | 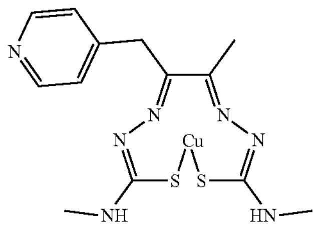 | C |
| 2 | 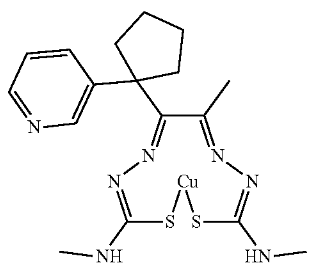 | A |
| 3 | 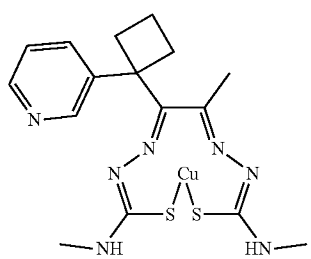 | C |
| 4 | 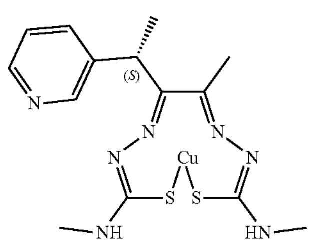 | B |
| 5 | 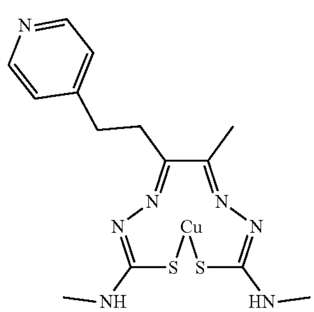 | C |

TABLE 1-continued

| Cpd # | Structure | Activity |
|---|---|---|
| 6 | 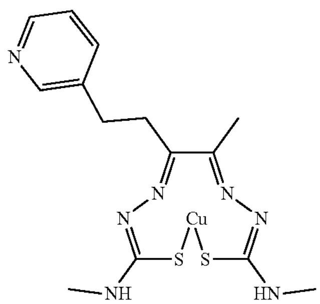 | C |
| 7 | 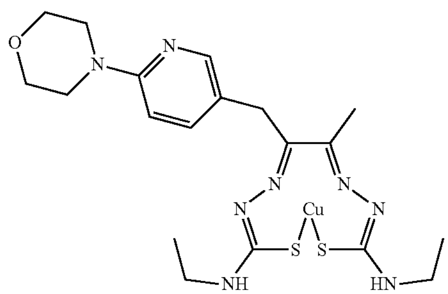 | E |
| 8 | 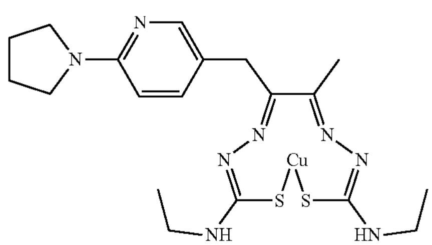 | D |
| 9 | 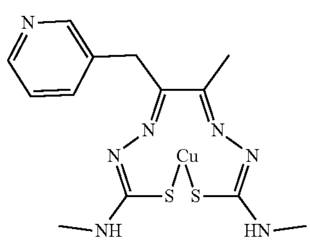 | C |
| 10 | 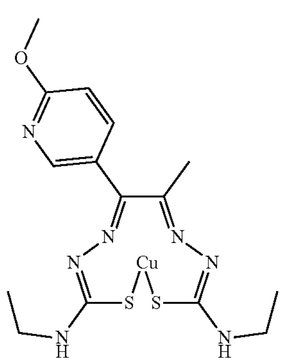 | C |

TABLE 1-continued

| Cpd # | Structure | Activity |
|---|---|---|
| 11 | 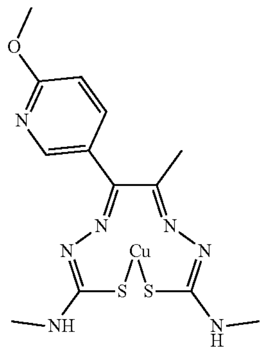 | B |
| 12 | 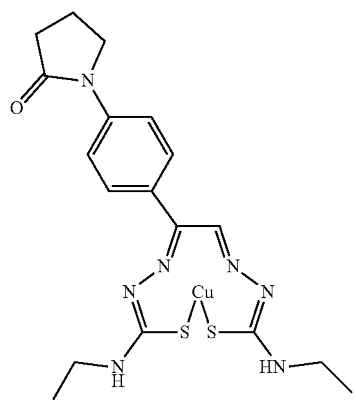 | A |
| 13 | 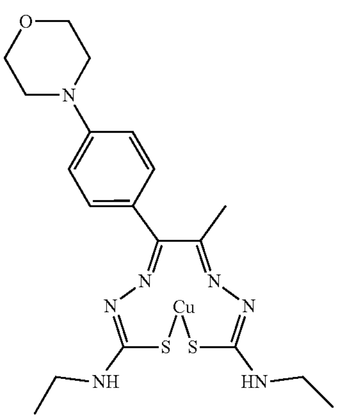 | D |
| 14 | 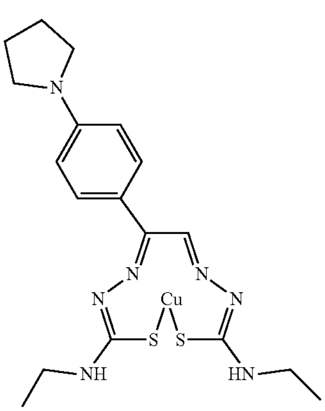 | D |

TABLE 1-continued
| Cpd # | Structure | Activity |
|---|---|---|
| 15 | 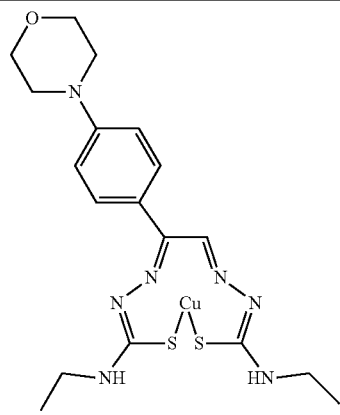 | B |
| 17 | 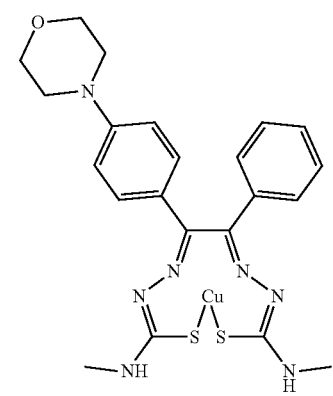 | B |
| 18 | 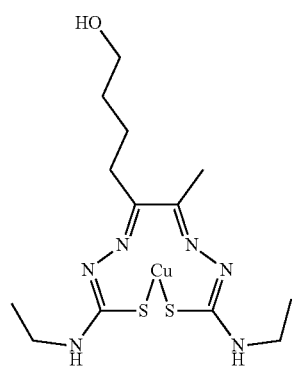 | D |

TABLE 1-continued
| Cpd # | Structure | Activity |
|---|---|---|
| 19 | 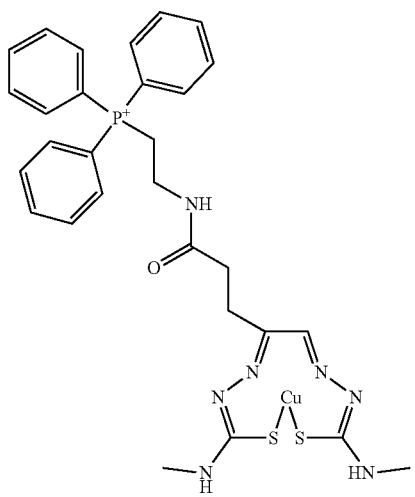 | E |
| 20 | 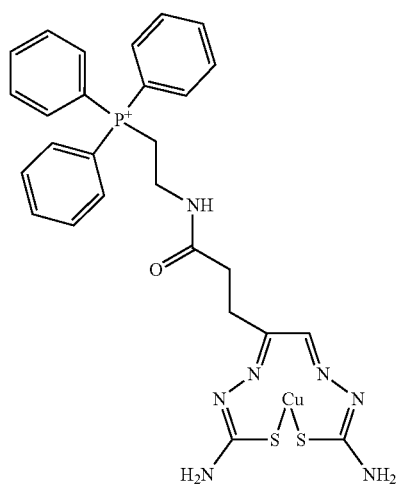 | E |
| 21 | 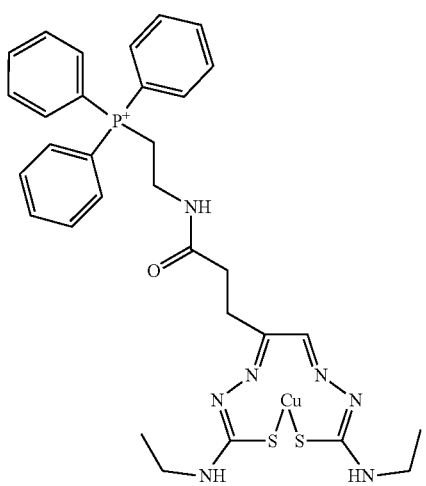 | D |

TABLE 1-continued

| Cpd # | Structure | Activity |
|---|---|---|
| 24 | 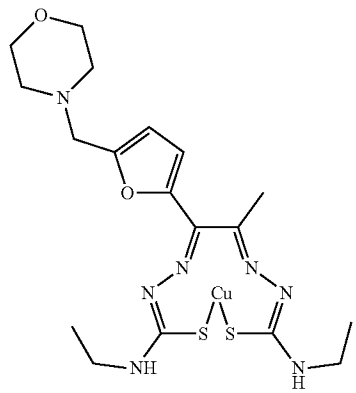 | C |
| 25 | 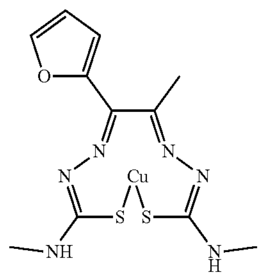 | A |
| 29 | 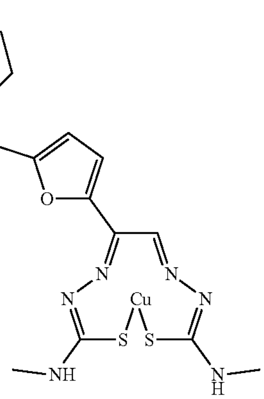 | B |
| 30 | 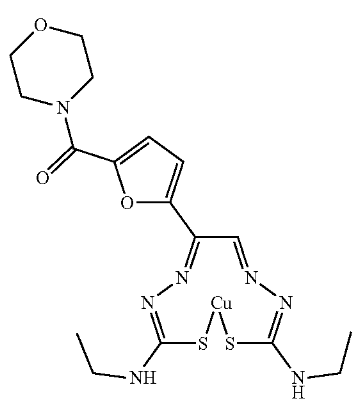 | B |

TABLE 1-continued
| Cpd # | Structure | Activity |
|---|---|---|
| 31 | 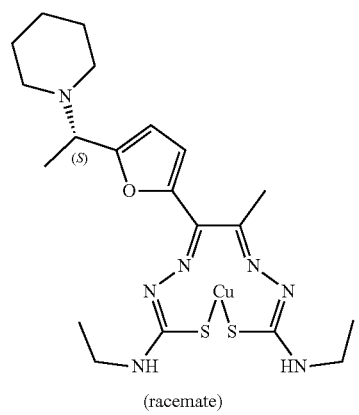<br>(racemate) | C |
| 32 | 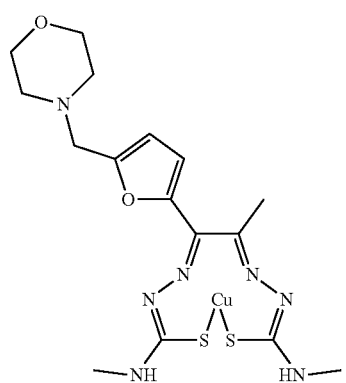 | A |
| 33 | 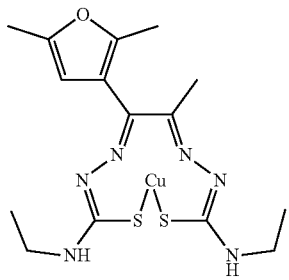 | C |
| 34 | 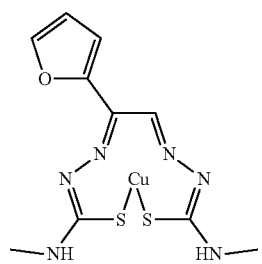 | A |

TABLE 1-continued
| Cpd # | Structure | Activity |
|---|---|---|
| 35 | 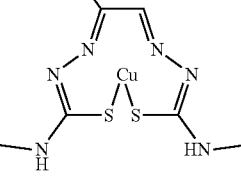 | B |
| 36 | 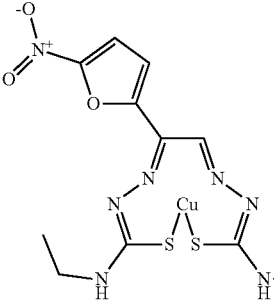 | C |
| 37 | 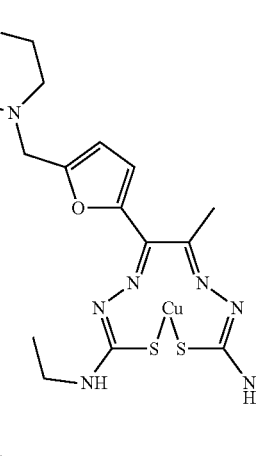 | B |
| 38 | 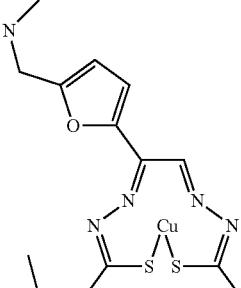 | C |

TABLE 1-continued
| Cpd # | Structure | Activity |
|---|---|---|
| 39 | 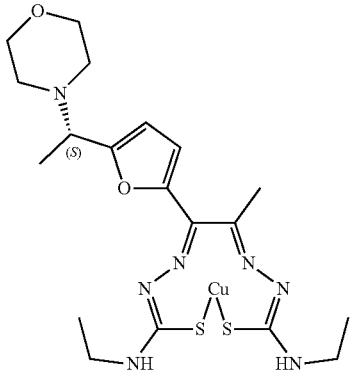<br>(racemate) | D |
| 41 | 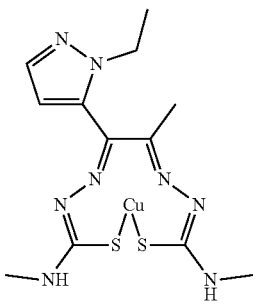 | B |
| 43 | 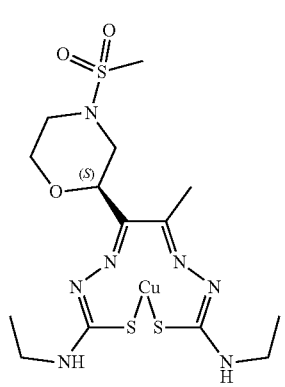<br>(racemate) | B |
| 44 | 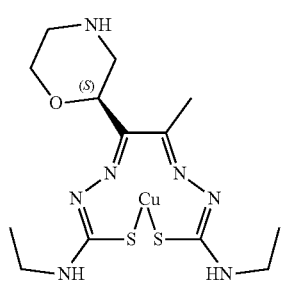<br>(racemate) | A |

TABLE 1-continued
| Cpd # | Structure | Activity |
|---|---|---|
| 45 | 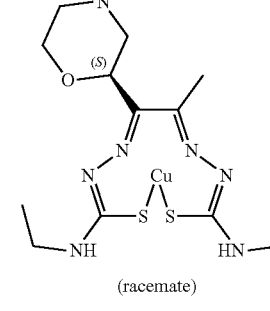<br>(racemate) | C |
| 46 | 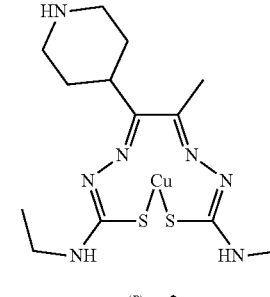 | C |
| 47 | 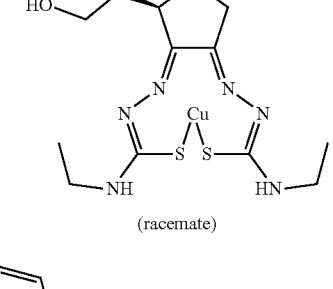<br>(racemate) | E |
| 48 | 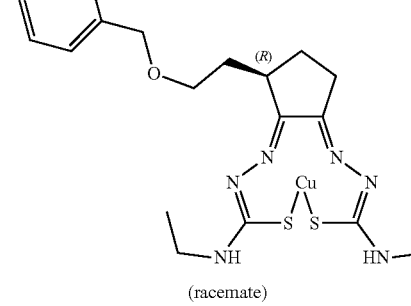<br>(racemate) | E |
| 49 | 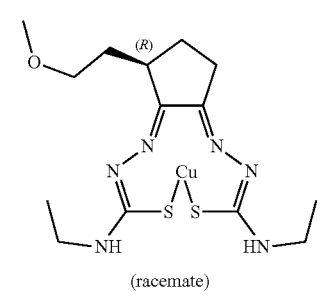<br>(racemate) | D |

TABLE 1-continued

| Cpd # | Structure | Activity |
|---|---|---|
| 50 | (racemate) | D |
| 53 | (racemate) | C |
| 54 | 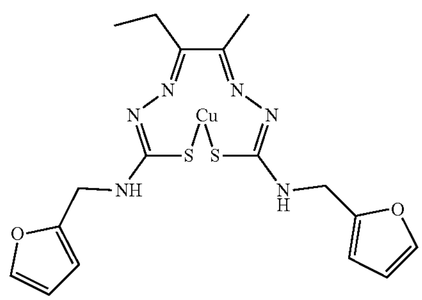 | A |
| 55 | 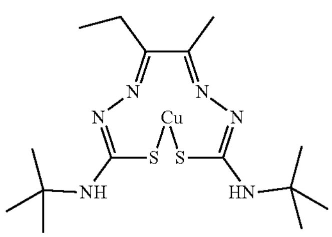 | C |
| 56 | 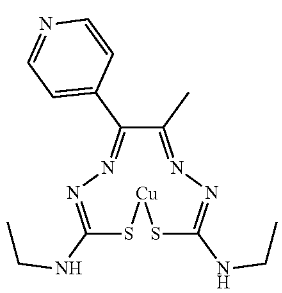 | B |

TABLE 1-continued

| Cpd # | Structure | Activity |
|---|---|---|
| 58 | 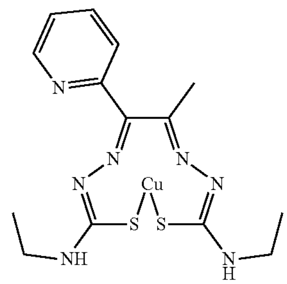 | B |
| 59 | 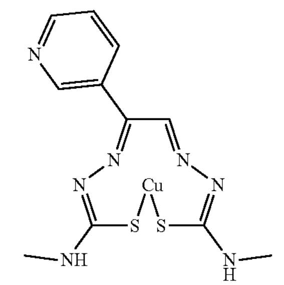 | A |
| 60 | 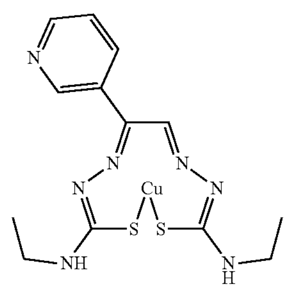 | A |
| 61 | 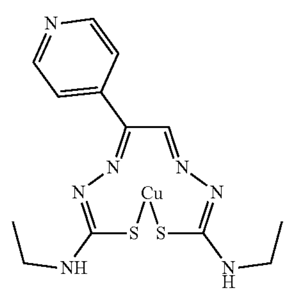 | A |
| 62 | 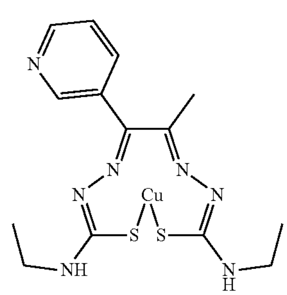 | B |

TABLE 1-continued
| Cpd # | Structure | Activity |
|---|---|---|
| 63 | 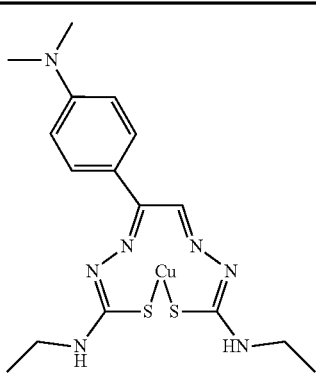 | C |
| 65 | 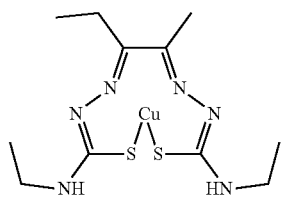 | C |
| 66 | 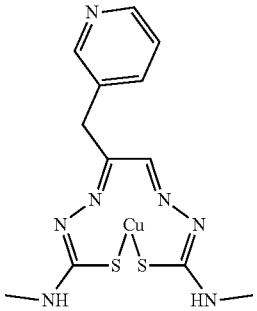 | A |
| 68 | 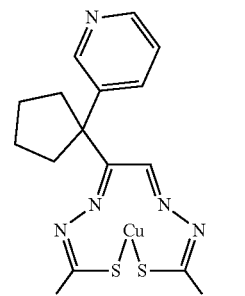 | D |
| 69 | 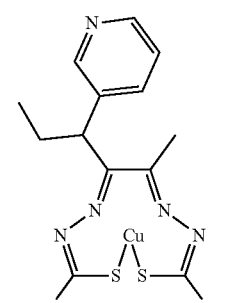 | C |

TABLE 1-continued
| Cpd # | Structure | Activity |
|---|---|---|
| 71 | 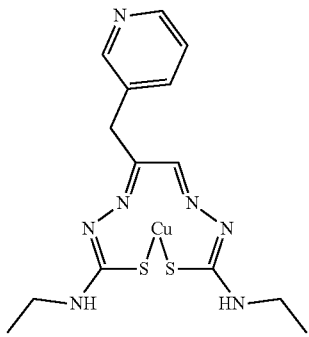 | B |
| 73 | 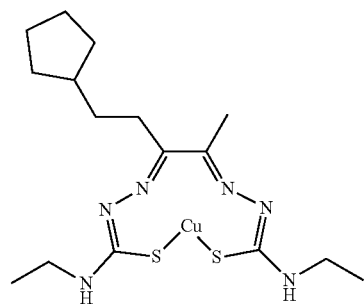 | D |
| 74 | 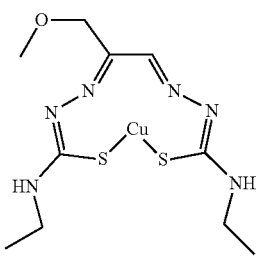 | A |
| 75 | 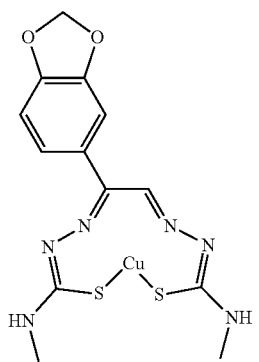 | B |

TABLE 1-continued

| Cpd # | Structure | Activity |
|---|---|---|
| 77 | 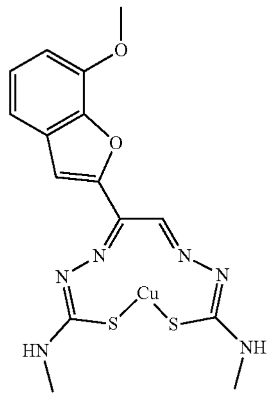 | A |
| 78 | 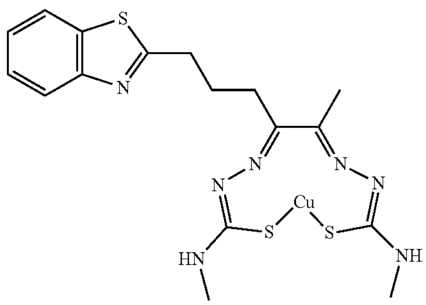 | D |
| 79 | 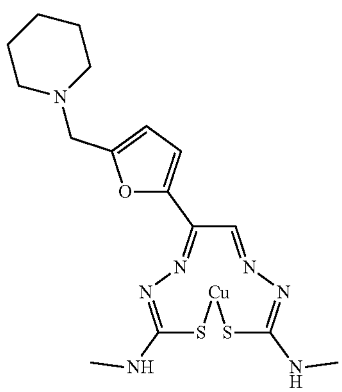 | B |
| 80 | 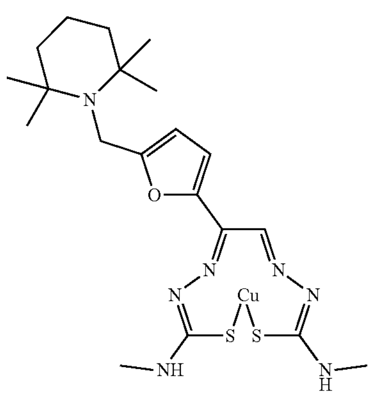 | B |

TABLE 1-continued

| Cpd # | Structure | Activity |
|---|---|---|
| 81 | 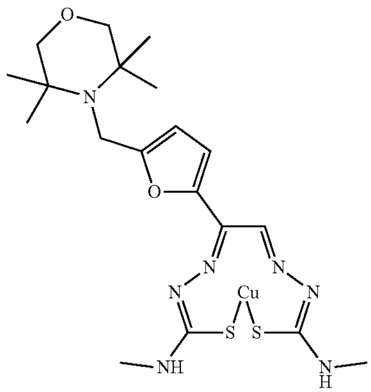 | B |
| 82 | 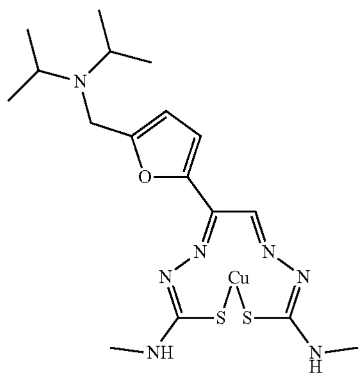 | A |
| 83 | 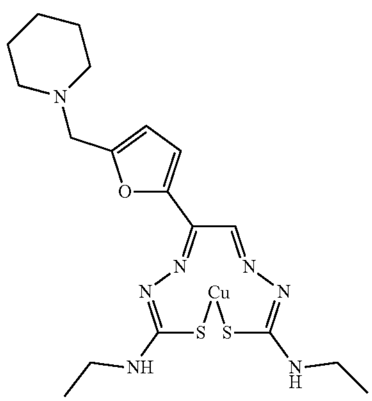 | B |
| 84 | 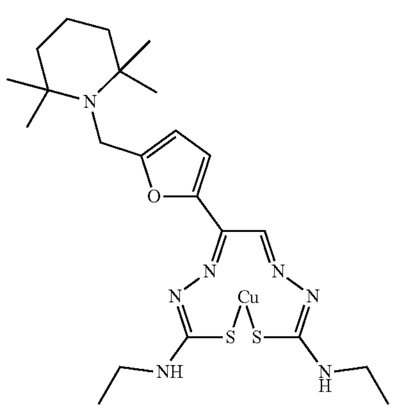 | B |

TABLE 1-continued

| Cpd # | Structure | Activity |
|---|---|---|
| 85 | 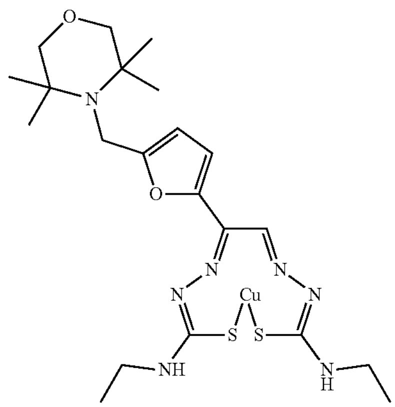 | B |
| 86 | 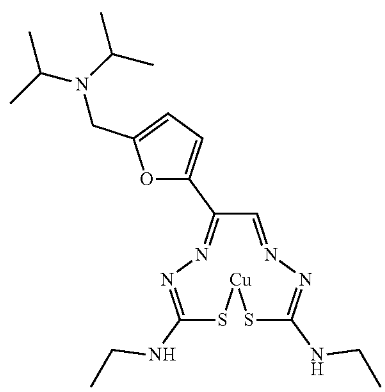 | B |
| 87 | 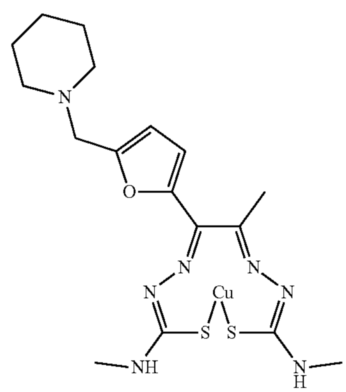 | A |
| 88 | 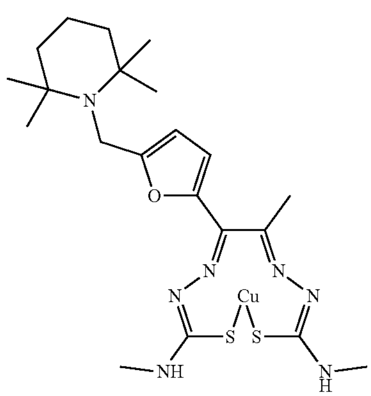 | B |

TABLE 1-continued

| Cpd # | Structure | Activity |
|---|---|---|
| 89 | 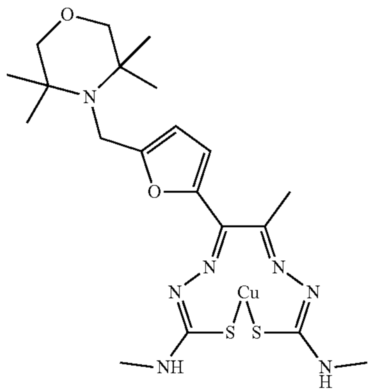 | C |
| 90 | 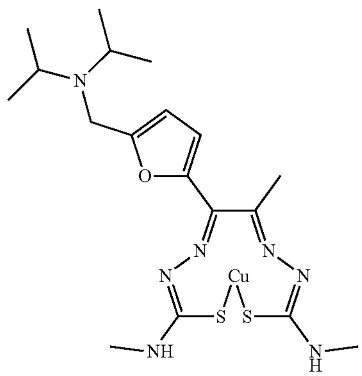 | A |
| 91 | 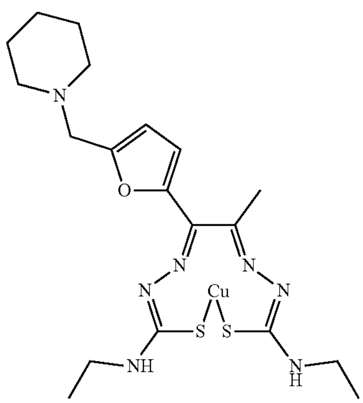 | A |
| 92 | 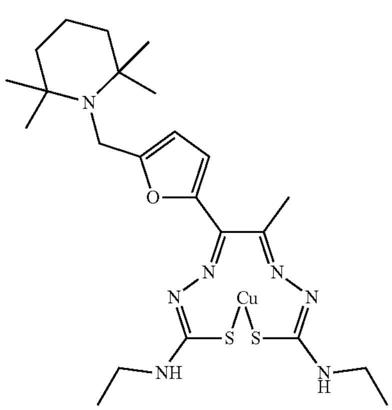 | E |

TABLE 1-continued
| Cpd # | Structure | Activity |
|---|---|---|
| 93 | 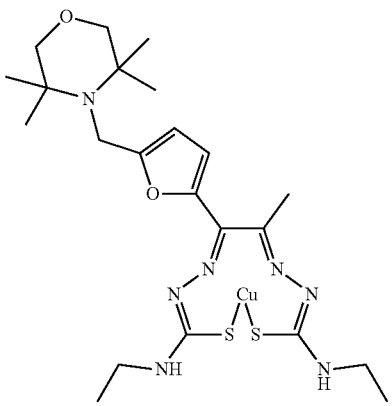 | D |
| 94 | 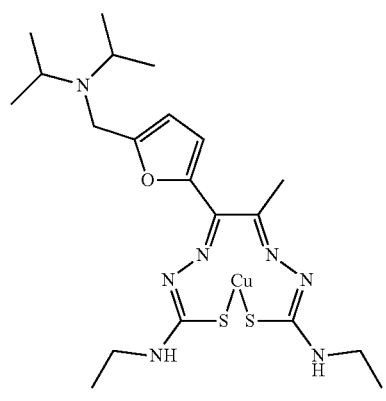 | A |
| 95 | 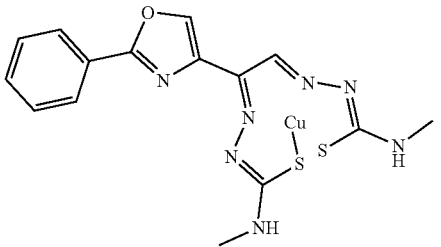 | A |
| 96 | 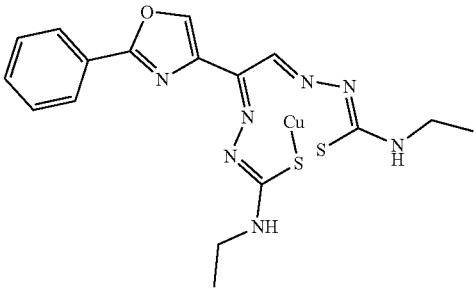 | B |

TABLE 1-continued

| Cpd # | Structure | Activity |
|---|---|---|
| 98 | 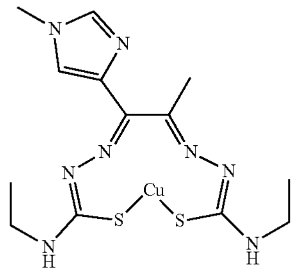 | A |
| 99 | 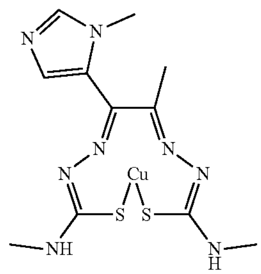 | C |
| 100 | 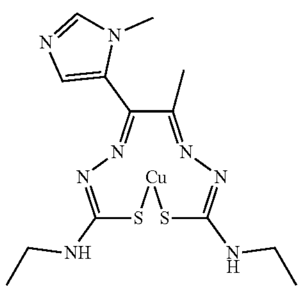 | A |
| 101 | 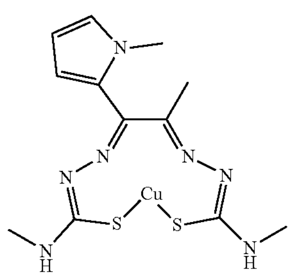 | B |
| 102 | 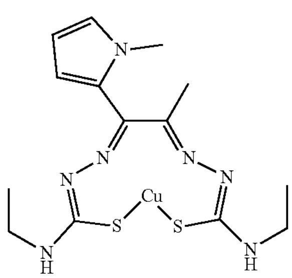 | E |

TABLE 1-continued
| Cpd # | Structure | Activity |
|---|---|---|
| 104 | 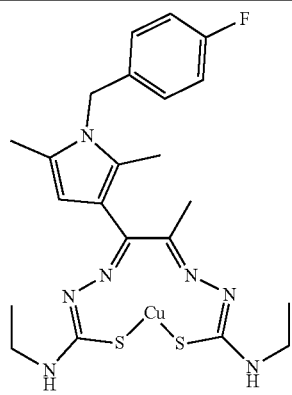 | B |
| 105 | 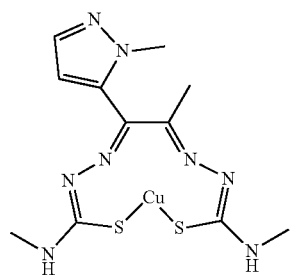 | A |
| 106 | 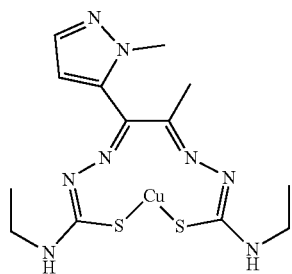 | A |
| 107 | 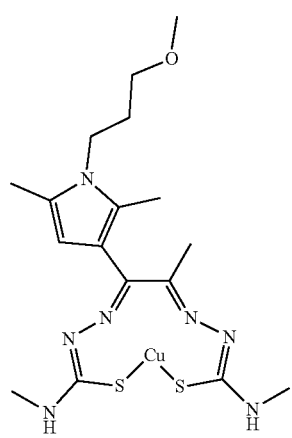 | C |

TABLE 1-continued

| Cpd # | Structure | Activity |
|---|---|---|
| 109 | 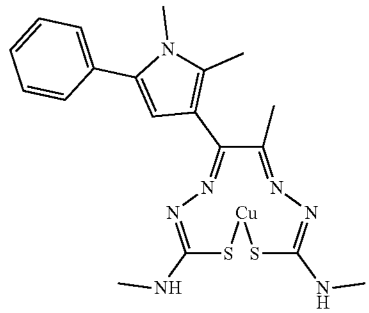 | B |
| 110 | 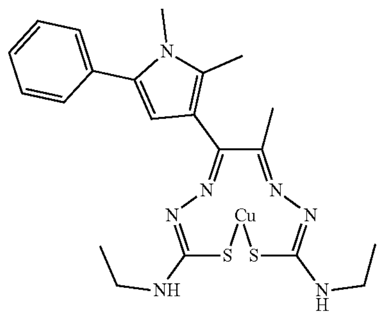 | D |
| 111 | 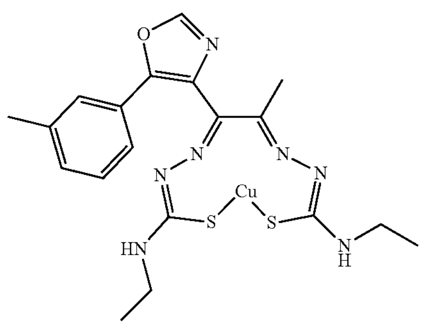 | E |
| 112 | 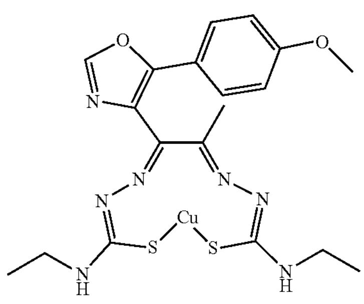 | E |
| 113 | 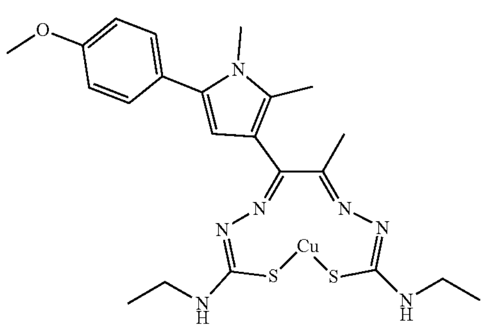 | D |

TABLE 1-continued

| Cpd # | Structure | Activity |
|---|---|---|
| 114 | 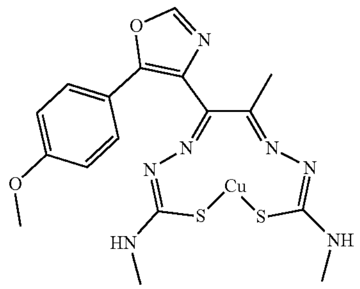 | D |
| 115 | 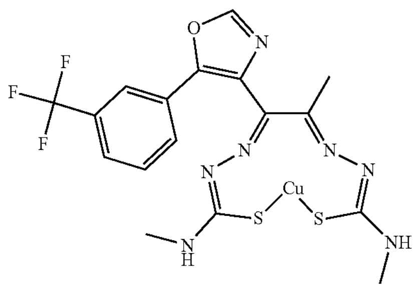 | C |
| 116 | 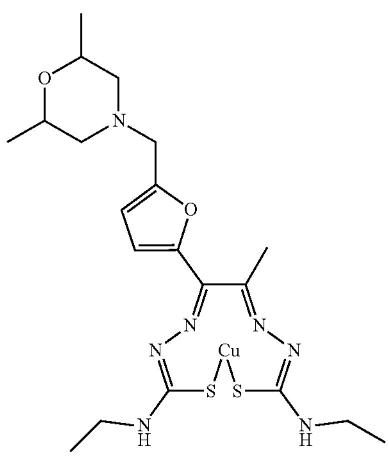 | B |
| 118 | 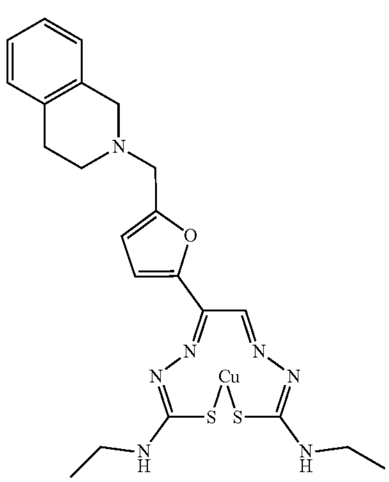 | D |

TABLE 1-continued
| Cpd # | Structure | Activity |
|---|---|---|
| 119 | 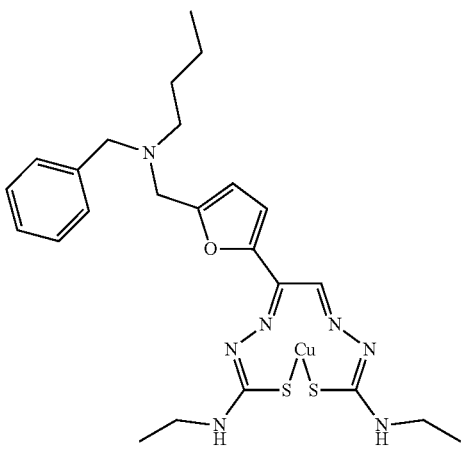 | C |
| 120 | 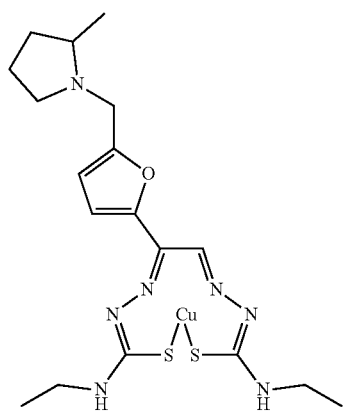 | A |
| 121 | 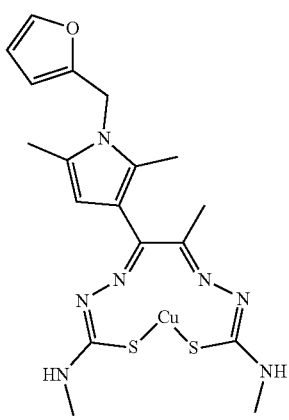 | C |

TABLE 1-continued
| Cpd # | Structure | Activity |
|---|---|---|
| 122 | 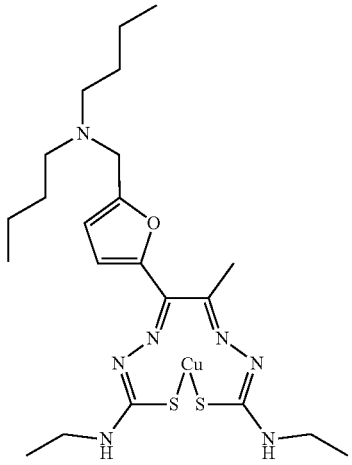 | B |
| 123 | 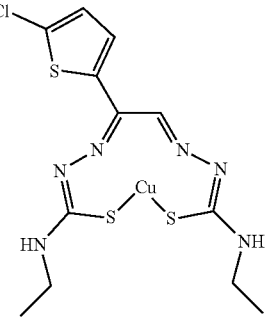 | A |
| 126 | 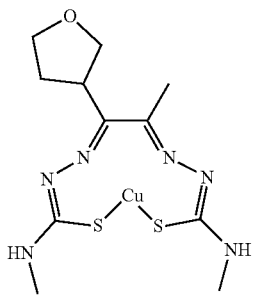 | C |
| 127 | 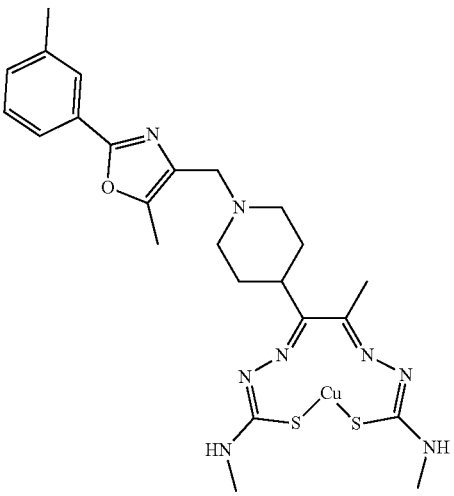 | B |

Example 9: Analysis of Compounds 25 and 34 in Mouse Plasma and Spinal Cord Tissue Mouse spinal cord samples were homogenized by first thawing frozen tissues in an ice bath, where samples were kept when not actively being processed. Phosphate buffered saline (200 µL), pH 7.4, was added to each tissue, which was homogenized by ultrasonication with a microprobe at 40% output for approximately 15 sec. Homogenate samples were stored frozen at −70° C. until analysis.

Mouse plasma samples or spinal cord homogenate samples (20 µL) were added to polypropylene test tubes containing 150 µL of extraction buffer [ammonium phosphate dibasic:ammonium citrate tribasic:ammonium hydroxide:water (0.880:1.05:1.70:~98.3, w/w/v/v)]. Internal standard solution (10 µL of 100 ng/mL) was added to each tube. Compound 25 was the internal standard for Compound 34 and vice versa. All tubes were mixed by vortexing. The contents of each tube were transferred to appropriate wells of a Biotage Isolute SLE+ plate (200 µL size; Uppsala, Sweden). Samples were briefly loaded onto the plate with positive pressure (~1 psi) and allowed to rest for 5 minutes. Dichloromethane (1 mL) was added to each well and allowed to flow through via gravity. Brief positive pressure (~1 psi) was used to complete the elution process. All wells of the receiver plate were supplemented with 25 µL of 4% propylene glycol in isopropanol (v/v). The solvent was evaporated under a stream of nitrogen, and the samples were reconstituted with 300 µL of [0.2% formic acid, 10 mM ammonium formate in water]:[0.2% formic acid, 10 mM ammonium formate in acetonitrile:water (9:1, v/v)], (1:1, v/v). The plate was capped, lightly vortex mixed, and stored at 10° C. pending analysis.

Separate tubes for the calibrators were prepared similarly using blank mouse plasma ($K_2$EDTA) or blank spinal cord homogenate as appropriate.

The extracts were analyzed using an Agilent 1200 HPLC system (Agilent, Santa Clara, CA) coupled to an API5500 mass analyzer (SCIEX, Foster City, CA). Analytes were chromatographically separated using a Kinetex® Phenyl-Hexyl column (50×2.1 mm, 2.6 µm; Phenomenex, Torrance, CA) using a mobile phase system consisting of Mobile Phase A (0.2% formic acid, 10 mM ammonium formate in water) and Mobile Phase B (0.2% formic acid, 10 mM ammonium formate in acetonitrile:water (9:1, v/v)). The following gradient profile was used.

| Time (min) | Flow Rate (mL/min) | % A | % B |
| --- | --- | --- | --- |
| Initial | 300 | 50 | 50 |
| 0.50 | 300 | 50 | 50 |
| 2.50 | 300 | 20 | 80 |
| 2.51 | 300 | 2 | 98 |
| 3.00 | 300 | 2 | 98 |
| 3.01 | 300 | 50 | 50 |
| 4.00 | 300 | 50 | 50 |

The mobile phase was nebulized using heated nitrogen in a Turbo-V source/interface set to electrospray positive ionization mode. The ionized compounds were detected using multiple reaction monitoring with transitions m/z 373.95>300.9 (Compound 25) and 360>286.9 (Compound 34).

The peak heights of Compounds 25 and 34 were acquired using Analyst v. 1.6.2 (SCIEX, Framingham, MA). The calibration curve was obtained by fitting the peak height ratios of the analyte/I.S. and the standard concentrations to a quadratic equation with $1/x^2$ weighting, using Analyst. The equation of the calibration curve was then used to interpolate the concentrations of the analyte in the samples using their peak height ratios. Results for Compound 25 are depicted in FIGS. 11A, 11B, 12A, 12B. Results for Compound 34 are depicted in FIGS. 13A, 13B, 14A, 14B.

Example 10: Analysis of Compounds 32 and 29 in Mouse Plasma and Spinal Cord Tissue Mouse spinal cord samples were homogenized by first thawing frozen tissues in an ice bath, where samples were kept when not actively being processed. Phosphate buffered saline (200 µL), pH 7.4, was added to each tissue, which was homogenized by ultrasonication with a microprobe at 40% output for approximately 15 sec. Homogenate samples were stored frozen at −70° C. until analysis.

Mouse plasma samples or spinal cord homogenate samples (20 µL) were added to wells of a Biotage Isolute PPT+ plate (Uppsala, Sweden) containing 200 µL of acetonitrile. Internal standard solution (20 µL of 50 ng/mL) was added to each tube. Compound 32 was the internal standard for Compound 29 and vice versa. The samples were mixed gently by aspiration and dispensing using a multichannel pipette, then they were allowed to rest for 5 min. Positive pressure was used to push the samples into the receiver plate. Deionized water (300 µL) was added to each well, and the plate was capped and lightly vortex mixed prior to storage at 10° C. pending analysis.

Separate tubes for the calibrators were prepared similarly using blank mouse plasma ($K_2$EDTA) or blank spinal cord homogenate as appropriate.

The extracts were analyzed using an Agilent 1200 HPLC system (Agilent, Santa Clara, CA) coupled to an API5500 mass analyzer (SCIEX, Foster City, CA). Analytes were chromatographically separated using an ACE Excel 2 C18-PFP column (100×2.1 mm, 2 µm; Mac-Mod, Chadds Ford, PA) using a mobile phase system consisting of Mobile Phase A (0.2% formic acid, 10 mM ammonium formate in water) and Mobile Phase B (0.2% formic acid, 10 mM ammonium formate in acetonitrile:water (9:1, v/v)). The following gradient profile was used.

| Time (min) | Flow Rate (mL/min) | % A | % B |
| --- | --- | --- | --- |
| Initial | 300 | 60 | 40 |
| 0.50 | 300 | 60 | 40 |
| 2.50 | 300 | 10 | 90 |
| 3.00 | 300 | 10 | 90 |
| 3.01 | 300 | 60 | 40 |
| 4.00 | 300 | 60 | 40 |

The mobile phase was nebulized using heated nitrogen in a Turbo-V source/interface set to electrospray positive ionization mode. The ionized compounds were detected using multiple reaction monitoring with transitions m/z 473.05>385.9 (Compound 32) and 458.95>371.9 (Compound 29).

The peak heights of Compound 32 and Compound 29 were acquired using Analyst v. 1.6.2 (SCIEX, Framingham, MA). The calibration curve was obtained by fitting the peak height ratios of the analyte/I.S. and the standard concentrations to a quadratic equation with $1/x^2$ weighting, using Analyst. The equation of the calibration curve was then used to interpolate the concentrations of the analyte in the samples using their peak height ratios. The peak heights used for the calculations were not rounded. Results for Compound 32 are depicted in FIGS. 15A, 15B, 16A, 16B. Results for Compound 29 are depicted in FIGS. 17A, 17B, 18A, 18B.

The invention claimed is:

1. A compound of Formula (V):

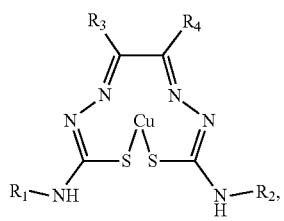

(V)

or pharmaceutically acceptable salts thereof, wherein:

$R_1$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;

$R_2$ is $C_1$-$C_6$ alkyl optionally substituted with 5- to 10-membered heteroaryl, $NH_2$, $NH(C_1$-$C_6$ alkyl), or $N(C_1$-$C_6$ alkyl)$_2$;

$R_3$ is furyl optionally substituted one time with $C_1$-$C_3$ alkyl-N($C_1$-$C_4$ alkyl)$_2$ or $C_1$-$C_3$ alkyl-(5- to 6-membered heterocycle), wherein the 5- to 6-membered heterocycle is optionally further substituted one to four times with $C_1$-$C_3$ alkyl; and $R_4$ is hydrogen or $C_{1-3}$ alkyl.

2. The compound of claim 1, wherein:

$R_1$ is methyl or ethyl; and $R_2$ is methyl or ethyl.

3. The compound of claim 1, wherein $R_3$ is selected from the group consisting of:

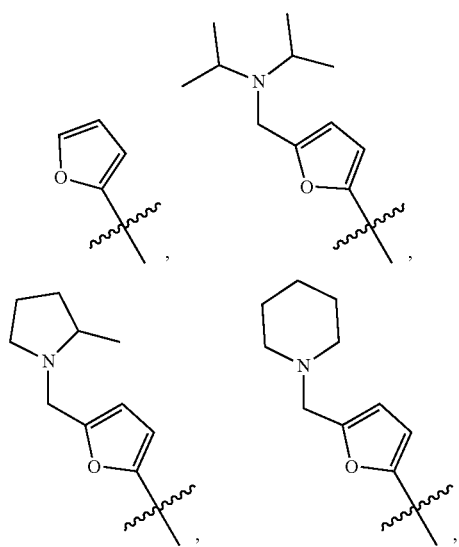

-continued

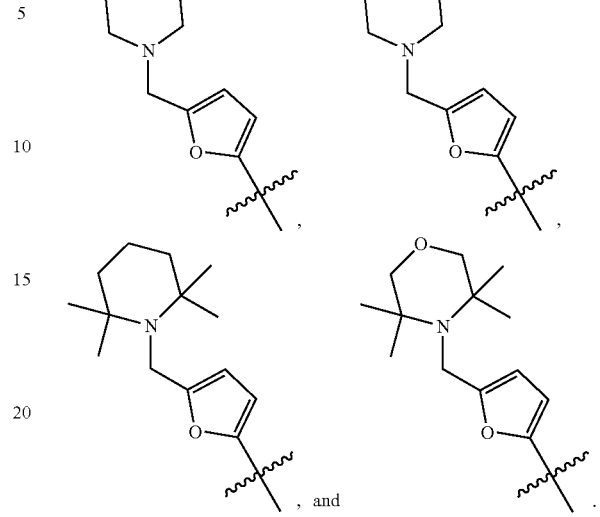

4. The compound of claim 1, wherein $R_4$ is hydrogen or methyl.

5. The compound of claim 1, wherein $R_1$ is methyl and $R_2$ is methyl.

6. The compound of claim 1, wherein $R_1$ is ethyl and $R_2$ is ethyl.

7. The compound of claim 1, wherein $R_3$ is furyl substituted one time with $C_1$-$C_3$ alkyl-N($C_1$-$C_4$ alkyl)$_2$ or $C_1$-$C_3$ alkyl-(5- to 6-membered heterocycle), wherein the 5- to 6-membered heterocycle is optionally further substituted one to four times with $C_1$-$C_3$ alkyl.

8. The compound of claim 1, wherein $R_3$ is furyl substituted one time with $C_1$-$C_3$ alkyl-(5- to 6-membered heterocycle), wherein the 5- to 6-membered heterocycle is optionally further substituted one to four times with $C_1$-$C_3$ alkyl.

9. The compound of claim 1, wherein $R_4$ is hydrogen.

10. The compound of claim 1, wherein $R_4$ is methyl.

11. The compound of claim 1, selected from the group consisting of:

Compound 23

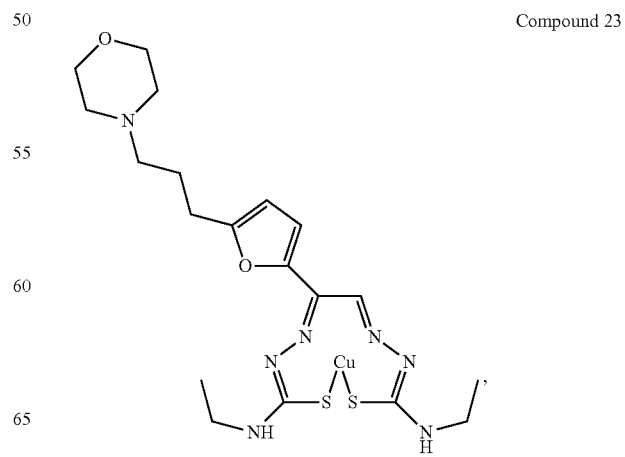

Compound 24
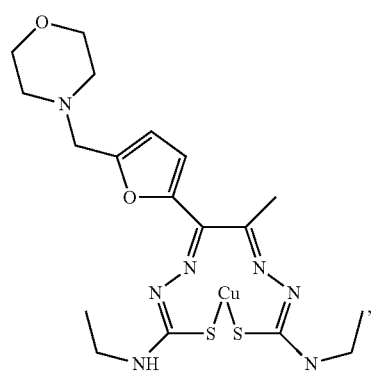
Compound 28
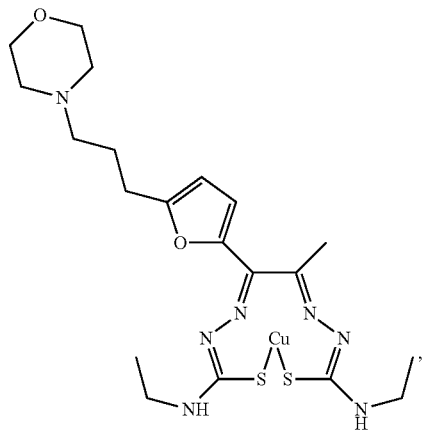
Compound 25
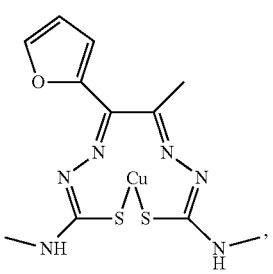
Compound 29
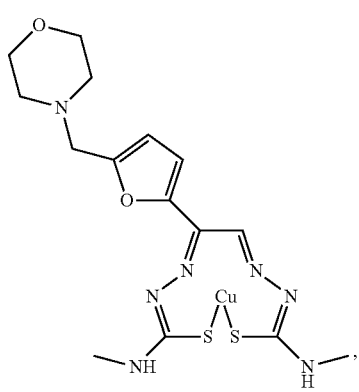
Compound 26
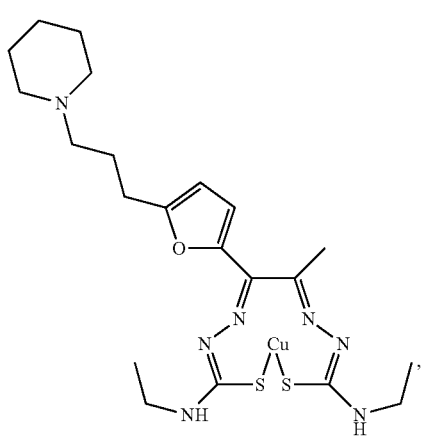
Compound 31
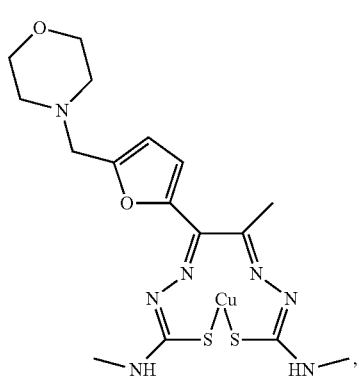
Compound 27
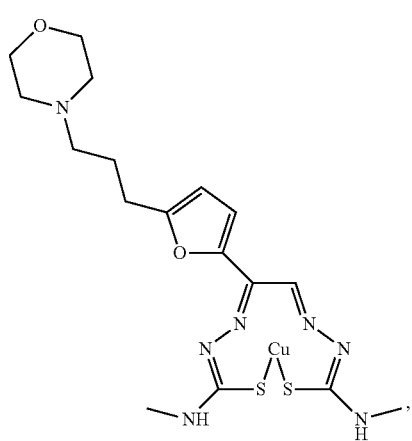
Compound 32

-continued
Compound 34
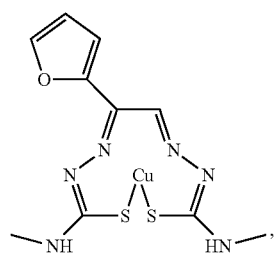
Compound 35
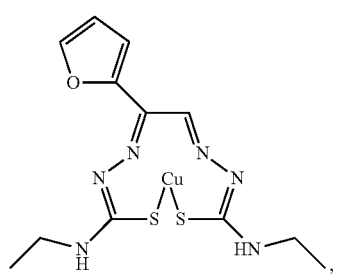
Compound 37
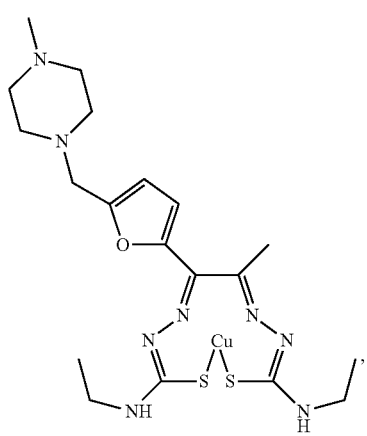
Compound 38
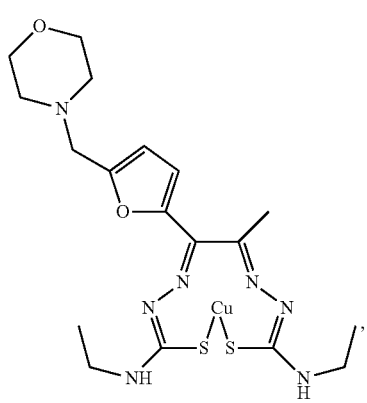
-continued
Compound 39
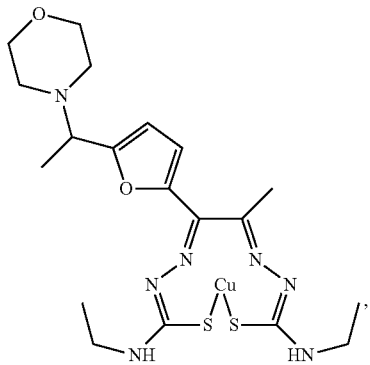
Compound 79
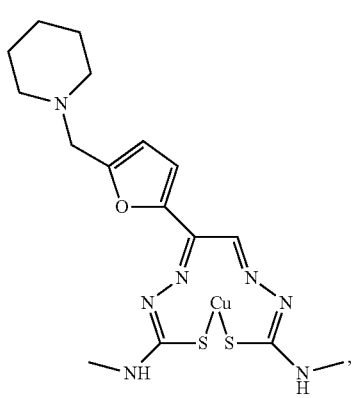
Compound 80
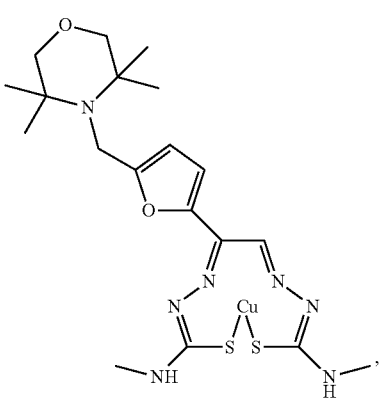
Compound 81

Compound 82
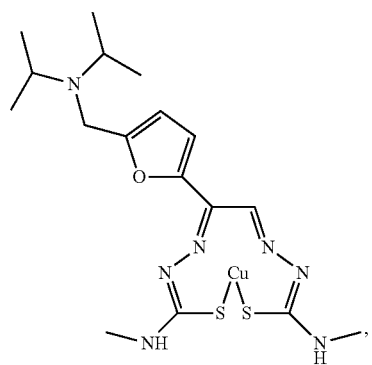
Compound 86
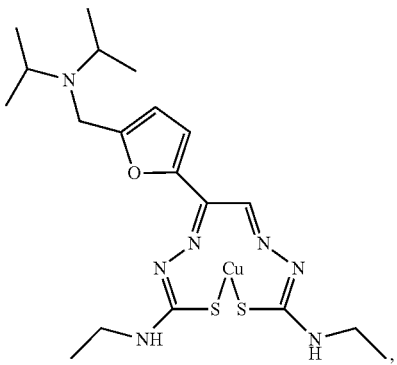
Compound 83
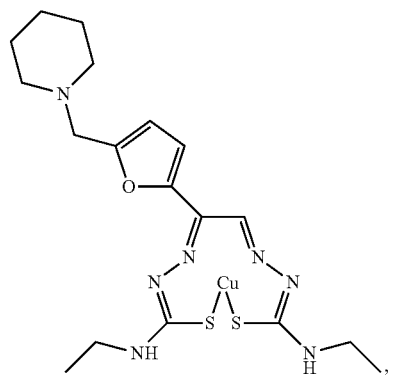
Compound 87
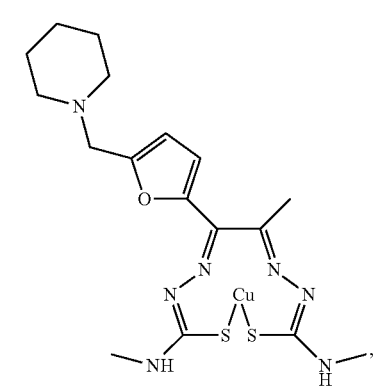
Compound 84
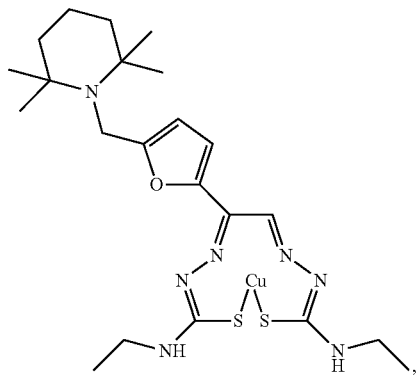
Compound 88
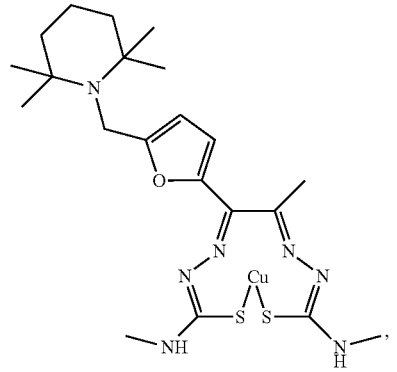
Compound 85
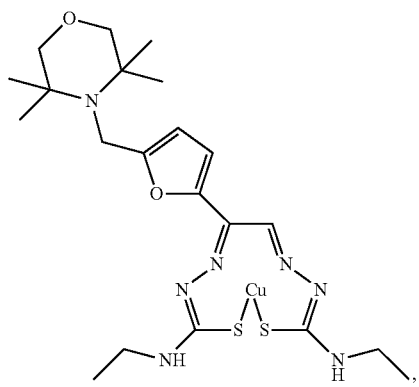
Compound 89
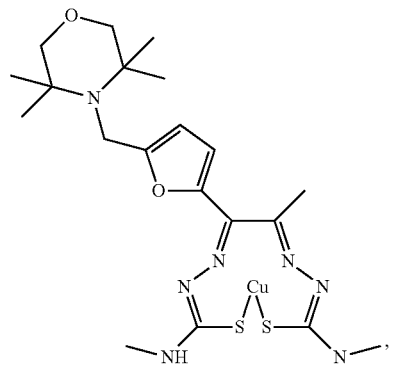

Compound 90
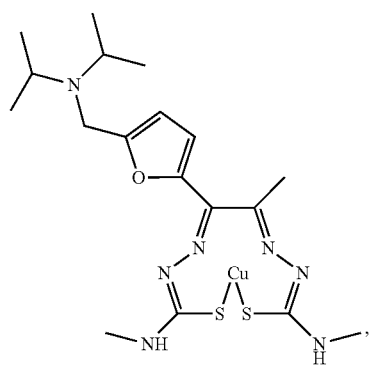
Compound 91
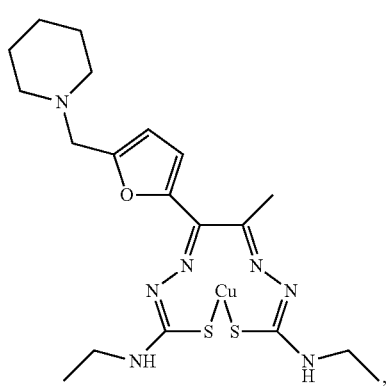
Compound 92
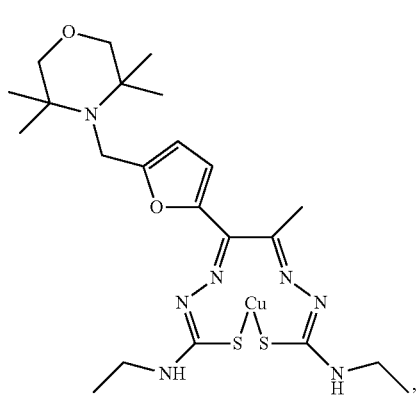
Compound 93
Compound 94
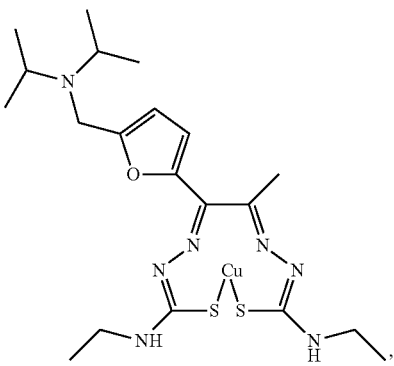
Compound 116
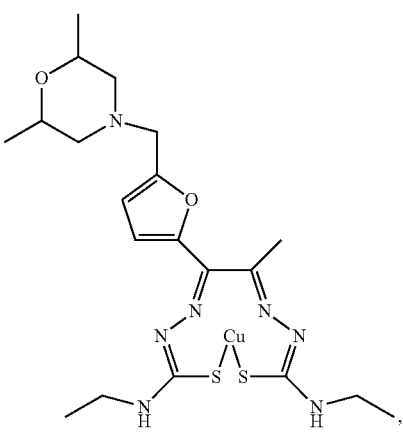
Compound 120
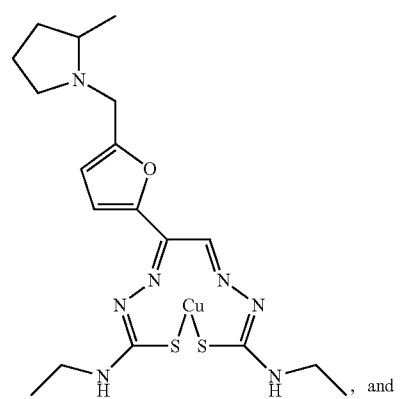
, and -continued Compound 122

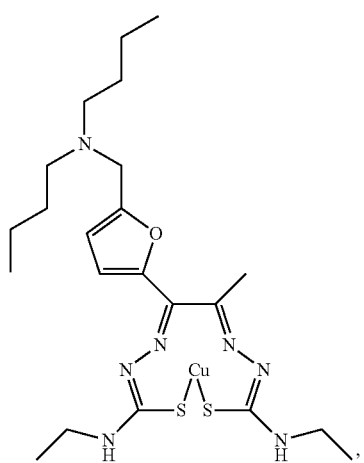

or a pharmaceutically acceptable salt thereof.

12. The compound of claim 11, selected from the group consisting of Compounds 25, 29, 32, 34, 79, 80, 81, 82, 83, 84, 85, 86, 87, 88, 90, 91, 94, and 120, or a pharmaceutically acceptable salt thereof.

13. The compound of claim 1, having the structure of Compound 32:

Compound 23

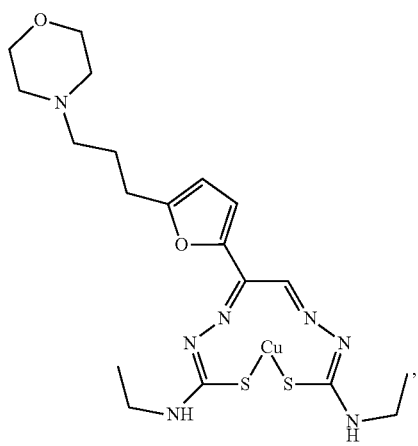

-continued

Compound 24

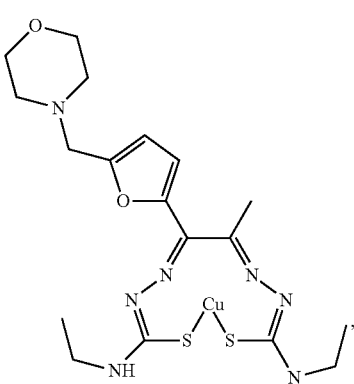

Compound 25

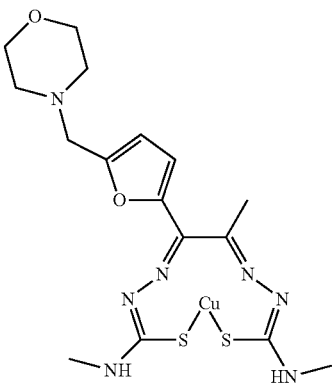

Compound 32 or a pharmaceutically acceptable salt thereof.

14. A pharmaceutical composition comprising a compound of claim 1, or a pharmaceutically acceptable salt thereof, and at least one pharmaceutically acceptable excipient, diluent, or carrier.

* * * * *